US011638760B2

(12) United States Patent
Thomas et al.

(10) Patent No.: US 11,638,760 B2
(45) Date of Patent: May 2, 2023

(54) PYRROLOBENZODIAZEPINE ANTIBODY CONJUGATES

(71) Applicant: Mersana Therapeutics, Inc., Cambridge, MA (US)

(72) Inventors: Joshua D. Thomas, Natick, MA (US); Brian D. Jones, Allston, MA (US); Timothy B. Lowinger, Carlisle, MA (US); Shuyi Tang, Shanghai (CN); Mao Yin, Needham, MA (US); Aleksandr V. Yurkovetskiy, Littleton, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 301 days.

(21) Appl. No.: 16/766,914

(22) PCT Filed: Nov. 27, 2018

(86) PCT No.: PCT/US2018/062505
§ 371 (c)(1),
(2) Date: May 26, 2020

(87) PCT Pub. No.: WO2019/104289
PCT Pub. Date: May 31, 2019

(65) Prior Publication Data
US 2022/0296725 A1 Sep. 22, 2022

Related U.S. Application Data

(60) Provisional application No. 62/701,090, filed on Jul. 20, 2018, provisional application No. 62/653,757, filed on Apr. 6, 2018, provisional application No. 62/590,893, filed on Nov. 27, 2017.

(51) Int. Cl.
*A61K 47/64* (2017.01)
*A61K 45/06* (2006.01)

(52) U.S. Cl.
CPC .............. *A61K 47/64* (2017.08); *A61K 45/06* (2013.01)

(58) Field of Classification Search
None
See application file for complete search history.

(56) References Cited

U.S. PATENT DOCUMENTS

| | | | |
|---|---|---|---|
| 5,811,097 A | 9/1998 | Allison et al. | |
| 5,855,887 A | 1/1999 | Allison et al. | |
| 5,898,031 A | 4/1999 | Crooke | |
| 5,977,318 A | 11/1999 | Linsley et al. | |
| 6,051,227 A | 4/2000 | Allison et al. | |
| 6,107,094 A | 8/2000 | Crooke | |
| 6,207,156 B1 | 3/2001 | Kuchroo et al. | |
| 6,210,669 B1 | 4/2001 | Aruffo et al. | |
| 6,303,121 B1 | 10/2001 | Kwon | |
| 6,355,476 B1 | 3/2002 | Kwon et al. | |
| 6,362,325 B1 | 3/2002 | Kwon | |
| 6,506,559 B1 | 1/2003 | Fire et al. | |
| 6,569,997 B1 | 5/2003 | Kwon | |
| 6,682,736 B1 | 1/2004 | Hanson et al. | |
| 6,808,710 B1 | 10/2004 | Wood et al. | |
| 6,887,673 B2 | 5/2005 | Kunkel et al. | |
| 6,905,685 B2 | 6/2005 | Kwon | |
| 6,974,863 B2 | 12/2005 | Kwon | |
| 6,984,720 B1 | 1/2006 | Korman et al. | |
| 7,029,674 B2 | 4/2006 | Carreno et al. | |
| 7,056,704 B2 | 6/2006 | Tuschl et al. | |
| 7,078,196 B2 | 6/2006 | Tuschl et al. | |
| 7,109,003 B2 | 9/2006 | Hanson et al. | |
| 7,132,281 B2 | 11/2006 | Hanson et al. | |
| 7,214,493 B2 | 5/2007 | Kunkel et al. | |
| 7,282,564 B2 | 10/2007 | Mello et al. | |
| 7,288,638 B2 | 10/2007 | Jure-Kunkel et al. | |
| 7,303,749 B1 | 12/2007 | Chari | |
| 7,432,249 B2 | 10/2008 | Crooke | |
| 7,432,250 B2 | 10/2008 | Crooke | |
| 7,514,546 B2 | 4/2009 | Kingsman et al. | |
| 7,538,095 B2 | 5/2009 | Fire et al. | |
| 7,560,438 B2 | 7/2009 | Fire et al. | |
| 8,044,178 B2 | 10/2011 | Boghaert et al. | |
| 8,309,094 B2 | 11/2012 | Gerber et al. | |
| 8,367,065 B2 | 2/2013 | Zhao et al. | |
| 8,524,696 B2 | 9/2013 | Borowy-Borowski et al. | |
| 10,143,695 B2 | 12/2018 | Yin et al. | |
| 10,526,294 B2 | 1/2020 | Thomas et al. | |
| 10,660,901 B2 | 5/2020 | Yin et al. | |

(Continued)

FOREIGN PATENT DOCUMENTS

| | | |
|---|---|---|
| CN | 101104640 | 1/2008 |
| WO | WO 96/40915 | 12/1996 |

(Continued)

OTHER PUBLICATIONS

Alley et al., "SJG-136 (NSC 694501), A Novel Rationally Designed DNA Minor Groove Interstrand Cross-Linking Agent with Potent and Broad Spectrum Antitumor Activity: Part 2: Efficacy Evaluations", Cancer Res., 2004, vol. 64, No. 18, p. 6700-6706.

Arnould et al. "Time-dependent cytotoxicity induced by SJG-136 (NSC 694501): influence of the rate of interstrand cross-link formation on DNA damage signaling", Mol Cancer Ther., 2006, vol. 5, No. 6, p. 1602-1609.

Baraldi, P. et al. "Design, Synthesis and Biological Activity of Pyrrolo [2,1-c][1,4] Benzodiazepine (PBD)-Distanycin Hybrid", Bioorganic & Medicinal Chemistry Letters, 1998, vol. 8, p. 3019-3024.

(Continued)

*Primary Examiner* — Samantha L Shterengarts
(74) *Attorney, Agent, or Firm* — Cooley LLP; Heidi A. Erlacher; Christine E Dunne

(57) ABSTRACT

The present disclosure relates generally to antibody-drug conjugates comprising pyrrolo[2, 1-c][1, 4]benzodiazepine (PBD) drug moieties. The present disclosure also relates to methods of using these conjugates, e.g., as therapeutics and/or diagnostics.

21 Claims, 2 Drawing Sheets

Specification includes a Sequence Listing.

(56) References Cited

U.S. PATENT DOCUMENTS

| | | | |
|---|---|---|---|
| 10,947,317 | B2 | 3/2021 | Bergstrom et al. |
| 11,135,307 | B2 | 10/2021 | Yurkovetskiy et al. |
| 2002/0039581 | A1 | 4/2002 | Carreno et al. |
| 2002/0086014 | A1 | 7/2002 | Korman et al. |
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2004/0265839 | A1 | 12/2004 | Mello et al. |
| 2005/0095244 | A1 | 5/2005 | Jure-Kunkel et al. |
| 2005/0100913 | A1 | 5/2005 | Mello et al. |
| 2005/0159351 | A1 | 7/2005 | Grate et al. |
| 2005/0201994 | A1 | 9/2005 | Korman et al. |
| 2005/0250106 | A1 | 11/2005 | Epstein et al. |
| 2006/0024798 | A1 | 2/2006 | Mello et al. |
| 2008/0050342 | A1 | 2/2008 | Fire et al. |
| 2008/0081373 | A1 | 4/2008 | Fire et al. |
| 2008/0248576 | A1 | 10/2008 | Fire et al. |
| 2010/0173382 | A1 | 7/2010 | Boghaert et al. |
| 2014/0294898 | A1 | 10/2014 | Miller et al. |
| 2015/0366987 | A1 | 12/2015 | Bodyak et al. |
| 2016/0082114 | A1 | 3/2016 | Chari et al. |
| 2017/0050971 | A1 | 2/2017 | Thurston et al. |

FOREIGN PATENT DOCUMENTS

| | | |
|---|---|---|
| WO | WO 1997/020574 | 6/1997 |
| WO | WO 98/42752 | 10/1998 |
| WO | WO 1999/032619 | 7/1999 |
| WO | WO 2000/12506 A2 | 3/2000 |
| WO | WO 00/29428 | 5/2000 |
| WO | WO 2000/037504 | 6/2000 |
| WO | WO 01/014557 | 3/2001 |
| WO | WO 2001/014424 | 3/2001 |
| WO | WO 2001/029058 | 4/2001 |
| WO | WO 2002/078731 | 10/2002 |
| WO | WO 2003/011911 | 2/2003 |
| WO | WO 2003/086459 | 10/2003 |
| WO | WO 2004/004771 | 1/2004 |
| WO | WO 2004/035607 | 4/2004 |
| WO | WO 2004/056875 | 7/2004 |
| WO | WO 2004/072286 | 8/2004 |
| WO | WO 2004/078928 | 9/2004 |
| WO | WO 2004/081021 | 9/2004 |
| WO | WO 2005/082023 | 9/2005 |
| WO | WO 2005/085177 A2 | 9/2005 |
| WO | WO 2005/085250 A1 | 9/2005 |
| WO | WO 2005/092380 | 10/2005 |
| WO | WO 2006/09649 | 1/2006 |
| WO | WO 2006/029219 | 3/2006 |
| WO | WO 2006/121168 | 11/2006 |
| WO | WO 2006/133396 | 12/2006 |
| WO | WO 2007/005874 | 1/2007 |
| WO | WO 2007/123737 | 1/2007 |
| WO | WO 2007/039752 | 4/2007 |
| WO | WO 2008/099416 | 8/2008 |
| WO | WO 2008/132601 | 11/2008 |
| WO | WO 2008/156712 | 12/2008 |
| WO | WO 2009/052623 | 4/2009 |
| WO | WO 2009/060208 | 5/2009 |
| WO | WO 2009/100140 | 8/2009 |
| WO | WO 2010/001617 | 1/2010 |
| WO | WO 2010/019570 | 2/2010 |
| WO | WO 2010/029434 | 3/2010 |
| WO | WO 2010/036959 | 4/2010 |
| WO | WO 2010/077634 | 7/2010 |
| WO | WO 2010/089411 | 8/2010 |
| WO | WO 2010/091150 | 8/2010 |
| WO | WO 2011/110604 | 9/2011 |
| WO | WO 2011/110621 | 9/2011 |
| WO | WO 2011/117882 | 9/2011 |
| WO | WO 2011/127180 | 10/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2011/159877 | 12/2011 |
| WO | WO 2012/120125 | 9/2012 |
| WO | WO 2012/128868 | 9/2012 |
| WO | WO 2012/145493 | 10/2012 |
| WO | WO 2013/006490 | 1/2013 |
| WO | WO 2013/019096 | 2/2013 |
| WO | WO 2013/022091 | 2/2013 |
| WO | WO 2013/041606 | 3/2013 |
| WO | WO 2013/041687 | 3/2013 |
| WO | WO 2013/053871 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2013/056716 | 4/2013 |
| WO | WO 2013/079174 | 6/2013 |
| WO | WO 2013/132317 | 9/2013 |
| WO | WO 2013/164592 | 11/2013 |
| WO | WO 2013/164593 | 11/2013 |
| WO | WO 2013/177481 | 11/2013 |
| WO | WO 2013/181634 | 12/2013 |
| WO | WO 2014/011518 | 1/2014 |
| WO | WO 2014/011519 | 1/2014 |
| WO | WO 2014/022679 | 2/2014 |
| WO | WO 2014/036412 | 3/2014 |
| WO | WO 2014/057073 | 4/2014 |
| WO | WO 2014/057074 | 4/2014 |
| WO | WO 2014/057122 | 4/2014 |
| WO | WO 2014/062697 | 4/2014 |
| WO | WO 2014/096365 | 6/2014 |
| WO | WO 2014/096368 | 6/2014 |
| WO | WO 2014/130879 | 8/2014 |
| WO | WO 2014/140174 | 9/2014 |
| WO | WO 2014/174111 | 10/2014 |
| WO | WO 2014/204988 | 12/2014 |
| WO | WO 2015/038426 | 3/2015 |
| WO | WO 2015/052321 | 4/2015 |
| WO | WO 2015/052322 | 4/2015 |
| WO | WO 2015/052534 | 4/2015 |
| WO | WO 2015/052535 | 4/2015 |
| WO | WO 2015/057699 | 4/2015 |
| WO | WO 2015/095124 | 6/2015 |
| WO | WO 2015/095227 | 6/2015 |
| WO | WO 2015/159076 | 10/2015 |
| WO | WO 2016/037644 | 3/2016 |
| WO | WO 2016/044396 | 3/2016 |
| WO | WO 2016/044560 | 3/2016 |
| WO | WO 2016/198869 | 12/2016 |
| WO | WO 2017/032983 | 3/2017 |
| WO | WO 2017/051249 | 3/2017 |
| WO | WO 2017/172930 | 10/2017 |
| WO | WO 2017/201132 A2 | 11/2017 |
| WO | WO 2017/223275 A1 | 12/2017 |
| WO | WO 2018/098269 A2 | 5/2018 |
| WO | WO 2019/133652 A1 | 7/2019 |
| WO | WO 2020/049286 A1 | 3/2020 |

OTHER PUBLICATIONS

Baraldi, P. et al. "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers", J. Med. Chem. 1999, vol. 42, p. 5131-5141.

Basher, M. et al. "Sequence-selective binding of C8-conjugated pyrrolobenzodiazepines (PBDs) to DNA", Biophysical Chemistry, 2017, 9 pages.

Brahmer et al. "Phase I Study of Single-Agent Anti-Programmed Death-1 (MDX-1106) in Refractory Solid Tumors: Safety, Clinical Activity, Pharmacodynamics, and Immunologic Correlates", Journal of Clinical Oncology, 2010, vol. 28, No. 19, p. 3167-3175.

Brucoli, F. et al. "Novel C8-linked pyrrolobenzodiazepine (PBD)-heterocycle conjugates that recognize DNA sequences containing an inverted CCAAT box", Bioorganic & Medicinal Chemistry Letters, 2011, vol. 21, p. 3780-3783.

Brucoli, F. et al. "An Extended Pyrrolobenzodiazepine-Polyamide Conjugate with Selectivity for a DNA Sequence Containing the

(56) References Cited

OTHER PUBLICATIONS

ICB2 Transcription Factor Binding Site", Journal of Medicinal Chemistry, 2013, vol. 56, p. 6339-6351.
Camacho et al, "Phase 1 clinical trial of anti-CTLA4 human monoclonal antibody CP-675,206 in patients (pts) with advanced solid malignancies: 2505", 2004, J. Clin. Oncol., vol. 22, sup 14, Abstract No. 2505, p. 164s.
Damayanthi, Y. et al. "Design and Synthesis of NovelPyrrolo[2,1-c][1,4]benzodiazepine-Lexitropsin Conjugates", J. Org. Chem. 1999, vol. 64, p. 290-292.
Francisco et al., cAC10-vcMMAE, an anti-CD30-monomethyl auristatin E conjugate with potent and selective antitumor activity, Blood, 2003, vol. 102, No. 4, p. 1458-1465.
Goldberg et al, "Role of PD-1 and its ligand, B7-H1, in early fate decisions of CD8 T cells", Blood, 2007, vol. 110, No. 1, p. 186-192.
Gregson et al., "Design, Synthesis, and Evaluation of a Novel Pyrrolobenzodiazepine DNA-Interactive Agent with Highly Efficient Cross-Linking Ability and Potent Cytotoxicity", J. Med. Chem., 2001, vol. 44, No. 5, p. 737-748.
Hartley et al., "SJG-136 (NSC 694501), a Novel Rationally Designed DNA Minor Groove Interstrand Cross-Linking Agent with Potent and Broad Spectrum Antitumor Activity. Part 1: Cellular Pharmacology, In vitro and Initial In vivo Antitumor Activity", Cancer Research, 2004, vol. 64, p. 6693-6699.
Hermanson, G.T. Homobifunctional Crosslinkers: Bioconjugate Techniques, 1996 Academic Press: New York, p. 234-242.
Hurley et al. "Covalent binding of antitumor antibiotics in the minor groove of DNA. Mechanism of action of CC-1065 and the pyrrolo(1,4)benzodiazepines", Acc. Chem. Res.,1986, vol. 19, p. 230-237.
Hurwitz et al. "CTLA-4 blockade synergizes with tumor-derived granulocyte-macrophage colony-stimulating factor for treatment of an experimental mammary carcinoma", Proc. Natl. Acad. Sci. USA, 1998, vol. 95, No. 17, p. 10067-10071.
Kamal, A. et al. "AlCl3-NaI assisted cleavage of polymer-bound esters with concomitant amine coupling and azido-reductive cyclization: synthesis of pyrrolobenzodiazepine derivat", Tetrahedron Letters, 2013, vol. 54, No. 33, p. 4435-4441.
Kohn K.W. "Anthramycin", Antibiotics III, 1975, SpringerVerlag, New York, p. 3-11.
Kotecha, M. et al. "Inhibition of DNA binding of the NF-Y transcription factor by the pyrrolobenzodiazepine-polyamide conjugate GWL-78", Mol Cancer Ther 2008, vol. 7, No. 5, p. 1319-1328.
Leimgruber et al. "Isolation and Characterization of Anthramycin, a New Antitumor Antibiotic" Journal of the American Chemical Society, 1965, vol. 87, p. 5791-5793.
Leimgruber et al. "The Structure of Anthramycin", Journal of the American Chemical Society, 1965, vol. 87, p. 5793-5795.
Lyon R. et al. "Reducing hydrophobicity of homogeneous antibody-drug conjugates improves pharmacokinetics and therapeutic index" Nature Biotechnology, 2015, vol. 33, No. 7, p. 733-735.
Martin et al., "Sequence-Selective Interaction of the Minor-Groove Interstrand Cross-Linking Agent SJG-136 with Naked and Cellular DNA: Footprinting and Enzyme Inhibition Studies", Biochemistry, 2005, vol. 44, No. 11, p. 4135-4147.
Masterson, L. et al. "Synthesis and biological evaluation of pyrrolo[2,1-c][1,4]benzodiazepine (PBD) C8 cyclic amine conjugates", Bioorganic & Medicinal Chemistry Letters, 2004, vol. 14, p. 901-904.
Mokyr et al, "Realization of the Therapeutic Potential of CTLA-4 Blockade in Low-Dose Chemotherapy-treated Tumor-bearing Mice", Cancer Research, 1998, vol. 58, p. 5301-5304.
Rahman, K. et al. "GC-Targeted C8-linked Pyrrolobenzodiazepine (PBD)-Biaryl Conjugates with Femtomolar In Vitro Cytotoxicity and In Vivo Antitumour Activity in Mouse Models", Journal of Medicinal Chemistry, 2013, vol. 56, p. 2911-2935.
Rahman, K. et al. "GC-Targeted C8-linked Pyrrolobenzodiazepine (PBD)-Biaryl Conjugates with Femtomolar In Vitro Cytotoxicity and In Vivo Antitumour Activity in Mouse Models", Journal of Medicinal Chemistry, 2013, Supporting Information, 28 pages.
Rahman, K. et al. "Antistaphylococcal activity of DNA-interactive pyrrolobenzodiazepine (PBD) dimers and PBD-biaryl conjugates", Journal of Antimicrobial Chemotherapy, 2012, vol. 67, p. 1683-1696.
Reddy B. et al. "Design, synthesis and in vitro cytotoxicity studies of novel pyrrolo [2,1-c] [1,4]benzodiazepine (PBD)—polymade conjugates and 2,2'-PBD Dimers", Anti-Cancer Drug Design, 2000, vol. 15, p. 225-238.
Reid E. et al. "Design, synthesis and evaluation of novel, potent DNA alkylating agents and their antibody-drug conjugates (ADCs)", Bioorganic & Medicinal Chemistry Letters, 2019, 4 pages.
Sapra et al., "Long-term Tumor Regression Induced by an Antibody-Drug Conjugate That Targets 5T4, an Oncofetal Antigen Expressed on Tumor-Initiating Cells", Mol Cancer Ther. 2013, vol. 12, p. 38-47.
Thompson et al, "PD-1 Is Expressed by Tumor-Infiltrating Immune Cells and Is Associated with Poor Outcome for Patients with Renal Cell Carcinoma", Clinical Cancer Research, 2007, vol. 13, No. 6, p. 1757-1761.
Tiberghien et al. "Design and Synthesis of Tesirine, a Clinical Antibody-Drug Conjugate Pyrrolobenzodiazepine Dimer Payload", ACS Medical Chemistry Letters, 2016, vol. 7, p. 983-987.
Wells, G. et al. "Design, Synthesis, and Biophysical and Biological Evaluation of a Series of Pyrrolobenzodiazepine-Poly(N-methylpyrrole) Conjugates", J. Med. Chem. 2006, vol. 49, p. 5442-5461.

PYRROLOBENZODIAZEPINE ANTIBODY CONJUGATES

RELATED APPLICATIONS

This application is a U.S. National Phase application, filed under U.S.C. § 371, of International Application No. PCT/US2018/062505, filed Nov. 27, 2018, which claims priority to, and the benefit of, U.S. Provisional Application Nos. 62/590,893, filed Nov. 27, 2017, 62/653,757, filed Apr. 6, 2018, and 62/701,090, filed Jul. 20, 2018, under 35 U.S.C. § 119(e). The content of each of these applications are hereby incorporated by reference in their entireties.

INCORPORATION BY REFERENCE OF SEQUENCE LISTING

The contents of the text file named "MRSN-022N01US_SeqList.txt", which was created on May 27, 2020 and is 3 KB in size, are hereby incorporated by reference in their entirety.

BACKGROUND

The pyrrolo[2, 1-c][1, 4]benzodiazepines (PBDs) area family of naturally occurring, monofunctional DNA alkylating antitumor antibiotics, which includes anthramycin, DC-81, tomaymycin, and sibiromycin. These compounds bind exclusively to the exocyclic N2 of guanine in the minor groove and span 3 base pairs in a sequence specific manner (5'PuGPu). The first PBD antitumor antibiotic, anthramycin, was discovered in 1965 (Leimgruber et al., 1965. *J. Am. Chem. Soc.*, 87, 5793-5795; and Leimgruber et al., 1965 *J. Am. Chem. Soc.*, 87, 5791-5793). Since then, a number of naturally occurring PBDs and variety of analogues have been reported.

PBDs have the general structure:

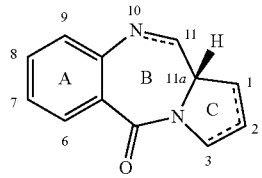

The PBDs differ in the number, type and position of substituents, in both their aromatic A rings and pyrrolo C rings, and in the degree of saturation of the C ring. In the B-ring there is either an imine (N=C), a carbinolamine (NH—CH(OH)) or a carbinolamine methyl ether (NH—CH(OMe)) at the N10-C11 position which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III*. Springer-Verlag, New York, pp. 3-11; and Hurley and Needham-VanDevanter, 1986 *Acc. Chem. Res.*, 19, 230-237). Their ability to form an adduct in the minor groove enables them to interfere with DNA processing, hence their use as antitumor agents.

The first PBD to enter the clinic, SJG-136 (NSC 694501) is a potent cytotoxic agent that causes DNA inter-strand crosslinks (S. G Gregson et al., 2001, J. Med. Chem., 44: 737-748; M. C. Alley et al., 2004, Cancer Res., 64: 6700-6706; J. A. Hartley et al., 2004, Cancer Res., 64: 6693-6699; C. Martin et al., 2005, Biochemistry., 44: 4135-4147; S. Arnould et al., 2006, Mol. Cancer Ther., 5: 1602-1509). Results from a Phase I clinical evaluation of SJG-136 revealed that this drug was toxic at extremely low doses (maximum tolerated dose of 45 µg/m, and several adverse effects were noted, including vascular leak syndrome, peripheral edema, liver toxicity and fatigue. DNA damage was noted at all doses in circulating lymphocytes.

Accordingly, there exists a need for more selective and efficacious drugs that can deliver critical DNA damage with minimal side effects continues.

SUMMARY

The present disclosure provides, inter alia, an antibody-drug conjugate (ADC) of Formula (I):

$$\text{PBRM-}[L^C\text{-D}]_{d15} \quad (I)$$

or a pharmaceutically acceptable salt or solvate thereof, wherein:
  PBRM denotes a protein based recognition-molecule;
  $L^C$ is a linker unit connecting the PBRM to D;
  D is a PBD drug moiety; and
  $d_{15}$ is an integer from about 1 to about 20.

In some embodiments, the conjugate is of Formula (II):

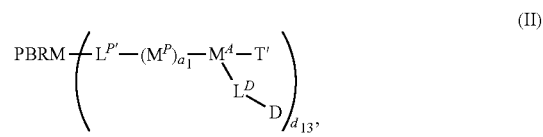

or a pharmaceutically acceptable salt or solvate thereof, wherein:
  PBRM denotes a protein based recognition-molecule;
  each occurrence of D is independently a PBD drug moiety;
  $L^{P'}$ is a divalent linker moiety connecting the PBRM to $M^P$; of which the corresponding monovalent moiety $L^P$ contains a functional group $W^P$ that is capable of forming a covalent bond with a functional group of the PBRM;
  $M^P$ is a Stretcher unit;
  $a_1$ is an integer from 0 to 1;
  $M^A$ comprises a peptide moiety that contains at least two amino acids;
  T' is a hydrophilic group and the

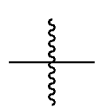

between T' and $M^A$ denotes direct or indirect attachment of T' and $M^A$;
  each occurrence of $L^D$ is independently a divalent linker moiety connecting D to $M^A$ and comprises at least one cleavable bond such that when the bond is broken, D is released in an active form for its intended therapeutic effect; and
  $d_{13}$ is an integer from 1 to 20.

In some embodiments, $d_{13}$ is an integer from 2 to 14, from 2 to 12, from 2 to 10, from 2 to 8, from 2 to 6, from 2 to 4, from 4 to 10, from 4 to 8, from 4 to 6, from 6 to 14, from 6 to 12, from 6 to 10, from 6 to 8, from 8 to 14, from 8 to 12, or from 8 to 10.
In some embodiments, $d_{13}$ is 3 to 5
In some embodiments, $d_{13}$ is 4 or 5.
In some embodiments, $L^P$, when not connected to PBRM, comprises a terminal group $W^P$, in which each $W^P$ independently is:
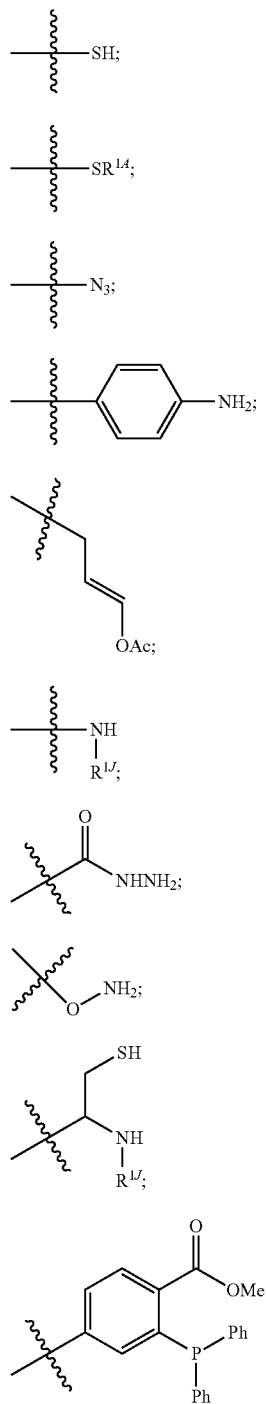
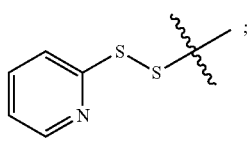
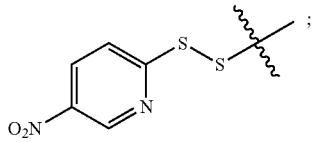
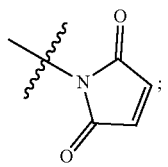
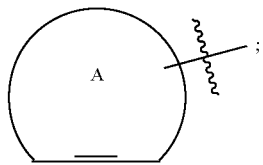
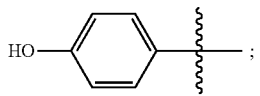
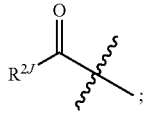
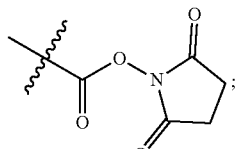
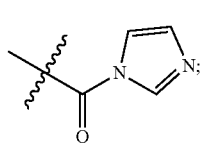
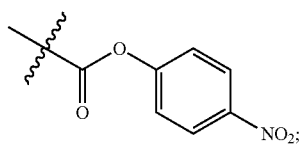
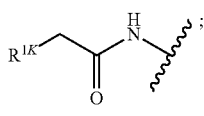
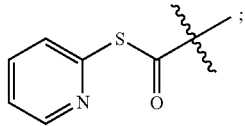

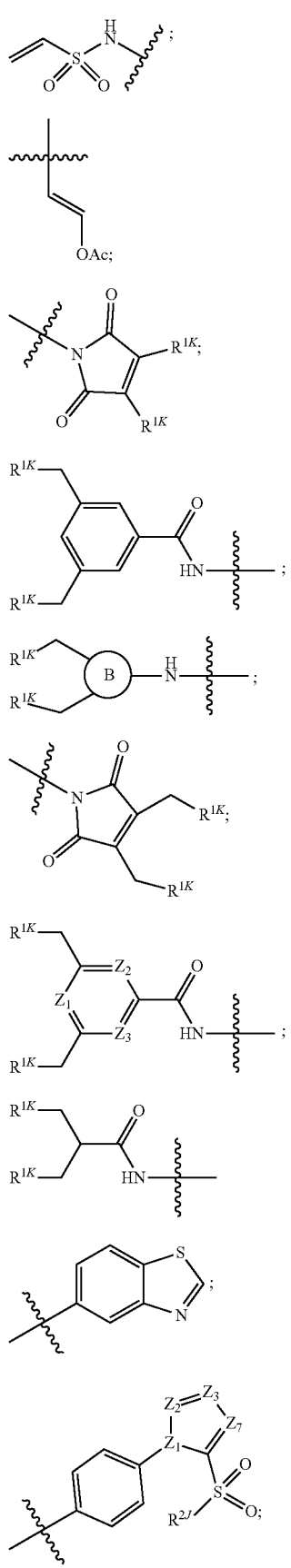
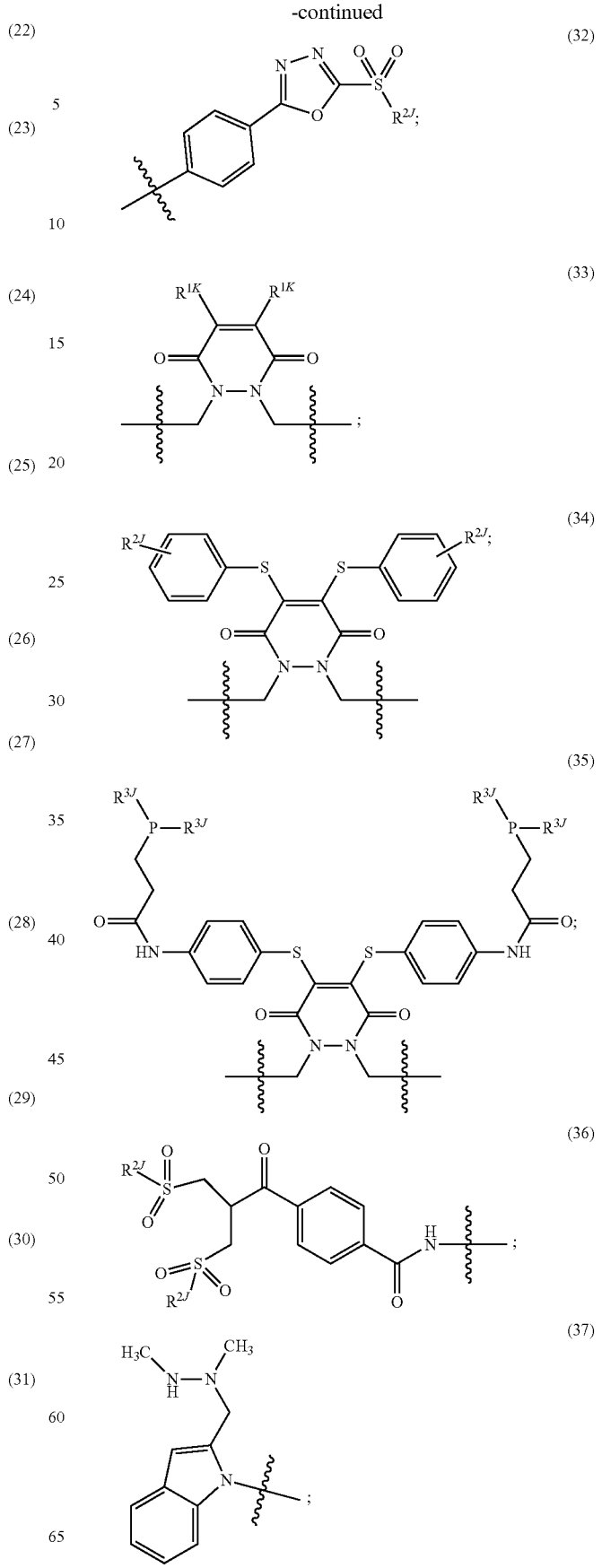

-continued

(38)
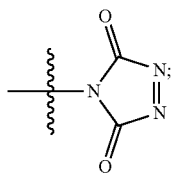

(39)
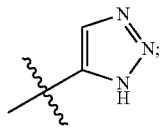

(40)
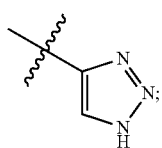

(41)
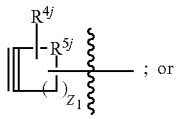; or

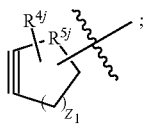;

wherein $R^{1K}$ is a leaving group;

$R^{1A}$ is a sulfur protecting group;

ring A is cycloalkyl or heterocycloalkyl;

ring B is cycloalkyl, heterocycloalkyl, aryl, or heteroaryl;

$R^{1J}$ is hydrogen or an aliphatic, heteroaliphatic, carbocyclic, or heterocycloalkyl moiety;

$R^{2J}$ is hydrogen or an aliphatic, aryl, heteroaliphatic, or carbocyclic moiety;

$R^{3J}$ is $C_{1-6}$ alkyl;

$Z_1$, $Z_2$, $Z_3$ and $Z_7$ are each independently a carbon or nitrogen atom;

$R^{4j}$ is hydrogen, halogen, OR, —NO$_2$, —CN, —S(O)$_2$R, $C_{1-24}$ alkyl (e.g., $C_{1-6}$alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl; or two $R^{4j}$ together form an annelated cycloalkyl, heterocycloalkyl, aryl, or heteroaryl; R is hydrogen, alkyl, heteroalkyl, cycloalkyl, or heterocycloalkyl R is hydrogen or aliphatic, heteroaliphatic, carbocyclic, or heterocycloalkyl moiety;

$R^{5j}$ is $C(R^{4j})_2$, O, S or NR; and $z_1$ is an integer 1, 2, 3, 4, 5, 6, 7, 8, 9 or 10.

In some embodiments, each $R^{1K}$ is halo or RC(O)O— in which R is hydrogen or an aliphatic, heteroaliphatic, carbocyclic, or heterocycloalkyl moiety.

In some embodiments, each $R^{1A}$ independently is

 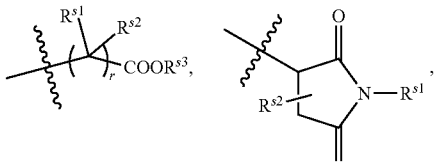

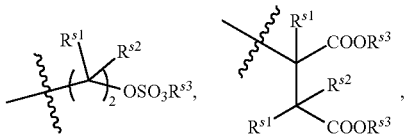

in which r is 1 or 2 and each of $R^{s1}$, $R^{s2}$, and $R^{s3}$ is hydrogen or an aliphatic, heteroaliphatic, carbocyclic, or heterocycloalkyl moiety.

In some embodiments, $L^P$, when not connected to PBRM is

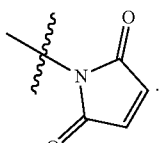

In some embodiments, $M^P$, when present, is —($Z_4$)—[($Z_5$)—($Z_6$)]$_z$—, with $Z_4$ connected to $L^{P'}$ or $L^P$ and $Z_6$ connected to $L^M$; in which z is 1, 2, or 3;

$Z_4$ is:

(1)
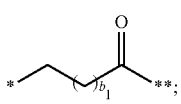

(2)
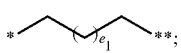

(3)
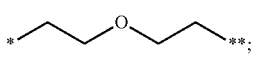

(4)
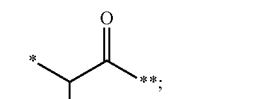

(5)
$R_{17}$;

(6)
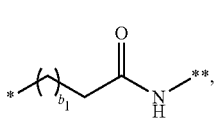

(7)
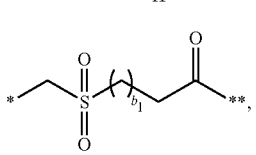

-continued

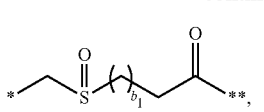
(8)

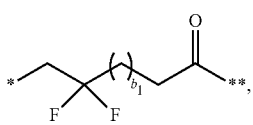
(9)

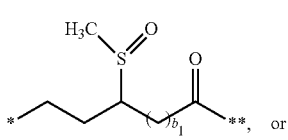
, or
(10)

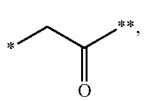
,
(11)

wherein * denotes attachment to $L^{P'}$ or $L^P$ and ** denotes attachment to $Z_5$ or $Z_6$ when present or to $M^A$ when $Z_5$ and $Z_6$ are both absent
$b_1$ is an integer from 0 to 6;
$e_1$ is an integer from 0 to 8,
$R_{17}$ is $C_{1-10}$ alkylene, $C_{1-10}$ heteroalkylene, $C_{3-8}$ cycloalkylene, O—($C_{1-8}$ alkylene, arylene, —$C_{1-10}$ alkylene-arylene-, -arylene-$C_{1-10}$ alkylene-, —$C_{1-10}$ alkylene-($C_{3-8}$ cycloalkylene)-, —($C_{3-8}$ cycloalkylene —$C_{1-10}$ alkylene-, 4 to 14-membered heterocycloalkylene, —$C_{1-10}$ alkylene-(4 to 14-membered heterocycloalkylene)-, -(4 to 14-membered heterocycloalkylene)-$C_{1-10}$ alkylene-, —$C_{1-10}$ alkylene-C(=O)—, —$C_{1-10}$ heteroalkylene-C(=O)—, —$C_{3-8}$ cycloalkylene-C(=O)—, —O—($C_{1-8}$ alkyl)-C(=O)—, -arylene-C(=O)—, —$C_{1-10}$ alkylene-arylene-C(=O)—, -arylene—$C_{1-10}$ alkylene-C(=O)—, —$C_{1-10}$ alkylene-($C_{3-8}$ cycloalkylene)-C(=O)—, —($C_{3-8}$ cycloalkylene)-$C_{1-10}$ alkylene-C(=O)—, -4 to 14-membered heterocycloalkylene-C(=O)—, —$C_{1-10}$ alkylene-(4 to 14-membered heterocycloalkylene)-C(=O)—, -(4 to 14-membered heterocycloalkylene)-$C_{1-10}$ alkylene-C(=O)—, —$C_{1-10}$ alkylene-NH—, —$C_{1-10}$ heteroalkylene-NH—, —$C_{3-8}$ cycloalkylene-NH—, —O—($C_{1-8}$ alkyl)-NH—, -arylene-NH—, —$C_{1-10}$ alkylene-arylene-NH—, -arylene-$C_{1-10}$ alkylene-NH—, —$C_{1-10}$ alkylene-($C_{3-8}$ cycloalkylene)-NH—, —($C_{3-8}$ cycloalkylene)-$C_{1-10}$ alkylene-NH—, -4 to 14-membered heterocycloalkylene-NH—, —$C_{1-10}$ alkylene-(4 to 14-membered heterocycloalkylene)-NH—, -(4 to 14-membered heterocycloalkylene)-$C_{1-10}$ alkylene-NH—, —$C_{1-10}$ alkylene-S—, —$C_{1-10}$ heteroalkylene-S—, —$C_{3-8}$ cycloalkylene-S—, —O—$C_{1-8}$ alkyl)-S—, -arylene-S—, —$C_{1-10}$ alkylene-arylene-S—, -arylene-$C_{1-10}$ alkylene-S—, —$C_{1-10}$ alkylene-($C_{3-8}$ cycloalkylene)-S—, —($C_{3-8}$ cycloalkylene)-$C_{1-10}$ alkylene-S—, -4 to 14-membered heterocycloalkylene-S—, —$C_{1-10}$ alkylene-(4 to 14-membered heterocycloalkylene)-S—, or -(4 to 14-membered heterocycloalkylene)-$C_1$-$C_{10}$ alkylene-S—;
each $Z_5$ independently is absent, $R_{57}$—$R_{17}$ or a polyether unit,
each $R_{57}$ independently is a bond, $NR_{23}$, S or O;
each $R_{23}$ independently is hydrogen, $C_{1-6}$ alkyl, $C_{6-10}$ aryl, $C_{3-8}$ cycloalkyl, —COOH, or —COO—$C_{1-6}$ alkyl; and
each $Z_6$ independently is absent, —$C_{1-10}$ alkyl-$R_3$—, —$C_{1-10}$ alkyl-$NR_5$—, —$C_{1-10}$ alkyl-C(O)—, —$C_{1-10}$ alkyl-O—, —$C_{1-10}$ alkyl-S— or —($C_{1-10}$ alkyl-$R_3$)$_{g1}$—$C_{1-10}$ alkyl-C(O)—;

each $R_3$ independently is —C(O)—$NR_5$— or —$NR_5$—C(O)—;
each $R_5$ independently is hydrogen, $C_{1-6}$ alkyl, $C_{6-10}$ aryl, $C_{3-8}$ cycloalkyl, COOH, or COO—$C_{1-6}$ alkyl; and
$g_1$ is an integer from 1 to 4.
In some embodiments, $Z_4$ is

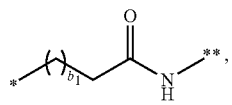
, in which $b_1$ is 1 or 4.
In some embodiments, $Z_4$ is

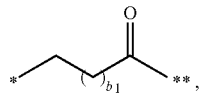
, in which $b_1$ is 1 or 4.
In some embodiments, $Z_4$ is

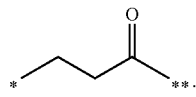
.

In some embodiments, $Z_4$ is

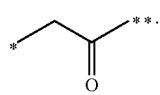
.

In some embodiments, each $Z_5$ independently is a polyalkylene glycol (PAO).
In some embodiments, $M^P$, when present, is

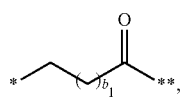
,
(1)

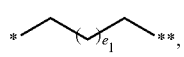
,
(2)

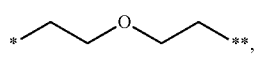
,
(3)

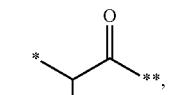
,
(4)

$R_{17}$,
(5)

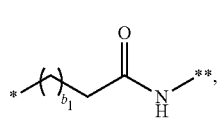
,
(6)

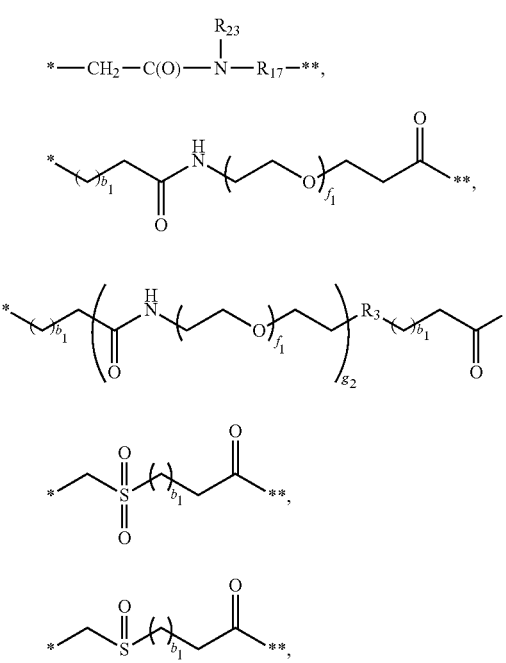

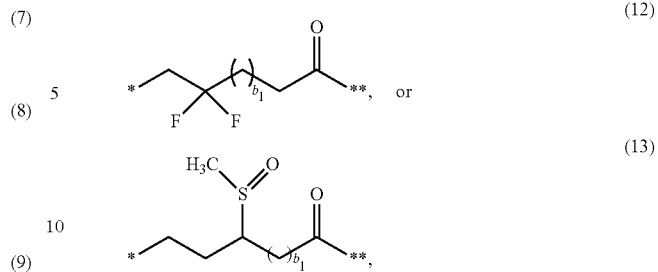

wherein * denotes attachment to $L^{P'}$ or $L^P$ and ** denotes attachment to $L^M$;

$R_3$, $R_5$, $R_{17}$, and $R_{23}$ are as defined herein;

$R_4$ is a bond or —$NR_5$—$(CR_{20}R_{21})$—$C(O)$—;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

each $b_1$ independently is an integer from 0 to 6;

$e_1$ is an integer from 0 to 8, each $f_1$ independently is an integer from 1 to 6; and $g_2$ is an integer from 1 to 4.

In some embodiments, $M^P$, when present, is:

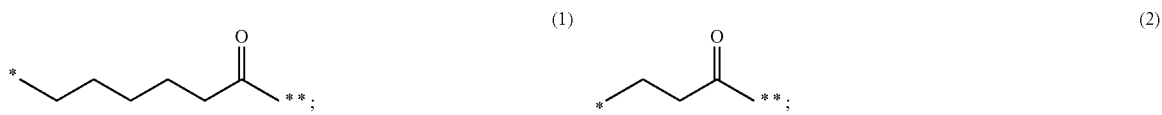

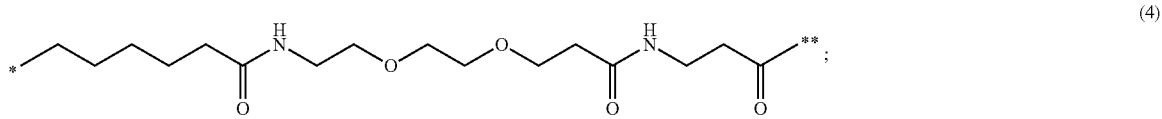

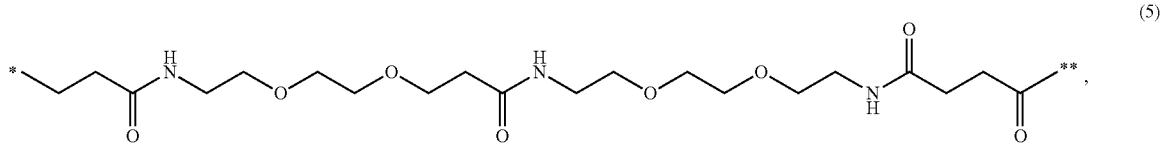

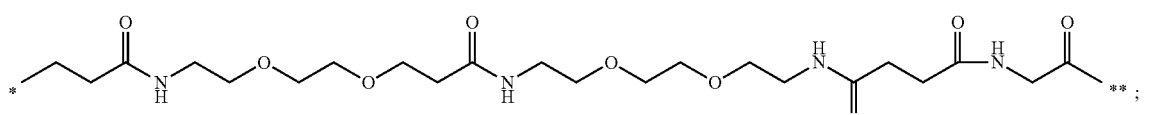

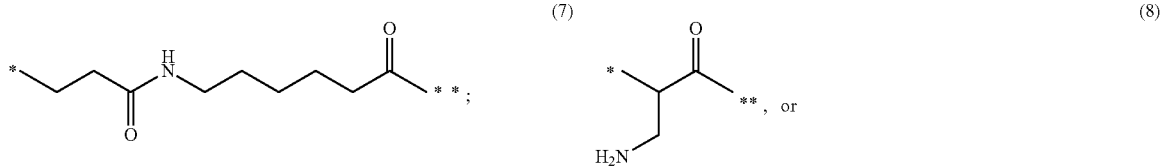

(9)

[Chemical structure: a small fragment with * on left, ** on right, and C=O group]

wherein * denotes attachment to $L^{P'}$ or $L^P$ and ** denotes attachment to $L^M$.

In some embodiments, $M^P$, when present, is:

[Chemical structure showing: *-CH2-C(=O)-NH-(CH2CH2-O)2-CH2CH2-C(=O)-**]

wherein * denotes attachment to $L^{P'}$ or $L^P$ and ** denotes attachment to $M^A$.

In some embodiments, $M^A$ comprises a peptide moiety of at least two amino acid (AA) units.

In some embodiments, $L^D$ comprises a peptide of 1 to 12 amino acids, wherein each amino acid is independently selected from alanine, 3-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In some embodiments, $L^D$ comprises β-alanine.

In some embodiments, $L^D$ comprises (β-alanine)-(alanine)-(alanine) or (β-alanine)-(valine)-(alanine).

In some embodiments, T' comprises a polyalcohol or a derivative thereof, a polyether or a derivative thereof, or a combination thereof.

In some embodiments, T' comprises an amino polyalcohol.

In some embodiments, T' comprises one or more of the following fragments of the formula:

[Chemical structure: —NH—R60—(CR58OH)n1—R61]

in which
  $n_1$ is an integer from 0 to about 6;
  each $R_{58}$ is independently hydrogen or $C_{1-8}$ alkyl;
  $R_{60}$ is a bond, a $C_{1-6}$ alkyl linker, or —CHR59— in which $R_{59}$ is H, alkyl, cycloalkyl, or arylalkyl;
  $R_{61}$ is $CH_2OR_{62}$, $COOR_{62}$, —$(CH_2)_{n2}COOR_{62}$, or a heterocycloalkyl substituted with one or more hydroxyl;
  $R_{62}$ is H or $C_{1-8}$ alkyl; and
  $n_2$ is an integer from 1 to about 5.

In some embodiments, T' comprises glucamine.
In some embodiments, T' comprises:

[Chemical structures showing glucamine-type and branched glutamic-acid-linked tri-glucamine moieties with multiple OH groups]

In some embodiments, T' comprises:

[Chemical structure: —NH—R64—(C(R63)(R63)—C(R63)(R63)—O)n4—R65]

in which
  $n_4$ is an integer from 1 to about 25;
  each $R_{63}$ is independently hydrogen or $C_{1-8}$ alkyl;
  $R_{64}$ is a bond or a $C_{1-8}$ alkyl linker;
  $R_{65}$ is H, $C_{1-8}$ alkyl, —$(CH_2)_{n2}COOR_{62}$, or —$(CH_2)_{n2}COR_{66}$;
  $R_{62}$ is H or $C_{1-8}$ alkyl;
  $R_{66}$ is

[Chemical structures showing glucamine and branched glutamic acid-linked di-glucamine moieties]

and
  $n_2$ is an integer from 1 to about 5.

In some embodiments, T' comprises polyethylene glycol, e.g., polyethylene glycol with from about 6 to about 24 PEG subunits, preferably from about 6 to about 12 PEG subunits, or from about 8 to about 12 PEG subunits.

In some embodiments, T' comprises:

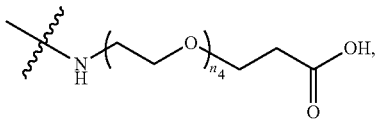

in which $n_4$ is an integer from about 2 to about 20, from about 4 to about 16, from about 6 to about 12, from about 8 to about 12.

In some embodiments, $n_4$ is 6, 7, 8, 9, 10, 11, or 12.
In some embodiments, $n_4$ is 8 or 12.
In some embodiments, T' comprises:

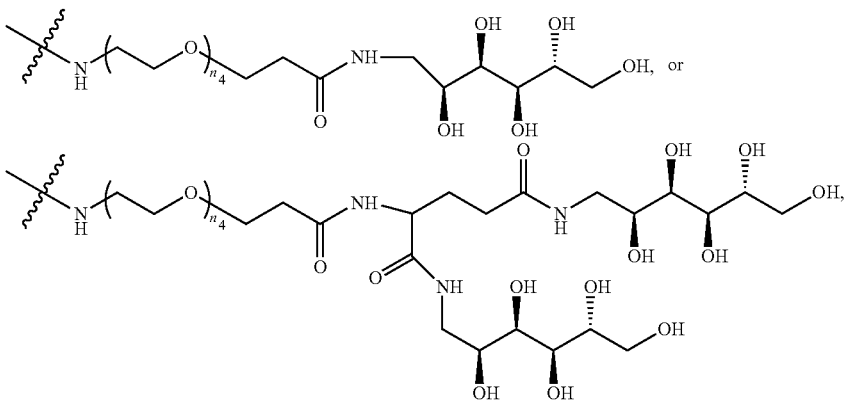

in which $n_4$ is an integer from about 2 to about 20, from about 4 to about 16, from about 6 to about 12, or from about 8 to about 12.

In some embodiments, $n_4$ is 6, 7, 8, 9, 10, 11, or 12.
In some embodiments, $n_4$ is 8 or 12.
In some embodiments, the conjugate is of Formula (III):

$$\text{PBRM-}(A^1_{a6}\text{-}L^1_{s2}L^2_{y1}\text{-}D)_{d13} \quad (III)$$

or pharmaceutically acceptable salt or solvate thereof, wherein:

PBRM denotes a protein based recognition-molecule;
each occurrence of D is independently a PBD drug moiety;
$A^1$ is a stretcher unit;
$a_6$ is an integer 1 or 2;
$L^1$ is a specificity unit;
$s_2$ is an integer from about 0 to about 12;
$L^2$ is a spacer unit;
y1 is an integer from 0 to 2; and
$d_{13}$ is an integer from about 1 to about 20.

In some embodiments, the conjugate is of any one of Formulae (IIIa) to (IIIf):

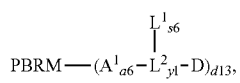
(IIIa)

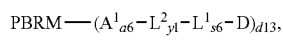
(IIIb)

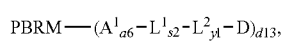
(IIIc)

-continued

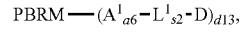
(IIId)

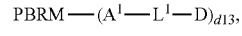
(IIIe)

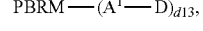
(IIIf)

or a pharmaceutically acceptable salt or solvate thereof, wherein:

PBRM denotes a protein based recognition-molecule;
each occurrence of D is independently a PBD drug moiety;
$A^1$ is a stretcher unit linked to the spacer unit $L^2$;
$a_6$ is an integer 1 or 2;
$L^1$ is a specificity unit linked to the spacer unit $L^2$;
$s_2$ is an integer from about 0 to about 12;
$s_6$ is an integer from about 0 to about 12.
$L^2$ is a spacer unit;
$y_1$ is an integer 0, 1 or 2; and
$d_{13}$ is an integer from about 1 to about 20.

In some embodiments, the PBD drug moiety (D) is of Formula (IV):

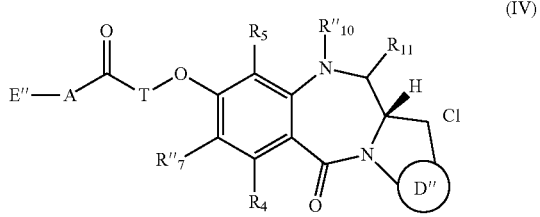

a tautomer thereof, a pharmaceutically acceptable salt or solvate thereof, or a pharmaceutically acceptable salt or solvate of the tautomer, wherein:

E" is a direct or indirect linkage to the PBRM (e.g., antibody or antibody fragment), E, or

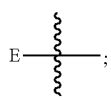

;

in which

denotes direct or indirect linkage to the PBRM (e.g., antibody or antibody fragment) via a functional group of E;

D" is D' or

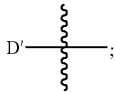

in which

denotes direct or indirect linkage to the PBRM (e.g., antibody or antibody fragment) via a functional group of D';

$R''_7$ is a direct or indirect linkage to the PBRM (e.g., antibody or antibody fragment), $R_7$, or

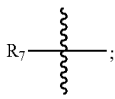

in which

denotes direct or indirect linkage to the PBRM (e.g., antibody or antibody fragment) via a functional group of $R_7$;

$R''_{10}$ is a direct or indirect linkage to the PBRM (e.g., antibody or antibody fragment), $R_{10}$ or

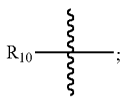

in which

denotes direct or indirect linkage the PBRM (e.g., antibody or antibody fragment) via a functional group of $R_{10}$; and wherein the PBD drug moiety (D) is directly or indirectly linked to the PBRM (e.g., antibody or antibody fragment) via a functional group of one of E", D", $R''_7$, and $R''_{10}$.

In some embodiments, E" is a direct or indirect linkage to $L^C$, E, or

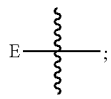

in which

denotes direct or indirect linkage to $L^C$ via a functional group of E.

In some embodiments, E" is a direct or indirect linkage to $L^D$, E, or

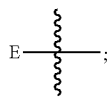

in which

denotes direct or indirect linkage to $L^D$ via a functional group of E.

In some embodiments, D" is D' or

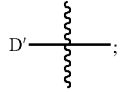

in which

denotes direct or indirect linkage to $L^C$ via a functional group of D'.

In some embodiments, D" is D' or

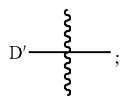

in which

denotes direct or indirect linkage to $L^D$ via a functional group of D'.

In some embodiments, R"$_7$ is a director indirect linkage to $L^C$, R$_7$ or

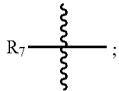

in which

denotes direct or indirect linkage to $L^C$ via a functional group of R$_7$.

In some embodiments, R"$_7$ is a direct or indirect linkage to $L^D$, R$_7$ or

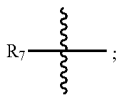

in which

denotes direct or indirect linkage to $L^D$ via a functional group of R$_7$.

In some embodiments, R"$_{10}$ is a director indirect linkage to $L^C$, R$_{10}$, or

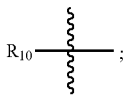

in which

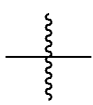

denotes direct or indirect linkage $L^C$ via a functional group of R$_{10}$.

In some embodiments, R"$_{10}$ is a direct or indirect linkage to $L^D$, R$_{10}$, or

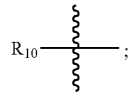

in which

denotes direct or indirect linkage $L^C$ via a functional group of R$_{10}$.

In some embodiments, E" is a direct or indirect linkage to the PBRM; D" is D'; R"$_7$ is R$_7$ and R"$_{10}$ is R$_{10}$.

In some embodiments, E" is a director indirect linkage to $L^C$; D" is D'; R"$_7$ is R$_7$ and R"$_{10}$ is R$_{10}$.

In some embodiments, E" is a direct or indirect linkage to $L^D$; D" is D'; R"$_7$ is R$_7$ and R"$_{10}$ is R$_{10}$.

In some embodiments, E" is

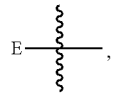

in which

denotes direct or indirect linkage to the PBRM via a functional group of E; D" is D'; R"$_7$ is R$_7$; and R"$_{10}$ is R$_{10}$.

In some embodiments, E" is

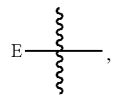

in which

denotes direct or indirect linkage to $L^C$ via a functional group of E; D" is D'; R"$_7$ is R$_7$; and R"$_{10}$ is R$_{10}$.

In some embodiments, E" is

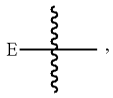

in which

denotes direct or indirect linkage to $L^D$ via a functional group of E; D" is D'; R"$_7$ is R$_7$; and R"$_{10}$ is R$_{10}$.

In some embodiments, D" is

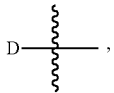

in which

denotes direct or indirect linkage to the PBRM via a functional group of D; E" is E; R"$_7$ is R$_7$; and R"$_{10}$ is R$_{10}$.

In some embodiments, D" is

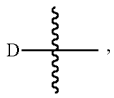

in which

denotes direct or indirect linkage to $L^C$ via a functional group of D; E" is E; R"$_7$ is R$_7$; and R"$_{10}$ is R$_{10}$.

In some embodiments, D" is

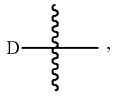

in which

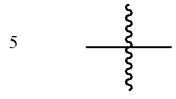

denotes direct or indirect linkage to $L^D$ via a functional group of D; E" is E; R"$_7$ is R$_7$; and R"$_{10}$ is R$_{10}$.

In some embodiments, R"$_7$ is a direct or indirect linkage to the PBRM; E" is E; D" is D'; and R"$_{10}$ is R$_{10}$.

In some embodiments, R"$_7$ is a direct or indirect linkage to $L^C$; E" is E; D" is D'; and R"$_{10}$ is R$_{10}$.

In some embodiments, R"$_7$ is a direct or indirect linkage to $L^D$; E" is E; D" is D'; and R"$_{10}$ is R$_{10}$.

In some embodiments, R"$_7$ is

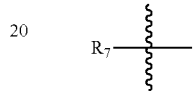

in which

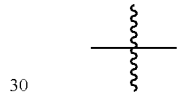

denotes direct or indirect linkage to the PBRM via a functional group of R$_7$; E" is E; D" is D'; and R"$_{10}$ is R$_{10}$.

In some embodiments, R"$_7$ is

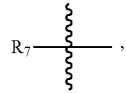

in which

denotes direct or indirect linkage to $L^C$ via a functional group of R$_7$; E" is E; D" is D'; and R"$_{10}$ is R$_{10}$.

In some embodiments, R"$_7$ is

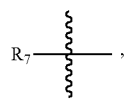

in which

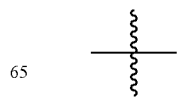

denotes direct or indirect linkage to $L^D$ via a functional group of $R_7$; E" is E; D" is D'; and R"$_{10}$ is $R_{10}$.

In some embodiments, R"$_{10}$ is a direct or indirect linkage to the PBRM; E" is E; D" is D'; and R"$_7$ is $R_7$.

In some embodiments, R"$_{10}$ is a direct or indirect linkage to $L^C$; E" is E, D" is D'; and R"$_7$ is $R_7$.

In some embodiments, R"$_{10}$ is a direct or indirect linkage to $L^D$; E" is E; D" is D'; and R"$_7$ is $R_7$.

In some embodiments, R"$_{10}$ is

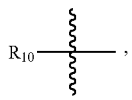

in which

denotes direct or indirect linkage to the PBRM via a functional group of $R_{10}$; E" is E; D" is D'; and R"$_7$ is $R_7$.

In some embodiments, R"$_{10}$ is

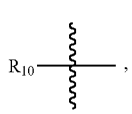

in which

denotes direct or indirect linkage to $L^C$ via a functional group of $R_{10}$; E" is E; D" is D'; and R"$_7$ is $R_7$.

In some embodiments, R"$_{10}$ is

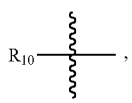

in which

denotes direct or indirect linkage to $L^D$ via a functional group of $R_{10}$, E" is E; D" is D'; and R"$_7$ is $R_7$.

In some embodiments, D' is D1, D2, D3, or D4:

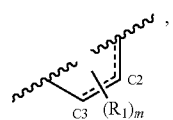
(D1)

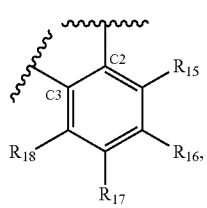
(D2)

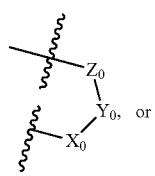
(D3)

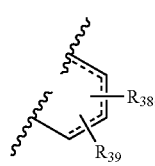
(D4)

wherein the dotted line between $C_2$ and $C_3$ or between $C_2$ and $C_1$ in D1 or the dotted line in D4 indicates the presence of a single or double bond; and m is 0, 1 or 2;

when D' is D1, the dotted line between $C_2$ and $C_3$ is a double bond, and m is 1, then $R_1$ is:

(i) $C_{6-10}$ aryl group, optionally substituted by one or more substituents selected from —OH, halo, —NO$_2$, —CN, —N$_3$, —OR$_2$, —COOH, —COOR$_2$, —COR$_2$, —OCONR$_{13}$R$_{14}$, $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—OR$_a$, 3- to 14-membered heterocycloalkyl, 5- to 12-membered heteroaryl, bis-oxy-$C_{1-3}$ alkylene, —NR$_3$R$_4$, —S(=O)$_2$R$_{12}$, —S(=O)$_2$NR$_{13}$R$_{14}$, —SR$_{12}$, —SO$_x$M, —OSO$_x$M, —NR$_9$COR$_{19}$, —NH(C=NH)NH$_2$;

(ii) $C_{1-8}$ alkyl;

(iii) $C_{3-6}$ cycloalkyl;

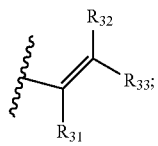
(iv)

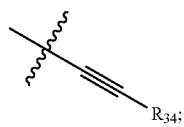
(vi)

-continued

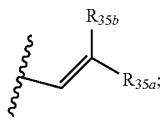

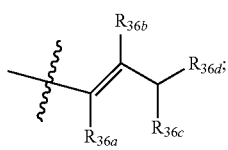

or (viii) halo;

when D' is D1, the dotted line between C2 and C3 is a single bond, and m is 1, then $R_1$ is:

(i) —OH, =O, =CH$_2$, —CN, —R$_2$, —OR$_2$, halo, =CH—R$_6$, =C(R$_6$)$_2$, —O—SO$_2$R$_2$, —CO$_2$R$_2$, —COR$_2$, —CHO, or —COOH; or

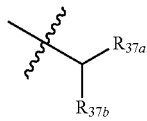

when D' is D1 and m is 2, then each $R_1$ independently is halo and either both $R_1$ are attached to the same carbon atom or one is attached to $C_2$ and the other is attached to $C_3$;

T is $C_{1-10}$ alkylene linker;

A is

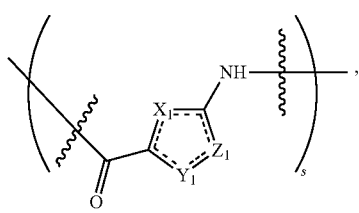

wherein the —NH group of A is connected to the —C(O)-T- moiety of Formula (I) and the C=O moiety of A is connected to E; and each independently is

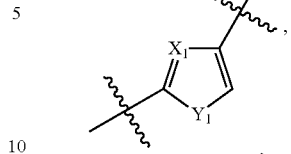, 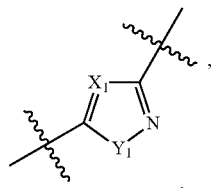

, or 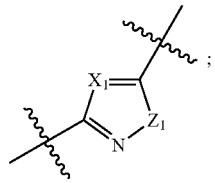;

E is E1, E2, E3, E4, —OH, —NH—(C$_{1-6}$ alkylene)-R$_{13a}$, —O—(CH$_2$)$_3$—NH$_2$, —O—CH(CH$_3$)—(CH$_2$)$_2$—NH$_2$, or —NH—(CH$_2$)$_3$—O—C(=O)—CH(CH$_3$)—NH$_2$:

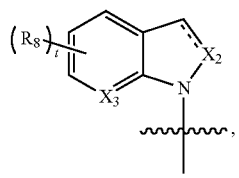 (E1)

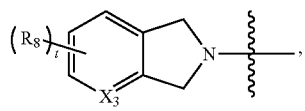 (E2)

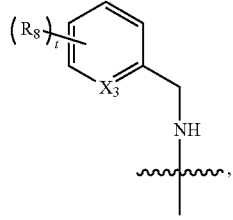 (E3)

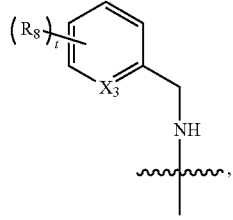 (E4)

wherein the dotted line in E1 or E4 indicates the presence of a single or double bond;

each occurrence of $R_2$ and $R_3$ independently is an optionally substituted $C_{1-8}$ alkyl, optionally substituted $C_{2-8}$ alkenyl, optionally substituted $C_{2-8}$ alkynyl, optionally substituted $C_{3-8}$ cycloalkyl, optionally substituted 3- to 20-membered heterocycloalkyl, optionally substituted $C_{6-20}$ aryl or optionally substituted 5- to 20-membered heteroaryl, and, optionally in relation to the group NR$_2$R$_3$, R$_2$ and R$_3$ together with the nitrogen atom to which they are attached form an optionally substituted 4-, 5-, 6- or 7-membered heterocycloalkyl or an optionally substituted 5- or 6-membered heteroaryl;

$R_4$, $R_5$ and $R_7$ are each independently —H, —$R_2$, —OH, —$OR_2$, —SH, —$SR_2$, —$NH_2$, —$NHR_2$, —$NR_2R_3$, —$NO_2$, —$SnMe_3$, halo or a polyethylene glycol unit —$(OCH_2CH_2)_r$—$OR_a$; or $R_4$ and $R_7$ together form bis-oxy-$C_{1-3}$ alkylene;

each $R_6$ independently is —H, —$R_2$, —$C_2R_2$, —$COR_2$, —CHO, —$CO_2H$, or halo;

each $R_8$ independently is —OH, halo, —$NO_2$, —CN, —$N_3$, —$OR_2$, —COOH, —$COOR_2$, —$COR_2$, —$OCONR_{13}R_{14}$, —$CONR_{13}R_{14}$, —CO—NH—($C_{1-6}$ alkylene)-$R_{13a}$, $C_{1-10}$alkyl, $C_{3-10}$cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, —$S(=O)_2R_2$, —$S(=O)_2NR_{13}R_{14}$, —$SR_{12}$, —$SO_xM$, —$OSO_xM$, —$NR_9COR_{19}$, —NH(C=NH)$NH_2$, —$R_{20}$—$R_{21}$—$NR_{13}R_{14}$, —$R_{20}$—$R_{21}$—NH—P(O)(OH)—$(OCH_2CH_2)_{n9}$—$OCH_3$, or —O—P(O)(OH)—$(OCH_2CH_2)_{n9}$—$OCH_3$;

each $R_9$ independently is $C_{1-10}$ alkyl, $C_{3-10}$ cycloalkyl, $C_{2-10}$ alkenyl or $C_{2-10}$ alkynyl;

$R^{10}$ is —H or a nitrogen protecting group, $R^{11}$ is -$QR^Q$ or —$SO_xM$;

or $R^{10}$ and $R^{11}$ taken together with the nitrogen atom and carbon atom to which they are respectively attached, form a N=C double bond;

each $R_{12}$ independently is $C_{1-7}$ alkyl, 3- to 20-membered heterocycloalkyl, 5- to 20-membered heteroaryl, or $C_{6-20}$ aryl each occurrence of $R_{13}$ and $R_{14}$ are each independently H, $C_{1-10}$ alkyl, 3- to 20-membered heterocycloalkyl, 5- to 20-membered heteroaryl, or $C_{6-20}$ aryl;

each $R_{13a}$ independently is —OH or —$NR_{13}R_{14}$;

$R_{15}$, $R_{16}$, $R_{17}$ and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3-14 membered heterocycloalkyl, 5- to 12-membered heteroaryl, —$NR_{13}R_{14}$, —$S(=O)_2R_2$, —$S(=O)_2NR_{13}R_{14}$, —$SR_{12}$, —$SO_xM$, —$OSO_xM$, —$NR_9COR_{19}$ or —NH(C=NH)$NH_2$;

each $R_{19}$ independently is $C_{1-10}$ alkyl, $C_{3-10}$ cycloalkyl, $C_{2-10}$ alkenyl or $C_{2-10}$ alkynyl;

each $R_{20}$ independently is a bond, $C_{6-10}$ arylene, 3-14 membered heterocycloalkylene or 5- to 12-membered heteroarylene;

each $R_{21}$ independently is a bond or $C_{1-10}$ alkylene;

$R_{31}$, $R_{32}$ and $R_{33}$ are each independently —H, $C_{1-3}$ alkyl, $C_{2-3}$ alkenyl, $C_{2-3}$ alkynyl or cyclopropyl, wherein the total number of carbon atoms in the $R_1$ group is no more than 5;

$R_{34}$ is —H, $C_{1-3}$ alkyl, $C_{2-3}$ alkenyl, $C_{2-3}$ alkynyl, cyclopropyl, or phenyl wherein the phenyl is optionally substituted by one or more of halo, methyl, methoxy, pyridyl or thiophenyl;

one of $R_{35a}$ and $R_{35b}$ is —H and the other is a phenyl group optionally substituted with one or more of halo, methyl, methoxy, pyridyl or thiophenyl;

$R_{36a}$, $R_{36b}$, $R_{36c}$ are each independently —H or $C_{1-2}$ alkyl;

$R_{36d}$ is —OH, —SH, —COOH, —C(O)H, —N=C=, —$NHNH_2$, —$CONHNH_2$,

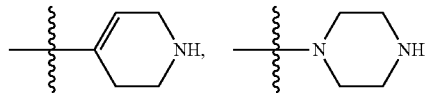

or $NHR^N$, wherein $R^N$ is —H or $C_{1-4}$ alkyl;

$R_{37a}$ and $R_{37b}$ are each independently is —H, —F, $C_{1-4}$ alkyl, $C_{2-3}$ alkenyl, wherein the alkyl and alkenyl groups are optionally substituted by $C_{1-4}$ alkyl amido or $C_{1-4}$ alkyl ester; or when one of $R_{37a}$ and $R_{37b}$ is —H, the other is —CN or a $C_{1-4}$ alkyl ester;

$R_{38}$ and $R_{39}$ are each independently H, $R_{13}$, =$CH_2$, =CH—$(CH_2)_{s1}$—$CH_3$, =O, $(CH_2)_{s1}$—$OR_{13}$, $(CH_2)_{s1}$—$CO_2R_{13}(CH_2)_{s1}$—$NR_{13}R_{14}$, O—$(CH_2)_2$—$NR_{13}R_{14}$, NH—C(O)—$R_{13}$, O—$(CH_2)$s-NH—C(O)—$R_{13}$, O—$(CH_2)$s-C(O)$NHR_3$, $(CH_2)_{s1}$OS(=O)$_2R_{13}$, O—$SO_2R_3$, $(CH_2)_{s1}$—C(O)$R_1$ and $(CH_2)_{s1}$—C(O)$NR_{13}R_{14}$;

$X_0$ is $CH_2$, $NR_6$, C=O, BH, SO or $SO_2$;

$Y_0$ is O, $CH_2$, $NR_6$ or S;

$Z_0$ is absent or $(CH_2)_n$;

each $X_1$ independently is $CR_b$, or N;

each $Y_1$ independently is CH, $NR_a$, O or S;

each $Z_1$ independently is CH, $NR_a$, O or S;

each $R_a$ independently is H or $C_{1-4}$ alkyl;

each $R_b$ independently is H, OH, $C_{1-4}$ alkyl, or $C_{1-4}$ alkoxyl;

$X_2$ is CH, $CH_2$ or N;

$X_3$ is CH or N;

$X_4$ is NH, O or S;

$X_8$ is NH, O or S;

Q is O, S or NH;

when Q is S or NH, then $R^Q$ is —H or optionally substituted $C_{1-2}$ alkyl; or when Q is O, then $R^Q$ is —H or optionally substituted $C_{1-2}$ alkyl, —$SO_xM$, —$PO_3M$, —$(CH_2$—$CH_2$—O$)_{n9}CH_3$, —$(CH_2$—$CH_2O)_{n1}$—$CH_2)_2$—$R_{40}$, —C(O)—$(CH_2$—$CH_{2-0})_{n9}CH_3$, —C(O)O—$(CH_2$—$CH_2$—O$)_{n9}CH_3$, —C(O)NH—$(CH_2$—$CH_2$—O$)_{n9}$, $CH_3$, —$(CH_2)_n$—NH—C(O)—$CH_2$—O—$CH_2$—C(O)—NH—$(CH_2$—$CH_2$—O$)_{n9}$$CH_3$, —(CH$)_n$—NH—C(O)—$(CH_2)_n$—$(CH_2$—$CH_2$—O$)_{n9}$$CH_3$, a sugar moiety,

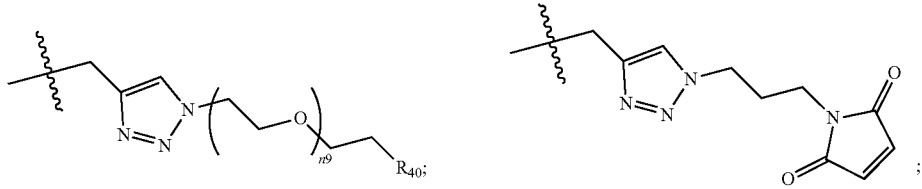

-continued

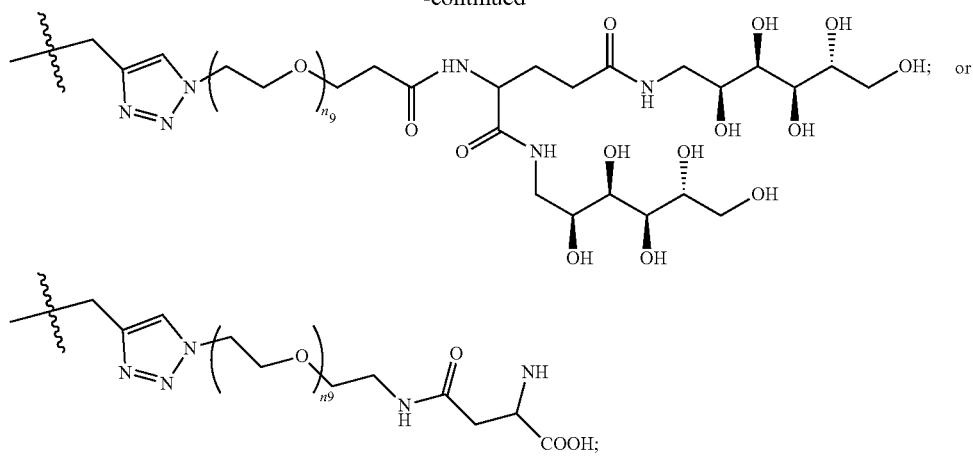

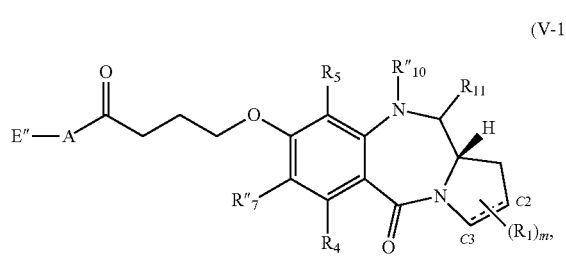

each M independently is H or a monovalent pharmaceutically acceptable cation;

n is 1, 2 or 3;

$n_9$ is 1, 2, 3, 4, 5, 6, 8, 12 or 24.

each r independently is an integer from 1 to 200;

s is 1, 2, 3, 4, 5 or 6;

$s_1$ is 0, 1, 2, 3, 4, 5 or 6;

t is 0, 1, or 2;

$R_{40}$ is —$SO_3H$, —COOH, —C(O)NH(CH$_2$)$_2$SO$_3$H or —C(O)NH(CH$_2$)$_2$COOH; and each x independently is 2 or 3.

In some embodiments, the PBD drug moiety (D) is of Formula (IV-a),

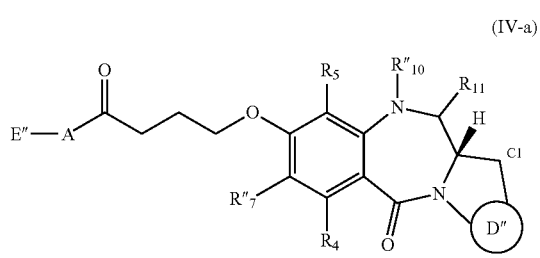

a tautomer thereof, a pharmaceutically acceptable salt or solvate thereof, or a pharmaceutically acceptable salt or solvate of the tautomer.

In some embodiments, D' is D1.

In some embodiments, the PBD drug moiety (D) is of any one of formulae (V-1), (V-2), and (V-3):

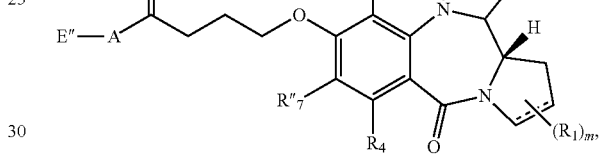

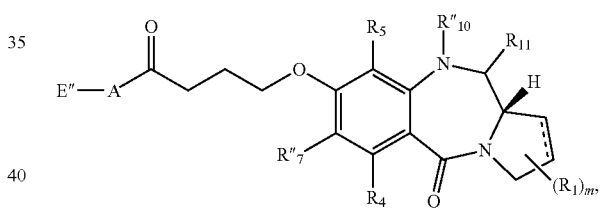

a tautomer thereof, a pharmaceutically acceptable salt or solvate thereof, or a pharmaceutically acceptable salt or solvate of the tautomer.

In some embodiments, the PBD drug moiety (D) is of Formula (VI-1):

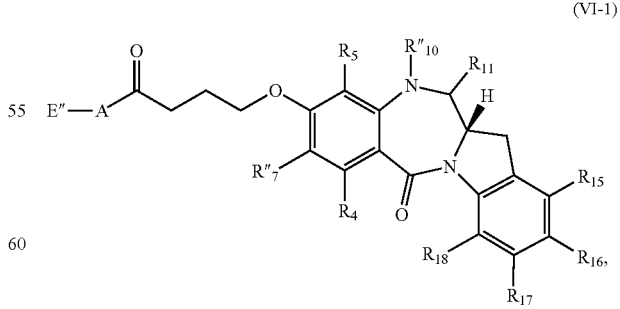

a tautomer thereof, a pharmaceutically acceptable salt or solvate thereof, or a pharmaceutically acceptable salt or solvate of the tautomer.

In some embodiments, the PBD drug moiety (D) is of Formula (VII), (VII-1), (VII-2), or (VII-3):

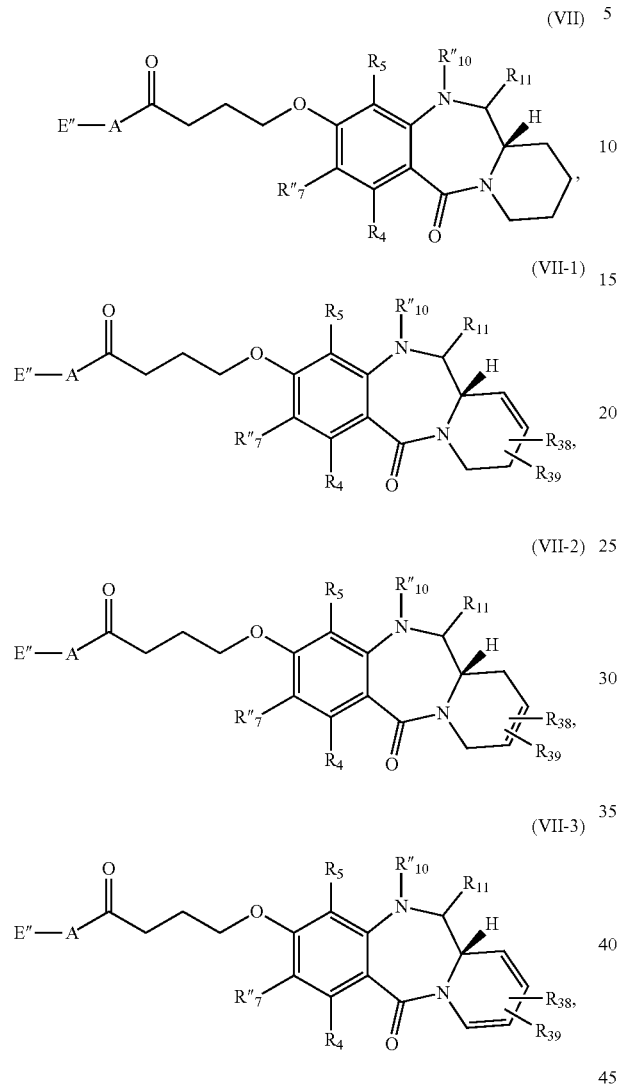

a tautomer thereof, a pharmaceutically acceptable salt or solvate thereof, or a pharmaceutically acceptable salt or solvate of the tautomer.

In some embodiments, the PBD drug moiety (D) is of Formula (VIII):

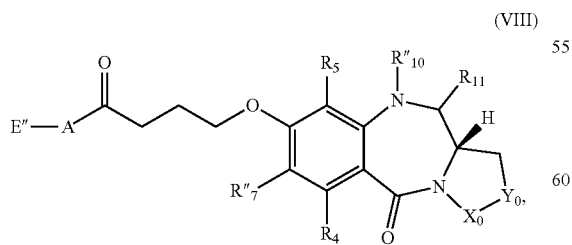

a tautomer thereof, a pharmaceutically acceptable salt or solvate thereof, or a pharmaceutically acceptable salt or solvate of the tautomer.

In some embodiments, T is $C_{2-4}$ alkylene linker.

In some embodiments, A is

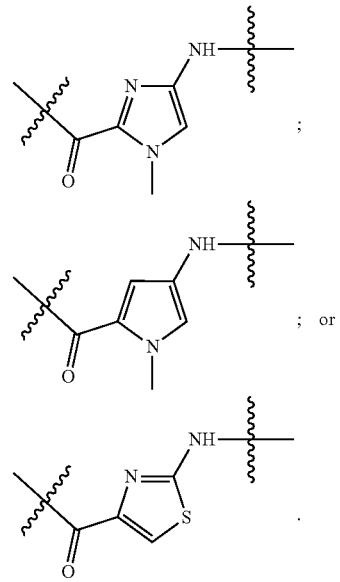

In some embodiments, A is

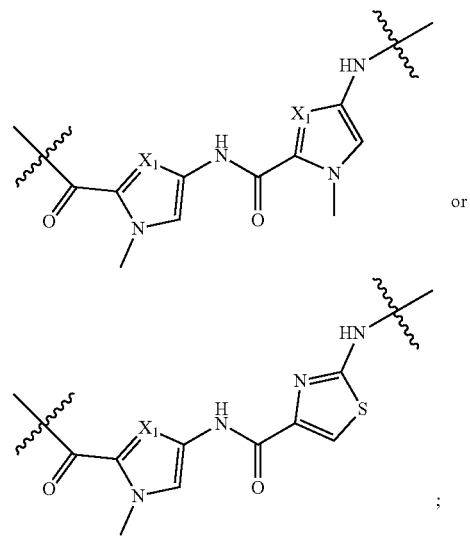

wherein each $X_1$ independently is CH or N.

In some embodiments, A is

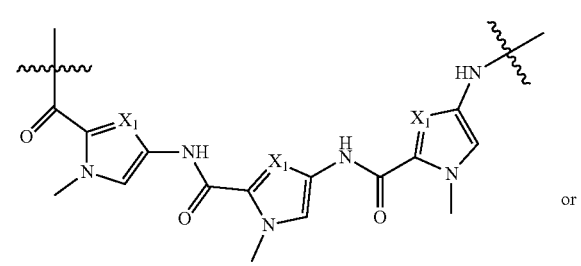

-continued
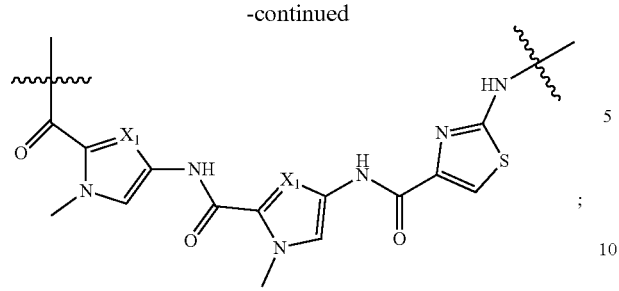
wherein each $X_1$ independently is CH or N.
In some embodiments, A is:
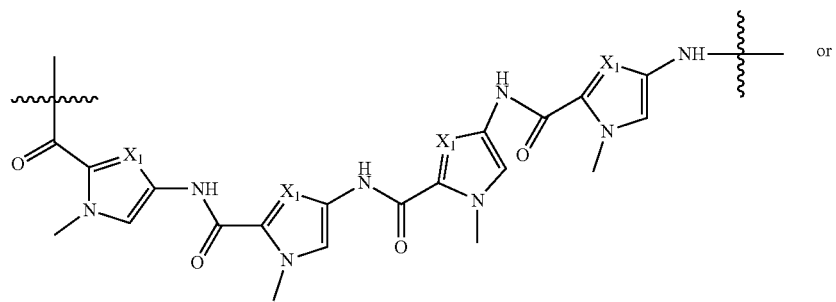
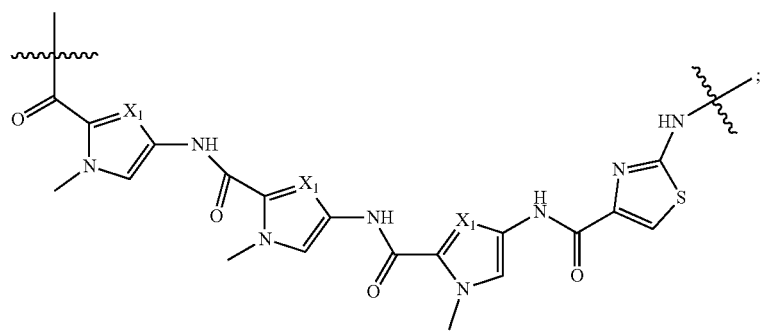
wherein each $X_1$ independently is CH or N.
In some embodiments, E is —OH, —NH—($C_{1-6}$ alkylene)-OH,
In some embodiments, E is
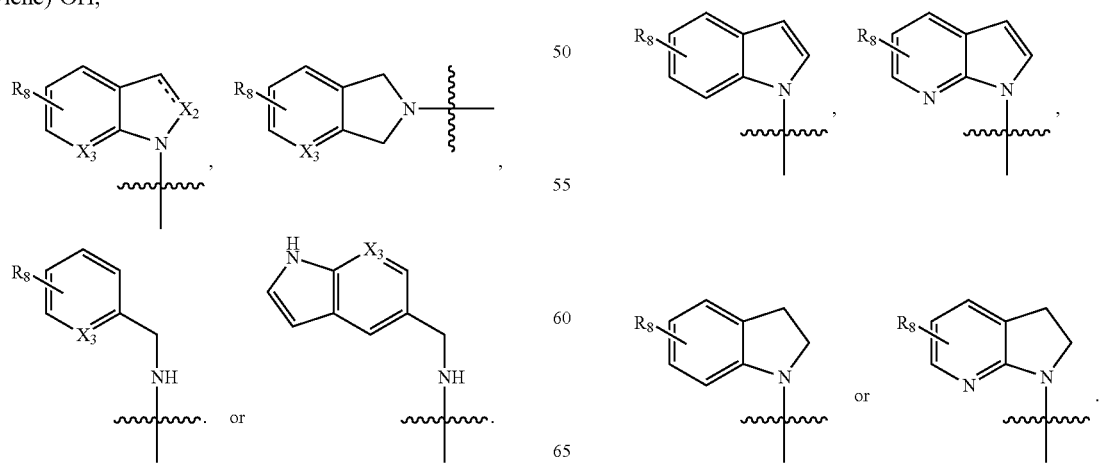

In some embodiments, the PBD drug moiety (D) is of any one of Formulae (IX-a) to (IX-r):
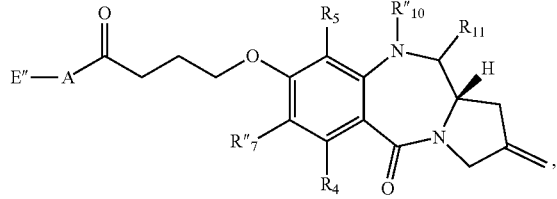
(IX-a)
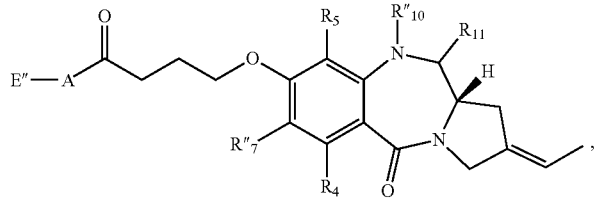
(IX-b)
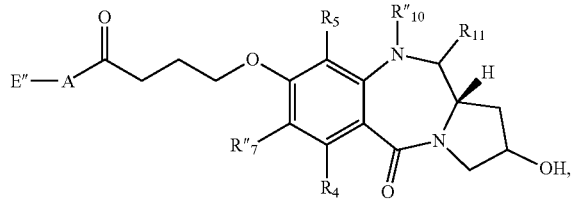
(IX-c)
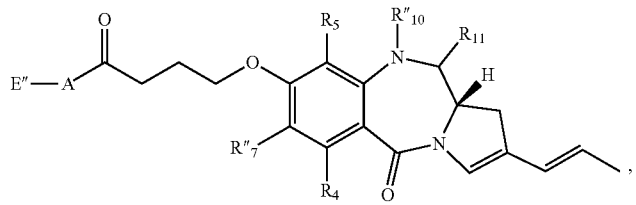
(IX-d)
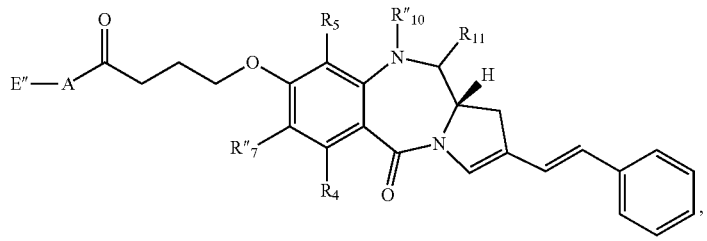
(IX-e)
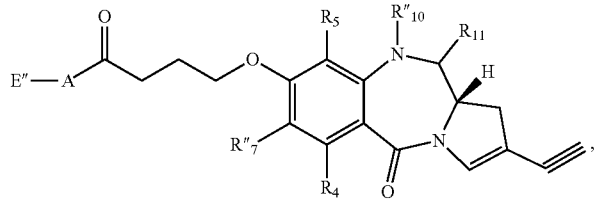
(IX-f)
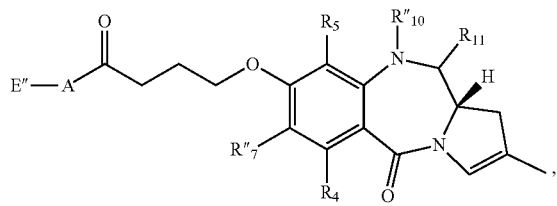
(IX-g)

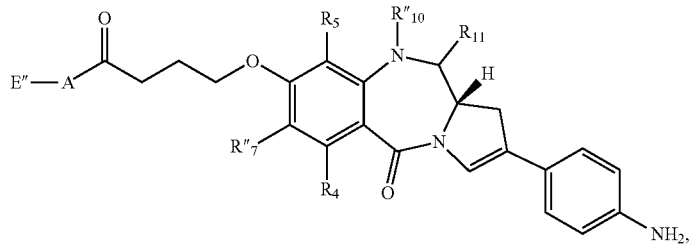
(IX-h)
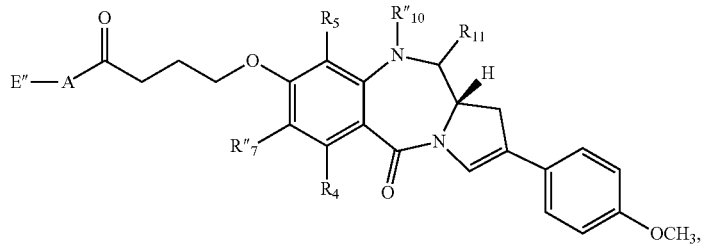
(IX-i)
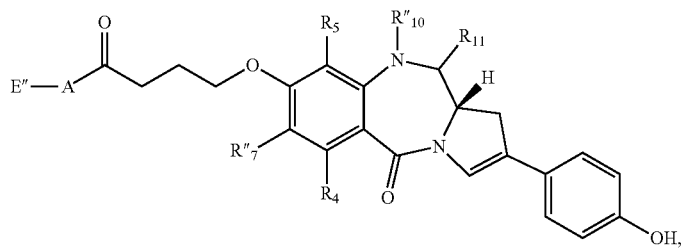
(IX-j)
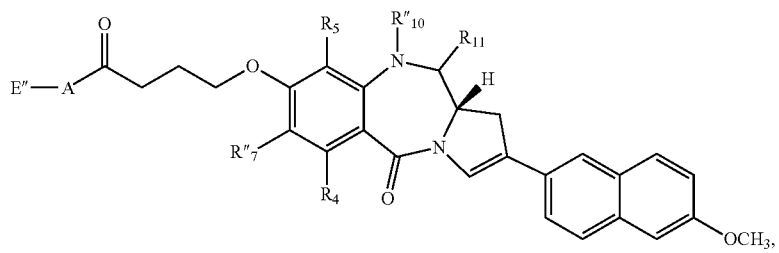
(IX-k)
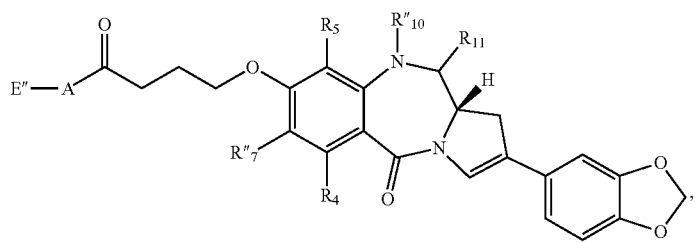
(IX-l)
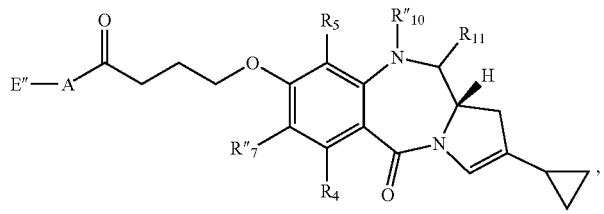
(IX-m)

-continued

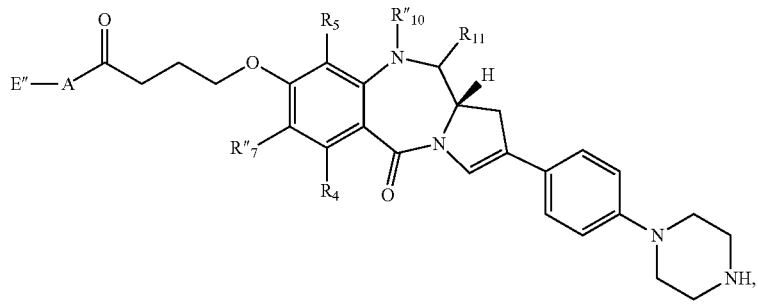
(IX-n)

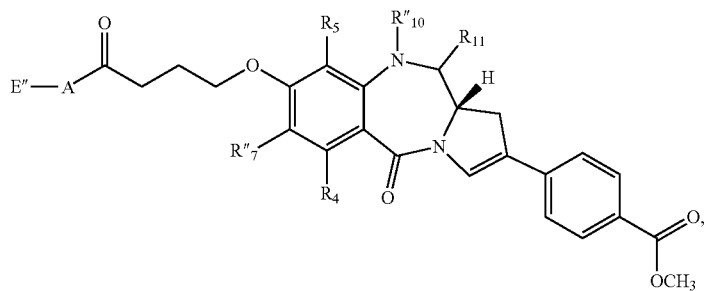
(IX-o)

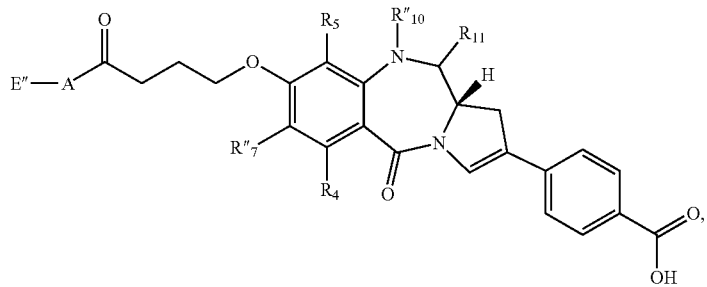
(IX-p)

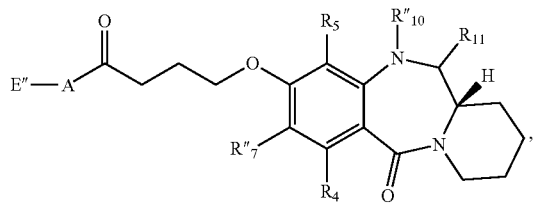
(IX-q)

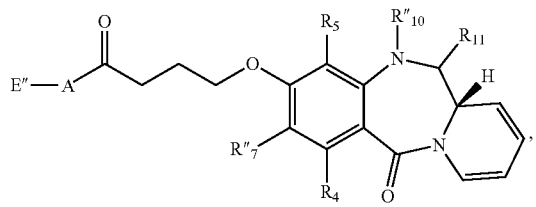
(IX-r)

a tautomer thereof, a pharmaceutically acceptable salt or solvate thereof, or a pharmaceutically acceptable salt or solvate of the tautomer.

In some embodiments, the PBD drug moiety (D), prior to being connected to another portion of the conjugate, corresponds to a compound selected from the compounds listed in Table 1, tautomers thereof, pharmaceutically acceptable salts or solvates thereof, or pharmaceutically acceptable salts or solvates of the tautomers.

In some embodiments, the PBD drug moiety (D), prior to being connected to another portion of the conjugate, corresponds to a compound of any one of Formula (XIIIa) to (XIIIm):
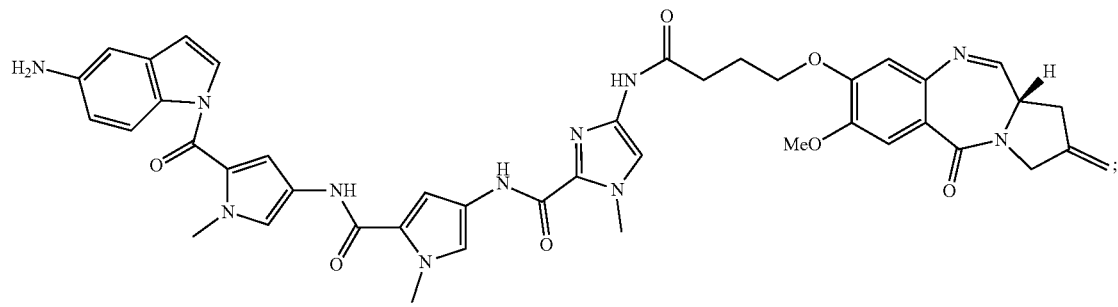
(XIIIa)
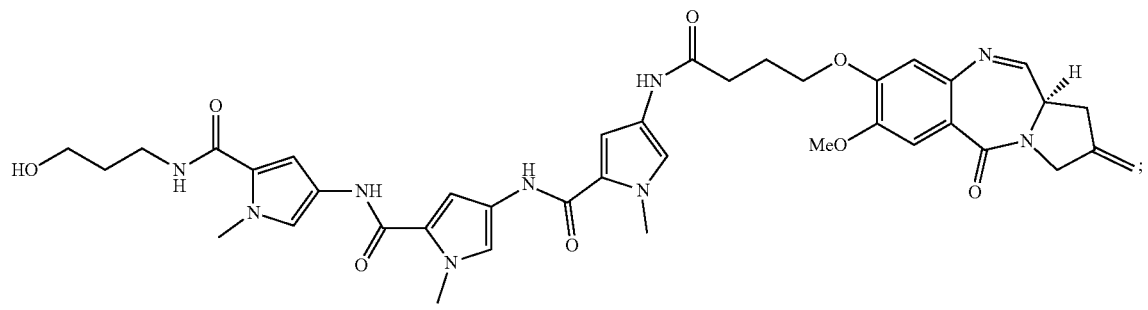
(XIIIb)
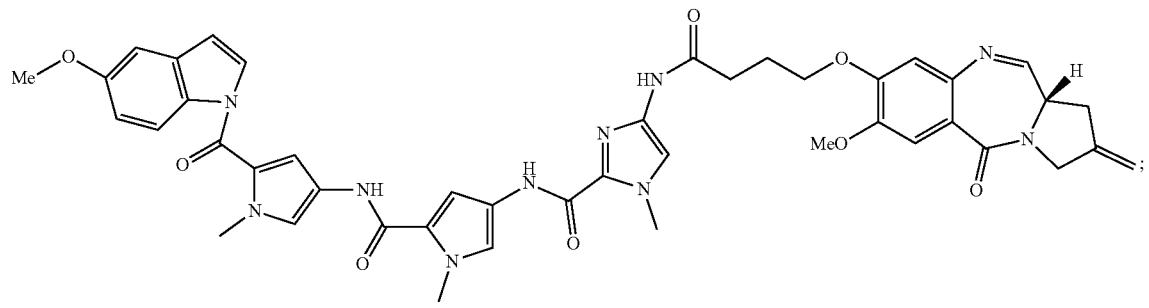
(XIIIc)
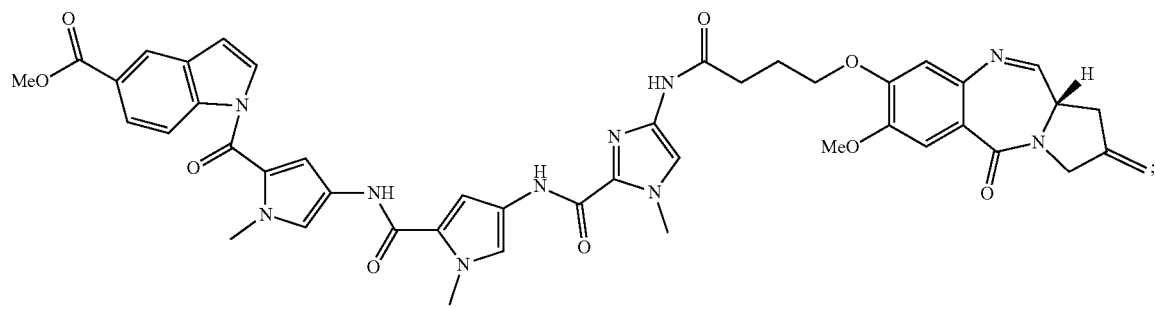
(XIIId)

-continued
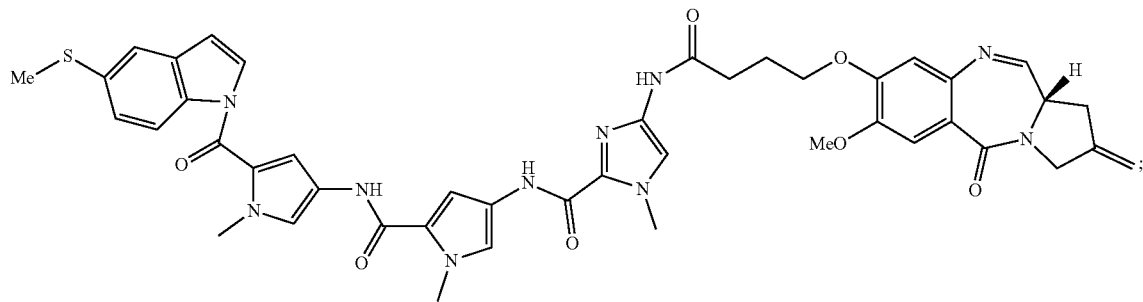
(XIIIe)
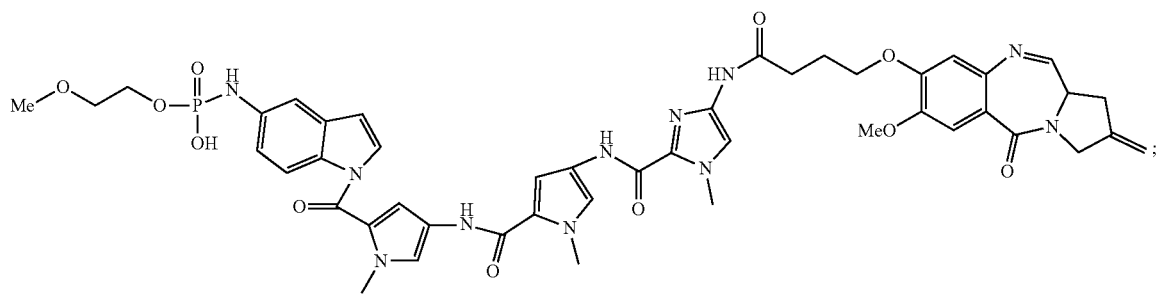
(XIIIf)
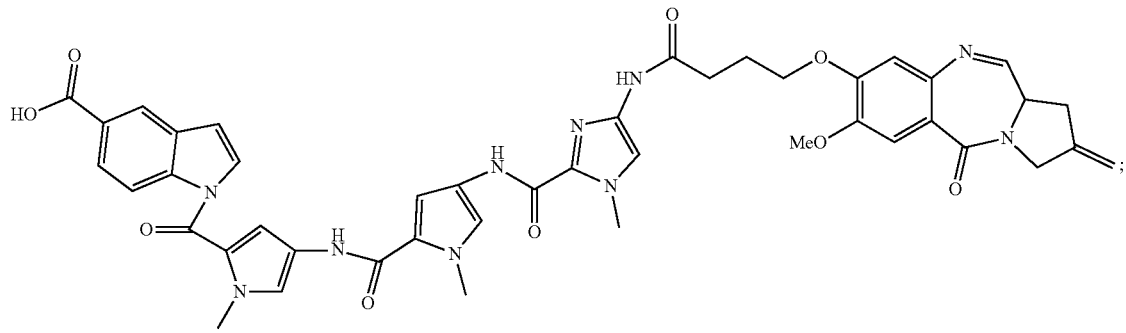
(XIIIg)
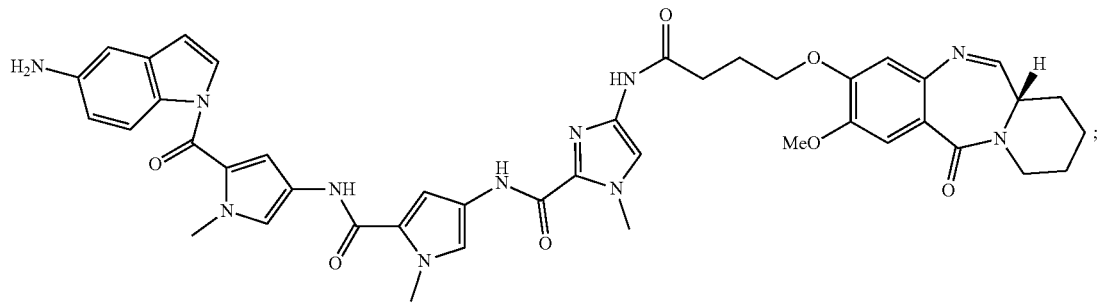
(XIIIh)
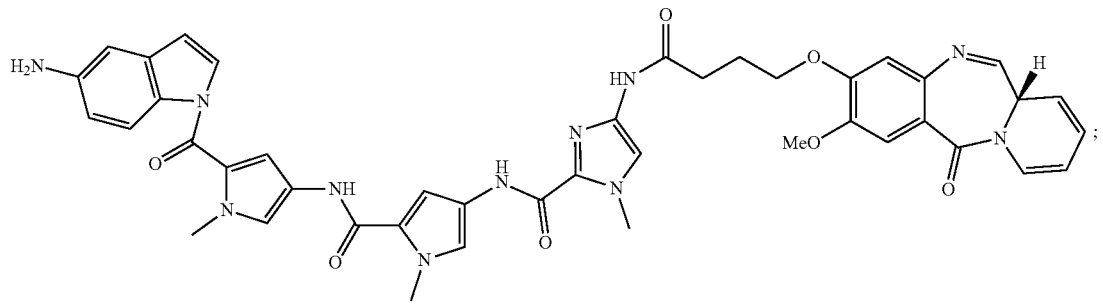
(XIIIi)

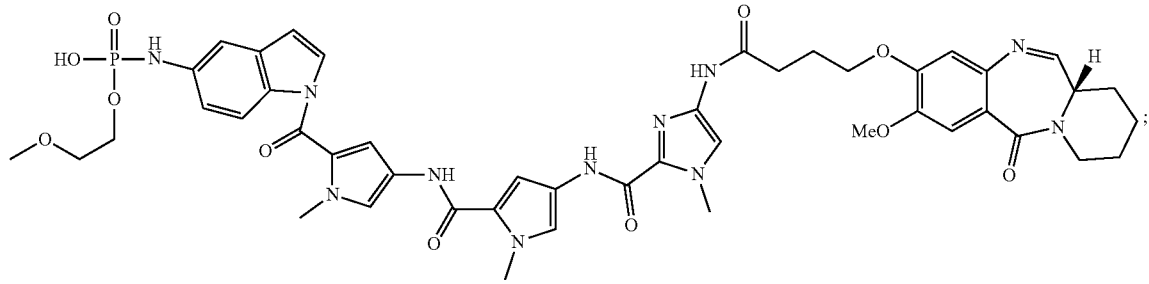

(XIIIj)

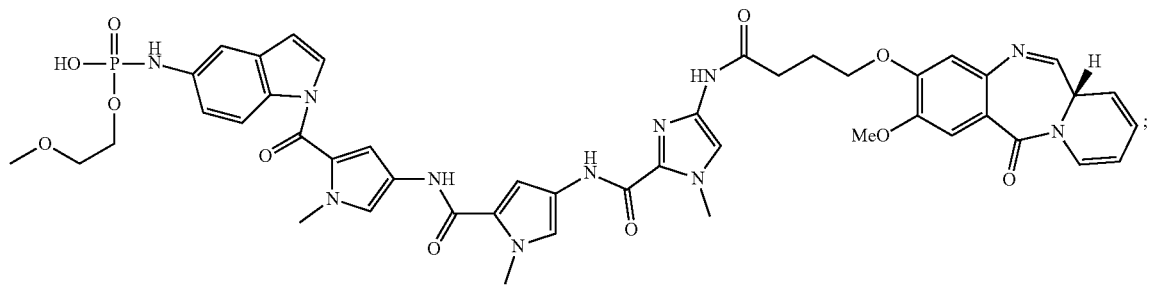

(XIIIk)

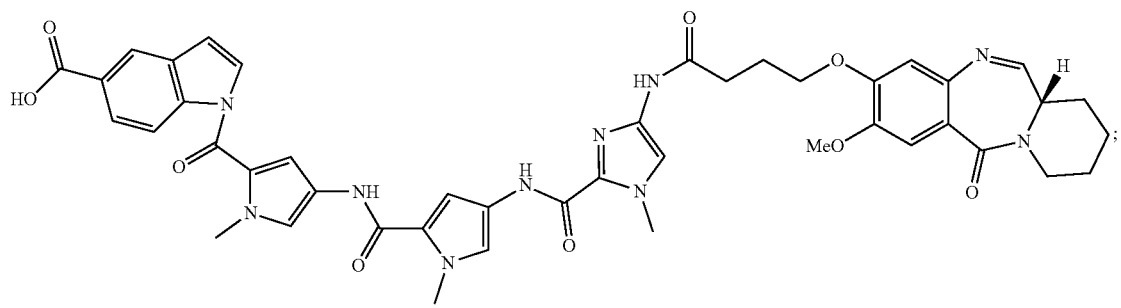

(XIIIl)

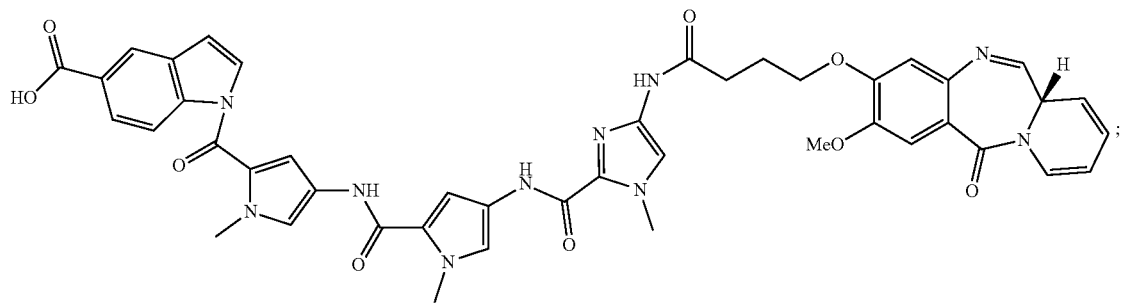

(XIIIm)

a tautomer thereof, a pharmaceutically acceptable salt or solvate thereof, or a pharmaceutically acceptable salt or solvate of the tautomer.

In some embodiments, the PBD drug moiety (D) is selected from the conjugates listed in Table 1A, tautomers thereof, pharmaceutically acceptable salts or solvates thereof, and pharmaceutically acceptable salts or solvates of the tautomers.

In some embodiments, the conjugate is selected from the conjugates listed in Table 2, tautomers thereof, pharmaceutically acceptable salts or solvates thereof, and pharmaceutically acceptable salts or solvates of the tautomers.

In some aspects, the present disclosure provides a pharmaceutical composition comprising the conjugate of any one of the preceding claims and a pharmaceutically acceptable carrier.

In some aspects, the present disclosure provides a method of treating or preventing a disease or disorder, comprising administering to a subject in need thereof a pharmaceutically effective amount of the conjugate of any one of the preceding claims.

In some embodiments, the disease or disorder is cancer.

In some aspects, the present disclosure provides a conjugate disclosed herein for use in treating or preventing a disease or disorder.

In some aspects, the present disclosure provides use of a conjugate disclosed herein in treating or preventing a disease or disorder.

In some aspects, the present disclosure provides use of a conjugate disclosed herein in the manufacture of a medicament for treating or preventing a disease or disorder.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the disclosure will be apparent from the following detailed description and claims.

DETAILED DESCRIPTION

Figure 1:
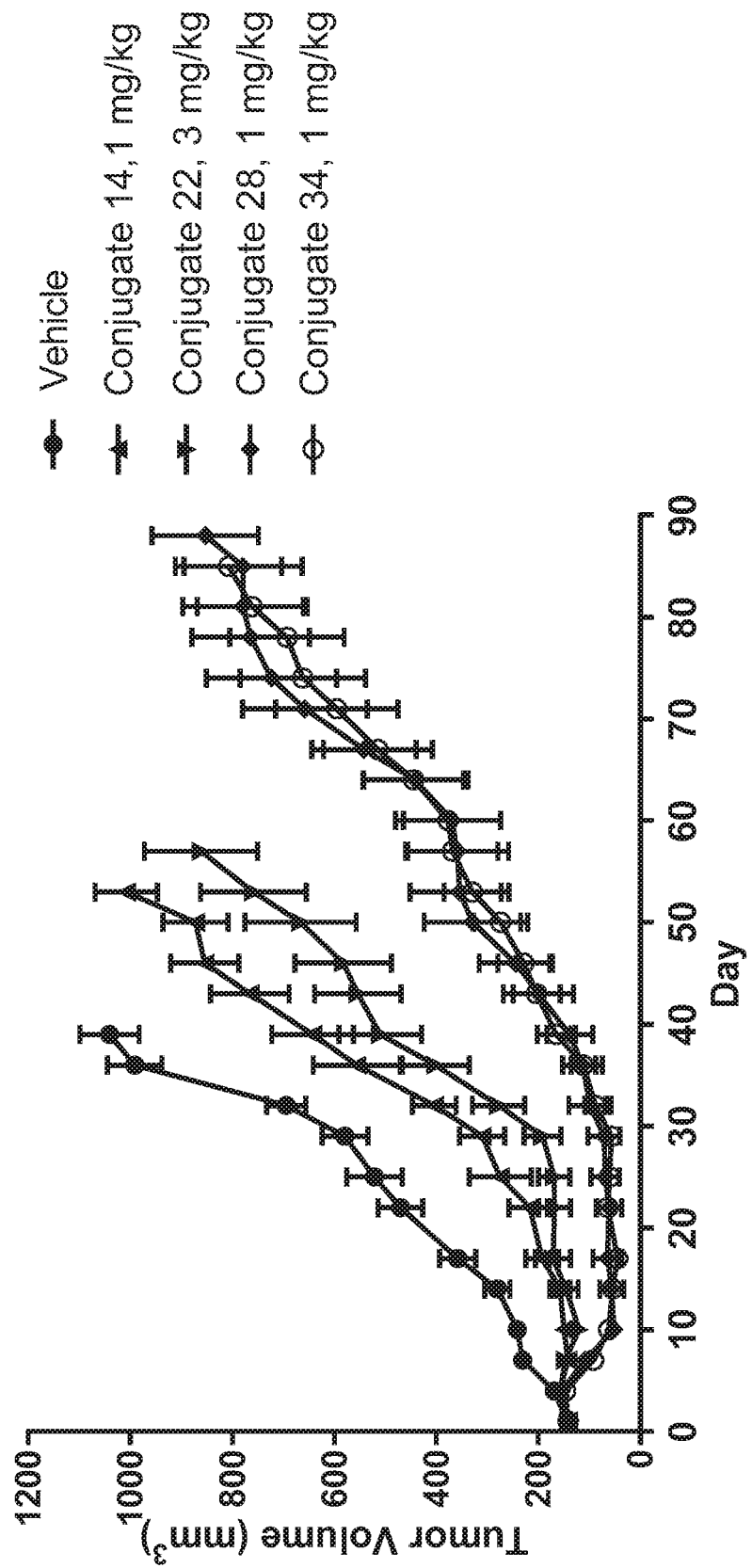
FIG. 1 is a plot of tumor volume vs. time, showing the tumor response in mice inoculated subcutaneously with Calu-3 cells (n=10 for each group) after IV administration as a single dose on day 1 of vehicle or trastuzumab-PBD conjugates: Example 4, Conjugate 14; Example 5, Conjugate 22; Example 6, Conjugate 28; and Example 7, Conjugate 34; each at 1 mg/kg.

In some aspects, the present disclosure provides, inter alia, a conjugate (e.g., an antibody-drug conjugate (ADC)) of Formula (I):

PBRM-[$L^C$-D]$_{d15}$ (I)

or a pharmaceutically acceptable salt or solvate thereof, wherein:
PBRM denotes a protein based recognition-molecule;
$L^C$ is a linker unit connecting the PBRM to D;
D is a PBD drug moiety; and
$d_{15}$ an integer from about 1 to about 20.

In some embodiments, the conjugates of Formula (I) include those where each of the moieties defined for one of PBRM, $L^C$, D, and $d_{15}$ can be combined with any of the moieties defined for the others of PBRM, $L^C$, D, and $d_{15}$.

In some embodiments, the PBRM is a targeting agent that binds to a target moiety. In some embodiments, the PBRM is a cell binding agent specifically binding to a cell component. In some embodiments, the PBRM specifically binds to a target molecule of interest.

In some embodiments, the conjugate allows for delivery of the PBD drug moiety (D) to a preferred site in a subject (e.g., a human). In some embodiments, the conjugate allows for the release of the PBD drug moiety (D) in an active form for its intended therapeutic effect.

In some embodiments, the conjugate comprises the PBD drug moiety (D) being covalently attached to a cell binding agent via the linker unit ($L^C$).

In some embodiments, the linker unit is a bifunctional or multifunctional moiety which being capable of linking one or more PBD drug moiety (D) and an antibody unit (Ab) to form an antibody-drug conjugate (ADC). The linker unit may be stable outside a cell (i.e., extracellularly), or it may be cleavable by enzymatic activity, hydrolysis, or other metabolic conditions.

In some embodiments, the linker unit of the ADC prevents aggregation of the ADC and/or keep the ADC freely soluble in aqueous media and in a monomeric state.

In some embodiments, the linker unit of the ADC is stable extracellularly. In some embodiments, before transport or delivery into a cell, the ADC is preferably stable and remains intact (i.e., the antibody remains linked to the drug moiety). In some embodiments, the linker unit is stable outside the target cell and may be cleaved at an efficacious rate inside the cell. In some embodiments, the linker unit may (i) maintain the specific binding properties of the antibody; (ii) allow for intracellular delivery of the conjugate or therapeutic agent; (iii) remain stable and intact (i.e., not cleaved) until the conjugate has been delivered or transported to its targeted site; and/or (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Covalent attachment of the antibody and the PBD drug moiety requires the linker unit to have two reactive functional groups (i.e., bivalency in a reactive sense). Useful bivalent linker units for attaching two or more functional or biologically active moieties include, but are not limited to, peptides, nucleic acids, drugs, toxins, antibodies, haptens, and reporter groups. Some known bivalent linker units and their resulting conjugates have been described (Hermanson, G. T. (1996) Bioconjugate Techniques; Academic Press: New York, p 234-242).

In some embodiments, the linker unit may be substituted with one or more groups which modulate aggregation, solubility, and/or reactivity. In some embodiments, a sulfonate substituent may increase water solubility of the reagent and facilitate the coupling reaction of the linker reagent with the antibody or the PBD drug moiety, or facilitate the coupling reaction of an antibody-linker reagent (Ab-L) with a PBD drug moiety (D), or a PBD drug-linker reagent (D-L) with an antibody unit (Ab), depending on the synthetic route employed to prepare the ADC. In some aspects, the present disclosure provides a method of preparing a conjugate (e.g., an antibody-drug conjugate (ADC)) of the present disclosure. Antibody-drug conjugates (ADC) can be conveniently prepared using a linker unit having reactive functionality for binding to the PBD drug moiety (D) and to the antibody unit (Ab). In some embodiments, a cysteine thiol, or an amine (e.g. N-terminus or amino acid side chain such as lysine) of the antibody (Ab) can form a bond with a functional group of a linker or spacer reagent, a PBD drug moiety (D), or a PBD drug-linker reagent (D-RL).

Antibody-Drug Conjugate (ADC) Type I:

In some embodiments, the conjugate (e.g., the antibody-drug conjugate (ADC)) of the present disclosure is of Formula (II):

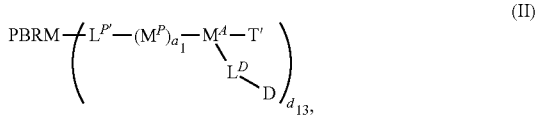
(II)

or a pharmaceutically acceptable salt or solvate thereof, wherein:

PBRM denotes a protein based recognition-molecule;

each occurrence of D is independently a PBD drug moiety;

$L^{P'}$ is a divalent linker moiety connecting the PBRM to $M^P$; of which the corresponding monovalent moiety $L^P$ contains a functional group $W^P$ that is capable of forming a covalent bond with a functional group of the PBRM;

$M^P$ is a Stretcher unit;

$a_1$ is an integer from 0 to 1;

$M^A$ comprises a peptide moiety that contains at least two amino acids;

T' is a hydrophilic group and the

between T' and $M^A$ denotes direct or indirect attachment of T' and $M^A$;

each occurrence of $L^D$ is independently a divalent linker moiety connecting D to $M^A$ and comprises at least one cleavable bond such that when the bond is broken, D is released in an active form for its intended therapeutic effect; and $d_{13}$ is an integer from 1 to 20.

In some embodiments, the conjugates of Formula (II) include those where each of the moieties defined for one of PBRM, D, $L^{P'}$, $L^P$, $W^P$, $M^P$, $a_1$, $M^A$, T', $L^D$, and $d_{13}$ can be combined with any of the moieties defined for the others of PBRM, D, $L^{P'}$, $L^P$, $W^P$, $M^P$, $a_1$, $M^A$, T', $L^D$, and $d_{13}$.

In some aspects, the present disclosure provides a scaffold of any one of Formulae (IIa) to (IIe):

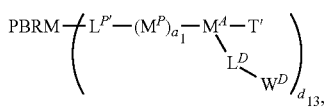
(IIa)

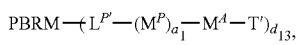
(IIb)

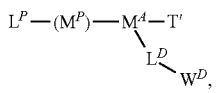
(IIc)

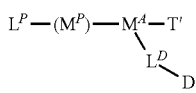
(IId)

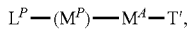
(IIe)

or a pharmaceutically acceptable salt or solvate thereof, wherein

PBRM denotes a protein based recognition-molecule;

each occurrence of D is independently a PBD drug moiety;

$L^{P'}$ is a divalent linker moiety connecting the PBRM to M; of which the corresponding monovalent moiety $L^P$ contains a functional group $W^P$ that is capable of forming a covalent bond with a functional group of the PBRM;

$M^P$ is a Stretcher unit;

$a_1$ is an integer from 0 to 1; $M^A$ comprises a peptide moiety that contains at least two amino acids;

T' is a hydrophilic group and the

between T' and $M^A$ denotes direct or indirect attachment of T' and $M^A$;

each occurrence of $W^D$ is independently a functional group that is capable of forming a covalent bond with a functional group of D; each occurrence of $L^D$ is independently a divalent linker moiety connecting $W^D$ or D to $M^A$ and $L^D$ comprises at least one cleavable bond such that when the bond is broken, D is released in an active form for its intended therapeutic effect; and $d_{13}$ is an integer from 1 to 10.

In some embodiments, the conjugates of any one of Formulae (IIa)-(IIe) include those where each of the moieties defined for one of PBRM, D, $L^{P'}$, $L^P$, $W^P$, $M^P$, $a_1$, $M^A$, T', $L^D$, $W^D$, and $d_{13}$ can be combined with any of the moieties defined for the others of PBRM, D, $L^{P'}$, $L^P$, $W^P$, $M^P$, $a_1$, $M^A$, T', $L^D$, $W^D$, and $d_{13}$.

The conjugates and scaffolds of the disclosure can include one or more of the following features when applicable.

In some embodiments, $d_{13}$ is an integer from 2 to 14, from 2 to 12, from 2 to 10, from 2 to 8, from 2 to 6, from 2 to 4, from 4 to 10, from 4 to 8, from 4 to 6, from 6 to 14, from 6 to 12, from 6 to 10, from 6 to 8, from 8 to 14, from 8 to 12, or from 8 to 10.

In some embodiments, di is an integer from 2 to 6 (e.g., $d_{13}$ is 2, 3, 4, 5 or 6).

In some embodiments, $d_{13}$ is an integer from 2 to 4 (e.g., $d_{13}$ is 2, 3, or 4).

In some embodiments, $d_{13}$ is an integer from 4 to 6 (e.g., $d_{13}$ is 4, 5, or 6).

In some embodiments, $d_{13}$ is an integer from 6 to 8 (e.g., $d_{13}$ is 6, 7, or 8).

In some embodiments, di is an integer from 6 to 10 (e.g., $d_{13}$ is 6, 7, 8, 9, or 10).

In some embodiments, do is 3 to 5.

In some embodiments, $d_{13}$ is 4 or 5.

$L^P$ and $L^{P'}$

In some embodiments, $L^{P'}$ is a divalent linker moiety connecting the PBRM to $M^P$; of which the corresponding monovalent moiety is $L^P$.

In some embodiments, $L^P$, when not connected to PBRM, comprises a terminal group $W^P$, in which each $W^P$ independently is:

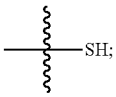
(1)

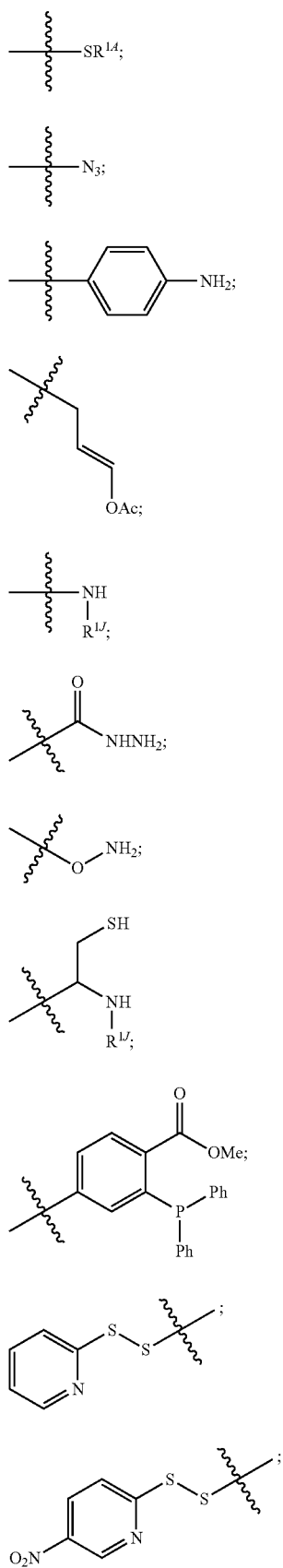
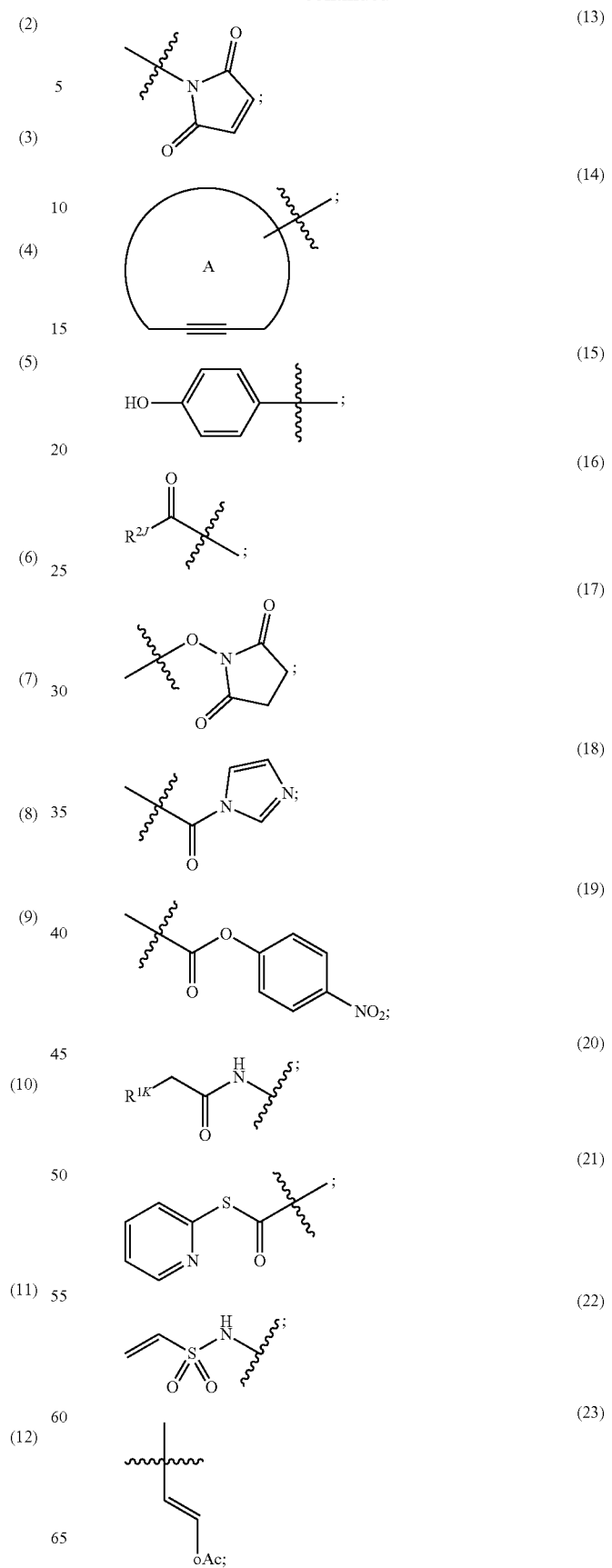

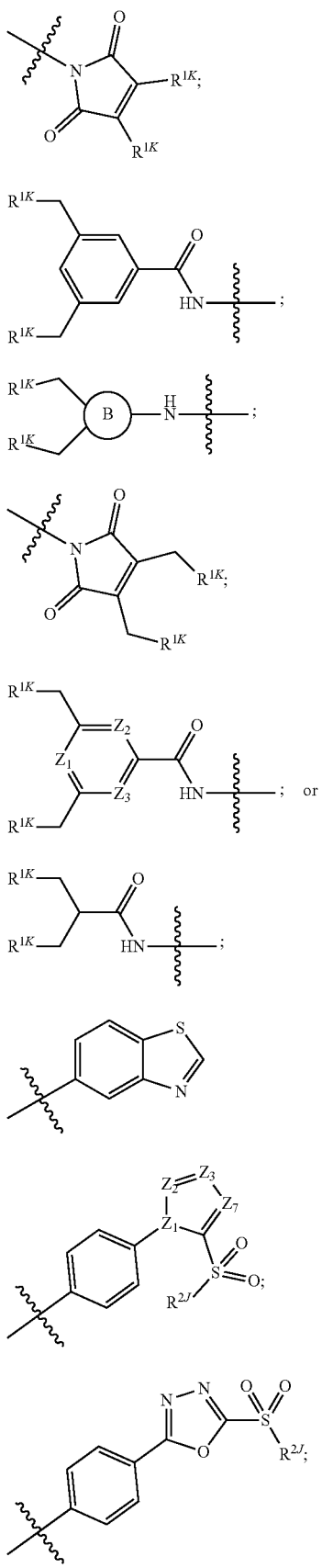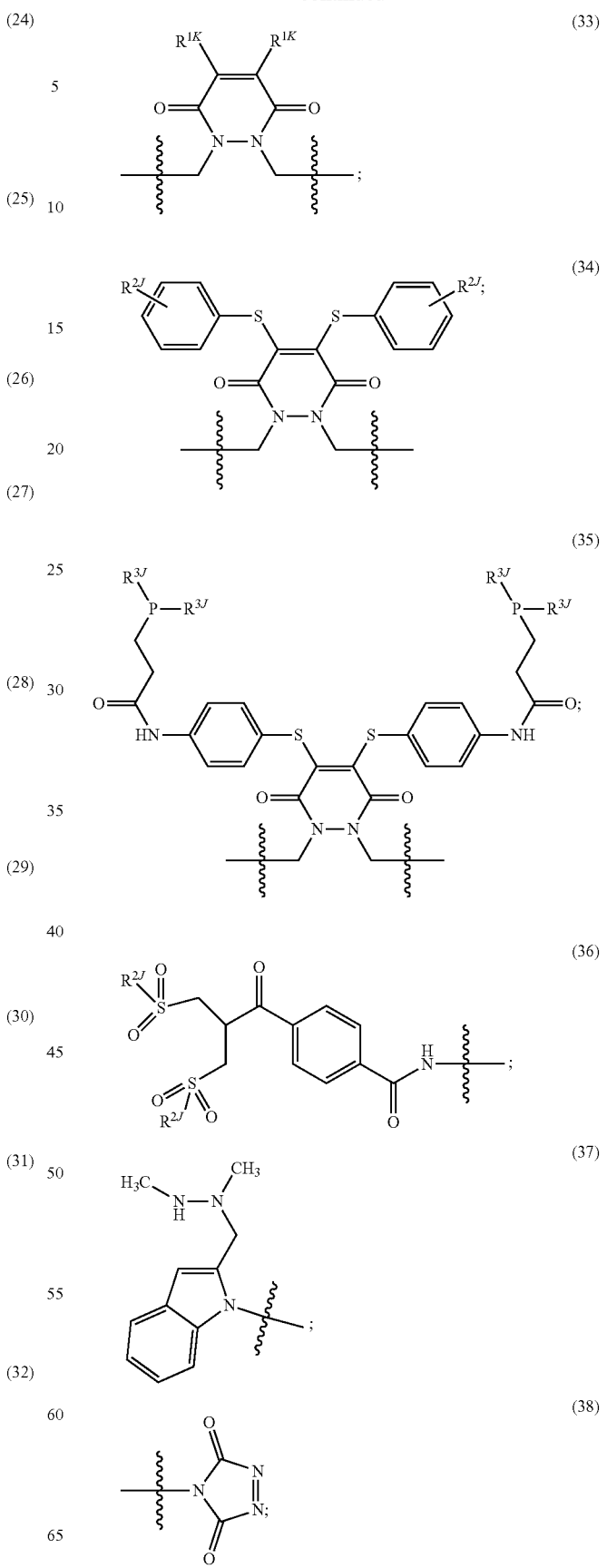

-continued

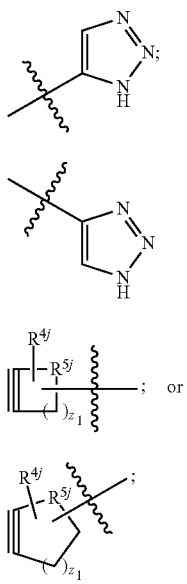

(39)

(40)

(41)

(43)

in which
R$^{1K}$ is a leaving group (e.g., halide or RC(O)O— in which R is hydrogen or an aliphatic, heteroaliphatic, carbocyclic, or heterocycloalkyl moiety);
R$^{1A}$ is a sulfur protecting group;
ring A is cycloalkyl or heterocycloalkyl;
ring B is cycloalkyl, heterocycloalkyl, aryl, or heteroaryl;
R$^{1J}$ is hydrogen or an aliphatic, heteroaliphatic, carbocyclic, or heterocycloalkyl moiety;
R$^{2J}$ is hydrogen, an aliphatic, aryl, heteroaliphatic, or carbocyclic moiety;
R$^{4j}$ is C$_{1-6}$ alkyl; Z$_1$, Z$_2$, Z$_3$ and Z$_7$ are each independently a carbon or nitrogen atom; R$^4$ is hydrogen, halogen, OR, —NO$_2$, —CN, —S(O)$_2$R, C$_{1-24}$ alkyl (e.g., C$_{1-6}$ alkyl), or 6-24 membered aryl or heteroaryl, wherein the C$_{1-24}$ alkyl (e.g., C$_{1-6}$ alkyl), or 6-24 membered aryl or heteroaryl, is optionally substituted with one or more aryl or heteroaryl; or two R$^{4j}$ together form an annelated cycloalkyl, heterocycloalkyl, aryl, or heteroaryl; R is hydrogen, alkyl, heteroalkyl, cycloalkyl, or heterocycloalkyl
R$^{5j}$ is C(R$^{4j}$)$_2$, O, S or NR; and
z$_1$ is an integer 1, 2, 3, 4, 5, 6, 7, 8, 9 or 10.
In some embodiments, each R$^{1K}$ is halo or RC(O)O— in which R is hydrogen or an aliphatic, heteroaliphatic, carbocyclic, or heterocycloalkyl moiety.
In some embodiments, each R$^{1A}$ independently is

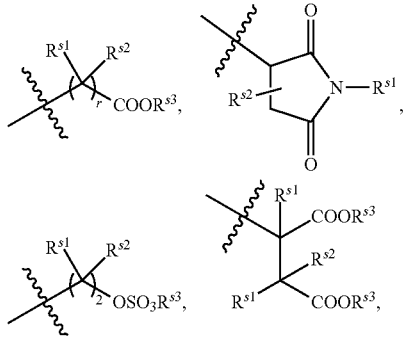

in which r is 1 or 2 and each of R$^{s1}$, R$^{s2}$, and R$^{s3}$ is hydrogen or an aliphatic, heteroaliphatic, carbocyclic, or heterocycloalkyl moiety.

In some embodiments, ring A is C$_{3-8}$ cycloalkyl or 5-19 membered heterocycloalkyl.

In some embodiments, ring A is

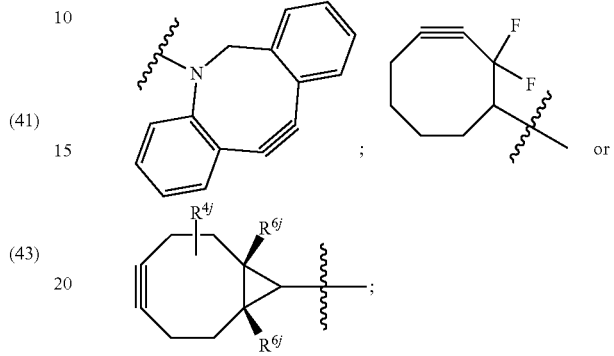

wherein R$^{6j}$ is hydrogen, halogen, C$_{1-24}$ alkyl (e.g., C$_{1-6}$ alkyl), or 6-24 membered aryl or heteroaryl, wherein the C$_{1-24}$ alkyl (e.g., C$_{1-6}$ alkyl), or 6-24 membered aryl or heteroaryl, is optionally substituted with one or more aryl or heteroaryl.

In some embodiments, ring A is

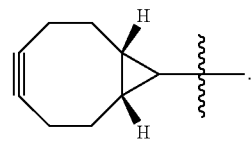 [SMILES: *C1[C@H]2CCC#CCC[C@@H]12]

In some embodiments, ring A or B is C$_{3-8}$ cycloalkyl or 3-12 membered heterocycloalkyl.

In some embodiments, ring A or B is piperazinyl or piperidinyl.

In some embodiments, each of R$^{s1}$, R$^{s2}$, and R$^{s3}$ is hydrogen or C$_{1-6}$ alkyl.

In some embodiments, W$^P$ is

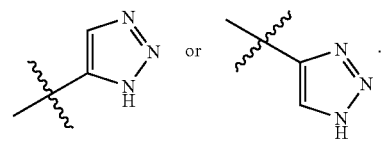 [SMILES: *c1cnn[nH]1 ; "or" ; *c1c[nH]nn1 ; "."]

In some embodiments, W$^P$ is

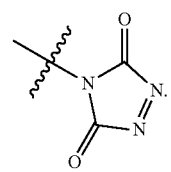 [SMILES: *N1C(=O)N=NC1=O]

In some embodiments, $W^P$ is

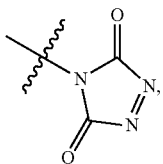 [SMILES: *N1C(=O)N=NC1=O]

$L^{P'}$ comprises

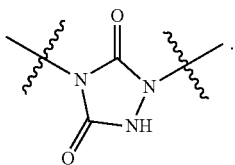 [SMILES: *n1[nH]c(=O)n(*)c1=O]

In some embodiments, $W^P$ is

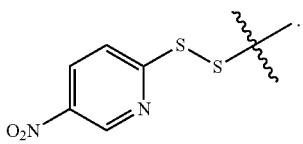

In some embodiments, when $W^P$ is

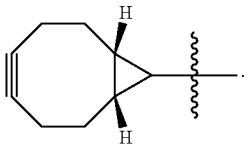 [SMILES: *C1[C@H]2CCC#CCC[C@@H]12]

In some embodiments, when $W^P$ is

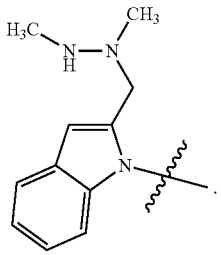 [SMILES: *n1c(CN(C)NC)cc2ccccc21]

In some embodiments, when $W^P$ is

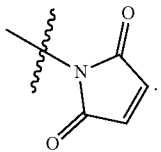 [SMILES: *N1C(=O)C=CC1=O]

In some embodiments, when $W^P$ is

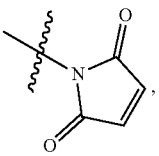 [SMILES: *N1C(=O)C=CC1=O]

$L^{P'}$ comprise

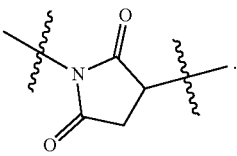 [SMILES: *C1CC(=O)N(*)C1=O]

In some embodiments, $W^P$ is

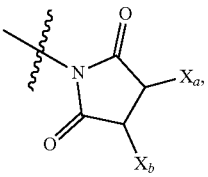

wherein one of $X_a$ and $X_b$ is H and the other is a maleimido blocking moiety. In some embodiments, a maleimido blocking compound (i.e., a compound that can react with maleimide to convert it to succinimide) may be used to quench the reaction between, e.g., the Linker-Drug moiety and PBRM, and a maleimido blocking moiety refers to the chemical moiety attached to the succinimide upon conversion. In some embodiments, the maleimido blocking moieties are moieties that can be covalently attached to one of the two olefin carbon atoms upon reaction of the maleimido group with a thiol-containing compound of Formula (II'):

$$R_{90}-(CH_2)_d-SH \quad (II')$$

wherein:
$R_{90}$ is $NHR_{91}$, OH, $COOR_{93}$, $CH(NHR_{91})COOR_{93}$ or a substituted phenyl group;
$R_{93}$ is hydrogen or $C_{1-4}$ alkyl;
$R_{91}$ is hydrogen, $CH_3$ or $CH_3CO$ and
d is an integer from 1 to 3.

In some embodiments, the maleimido blocking compound is cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH CHO, $COC_{1-4}$ alkyl, $NH_2$, F, cyano, $SO_3H$, $PO_3H$, and the like.

In some embodiments, the maleimido blocking group is $-S-(CH_2)_d-R_{90}$, wherein:
$R_{90}$ is OH, COOH, or $CH(NHR_{91})COOR_{93}$;
$R_{93}$ is hydrogen or $CH_3$;
$R_{91}$ is hydrogen or $CH_3CO$; and
d is 1 or 2.

In some embodiments, the maleimido blocking group is —S—CH$_2$—CH(NH$_2$)COOH.

Stretcher Unit M$^P$

In some embodiments, M$^P$, when present, is —(Z$_4$)—[(Z$_5$)—(Z$_6$)]$_z$—, with Z$_4$ connected to L$^{P'}$ or L$^P$ and Z$_6$ connected to M$^A$; in which z is 1, 2, or 3;

Z$_4$ is

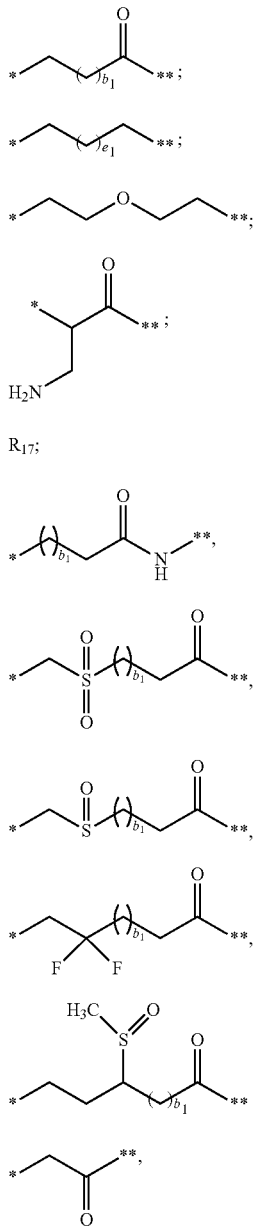

wherein * denotes attachment to L$^{P'}$ or L$^P$ and ** denotes attachment to Z$_5$ or Z$_6$ when present or to M$^A$ when Z$_5$ and Z$_6$ are both absent;

b$_1$ is an integer from 0 to 6;

e$_1$ is an integer from 0 to 8,

R$_{17}$ is C$_{1-10}$ alkylene, C$_{1-10}$ heteroalkylene, C$_{3-8}$ cycloalkylene, O—(C$_{1-8}$ alkylene, arylene, —C$_{1-10}$ alkylene-arylene-, -arylene-C$_{1-10}$ alkylene-, —C$_{1-10}$ alkylene-(C$_{3-8}$ cycloalkylene)-, —(C$_{3-8}$ cycloalkylene —C$_{1-10}$ alkylene-, 4 to 14-membered heterocycloalkylene, —C$_{1-10}$ alkylene-(4 to 14-membered heterocycloalkylene)-, -(4 to 14-membered heterocycloalkylene)-C$_{1-10}$ alkylene-, —C$_{1-10}$ alkylene-C(═O)—, —C$_{1-10}$ heteroalkylene-C(═O)—, —C$_{3-8}$ cycloalkylene-C(═O)—, —O—(C$_{1-8}$ alkyl)-C(═O)—, -arylene-C(═O)—, —C$_{1-10}$ alkylene-arylene-C(═O)—, -arylene —C$_{1-10}$ alkylene-C(═O)—, —C$_{1-10}$ alkylene-(C$_{3-8}$ cycloalkylene)-C(═O)—, —(C$_{3-8}$ cycloalkylene)-C$_{1-10}$ alkylene-C(═O)—, -4 to 14-membered heterocycloalkylene-C(═O)—, —C$_{1-10}$ alkylene-(4 to 14-membered heterocycloalkylene)-C(═O)—, -(4 to 14-membered heterocycloalkylene)-C(═O)—C$_{1-10}$ alkylene-, —C$_{1-10}$ alkylene-NH—, —C$_{1-10}$ heteroalkylene-NH—, —C$_{3-8}$ cycloalkylene-NH—, —O—(C$_{1-8}$ alkyl)-NH—, -arylene-NH—, —C$_{1-10}$ alkylene-arylene-NH—, -arylene-C$_{1-10}$ alkylene-NH—, —C$_{1-10}$ alkylene-(C$_{3-8}$ cycloalkylene)-NH—, —(C$_{3-8}$ cycloalkylene)-C$_{1-10}$ alkylene-NH—, -4 to 14-membered heterocycloalkylene-NH—, —C$_{1-10}$ alkylene-(4 to 14-membered heterocycloalkylene)-NH—, -(4 to 14-membered heterocycloalkylene)-C$_{1-10}$ alkylene-NH—, —C$_{1-10}$ alkylene-S—, —C$_{1-10}$ heteroalkylene-S—, —C$_{3-8}$ cycloalkylene-S—, —O—C$_{1-8}$ alkyl)-S—, -arylene-S—, —C$_{1-10}$ alkylene-arylene-S—, -arylene-C$_{1-10}$ alkylene-S—, —C$_{1-10}$ alkylene-(C$_{3-8}$ cycloalkylene)-S—, —(C$_{3-8}$ cycloalkylene)-C$_{1-10}$ alkylene-S—, -4 to 14-membered heterocycloalkylene-S—, —C$_{1-10}$ alkylene-(4 to 14-membered heterocycloalkylene)-S—, or -(4 to 14-membered heterocycloalkylene)-C$_1$-C$_{10}$ alkylene-S—;

each Z$_5$ independently is absent, R$_{57}$—R$_{17}$ or a polyether unit:

each R$_{57}$ independently is a bond, NR$_{23}$, S or O;

each R$_{23}$ independently is hydrogen. C$_{1-6}$ alkyl, C$_{6-10}$ aryl, C$_{3-8}$ cycloalkyl, —COOH, or —COO—C$_{1-6}$ alkyl; and each Z$_6$ independently is absent, —C$_{1-10}$ alkyl-R$_3$—, —C$_{1-10}$ alkyl-NR$_5$—, —C$_{1-10}$ alkyl-C(O)—, —C$_{1-10}$ alkyl-O—, —C$_{1-10}$ alkyl-S— or —(C$_{1-10}$ alkyl-R$_3$)$_{g1}$—C$_{1-10}$ alkyl-C(O)—;

each R$_3$ independently is —C(O)—NR$_5$— or —NR$_5$—C(O)—;

each R$_5$ independently is hydrogen, C$_{1-6}$ alkyl, C$_{6-10}$ aryl, C$_{3-8}$ cycloalkyl, COOH, or COO—C$_{1-6}$ alkyl; and g$_1$ is an integer from 1 to 4.

In some embodiments, Z$_4$ is

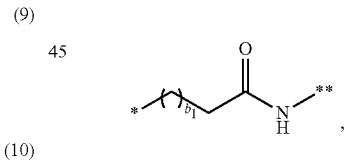

e.g., wherein b$_1$ is 0, 1 or 4.

In some embodiments, Z$_4$ is

e.g., wherein b$_1$ is 1 or 4.

In some embodiments, Z$_4$ is

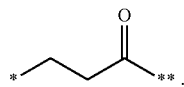

In some embodiments, $Z_4$ is

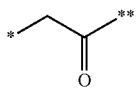

In some embodiments, each $Z_5$ independently is a polyalkylene glycol (PAO), including but are not limited to, polymers of lower alkylene oxides, in particular polymers of ethylene oxide, such as, for example, propylene oxide, polypropylene glycols, polyethylene glycol (PEG), polyoxyethylenated polyols, copolymers thereof and block copolymers thereof. In some embodiments, the polyalkylene glycol is a polyethylene glycol (PEG) including, but not limited to, polydisperse PEG, monodisperse PEG and discrete PEG. Polydisperse PEGs are a heterogeneous mixture of sizes and molecular weights whereas monodisperse PEGs are typically purified from heterogeneous mixtures and are therefore provide a single chain length and molecular weight. In some embodiments, the PEG units are discrete PEGs provide a single molecule with defined and specified chain length. In some embodiments, the polyethylene glycol is mPEG.

As used herein a subunit when referring to the PEG unit refers to a polyethylene glycol subunit having the formula

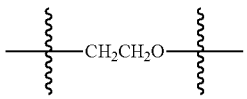

In some embodiments, the PEG unit comprises multiple PEG subunits.

In some embodiments, when z is 2 or 3, at least one $Z_5$ is a polyalkylene glycol (PAO), e.g., a PEG unit.

In some embodiments, the PEG unit comprises 1 to 6 subunits.

In some embodiments, the PEG unit comprises 1 to 4 subunits.

In some embodiments, the PEG unit comprises 1 to 3 subunits.

In some embodiments, the PEG unit comprises 2 subunits.

In some embodiments, the PEG unit comprises 1 subunit.

In some embodiments, the PEG unit comprises one or multiple PEG subunits linked together by a PEG linking unit. The PEG linking unit that connects one or more chains of repeating $CH_2CH_2O$— subunits can be $Z_6$. In some embodiments, $Z_6$ is —$C_{1-10}$ alkyl-$R_3$—, —$C_{2-10}$ alkyl-NH—, —$C_{2-10}$ alkyl-C(O)—, —$C_{2-10}$ alkyl-O— or —$C_{1-10}$ alkyl-S, wherein $R_3$ is —C(O)—$NR_5$— or —$NR_5$—C(O)—.

In some embodiments, the PEG linking unit is —$C_{1-10}$ alkyl-C(O)—NH— or —$C_{1-10}$ alkyl-NH—C(O)—. In one embodiment, the PEG linking unit is —$(CH_2)_2$—C(O)—NH—.

In some embodiments, each $Z_5$ is absent.

In some embodiments, when z is 2 or 3, at least one $Z_5$ is absent.

In some embodiments, each $Z_5$ is —$(CH_2$—$CH_2$—O—$)_2$—.

In some embodiments, when z is 2 or 3, at least one $Z_5$ is —$(CH_2$—$CH_2$—O—$)_2$—.

In some embodiments, each $Z_5$ independently is $R_{57}$—$R_{17}$. In some embodiments, each $Z_5$ independently is $R_{17}$, $NHR_{17}$, $OR_{17}$, or $SR_{17}$.

In some embodiments, when z is 2 or 3, at least one $Z_5$ is $R_{57}$—$R_{17}$, e.g., $R_{17}$, $NHR_{17}$, $OR_{17}$, or $SR_{17}$.

In some embodiments, each $Z_6$ is absent.

In some embodiments, when z is 2 or 3, at least one $Z_6$ is absent.

In some embodiments, at least one of $Z_5$ and $Z_6$ is not absent.

In some embodiments, each Z (independently is —$C_{1-10}$ alkyl-$R_3$—, —$C_{1-10}$ alkyl-NH—, —$C_{1-10}$ alkyl-C(O)—, —$C_{1-10}$ alkyl-O—, —$C_{1-10}$ alkyl-S— or —($C_{1-10}$ alkyl-$R_3$)$_{g1}$—$C_{1-10}$ alkyl-C(O)—. In some embodiments, $g_1$ is an integer from 1 to 4.

In some embodiments, when z is 2 or 3, at least one $Z_6$ is —$C_{1-10}$ alkyl-$R_3$—, —$C_{1-10}$ alkyl-NH—, —$C_{1-10}$ alkyl-C(O)—, —$C_{1-10}$ alkyl-O—, —$C_{1-10}$ alkyl-S— or —($C_{1-10}$ alkyl-$R_3$)$_{g1}$—$C_{1-10}$ alkyl-C(O)—.

In some embodiments, $g_1$ is an integer from 1 to 4.

In some embodiments, each $Z_6$ independently or at least one $Z_6$ is —$C_{2-10}$ alkyl-C(O)—, e.g., —$(CH_2)_2$—C(O)—.

In some embodiments, each $Z_6$ independently or at least one Z is —$C_{2-10}$ alkyl-$R_3$—$C_{2-10}$ alkyl-C(O)—, e.g., —$(CH_2)_2$—C(O)NH—$(CH_2)_2$—C(O)—.

In some embodiments, each $Z_6$ independently or at least one $Z_6$ is —($C_{2-10}$ alkyl-$R_3$)$_{g1}$—$C_{2-10}$ alkyl-C(O)—, e.g., —$(CH_2)_2$—C(O)NH—$(CH_2)_2$—NHC(O)—$(CH_2)$—C(O)—.

In some embodiments, —[($Z_5$)—($Z_6$)]$_z$— is not absent.

In some embodiments, —[($Z_5$)—($Z_6$)]$_z$— is a bond.

In some embodiments, —[($Z_5$)—($Z_6$)]$_z$— is —$(CH_2CH_2O)_2$—$(CH_2)_2$—C(O)—NH—$(CH_2CH_2O)_2$—.

In some embodiments, $M^P$, when present, is

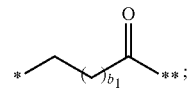
(1)

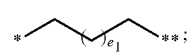
(2)

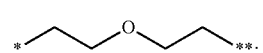
(3)

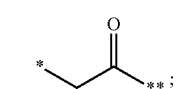
(4)

$R_{17}$;
(5)

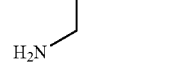
(6)

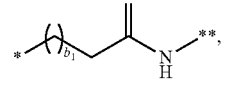
(6)

*—$CH_2$—C(O)—$\overset{R_{23}}{\underset{|}{N}}$—$R_{17}$—**,
(7)

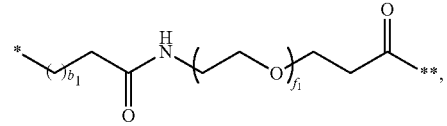
(8)

-continued

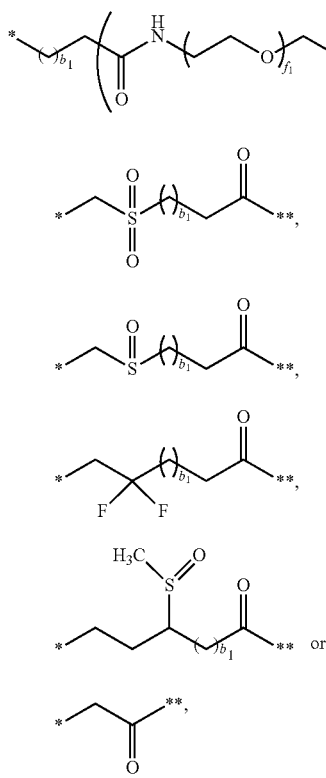

(9)

(10)

(11)

(12)

(13)

(14)

wherein * denotes attachment to $L^{P'}$ or $L^P$ and ** denotes attachment to $L^M$;

$R_3$, $R_5$, $R_{17}$, and $R_{23}$ are as defined herein;

$R_4$ is a bond or $-NR_5-(CR_{20}R_{21})-C(O)-$;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

each $b_1$ independently is an integer from 0 to 6;

$e_1$ is an integer from 0 to 8, each $f_1$ independently is an integer from 1 to 6; and $g_2$ is an integer from 1 to 4.

In some embodiments, $b_1$ is 1.

In some embodiments, $b_1$ is 0

In some embodiments, each $f_1$ independently is 1 or 2.

In some embodiments, $f_1$ is 2.

In some embodiments, $g_2$ is 1 or 2.

In some embodiments, $g_2$ is 2.

In some embodiments, $R_{17}$ is unsubstituted.

In some embodiments, $R_{17}$ is optionally substituted.

In some embodiments, $R_{17}$ is optionally substituted by a basic unit, e.g., $-(CH_2)_xNH_2$, $-(CH_2)_xNHR^a$, and $-(CH_2)_xN(R^a)_2$, wherein x is an integer from 1 to 4 and each $R^a$ is independently selected from $C_{1-6}$ alkyl and $C_{1-6}$ haloalkyl, or two $R^a$ groups are combined with the nitrogen to which they are attached to form an azetidinyl, pyrrolidinyl or piperidinyl group.

In some embodiments, $R^{17}$ is $-C_{2-3}$ alkylene-$C(=O)-$ wherein the alkylene is optionally substituted by a basic unit, e.g., $-(CH_2)_xNH_2$, $-(CH_2)_xNHR^a$, and $-(CH_2)_xN(R^a)_2$, wherein x and $R^a$ are as defined herein.

In some embodiments, wherein $M^P$, when present, is:

(1)
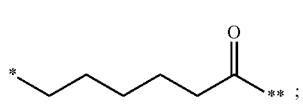

(2)
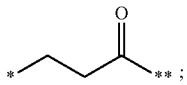

(3)
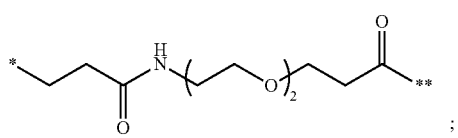

(4)
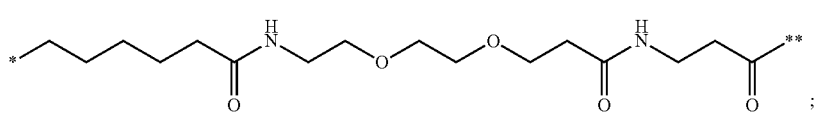

(5)
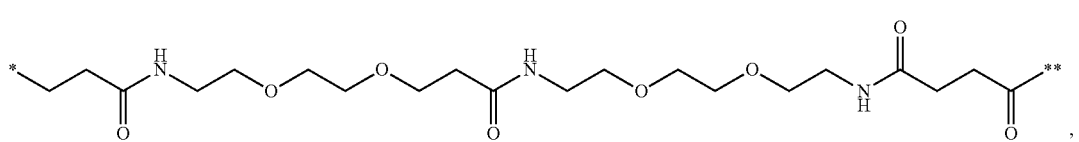

(6)
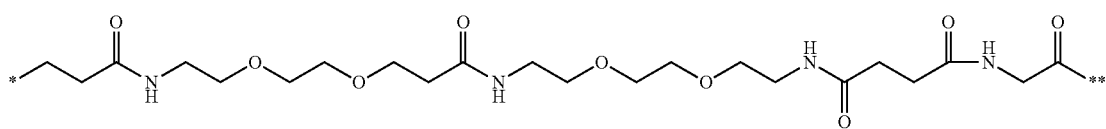

-continued

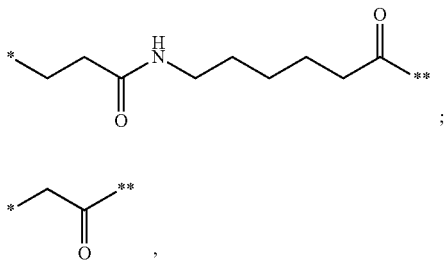
(7)

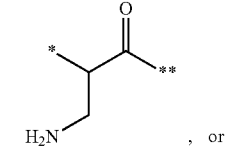
(8)

, or (9)

wherein * denotes attachment to $L^{P'}$ or $L^P$ and ** denotes attachment to $M^A$.

In some embodiments, wherein $M^P$, when present, is:

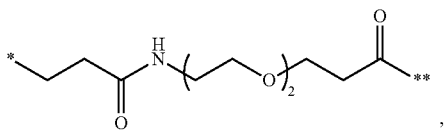

wherein * denotes attachment to $L^{P'}$ or $L^P$ and ** denotes attachment to $M^A$.

In some embodiments, wherein $M^P$, when present, is:

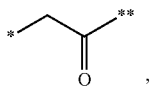

wherein * denotes attachment to $L^{P'}$ or $L^P$ and ** denotes attachment to $M^A$.

$M^A$

In some embodiments, $M^A$ is a linker moiety that is capable of connecting one or more drugs and one or more hydrophilic groups to $L^P$ or $L^{P'}$. In some embodiments, $M^A$ comprises a peptide moiety of at least two amino acid (AA) units.

The peptide moiety is a moiety that is capable of forming a covalent bond with a $-L^D$-D unit and allows for the attachment of multiple drugs. In some embodiments, peptide moiety comprises a single AA unit or has two or more AA units (e.g., 2 to 10, preferably from 2 to 6, e.g., 2, 3, 4, 5 or 6) wherein the AA units are each independently a natural or non-natural amino acid, an amino alcohol, an amino aldehyde, a diamine, or a polyamine or combinations thereof. If necessary in order to have the requisite number of attachments, at least one of AA units will have a functionalized side chain to provide for attachment of the $-L^D$-D unit. Exemplary functionalized AA units (e.g., amino acids, amino alcohols, or amino aldehydes) include, for example, azido or alkyne functionalized AA units (e.g., amino acid, amino alcohol, or amino aldehyde modified to have an azide group or alkyne group for attachment using click chemistry).

In some embodiments, the peptide moiety has 2 to 12 AA units.

In some embodiments, the peptide moiety has 2 to 10 AA units.

In some embodiments, the peptide moiety has 2 to 6 AA units.

In some embodiments, the peptide moiety has 2, 3, 4, 5 or 6 AA units.

In some embodiments, an AA unit has three attachment sites, (e.g., for attachment to $L^M$, the hydrophilic group (T') or another AA unit, and to the $-L^D$-D unit). In some embodiments, the AA unit has the formula:

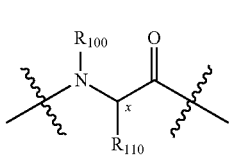

wherein the wavy line indicates attachment sites within the conjugate (e.g., the antibody-drug conjugate (ADC)) of the disclosure or intermediates thereof; and $R_{100}$ and $R_{110}$ are as defined herein.

In some embodiments, an AA unit has two attachment sites (i.e., a terminal unit) and one of the attachment sites shown above can replaced, for example, by H, OH, or an unsubstituted $C_{1-3}$ alkyl group.

In some embodiments, the peptide moiety comprises at least two AA units of the following formula:

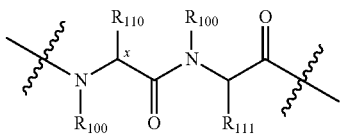

wherein:

each $R_{111}$ independently is H, p-hydroxybenzyl, methyl, isopropyl, isobutyl, sec-butyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)NHC(=NH)NH$_2$, —(CH$_2$)$_4$NH$_2$, —(CH$_2$)$_3$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl,

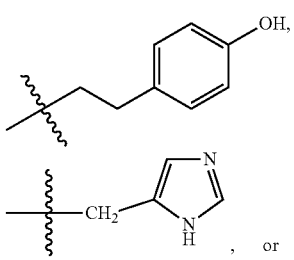

, or

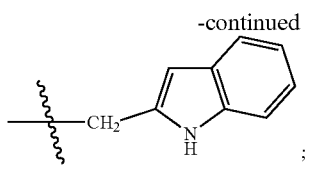

the wavy line indicates the attachment sites within the conjugate or intermediates thereof; and $R_{100}$ and $R_{110}$ are as defined herein.

In some embodiments, the peptide moiety comprises at least two AA units, e.g., cysteine-alanine is:

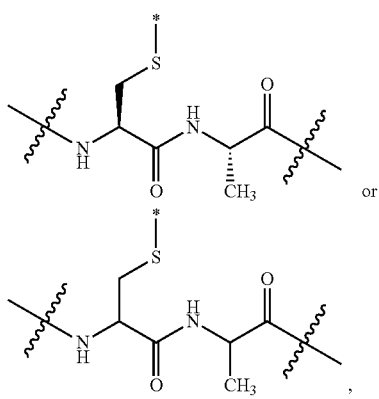

wherein the wavy lines and asterisk indicates attachment sites within the conjugate or intermediates thereof. For example, asterisk indicates attachment site of -$L^P$-D unit or a hydrophilic group. For example, the wavy line next to the carbonyl group indicates attachment site of -$L^P$-D unit or a hydrophilic group. For example, the wavy line next to the amine group indicates attachment site of -$L^P$-D unit or a hydrophilic group. For example, one or two of the wavy lines and asterisk indicate attachment site(s) of one or more -$L^P$-D units or one or more hydrophilic groups.

In some embodiments, the peptide moiety comprises at least two AA units, which provide two attachment sites, e.g., cysteine-alanine is:

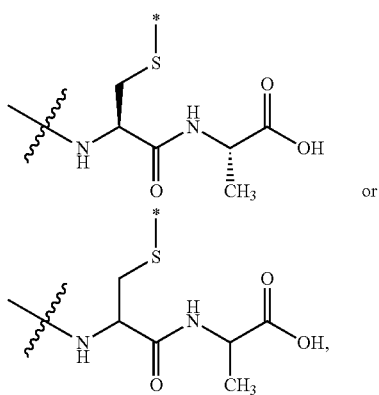

wherein the wavy line and asterisk indicates attachment sites within the conjugate or intermediates thereof. In some embodiments, asterisk indicates attachment site of -$L^P$-D unit or a hydrophilic group. In some embodiments, the wavy line indicates attachment site of -$L^P$-D unit or a hydrophilic group.

One or more AA units (e.g., an amino acid, amino alcohol, amino aldehyde or polyamine) of the peptide moiety can be replaced by an optionally substituted $C_{1-20}$ heteroalkylene (e.g., optionally substituted $C_{1-12}$ heteroalkylene), optionally substituted $C_{3-8}$ heterocyclo, optionally substituted $C_{6-14}$ arylene, or optionally substituted $C_{3-8}$ carbocyclo as described herein. The optionally substituted heteroalkylene, heterocycle, arylene or carbocyclo may have one or more functional groups for attachment within a conjugate or intermediates thereof. Suitable substituents include, but are not limited to (=O), —$R^{1C}$, —$R^{1B}$, —$OR^{1B}$, —$SR^{1B}$, —$N(R^{1B})_2$, —$N(R^{1B})_3$, =$NR^{1B}$, $C(R^{1C})_3$, CN, OCN, SCN, N=C=O, NCS, NO, $NO_2$, =$N_2$, $N_3$, $NR^{1B}C(=O)R^{1B}$, —$C(=O)R^{1B}$, —$C(=O)N(R^{1B})_2$, $SO_3^-$, $SO_3H$, $S(=O)_2R^{1B}$, —$OS(=O)_2OR^{1B}$, —$S(=O)_2NR^{1B}$, —$S(=O)R^{1B}$, —$OP(=O)(OR^{1B})_2$, —$P(=O)(OR^{1B})_2$, $PO_3^-$, $PO_3H_2$, $AsO_2H_2$, $C(=O)R^{1B}$, $C(=O)R^{1C}$, $C(=S)R^{1B}$, $CO_2R^{1B}$, $CO_2^-$, $C(=S)OR^{1B}$, $C(=O)SR^{1B}$, $C(=S)SR^{1B}$, $C(=O)N(R^{1B})_2$, $C(=S)N(R^{1B})_2$, and $C(=NR^{1B})N(R^{1B})_2$, wherein each $R^{1C}$ is independently a halogen (e.g., —F, —Cl, —Br, or —I), and each $R^{1B}$ is independently —H, —$C_{1-20}$ alkyl, —$C_{6-20}$ aryl, —$C_{3-14}$ heterocycle, a protecting group or a prodrug moiety.

In some embodiments, the one or more substituents for the heteroalkylene, heterocycle, arylene or carbocyclo are selected from (=O), $R^{1C}$, $R^{1B}$, $OR^{1B}$, $SR^{1B}$, and $N(R^{1B})_2$.

In some embodiments, the peptide moiety can be a straight chain or branched moiety of having the Formula:

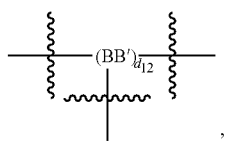

wherein:

each BB' is independently an amino acid, optionally substituted $C_{1-20}$ heteroalkylene (e.g., optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo;

$d_{12}$ is an integer from 1 to 10; and the wavy line indicates the covalent attachment sites within the conjugate or intermediate thereof.

In some embodiments, $d_{12}$ is an integer from 2 to 10.

In some embodiments, $d_{12}$ is an integer from 2 to 6.

In some embodiments, $d_{12}$ is an integer from 4, 5 or 6.

In some embodiments, di is an integer from 5 or 6.

In some embodiments, the optionally substituted heteroalkylene, heterocycle, arylene or carbocyclo have functional groups for attachments between the BB' subunits and/or for attachments within a conjugate or intermediates thereof disclosed herein.

In some embodiments, the peptide moiety comprises no more than 2 optionally substituted $C_{1-20}$ heteroalkylenes, optionally substituted $C_{3-18}$ heterocyclos, optionally substituted $C_{6-14}$ arlenes, or optionally substituted $C_{3-8}$ carbocyclos.

In other embodiments, the peptide moiety comprises no more than 1 optionally substituted $C_{1-20}$ heteroalkylenes, optionally substituted $C_{3-8}$ heterocyclos, optionally substituted $C_{6-14}$ arylenes, or optionally substituted $C_{3-8}$ carbocyclos. The optionally substituted heteroalkylene, heterocycle, arylene or carbocyclo will have functional groups for attachment between the BB' subunits and/or for attachments within a conjugate or intermediates thereof disclosed herein.

In some embodiments, at least one BB' is an amino acid. In some embodiments, the amino acid can be an alpha, beta, or gamma amino acid, which can be natural or non-natural. The amino acid can be a D or L isomer.

In some embodiments, attachment within the peptide moiety or with the other components of the conjugate (or intermediate thereof, or scaffold) can be, for example, via amino, carboxy, or other functionalities.

In some embodiments, each amino acid of the peptide moiety can be independently D or L isomer of a thiol containing amino acid. The thiol containing amino acid can be, for example, cysteine, homocysteine, or penicillamine.

In some embodiments, each amino acid that comprises the peptide moiety can be independently the L- or D-isomers of the following amino acids: alanine (including β-alanine), arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, stereoisomers thereof (e.g., isoaspartic acid and isoglutamic acid), and derivatives thereof.

In some embodiments, each amino acid that comprises the peptide moiety is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, alanine, or a stereoisomers thereof (e.g., isoaspartic acid and isoglutamic acid).

In some embodiments, the peptide moiety comprises a monopeptide, a dipeptide, tripeptide, tetrapeptide, or pentapeptide.

In some embodiments, the peptide moiety contains at least about five amino acids (e.g., 5, 6, 7, 8, 9, or 10 amino acids).

In some embodiments, the peptide moiety contains at most about ten amino acids.

In some embodiments, the peptide moiety comprises a pentapeptide.

In some embodiments, each amino acid that comprises the peptide moiety is independently glycine, serine, glutamic acid, lysine, aspartic acid and cysteine.

In some embodiments, the peptide moiety comprises at least four glycines and at least one serine, e.g., (glycine)$_4$ and serine wherein the serine is at any position along the peptide chain, such as, for example, (serine)-(glycine)$_4$; (glycine)-(serine)-(glycine)$_3$; (glycine)$_2$-(serine)-(glycine)$_2$; (glycine)$_3$-(serine)-(glycine); or (glycine)$_4$-(serine).

In some embodiments, the peptide moiety comprises (glycine)$_4$-(serine) or (serine)-(glycine)$_4$.

In some embodiments, the peptide moiety comprises at least four glycines and at least one glutamic acid e.g., (glycine)$_4$ and glutamic acid wherein the glutamic acid is at any position along the peptide chain, such as, for example, (glutamic acid)-(glycine; (glycine)-(glutamic acid)-(glycine)$_3$; (glycine)$_2$-(glutamic acid)-(glycine)$_2$; (glycine)$_3$-(glutamic acid)-(glycine); or (glycine)$_4$-(glutamic acid).

In some embodiments, the peptide moiety comprises (glutamic acid)-(glycine)$_4$; or (glycine)$_4$-(glutamic acid).

In some embodiments, the peptide moiety comprises (β-alanine)-(glycine)$_4$-(serine) wherein the serine is at any position along the peptide chain, such as, for example, (β-alanine)-(serine)-(glycine)$_4$; (β-alanine)-(glycine)-(serine)-(glycine)$_3$; (β-alanine)-(glycine)$_2$-(serine)-(glycine)$_2$; (β-alanine)-(glycine)$_3$-(serine)-(glycine); or (β-alanine)-(glycine)$_4$-(serine).

In some embodiments, the peptide moiety comprises (glycine)$_4$-(serine)-(glutamic acid) wherein the serine is at any position along the peptide chain, such as, for example, (serine)-(glycine)$_4$-(glutamic acid); (glycine)-(serine)-(glycine)$_3$-(glutamic acid); (glycine)$_2$-(serine)-(glycine)$_2$-(glutamic acid); (glycine)$_3$-(serine)-(glycine)-(glutamic acid); or (glycine)$_4$-(serine)-(glutamic acid). In another embodiment, the peptide moiety comprises (β-alanine)-(glycine)$_4$-(serine)-(glutamic acid) wherein the serine is at any position along the peptide chain, such as, for example, (β-alanine)-(serine)-(glycine)$_4$-(glutamic acid); (β-alanine)-(glycine)-(serine)-(glycine)$_3$-(glutamic acid); (β-alanine)-(glycine)$_2$-(serine)-(glycine)$_2$-(glutamic acid); (β-alanine)-(glycine)$_3$-(serine)-(glycine)-(glutamic acid); or (β-alanine)-(glycine)$_4$-(serine)-(glutamic acid).

In some embodiments, when at least one of hydrophilic groups (T') is a polyalcohol or derivative thereof (e.g., an amino polyalcohol) or a glucosyl-amine or a di-glucosyl-amine or a tri-glucosyl-amine, $M^4$ does not have to comprise a peptide moiety. In some embodiments, $M^4$ comprises one or more of the following:

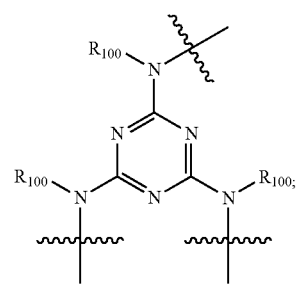

(1)

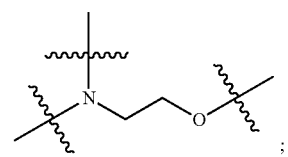

(2)

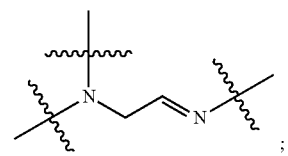

(3)

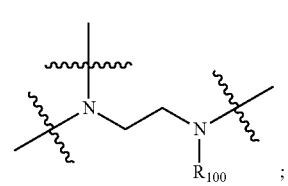

(4)

-continued (5)

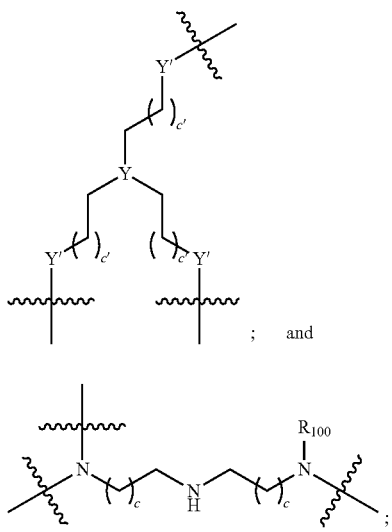

and (6)

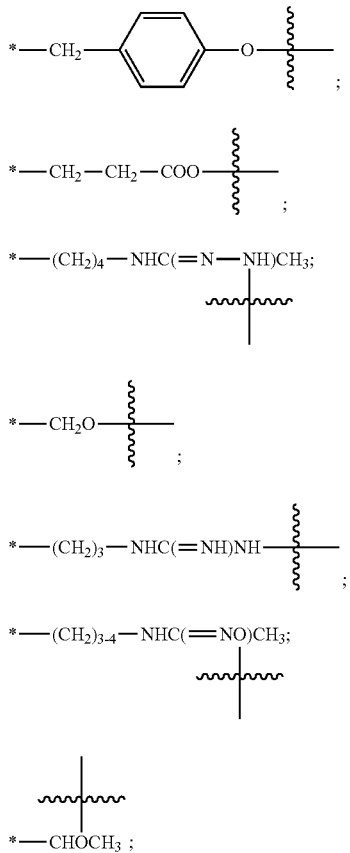

wherein
the wavy line indicates attachment sites within the conjugate (e.g., the antibody-drug conjugate (ADC)) of the disclosure or intermediates thereof; $R_{100}$ and $R_{110}$ and $R_{10}$ are as defined herein.

In some embodiments, $R_{110}$ is:

(1)

*—$CH_2$—⟨phenyl⟩—O—∿ ;

(2)

*—$CH_2$—$CH_2$—COO—∿ ;

(3)

*—$(CH_2)_4$—NHC(=N—NH)$CH_3$; ∿

(4)

*—$CH_2$O—∿ ;

(5)

*—$(CH_2)_3$—NHC(=NH)NH—∿ ;

(6)

*—$(CH_2)_{3-4}$—NHC(=NO)$CH_3$; ∿

(7)

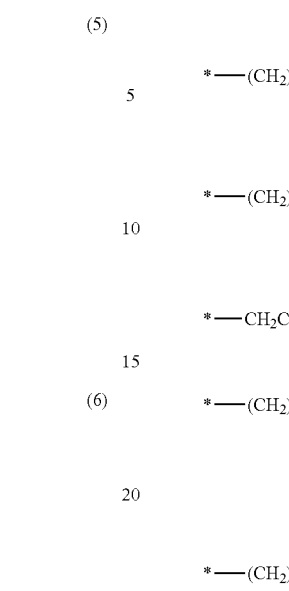

*—CHOCH$_3$ ;

-continued (8)

*—$(CH_2)_3$NH—∿ ;

(9)

*—$(CH_2)_{3-4}$—NHCONH—∿ ;

(10)

*—$CH_2$CONH—∿ ;

(11)

*—$(CH_2)_3$—NHC(=N—NH)$CH_3$; ∿

(12)

*—$(CH_2)_2$CH(OH)$CH_2$NH—∿ ;

(13)

*—$CH_2$COO—∿ ;

(14)

*—$(CH_2)_2$CH(O)$CH_2$NH$_2$; ∿

(15)

*—$(CH_2)_2$CONH—∿ ;

(16)

*—$(CH_2)_3$—NHCH=N—NH—∿ ;

(17)

*—$(CH_2)_3$—NHCH=N—O—∿ ;

(18)

*—$(CH_2)_4$—NHC(=NH)NH—∿ ;

(19)

*—$(CH_2)_{1-4}$NH—∿ ;

(20)

*—$(CH_2)_{1-4}$S—∿ ;

(21)

*—$(C(CH_3)_2$S—∿ ;

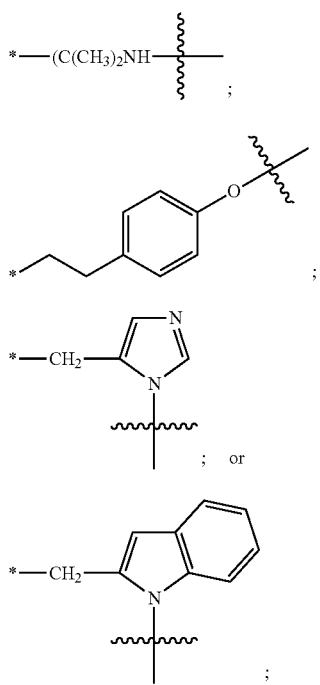

wherein the asterisk indicates attachment to the carbon labeled x and the wavy line indicates one of the three attachment sites.

In some embodiments, $R_{100}$ is independently selected from hydrogen and $CH_3$.

In some embodiments, Y is N.

In some embodiments, Y is CH.

In some embodiments, $R_{100}$ is H or $CH_3$.

In some embodiments, each c' is independently an integer from 1 to 3.

In some embodiments, $R_{110}$ is not

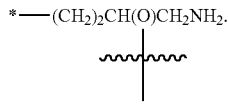

$L^D$ and $W^D$

In some embodiments, each occurrence of $L^D$ is independently a divalent linker moiety connecting D to $M^A$ and comprises at least one cleavable bond such that when the bond is broken, D is released in an active form for its intended therapeutic effect.

In some embodiments, $L^D$ is a component of the Releasable Assembly Unit. In other embodiments, $L^D$ is the Releasable Assembly Unit.

In some embodiments, $L^D$ comprises one cleavable bond.

In some embodiments, $L^D$ comprises multiple cleavage sites or bonds.

Functional groups for forming a cleavable bond can include, for example, sulfhydryl groups to form disulfide bonds, aldehyde, ketone, or hydrazine groups to form hydrazone bonds, hydroxylamine groups to form oxime bonds, carboxylic or amino groups to form peptide bonds, carboxylic or hydroxy groups to form ester bonds, and sugars to form glycosidic bonds. In some embodiments, $L^D$ comprises a disulfide bond that is cleavable through disulfide exchange, an acid-labile bond that is cleavable at acidic pH, and/or bonds that are cleavable by hydrolases (e.g., peptidases, esterases, and glucuronidases). In some embodiments, $L^D$ comprises a carbamate bond (i.e., —O—C(O)—NR—, in which R is H or alkyl or the like).

The structure and sequence of the cleavable bond(s) in $L^D$ can be such that the bond(s) is cleaved by the action of enzymes present at the target site. In other embodiments, the cleavable bond(s) can be cleavable by other mechanisms.

In some embodiments, the cleavable bond(s) can be enzymatically cleaved by one or more enzymes, including a tumor-associated protease, to liberate the Drug moiety or D, which in one embodiment is protonated in vivo upon release to provide a Drug moiety or D.

In certain embodiments, $L^D$ can comprise one or more amino acids. In some embodiments, each amino acid in $L^D$ can be natural or unnatural and/or a D- or L-isomer provided that there is a cleavable bond. In some embodiments, $L^D$ comprising an alpha, beta, or gamma amino acid that can be natural or non-natural. In some embodiments, $L^D$ comprises 1 to 12 (e.g., 1 to 6, or 1 to 4, or 1 to 3, or 1, 2, 3, 4, 5, 6, 7, 8, 9, 10, 11, or 12) amino acids in contiguous sequence. In certain embodiments, $L^D$ can comprise only natural amino acids. In other embodiments, $L^D$ can comprise only non-natural amino acids. In some embodiments, $L^D$ can comprise a natural amino acid linked to a non-natural amino acid. In some embodiments, $L^D$ can comprise a natural amino acid linked to a D-isomer of a natural amino acid. An exemplary $L^D$ comprises a dipeptide such as -Val-Cit-, -Phe-Lys-, -Ala-Ala- or -Val-Ala-.

In some embodiments, $L^D$ comprises, a monopeptide, a dipeptide, a tripeptide, a tetrapeptide, a pentapeptide, a hexapeptide, a heptapeptide, an octapeptide, a nonapeptide, a decapeptide, an undecapeptide or a dodecapeptide unit.

In some embodiments, $L^D$ comprises a peptide (e.g., of 1 to 12 amino acids), which is conjugated directly to the drug moiety. In some such embodiments, the peptide is a single amino acid or a dipeptide.

In some embodiments, each amino acid in $L^D$ is independently selected from alanine, -alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In some embodiments, each amino acid is independently selected from alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, citrulline and selenocysteine.

In some embodiments, each amino acid is independently selected from the group consisting of alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, citrulline and derivatives thereof.

In some embodiments, each amino acid is selected from the proteinogenic or the non-proteinogenic amino acids.

In some embodiments, each amino acid in $L^D$ can be independently selected from L- or D-isomers of the following amino acids: alanine, β-alanine, arginine, aspartic acid, asparagine, cysteine, histidine, glycine, glutamic acid, glutamine, phenylalanine, lysine, leucine, methionine, serine, tyrosine, threonine, tryptophan, proline, ornithine, penicillamine, aminoalkynoic acid, aminoalkanedioic acid, heterocyclo-carboxylic acid, citrulline, statine, diaminoalkanoic acid, valine, citrulline or derivatives thereof.

In some embodiments, each amino acid in $L^D$ is independently cysteine, homocysteine, penicillamine, ornithine, lysine, serine, threonine, glycine, glutamine, alanine, aspartic acid, glutamic acid, selenocysteine, proline, glycine, isoleucine, leucine, methionine, valine, citrulline or alanine.

In some embodiments, each amino acid in $L^D$ is independently selected from L-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline or valine.

In some embodiments, each amino acid in $L^D$ is independently selected from D-isomers of the following amino acids: alanine, β-alanine, arginine, aspartic acid, asparagine, histidine, glycine, glutamic acid, glutamine, phenylalanine, lysine, leucine, serine, tyrosine, threonine, isoleucine, tryptophan, citrulline or valine.

In some embodiments, each amino acid in $L^D$ is alanine, β-alanine, glycine, glutamic acid, isoglutamic acid, isoaspartic acid, valine, citrulline or aspartic acid.

In one embodiment, $L^D$ comprises β-alanine.

In another embodiment, $L^D$ comprises (β-alanine)-(alanine).

In another embodiment, $L^D$ comprises (β-alanine)-(glutamic acid).

In another embodiment, $L^D$ comprises (β-alanine)-(isoglutamic acid).

In another embodiment, $L^D$ comprises (β-alanine)-(aspartic acid).

In another embodiment, $L^D$ comprises (β-alanine)-(isoaspartic acid).

In another embodiment, $L^D$ comprises (β-alanine)-(valine).

In another embodiment, $L^D$ comprises (β-alanine)-(valine)-(alanine).

In another embodiment, $L^D$ comprises (β-alanine)-(alanine)-(alanine).

In another embodiment, $L^D$ comprises (β-alanine)-(valine)-(citruline).

In another embodiment, $L^D$ comprises (β-alanine)-(valine)-(lys).

In another embodiment, $L^D$ comprises (β-alanine)-(lys).

In another embodiment, $L^D$ comprises (β-alanine)-(gly)-(gly)-(gly).

In some embodiments, $L^D$ comprises:
(i) (β-alanine)-(alanine)-(alanine); or
(ii) (β-alanine)-(valine)-(alanine).

In some embodiments, $L^D$ comprises a carbamate bond in addition to one or more amino acids.

In some embodiments, $L^D$ can be designed and optimized in their selectivity for enzymatic cleavage by a particular enzyme, e.g., a tumor-associated protease.

In some embodiments, $L^D$ comprises a bond whose cleavage is catalyzed by cathepsin B, C and D, or a plasmin protease.

In some embodiments, $L^D$ comprises a sugar cleavage site. In some such embodiments, $L^D$ comprises a sugar moiety (Su) linked via an oxygen glycosidic bond to a self-immolative group. A "self-immolative group" can be a tri-functional chemical moiety that is capable of covalently linking together three spaced chemical moieties (i.e., the sugar moiety (via a glycosidic bond), a drug moiety (directly or indirectly), and $M^A$ (directly or indirectly). The glycosidic bond will be one that can be cleaved at the target site to initiate a self-immolative reaction sequence that leads to a release of the drug.

In some embodiments, $L^D$ comprises a sugar moiety (Su) linked via a glycoside bond (—O'—) to a self-immolative group (K) of the formula:

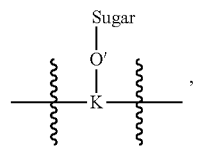

wherein the self-immolative group (K) forms a covalent bond with the drug moiety (directly or indirectly) and also forms a covalent bond with $M^A$ (directly or indirectly). Examples of self-immolative groups are described in, e.g., WO 2015/057699, the contents of which are hereby incorporated by reference in its entirety.

In some embodiments, when not connected to or prior to connecting to the PBD drug moiety, $L^D$ comprises a functional a functional group $W^D$. Each $W^D$ independently can be a functional group as listed for $W^P$. In some embodiments, each W independently is

(1)

(2)

(3)

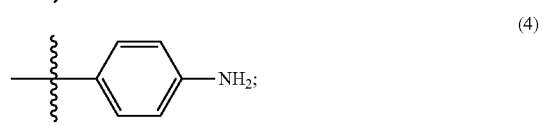

(4)

(5)

(6)

(7)

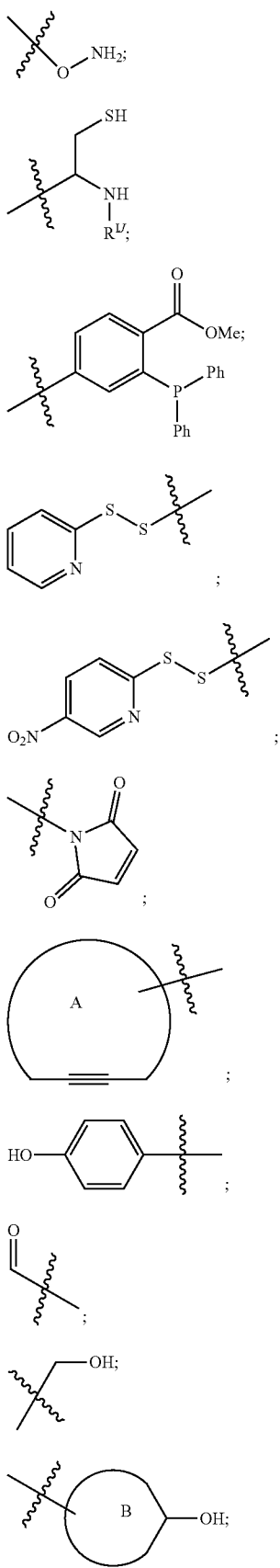
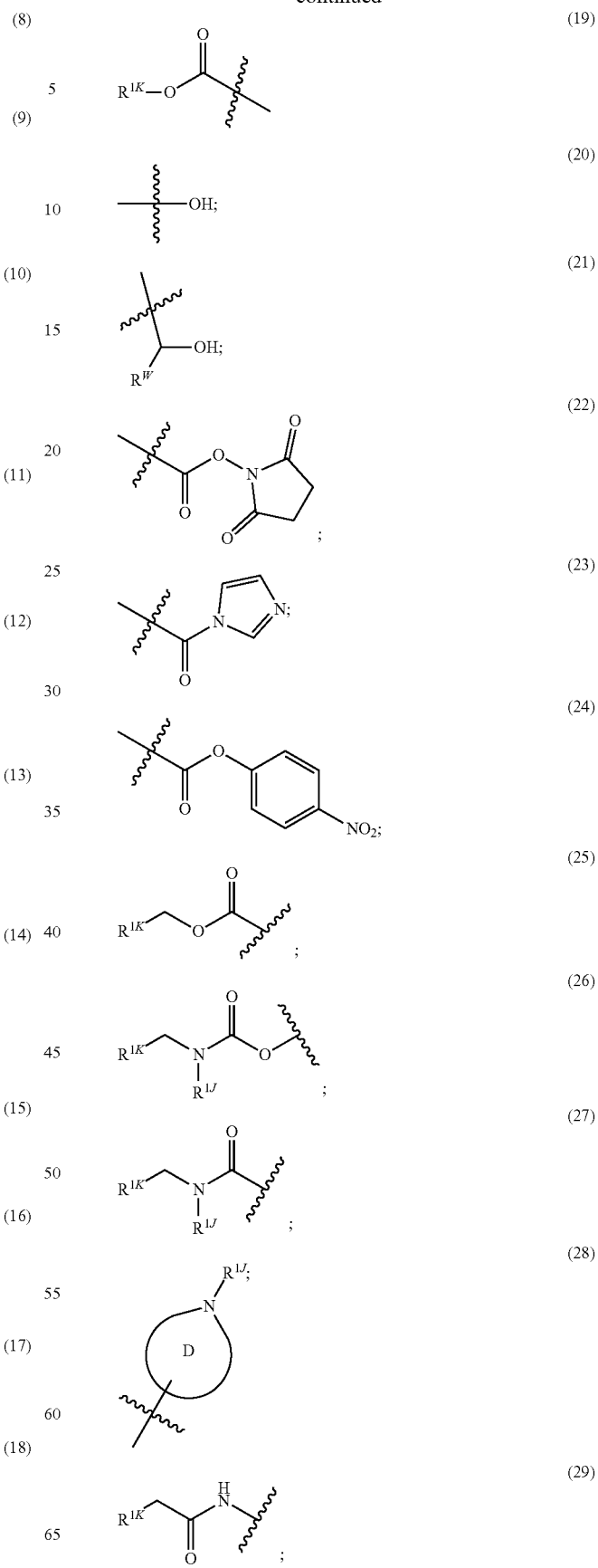

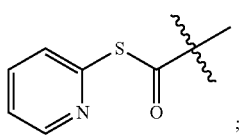

(30)

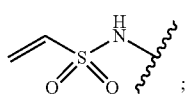

(31)

—COOH;  or (32)

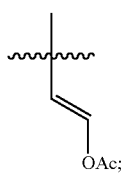

(33)

in which $R^{1A}$ is a sulfur protecting group, each of ring A and B, independently, is cycloalkyl or heterocycloalkyl, $R^W$ is an aliphatic, heteroaliphatic, carbocyclic or heterocycloalkyl moiety; ring D is heterocycloalkyl; $R^{1J}$ is hydrogen or an aliphatic, heteroaliphatic, carbocyclic, or heterocycloalkyl moiety; and $R^{1K}$ is a leaving group (e.g., halide or RC(O)— in which R is hydrogen or an aliphatic, heteroaliphatic, carbocyclic, or heterocycloalkyl moiety).

In some embodiments, $W^D$ is

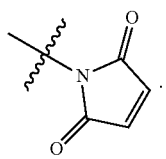

In some embodiments, $W^D$ is

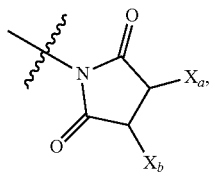

wherein one of $X_a$ and $X_b$ is H and the other is a maleimido blocking moiety.

In some embodiments, $W^D$ is

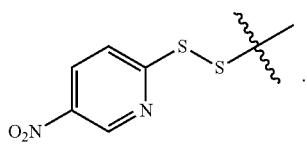 [SMILES: *SSc1ccc([N+](=O)[O-])cn1]

T'

In some embodiments, the hydrophilic group (T') included in the conjugates or scaffolds of the disclosure is a water-soluble and substantially non-antigenic polymer. Examples of the hydrophilic group, include, but are not limited to, polyalcohols, polyethers, polyanions, polycations, polyphosphoric acids, polyamines, polysaccharides, polyhydroxy compounds, polylysines, and derivatives thereof. One end of the hydrophilic group (T') can be functionalized so that it can be covalently attached to the Multifunctional Linker or $M^A$ linker (e.g., to an amino acid in the $M^A$ linker) by means of a non-cleavable linkage or via a cleavable linkage. Functionalization can be, for example, via an amine, thiol, NHS ester, maleimide, alkyne, azide, carbonyl, or other functional group. The other terminus (or termini) of the hydrophilic group (T') will be free and untethered. By "untethered", it is meant that the hydrophilic group (T') will not be attached to another moiety, such as D or a Drug Moiety, Releasable Assembly Unit, or other components of the conjugates or scaffolds of the disclosure. The free and untethered end of the hydrophilic group (T') may include a methoxy, carboxylic acid, alcohol or other suitable functional group. The methoxy, carboxylic acid, alcohol or other suitable functional group acts as a cap for the terminus or termini of the hydrophilic group.

A cleavable linkage refers to a linkage that is not substantially sensitive to cleavage while circulating in the plasma but is sensitive to cleavage in an intracellular or intratumoral environment. A non-cleavable linkage is one that is not substantially sensitive to cleavage in any biological environment. Chemical hydrolysis of a hydrazone, reduction of a disulfide, and enzymatic cleavage of a peptide bond or glycosidic linkage are examples of cleavable linkages. Exemplary attachments of the hydrophilic group (T') are via amide linkages, ether linkages, ester linkages, hydrazone linkages, oxime linkages, disulfide linkages, peptide linkages or triazole linkages. In some embodiments, the attachment of the hydrophilic group (T') to the Multifunctional Linker or $M^A$ linker (e.g., to an amino acid in the $M^A$ linker) is via an amide linkage.

For those embodiments wherein the conjugate or scaffold of the disclosure comprises more than one hydrophilic groups, the multiple hydrophilic groups may be the same or different chemical moieties (e.g., hydrophilic groups of different molecular weight, number of subunits, or chemical structure). The multiple hydrophilic groups can be attached to the Multifunctional Linker or $M^A$ linker at a single attachment site or different sites.

The addition of the hydrophilic group (T') may have two potential impacts upon the pharmacokinetics of the resulting conjugate. The desired impact is the decrease in clearance (and consequent in increase in exposure) that arises from the reduction in non-specific interactions induced by the exposed hydrophobic elements of the drug or drug-linker. The second impact is undesired impact and is the decrease in volume and rate of distribution that may arise from the increase in the molecular weight of the conjugate. Increasing the molecular weight of the hydrophilic group (T') increases the hydrodynamic radius of a conjugate, resulting in decreased diffusivity that may diminish the ability of the conjugate to penetrate into a tumor. Because of these two competing pharmacokinetic effects, it is desirable to use a hydrophilic group (T') that is sufficiently large to decrease the conjugate clearance thus increasing plasma exposure, but not so large as to greatly diminish its diffusivity, which may reduce the ability of the conjugate to reach the intended target cell population.

In some embodiments, the hydrophilic group, includes, but is not limited to, a sugar alcohol (also known as polyalcohol, polyhydric alcohol, alditol or glycitol, such as inositol, glycerol, erythritol, threitol, arabitol, xylitol, ribitol, galactitol, mannitol, sorbitol, and the like) or a derivative thereof (e.g., amino polyalcohol), carbohydrate (e.g., a saccharide), a polyvinyl alcohol, a carbohydrate-based polymer (e.g., dextrans), a hydroxypropylmethacrylamide (HPMA), a polyalkylene oxide, and/or a copolymer thereof.

In some embodiments, the hydrophilic group (T') comprises a plurality of hydroxyl ("—OH") groups, such as moieties that incorporate monosaccharides, oligosaccharides, polysaccharides, and the like. In yet another embodiment the hydrophilic group (T') comprises a plurality of —(CR$_{58}$OH)— groups, wherein R$_{58}$ is hydrogen or C$_{1-8}$ alkyl.

In some embodiments, the hydrophilic group (T') comprises one or more of the following fragments of the formula:

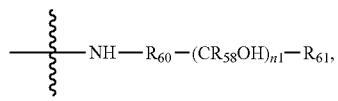

in which n$_1$ is an integer from 0 to about 6;

each R$_{58}$ is independently hydrogen or C$_{1-8}$ alkyl;

R$_{60}$ is a bond, a C$_{1-6}$ alkyl linker, or —CHR$_{59}$— in which R$_{59}$ is H, alkyl, cycloalkyl, or arylalkyl;

R$_{61}$ is CH$_2$OR$_{62}$, COOR$_{62}$, —(CH$_2$)$_{n2}$COOR$_{62}$, or a heterocycloalkyl substituted with one or more hydroxyl;

R$_{62}$ is H or C$_{1-8}$ alkyl; and n$_2$ is an integer from 1 to about 5.

In some embodiments, R$_{58}$ is hydrogen, R$_{60}$ is a bond or a C$_{1-6}$ alkyl linker, n$_1$ is an integer from 1 to about 6, and R$_{61}$ is CH$_2$OH or COOH. In some embodiments, R$_{58}$ is hydrogen, R$_{60}$ is —CHR$_{59}$—, n$_1$ is 0, and R$_{61}$ is a heterocycloalkyl substituted with one or more hydroxyl, e.g., a monosaccharide.

In some embodiments, the hydrophilic group (T') comprises a glucosyl-amine, a diamine or a tri-amine.

In some embodiments, the hydrophilic group (T') comprises one or more of the following fragments or a stereoisomer thereof:

(1)
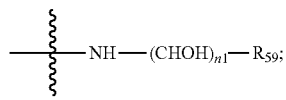

(2)
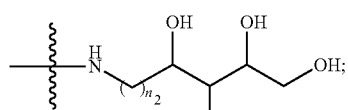

(3)
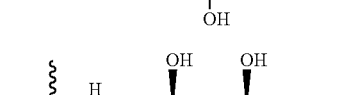

(4)
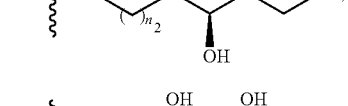

(5)
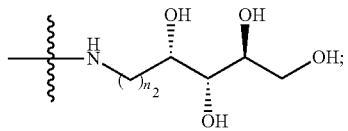

(6)
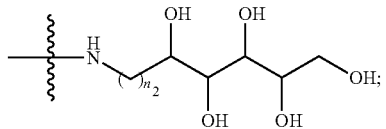

(7)
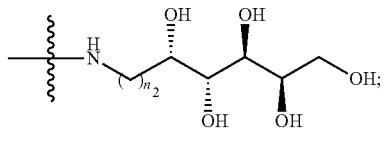

(8)
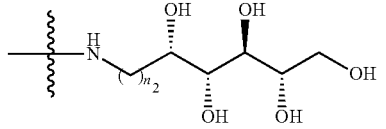

(9)
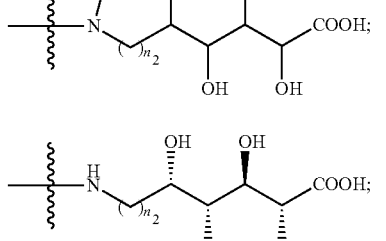

(10)
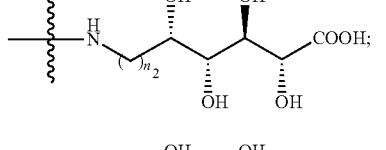

(11)
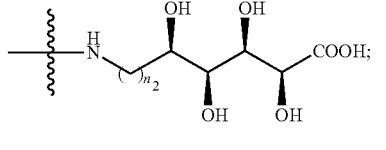

(12)
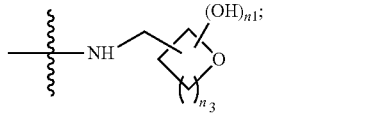

(13)
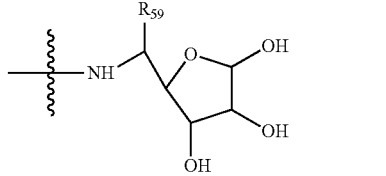

(14)
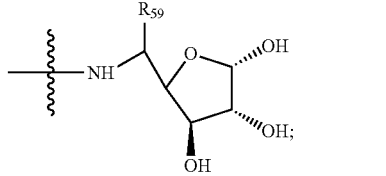

-continued

(15)
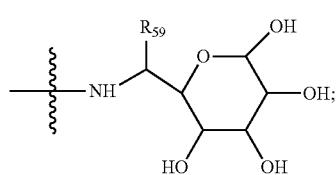

(16)
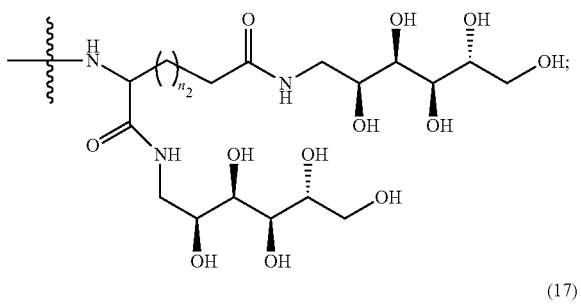

(17)
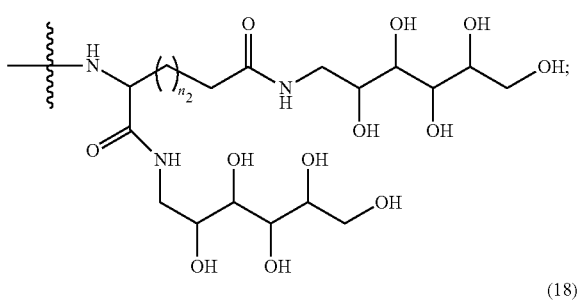

(18)
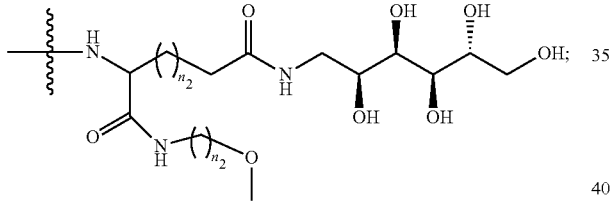

(19)
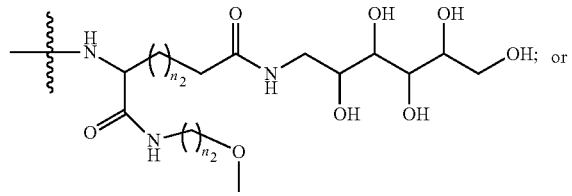

(20)
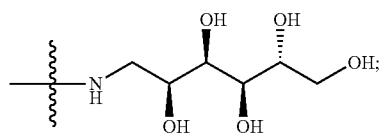

wherein:
$R_{59}$ is H, alkyl, cycloalkyl, or arylalkyl;
$n_1$ is an integer from 1 to about 6;
$n_2$ is an integer from 1 to about 5; and
$n_3$ is an integer from about 1 to about 3.

It is understood that all stereochemical forms of the hydrophilic groups are contemplated herein. In some embodiments, in the above formula, the hydrophilic group (T') may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, one or more of the following features are contemplated for the hydrophilic groups when applicable:

In some embodiments, $n_3$ is 2 or 3.
In some embodiments, $n_1$ is 1, 2, or 3.
In some embodiments, $n_2$ is 1.
In some embodiments, $R_{59}$ is hydrogen.
In some embodiments, the hydrophilic group (T') comprises:

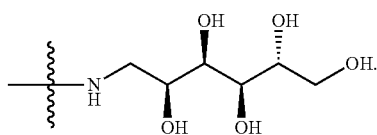 [SMILES: *NC[C@H](O)[C@@H](O)[C@H](O)[C@H](O)CO]

In some embodiments, the hydrophilic group (T') comprises:

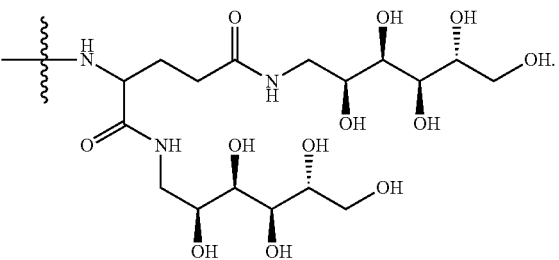 [SMILES: *NC(CCC(=O)NC[C@H](O)[C@@H](O)[C@H](O)[C@H](O)CO)C(=O)NC[C@H](O)[C@@H](O)[C@H](O)[C@H](O)CO]

In some embodiments, the hydrophilic group (T') comprises:

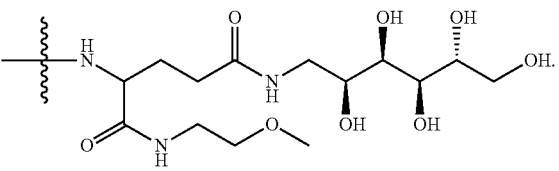 [SMILES: *NC(CCC(=O)NC[C@H](O)[C@@H](O)[C@H](O)[C@H](O)CO)C(=O)NCCOC]

In some embodiments, the hydrophilic group (T') comprises

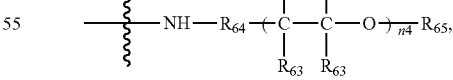

in which
$n_4$ is an integer from 1 to about 25;
each $R_{63}$ is independently hydrogen or $C_{1-8}$ alkyl;
$R_{64}$ is a bond or a $C_{1-8}$ alkyl linker;
$R_{65}$ is H, $C_{1-8}$ alkyl, $-(CH_2)_{n2}COOR_{62}$, or $-(CH_2)_{n2}COR_{66}$;
$R_{62}$ is H or $C_{1-8}$ alkyl;

$R_{66}$ is

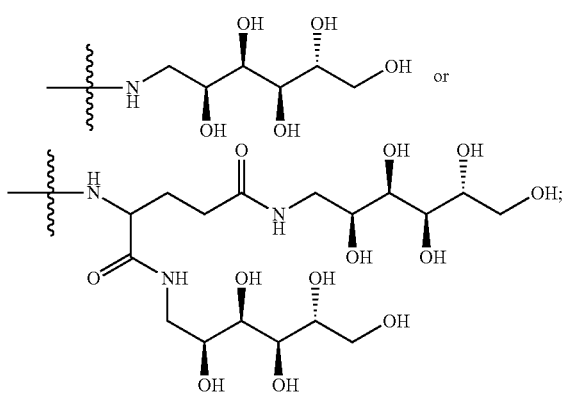

and $n_2$ is an integer from 1 to about 5.

In some embodiments, the hydrophilic group (T') comprises:

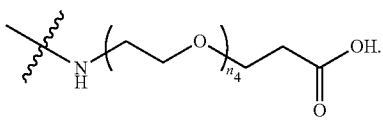

In some embodiments, $n_4$ is an integer from about 2 to about 20, from about 4 to about 16, from about 6 to about 12, from about 8 to about 12.

In some embodiments, $n_4$ is 6, 7, 8, 9, 10, 11, or 12.

In some embodiments, $n_4$ is 8 or 12.

In some embodiments, the hydrophilic group (T') comprises:

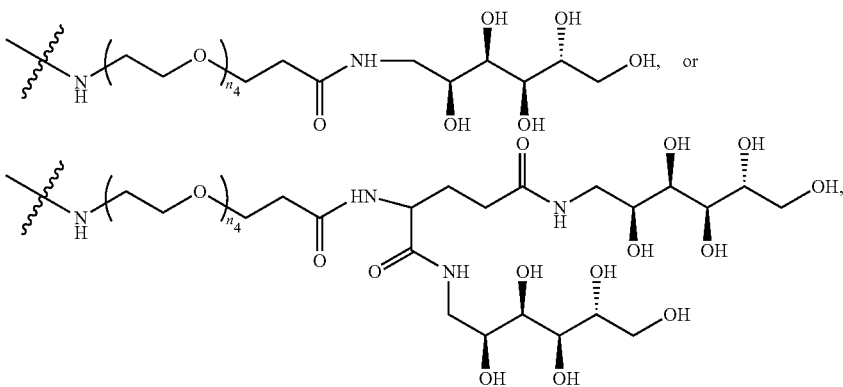

in which $n_4$ is an integer from about 2 to about 20, from about 4 to about 16, from about 6 to about 12, from about 8 to about 12.

In some embodiments, $n_4$ is 6, 7, 8, 9, 10, 11, or 12.

In some embodiments, $n_4$ is 8 or 1

In some embodiments, the hydrophilic group (T') comprises a polyether, e.g., a polyalkylene glycol (PAO). PAO includes but is not limited to, polymers of lower alkylene oxides, in particular polymers of ethylene oxide, such as, for example, propylene oxide, polypropylene glycols, polyethylene glycol (PEG), polyoxyethylenated polyols, copolymers thereof and block copolymers thereof. In other embodiments the polyalkylene glycol is a polyethylene glycol (PEG) including, but not limited to, polydisperse PEG, monodisperse PEG and discrete PEG. Polydisperse PEGs are a heterogeneous mixture of sizes and molecular weights whereas monodisperse PEGs are typically purified from heterogeneous mixtures and are therefore provide a single chain length and molecular weight. In another embodiment, the PEG units are discrete PEGs provide a single molecule with defined and specified chain length. In some embodiments, the polyethylene glycol is mPEG.

In some embodiments, the hydrophilic group (T') comprises a PEG unit which comprises one or multiple polyethylene glycol chains. The polyethylene glycol chains can be linked together, for example, in a linear, branched or star shaped configuration. The PEG unit, in addition to comprising repeating polyethylene glycol subunits, may also contain non-PEG material (e.g., to facilitate coupling of multiple PEG chains to each other or to facilitate coupling to the amino acid). Non-PEG material refers to the atoms in the PEG chain that are not part of the repeating —$CH_2CH_2O$— subunits. In one embodiment, the PEG chain can comprise two monomeric PEG chains linked to each other via non-PEG elements. In another embodiment, the PEG Unit can comprise two linear PEG chains attached to a central core that is attached to the amino acid (i.e., the PEG unit itself is branched).

The PEG unit may be covalently bound to the Multifunctional Linker or $M^4$ linker (e.g., to an amino acid in the $M^4$ linker) via a reactive group. Reactive groups are those to which an activated PEG molecule may be bound (e.g., a free amino or carboxyl group). For example, N-terminal amino acids and lysines (K) have a free amino group; and C-terminal amino acid residues have a free carboxyl group. Sulfhydryl groups (e.g., as found on cysteine residues) may also be used as a reactive group for attaching PEG.

In some embodiments, the PEG unit may be attached to the Multifunctional Linker or $M^4$ linker (e.g., to an amino acid in the $M^4$ linker) by using methoxylated PEG ("mPEG") having different reactive moieties, including, but not limited to, succinimidyl succinate (SS), succinimidyl carbonate (SC), mPEG-imidate, para-nitrophenylcarbonate (NPC), succinimidyl propionate (SPA), and cyanuric chloride. Examples of mPEGs include, but are not limited to, mPEG-succinimidyl succinate (mPEG-SS), $mPEG_2$-succinimidyl succinate ($mPEG_2$-SS), mPEG-succinimidyl carbonate (mPEG-SC), $mPEG_2$-succinimidyl carbonate ($mPEG_2$-SC), mPEG-imidate, mPEG-para-nitrophenylcarbonate (mPEG-NPC), mPEG-imidate, $mPEG_2$-para-nitrophenylcarbonate (mPEG$_2$-NPC), mPEG-succinimidyl propionate (mPEG-SPA), mPEG$_2$-succinimidyl propionate (mPEG$_2$-SPA), mPEG-N-hydroxy-succinimide (mPEG-NHS), mPEG$_2$-N-hydroxy-succinimide (mPEG-NHS), mPEG$_2$-cyanuric chloride, mPEG$_2$-cyanuric chloride, mPEG$_2$-Lysinol-NPC, and mPEG$_2$-Lys-NHS. A wide variety of PEG species can be used, and substantially any suitable reactive PEG reagent can be used. In some embodiments, the reactive PEG reagent will result in formation of a carbamate or amide bond upon attachment to the Multifunctional Linker or M$^4$ linker (e.g., to an amino acid in the M$^4$ linker). The reactive PEG reagents include, but are not limited to, mPEG$_2$-N-hydroxy-succinimide (mPEG$_2$-NHS), bifunctional PEG propionaldehyde (mPEG$_2$-ALD), multi-Arm PEG, maleimide-containing PEG (mPEG(MAL)$_2$, mPEG$_2$(MAL)), mPEG-NH$_2$, mPEG-succinimidyl propionate (mPEG-SPA), succinimide of mPEG butanoate acid (mPEG-SBA), mPEG-thioesters, mPEG-Double Esters, mPEG-BTC, mPEG-ButyrALD, mPEG-acetaldehyde diethyl acetal (mPEG-ACET), heterofunctional PEGs (e.g., NH$_2$-PEG-COOH, Boc-PEG-NHS, Fmoc-PEG-NHS, NHS-PEG-vinylsulfone (NHS-PEG-VS), or NHS-PEG-MAL), PEG acrylates (ACRL-PEG-NHS), PEG-phospholipids (e.g., mPEG-DSPE), multi-armed PEGs of the SUNBRITE™ series including the glycerine-based PEGs activated by a chemistry chosen by those skilled in the art, any SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In some such embodiments, the PEG unit comprises no more than about 72 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In some embodiments, the PEG unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, or at least 18 subunits.

In some embodiments, the PEG unit comprises at least 6 subunits, at least 7 subunits, at least 8 subunits, at least 9 subunits, at least 10 subunits, at least 11 subunits, or at least 12 subunits.

In some embodiments, the PEG unit comprises at least 8 subunits, at least 9 subunits, at least 10 subunits, at least 11 subunits, or at least 12 subunits.

In some embodiments, the PEG unit comprises at least 6 subunits, at least 7 subunits, or at least 8 subunits.

In some embodiments, the PEG unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In another embodiment, the PEG unit comprises a combined total of at least 6 subunits, at least 8, at least 10 subunits, or at least 12 subunits. In some such embodiments, the PEG unit comprises no more than a combined total of about 72 subunits, preferably no more than a combined total of about 36 subunits.

In some embodiments, the PEG unit comprises a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or from 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In some embodiments, the PEG unit comprises one or more linear PEG chains having a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In some embodiments, the PEG unit is a derivatized linear single PEG chain having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In some embodiments, the PEG unit is a derivatized linear single PEG chain having from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In some embodiments, the PEG unit is a derivatized linear single PEG chain having from 2 to 72, 2 to 60, 2 to 48, 2 to 36 or 2 to 24 subunits, from 2 to 72, 2 to 60, 2 to 48, 2 to 36 or 2 to 24 subunits, from 3 to 72, 3 to 60, 3 to 48, 3 to 36 or 3 to 24 subunits, from 3 to 72, 3 to 60, 3 to 48, 3 to 36 or 3 to 24 subunits, from 4 to 72, 4 to 60, 4 to 48, 4 to 36 or 4 to 24 subunits, from 5 to 72, 5 to 60, 5 to 48, 5 to 36 or 5 to 24 subunits.

In some embodiments, a linear PEG unit is:

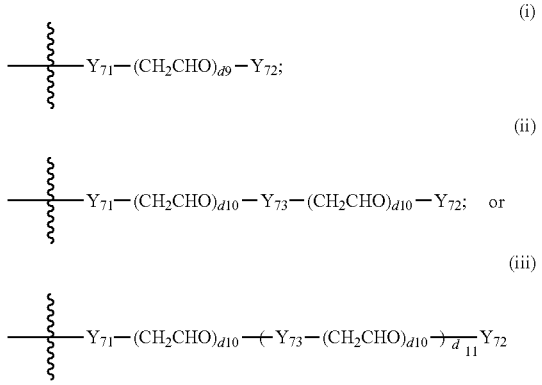

wherein;

the wavy line indicates site of attachment to the Multifunctional Linker or $M^A$ linker (e.g., to an amino acid in the $M^A$ linker);

$Y_{71}$ is a PEG attachment unit;

$Y_{72}$ is a PEG capping unit;

$Y_{73}$ is an PEG coupling unit (i.e., for coupling multiple PEG subunit chains together);

$d_9$ is an integer from 2 to 72, preferably from 4 to 72, more preferably from 6 to 72, from 8 to 72, from 10 to 72, from 12 to 72 or from 6 to 24;

each $d_{10}$ is independently an integer from 1 to 72.

$d_{11}$ is an integer from 2 to 5.

In some embodiments, there are at least 6, preferably at least 8, at least 10, or at least 12 PEG subunits in the PEG unit. In some embodiments, there are no more than 72 or 36 PEG subunits in the PEG unit.

In some embodiments, $d_9$ is 8 or about 8, 12 or about 12, 24 or about 24.

In some embodiments, each $Y_{72}$ is independently —$C_{1-10}$ alkyl, —$C_{2-10}$ alkyl-$CO_2H$, —$C_{2-10}$ alkyl-OH, —$C_{2-10}$ alkyl-$NH_2$, —$C_{2-10}$ alkyl-NH($C_{1-3}$ alkyl), or $C_{2-10}$ alkyl-N($C_{1-3}$ alkyl)$_2$.

In some embodiments, $Y_{72}$ is —$C_{1-10}$ alkyl, —$C_{2-10}$ alkyl-$CO_2H$, —$C_{2-10}$ alkyl-OH, or —$C_{2-10}$ alkyl-$NH_2$.

The PEG coupling unit is part of the PEG unit and is non-PEG material that acts to connect two or more chains of repeating $CH_2CH_2O$— subunits. In some embodiments, the PEG coupling unit $Y_{73}$ is —$C_{2-10}$ alkyl-C(O)—NH—, —$C_{2-10}$ alkyl-NH—C(O)—, —$C_{2-10}$ alkyl-NH—, —$C_{2-10}$ alkyl-C(O)—, —$C_{2-10}$ alkyl-O— or —$C_{2-4}$ alkyl-S—.

In some embodiments, each $Y_{73}$ is independently —$C_{1-10}$ alkyl-C(O)—NH—, —$C_{1-10}$ alkyl-NH—C(O)—, —$C_{2-10}$ alkyl-NH—, —$C_{2-10}$ alkyl-O—, —$C_{1-10}$ alkyl-S—, or —$C_{1-10}$ alkyl-NH—.

The PEG attachment unit is part of the PEG unit and acts to link the PEG unit to the Multifunctional Linker or $M^A$ linker (e.g., to an amino acid in the $M^A$ linker). In some embodiments, the amino acid has a functional group that forms a bond with the PEG Unit. Functional groups for attachment of the PEG unit to the amino acid include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG unit can be attached to the amino acid, for example, via a disulfide, thioether, hydrazone, oxime, peptide, ester, sulfonamide, carbamate, or amide bond. Typically, the reaction for attaching the PEG unit can be a cycloaddition, addition, addition/elimination or substitution reaction, or a combination thereof when applicable.

In some embodiments, the PEG attachment unit $Y_{71}$ is a bond, —C(O)—, —O—, —S—, —S(O)—, —S(O)$_2$—, —NR$_5$—, —C(O)O—, —C(O)—$C_{1-10}$ alkyl, —C(O)—$C_{1-10}$ alkyl-O—, —C(O)—$C_{1-10}$ alkyl-$CO_2$—, —C(O)—$C_{1-10}$ alkyl-NR$_5$—, —C(O)—$C_{1-10}$ alkyl-S—, —C(O)—$C_{1-10}$ alkyl-C(O)—NR$_5$—, —C(O)—$C_{1-10}$ alkyl-NR$_5$—C(O)—, —$C_{1-10}$ alkyl, —$C_{1-10}$ alkyl-O—, —$C_{1-10}$ alkyl-$CO_2$—, —$C_{1-10}$ alkyl-NR$_5$—, —$C_{1-10}$ alkyl-S—, —$C_{1-10}$ alkyl-C(O)—NR$_5$—, —$C_{1-10}$ alkyl-NR$_5$—C(O)—, —$CH_2CH_2SO_2$—$C_{1-10}$ alkyl-, —$CH_2C(O)$—$C_{1-10}$ alkyl-, =N—(O or N)—$C_{1-10}$ alkyl-O—, =N—(O or N)—$C_{1-10}$ alkyl-NR$_5$—, =N—(O or N)—$C_{1-10}$ alkyl-$CO_2$—, =N—(O or N—$C_{1-10}$-alkyl-S—,

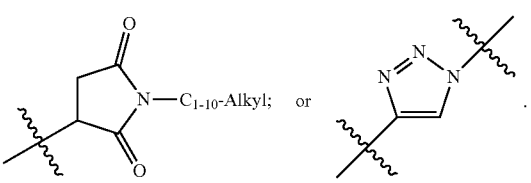

In some embodiments, $Y_{71}$ is —NH—, —C(O)—, a triazole group, —S—, or a maleimido-group such as

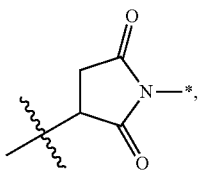

wherein the wavy line indicates attachment to the Multifunctional Linker or $M^A$ linker (e.g., to an amino acid in the $M^A$ linker) and the asterisk indicates the site of attachment within the PEG Unit.

Examples of linear PEG units include, but are not limited to:

(i)

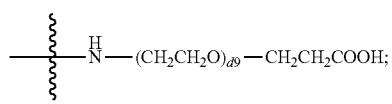

(ii)

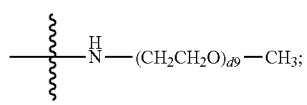

(iii)

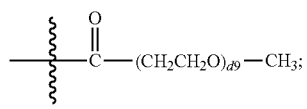

(iv)

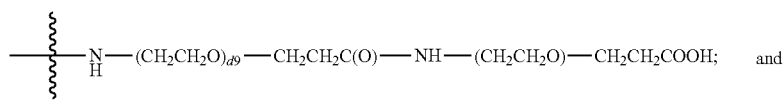 and (v)

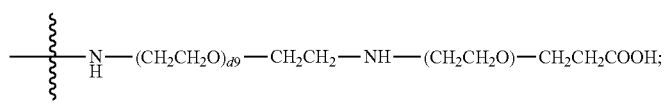

wherein the wavy line indicates site of attachment to the $M^A$ linker (e.g., to an amino acid in the $M^A$ linker), and each $d_9$ is independently an integer from 4 to 24, 6 to 24, 8 to 24, 10 to 24, 12 to 24, 14 to 24, or 16 to 24.

In some embodiments, $d_9$ is about 8, about 12, or about 24.

In some embodiments, the PEG unit is from about 300 daltons to about 5 kilodaltons; from about 300 daltons, to about 4 kilodaltons; from about 300 daltons, to about 3 kilodaltons; from about 300 daltons, to about 2 kilodaltons; or from about 300 daltons, to about 1 kilodalton. In some such aspects, the PEG unit has at least 6 subunits or at least 8, 10 or 12 subunits. In some embodiments, the PEG unit has at least 6 subunits or at least 8, 10 or 12 subunits but no more than 72 subunits, preferably no more than 36 subunits.

Suitable polyethylene glycols may have a free hydroxy group at each end of the polymer molecule, or may have one hydroxy group etherified with a lower alkyl, e.g., a methyl group. Also suitable for the practice of the disclosure are derivatives of polyethylene glycols having esterifiable carboxy groups. Polyethylene glycols are commercially available under the trade name PEG, usually as mixtures of polymers characterized by an average molecular weight. Polyethylene glycols having an average molecular weight from about 300 to about 5000 are preferred, those having an average molecular weight from about 600 to about 1000 being particularly preferred.

Other examples of hydrophilic groups that are suitable for the conjugates, scaffolds, and methods disclosed herein can be found in e.g., U.S. Pat. No. 8,367,065 column 13: U.S. Pat. No. 8,524,696 column 6; WO2015/057699 and WO 2014/062697, the contents of each of which are hereby incorporated by reference in their entireties.

Antibody-Drug Conjugate (ADC) Type II

In some embodiments, the conjugate (e.g., the antibody-drug conjugate (ADC)) of the present disclosure is of Formula (III):

(III)

or pharmaceutically acceptable salt or solvate thereof, wherein:

PBRM denotes a protein based recognition-molecule;

each occurrence of D is independently a PBD drug moiety;

$A^1$ is a stretcher unit;

$a_6$ is an integer 1 or 2;

$L^1$ is a specificity unit;

$s_2$ is an integer from about 0 to about 12;

$L^2$ is a spacer unit;

$y_1$ is an integer from 0 to 2; and $d_{13}$ is an integer from about 1 to about 20.

In some embodiments, the conjugates of Formula (III) include those where each of the moieties defined for one of PBRM, D, $A^1$, $a_6$, $L^1$, $s_2$, $L^2$, $y_1$, and $d_{13}$ can be combined with any of the moieties defined for the others of PBRM, D, $A^1$, $a_6$, $L^1$, $s_2$, $L^2$, $y_1$, and $d_{13}$.

In some embodiments, the conjugate (e.g., the antibody-drug conjugate (ADC)) of the present disclosure is of Formula (IIIa) or (IIIb):

(IIIa)

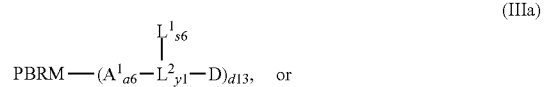

(IIIb)

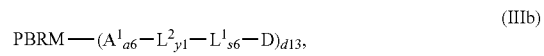

or a pharmaceutically acceptable salt or solvate thereof, wherein:

PBRM denotes a protein based recognition-molecule;

each occurrence of D is independently a PBD drug moiety;

$A^1$ is a stretcher unit linked to the spacer unit $L^2$;

$a_6$ is an integer 1 or 2;

$L^1$ is a specificity unit linked to the spacer unit $L^2$;

$s_6$ is an integer from about 0 to about 12.

$L^2$ is a spacer unit;

$y_1$ is an integer 0, 1 or 2; and $d_{13}$ is an integer from about 1 to about 20.

In some embodiments, the conjugates of any one of Formulae (IIIa)-(IIIb) include those where each of the moieties defined for one of PBRM, D, $A^1$, $a_6$, $L^1$, $s_6$, $L^2$, $y_1$, and $d_{13}$ can be combined with any of the moieties defined for the others of PBRM, D, $A^1$, $a_6$, $L^1$, $s_6$, $L^2$, $y_1$, and $d_{13}$.

In some embodiments, the conjugate (e.g., the antibody-drug conjugate (ADC)) of the present disclosure is of any one of Formulae (IIIc) to (IIIf):

  (IIIc)

  (IIId)

  (IIIe)

  (IIIf)

or a pharmaceutically acceptable salt or solvate thereof, wherein PBRM, $A^1$, $a_6$, $L^1$ $s_2$, $L^2$, $y_1$ D and $d_{13}$ are as defined herein.

In some embodiments, the conjugates of any one of Formulae (IIIc)-(IIIf) include those where each of the moieties defined for one of PBRM, $A^1$, $a_6$, $L^1$ $s_2$, $L^2$, $y_1$, D, and $d_{13}$ can be combined with any of the moieties defined for the others of PBRM, $A^1$, $a_6$, $L^1{}_{s2}$, $L^2$, $y_1$, D, and $d_{13}$.

In some embodiments, the PBRM specifically binds to a target molecule on the surface of a target cell. An exemplary formula is:

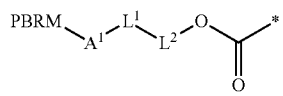

wherein the asterisk indicates the point of attachment to the Drug moiety (D), PRBM is targeting moiety, $L^1$ is a Specificity unit, $A^1$ is a Stretcher unit connecting L to the PBRM, $L^2$ is a Spacer unit, which is a covalent bond, a self-immolative group or together with —OC(=O)— forms a self-immolative group, and $L^2$ is optional. —OC(=O)— may be considered as being part of $L^1$ or $L^2$, as appropriate.

In some embodiments, the PBRM specifically binds to a target molecule on the surface of a target cell. An exemplary formula is:

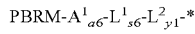

wherein the asterisk indicates the point of attachment to the Drug moiety (D), PBRM is the targeting moiety, $L^1$ is a Specificity unit, $A^1$ is a Stretcher unit connecting L to the PBRM, $L^2$ is a Spacer unit which is a covalent bond or a self-immolative group, and $a_6$ is an integer 1 or 2, $s_6$ is an integer 0, 1 or 2, and $y_1$ is an integer 0, 1 or 2.

In the embodiments above, L can be a cleavable Specificity unit, and may be referred to as a "trigger" that when cleaved activates a self-immolative group (or self-immolative groups) $L^2$, when a self-immolative group(s) is present.

When the Specificity unit $L^1$ is cleaved, or the linkage (i.e., the covalent bond) between $L^1$ and $L^2$ is cleaved, the self-immolative group releases the PBD Drug moiety (D).

In some embodiments, the PBRM specifically binds to a target molecule on the surface of a target cell. An exemplary formula is:

wherein the asterisk indicates the point of attachment to the PBD Drug moiety (D), PBRM is the targeting moiety, $L^1$ is a Specificity unit connected to $L^2$, $A^1$ is a Stretcher unit connecting $L^2$ to the PBRM, $L^2$ is a self-immolative group, and $a_6$ is an integer 1 or 2, $s_6$ is an integer 0, 1 or 2, and $y_1$ is an integer 0, 1 or 2.

In the various embodiments discussed herein, the nature of L and $L^2$ can vary widely. These groups are chosen on the basis of their characteristics, which may be dictated in part, by the conditions at the site to which the conjugate is delivered. Where the Specificity unit Lt is cleavable, the structure and/or sequence of L is selected such that it is cleaved by the action of enzymes present at the target site (e.g., the target cell). $L^1$ units that are cleavable by changes in pH (e.g. acid or base labile), temperature or upon irradiation (e.g. photolabile) may also be used. $L^1$ units that are cleavable under reducing or oxidizing conditions may also find use in the conjugates of the present disclosure.

In some embodiments, $L^1$ may comprise one amino acid or a contiguous sequence of amino acids. The amino acid sequence may be the target substrate for an enzyme.

In some embodiments, $L^1$ is cleavable by the action of an enzyme. In one embodiment, the enzyme is an esterase or a peptidase. In some embodiments, $L^1$ may be cleaved by a lysosomal protease, such as, for example, a cathepsin.

In some embodiments, $L^2$ is present and together with —C(=O)O— forms a self-immolative group or self-immolative groups. In some embodiments, —C(=O)O— also is a self-immolative group.

In some embodiments, where $L^1$ is cleavable by the action of an enzyme and $L^2$ is present, the enzyme cleaves the bond between $L^1$ and $L^2$, whereby the self-immolative group(s) release the Drug moiety.

In some embodiments, $L^1$ and $L^2$, where present, may be connected by a bond selected from: (i) —C(=O)NH: (ii) —C(=O)O—; (iii) —NHC(=O)—; (iv) —OC(=O)—; (v) —OC(=O)O—; (vi) —NHC(=O)O—; (vii) —OC(=O) NH—; (viii) —NHC(=O)NH—; and (ix) —O— (a glycosidic bond).

In some embodiments, an amino group of $L^1$ that connects to $L^2$ may be the N-terminus of an amino acid or may be derived from an amino group of an amino acid side chain, for example a lysine amino acid side chain.

In some embodiments, a carboxyl group of $L^1$ that connects to $L^2$ may be the C-terminus of an amino acid or may be derived from a carboxyl group of an amino acid side chain, for example a glutamic acid amino acid side chain.

In some embodiments, a hydroxy group of $L^1$ that connects to $L^2$ may be derived from a hydroxy group of an amino acid side chain, such as, for example, a serine amino acid side chain.

In some embodiments, —C(=O)O— and $L^2$ together form the group:

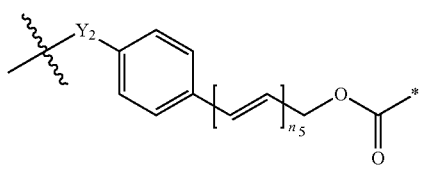

wherein the asterisk indicates the point of attachment to the Drug moiety, the wavy line indicates the point of attachment to the $L^1$, $Y_2$ is —N(H)—, —O—, —C(=O)N(H)— or —C(=O)O—, and $n_5$ is an integer from 0 to 3. The phenylene ring is optionally substituted with one, two or three substituents as described herein.

In some embodiments, $Y_2$ is NH.

In some embodiments, $n_5$ is 0 or 1. Preferably, $n_5$ is 0.

In some embodiments, when $Y_2$ is NH and $n_5$ is 0, the self-immolative group may be referred to as a p-aminobenzylcarbonyl linker (PABC). The self-immolative group will allow for release of the Drug moiety (i.e., the PBD) when a remote site in the linker is activated, proceeding along the lines as shown below (for $n_5$=0):

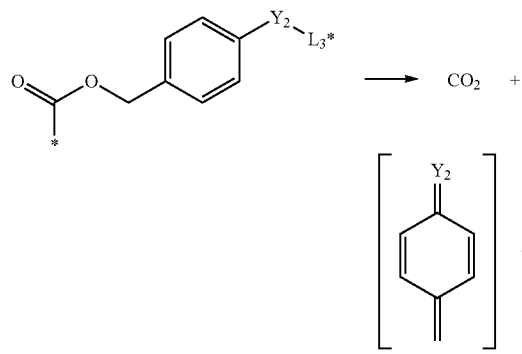

wherein the asterisk indicates the attachment to the Drug, $L^3$ is the activated form of the remaining portion of the linker and the released Drug moiety is not shown. These groups have the advantage of separating the site of activation from the Drug.

In some embodiments, —C(=O)O— and $L^2$ together form a group selected from:

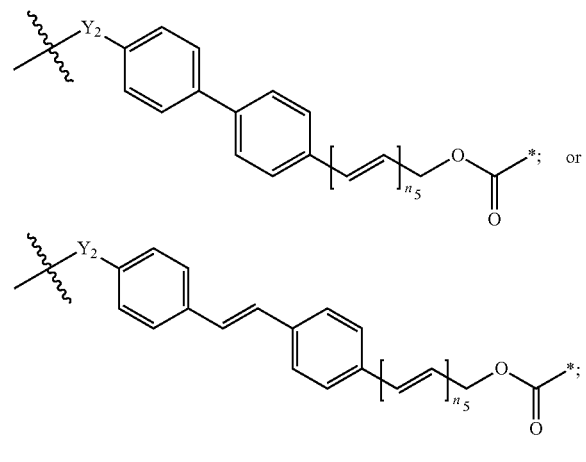

wherein the asterisk, the wavy line, $Y_2$, and $n_5$ are as defined above. Each phenylene ring is optionally substituted with one, two or three substituents as described herein. In one embodiment, the phenylene ring having the $Y_1$ substituent is optionally substituted and the phenylene ring not having the $Y_1$ substituent is unsubstituted.

In some embodiments, —C(=O)O— and $L^2$ together form a group selected from:

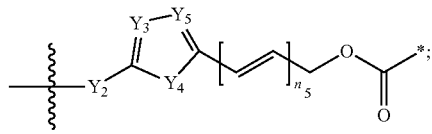

wherein the asterisk, the wavy line, $Y_2$, and $n_5$ are as defined herein, $Y_4$ is O, S or NR, $Y_3$ is N, CH, or CR, and $Y_5$ is N, CH, or CR.

In some embodiments, $Y_3$ is N.
In some embodiments, $Y_3$ is CH.
In some embodiments, $Y_4$ is O or S.
In some embodiments, $Y_5$ is CH.

In some embodiments, the covalent bond between $L^1$ and $L^2$ is a cathepsin labile (e.g., cleavable) bond.

In some embodiments, $L^1$ comprises a dipeptide. The amino acids in the dipeptide may be any combination of natural amino acids and non-natural amino acids. In some embodiments, the dipeptide comprises natural amino acids. When the linker is a cathepsin labile linker, the dipeptide is the site of action for cathepsin-mediated cleavage. The dipeptide then is a recognition site for cathepsin.

In some embodiments, the group —$X_5$—$X_6$— in dipeptide, —NH—$X_5$—$X_6$—CO—, is selected from: (i) -Phe-Lys-; (ii) -Val-Ala; (iii) -Val-Lys-; (iv) -Ala-Lys; (v) -Ala-Ala; (vi) -Val-Cit; (vii) -Phe-Cit; (viii) -Leu-Cit; (ix) -Ile-Cit-Phe-Arg-, and (x) -Trp-Cit-; wherein Cit is citrulline. In such a dipeptide, —NH— is the amino group of $X_5$, and CO is the carbonyl group of $X_6$.

In some embodiments, the group —$X_5$—$X_6$— in dipeptide, is selected from: (i) -Phe-Lys-, (ii) -Val-Ala-, (iii) -Ala-Ala-, (iv) -Val-Lys-, (v) -Ala-Lys-, and (vi) -Val-Cit-.

In some embodiments, the group —$X_5$—$X_6$— in dipeptide, is -Phe-Lys-, Val-Cit, -Ala-Ala- or -Val-Ala-.

Other dipeptide combinations of interest include: (i) -Gly-Gly-, (ii) -Pro-Pro-, and (iii) -Val-Glu-.

Other dipeptide combinations may be used, including those described by Dubowchik et al., which is incorporated herein by reference.

In some embodiments, the amino acid side chain is chemically protected, where appropriate. The side chain protecting group may be a group as discussed below. Protected amino acid sequences are cleavable by enzymes. In some embodiments, a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective groups in Organic Synthesis, Greene and Wuts.

Possible side chain protecting groups are amino acids having reactive side chain functionality, such as, for example:

(i) Arg: Z, Mtr, Tos;
(ii) Asn: Trt, Xan;
(iii) Asp: Bzl, t-Bu;
(iv) Cys: Acm, Bzl, Bzl-OMe, Bzl-Me, Trt;

(v) Glu: Bzl, t-Bu; Gln: Trt, Xan;

(vi) His: Boc, Dnp, Tos, Trt;

(vii) Lys: Boc, Z—Cl, Fmoc, Z;

(viii) Ser: Bzl, TBDMS, TBDPS;

(ix) Thr: Bz;

(x) Trp: Boc; or (xi) Tyr: Bzl, Z, Z—Br.

In some embodiments, —$X_6$— is connected indirectly to the Drug moiety. In such an embodiment, the Spacer unit $L_2$ is present.

In some embodiments, the dipeptide is used in combination with a self-immolative group(s) (the Spacer unit). The self-immolative group(s) may be connected to —$X_6$—.

When a self-immolative group is present, —$X_6$— is connected directly to the self-immolative group. In one embodiment, —$X_6$— is connected to the group $Y_2$ of the self-immolative group. Preferably the group —$X_6$—CO— is connected to $Y_2$, wherein $Y_2$ is NH.

In some embodiments, —$X_5$ is connected directly to $A^1$. Preferably the group NH—$X_5$— (the amino terminus of $X_5$) is connected to $A^1$. $A^1$ may comprise the functionality —CO— thereby to form an amide link with —$X_5$.

In some embodiments, $L^1$ and $L^2$ together with —OC(=O)— comprise the group —$X_5$—$X_6$-PABC-. The PABC group is connected directly to the Drug moiety. In one example, the self-immolative group and the dipeptide together form the group -Phe-Lys-PABC-, is:

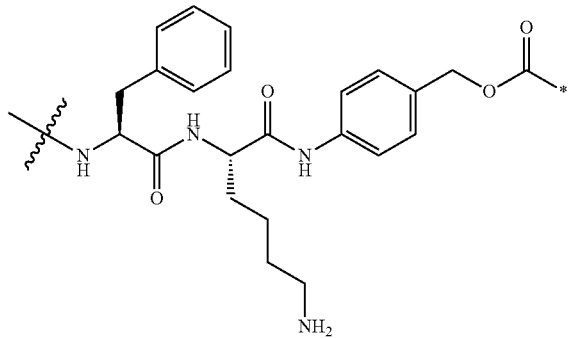 [SMILES: *N[C@@H](Cc1ccccc1)C(=O)N[C@@H](CCCCN)C(=O)Nc1ccc(COC(*)=O)cc1]

wherein the asterisk indicates the point of attachment to the Drug moiety, and the wavy line indicates the point of attachment to the remaining portion of $L^1$ or the point of attachment to A. In some embodiments, the wavy line indicates the point of attachment to $A^1$.

In some embodiments, the self-immolative group and the dipeptide together form the group -Val-Ala-PABC- or -Ala-Ala-PABC are;

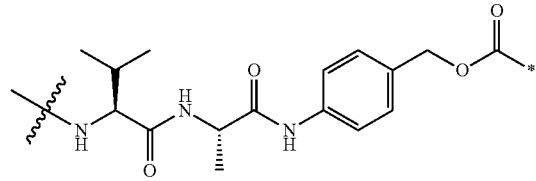

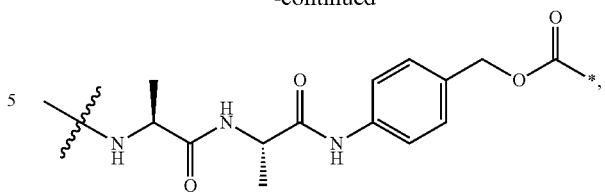

wherein the asterisk and the wavy line are as defined above.

In some embodiments, $L^1$ and $L^2$ together with —OC(=O)— are:

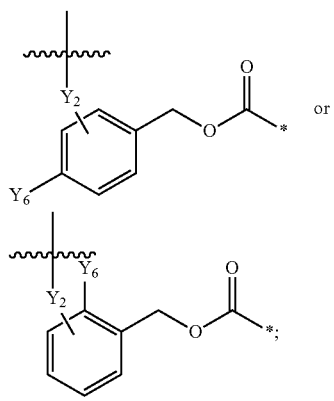

wherein the asterisk indicates the point of attachment to the Drug moiety, the wavy line indicates the point of attachment to $A^1$, $Y_2$ is a covalent bond or a functional group, and $Y_6$ is a group that is susceptible to cleavage thereby to activate a self-immolative group.

In some embodiments, $Y_6$ is selected such that the group is susceptible to cleavage, e.g., by light or by the action of an enzyme. In some embodiments, $Y_6$ may be —$NO_2$ or glucuronic acid (e.g., p-glucuronic acid). The former may be susceptible to the action of a nitroreductase, the latter to the action of a β-glucuronidase.

In some embodiments, the group $Y_2$ may be a covalent bond.

In some embodiments, the group $Y_2$ may be a functional group selected from (i) —C(=O)—; (ii) —NH—; (iii) —O—; (iv) —C(=O)NH—; (v) —C(=O)O—; (vi) —NHC(=O)—; (vii) —OC(=O)—; (viii) —OC(=O)O—; (ix) —NHC(=O)O—; (x) —OC(=O)NH—; (xi) —NHC(=O)NH—; (xii) —NHC(=O)NH; (xiii) —C(=O)NHC(=O)—; (xiv) $SO_2$; and (v) —S—.

In some embodiments, the group $Y_2$ is preferably —NH—, —$CH_2$—, —O—, and —S—.

In some embodiments, $L^1$ and $L^2$ together with —OC(=O)— is:

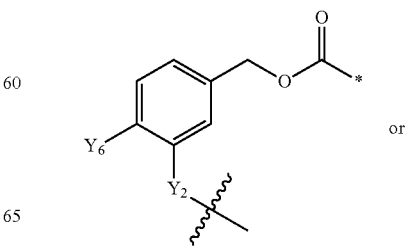

or

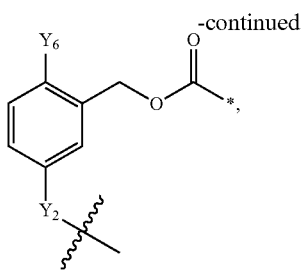

wherein the asterisk indicates the point of attachment to the Drug moiety, the wavy line indicates the point of attachment to $A^1$, $Y_2$ is a covalent bond or a functional group and $Y_6$ is glucuronic acid (e.g., β-glucuronic acid). $Y_2$ is preferably a functional group selected from —NH—.

In some embodiments, $L^1$ and $L^2$ together are:

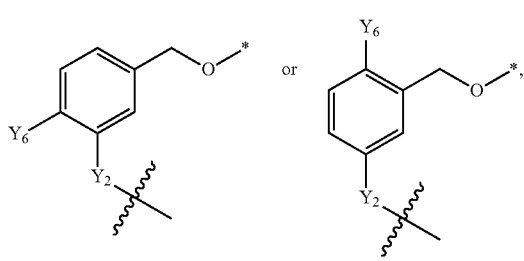

wherein the asterisk indicates the point of attachment to the remainder of $L^2$ or the Drug moiety, the wavy line indicates the point of attachment to $A^1$, $Y_2$ is a covalent bond or a functional group and $Y_6$ is glucuronic acid (e.g., β-glucuronic acid). $Y_2$ is preferably a functional group selected from —NH—, —CH$_2$—, —O—, and —S—.

In some embodiments, $Y_2$ is a functional group as set forth above, the functional group is linked to an amino acid, and the amino acid is linked to the Stretcher unit A. In some embodiments, amino acid is β-alanine. In such an embodiment, the amino acid is equivalently considered part of the Stretcher unit.

In some embodiments, the Specificity unit $L^1$ and the PBRM are indirectly connected via the Stretcher unit.

In some embodiments, $L^1$ and $A^1$ may be connected by a bond selected from: (i) —C(=O)NH—; (ii) —C(=O)O—; (iii) —NHC(=O)—; (iv) —OC(=O)—; (v) —OC(=O)O—; (vi) —NHC(=O)O—; (vii) —OC(=O)NH—; and (viii) —NHC(=O)NH—.

In some embodiments, the group $A^1$ is:

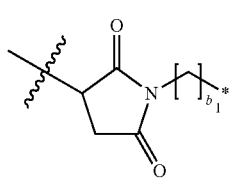

wherein the asterisk indicates the point of attachment to $L^1$, the wavy line indicates the point of attachment to the PRBM moiety, and $b_1$ is an integer from 0 to 6. In one embodiment, $b_1$ is 5.

In some embodiments, the group $A^1$ is:

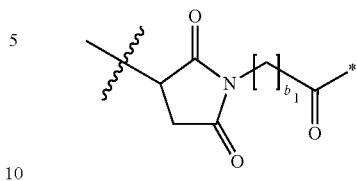

wherein the asterisk indicates the point of attachment to $L^1$, the wavy line indicates the point of attachment to the PBRM moiety, and $b_1$ is an integer from 0 to 6. In one embodiment, $b_1$ is 5.

In some embodiments, the group $A^1$ is:

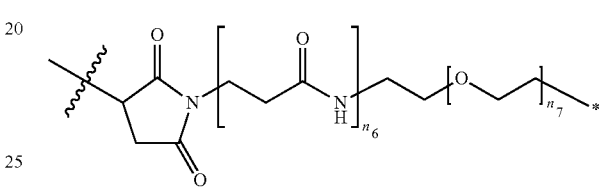

wherein the asterisk indicates the point of attachment to $L^1$, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the group $A^1$ is:

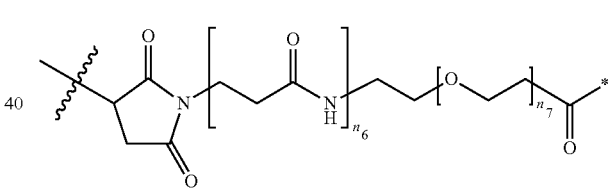

wherein the asterisk indicates the point of attachment to $L^1$, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the group $A^1$ is:

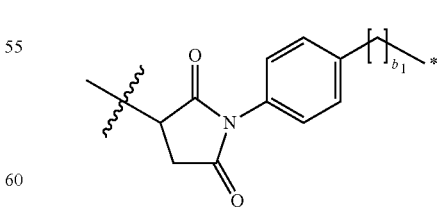

wherein the asterisk indicates the point of attachment to $L^1$, the wavy line indicates the point of attachment to the PBRM moiety, and $b_1$ is an integer from 0 to 6. In one embodiment, $b_1$ is 5.

In some embodiments, the group $A^1$ is:

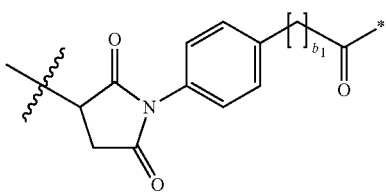

wherein the asterisk indicates the point of attachment to $L^1$, the wavy line indicates the point of attachment to the PBRM moiety, and $b_1$ is an integer from 0 to 6. In one embodiment, $b_1$ is 5.

In some embodiments, the group $A^1$ is:

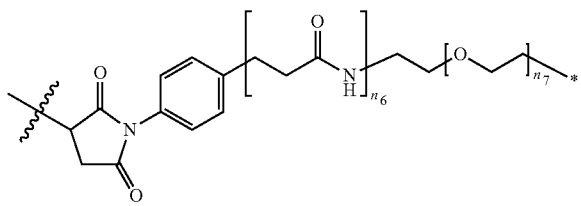

wherein the asterisk indicates the point of attachment to $L^1$, the wavy line indicates the point of attachment to the PBRM moiety, $n_6$ is an integer 0 or 1, and $n_7$ is an integer from 0 to 30. In a preferred embodiment, $n_6$ is 1 and n is 0 to 10, 1 to 8, preferably 4 to 8, most preferably 4 or 8.

In some embodiments, the group $A^1$ is:

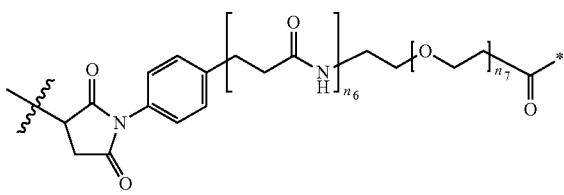

wherein the asterisk indicates the point of attachment to $L^1$, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the connection between the PBRM moiety and $A^1$ is through a thiol residue of the PBRM moiety and a maleimide group of A.

In some embodiments, the connection between the PBRM moiety and $A^1$ is:

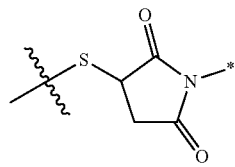 [SMILES: *SC1CC(=O)N(*)C1=O]

wherein the asterisk indicates the point of attachment to the remaining portion of $A^1$, $L^1$, $L^2$ or D, and the wavy line indicates the point of attachment to the remaining portion of the PBRM moiety. In this embodiment, the S atom is typically derived from the PBRM moiety.

In each of the embodiments above, an alternative functionality may be used in place of the malemide-derived group is:

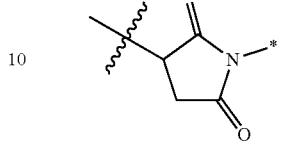

wherein the wavy line indicates the point of attachment to the PBRM moiety as before, and the asterisk indicates the bond to the remaining portion of the $A^1$ group, or to $L^1$, $L^2$ or D.

In some embodiments, the maleimide-derived group is replaced with the group:

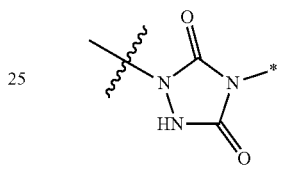

wherein the wavy line indicates point of attachment to the PBRM moiety, and the asterisk indicates the bond to the remaining portion of the A group, or to $L^1$, $L^2$ or D.

In some embodiments, the maleimide-derived group is replaced with a group, which optionally together with a PBRM moiety (e.g., a PBRM), is selected from: (i) —C(=O)NH—; (ii) —C(=O)O—; (iii) —NHC(=O)—; (iv) —OC(=O)—; (v) —OC(=O)O—; (vi) —NHC(=O)O—; (vii) —OC(=O)NH—; (viii) —NHC(=O)NH—; (ix) —NHC(=O)NH; (x) —C(=O)NHC(=O)—; (xi) —S—; (xii) —S—S—; (xiii) —CH$_2$C(=O)—; (xiv) —C(=O)CH$_2$—; (xv)=N—NH—; and (xvi) —NH—N=. Of these —C(=O)CH$_2$— may be preferred especially when the carbonyl group is bound to —NH—.

In some embodiments, the maleimide-derived group is replaced with a group, which optionally together with the PBRM moiety, is selected from:

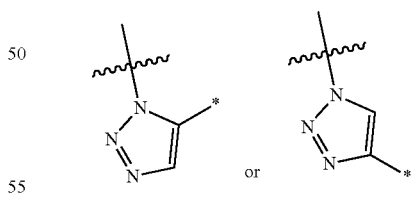

wherein the wavy line indicates either the point of attachment to the moiety or the bond to the remaining portion of the $A^1$ group, and the asterisk indicates the other of the point of attachment to the PBRM moiety or the bond to the remaining portion of the $A^1$ group.

Other groups suitable for connecting $L^1$ to the PBRM are described in WO 2005/082023. The Stretcher unit $A^1$ is present, the Specificity unit $L^1$ is present and Spacer unit $L^2$ is absent. Thus, $L^1$ and the Drug moiety are directly connected via a bond.

Equivalently in this embodiment, $L^2$ is a bond.

In some embodiments, $L^1$ and D may be connected by a bond selected from: (i) —C(=O)N<; (ii) —C(=O)O—; (iii) —NHC(=O)—; (iv) —OC(=O)—; (v) —OC(=O)O—; (vi) —NHC(=O)O; (vii) —OC(=O)N<; and (viii) —NHC(=O)N<; wherein N< or O— are part of D.

In some embodiments, $L^1$ and D are preferably connected by a bond selected from: —C(=O)N<, and —NHC(=O)—.

In some embodiments, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In some embodiments, the group —$X_5$—$X_6$— in dipeptide, —NH—$X_5$—$X_6$—CO—, is selected from: (i) -Phe-Lys-; (ii) -Val-Ala-; (iii) -Ala-Ala-; (iv) -Val-Lys-; (v) -Ala-Lys-; (vi) -Val-Cit-; (vii) -Phe-Cit-; (viii) -Leu-Cit-; (ix) -Ile-Cit-; (x) -Phe-Arg-; and (xi) -Trp-Cit-; wherein Cit is citrulline. In such a dipeptide, —NH— is the amino group of $X_5$, and CO is the carbonyl group of $X_6$.

In some embodiments, the group —$X_5$—$X_6$— in dipeptide, —NH—$X_5$—$X_6$—CO—, is selected from: (i) -Phe-Lys-; (ii) -Val-Ala-; (iii) -Ala-Ala-; (iv) -Val-Lys-; (v) -Ala-Lys-; and (vi) -Val-Cit-.

In some embodiments, the group —X X2- in dipeptide, is -Phe-Lys-, -Ala-Ala- or -Val-Ala-.

Other dipeptide combinations of interest include: (i) -Gly-Gly-; (ii) -Pro-Pro-; and (iii) -Val-Glu-.

Other dipeptide combinations may be used, including those described above.

In some embodiments, L-D is:

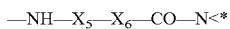

wherein —NH—$X_5$—$X_6$—CO— is the dipeptide, —N< is part of the Drug moiety, the asterisk indicates the points of attachment to the remainder of the Drug moiety, and the wavy line indicates the point of attachment to the remaining portion of $L^1$ or the point of attachment to A. Preferably, the wavy line indicates the point of attachment to $A^1$.

In some embodiments, the dipeptide is valine-alanine and $L^1$-D is:

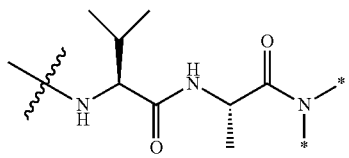 [SMILES: *N[C@H](C(=O)N[C@@H](C)C(=O)N(*)*)C(C)C]

wherein the asterisks, —N< and the wavy line are as defined above.

In some embodiments, the dipeptide is alanine-alanine and L-D is:

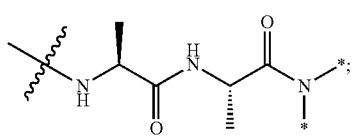

wherein the asterisks, —N< and the wavy line are as defined above.

In some embodiments, the dipeptide is phenylalanine-lysine and $L^1$-D is:

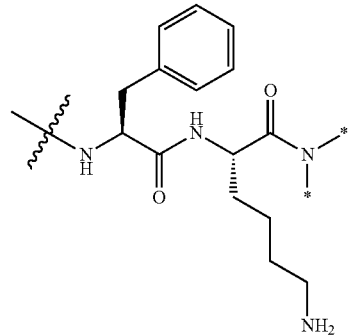 [SMILES: *N[C@@H](Cc1ccccc1)C(=O)N[C@@H](CCCCN)C(=O)N(*)*]

wherein the asterisks, —N< and the wavy line are as defined above.

In some embodiments, the dipeptide is valine-citrulline.

In some embodiments, the groups A -$L^1$ are:

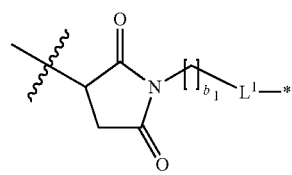

wherein the asterisk indicates the point of attachment to $L^2$ or D, the wavy line indicates the point of attachment to the PBRM moiety, and $b_1$ is an integer from 0 to 6. In some embodiments, $b_1$ is 5.

In some embodiments, the groups $A^1$-$L^1$ are:

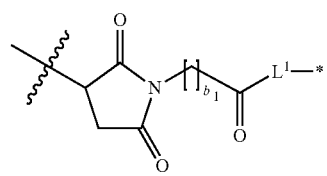

wherein the asterisk indicates the point of attachment to $L^2$ or D, the wavy line indicates the point of attachment to the PBRM moiety, and $b_1$ is an integer from 0 to 6. In some embodiments, $b_1$ is 5.

In some embodiments, the groups $A^1$-$L^1$ are:

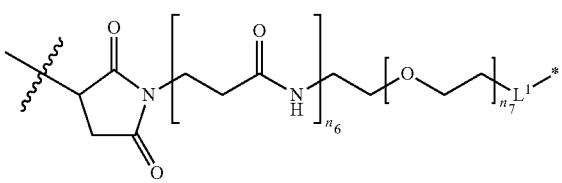

wherein the asterisk indicates the point of attachment to $L^2$ or D, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the groups $A^1$-$L^1$ are:

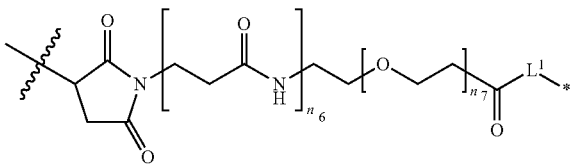

wherein the asterisk indicates the point of attachment to $L^2$ or D, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 7, preferably 3 to 7, most preferably 3 or 7. one embodiment, the groups A1

In some embodiments, the groups $A^1$-$L^1$ are:

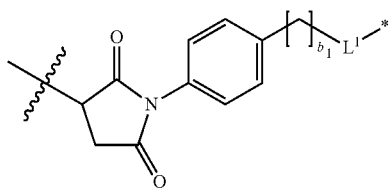

wherein the asterisk indicates the point of attachment to $L^2$ or D, the wavy line indicates the point of attachment to the PBRM moiety, and $b_1$ is an integer from 0 to 6. In some embodiments, $b_1$ is 5.

In some embodiments, the groups $A^1$-$L^1$ are:

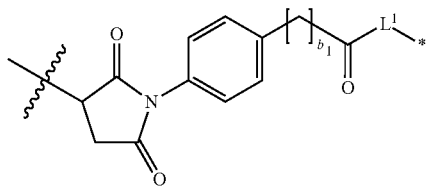

wherein the asterisk indicates the point of attachment to L or D, the wavy line indicates the point of attachment to the PBRM moiety, and $b_1$ is an integer from 0 to 6. In some embodiments, $b_1$ is 5.

In some embodiments, the groups $A^1$-$L^1$ are:

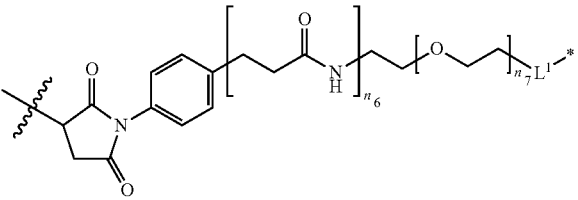

wherein the asterisk indicates the point of attachment to $L^2$ or D, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the groups $A^1$-$L^1$ are:

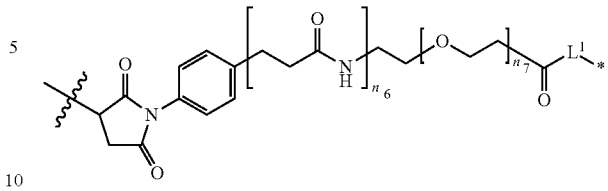

wherein the asterisk indicates the point of attachment to $L^2$ or D, the wavy line indicates the point of attachment to the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the groups PBRM-$A^1$-$L^1$ are:

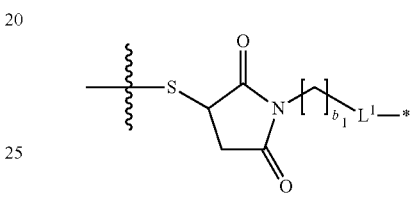

wherein the asterisk indicates the point of attachment to $L^2$ or D, S is a sulfur group of the PBRM moiety, the wavy line indicates the point of attachment to the rest of the PBRM moiety, and $b_1$ is an integer from 0 to 6. In some embodiments, $b_1$ is 5.

In some embodiments, the group PBRM-$A^1$-$L^1$ are:

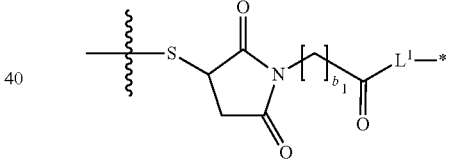

wherein the asterisk indicates the point of attachment to $L^2$ or D, S is a sulfur group of the PBRM moiety, the wavy line indicates the point of attachment to the remainder of the PBRM moiety, and $b_1$ is an integer from 0 to 6. In some embodiments, $b_1$ is 5.

In some embodiments, the groups PBRM-$A^1$-$L^1$ are:

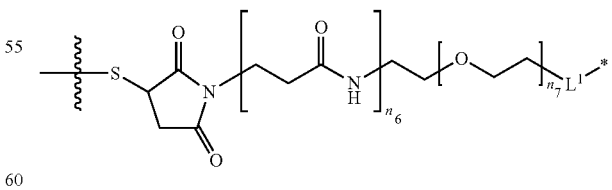

wherein the asterisk indicates the point of attachment to $L^2$ or D, S is a sulfur group of the PBRM moiety, the wavy line indicates the point of attachment to the remainder of the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the groups PBRM-$A^1$-$L^1$ are:

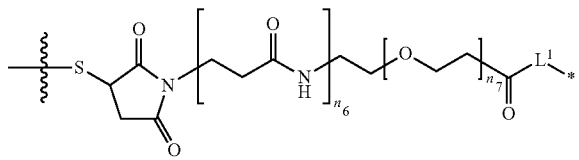

wherein the asterisk indicates the point of attachment to $L^2$ or D, S is a sulfur group of the PBRM moiety, the wavy line indicates the point of attachment to the remainder of the PBRM moiety, $n_6$ is an integer 0 or 1, and $n_7$ is an integer from 0 to 30. In a preferred embodiment, $n_6$ is 1 and $n_7$ is 0 to 10, 1 to 8, preferably 4 to 8, most preferably 4 or 8.

In some embodiments, the groups PBRM-$A^1$-$L^1$ are:

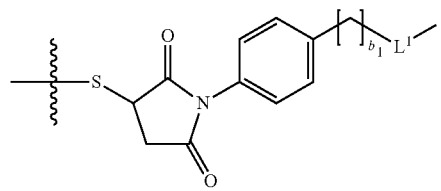

wherein the asterisk indicates the point of attachment to $L^2$ or D, S is a sulfur group of the PBRM moiety, the wavy line indicates the point of attachment to the remainder of the PBRM moiety, $b_1$ is an integer from 0 to 6. In some embodiments, $b_1$ is 5.

In some embodiments, the groups PBRM-$A^1$-$L^1$ are:

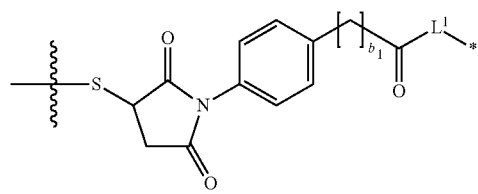

wherein the asterisk indicates the point of attachment to $L^2$ or D, S is a sulfur group of the PBRM moiety, the wavy line indicates the point of attachment to the remainder of the PBRM moiety, $b_1$ is an integer from 0 to 6. In some embodiments, $b_1$ is 5.

In some embodiments, the groups PBRM-$A^1$-$L^1$ are:

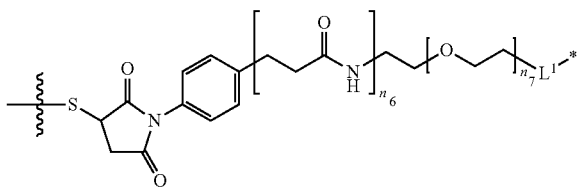

wherein the asterisk indicates the point of attachment to $L^2$ or D, S is a sulfur group of the PBRM moiety, the wavy line indicates the point of attachment to the remainder of the PBRM moiety, $b_1$ is an integer from 0 to 6. In some embodiments, $b_1$ is 5.

In some embodiments, the groups PBRM-$A^1$-$L^1$ are:

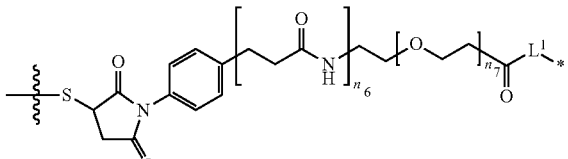

wherein the asterisk indicates the point of attachment to $L^2$ or D, S is a sulfur group of the PBRM moiety, the wavy line indicates the point of attachment to the remainder of the PBRM moiety, $b_1$ is an integer from 0 to 6. In some embodiments, $b_1$ is 5.

In some embodiments, the Stretcher unit is an acetamide unit, having the formula:

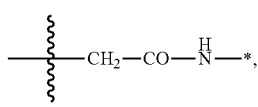

wherein the asterisk indicates the point of attachment to the remainder of the Stretcher unit, $L^1$ or D, and the wavy line indicates the point of attachment to the PBRM moiety.

Linker-Drugs

In other embodiments, Linker-Drug compounds are provided for conjugation to a PBRM moiety. In some embodiments, the Linker-Drug compounds are designed for connection to a PBRM.

In some embodiments, the Drug Linker is

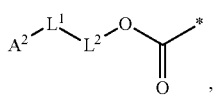

wherein the asterisk indicates the point of attachment to the Drug moiety (D, as defined above), $A^2$ is a Stretcher group ($A^1$) to form a connection to a PBRM moiety, $L^1$ is a Specificity unit, $L^2$ (a Spacer unit) is a covalent bond or together with —OC(=O)— forms a self-immolative group(s).

In another embodiment, the Drug Linker compound is

wherein the asterisk indicates the point of attachment to the Drug moiety (D), $A^2$ is a Stretcher unit (A1) to form a connection to a PBRM moiety, $L^1$ is a Specificity unit, $L^2$ (a Spacer unit) is a covalent bond or a self-immolative group(s).

$L^1$ and $L^2$ are as defined above. References to connection to $A^1$ can be construed here as referring to a connection to $A^2$.

In some embodiments, where $L^1$ comprises an amino acid, the side chain of that amino acid may be protected. Any suitable protecting group may be used. In some embodiments, the side chain protecting groups are removable with other protecting groups in the compound, where present. In other embodiments, the protecting groups may be orthogonal to other protecting groups in the molecule, where present.

Suitable protecting groups for amino acid side chains include those groups described in the Novabiochem Catalog 2006/2007. Protecting groups for use in a cathepsin labile linker are also discussed in Dubowchik et al.

In certain embodiments, the group $L^1$ includes a Lys amino acid residue. The side chain of this amino acid may be protected with a Boc or Alloc protected group. A Boc protecting group is most preferred.

The functional group $A^2$ forms a connecting group upon reaction with a PBRM moiety.

In some embodiments, the functional group $A^2$ is or comprises an amino, carboxylic acid, hydroxy, thiol, or maleimide group for reaction with an appropriate group on the PBRM moiety.

In a preferred embodiment, $A^2$ comprises a maleimide group.

In some embodiments, the group $A^2$ is an alkyl maleimide group. This group is suitable for reaction with thiol groups, particularly cysteine thiol groups, present in the PBRM, for example present in an antibody.

In some embodiments, the group $A^2$ is:

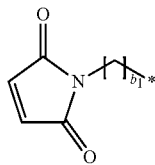

wherein the asterisk indicates the point of attachment to $L^1$, $L^2$ or D, and $b_1$ is an integer from 0 to 6. In some embodiments, $b_1$ is 5.

In some embodiments, the group $A^2$ is:

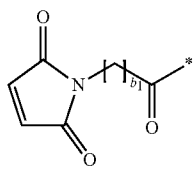

wherein the asterisk indicates the point of attachment to $L^1$, $L^2$ or D, and $b_1$ is an integer from 0 to 6. In some embodiments, $b_1$ is 5.

In some embodiments, the group $A^2$ is:

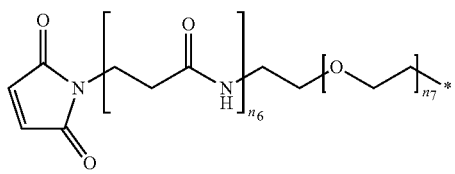

wherein the asterisk indicates the point of attachment to $L^1$, $n_6$ is an integer 0 or 1, and $n_7$ is an integer from 0 to 30. In a preferred embodiment, $n_6$ is 1 and $n_7$ is 0 to 10, 1 to 2, preferably 4 to 8, and most preferably 4 or 8.

In some embodiments, the group $A^2$ is:

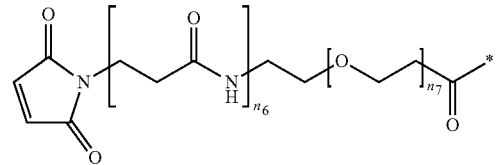

wherein the asterisk indicates the point of attachment to $L^1$, $n_6$ is an integer 0 or 1, and 7 is an integer from 0 to 30. In a preferred embodiment, $n_6$ is 1 and $n_7$ is 0 to 10, 1 to 8, preferably 4 to 8, and most preferably 4 or 8.

In some embodiments, the group $A^2$:

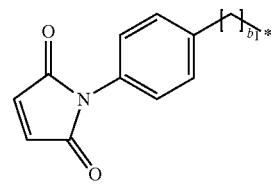

wherein the asterisk indicates the point of attachment to $L^1$, $L^2$ or D, and $b_1$ is an integer from 0 to 6. In some embodiments, $b_1$ is 5.

In some embodiments, the group $A^2$ is:

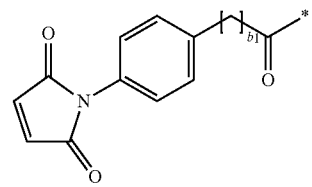

wherein the asterisk indicates the point of attachment to $L^1$, $L^2$ or D, and $b_1$ is an integer from 0 to 6. In some embodiments, $b_1$ is 5.

In some embodiments, the group $A^2$ is:

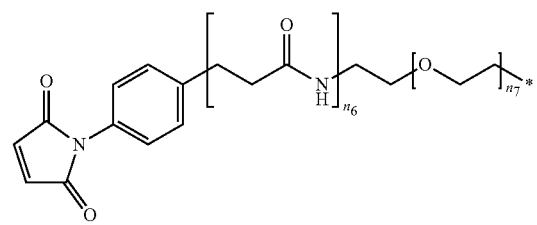

wherein the asterisk indicates the point of attachment to $L^1$, $n_6$ is an integer 0 or 1, and $n_7$ is an integer from 0 to 30. In a preferred embodiment, $n_6$ is 1 and $n_7$ is 0 to 10, 1 to 2 preferably 4 to 8, and most preferably 4 or 8.

In some embodiments, the group $A^2$ is:

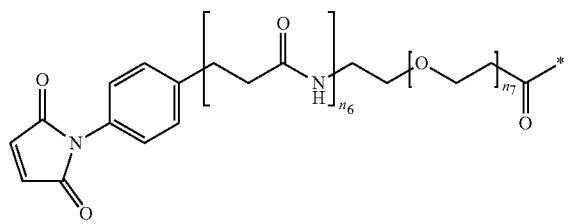

wherein the asterisk indicates the point of attachment to $L^1$, $n_6$ is an integer 0 or 1, and $n_7$ is an integer from 0 to 30. In a preferred embodiment, $n_6$ is 1 and $n_7$ is 0 to 10, 1 to 8, preferably 4 to 8, and most preferably 4 or 8.

In each of the embodiments above, an alternative functionality may be used in place of the malemide group shown below:

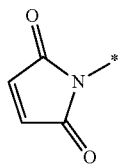 [SMILES: *N1C(=O)C=CC1=O]

wherein the asterisk indicates the bond to the remaining portion of the $A^2$ group.

In some embodiments, the maleimide-derived group is replaced with the group:

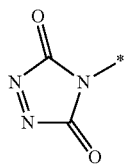

wherein the asterisk indicates the bond to the remaining portion of the $A^2$ group.

In some embodiments, the maleimide group is replaced with a group selected from: (i) —C(=O)OH; (ii) —OH; (iii) —NH$_2$; (iv) —SH; (v) —C(=O)CH$_2$X; wherein X$_7$ is Cl, Br or I; (vi) —CHO; (vii) —C≡CH; and (viii) —N$_3$ (azide). Of these, —C(=O)CH$_2$X$_7$ may be preferred, especially when the carbonyl group is bound to —NH—.

In some embodiments, $L^1$ is present, and $A^2$ is —NH$_2$, —NHMe, —COOH, —OH or —SH.

In some embodiments, where $L^1$ is present, $A^2$ is —NH$_2$ or —NHMe. Either group may be the N-terminal of an $L^1$ amino acid sequence.

In some embodiments, $L^1$ is present and $A^2$ is —NH$_2$, and $L^1$ is an amino acid sequence —X$_5$—X$_6$—, as defined above.

In some embodiments, $L^1$ is present and $A^2$ is COOH. This group may be the C-terminal of an $L^1$ amino acid sequence.

In some embodiments, $L^1$ is present and $A^2$ is OH.
In some embodiments, $L^1$ is present and $A^2$ is SH.

The group $A^2$ may be convertible from one functional group to another. In one embodiment, $L^1$ is present and $A^2$ is —NH$_2$. This group is convertible to another group $A^2$ comprising a maleimide group. In some embodiments, the group —NH$_2$ may be reacted with an acids or an activated acid (e.g., N-succinimide forms) of those $A^2$ groups comprising maleimide shown above.

The group $A^2$ may therefore be converted to a functional group that is more appropriate for reaction with a PBRM moiety.

As noted above, In some embodiments, $L^1$ is present and $A^2$ is —NH$_2$, —NHMe, —COOH, —OH or —SH. In a further embodiment, these groups are provided in a chemically protected form. The chemically protected form is therefore a precursor to the linker that is provided with a functional group.

In some embodiments, $A^2$ is —NH$_2$ in a chemically protected form. The group may be protected with a carbamate protecting group. The carbamate protecting group may be selected from the group consisting of: Alloc, Fmoc, Boc, Troc, Teoc, Cbz and PNZ.

Preferably, where $A^2$ is —NH$_2$, it is protected with an Alloc or Fmoc group.

In some embodiments, where $A^2$ is —NH$_2$, it is protected with an Fmoc group.

In some embodiments, the protecting group is the same as the carbamate protecting group of the capping group.

In some embodiments, the protecting group is not the same as the carbamate protecting group of the capping group. In this embodiment, it is preferred that the protecting group is removable under conditions that do not remove the carbamate protecting group of the capping group.

The chemical protecting group may be removed to provide a functional group to form a connection to a PBRM moiety. Optionally, this functional group may then be converted to another functional group as described above.

In some embodiments, the active group is an amine. This amine is preferably the N-terminal amine of a peptide, and may be the N-terminal amine of the preferred dipeptides of the present disclosure. The active group may be reacted to yield the functional group that is intended to form a connection to a PBRM moiety.

In other embodiments, the Linker unit is a precursor to the Linker unit having an active group. In this embodiment, the Linker unit comprises the active group, which is protected by way of a protecting group. The protecting group may be removed to provide the Linker unit having an active group.

Where the active group is an amine, the protecting group may be an amine protecting group, such as those described in Green and Wuts. The protecting group is preferably orthogonal to other protecting groups, where present, the Linker unit.

In some embodiments, the protecting group is orthogonal to the capping group. Thus, the active group protecting group is removable whilst retaining the capping group. In other embodiments, the protecting group and the capping group is removable under the same conditions as those used to remove the capping group.

In some embodiments, the Linker unit is:

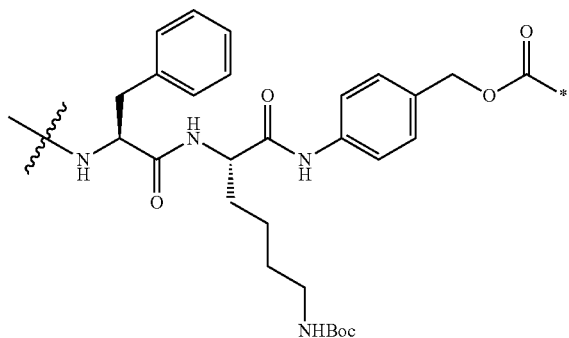 [SMILES: *N[C@@H](Cc1ccccc1)C(=O)N[C@@H](CCCCNC(=O)OC(C)(C)C)C(=O)Nc1ccc(COC(*)=O)cc1]

wherein the asterisk indicates the point of attachment to the Drug moiety, and the wavy line indicates the point of attachment to the remaining portion of the Linker unit, as applicable or the point of attachment to $A^2$. Preferably, the wavy line indicates the point of attachment to A.

In some embodiments, the Linker unit is:

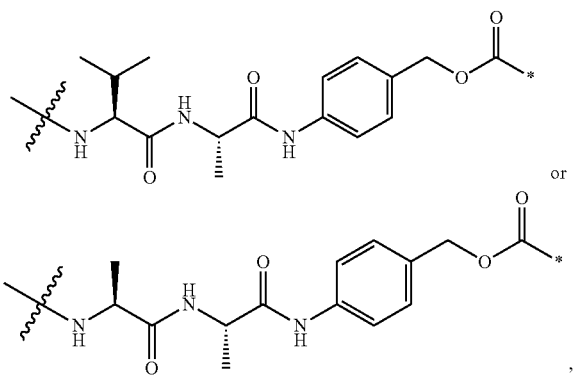

wherein the asterisk and the way line are as defined above.

Other functional groups suitable for use in forming a connection between L and the PBRM are described in WO 2005/082023.

Protein-Based Recognition Molecules (PBRMs)

The protein-based recognition molecule directs the conjugates comprising a peptide linker to specific tissues, cells, or locations in a cell. The protein-based recognition molecule can direct the conjugate in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the conjugate to tissues other than the liver. In other embodiments the protein-based recognition molecule targets the conjugate to a specific tissue such as the liver, kidney, lung or pancreas. The protein-based recognition molecule can target the conjugate to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the conjugate to specific types of cells such as specific targeting to hepatocytes in the liver as opposed to Kupffer cells. In other cases, protein-based recognition molecules can direct the conjugate to cells of the reticular endothelial or lymphatic system, or to professional phagocytic cells such as macrophages or eosinophils. (In such cases the conjugate itself might also be an effective delivery system, without the need for specific targeting).

In still other embodiments, the protein based recognition molecule can target the conjugate to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments the protein based recognition molecules include antibodies, proteins and peptides or peptide mimics.

In a preferred embodiment, the protein based recognition molecule comprises a sulfhydryl group and the protein based recognition molecule is conjugated to the Linker-Drug moiety by forming a covalent bond via the sulfhydryl group and a functional group of the Linker-Drug moiety.

Exemplary antibodies or antibodies derived from Fab, Fab2, scFv or camel antibody heavy-chain fragments specific to the cell surface markers, include, but are not limited to, 5T4, AOC3, ALK, AXL, C242, C4.4a, CA-125, CCL11, CCR 5, CD2, CD3, CD4, CD5, CD15, CA15-3, CD18, CD19, CA19-9, CDH6, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD138, CD141, CD147, CD152, CD 154, CD326, CEA, CEACAM-5, clumping factor, CTLA-4, CXCR2, EGFR (HER1), ErbB2, ErbB3, EpCAM, EPHA2, EPHB2, EPHB4, FGFR (i.e. FGFR1, FGFR2, FGFR3, FGFR4), FLT3, folate receptor, FAP, GD2, GD3, GPNMB, GCC (GUCY2C), HGF, HER2, HER3, HMI.24, ICAM, ICOS-L, IGF-1 receptor, VEGFR1, EphA2, TRPV1, CFTR, gpNMB, CA9, Cripto, c-KIT, c-MET, ACE, APP, adrenergic receptor-beta2, Claudine 3, LIV1, LY6E, Mesothelin, MUC1, MUC13, NaPi2b, NOTCH1, NOTCH2, NOTCH3, NOTCH4, RON, ROR1, PD-L1, PD-L2, PTK7, B7-H3, B7-B4, IL-2 receptor, IL-4 receptor, IL-13 receptor, TROP-2, frizzled-7, integrins (including $\alpha_4$, $\alpha_v\beta_3$, $\alpha_v\beta_5$, $\alpha_v\beta_6$, $\alpha_1\beta_4$, $\alpha_4\beta_1$, $\alpha_4\beta_7$, $\alpha_5\beta_1$, $\alpha_6\beta_4$, $\alpha_{IIb}\beta_3$ integrins), IFN-$\alpha$, IFN-$\gamma$, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, myostatin, NCA-90, NGF, PDGFR$\alpha$, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-$\beta$2, TGF-$\beta$, TNF-$\alpha$, TRAIL-R1, TRAIL-R2, tumor antigen CTAA16.88, VEGF-A, VEGFR2, vimentin, and the like.

In some embodiments, the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR (HER1), ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR $\alpha$, phosphatidylserine, prostatic carcinoma cells, adrenergic receptor-beta2, Claudine 3, mucin, MUC1, NaPi2b, B7H3, B7H4, C4.4a, CEACAM-5, MUC13, TROP-2, frizzled-7, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ integrins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOLIRIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, fevizumab, fezakinumab, figitumumab, fontolizumab (HuZAF), foravirumab, fresolimumab, galiximab, gantenerumab, gavilimomab, gemtuzumab, girentuximab, glembatumumab, golimumab (SIMPONI), gomiliximab, ibalizumab, ibritumomab, igovomab (INDIMACIS-125), imciromab (MYOSCINT), infliximab (REMICADE), intetumumab, inolimomab, inotuzumab, ipilimumab, iratumumab, keliximab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO 140, rafivirumab, ramucirumab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, tefibazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), volociximab (HU-MASPECT), votumumab, zalutumumab (HuMEX-EGFr), zanolimumab (HuMAX-CD4), ziralimumab and zolimomab.

In some embodiments, the antibodies are directed to cell surface markers for 5T4, CA-125, CEA, CDH6, CD3, CD19, CD20, CD22, CD30, CD33, CD40, CD44, CD51, CTLA-4, CEACAM5, EpCAM, HER2, EGFR (HER1), FAP, folate receptor, GCC (GUCY2C), HGF, integrin $\alpha_v\beta_3$, integrin $\alpha_5\beta_1$, IGF-1 receptor, GD3, GPNMB, mucin, LIV1, LY6E, mesothelin, MUC1, MUC13, PTK7, phosphatidylserine, prostatic carcinoma cells, PDGFR $\alpha$, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab, sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, volociximab and zalutumumab.

In specific embodiments the antibodies directed to cell surface markers for HER2 are pertuzumab or trastuzumab and for EGFR (HER1) the antibody is cetuximab or panitumumab; and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRPI targeting, ApoE protein derived peptides, ApoA protein peptides, somatostatin receptor targeting peptides, chlorotoxin derived peptides, and bombesin.

In specific embodiments the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments, the protein-drug conjugates comprise broad spectrum cytotoxins in combination with cell surface markers for HER2 such as pertuzumab or trastuzumab; for EGFR such as cetuximab and panitumumab; for CEA such as labetuzumab; for CD20 such as rituximab; for VEGF-A such as bevacizumab; or for CD-22 such as epratuzumab or veltuzumab.

In other embodiments, the protein-drug conjugates or protein conjugates used in the disclosure comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3×CD19 plus CD28×CD22 bispecific antibodies.

In other embodiments, the protein-drug conjugates or protein conjugates used in the disclosure comprise protein based recognition molecules are antibodies against antigens, such as, for example, Trastuzumab, Cetuximab, Rituximab, Bevacizumab, Epratuzumab, Veltuzumab, Labetuzumab, B7-H4, B7-H3, CA125, CDH6, CD33, CXCR2, CEACAM5, EGFR, FGFR1, FGFR2, FGFR3, FGFR4, GCC (GUCY2C), HER2, LIV1, LY6E, NaPi2b, c-Met, mesothelin, NOTCH1, NOTCH2, NOTCH3, NOTCH4, PD-L1, PTK7, c-Kit, MUC1, MUC13. and 5T4.

In a specific embodiment, the protein-drug conjugates or protein conjugates of the disclosure comprise protein based recognition molecules which are antibodies against 5T4, such as, for example a humanized anti-5T4 scFvFc antibody.

Examples of suitable 5T4 targeting ligands or immunoglobulins include those which are commercially available, or have been described in the patent or non-patent literature, e.g., U.S. Pat. Nos. 8,044,178, 8,309,094, 7,514,546, EP1036091 (commercially available as TroVax™, Oxford Biomedica), EP2368914A1, WO 2013041687 A1 (Amgen), US 2010/0173382, and P. Sapra, et al., Mol. Cancer Ther. 2013, 12:38-47. An anti-5T4 antibody is disclosed in U.S. Provisional Application No. 61/877,439, filed Sep. 13, 2013 and U.S. Provisional Application No. 61/835,858, filed Jun. 17, 2013. The contents of each of the patent documents and scientific publications are herein incorporated by reference in their entireties.

As used herein, the term "5T4 antigen-binding portion" refers to a polypeptide sequence capable of selectively binding to a 5T4 antigen. In exemplary conjugates, the 5T4 antigen-binding portion generally comprises a single chain scFv-Fc form engineered from an anti-5T4 antibody. A single-chain variable fragment (scFv-Fc) is a fusion protein of the variable regions of the heavy (VH) and light chains (VL) of an immunoglobulin, connected with a linker peptide, and further connected to an Fc region comprising a hinge region and $CH_2$ and $CH_3$ regions of an antibody (any such combinations of antibody portions with each other or with other peptide sequences is sometimes referred to herein as an "immunofusion" molecule). Within such a scFvFc molecule, the scFv section may be C-terminally linked to the N-terminus of the Fc section by a linker peptide.

In other specific embodiments, the protein-drug conjugates or protein conjugates of the disclosure comprise protein based recognition molecules which are Her-2 or NaPi2b antibodies.

In some embodiments, the Her-2 antibody suitable for the conjugate or scaffold of the disclosure comprises a variable heavy chain complementarity determining region 1 (CDRH1) comprising the amino acid sequence FTFS-SYSMN (SEQ ID NO: 25); a variable heavy chain complementarity determining region 2 (CDRH2) comprising the amino acid sequence YISSSSSTIYYADSVKG (SEQ ID NO: 26); a variable heavy chain complementarity determining region 3 (CDRH3) comprising the amino acid sequence GGHGYFDL (SEQ ID NO: 27); a variable light chain complementarity determining region 1 (CDRL1) comprising the amino acid sequence RASQSVSSSYLA (SEQ ID NO: 28); a variable light chain complementarity determining region 2 (CDRL2) comprising the amino acid sequence GASSRAT (SEQ ID NO: 21); and a variable light chain complementarity determining region 3 (CDRL3) comprising the amino acid sequence QQYHHSPLT (SEQ ID NO: 29) (see, e.g., US20150366987(A1) published Dec. 24, 2015). In some embodiments, the NaPi2b antibody suitable for the conjugate or scaffold of the disclosure comprises a variable light chain complementarity determining region 1 (CDRL1) comprising the amino acid sequence SASQDIGNFLN (SEQ ID NO: 8); a variable light chain complementarity determining region 2 (CDRL2) comprising the amino acid sequence YTSSLYS (SEQ ID NO: 9); a variable light chain complementarity determining region 3 (CDRL3) comprising the amino acid sequence QQYSKLPLT (SEQ ID NO: 10); a variable heavy chain complementarity determining region 1 (CDRH1) comprising the amino acid sequence GYTFTGYNIH (SEQ ID NO: 5); a variable heavy chain complementarity determining region 2 (CDRH2) comprising the amino acid sequence AIYPGNGDTSYKQKFRG (SEQ ID NO: 6); and a variable heavy chain complementarity determining region 3 (CDRH3) comprising the amino acid sequence GETARATFAY (SEQ ID NO: 7)(see, e.g., co-pending application U.S. Ser. No. 15/457,574 filed Mar. 13, 2017).

PBD Drug Moiety (D)

In some embodiments, the PBD drug moiety (D) is of Formula (IV),

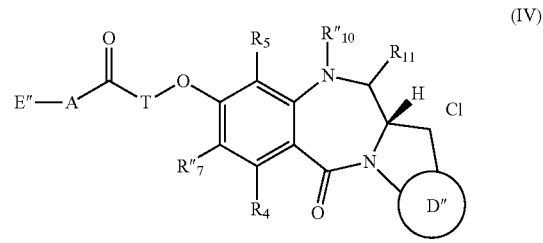

(IV)

a tautomer thereof, a pharmaceutically acceptable salt or solvate thereof, or a pharmaceutically acceptable salt or solvate of the tautomer, wherein:

E" is a direct or indirect linkage to the PBRM (e.g., antibody or antibody fragment), E or

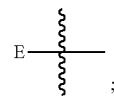

in which

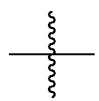

denotes direct or indirect linkage to the PBRM (e.g., antibody or antibody fragment) via a functional group of E;

D" is D' or

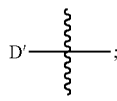

in which

denotes direct or indirect linkage to the PBRM (e.g., antibody or antibody fragment) via a functional group of D';

R"$_7$ is a direct or indirect linkage to the PBRM (e.g., antibody or antibody fragment), R or

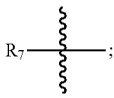

in which

denotes direct or indirect linkage to the PBRM (e.g., antibody or antibody fragment) via a functional group of R$_7$;

R"$_{10}$ is a direct or indirect linkage to the PBRM (e.g., antibody or antibody fragment), R$_{10}$ or

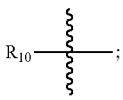

in which

denotes direct or indirect linkage the PBRM (e.g., antibody or antibody fragment) via a functional group of R$_{10}$; and wherein the PBD drug moiety (D) is directly or indirectly linked to the PBRM (e.g., antibody or antibody fragment) via a functional group of one of E", D", R"$_7$, and R"$_{10}$.

In some embodiments, E" is direct or indirect linkage to L$^C$, E, or

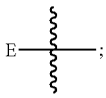

in which

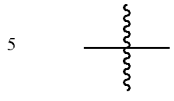

denotes direct or indirect linkage to L$^C$ via a functional group of E.

In some embodiments, E" is a direct or indirect linkage to L$^D$, E, or

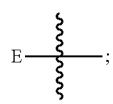

in which

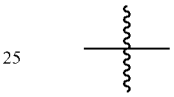

denotes direct or indirect linkage to L$^D$ via a functional group of E.

In some embodiments, D" is D' or

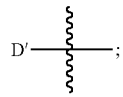

in which

denotes direct or indirect linkage to L$^C$ via a functional group of D'.

In some embodiments, D" is D' or

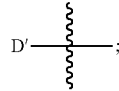

in which

denotes direct or indirect linkage to L$^D$ via a functional group of D'.

In some embodiments, R"$_7$ is a direct or indirect linkage to L$^C$, R$_7$ or

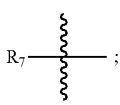

in which

denotes direct or indirect linkage to L$^C$ via a functional group of R$_7$.

In some embodiments, R"$_7$ is a direct or indirect linkage to L$^D$, R$_7$ or

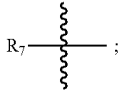

in which

denotes direct or indirect linkage to L$^D$ via a functional group of R$_7$.

In some embodiments, R"$_{10}$ is a direct or indirect linkage to L$^C$, R$_{10}$, or

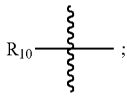

in which

denotes direct or indirect linkage L$^C$ via a functional group of R$_{10}$.

In some embodiments, R"$_{10}$ is a direct or indirect linkage to L$^D$, R$_{10}$, or

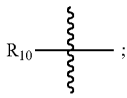

in which

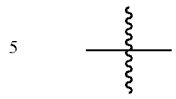

denotes direct or indirect linkage L$^C$ via a functional group of R$_{10}$.

In some embodiments, E" is a direct or indirect linkage to the PBRM; D" is D'; R"$_7$ is R and R"$_{10}$ is R$_{10}$.

In some embodiments, E" is a direct or indirect linkage to L$^C$; D" is D'; R"$_7$ is R$_7$ and R"$_{10}$ is R$_{10}$.

In some embodiments, E" is a direct or indirect linkage to L$^D$; D" is D'; R"$_7$ is R$_7$ and R"$_{10}$ is R$_{10}$.

In some embodiments, E" is

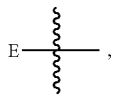

in which

denotes direct or indirect linkage to the PBRM via a functional group of E; D" is D'; R"$_7$ is R$_7$; and R"$_{10}$ is R$_{10}$.

In some embodiments, E" is

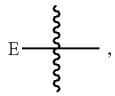

in which

denotes direct or indirect linkage to L$^C$ via a functional group of E; D" is D'; R"$_7$ is R$_7$; and R"$_{10}$ is R$_{10}$.

In some embodiments, E" is

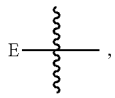

in which

denotes direct or indirect linkage to $L^D$ via a functional group of E; D" is D'; R"$_7$ is R$_7$; and R"$_{10}$ is R$_{10}$.

In some embodiments, D" is

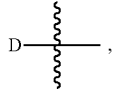, in which

denotes direct or indirect linkage to the PBRM via a functional group of D; E" is E; R"$_7$ is R$_7$ and R"$_{10}$ is R$_{10}$.

In some embodiments, D" is

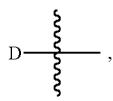, in which

denotes direct or indirect linkage to $L^C$ via a functional group of D; E" is E; R"$_7$ is R$_7$; and R"$_{10}$ is R$_{10}$.

In some embodiments, D" is

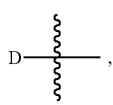, in which

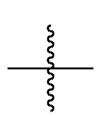

denotes direct or indirect linkage to $L^D$ via a functional group of D; E" is E; R"$_7$ is R$_7$; and R"$_{10}$ is R$_{10}$.

In some embodiments, R"$_7$ is a direct or indirect linkage to the PBRM; E" is E; D" is D'; and R"$_{10}$ is R$_{10}$.

In some embodiments, R"$_7$ is a direct or indirect linkage to $L^C$; E" is E; D" is D'; and R"$_{10}$ is R$_{10}$.

In some embodiments, R"$_7$ is a direct or indirect linkage to $L^D$; E" is E; D" is D'; and R"$_{10}$ is R$_{10}$.

In some embodiments, R"$_7$ is

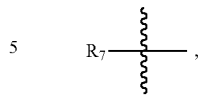, in which

denotes direct or indirect linkage to the PBRM via a functional group of R$_7$; E" is E; D" is D'; and R"$_{10}$ is R$_{10}$.

In some embodiments, R"$_7$ is

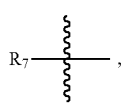, in which

denotes direct or indirect linkage to $L^C$ via a functional group of R$_7$; E" is E; D" is D'; and R"$_{10}$ is R$_{10}$.

In some embodiments, R"$_7$ is

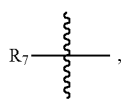, in which

denotes direct or indirect linkage to $L^D$ via a functional group of R$_7$, E" is E; D" is D'; and R"$_{10}$ is R$_{10}$.

In some embodiments, R"$_{10}$ is a direct or indirect linkage to the PBRM; E" is E; D" is D'; and R"$_7$ is R$_7$.

In some embodiments, R"$_{10}$ is a direct or indirect linkage to $L^C$; E" is E; D" is D'; and R"$_7$ is R$_7$.

In some embodiments, R"$_{10}$ is a direct or indirect linkage to $L^D$; E" is E; D" is D'; and R"$_7$ is R$_7$.

In some embodiments, R"$_{10}$ is

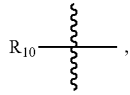, in which

denotes direct or indirect linkage to the PBRM via a functional group of $R_{10}$; E" is E; D" is D'; and $R''_7$ is $R_7$.

In some embodiments, $R''_{10}$ is

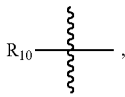

in which

denotes direct or indirect linkage to $L^C$ via a functional group of $R_{10}$; E" is E; D" is D'; and $R''_7$ is $R_7$.

In some embodiments, $R''_{10}$ is

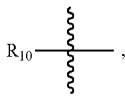

in which

denotes direct or indirect linkage to $L^D$ via a functional group of $R_{10}$; E" is E; D" is D'; and $R''_7$ is $R_7$.

In some embodiments, the conjugates of Formula (IV) include those where each of the moieties defined for one of E", D", $R''_7$, $R''_{10}$, D', T, E, A, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{31}$, $R_{32}$, $R_{33}$, $R_{34}$, $R_{35a}$, $R_{35b}$, $R_{36a}$, $R_{36b}$, $R_{36c}$, $R_{36d}$, $R_{37a}$, $R_{37b}$, $R_a$, $R^b$, $R^N$, $R^Q$, $X_0$, $Y_0$, $Z_0$, $X_1$, $Y_1$, $Z_1$, $X_2$, $X_3$, M, Q, m, n, r, s, t, and x, can be combined with any of the moieties defined for the others of E", D", $R''_7$, $R''_{10}$, D', T, E, A, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$ $R_{18}$, $R_{19}$, $R_{20}$, $R_{21}$, $R_{31}$, $R_{32}$, $R_{33}$, $R_{34}$, $R_{35a}$, $R_{35b}$, $R_{36a}$, $R_{36c}$, $R_{36d}$, $R_{37a}$, $R_{37b}$, $R_{40}$, $R_a$, $R^b$, $R^N$, $R^Q$, $X_0$, $Y_0$, $Z_0$, $X_1$, $Y_1$, $Z_1$, $X_2$, $X_3$, $X_4$, $X_8$, M, Q, m, n, r, s, t, and x.

In some embodiments, D' is D1, D2, D3, or D4:

(D1)

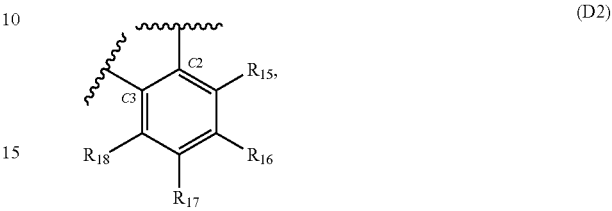

(D2)

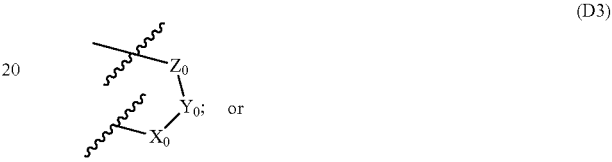

(D3)

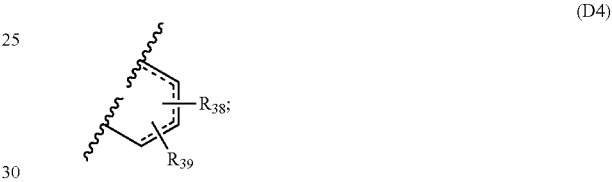

(D4)

wherein the dotted line between C2 and C3 or between C2 and C1 in D1 or the dotted line in D4 indicates the presence of a single or double bond; and m is 0, 1 or 2;

when D' is D1, the dotted line between C2 and C3 is a double bond, and m is 1, then $R_1$ is:

(i) $C_{6-10}$ aryl group, optionally substituted by one or more substituents selected from —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, bis-oxy-$C_{1-3}$ alkylene, —$NR_3R_4$, —$S(=O)_2R_{12}$, —$S(=O)_2NR_{13}R_{14}$, —$SR_{12}$, —$SO_xM$, —$OSO_xM$, —$NR_9COR_{19}$, —NH(C=NH)$NH_2$;

(ii) $C_{1-5}$ alkyl;

(iii) $C_{3-6}$ cycloalkyl;

(iv)

(vi)

vii)

-continued

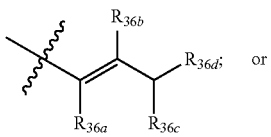
(viii)

(viii) halo;

when D' is D1, the dotted line between C2 and C3 is a single bond, and m is 1, then $R_1$ is:

(i) —OH, =O, =CH$_2$, —CN, —$R_2$, —O$R_2$, halo, =CH—$R_6$, =C($R_6$)$_2$, —O—SO$_2R_2$, —CO$_2R_2$, —CO$R_2$, —CHO, or —COOH; or

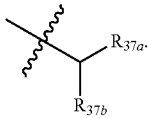
(ii)

when D' is D1 and m is 2, then each $R_1$ independently is halo and either both $R_1$ are attached to the same carbon atom or one is attached to $C_2$ and the other is attached to $C_3$;

T is $C_{1-10}$ alkylene linker;

A is

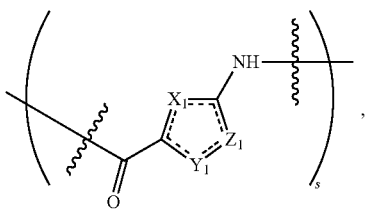

wherein the —NH group of A is connected to the —C(O)-T- moiety of Formula (I) and the C=O moiety of A is connected to E; and each

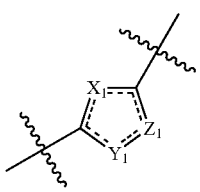

independently is

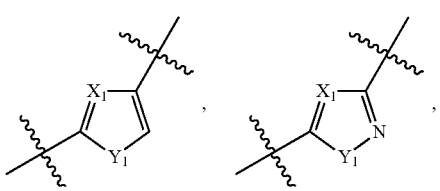

-continued

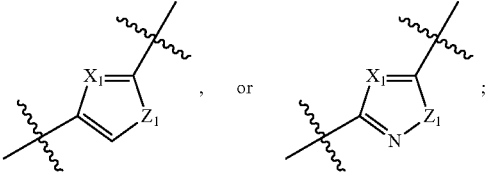

E is E1, E2, E3, E4, —OH, —NH—(C$_{1-6}$ alkylene)-$R_{13a}$, —O—(CH$_2$)$_3$—NH$_2$, —O—CH(CH$_3$)—(CH$_2$)$_2$—NH$_2$ or —NH—(CH$_2$)$_3$—O—C(=O)—CH(CH$_3$)—NH$_2$:

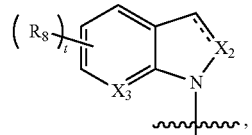
(E1)

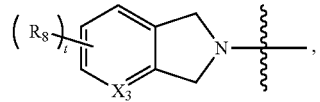
(E2)

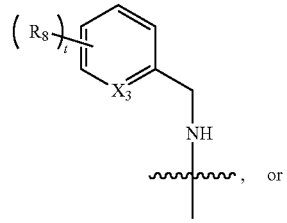
(E3)

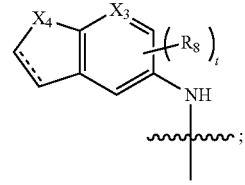
(E4)

wherein the dotted line in E1 or E4 indicates the presence of a single or double bond;

each occurrence of $R_2$ and $R_3$ independently is an optionally substituted $C_{1-8}$ alkyl, optionally substituted $C_{2-8}$ alkenyl, optionally substituted $C_{2-8}$ alkynyl, optionally substituted $C_{3-8}$ cycloalkyl, optionally substituted 3- to 20-membered heterocycloalkyl, optionally substituted $C_{6-20}$ aryl or optionally substituted 5- to 20-membered heteroaryl, and, optionally in relation to the group N$R_2R_3$, $R_2$ and $R_3$ together with the nitrogen atom to which they are attached form an optionally substituted 4-, 5-, 6- or 7-membered heterocycloalkyl or an optionally substituted 5- or 6-membered heteroaryl;

$R_4$, $R_5$ and $R_7$ are each independently —H, —$R_2$, —OH, —O$R_2$, —SH, —S$R_2$, —NH$_2$, —NH$R_2$, —N$R_2R_3$, —NO$_2$, —SnMe$_3$, halo or a polyethylene glycol unit —(OCH$_2$CH$_2$)$_r$—O$R_a$; or $R_4$ and $R_7$ together form bis-oxy-C$_{1-3}$ alkylene;

each $R_6$ independently is —H, —$R_2$, —CO$_2R_2$, —CO$R_2$, —CHO, —CO$_2$H, or halo;

each $R_8$ independently is —OH, halo, —NO$_2$, —CN, —N$_3$, —O$R_2$, —COOH, —COO$R_2$, —CO$R_2$, —OCON$R_{13}R_{14}$, —CON$R_{13}R_{14}$, —CO—NH—(C$_{1-6}$ alkylene)-$R_{13a}$, $C_{1-10}$ alkyl, $C_{3-10}$cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, —$S(=O)_2R_{12}$, —$S(=O)_2NR_{13}R_{14}$, —$SR_{12}$, —$SO_xM$, —$OSO_xM$, —$NR_9COR_{19}$, —NH(C=NH)NH$_2$, —$R_{20}$—$R_{21}$—$NR_3R_4$, —$R_{20}$—$R_{21}$—NH—P(O)(OH)—$(OCH_2CH_2)_{n9}$—$OCH_3$, or —O—P(O)(OH)—$(OCH_2CH_2)_{n9}$—$OCH_3$;

each $R_9$ independently is $C_{1-10}$ alkyl, $C_{3-10}$ cycloalkyl, $C_{2-10}$ alkenyl or $C_{2-10}$ alkynyl;

$R^{10}$ is —H or a nitrogen protecting group;

$R^{11}$ is -$QR^Q$ or —$SO_xM$;

or $R^{10}$ and $R^{11}$ taken together with the nitrogen atom and carbon atom to which they are respectively attached, form a N=C double bond;

each $R^{12}$ independently is $C_{1-7}$ alkyl, 3- to 20-membered heterocycloalkyl, 5- to 20-membered heteroaryl, or $C_{6-20}$ aryl;

each occurrence of $R_{13}$ and $R_{14}$ are each independently H, $C_{1-10}$ alkyl, 3- to 20-membered heterocycloalkyl, 5- to 20-membered heteroaryl, or $C_{6-20}$ aryl;

each $R_{13a}$ independently is —OH or —$NR_{13}R_{14}$, $R_{15}$, $R_{16}$, $R_{17}$ and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3-14 membered heterocycloalkyl, 5- to 12-membered heteroaryl, —$NR_{13}R_{14}$, —$S(=O)_2R_2$, —$S(=O)_2NR_{13}R_{14}$, —$SR_2$, —$SO_xM$, —$OSO_xM$, —$NR_9COR_{19}$ or —NH(C=NH)NH$_2$;

each $R_{19}$ independently is $C_{1-10}$ alkyl, $C_{3-10}$ cycloalkyl, $C_{2-10}$ alkenyl or $C_{2-10}$ alkynyl;

each $R_{20}$ independently is a bond, $C_{6-10}$ arylene, 3-14 membered heterocycloalkylene or 5- to 12-membered heteroarylene;

each $R_{21}$ independently is a bond or $C_{1-10}$ alkylene;

$R_{31}$, $R_{32}$ and $R_{33}$ are each independently —H, $C_{1-3}$ alkyl, $C_{2-3}$ alkenyl, $C_{2-3}$ alkynyl or cyclopropyl, wherein the total number of carbon atoms in the $R_1$ group is no more than 5;

$R_{34}$ is —H, $C_{1-3}$ alkyl, $C_{2-3}$ alkenyl, $C_{2-3}$ alkynyl, cyclopropyl, or phenyl wherein the phenyl is optionally substituted by one or more of halo, methyl, methoxy, pyridyl or thiophenyl;

one of $R_{35a}$ and $R_{35b}$ is —H and the other is a phenyl group optionally substituted with one or more of halo, methyl, methoxy, pyridyl or thiophenyl;

$R_{36a}$, $R_{36b}$, $R_{36c}$ are each independently —H or $C_{1-2}$ alkyl;
$R_{36d}$ is —OH, —SH, —COOH, —C(O)H, —N=C=, —NHNH$_2$, —CONHNH$_2$,

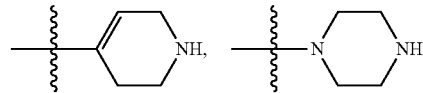

or NHR$^N$, wherein R$^N$ is —H or $C_{1-4}$ alkyl;

$R_{37a}$ and $R_{37b}$ are each independently is —H, —F, $C_{1-4}$ alkyl, $C_{2-3}$ alkenyl, wherein the alkyl and alkenyl groups are optionally substituted by $C_{1-4}$ alkyl amido or $C_{1-4}$ alkyl ester; or when one of $R_{37a}$ and $R_{37b}$ is —H, the other is —CN or a $C_{1-4}$ alkyl ester;

$R_{38}$ and $R_{39}$ are each independently H, $R_{13}$, =CH$_2$, =CH—(CH$_2$)$_{s1}$—CH$_3$, =O, (CH$_2$)$_{s1}$—OR$_{13}$, (CH$_2$)$_{s1}$—CO$_2$R$_{13}$(CH$_2$)$_{s1}$—NR$_{13}$R$_{14}$, O—(CH$_2$)$_2$—NR$_{13}$R$_{14}$, NH—C(O)—R$_{13}$, O—(CH$_2$)s-NH—C(O)—R$_{13}$, O—(CH$_2$)s-C(O)NHR$_3$, (CH$_2$)$_{s1}$OS(=O)$_2$R$_3$, O—SO$_2$R$_3$, (CH$_2$)$_{s1}$—C(O)R$_1$ and (CH$_2$)$_{s1}$—C(O)NR$_{13}$R$_{14}$;

$X_0$ is CH$_2$, NR$_6$, C=O, BH, SO or SO$_2$;

$Y_0$ is O, CH$_2$, NR$_6$ or S;

$Z_0$ is absent or (CH$_2$)$_n$;

each $X_1$ independently is CR$_b$, or N;

each $Y_1$ independently is CH, NR$_a$, O or S;

each $Z_1$ independently is CH, NR$_a$, O or S;

each $R_a$ independently is H or $C_{1-4}$ alkyl;

each $R_b$ independently is H, OH, $C_{1-4}$ alkyl, or $C_{1-4}$ alkoxyl;

$X_2$ is CH, CH$_2$ or N;

$X_3$ is CH or N;

$X_4$ is NH, O or S;

$X_8$ is NH, O or S;

Q is O, S or NH;

when Q is S or NH, then R$^Q$ is —H or optionally substituted $C_{1-2}$ alkyl; or when Q is O, then R$^Q$ is —H or optionally substituted $C_{1-2}$ alkyl, —SO$_x$M, —PO$_3$M, —(CH$_2$—CH$_2$—O)$_{n9}$CH$_3$, —(CH$_2$—CH$_2$O)$_{n9}$—(CH$_2$)$_2$—R$_{40}$, —C(O)—(CH$_2$—CH$_2$—O)$_{n9}$CH$_3$, —C(O)O—(CH$_2$—CH$_2$—O)$_{n9}$CH$_3$, —C(O)NH—(CH$_2$—CH$_2$—O)$_{n9}$CH$_3$, —(CH$_2$)$_n$—NH—C(O)—CH$_2$—O—CH$_2$—C(O)—NH—(CH$_2$—CH$_2$—O)$_9$CH$_3$, —(CH$_2$)$_n$—NH—C(O)—(CH$_2$)$_n$—(CH$_2$—CH$_2$—O)$_{n9}$CH$_3$, a sugar moiety,

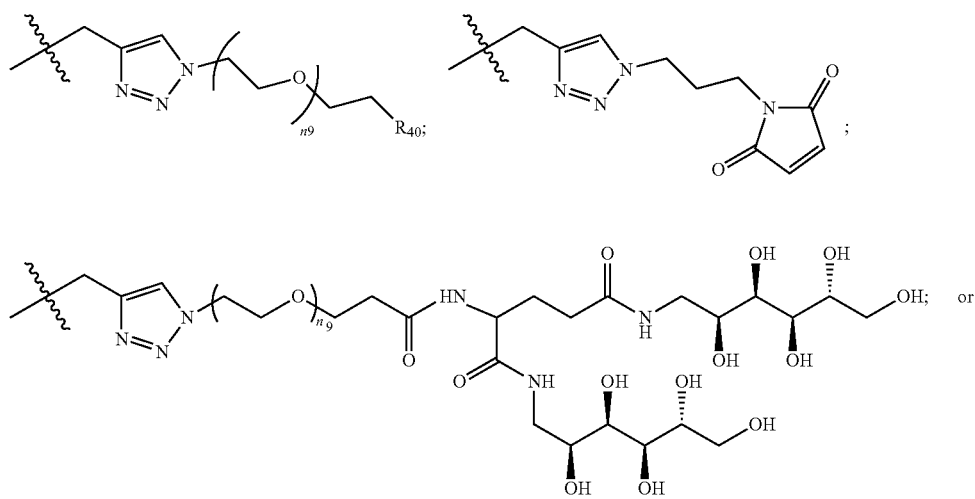

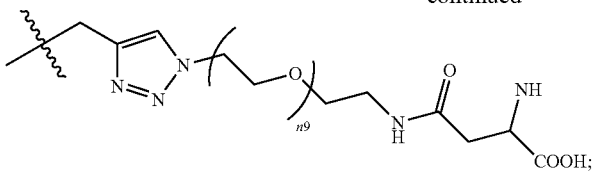

each M independently is H or a monovalent pharmaceutically acceptable cation;

n is 1, 2 or 3;

each r independently is an integer from 1 to 200;

s is 1, 2, 3, 4, 5 or 6;

$s_1$ is 0, 1, 2, 3, 4, 5 or 6:

$n_9$ is 1, 2, 3, 4, 5, 6, 8, 12 or 24;

t is 0, 1, or 2;

$R_{40}$ is —$SO_3H$, —COOH, —C(O)NH(CH$_2$)$_2$SO$_3$H or —C(O)NH(CH$_2$)$_2$COOH; and each x independently is 2 or 3.

The PBD drug moiety of Formula (IV) can have one or more of the following features when applicable:

In some embodiments, the PBD drug moiety of Formula (IV) is of Formula (IV-a),

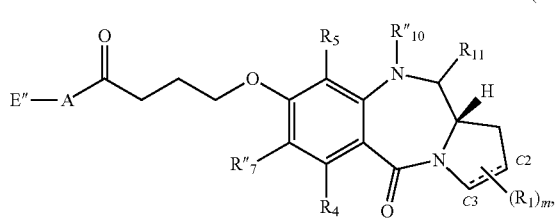

(IV-a)

a tautomer thereof, a pharmaceutically acceptable salt or solvate thereof, or a pharmaceutically acceptable salt or solvate of the tautomer.

In some embodiments, the conjugates of Formulae (IV-a) include those where each of the moieties defined for one of E″, A, $R_4$, $R_5$, $R″_7$, $R″_{10}$, $R_{11}$, and D″ can be combined with any of the moieties defined for the others of E″, A, $R_4$, $R_5$, $R″_7$, $R″_{10}$, $R_{11}$, and D″.

In some embodiments, D' is D1.

In some embodiments, D' is D2.

In some embodiments, D' is D3.

In some embodiments, D' is D4

In some embodiments, the PBD drug moiety of Formula (IV) is of any one of formulae (V-1), (V-2), and (V-3):

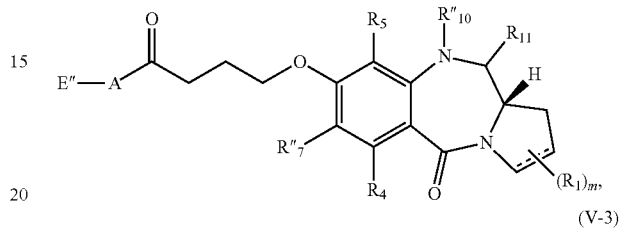

a tautomer thereof, a pharmaceutically acceptable salt or solvate thereof, or a pharmaceutically acceptable salt or solvate of the tautomer.

In some embodiments, the conjugates of any one of Formulae (V-1)-(V-3) include those where each of the moieties defined for one of E″, A, $R_1$, $R_4$, $R_5$, $R″_7$, $R″_{10}$, $R_{11}$, and m can be combined with any of the moieties defined for the others of E″, A, $R_1$, $R_4$, $R_5$, $R″_7$, $R″_{10}$, $R_{11}$, and m.

In some embodiments, the PBD drug moiety of Formula (IV) is of Formula (VI-1):

(VI-1)

a tautomer thereof, a pharmaceutically acceptable salt or solvate thereof, or a pharmaceutically acceptable salt or solvate of the tautomer.

In some embodiments, the conjugates of Formula (VI-1) include those where each of the moieties defined for one of E″, A, $R_4$, $R_5$, $R″_7$, $R″_{10}$, $R_{11}$, $R_{15}$, $R_{16}$, $R_{17}$, and $R_{18}$ can be combined with any of the moieties defined for the others of E″, A, $R_4$, $R_5$, $R″_7$, $R″_{10}$, $R_{15}$, $R_{16}$, $R_7$, and $R_{18}$.

In some embodiments, the PBD drug moiety of Formula (IV) is of Formula (VII), (VII-1), (VII-2), or (VII-3):

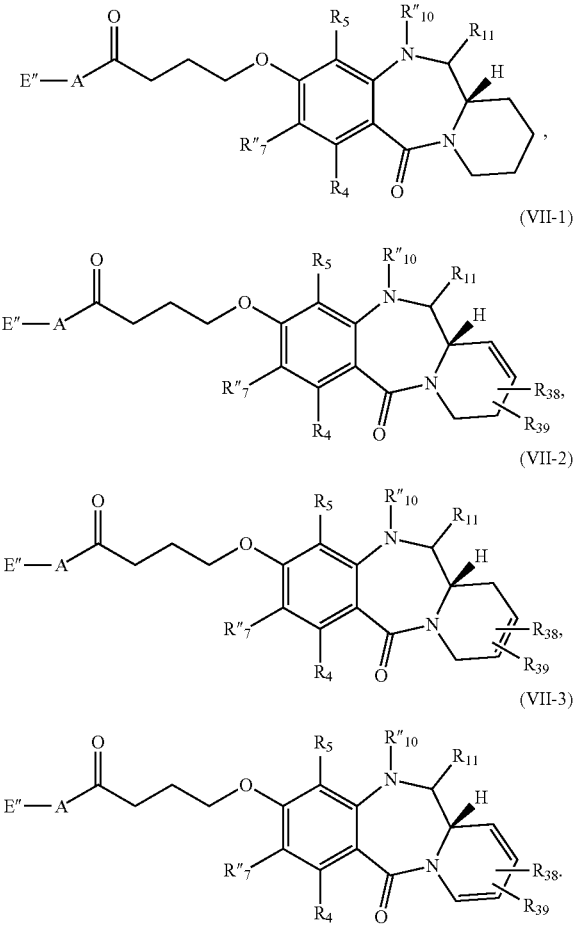

a tautomer thereof, a pharmaceutically acceptable salt or solvate thereof, or a pharmaceutically acceptable salt or solvate of the tautomer.

In some embodiments, the conjugates of any one of Formulae (VII), (VII-1), (VII-2), and (VII-3) include those where each of the moieties defined for one of E″, A, $R_4$, $R_5$, $R''_7$, $R''_{10}$, $R_{11}$, $R_{38}$, and $R_{39}$, where applicable, can be combined with any of the moieties defined for the others of E″, A, $R_4$, $R_5$, $R''_7$, $R''_{10}$, $R_{11}$, $R_{38}$, and $R_{39}$.

In some embodiments, the PBD drug moiety of Formula (IV) is of Formula (VIII):

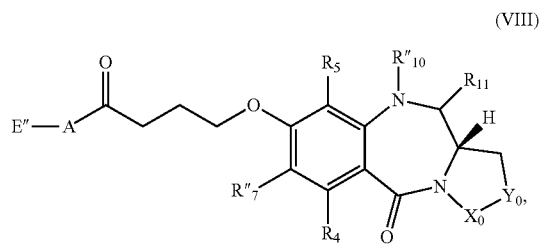

a tautomer thereof, a pharmaceutically acceptable salt or solvate thereof, or a pharmaceutically acceptable salt or solvate of the tautomer.

In some embodiments, the conjugates of Formula (VIII) include those where each of the moieties defined for one of E″, A, $R_4$, $R_5$, $R''_7$, $R''_{10}$, $R_{11}$, $X_0$, and $Y_0$ can be combined with any of the moieties defined for the others of E″, A, $R_5$, $R''_7$, $R''_{10}$, $R_{11}$, $X_0$, and $Y_0$.

In some embodiments, when D′ is D1, the dotted line between $C_2$ and $C_3$ is a double bond, and m is 1, then $R_1$ is $C_{6-10}$ aryl group, optionally substituted by one or more substituents selected from —OH, halo, —NO$_2$, —CN, —N$_3$, —OR$_2$, —COOH, —COOR$_2$, —COR$_2$, —OCONR$_{13}$R$_{14}$, $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—OR$_a$, 3- to 14-membered heterocycloalkyl, 5- to 12-membered heteroaryl, bis-oxy-$C_{1-3}$ alkylene, —NR$_{13}$R$_{14}$, —S(=O)$_2$R$_{12}$, —S(=O)$_2$NR$_{13}$R$_{14}$, —SR$_{12}$, —SO$_x$M, —OSO$_x$M, —NR$_9$COR$_{19}$, and —NH(C=NH)NH$_2$.

In some embodiments, when D′ is D1, the dotted line between $C_2$ and $C_3$ is a double bond, and m is 1, then $R_1$ is $C_{6-10}$ aryl group, optionally substituted by one or more substituents selected from —OH, halo, —NO$_2$, —CN, —N$_3$, —OR$_2$, —COOH, —COOR$_2$, —COR$_2$, —OCONR$_{13}$R$_{14}$. $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—OR$_a$, 3- to 14-membered heterocycloalkyl, 5- to 12-membered heteroaryl, —NR$_{13}$R$_{14}$, —S(=O)$_2$R$_2$, —S(=O)$_2$NR$_{13}$R$_{14}$, —SR$_{12}$, —NR$_9$COR$_{19}$, and —NH(C=NH)NH$_2$.

In some embodiments, when D′ is D1, the dotted line between $C_2$ and $C_3$ is a double bond, and m is 1, then $R_1$ is $C_{6-10}$ aryl group, optionally substituted by one or more substituents selected from —OH, halo, —OR$_2$, —COOH, —COOR$_2$, —COR$_2$, 3- to 14-membered heterocycloalkyl, and —NR$_{13}$R$_{14}$.

In some embodiments, when D′ is D1, the dotted line between $C_2$ and $C_3$ is a double bond, and m is 1, then $R_1$ is $C_{6-10}$ aryl group, substituted by one or more substituents selected from —OH, halo, —OR$_2$, —COH, —COOR$_2$, —COR$_2$, 3- to 14-membered heterocycloalkyl, and —NR$_{13}$R$_{14}$.

In some embodiments, when D′ is D1, the dotted line between $C_2$ and $C_3$ is a double bond, and m is 1, then $R_1$ is $C_{6-10}$ aryl group, substituted by one substituent selected from —OH, halo, —OR$_2$, —COOH, —COOR$_2$, —COR$_2$, 3- to 14-membered heterocycloalkyl, and —NR$_{13}$R$_{14}$.

In some embodiments, when D′ is D1, the dotted line between $C_2$ and $C_3$ is a double bond, and m is 1, then $R_1$ is $C_{6-10}$ aryl group, substituted by one substituent selected from —OH, —OR$_2$, —COOH, —COOR$_2$, 3- to 14-membered heterocycloalkyl, and —NR$_{13}$R$_{14}$.

In some embodiments, when D′ is D1, the dotted line between $C_2$ and $C_3$ is a double bond, and m is 1, then $R_1$ is $C_{6-10}$ aryl group, substituted by one substituent selected from —OH, and —COOH.

In some embodiments, when D′ is D1, the dotted line between $C_2$ and $C_3$ is a double bond, and m is 1, then $R_1$ is $C_{6-10}$ aryl group, substituted by one substituent selected from —OR$_2$— and —COOR$_2$.

In some embodiments, when D′ is D1, the dotted line between $C_2$ and $C_3$ is a double bond, and m is 1, then $R_1$ is $C_{6-10}$ aryl group, substituted by one 3- to 14-membered heterocycloalkyl.

In some embodiments, when D′ is D1, the dotted line between $C_2$ and $C_3$ is a double bond, and m is 1, then $R_1$ is $C_{6-10}$ aryl group, substituted by one —NR$_{13}$R$_{14}$.

In some embodiments, when D′ is D1, the dotted line between $C_2$ and $C_3$ is a double bond, and m is 1, then $R_1$ is $C_{1-5}$ alkyl.

In some embodiments, when D' is D1, the dotted line between $C_2$ and $C_3$ is a double bond, and m is 1, then $R_1$ is $C_{3-6}$ cycloalkyl.

In some embodiments, when D' is D1, the dotted line between $C_2$ and $C_3$ is a double bond, and m is 1, then $R_1$ is cyclopropyl.

In some embodiments, when D' is D1, the dotted line between $C_2$ and $C_3$ is a double bond, and m is 1, then $R_1$ is R

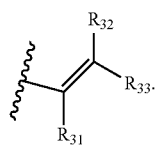

In some embodiments, when D' is D1, the dotted line between $C_2$ and $C_3$ is a double bond, and m is 1, then $R_1$ is

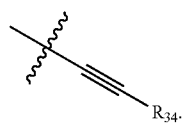

In some embodiments, when D' is D1, the dotted line between $C_2$ and $C_3$ is a double bond, and m is 1, then $R_1$ is

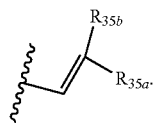

In some embodiments, when D' is D1, the dotted line between $C_2$ and $C_3$ is a double bond, and m is 1, then $R_1$ is

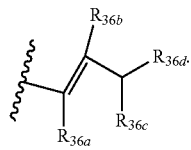

In some embodiments, when D' is D1, the dotted line between $C_2$ and $C_3$ is a double bond, and m is 1, then $R_1$ is halo.

In some embodiments, when D' is D1, the dotted line between $C_2$ and $C_3$ is a single bond, and m is 1, then $R_1$ is: —OH, =O, =$CH_2$, —CN, —$R_2$, —$OR_2$, halo, =CH—$R_6$, =C($R_6$)$_2$, —O—$SO_2R_2$, —$CO_2R_2$, —$COR_2$, —CHO, or —COOH.

In some embodiments, when D' is D1, the dotted line between $C_2$ and $C_3$ is a single bond, and m is 1, then $R_1$ is: =$CH_2$, =CH—$R_6$ or =C($R_6$)$_2$.

In some embodiments, when D' is D1 and m is 2, then each $R_1$ independently is halo and either both $R_1$ are attached to the same carbon atom or one is attached to $C_2$ and the other is attached to $C_3$.

In some embodiments, when D' is D4, the dotted line is a single bond, and $R_{38}$ and $R_{39}$ are each hydrogen.

In some embodiments, T is $C_{2-6}$ alkylene linker.
In some embodiments, T is $C_{2-4}$ alkylene linker.
In some embodiments, T is butylene.
In some embodiments, T is propylene
In some embodiments, T is n-propylene.
In some embodiments, T is ethylene.
In some embodiments, each

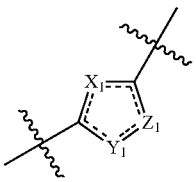

independently is

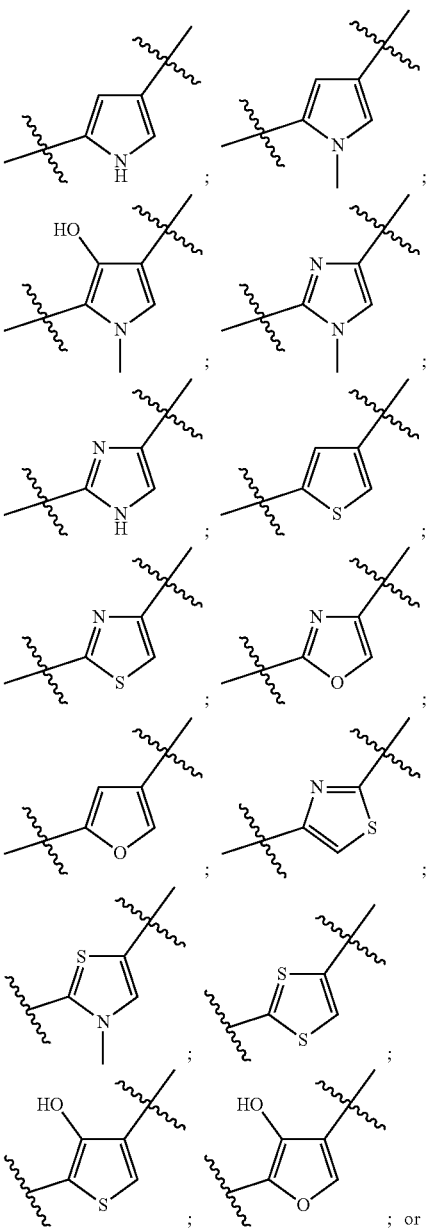

-continued

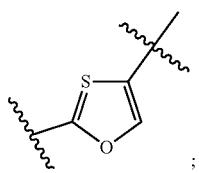

In some embodiments, each

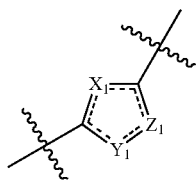

independently is

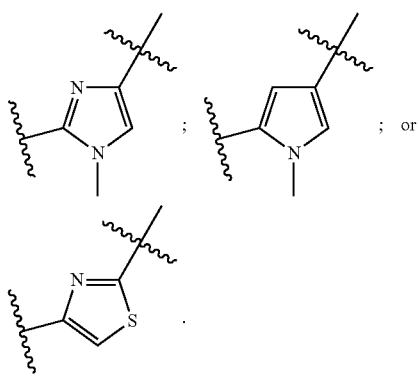

In some embodiments, s is 1, 2, 3, 4 or 5.
In some embodiments, s is 2, 3, 4, 5 or 6.
In some embodiments, s is 1, 2, 3 or 4.
In some embodiments, s is 2, 3, 4 or 5.
In some embodiments, s is 3, 4, 5 or 6.
In some embodiments, s is 1, 2 or 3.
In some embodiments, s is 2, 3 or 4.
In some embodiments, s is 3, 4 or 5.
In some embodiments, s is 4, 5 or 6.
In some embodiments, s is 1 or 2.
In some embodiments, s is 2 or 3.
In some embodiments, s is 3 or 4.
In some embodiments, s is 4 or 5.
In some embodiments, s is 5 or 6.
In some embodiments, s is 1.
In some embodiments, s is 2.
In some embodiments, s is 3.
In some embodiments, s is 4.
In some embodiments, s is 5.
In some embodiments, s is 6.

In some embodiments, A is

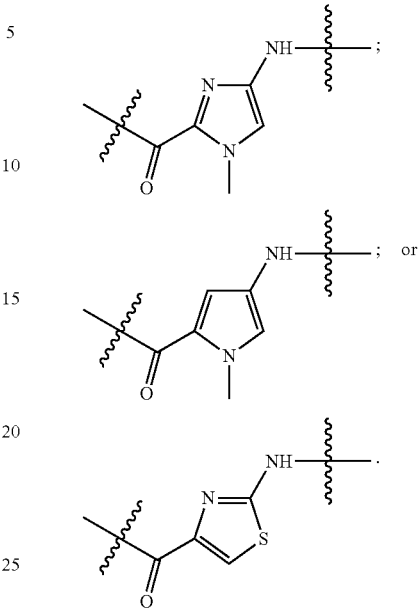

In some embodiments, A is

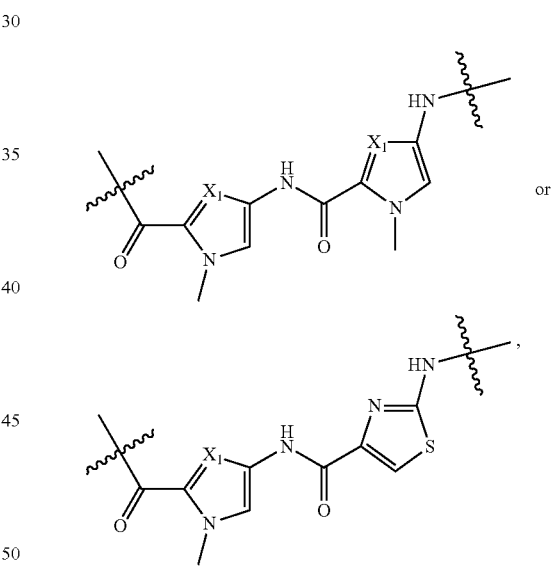

wherein each $X_1$ independently is CH or N.

In some embodiments, A is

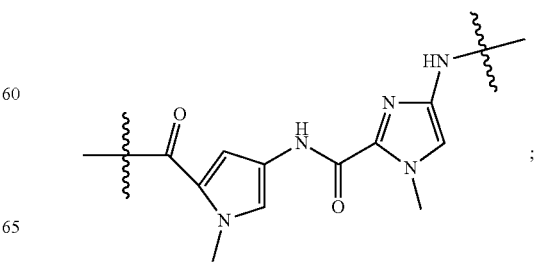

-continued
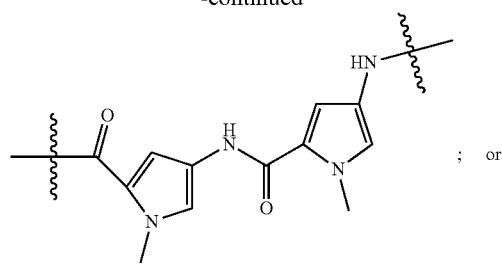
; or
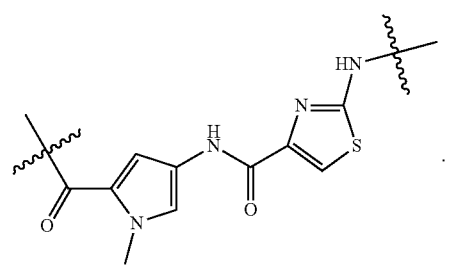
In some embodiments, A is
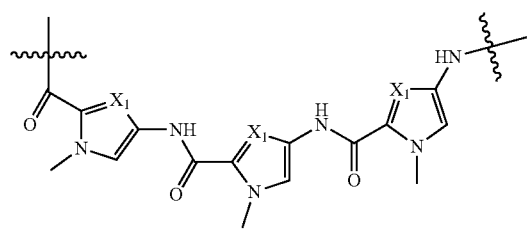
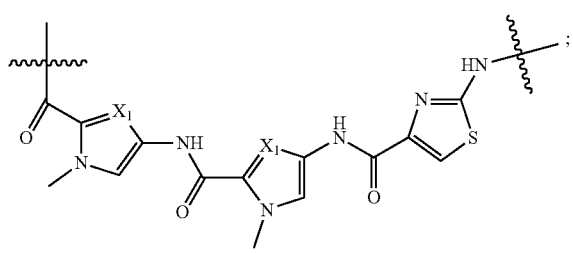
wherein each $X_1$ independently is CH or N.
In some embodiments, A is
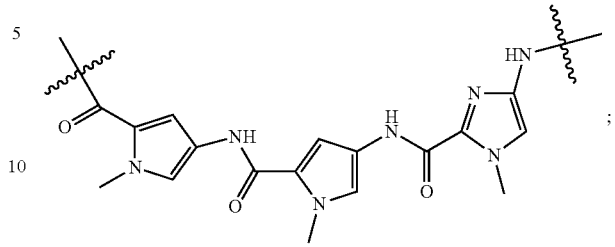
;
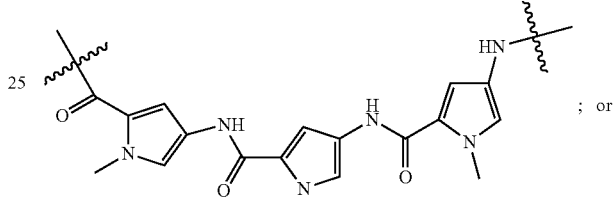
; or
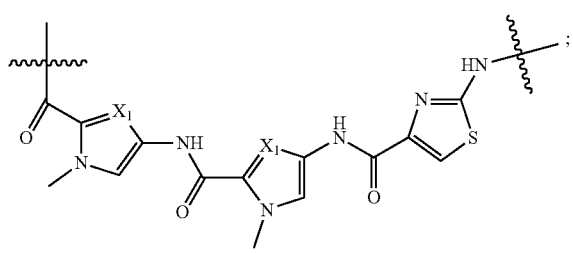
.
In some embodiments, A is:
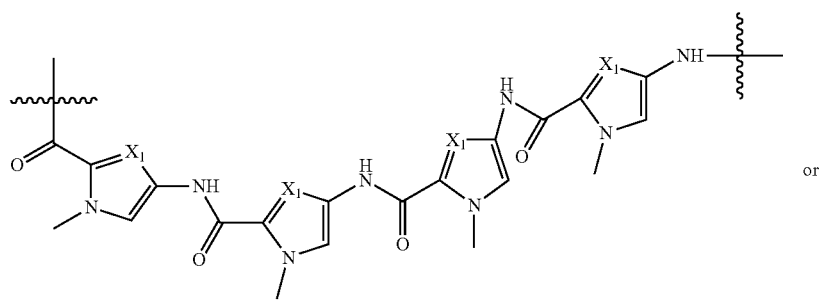
or

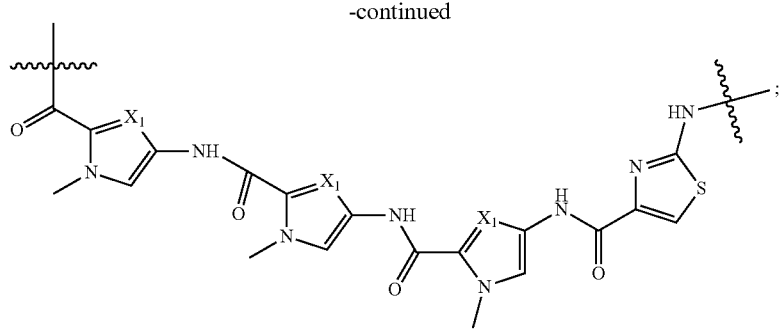
wherein each $X_1$ independently is CH or N.
In some embodiments, A is:
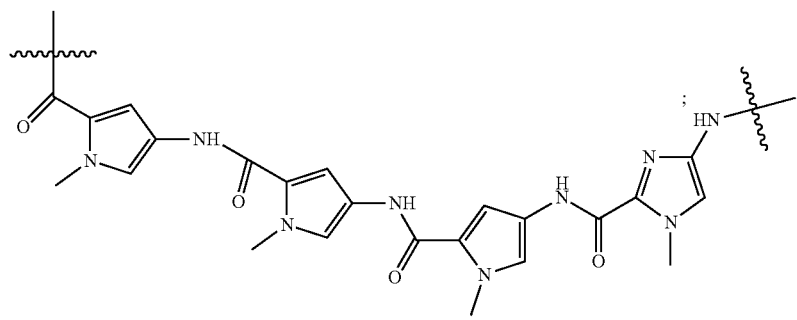
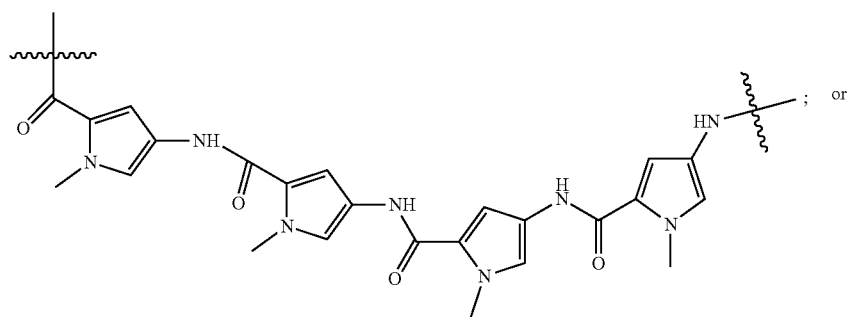
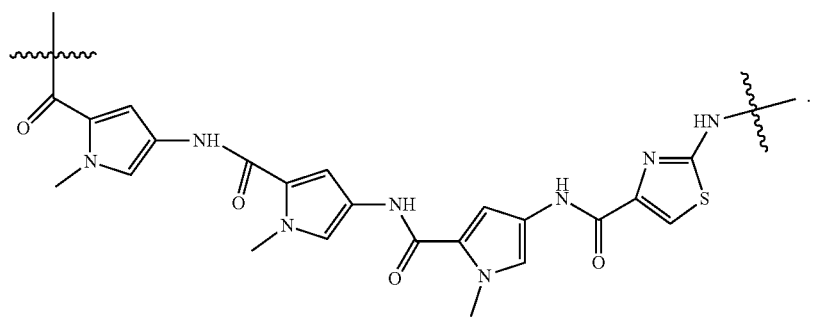

In some embodiments, t is 0.
In some embodiments, t is 1.
In some embodiments, t is 2.
In some embodiments E is -E1, E2, E3 E4, OH, —NH—(C$_{1-6}$ alkylene)-R$_{13a}$, —O—(CH$_2$)$_3$—NH$_2$, —O—CH(CH$_3$)—(CH$_2$)$_2$—NH$_2$ or —NH—(CH$_2$)$_3$—O—C(=O)—CH(CH$_3$)—NH$_2$

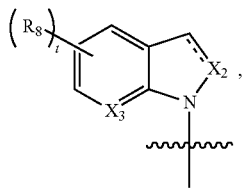
(E1)

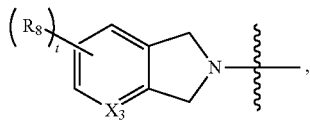
(E2)

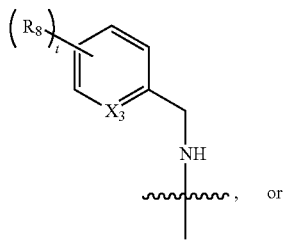
(E3)

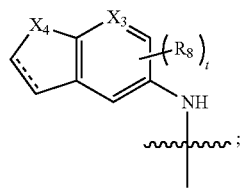
(E4)

wherein the dotted line in E1 or E4 indicates the presence of a single or double bond.

In some embodiments, E is

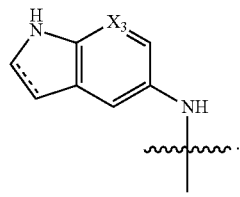

In some embodiments, E is

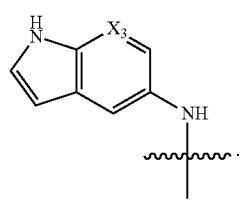

In some embodiments, X$_3$ is CH. In some embodiments, X$_3$ is N.

In some embodiments, when E is

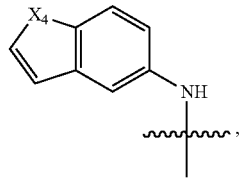

then s is 2, 3, 4, 5 or 6, In some embodiments, s is 2, s is 3, s is 4, s is 5 or s is 6.

In some embodiments, when X$_4$ is O or S, then s is 2, 3, 4, 5 or 6, In some embodiments, s is 2, s is 3, s is 4, s is 5 or s is 6.

In some embodiments, E is

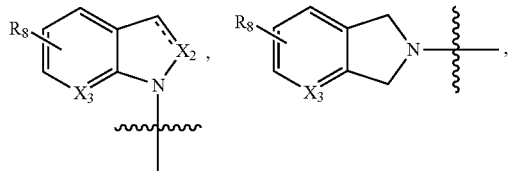

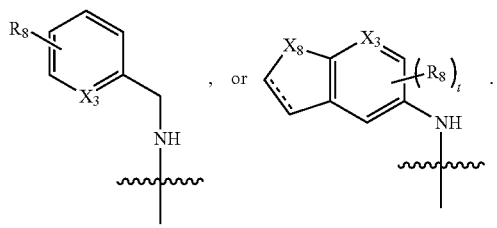

In some embodiments, E is —OH.

In some embodiments, E is —NH—(C$_{1-6}$ alkylene)-OH, wherein C$_{1-6}$ alkylene is a linear or branched alkylene.

In some embodiments, E is —NH—(CH$_2$)$_u$—OH, in which u is 1, 2, 3, 4, 5, or 6.

In some embodiments, E is —NH—(CH$_2$)$_3$—OH.

In some embodiments, E is —O—(CH$_2$)$_3$—NH$_2$.

In some embodiments, E is —O—CH(CH$_3$)—(CH$_2$)$_2$—NH$_2$,

In some embodiments, E is —NH—(CH$_2$)$_3$—O—C(=O)—CH(CH$_3$)—NH$_2$

In some embodiments, E is

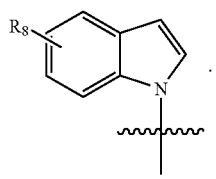

In some embodiments, E is
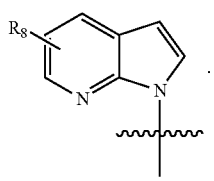
In some embodiments, E is
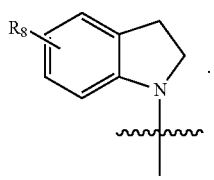
In some embodiments, E is
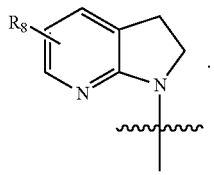
In some embodiments, E is
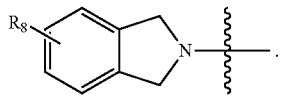
In some embodiments, E is
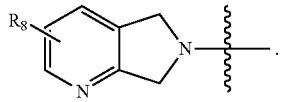
In some embodiments, E is N
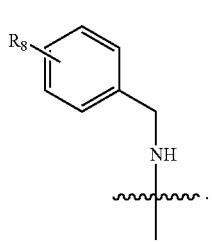
In some embodiments, E is
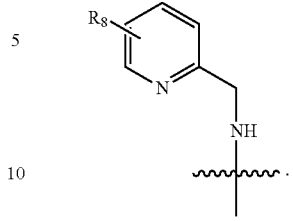
In some embodiments, E is
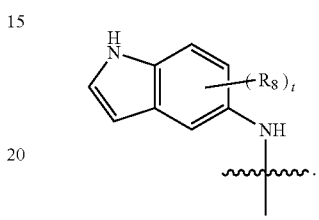
In some embodiments, E is
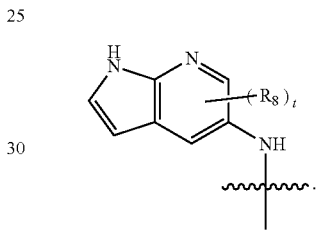
In some embodiments, E is
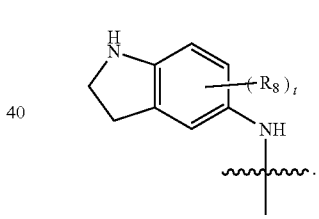
In some embodiments, E is
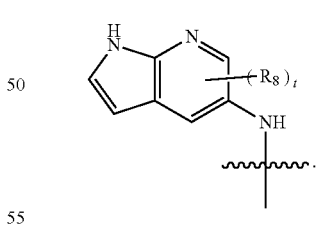
In some embodiments, E is
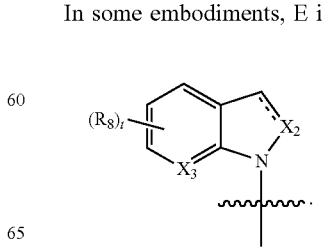

In some embodiments, E is
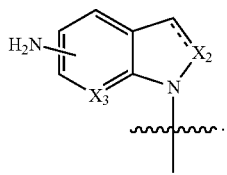
In some embodiments, E is
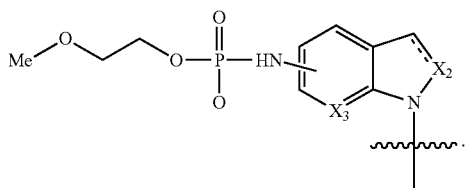
In some embodiments, E is
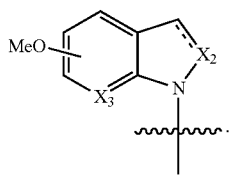
In some embodiments, E is
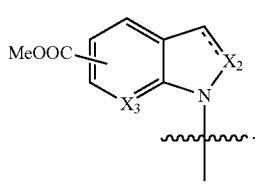
In some embodiments, E is
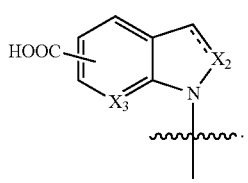
In some embodiments, E is
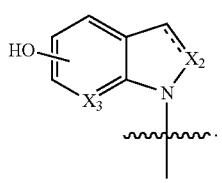
In some embodiments, E is
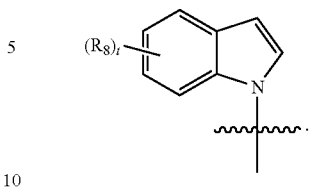
In some embodiments, E is
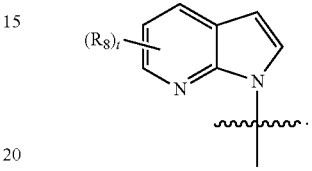
In some embodiments, E is
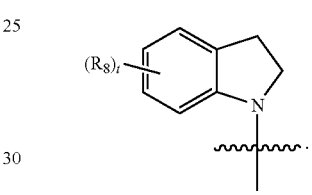
In some embodiments, E is
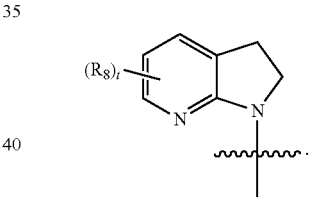
In some embodiments, E is
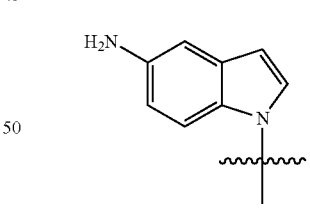
In some embodiments, E is
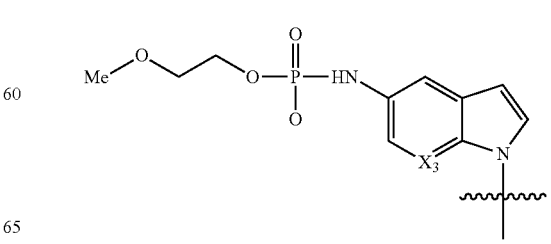

In some embodiments, E is
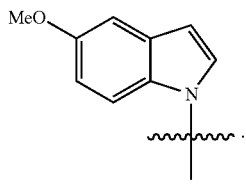 [SMILES: *n1ccc2cc(OC)ccc21]
In some embodiments, E is
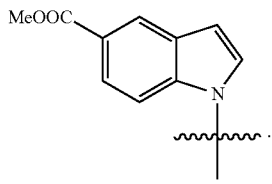 [SMILES: *n1ccc2cc(C(=O)OC)ccc21]
In some embodiments, E is
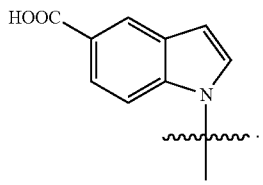
In some embodiments, E is
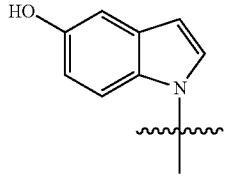 [SMILES: *n1ccc2cc(O)ccc21]
In some embodiments, E is
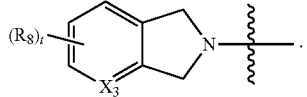
In some embodiments, E is
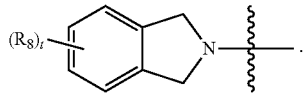
In some embodiments, E is
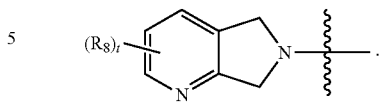
In some embodiments, E is
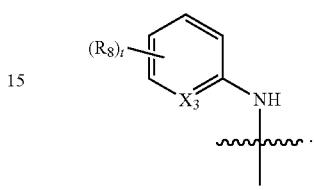
In some embodiments, E is
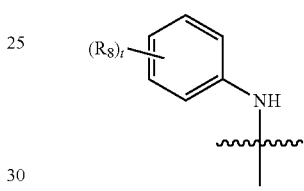
In some embodiments, E is
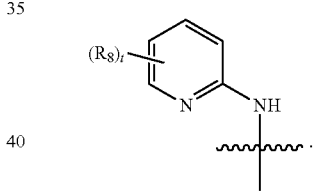
In some embodiments, E is
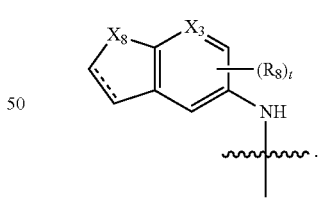
In some embodiments, E is
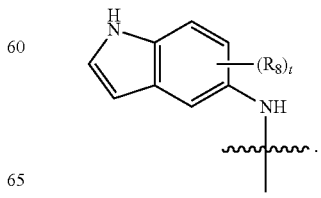

In some embodiments, E is

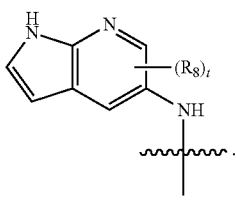

In some embodiments, E is

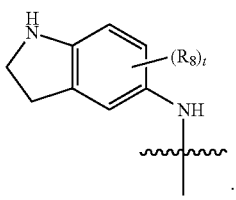

In some embodiments, E is

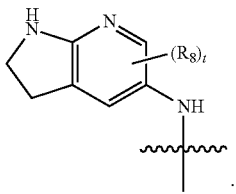

In some embodiments, E is

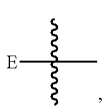

is the functional group of E.

In some embodiments, in

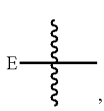

the

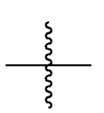

denotes direct or indirect linkage to the PBRM.

In some embodiments, in

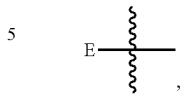

the

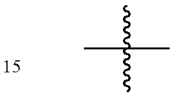

denotes direct or indirect linkage to $L^C$.

In some embodiments, in

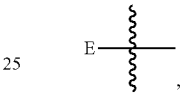

the

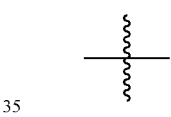

denotes direct or indirect linkage to $L^D$.

In some embodiments, in

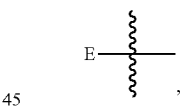

the functional group of E is $R_8$ or a portion thereof.

In some embodiments, in

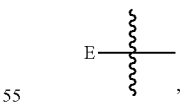

the

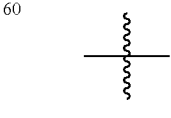

denotes direct or indirect linkage to the PBRM via $R_8$ or a portion thereof.

In some embodiments, in

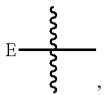, the

denotes direct or indirect linkage to $L^C$ via $R_8$ or a portion thereof.

In some embodiments, in

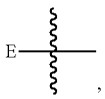, the

denotes direct or indirect linkage to $L^D$ via $R^8$ or a portion thereof.

In some embodiments, each $R_8$ independently is —OH, halo, —NO$_2$, —CN, —N$_3$, —OR$_2$, —COOH, —COOR$_2$, —COR$_2$, —OCONR$_{13}$R$_{14}$, —CO—NH—(C$_{1-6}$ alkylene)-R$_{13a}$, —OCO—NH—(C$_{1-6}$ alkylene)-R$_{13a}$, C$_{3-10}$ cycloalkyl, C$_{2-10}$ alkenyl, C$_{2-10}$ alkynyl, a polyethylene glycol unit —(OCH$_2$CH$_2$)$_r$—OR$_a$, 3- to 14-membered heterocycloalkyl, 5- to 12-membered heteroaryl, —S(=O)$_2$R$_{12}$, —S(=O)$_2$NR$_{13}$R$_{14}$, —SO$_x$M, —OSO$_x$M, —NR$_9$COR$_{19}$, —R$_{20}$—R$_{21}$—NR$_{13}$R$_{14}$, —R$_{20}$—R$_{21}$—NH—P(O)(OH)—(OCH$_2$CH$_2$)$_{n9}$—OCH$_3$, or —O—P(O)(OH)—(OCH$_2$CH$_2$)$_{n9}$—OCH$_3$ In some embodiments, each $R_8$ independently is —CONR$_{13}$R$_{14}$.

In some embodiments, when E is

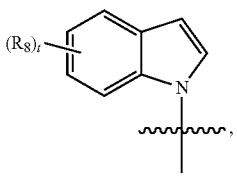, then at least one $R_8$ is —CONR$_{13}$R$_{14}$.

In some embodiments, when E is

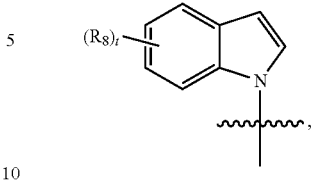, then at least one $R_8$ is —R$_{20}$—R$_{21}$—NH—P(O)(OH)—(OCH$_2$CH$_2$)$_{n9}$—OCH$_3$.

In some embodiments, when E is

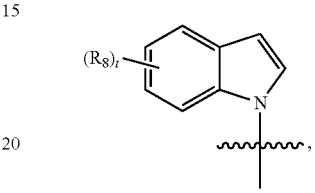, then at least one $R_8$ is —O—P(O)(OH)—(OCH$_2$CH$_2$)$_{n9}$—OCH$_3$.

In some embodiments, each $R_8$ independently is —CO—NH—(C$_{1-6}$ alkylene)-R$_{13a}$ or —OCO—NH—(C$_{1-6}$ alkylene)-R$_{13a}$.

In some embodiments, when E is

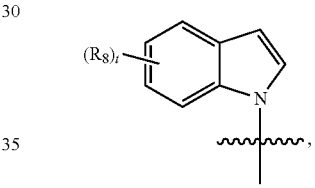, then at least one $R_8$ is —CO—NH—(C$_{1-6}$ alkylene)-R$_{13a}$ or —OCO—NH—(C$_{1-6}$ alkylene)-R$_{13a}$.

In some embodiments, each $R_8$ independently is —OH, halo, —NO$_2$, —CN, —N$_3$, —OR$_2$, —COOH, —COOR$_2$, —COR$_2$, —OCONR$_{13}$R$_{14}$, C$_{1-10}$ alkyl, C$_{3-10}$ cycloalkyl, C$_{2-10}$ alkenyl, C$_{2-10}$ alkynyl, a polyethylene glycol unit —(OCH$_2$CH$_2$)$_r$—OR$_a$, 3- to 14-membered heterocycloalkyl, 5- to 12-membered heteroaryl, —S(=O)$_2$R$_{12}$, —S(=O)$_2$NR$_{13}$R$_{14}$, —SR$_2$, —SO$_x$M, —OSO$_x$M, —NR$_9$COR$_{19}$, —NH(C=NH)NH$_2$, —R$_{20}$—R$_{21}$—NR$_{13}$OR$_{14}$, —R$_{20}$—R$_{21}$—NH—P(O)(OH)—(OCH$_2$CH$_2$)$_{n9}$—OCH$_3$, or —O—P(O)(OH)—(OCH$_2$CH$_2$)$_{n9}$—OCH$_3$.

In some embodiments, each $R_8$ independently is —OH, —OR$_2$, —COOH, —COOR$_2$, —COR$_2$, —OCONR$_{13}$R$_4$, —CONR$_{13}$R$_{14}$, —CO—NH—(C$_{1-6}$ alkylene)-R$_{13a}$, a polyethylene glycol unit —(OCH$_2$CH$_2$)$_r$—OR$_a$, 3- to 7-membered heterocycloalkyl, 5- to 6-membered heteroaryl, —S(=O)$_2$R$_2$, —S(=O)$_2$NR$_{13}$R$_{14}$, —SR$_2$, —R$_{20}$—R$_{21}$—NR$_{13}$R$_{14}$, —R$_{20}$—R$_{21}$—NH—P(O)(OH)—(OCH$_2$CH$_2$)$_{n9}$—OCH$_3$, or —O—P(O)(OH)—(OCH$_2$CH$_2$)$_{n9}$—OCH$_3$ wherein $R_{13}$ and $R_{14}$ are each independently —H or C$_{1-10}$ alkyl;

each $R_{20}$ is phenylene; and each $R_{21}$ independently is C$_{1-4}$ alkylene.

In some embodiments, each $R_8$ independently is —OH, —OR$_2$, —COOH, —COOR$_2$, —COR$_2$, —S(=O)$_2$R$_{12}$, —SR$_{12}$, —R$_{20}$—R$_{21}$—NR$_{13}$R$_{14}$, —R$_{20}$—R$_{21}$—NH—P(O)(OH)—(OCH$_2$CH$_2$)$_{n9}$—OCH$_3$, or —O—P(O)(OH)—(OCH$_2$CH$_2$)$_{n9}$—OCH$_3$.

In some embodiments, each $R_8$ independently is —OH or —$OR_2$.

In some embodiments, each $R_8$ independently is —COH, —$COOR_2$, or —$COR_2$.

In some embodiments, each $R_8$ independently is —S(=O)$_2R_2$ or —$SR_2$.

In some embodiments, each $R_8$ independently is —$CONR_{13}R_{14}$ or —CO—NH—($C_{1-6}$ alkylene)-$R_{13a}$.

In some embodiments, each $R_8$ independently is —$R_{20}$—$R_{21}$—$NR_3R_4$.

In some embodiments, $R_8$ is —$NH_2$.
In some embodiments, $R_8$ is —$CH_2NH_2$.
In some embodiments, $R_8$ is —$CH_2CH_2NH_2$.
In some embodiments, $R_8$ is —$CH_2CH_2CH_2NH_2$.
In some embodiments, $R_8$ is —NH—P(O)(OH)—(OCH$_2$CH$_2$)$_{n9}$—OCH$_3$.
In some embodiments, $R_8$ is —NH—P(O)(OH)—(OCH$_2$CH$_2$)—OCH$_3$.
In some embodiments, $R_8$ is —O—P(O)(OH)—(OCH$_2$CH$_2$)$_{n9}$—OCH$_3$.
In some embodiments, $R_8$ is —O—P(O)(OH)—(OCH$_2$CH$_2$)—OCH$_3$.

In some embodiments, each $R_{13a}$ independently is OH or $NHR_3$.

In some embodiments, each occurrence of $R_{13}$ is independently H or $C_{1-10}$ alkyl (e.g., $C_{1-6}$ alkyl).

In some embodiments, each occurrence of $R_{14}$ is independently H or $C_{1-10}$ alkyl (e.g., $C_{1-6}$ alkyl).

In some embodiments, each occurrence of $R_{13}$ is independently 3- to 20-membered (e.g., 4- to 14-membered) heterocycloalkyl or 5- to 20-membered (e.g., 5- to 10-membered) heteroaryl.

In some embodiments, each occurrence of $R_{14}$ is independently 3- to 20-membered (e.g., 4- to 14-membered) heterocycloalkyl or 5- to 20-membered (e.g., 5- to 10-membered) heteroaryl.

In some embodiments, $R_4$, $R_5$ and $R_7$ are each independently —H, —$R_2$, —OH, —$OR_2$, —SH, —$SR_2$, —$NH_2$, —$NHR_2$, —$NR_2R_3$, —$NO_2$, halo or a polyethylene glycol unit —(OCH$_2$CH$_2$)$_r$—$OR_a$.

In some embodiments, at least one of $R_4$, $R_5$ and $R_7$ is —$OR_2$.

In some embodiments, at least one of $R_4$, $R_5$ and $R_7$ is a polyethylene glycol unit —(OCH$_2$CH$_2$)$_r$—$OR_a$.

In some embodiments, at least two of $R_4$, $R_5$ and $R_7$ are —H.

In some embodiments, two of $R_4$, $R_5$ and $R_7$ are —H, and the other is —$OR_2$.

In some embodiments, two of $R_4$, $R_5$ and $R_7$ are —H, and the other is —$OCH_3$.

In some embodiments, $R_4$ and $R_5$ are each —H, and $R_7$ is —$OCH_3$.

In some embodiments, $R_4$ and $R_5$ are each —H, and $R_7$ is —(OCH$_2$CH$_2$)$_r$—$OR_a$.

In some embodiments, $R_4$ and $R_7$ together form bis-oxy-$C_{1-3}$ alkylene.

In some embodiments, each of $R_{20}$ and $R_{21}$ is a bond.

In some embodiments, one of $R_{20}$ and $R_{21}$ is a bond and the other is not a bond.

In some embodiments, $R_{20}$ is a bond and $R_{21}$ is not a bond.
In some embodiments, $R_{20}$ is a bond and $R_{21}$ is $C_{1-10}$ alkylene.

In some embodiments, $R_{21}$ is a bond and $R_{20}$ is not a bond.

In some embodiments, $R_{21}$ is a bond and $R_{20}$ is $C_{6-10}$ arylene, 3-14 membered heterocycloalkylene or 5- to 12-membered heteroarylene.

In some embodiments, $R^{10}$ and $R^{11}$ taken together with the nitrogen atom and carbon atom to which they are respectively attached, form a N=C double bond.

In some embodiments, $R^{10}$ is —H or a nitrogen protecting group, and R" is -QR$^Q$.

In some embodiments, $R^{10}$ is —H and $R^{11}$ is -QR$^Q$.

In some embodiments, $R^{10}$ is a nitrogen protecting group and R" is -QR$^Q$, wherein the nitrogen protecting group is allyloxycarbonyl (alloc), carbobenzyloxy (Cbz), p-methoxybenzyl carbonyl (Moz or MeOZ), acetyl (Ac), benzoyl (Bz), benzyl (Bn), trichloroethoxycarbonyl (Troc), t-butoxycarbonyl (BOC) or 9-fluorenylmethylenoxycarbonyl (Fmoc).

In some embodiments, $R^{11}$ is —OSO$_x$M.
In some embodiments, $R^{11}$ is —SO$_x$M.
In some embodiments, $R^{11}$ is —OH.
In some embodiments, $R^{11}$ is —OPO$_3$M.
In some embodiments, $R^{11}$ is —O(CH$_2$CH$_2$O)$_{n9}$CH$_3$.
In some embodiments, $R^{11}$ is —O—(CH$_2$—CH$_2$O)$_{n9}$—(CH$_2$)$_2$—$R_{40}$.
In some embodiments, $R^{11}$ is —OC(O)O—(CH$_2$—CH$_2$—O)$_{n9}$CH$_3$.
In some embodiments, $R^{11}$ is —OC(O)NH—(CH$_2$—CH$_2$—O)$_{n9}$CH$_3$.
In some embodiments, $R^{11}$ is -O—(CH$_2$)$_n$—NH—C(O)—CH$_2$—O—CH$_2$—C(O)—NH—(CH$_2$—CH$_2$—O)$_{n9}$CH$_3$.
In some embodiments, $R^{11}$ is —O—(CH$_2$), —NH—C(O)—(CH$_2$)—(CH$_2$—CH$_2$—O)$_{n9}$CH$_3$.
In some embodiments, $R^{11}$ is —O-sugar moiety.

In some embodiments, $R^{15}$, $R_{16}$, $R_{17}$ and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—$OR_a$, 3-14 membered heterocycloalkyl, 5- to 12-membered heteroaryl, —$NR_{13}R_{14}$, —S(=O)$_2R_{12}$, —S(=O)$_2NR_{13}R_{14}$, —$SR_{12}$ or —NH(C=NH)NH$_2$.

In some embodiments, at least one of $R_{15}$, $R_{16}$, $R_{17}$ and $R_{18}$ is —H.

In some embodiments, at least two of $R_{15}$, $R_{16}$, $R_{17}$ and $R_{18}$ is —H.

In some embodiments, at least three of $R_{15}$, $R_{16}$, $R_{17}$ and $R_{18}$ is —H.

In some embodiments, $R_{15}$, $R_{16}$, $R_{17}$ and $R_{18}$ are each —H or —$NR_{13}R_{14}$.

In some embodiments, at least one of $R_{15}$, $R_{16}$, $R_{17}$ and $R_{18}$ is —$NR_{13}R_{14}$.

In some embodiments, at least one of $R_{15}$, $R_{16}$, $R_{17}$ and $R_{18}$ is —$NH_2$.

In some embodiments, one of $R_{15}$, $R_{16}$, $R_{17}$ and $R_{18}$ is —$NR_3R_4$.

In some embodiments, one of $R_{15}$, $R_{16}$, $R_{17}$ and $R_{18}$ is —$NH_2$.

In some embodiments, $R_{16}$, $R_{17}$ and $R_{18}$ are each —H; and $R_{15}$ is —$NH_2$.

In some embodiments, $R_{15}$, $R_{17}$ and $R_{18}$ are each —H; and $R_{16}$ is —$NH_2$.

In some embodiments, $R_{15}$, $R_{16}$ and $R_{18}$ are each —H; and $R_{17}$ is —$NH_2$.

In some embodiments, $R_{15}$, $R_{16}$ and $R_{17}$ are each —H; and Rig is —$NH_2$.

In some embodiments, $X_0$ is $CH_2$, $NR_6$, or C=O.
In some embodiments, $Y_0$ is O, $CH_2$, or $NR_6$.
In some embodiments, $Z_0$ is absent.
In some embodiments, $Z_0$ is $(CH_2)_n$, and n is 1 or 2.
In some embodiments, when Q is S or NH, then R$^Q$ is —H.

In some embodiments, when Q is S or NH, then $R^Q$ is optionally substituted $C_{1-2}$ alkyl.

In some embodiments, when Q is O, then $R^Q$ is —H.

In some embodiments, when Q is O, then $R^Q$ is optionally substituted $C_{1-2}$ alkyl.

In some embodiments, when Q is O, then $R^Q$ is —$SO_xM$.

In some embodiments, when Q is O, then $R^Q$ is hydrogen.

In some embodiments, when Q is O, then $R^Q$ is —$PO_3M$.

In some embodiments, when Q is O, then $R^Q$ is —($CH_2$—$CH_2$—$O)_{n_9}CH_3$, and n is 6, 8, 12 or 24.

In some embodiments, when Q is O, then $R^Q$ is —C(O)—($CH_2$—$CH_2$—$O)_{n_9}CH_3$ and n is 6, 8, 12 or 24

In some embodiments, when Q is O, then $R^Q$ is —C(O)—($CH_2$—$CH_2$—$O)_9CH_3$ and $n_9$ is 6, 8, 12 or 24.

In some embodiments, when Q is O, then $R^Q$ is —C(O)NH—($CH_2$—$CH_2$—$O)_{n_9}CH_3$ and $n_9$ is 6, 8, 12 or 24.

In some embodiments, when Q is O, then $R^Q$ is —($CH_2$)—NH—C(O)—$CH_2$—O—$CH_2$—C(O)—NH—($CH_2$—$CH_2$—$O)_{n_9}CH_3$, and n is 2 and $n_9$ is 6, 8, 12 or 24.

In some embodiments, when Q is O, then $R^Q$ is —($CH_2$)$_n$—NH—C(O)—($CH_2$)$_n$—($CH_2$—$CH_2$—$O)_{n_9}CH_3$, and n is 2 and $n_9$ is 6, 8, 12 or 24.

In some embodiments, when Q is O, then $R^Q$ is a -sugar moiety.

In some embodiments, when Q is O, then $R^Q$ is

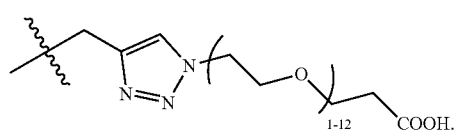

In some embodiments, when Q is O, then $R^Q$ is

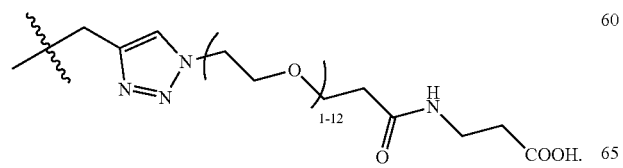

In some embodiments, when Q is O, then $R^Q$ is

In some embodiments, when Q is O, then $R^Q$ is

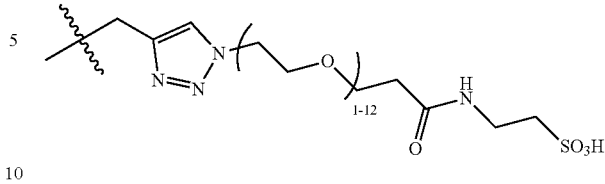

In some embodiments, when Q is O, then $R^Q$ is

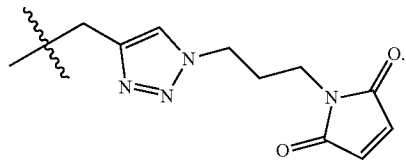 [SMILES: *Cc1cn(CCCN2C(=O)C=CC2=O)nn1]

In some embodiments, when Q is O, then $R^Q$ is.

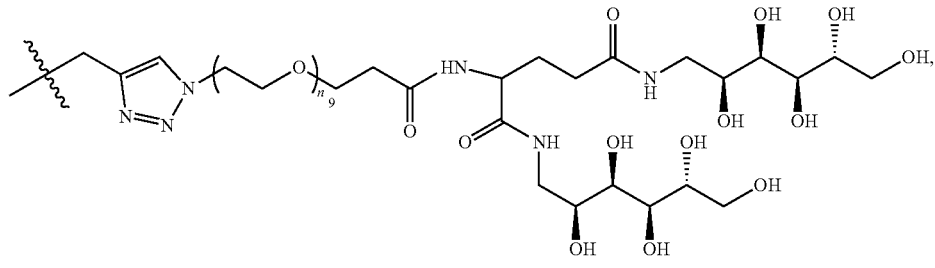

and $n_9$ is 6, 8, 12 or 24

In some embodiments, when Q is O, then $R^Q$

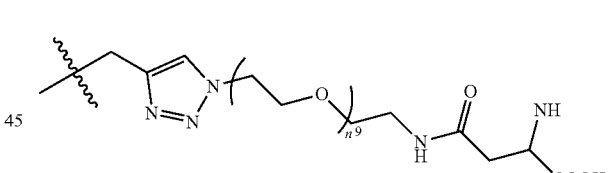

and $n_9$ is 6, 8, 12 or 24

In some embodiments, the compound of Formula (I) contains at most one —$SO_xM$ or —$OSO_xM$.

In some embodiments, $R^{11}$ is —$OSO_xM$, —$SO_xM$, —OH, —$OCH_3$, O—($CH_2$)$_2$—NH—C(O)—$CH_2$—O—$CH_2$—C(O)—NH—($CH_2$—$CH_2$—$O)_8CH_3$.

In some embodiments,

is

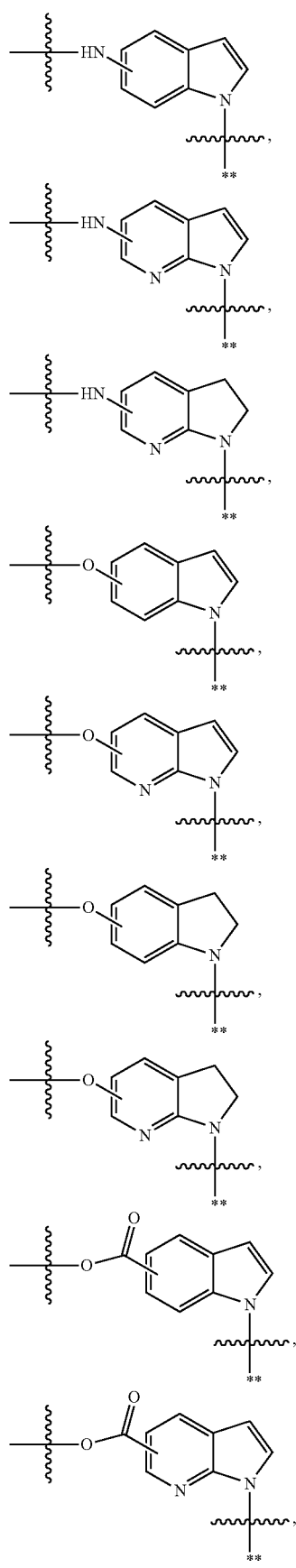
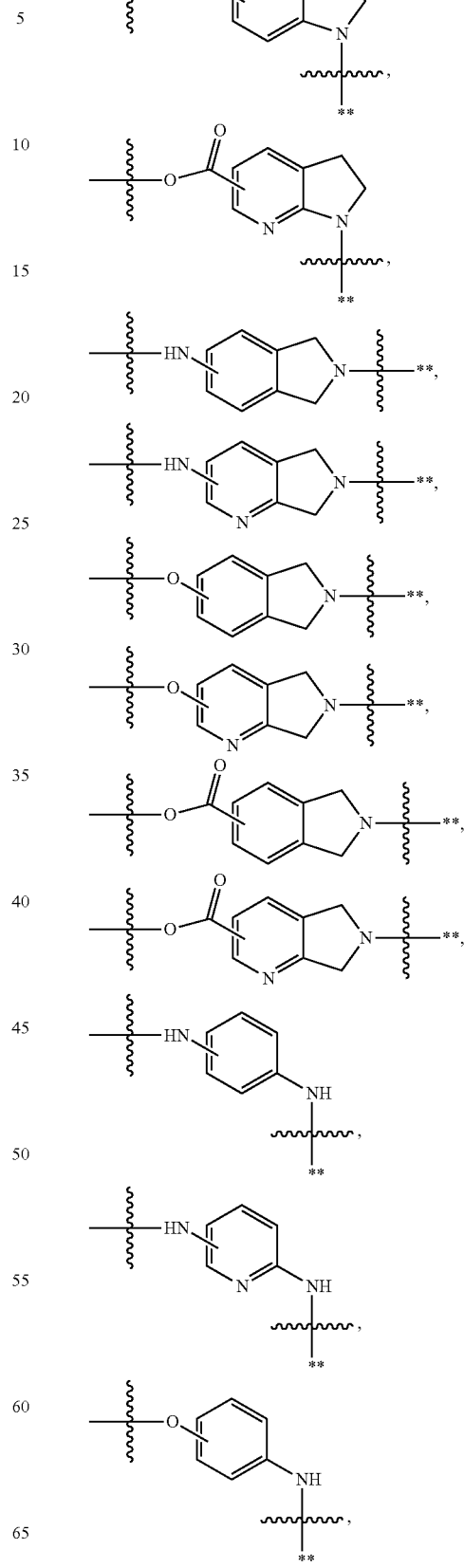

-continued
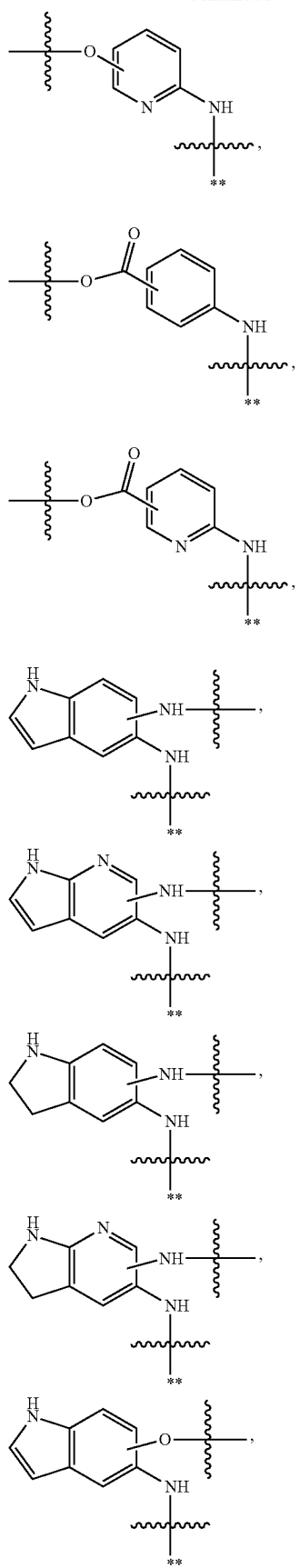
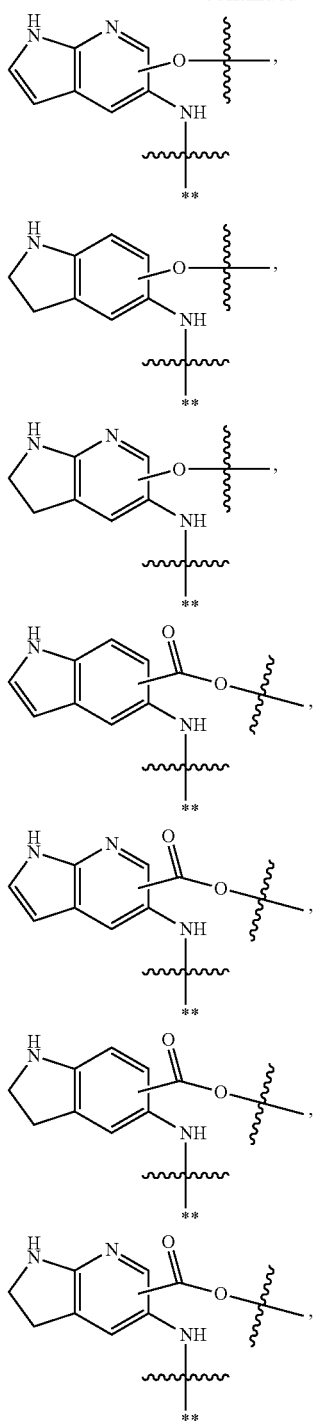
in which
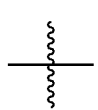
denotes a direct or indirect linkage to the PBRM, $L^C$, or $L^D$, and

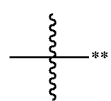
denotes a direct or indirect linkage to a remaining portion of D (e.g., a direct or indirect linkage to A).
In some embodiments,
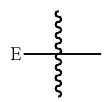
is
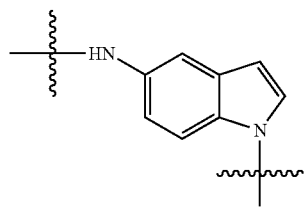
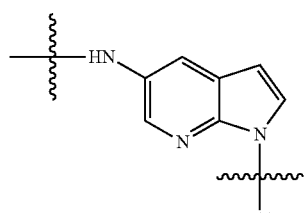
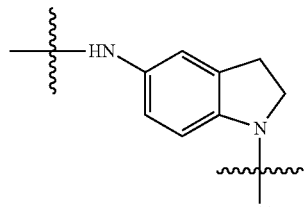
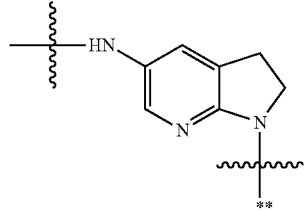
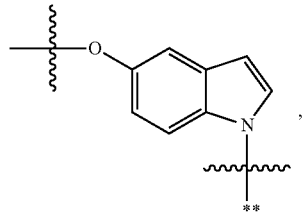
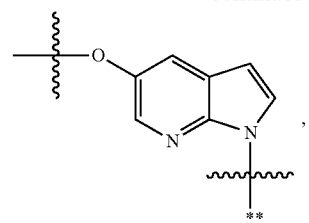
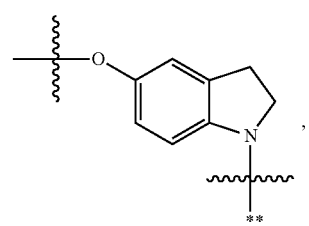
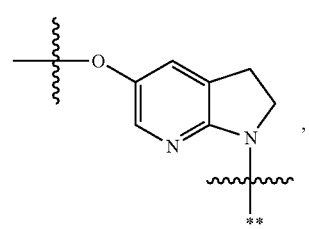
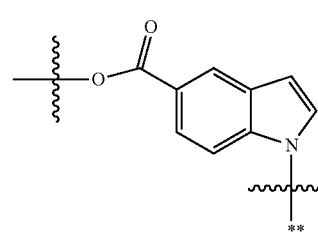
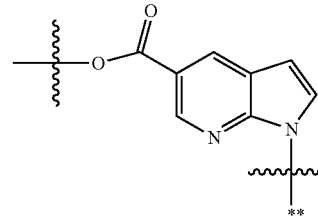
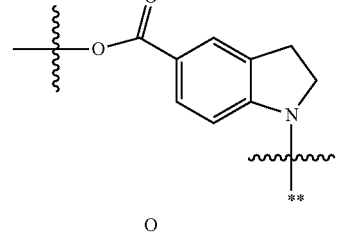, or
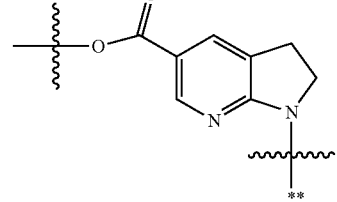
in which

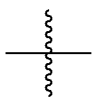

denotes a direct or indirect linkage to the PBRM, $L^C$, or $L^D$, and

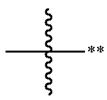

denotes a direct or indirect linkage to a remaining portion of D (e.g., a direct or indirect linkage to A).

In some embodiments,

is

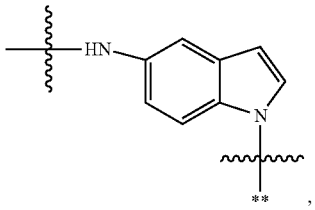

in which

denotes a direct or indirect linkage to the PBRM, $L^C$, or $L^D$, and

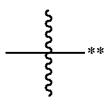

denotes a direct or indirect linkage to a remaining portion of D (e.g., a direct or indirect linkage to A).

In some embodiments,

is

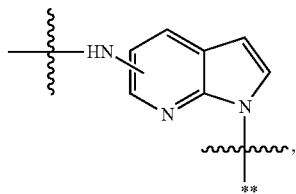

in which

denotes a direct or indirect linkage to the PBRM, $L^C$, or $L^D$, and

denotes a direct or indirect linkage to a remaining portion of D (e.g., a direct or indirect linkage to A).

In some embodiments, E is

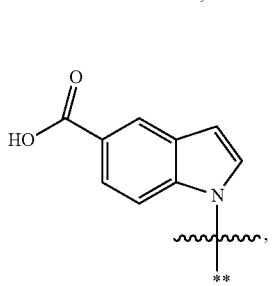

in which

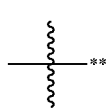

denotes a direct or indirect linkage to a remaining portion of D (e.g., a direct or indirect linkage to A).

In some embodiments, E is

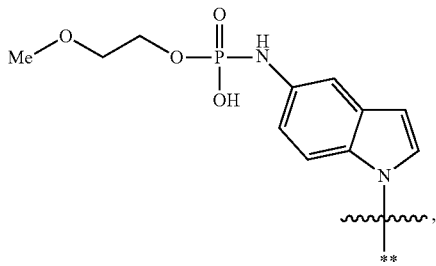

in which

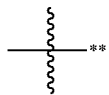
denotes a direct or indirect linkage to a remaining portion of D (e.g., a direct or indirect linkage to A).
In some embodiments, the PBD drug moiety of Formula (IV) is of any one of Formulae (IX-a to IX-r):
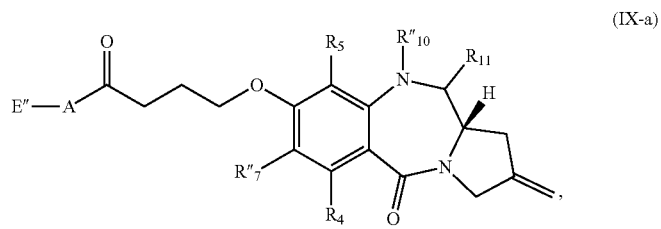
(IX-a)
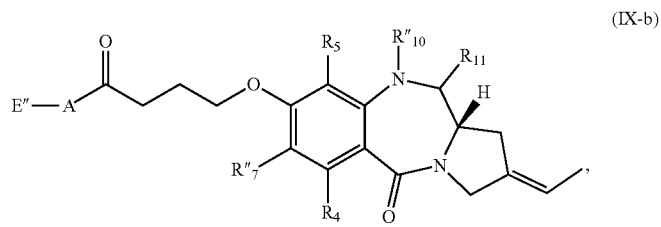
(IX-b)
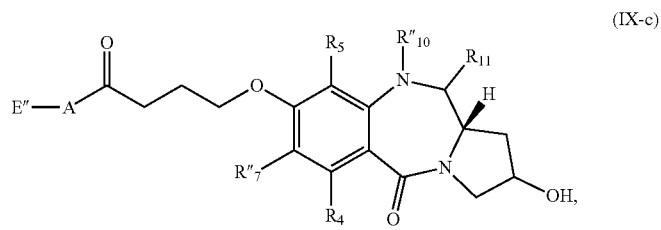
(IX-c)
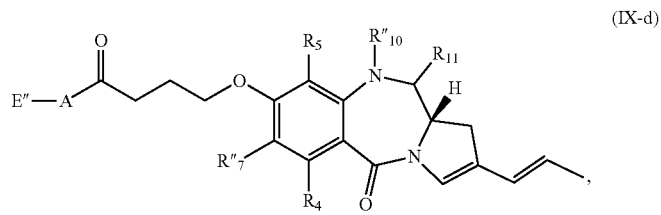
(IX-d)
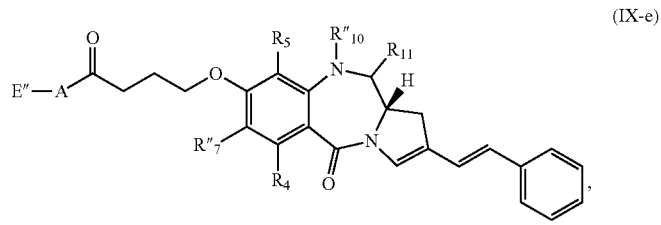
(IX-e)
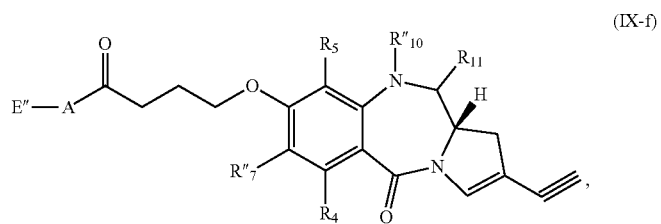
(IX-f)

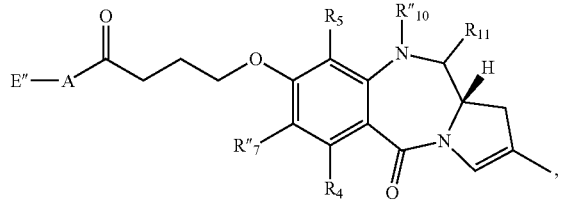
(IX-g)
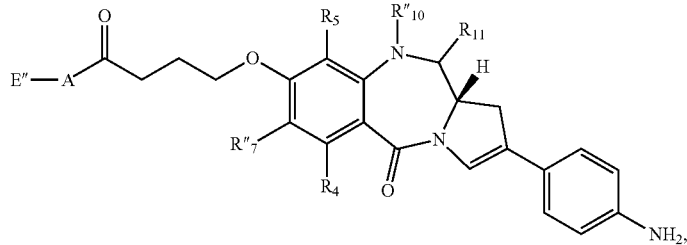
(IX-h)
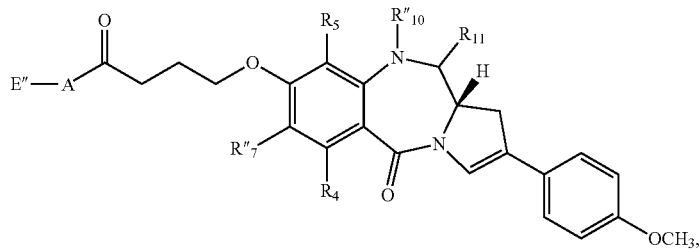
(IX-i)
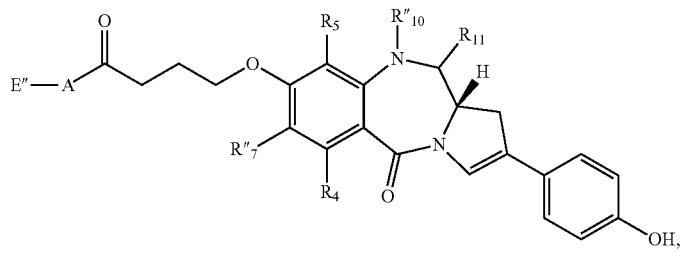
(IX-j)
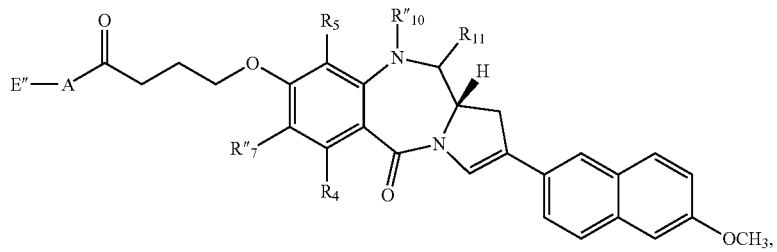
(IX-k)
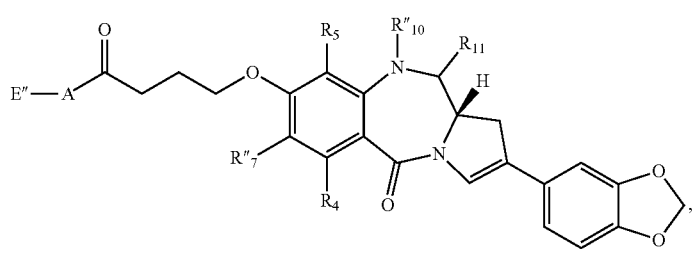
(IX-l)

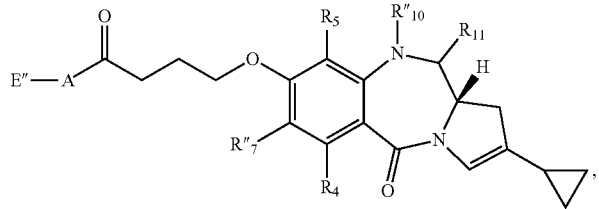
(IX-m)
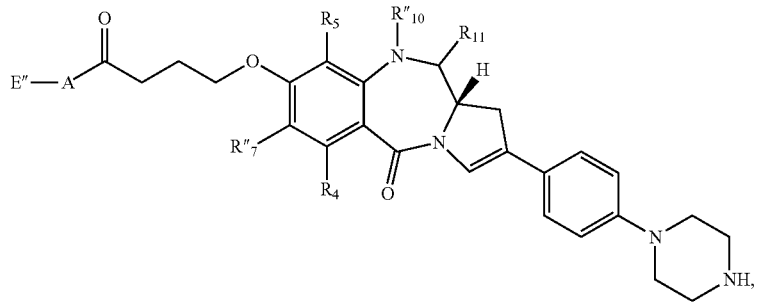
(IX-n)
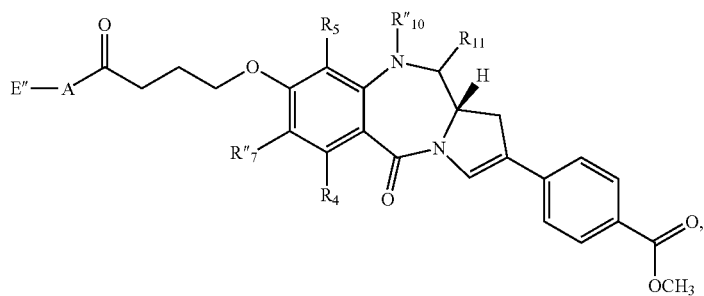
(IX-o)
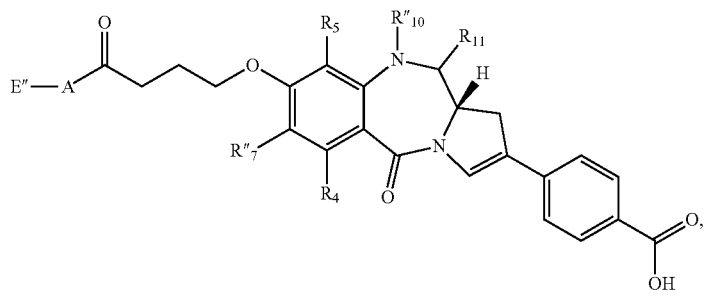
(IX-p)
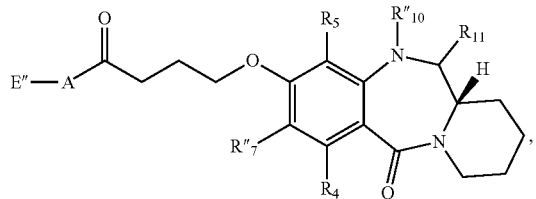
(IX-q)
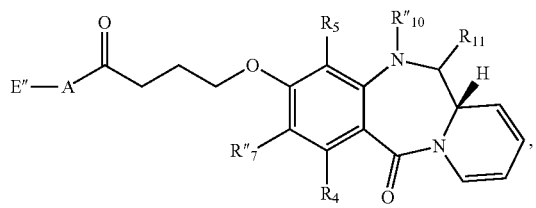
(IX-r)

a tautomer thereof, a pharmaceutically acceptable salt or solvate thereof, or a pharmaceutically acceptable salt or solvate of the tautomer.

In some embodiments, the conjugates of any one of Formulae (IX-a)-(IX-r) include those where each of the moieties defined for one of E", A, $R_4$, $R_5$, $R''_7$, $R''_{10}$, and $R_1$ can be combined with any of the moieties defined for the others of E", A, $R_4$, $R_5$, $R''_7$, $R''_{10}$, and $R_{11}$.

In some embodiments, the PBD drug moiety of Formula (IV) is of any one of Formulae (X-a) to (X-c):

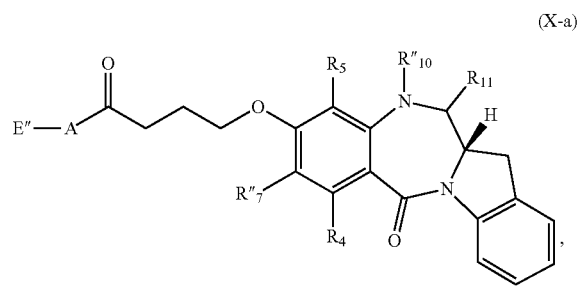
(X-a)

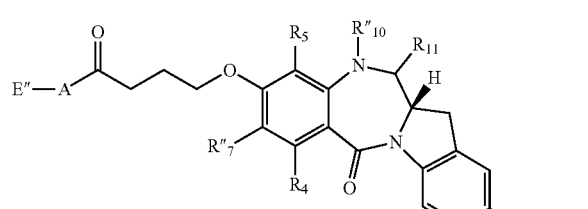
(X-b)

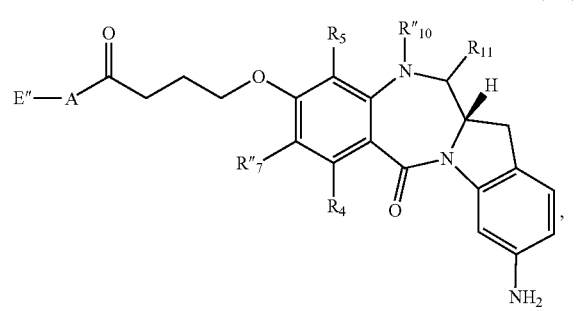
(X-c)

a tautomer thereof, a pharmaceutically acceptable salt or solvate thereof, or a pharmaceutically acceptable salt or solvate of the tautomer.

In some embodiments, the conjugates of any one of Formulae (X-a)-(X-c) include those where each of the moieties defined for one of E", A, $R_4$, $R_5$, $R''_7$, $R''_{10}$, and $R_{11}$ can be combined with any of the moieties defined for the others of E", A, $R_4$, $R_5$, $R''_7$, $R''_{10}$, and $R_{11}$.

In some embodiments, the PBD drug moiety of Formula (IV) is of any one of Formulae (XI-a) to (XI-c):

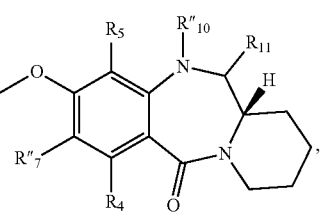
(XI-a)

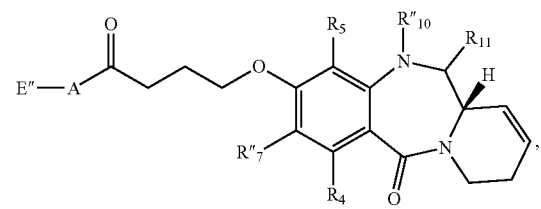
(XI-b)

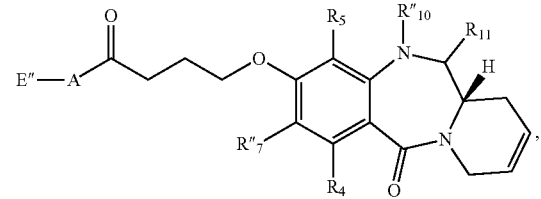
(XI-c)

a tautomer thereof, a pharmaceutically acceptable salt or solvate thereof, or a pharmaceutically acceptable salt or solvate of the tautomer.

In some embodiments, the conjugates of any one of Formulae (XI-a)-(XI-c) include those where each of the moieties defined for one of E", A, $R_4$, $R_5$, $R''_7$, $R''_{10}$, and $R_{11}$ can be combined with any of the moieties defined for the others of E", A, $R_4$, $R_5$, $R''_7$, $R''_{10}$, and $R_{11}$.

In some embodiments, the PBD drug moiety of Formula (IV) is

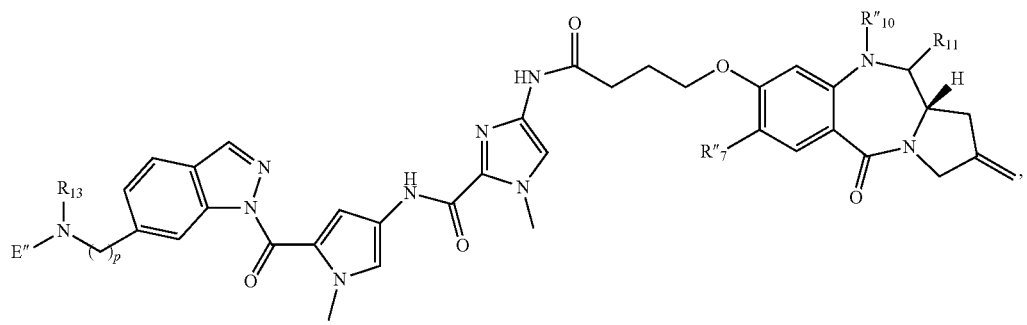

a tautomer thereof, a pharmaceutically acceptable salt or solvate thereof, or a pharmaceutically acceptable salt or solvate of the tautomer, wherein:

$R_{13}$ is H;

p is 1, 2, 3 or 4, and

E", $R''_7$, $R''_{10}$ and $R_{11}$ are as defined herein.

In some embodiments, the PBD drug moiety of Formula (IV) is of Formula (XII):

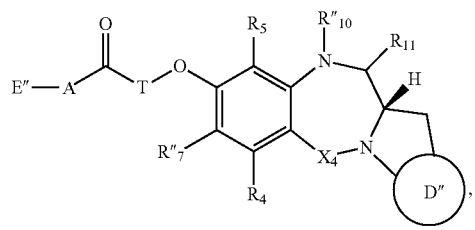

(XII)

a tautomer thereof, a pharmaceutically acceptable salt or solvate thereof, or a pharmaceutically acceptable salt or solvate of the tautomer.

In some embodiments, the conjugates of Formula (XII) include those where each of the moieties defined for one of E", A, T, $R_4$, $R_5$, $R''_7$, $R''_{10}$, $R_{11}$, $X_4$, and D" can be combined with any of the moieties defined for the others of E", A, T, $R_4$, $R_5$, $R''_7$, $R''_{10}$, $R_{11}$, $X_4$, and D".

In the PBD drug moiety of Formula (XII) above, $X_4$ is C=S, $CH_2$, SO, $SO_2$ or BH; and E", A, T, D", $R_4$, $R_5$, $R''_7$, $R''_{10}$ and $R_{11}$ are as defined herein.

In some embodiments, the PBD drug moiety of Formula (XII) is of any one of Formulae (XII-a) to (XII-e):

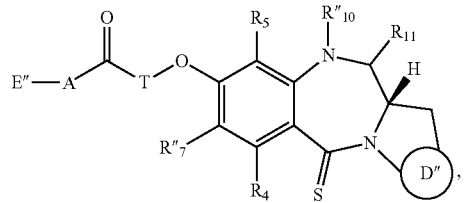

(XIIa)

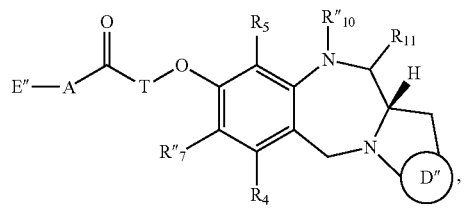

(XIIb)

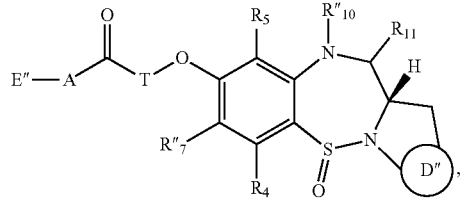

(XIIc)

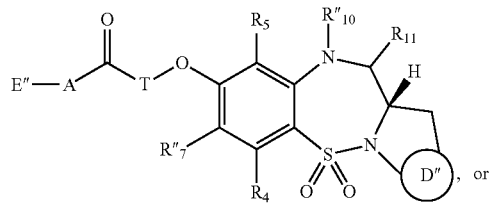

(XIId)

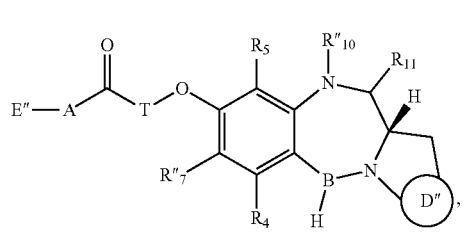

(XIIe)

a tautomer thereof, a pharmaceutically acceptable salt or solvate thereof, or a pharmaceutically acceptable salt or solvate of the tautomer.

In some embodiments, the conjugates of any one of Formulae (XIIa)-(XIIe) include those where each of the moieties defined for one of E", A, T, $R_4$, $R_5$, $R''_7$, $R''_{10}$, $R_{11}$, and D" can be combined with any of the moieties defined for the others of E", A, T, $R_4$, $R_5$, $R''_7$, $R''_{10}$, $R_{11}$, and D".

In some embodiments, the PBD drug moiety (D), prior to being connected to another portion of the conjugate (e.g., the linker unit ($L^C$)), corresponds to a compound selected from the compounds listed in Table 1, tautomers thereof, pharmaceutically acceptable salts or solvates thereof, or pharmaceutically acceptable salts or solvates of the tautomers.

TABLE I

| Structure |
| --- |
| 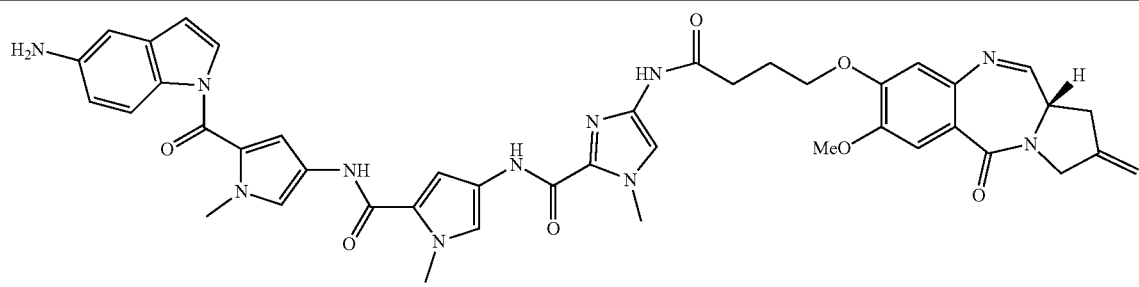 |

TABLE I-continued
Structure
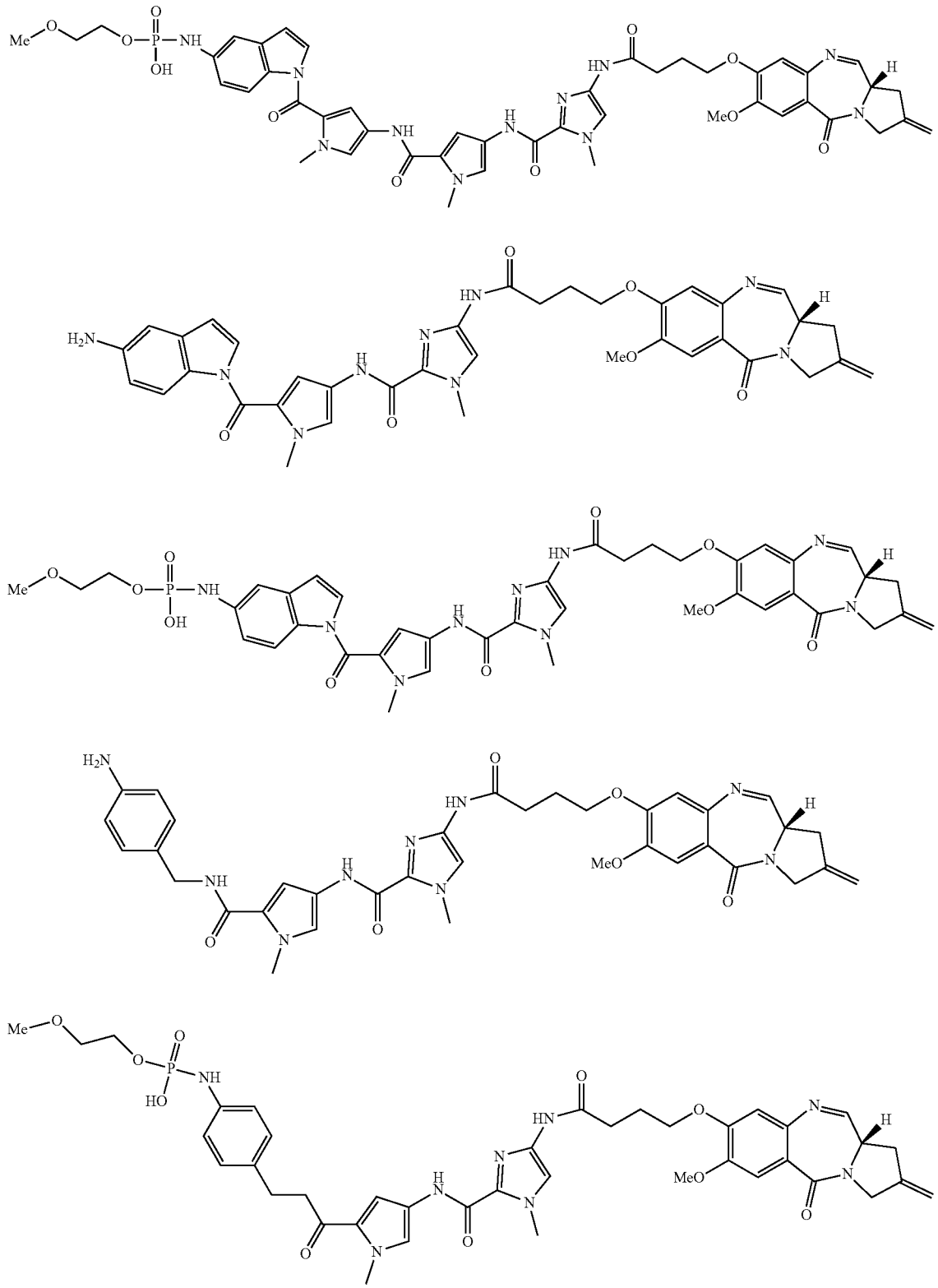

TABLE I-continued

Structure

TABLE I-continued
Structure
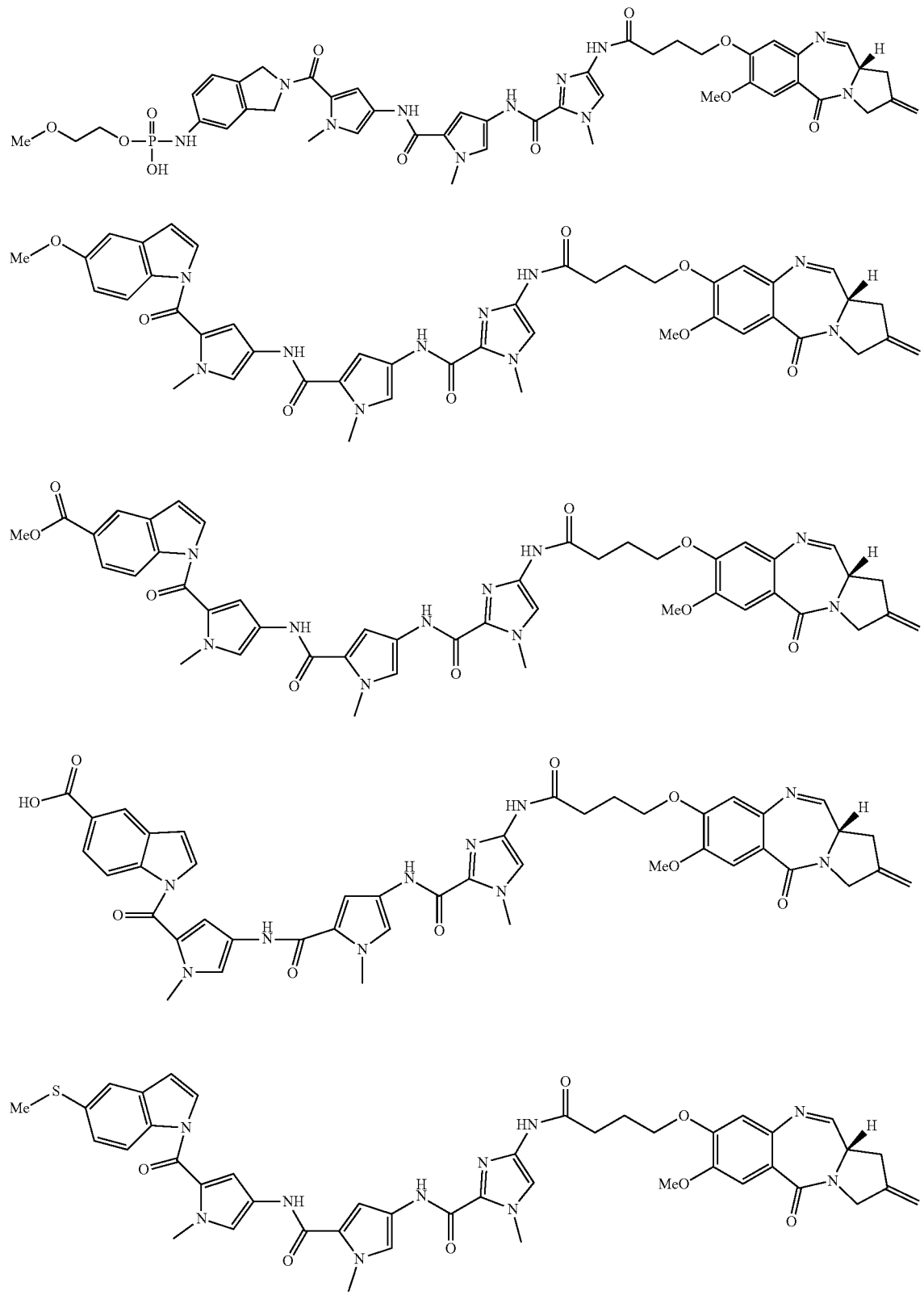

TABLE I-continued
Structure
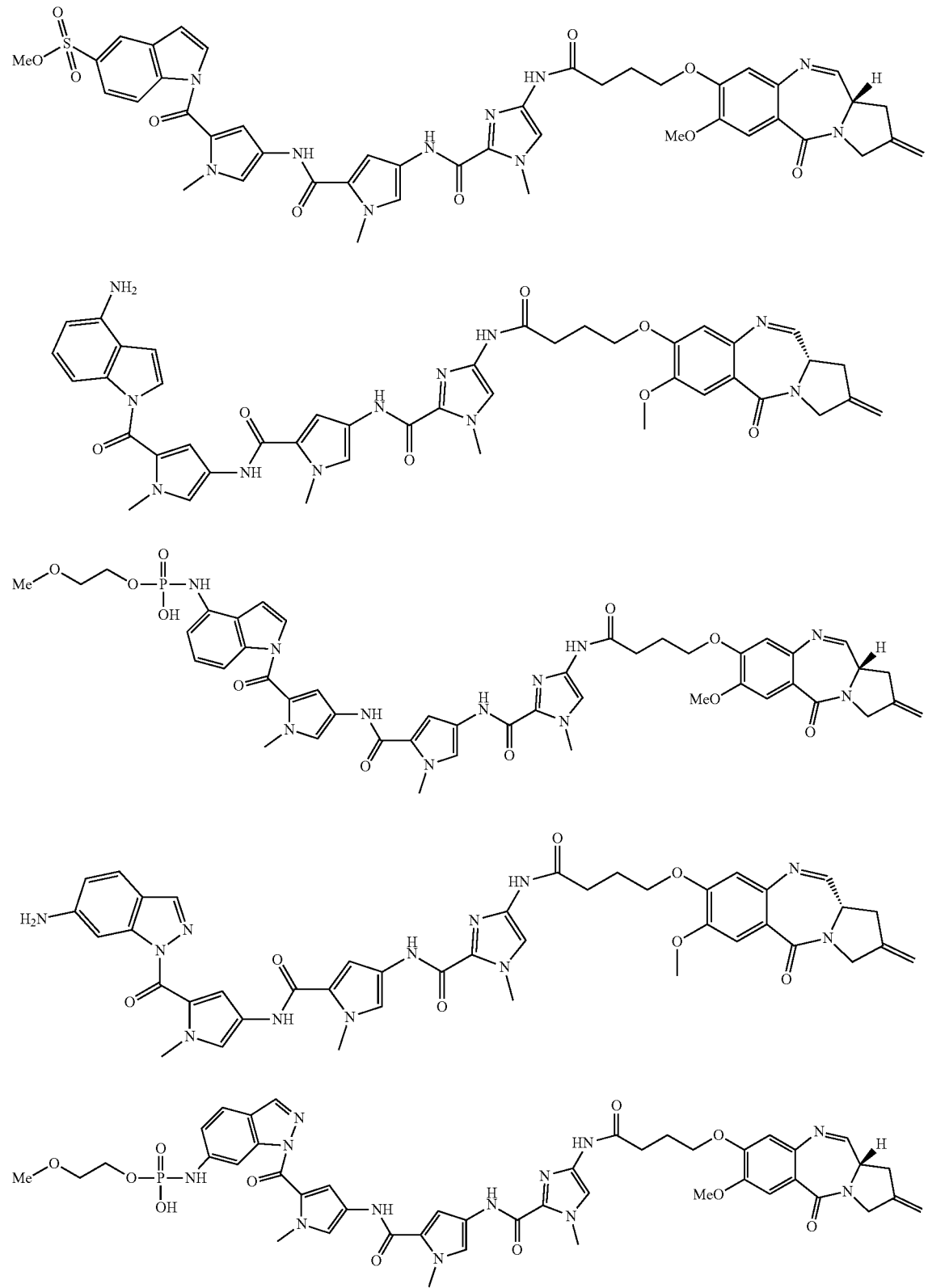

TABLE I-continued
Structure
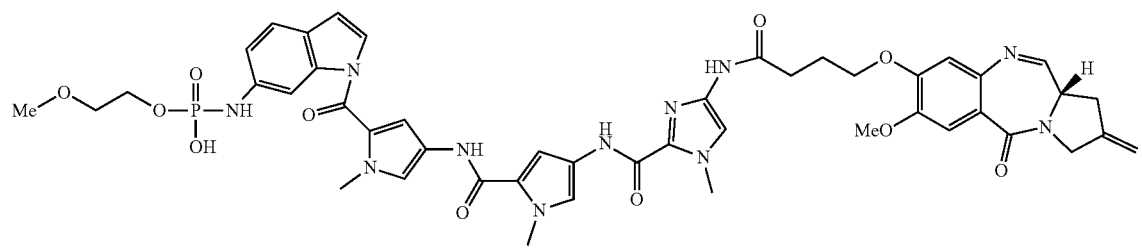 [SMILES: C=C1C[C@H]2C=Nc3cc(OCCCC(=O)Nc4cn(C)c(C(=O)Nc5cc(C(=O)Nc6cc(C(=O)n7ccc8ccc(NP(=O)(O)OCCOC)cc87)n(C)c6)n(C)c5)n4)c(OC)cc3C(=O)N2C1]
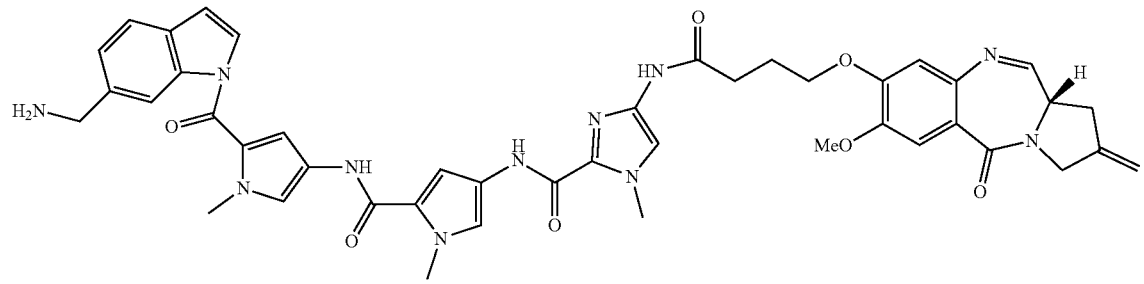 [SMILES: C=C1C[C@H]2C=Nc3cc(OCCCC(=O)Nc4cn(C)c(C(=O)Nc5cc(C(=O)Nc6cc(C(=O)n7ccc8ccc(CN)cc87)n(C)c6)n(C)c5)n4)c(OC)cc3C(=O)N2C1]
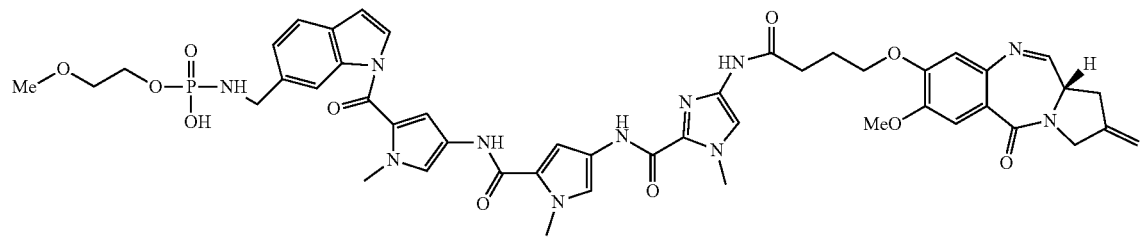 [SMILES: C=C1C[C@H]2C=Nc3cc(OCCCC(=O)Nc4cn(C)c(C(=O)Nc5cc(C(=O)Nc6cc(C(=O)n7ccc8ccc(CNP(=O)(O)OCCOC)cc87)n(C)c6)n(C)c5)n4)c(OC)cc3C(=O)N2C1]
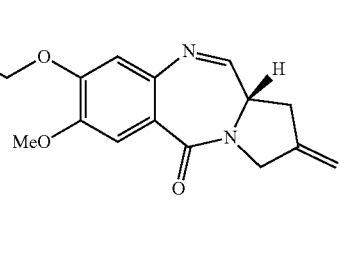
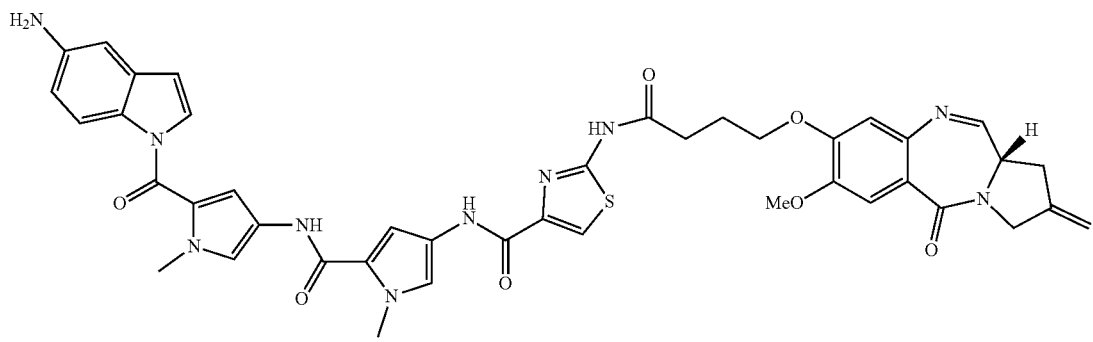 [SMILES: C=C1C[C@H]2C=Nc3cc(OCCCC(=O)Nc4nc(C(=O)Nc5cc(C(=O)Nc6cc(C(=O)n7ccc8cc(N)ccc87)n(C)c6)n(C)c5)cs4)c(OC)cc3C(=O)N2C1]

US 11,638,760 B2
187 188
TABLE I-continued
Structure
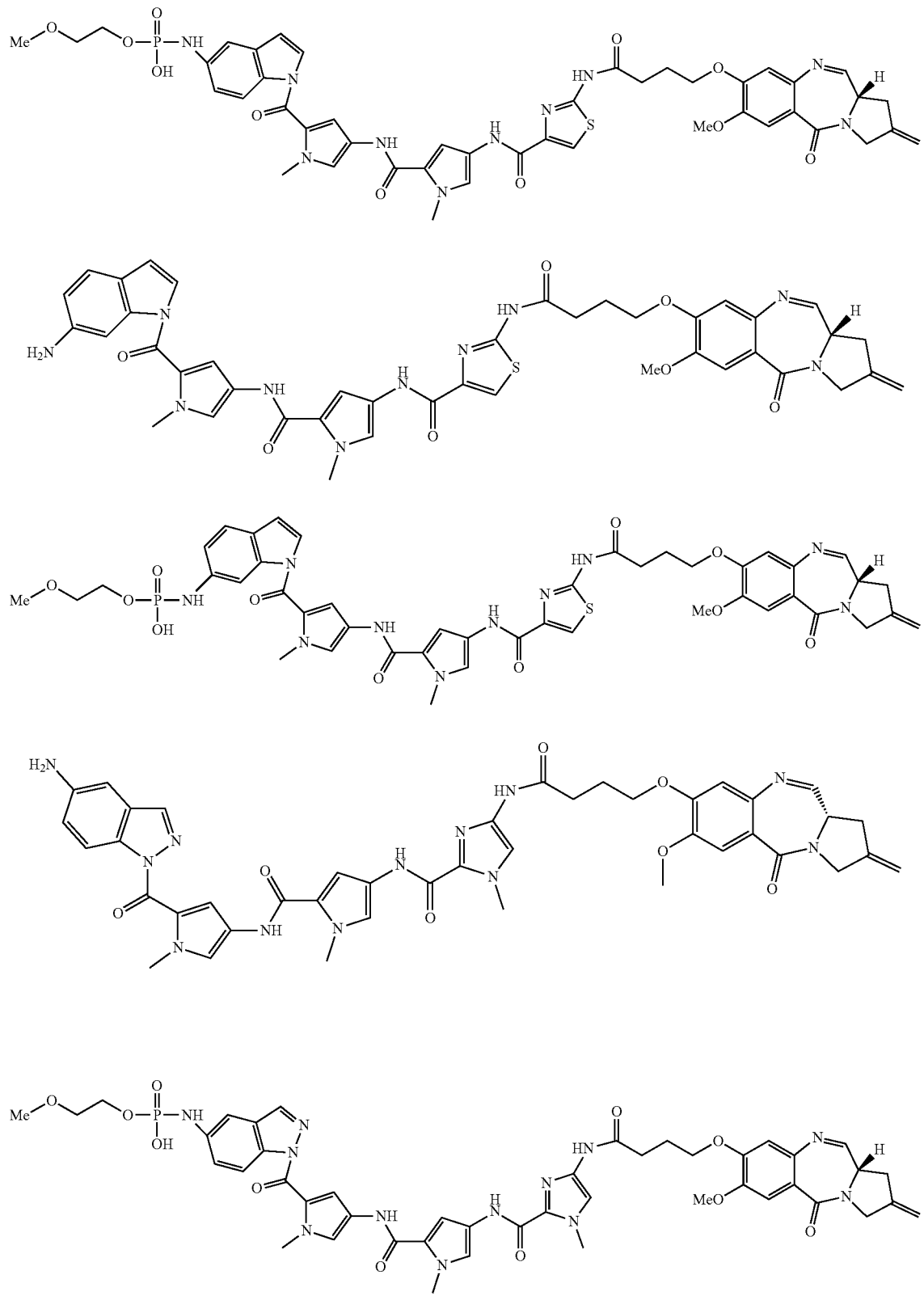

TABLE I-continued

Structure

TABLE I-continued

TABLE I-continued
Structure
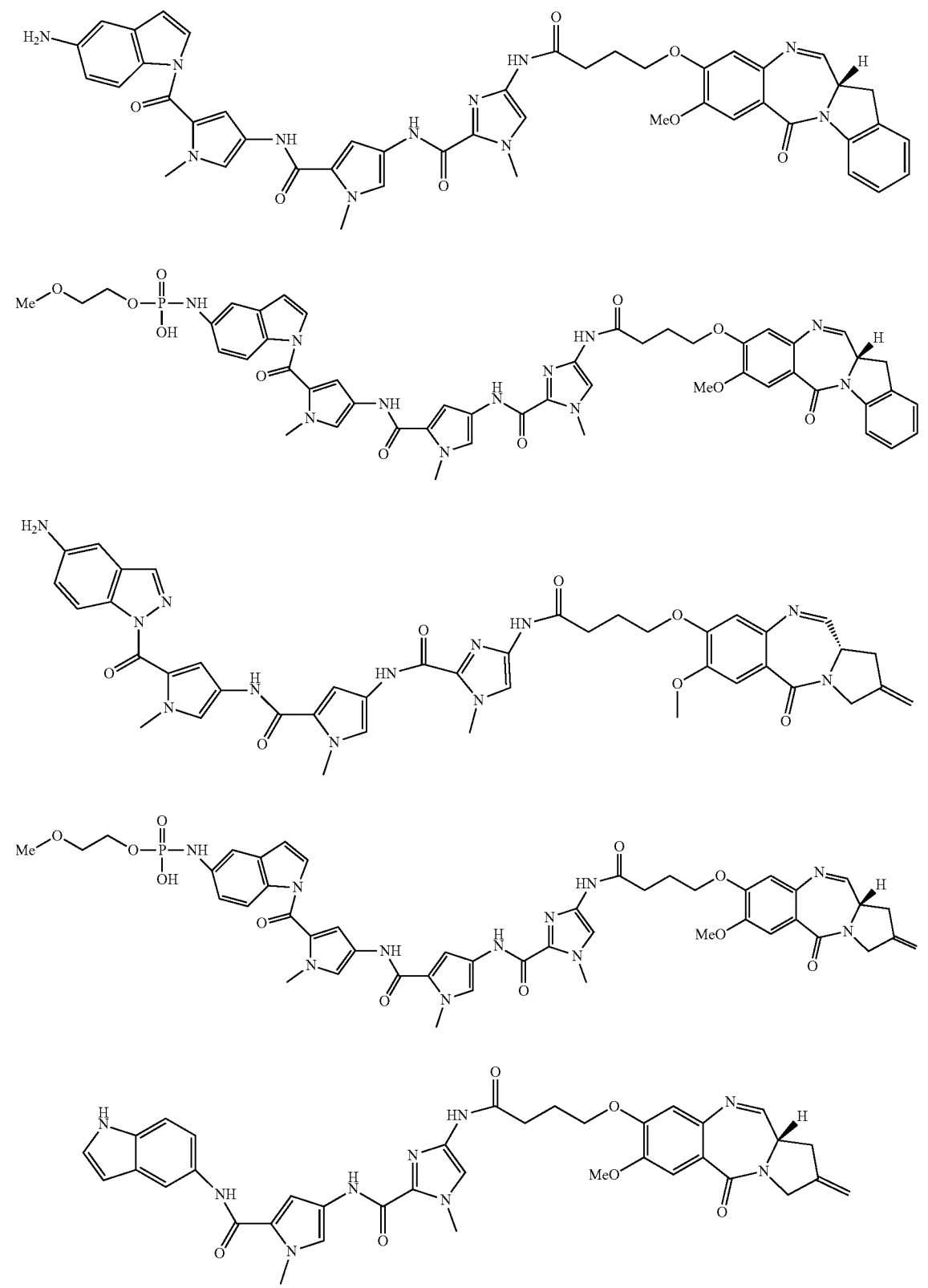

TABLE I-continued
Structure
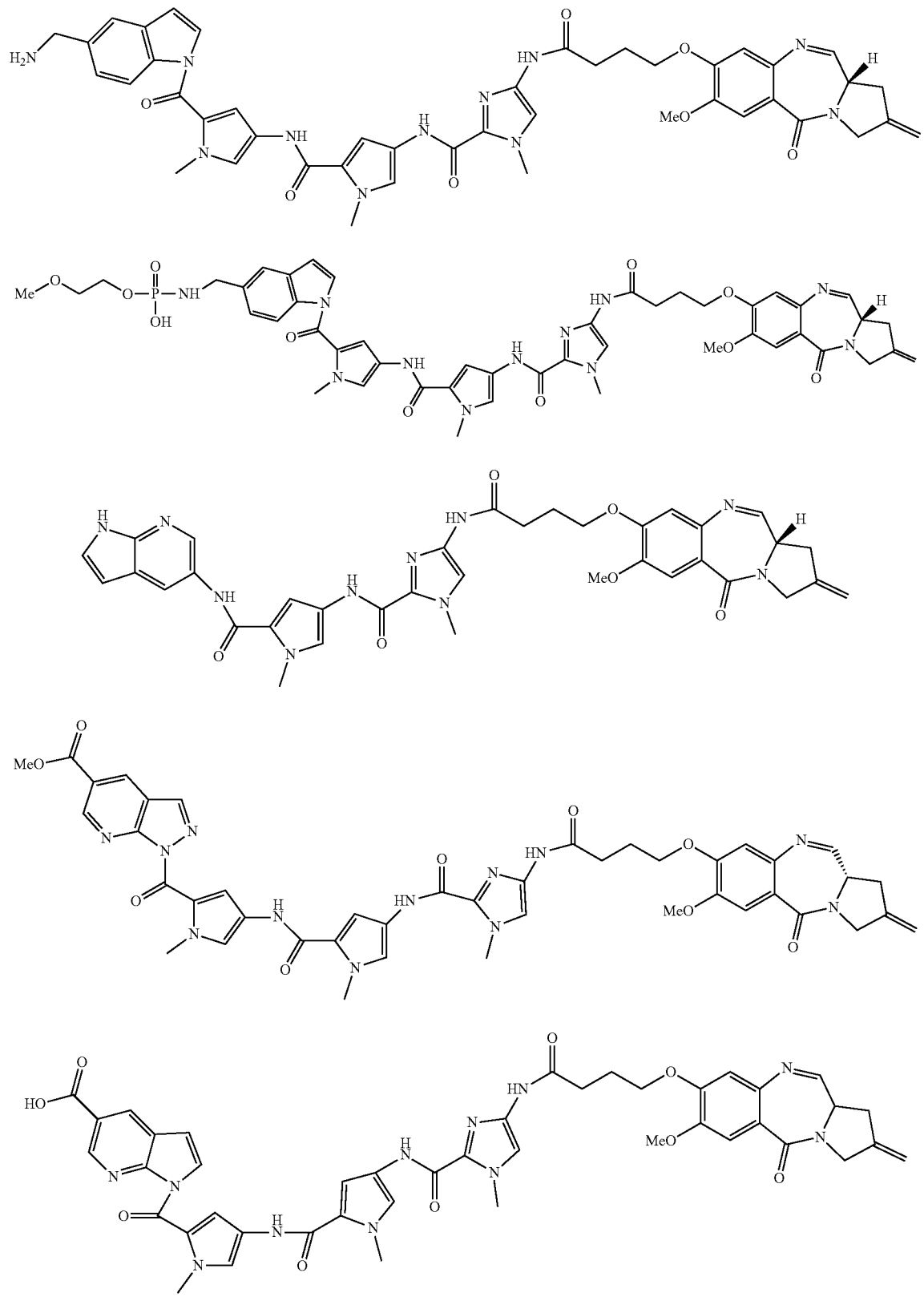

TABLE I-continued
Structure
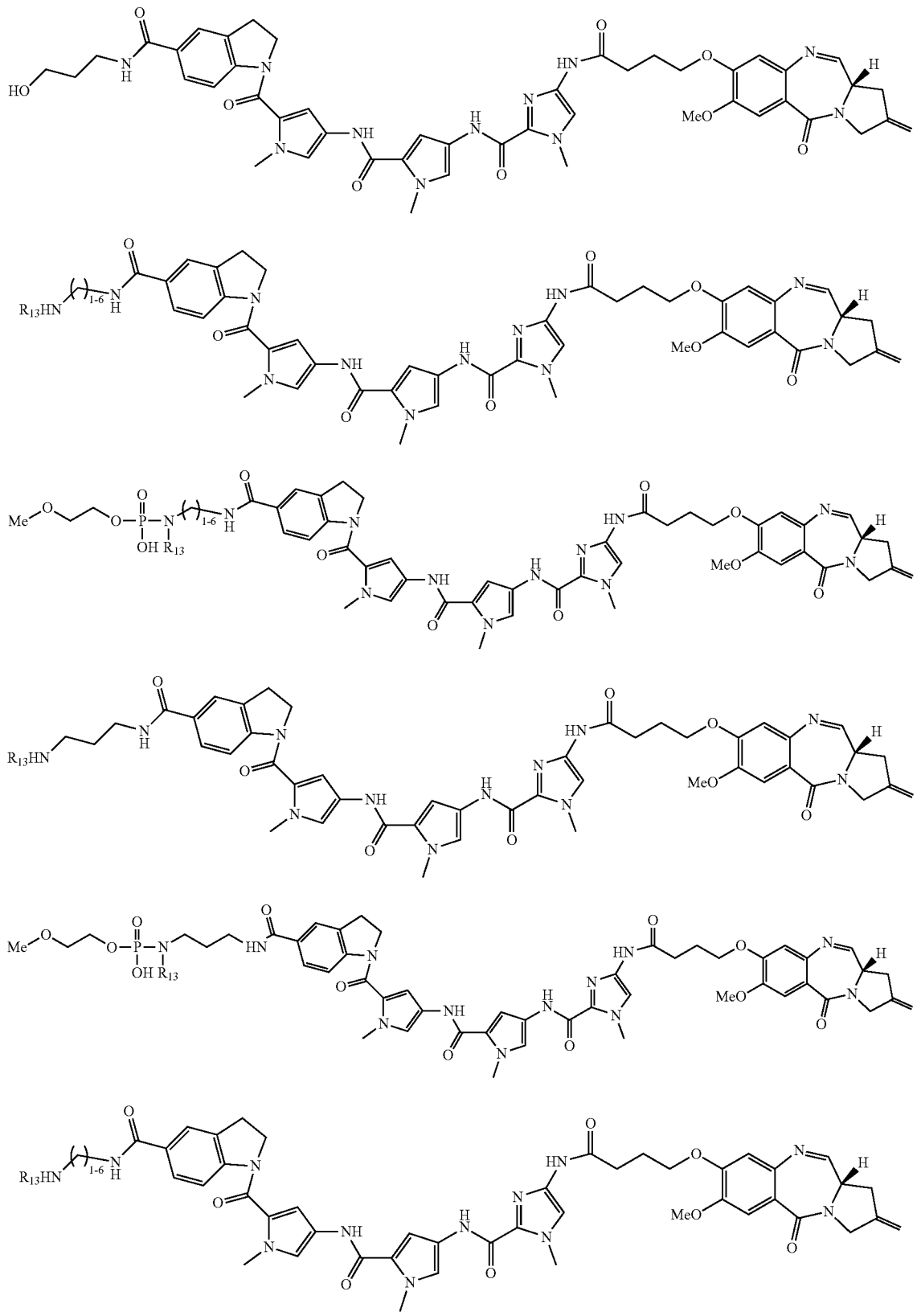

TABLE I-continued
Structure
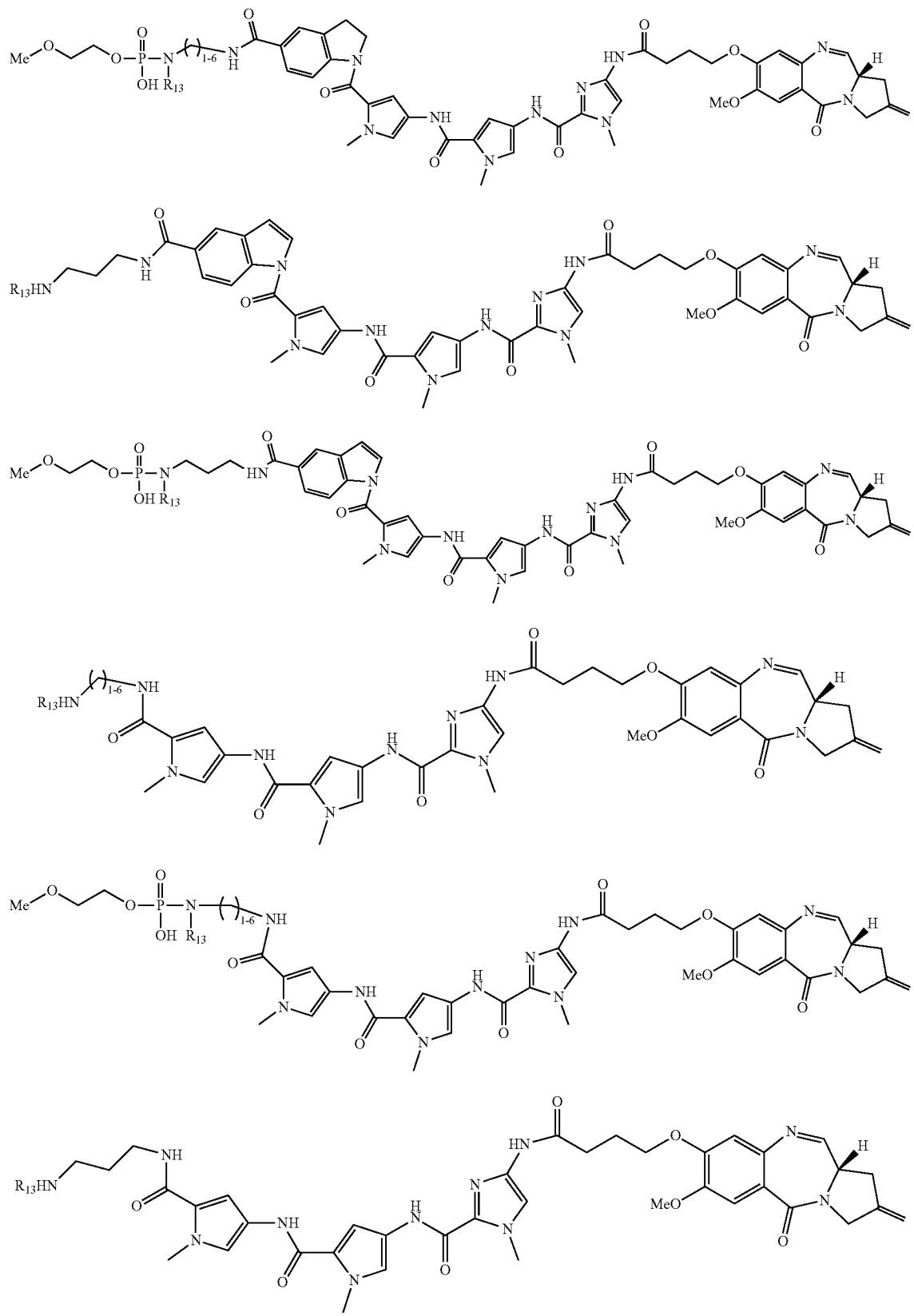

TABLE I-continued
Structure
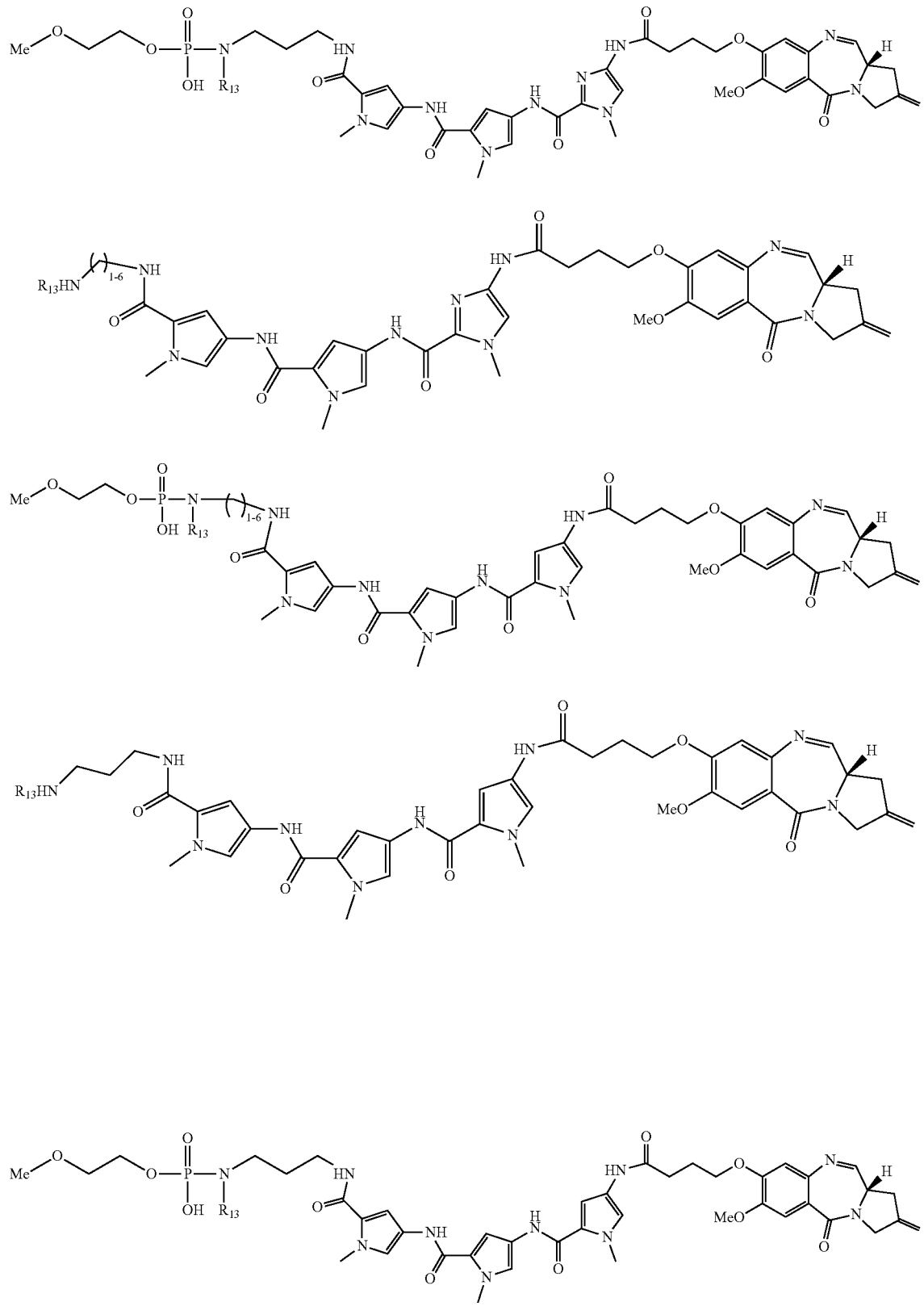

TABLE I-continued

Structure

TABLE I-continued
Structure
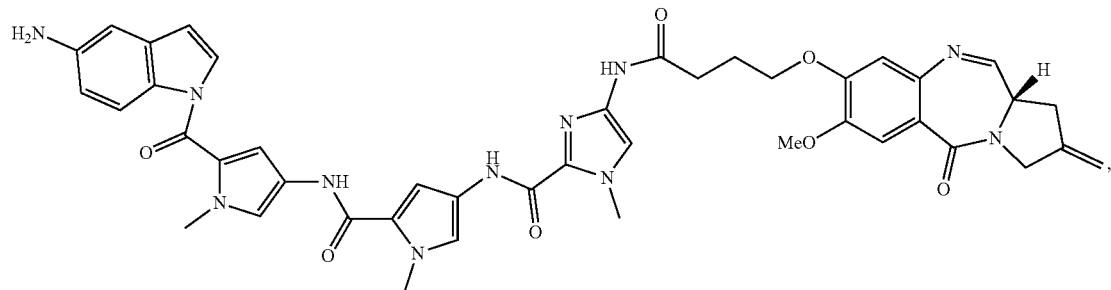
In some embodiments, the PBD drug moiety (D), prior to being connected to another portion of the conjugate (e.g., the linker unit ($L^C$)), corresponds to a compound of any one of Formula (XIIIa) to (XIIIm):
(XIIIa)
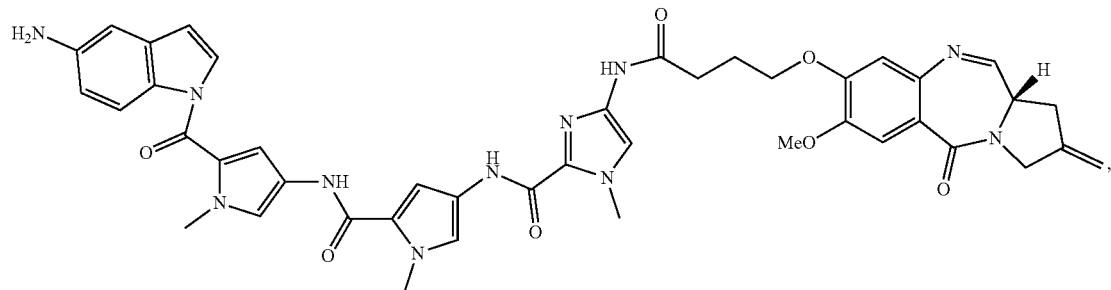
(XIIIb)
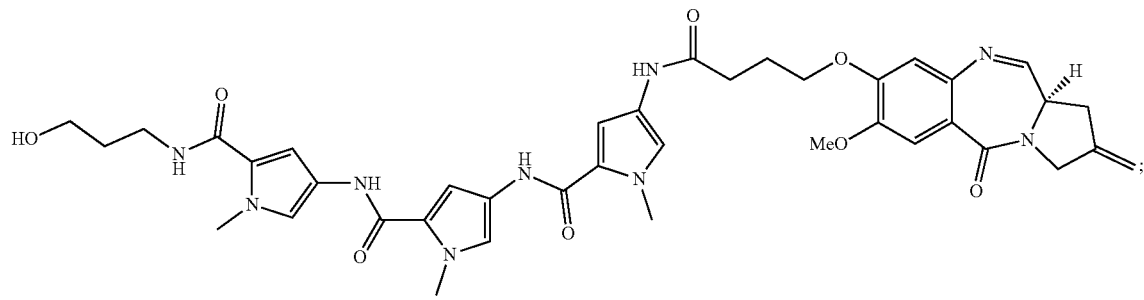
(XIIIc)
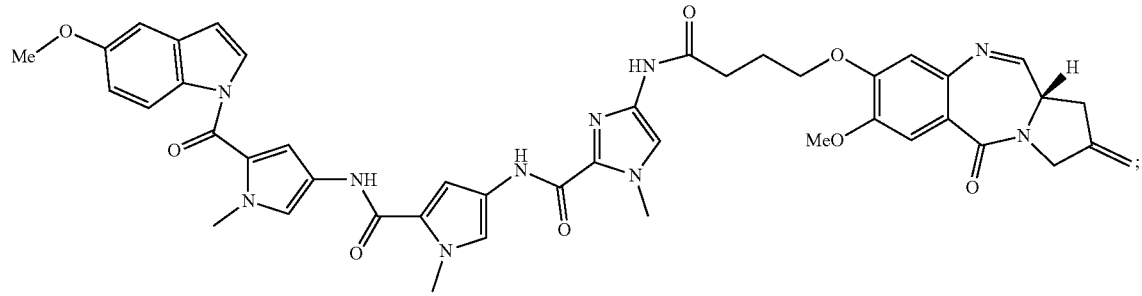

-continued
(XIIId)
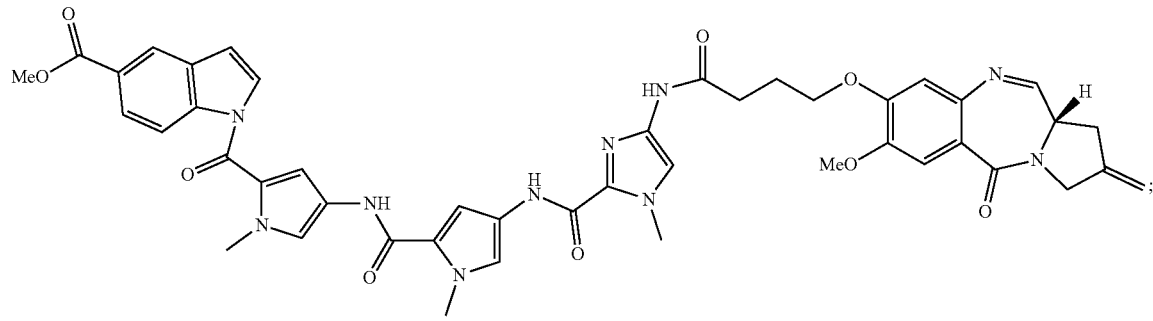
(XIIIe)
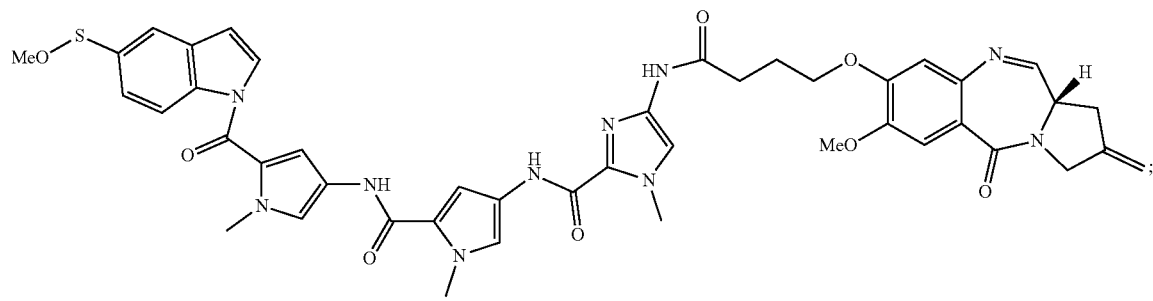
(XIIIf)
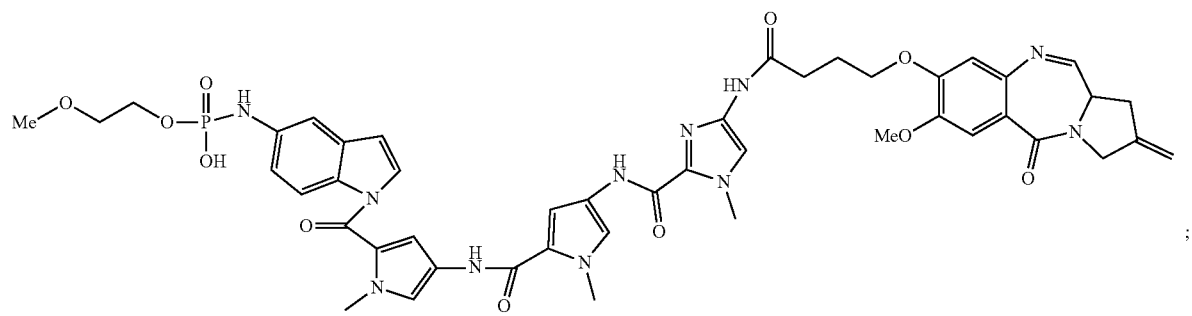
(XIIIg)
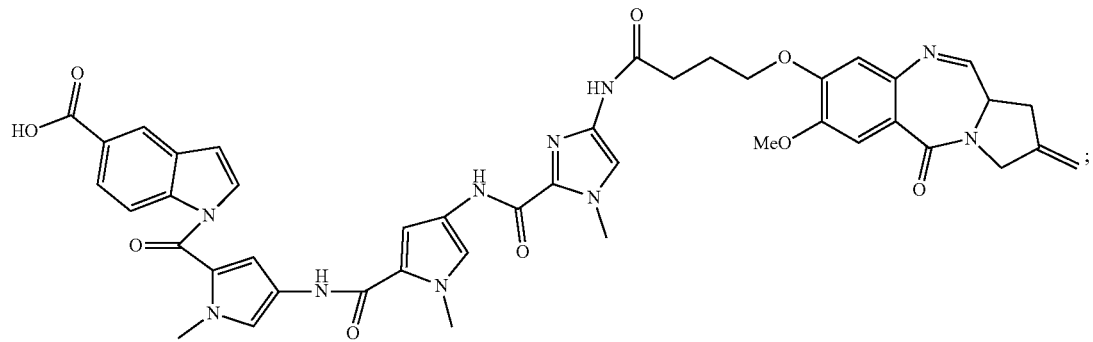

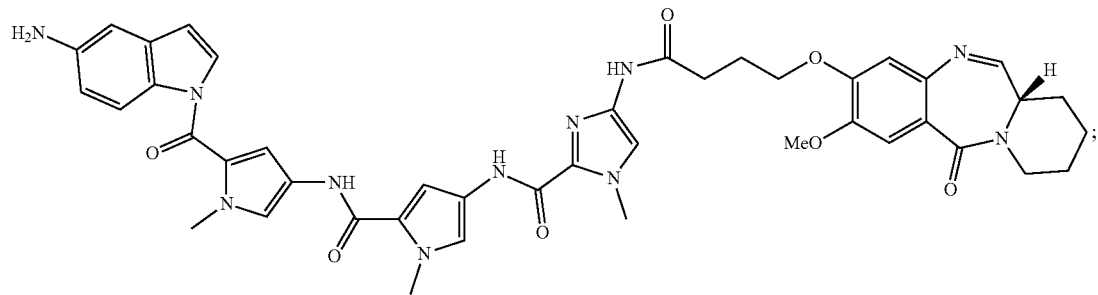
(XIIIh)
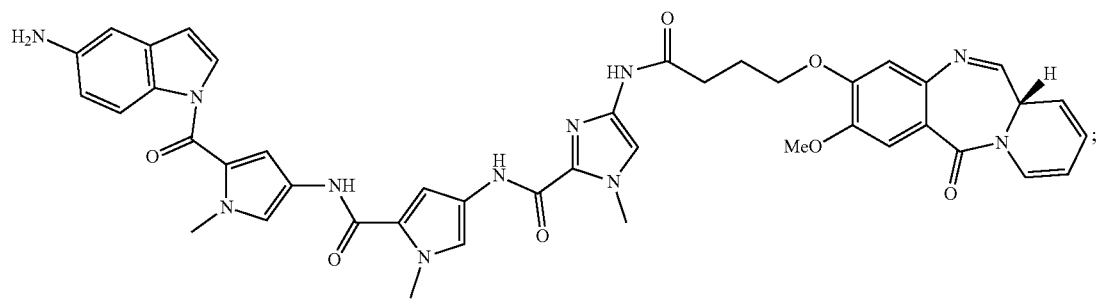
(XIIIi)
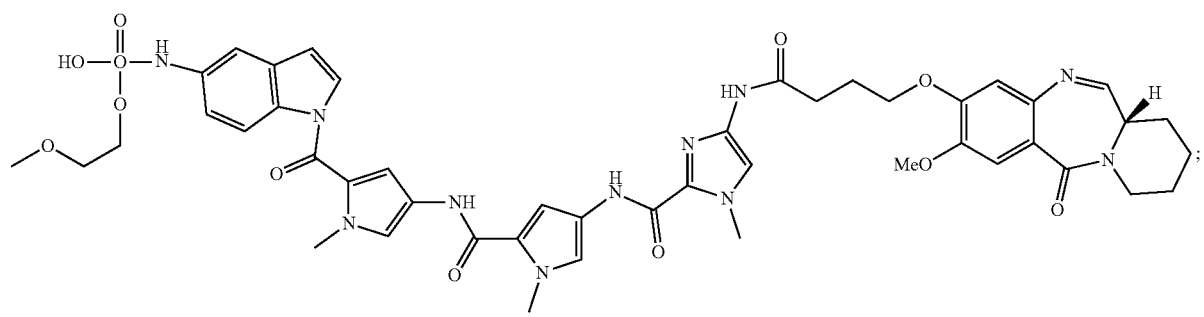
(XIIIj)
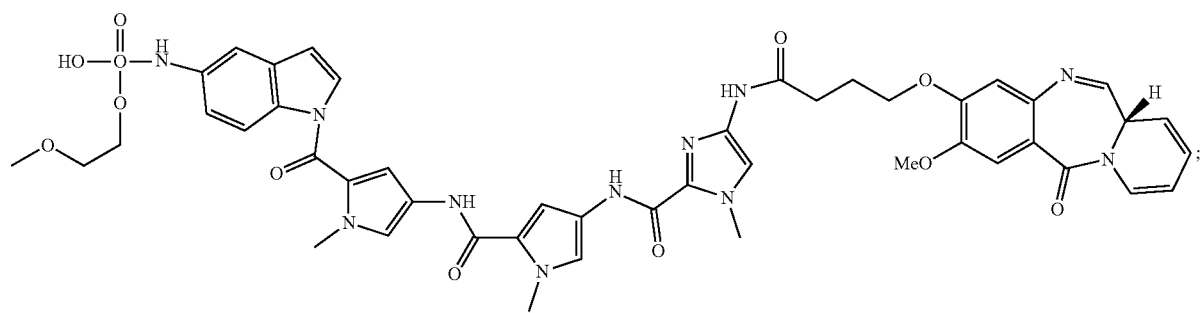
(XIIIk)
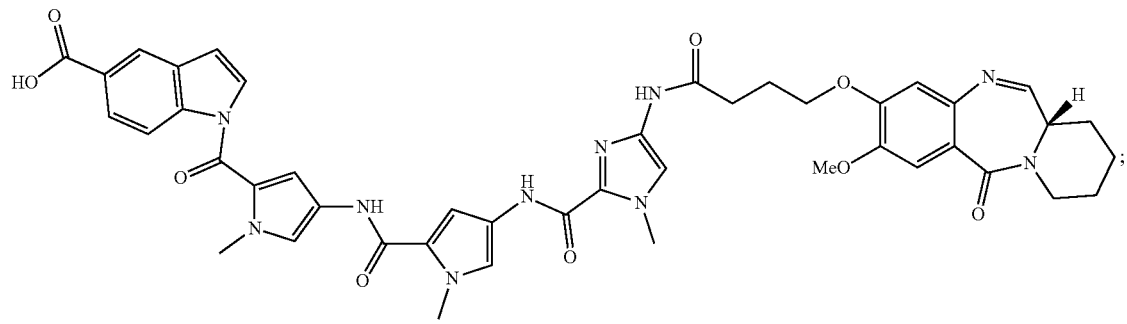
(XIIIl)

(XIIIm)

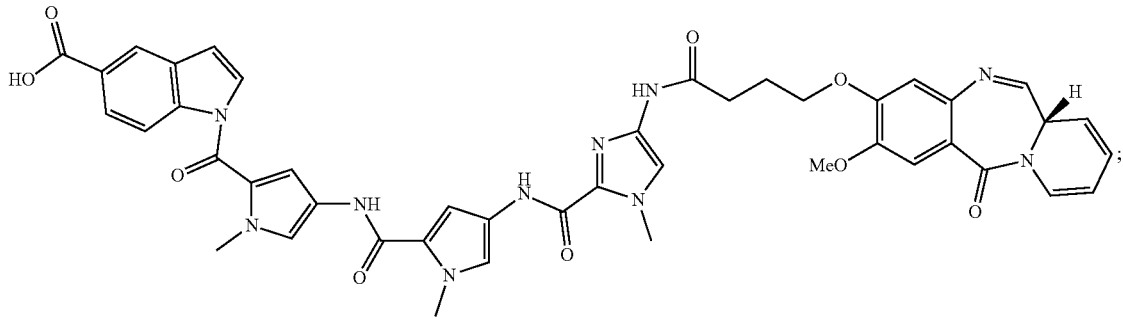

a tautomer thereof, a pharmaceutically acceptable salt or solvate thereof, or a pharmaceutically acceptable salt or solvate of the tautomer.

In some embodiments, the PBD drug moiety (D), connected to another portion of the conjugate (e.g., the linker unit ($L^C$)), corresponds to a conjugate selected from the conjugates listed in Table 1A, tautomers thereof, pharmaceutically acceptable salts or solvates thereof, or pharmaceutically acceptable salts or solvates of the tautomers, wherein

indicates the point of attachment to the linker unit.

TABLE 1A

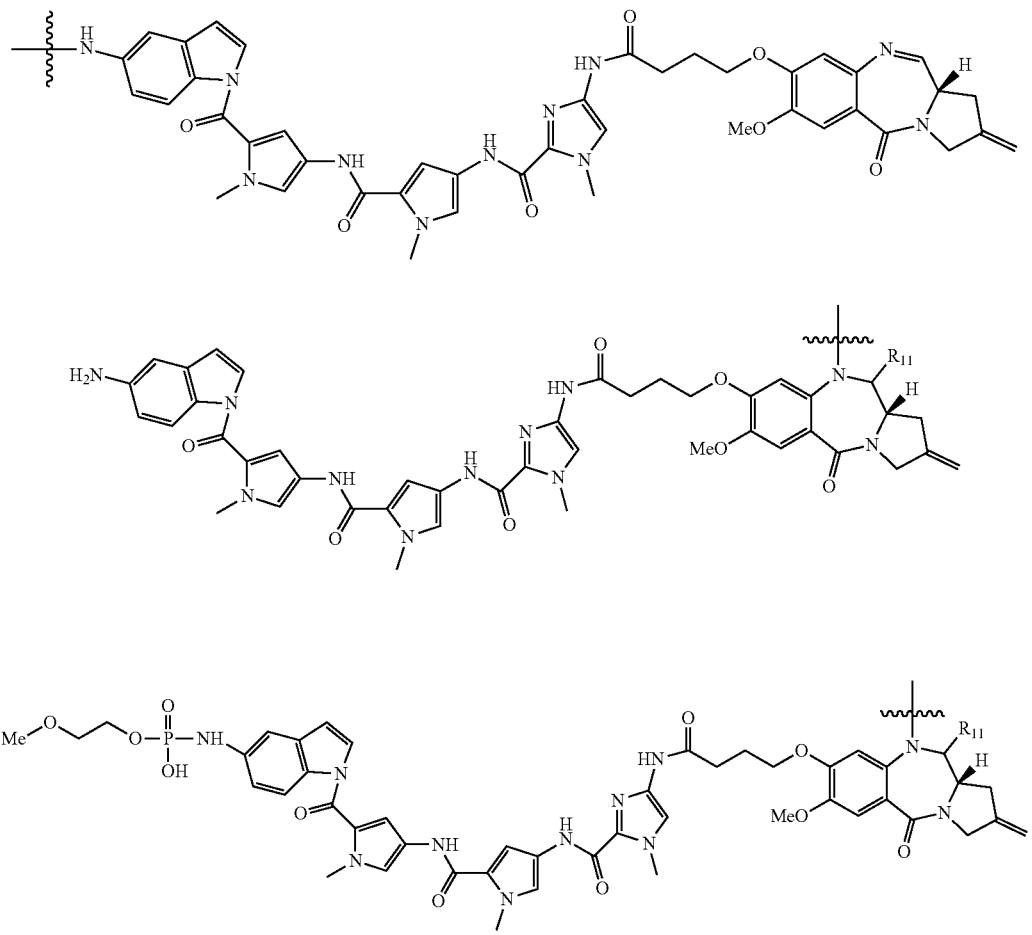

TABLE 1A-continued
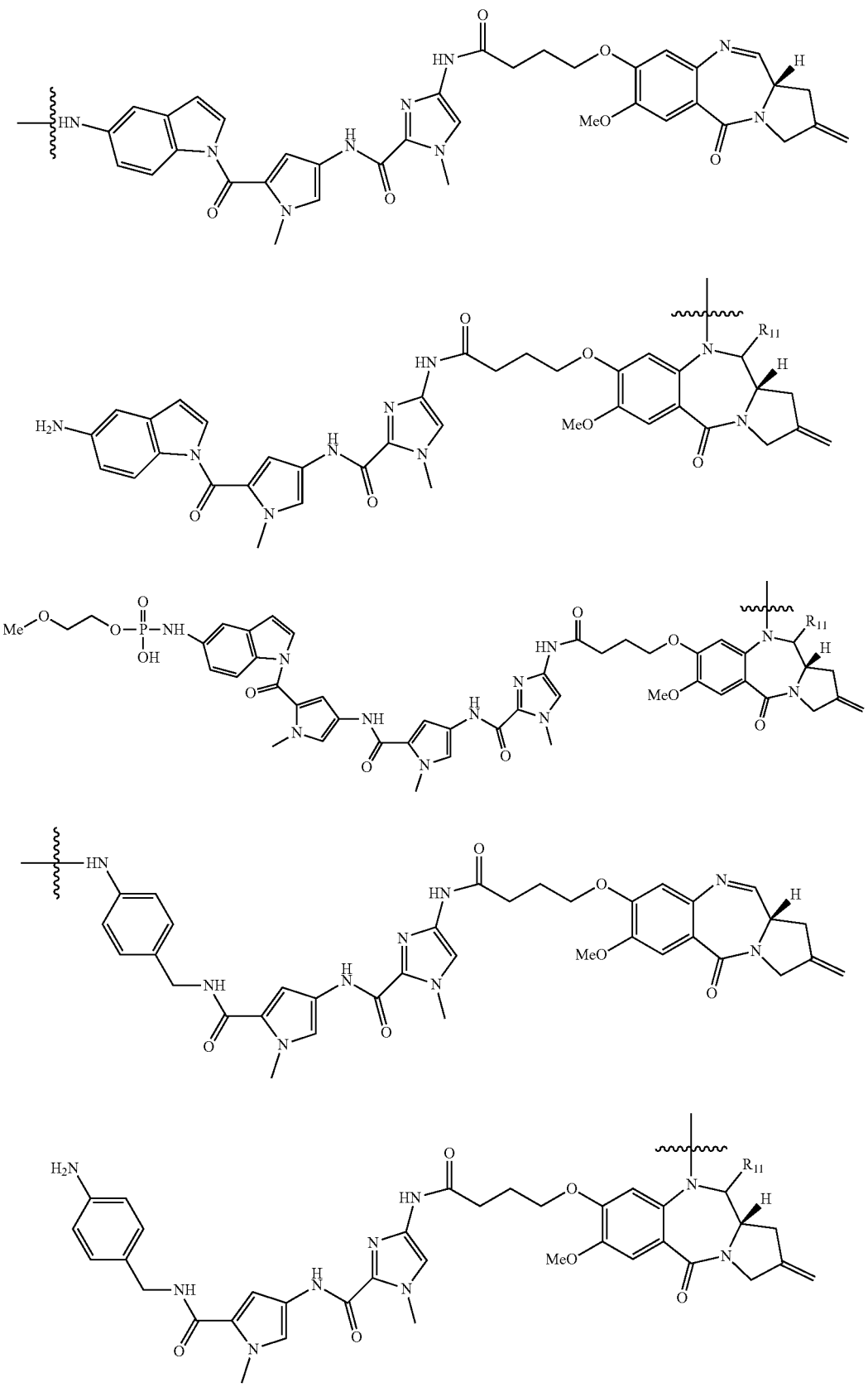

TABLE 1A-continued
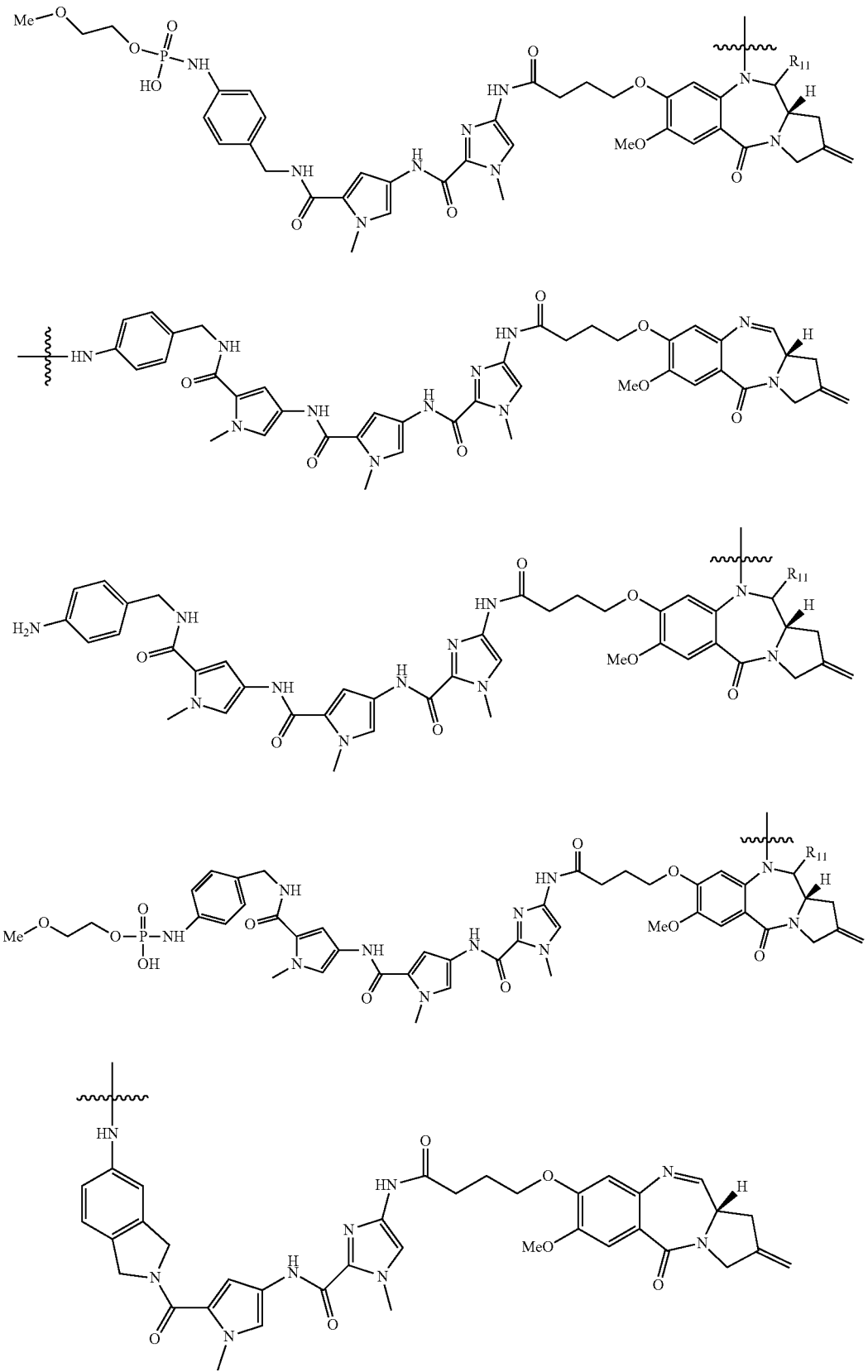

TABLE 1A-continued
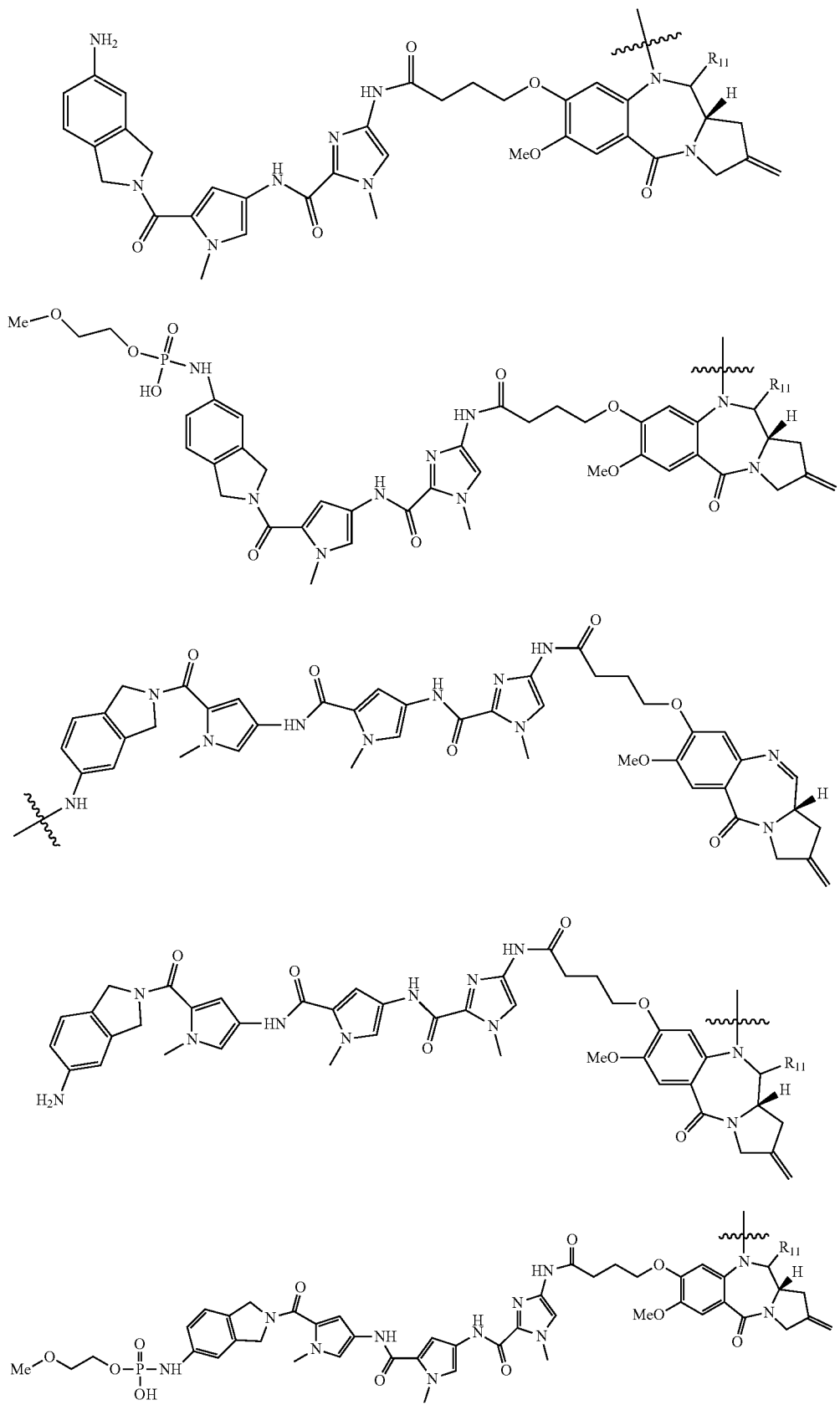

TABLE 1A-continued
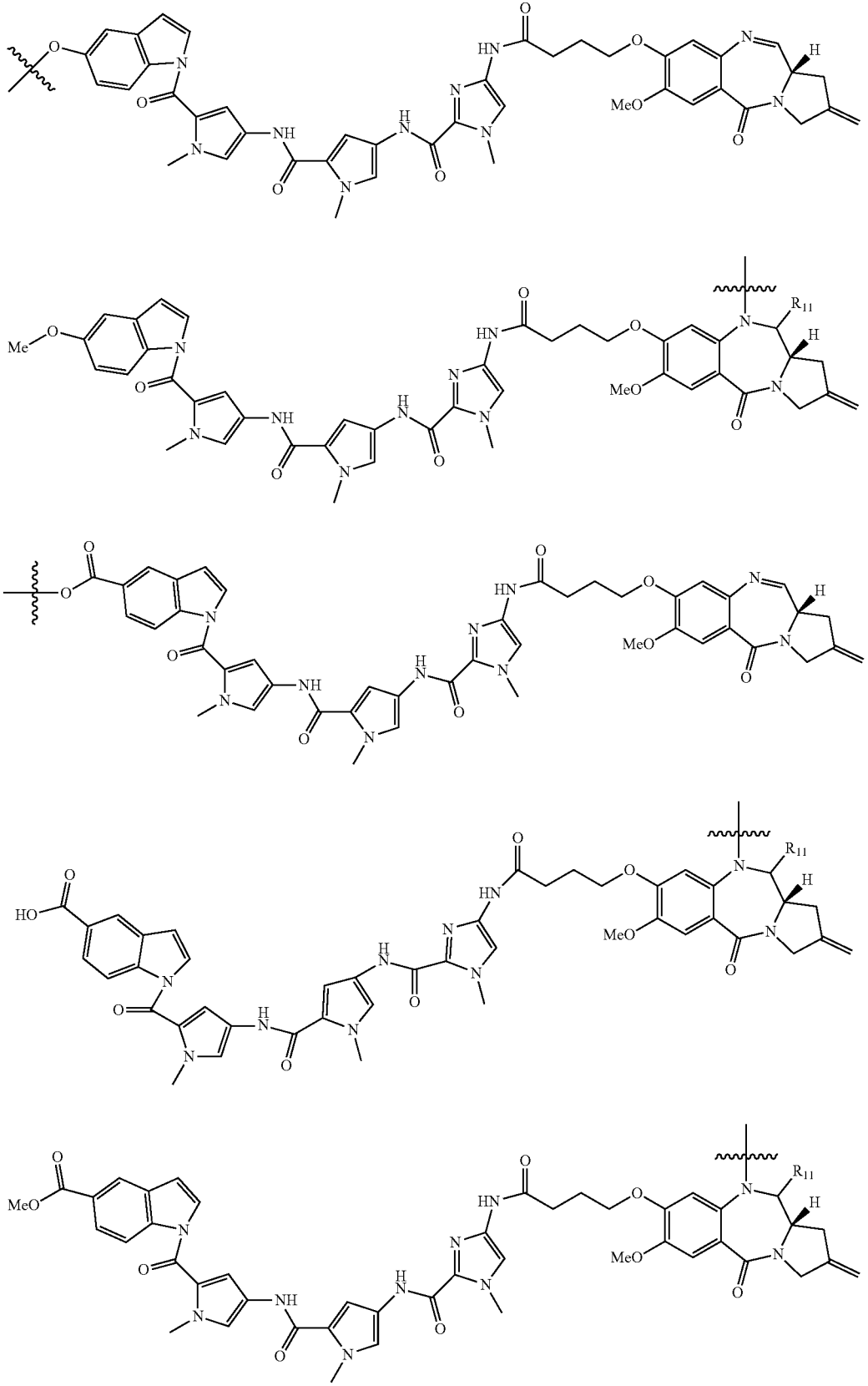

TABLE 1A-continued
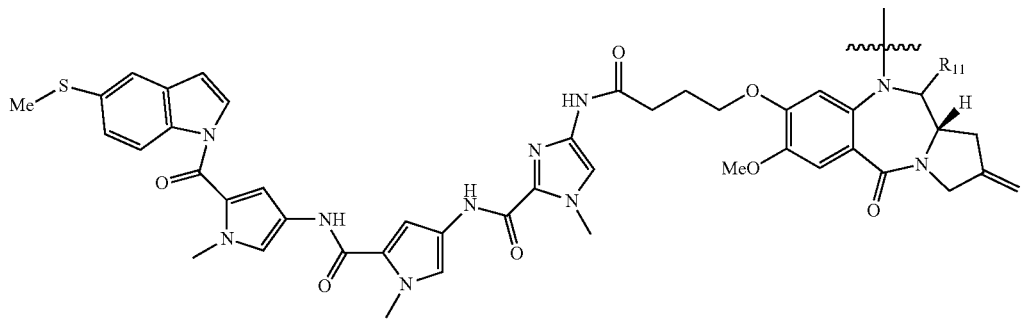
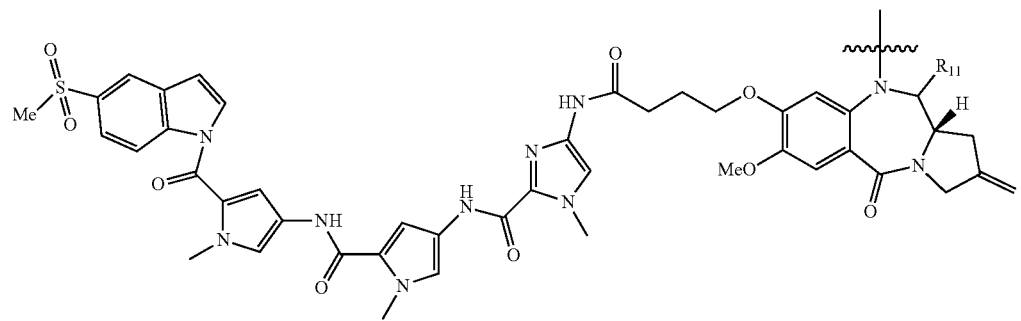
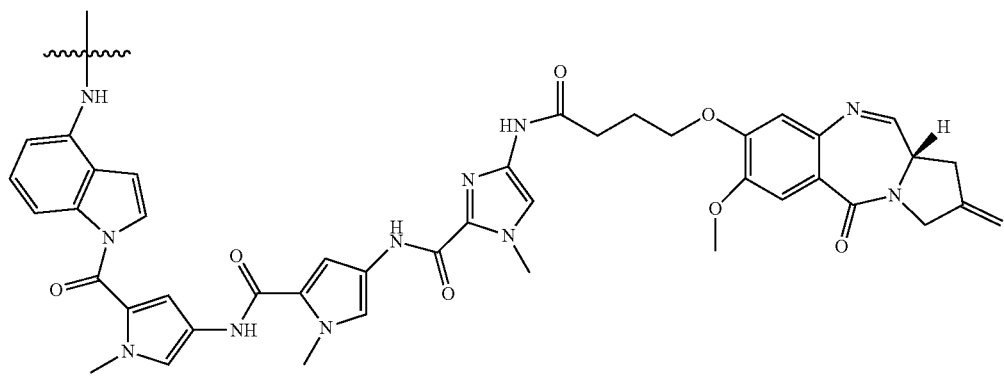 [SMILES: *Nc1cccc2c1ccn2C(=O)c1cc(NC(=O)c2cc(NC(=O)c3nc(NC(=O)CCCOc4cc5c(cc4OC)C(=O)N4CC(=C)C[C@H]4C=N5)cn3C)cn2C)cn1C]
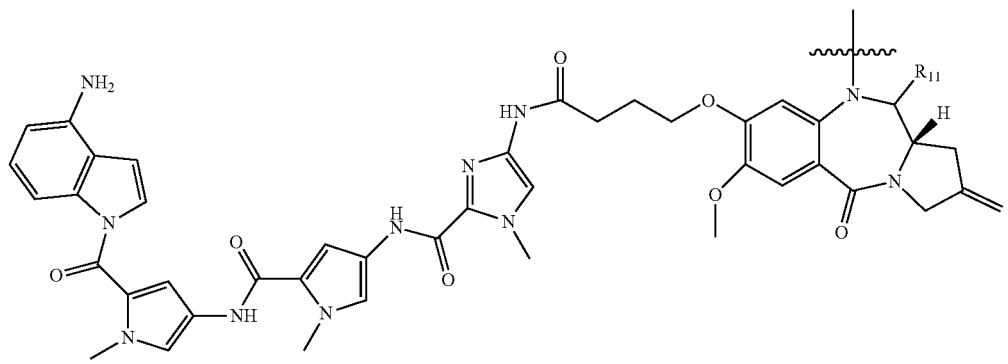

TABLE 1A-continued
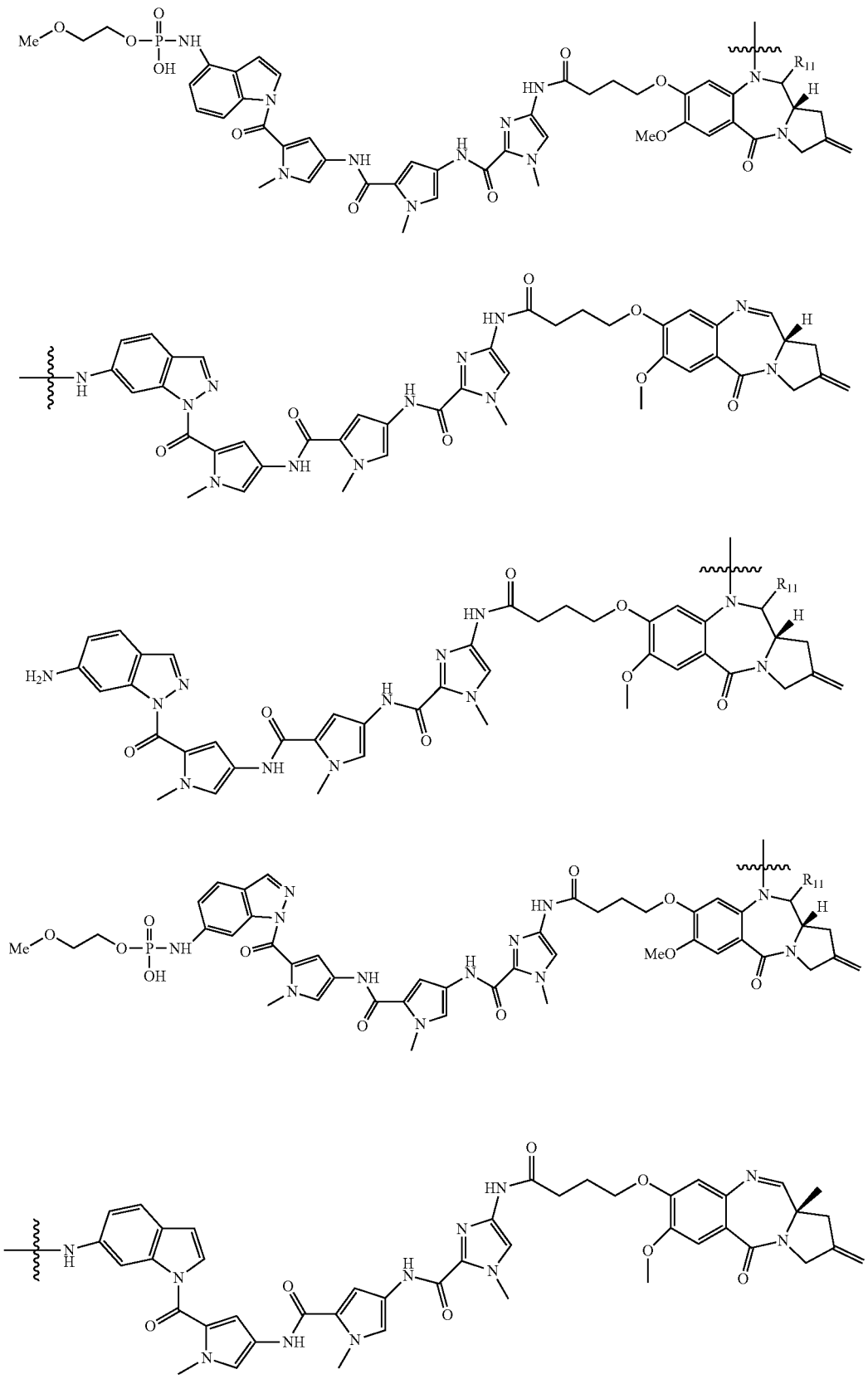

TABLE 1A-continued
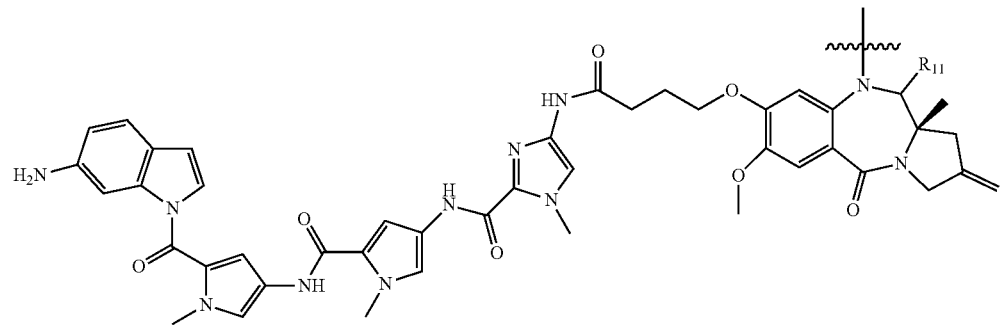
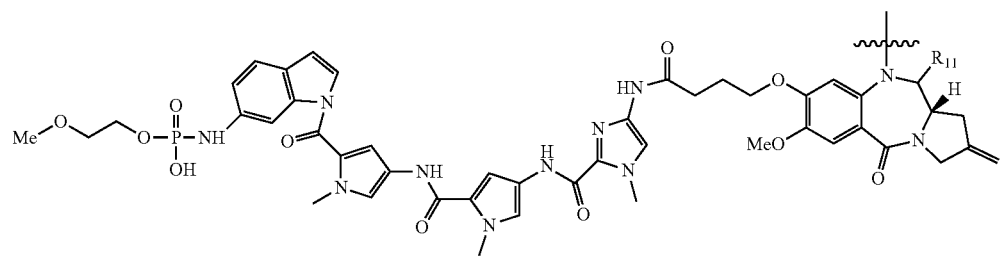
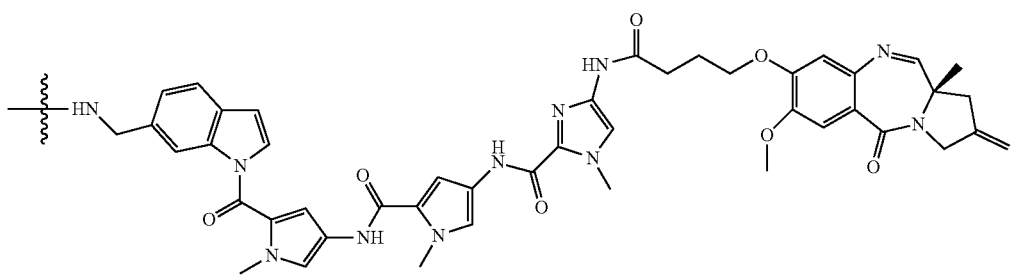 [SMILES: *NCc1ccc2ccn(C(=O)c3cc(NC(=O)c4cc(NC(=O)c5nc(NC(=O)CCCOc6cc7c(cc6OC)C(=O)N6CC(=C)C[C@@]6(C)C=N7)cn5C)cn4C)cn3C)c2c1]
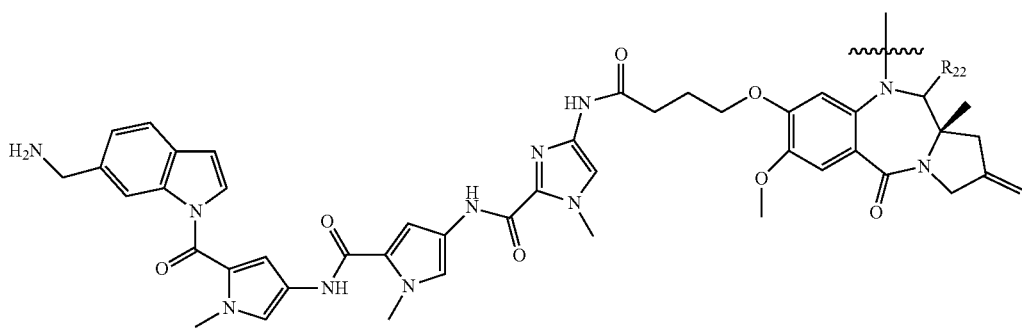
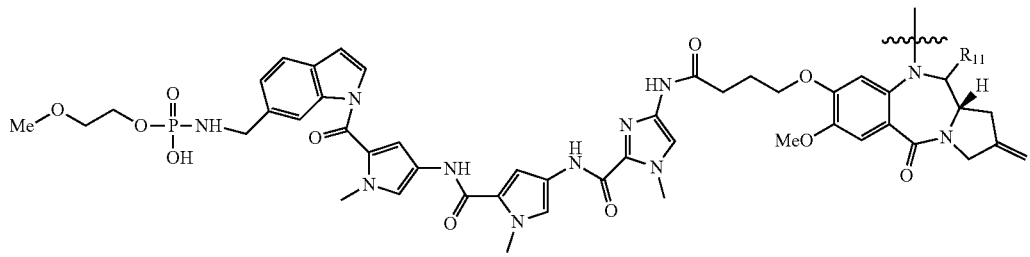

TABLE 1A-continued
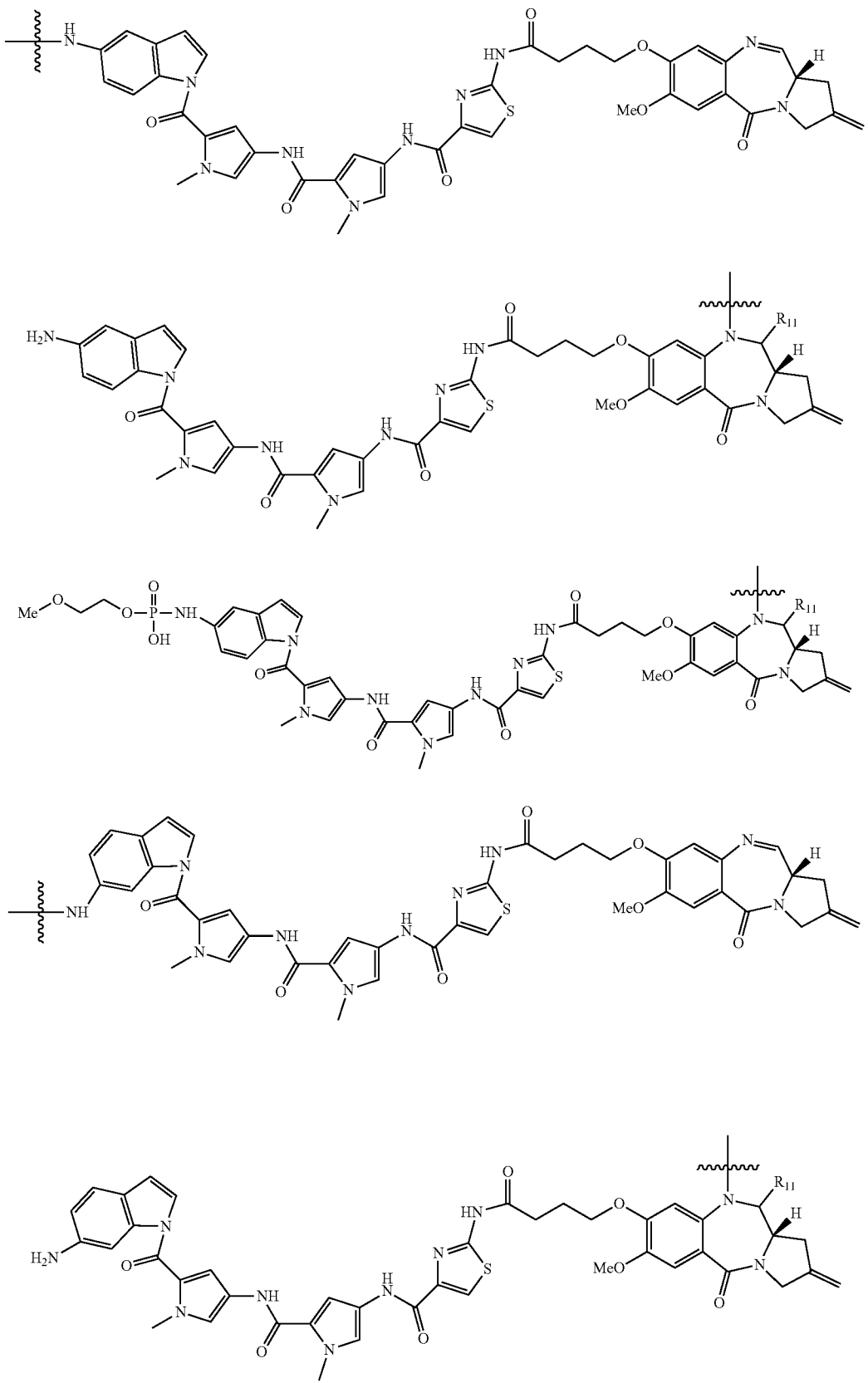

TABLE 1A-continued
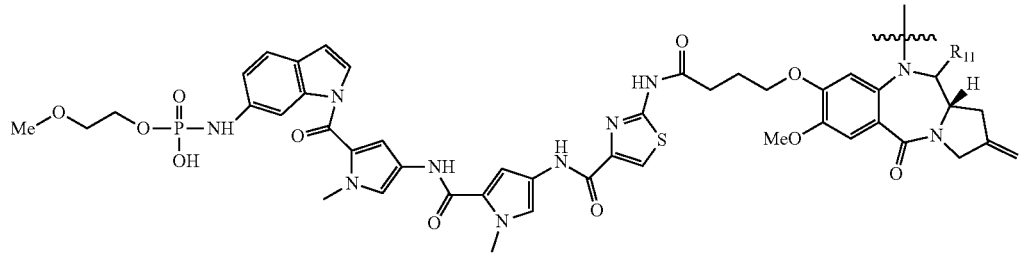
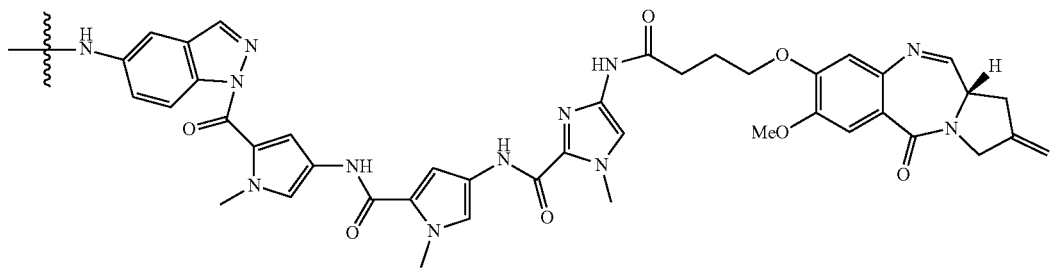 [SMILES: *Nc1ccc2c(cnn2C(=O)c2cc(NC(=O)c3cc(NC(=O)c4nc(NC(=O)CCCOc5cc6c(cc5OC)C(=O)N5CC(=C)C[C@H]5C=N6)cn4C)cn3C)cn2C)c1]
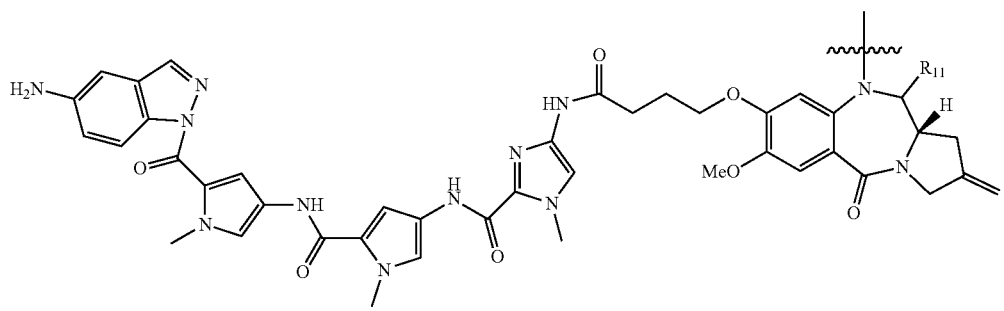
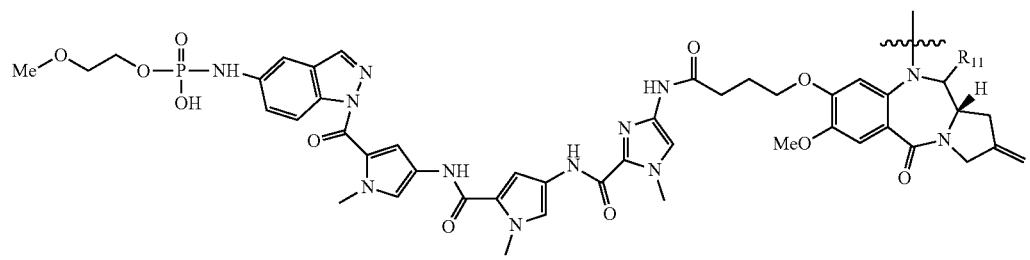
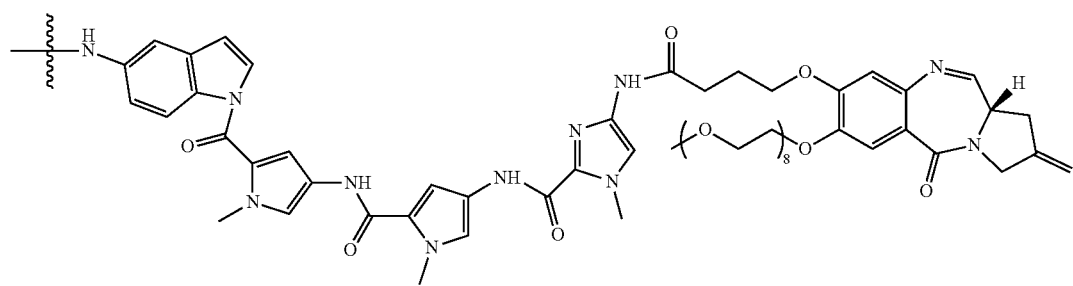

TABLE 1A-continued
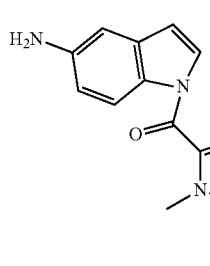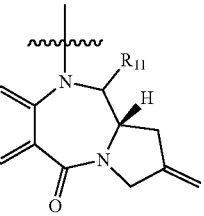
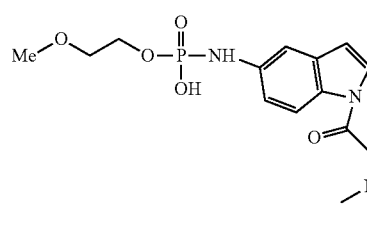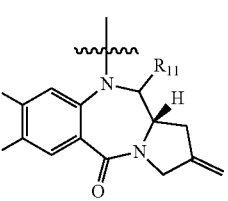
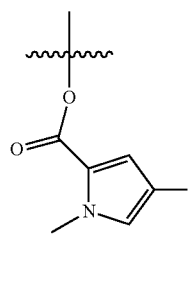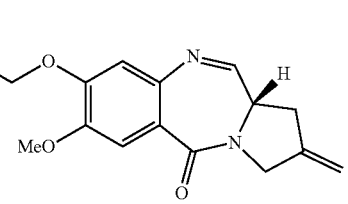
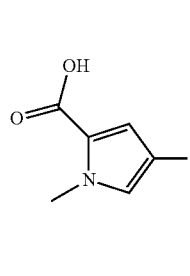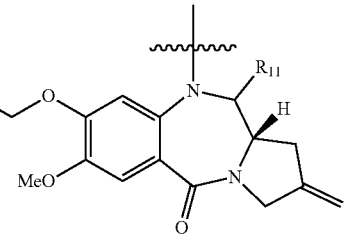
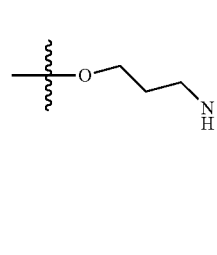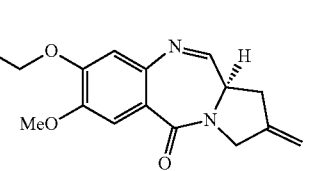

TABLE 1A-continued
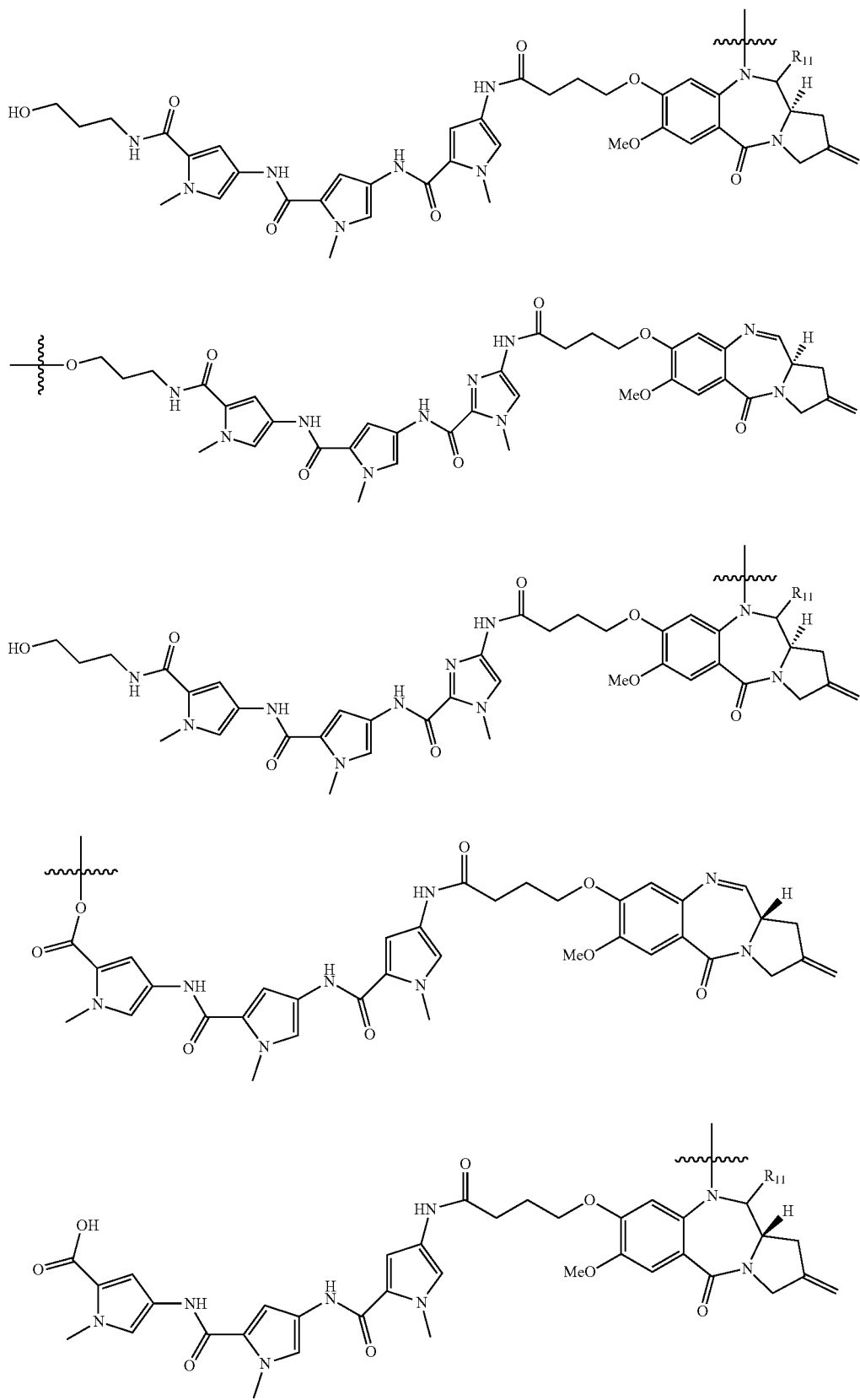

TABLE 1A-continued
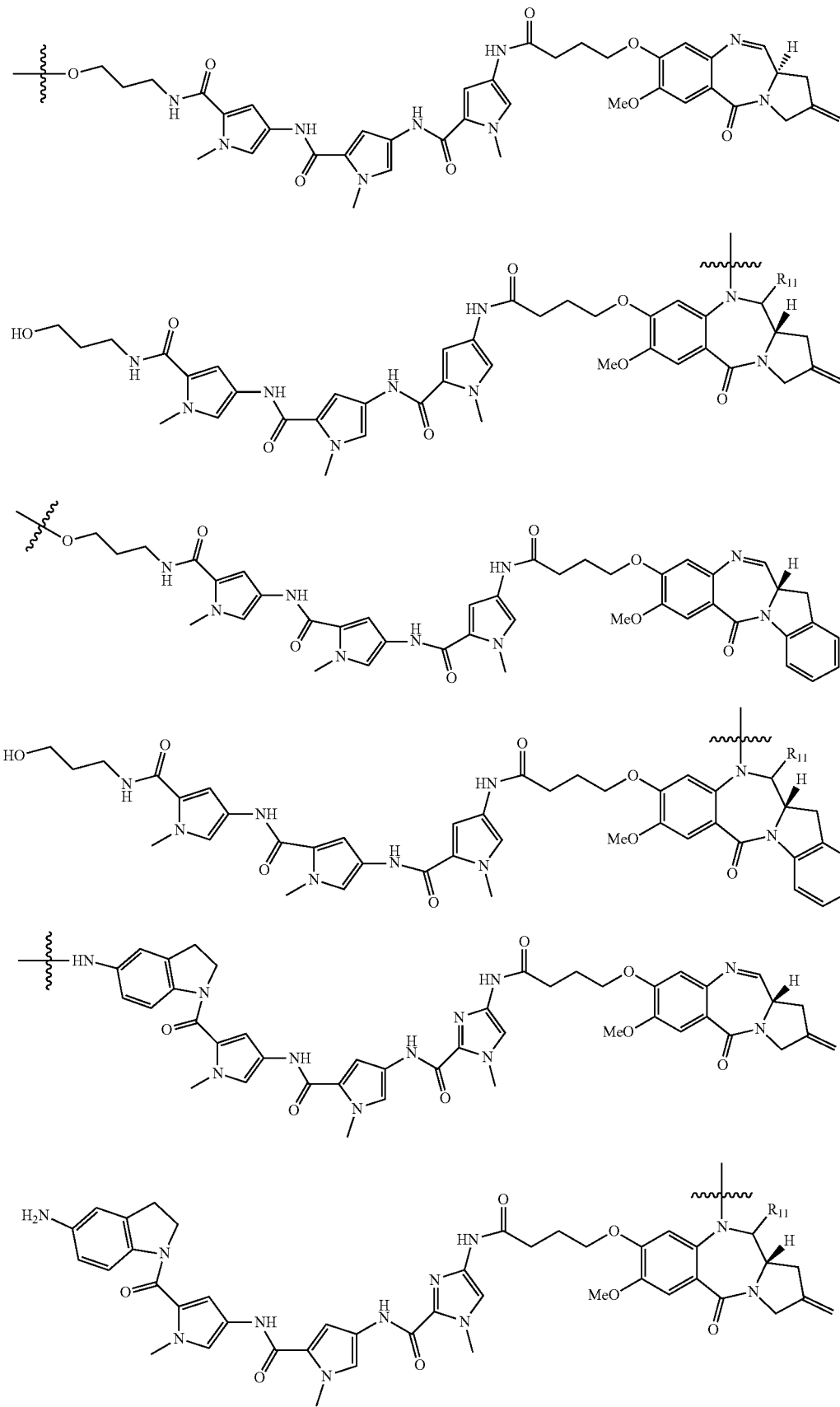

TABLE 1A-continued
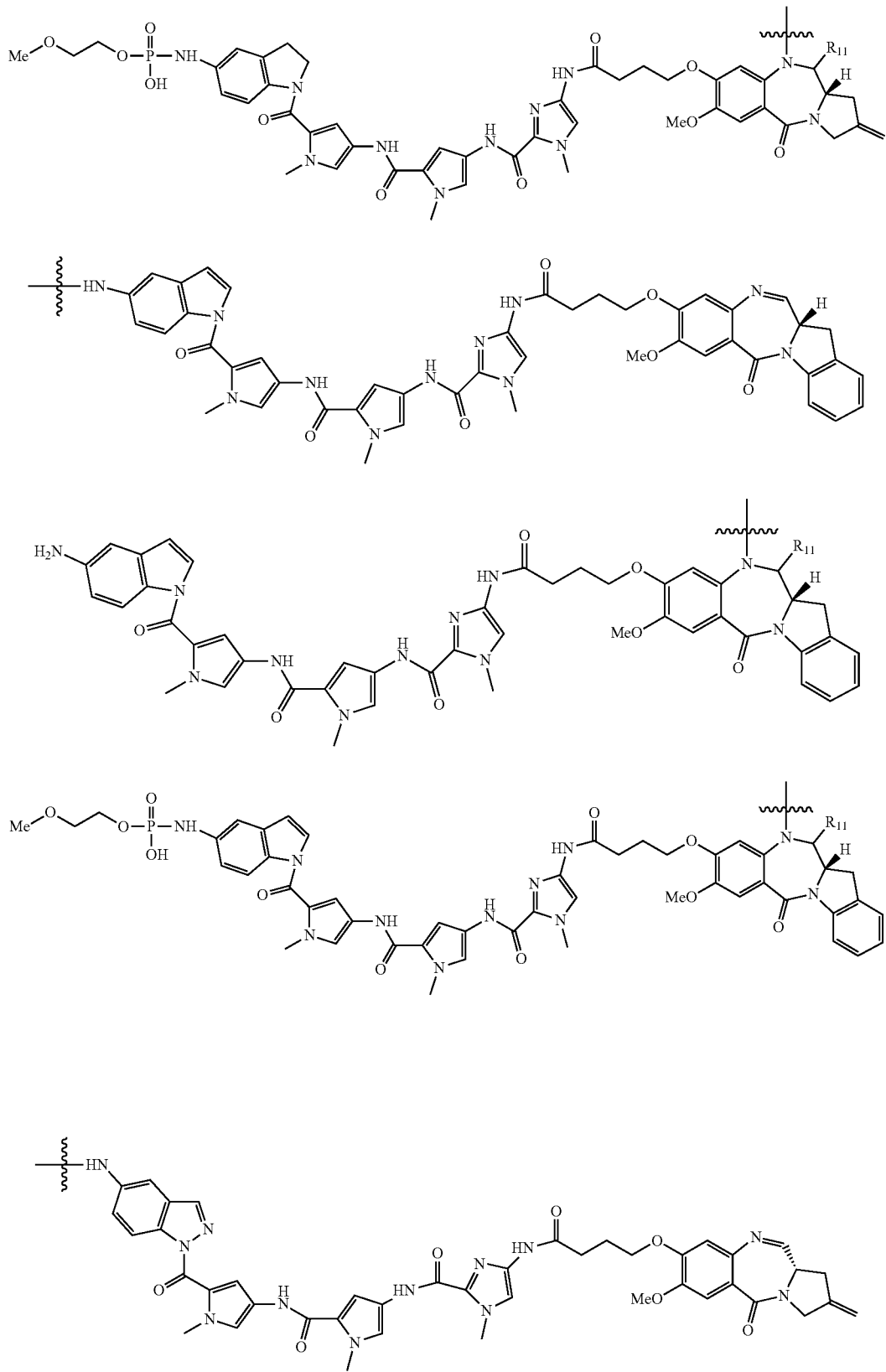

TABLE 1A-continued
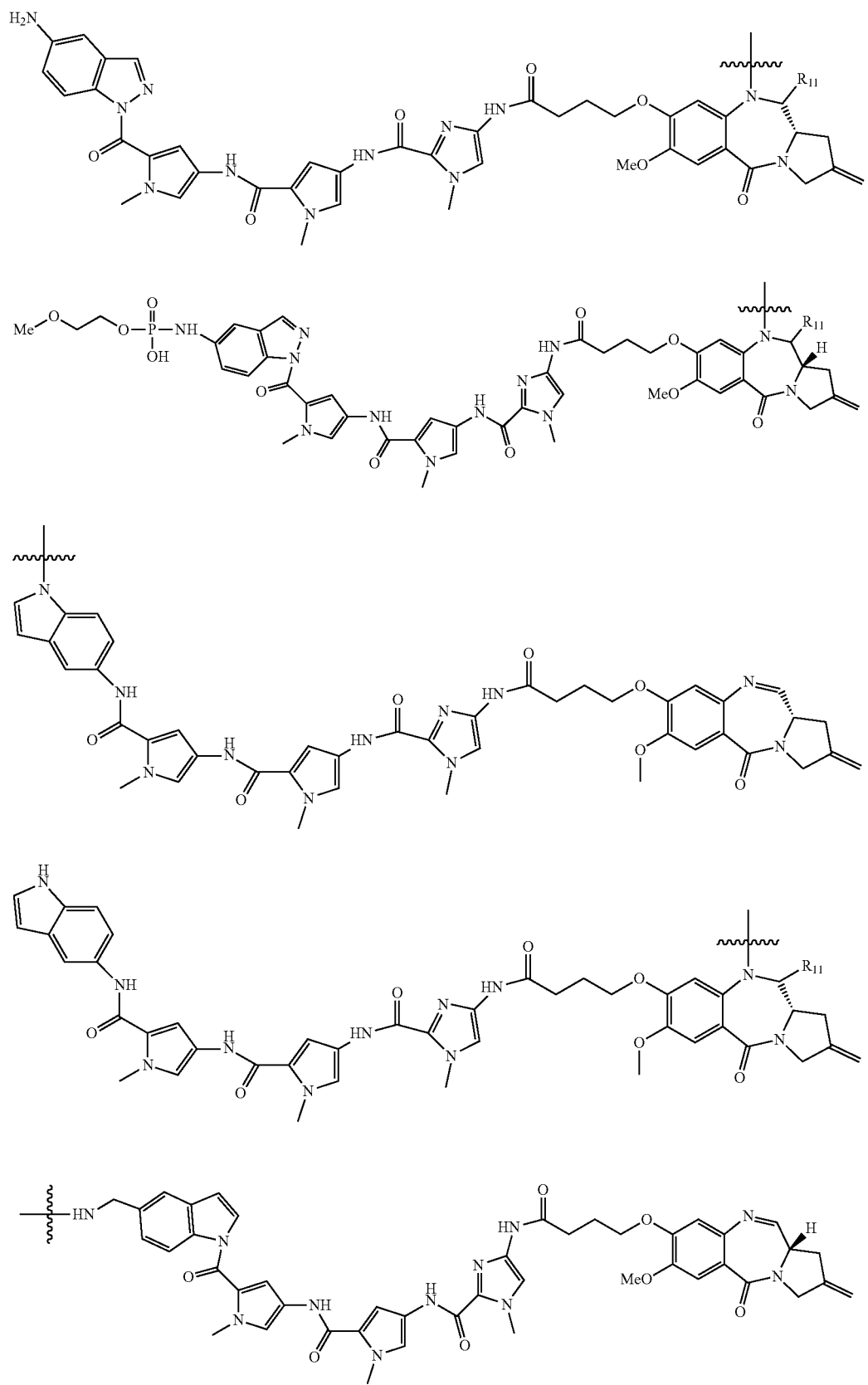

TABLE 1A-continued
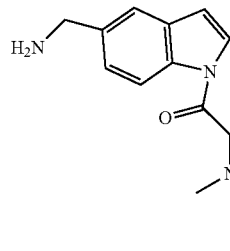 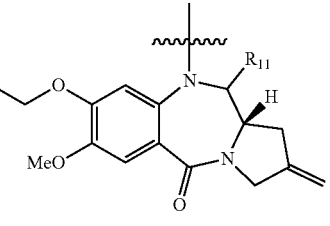
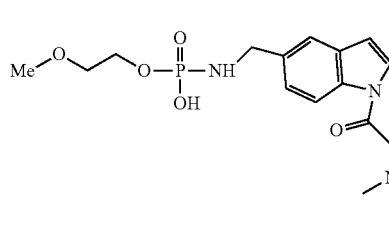 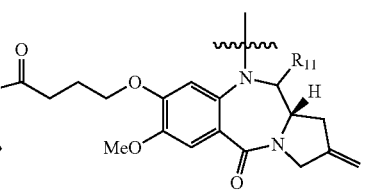
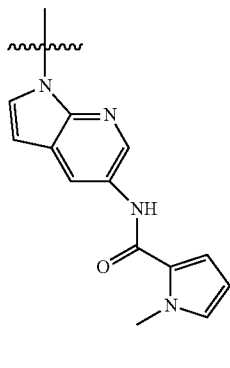 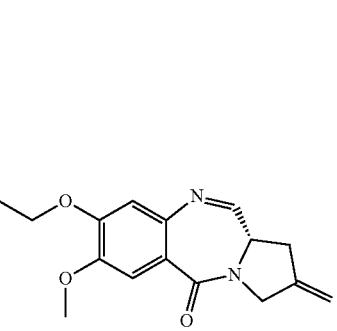
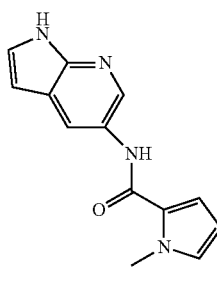 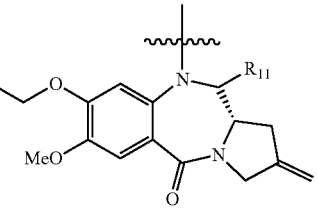
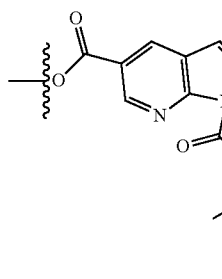 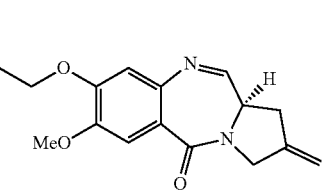

TABLE 1A-continued
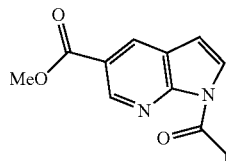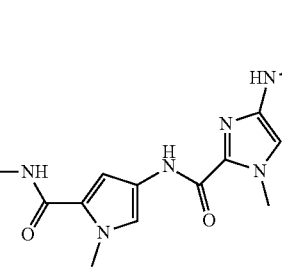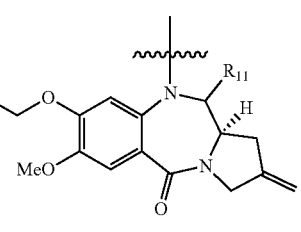
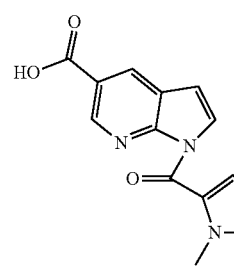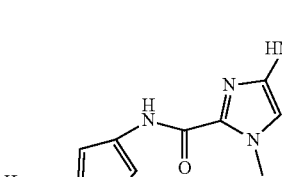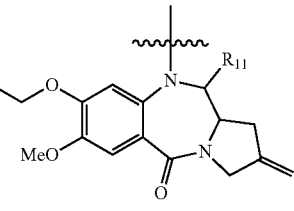
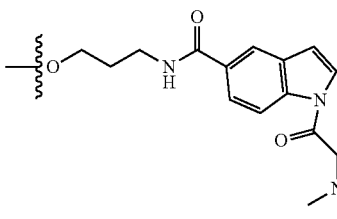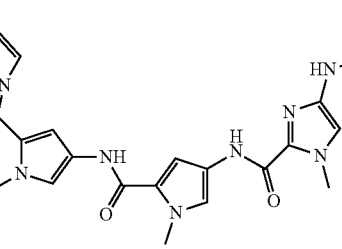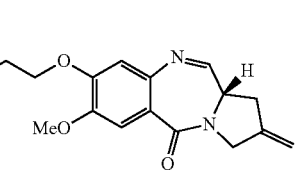
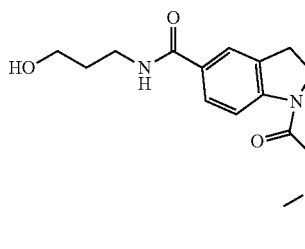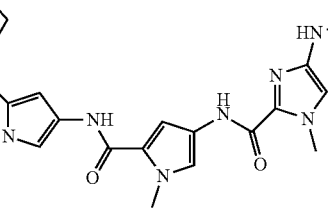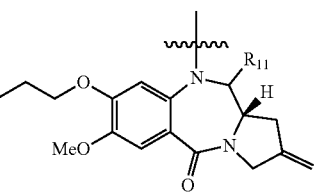
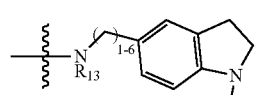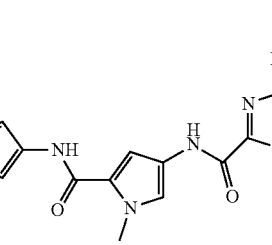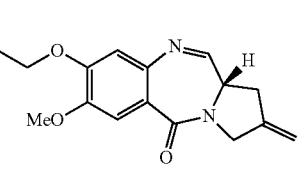

TABLE 1A-continued
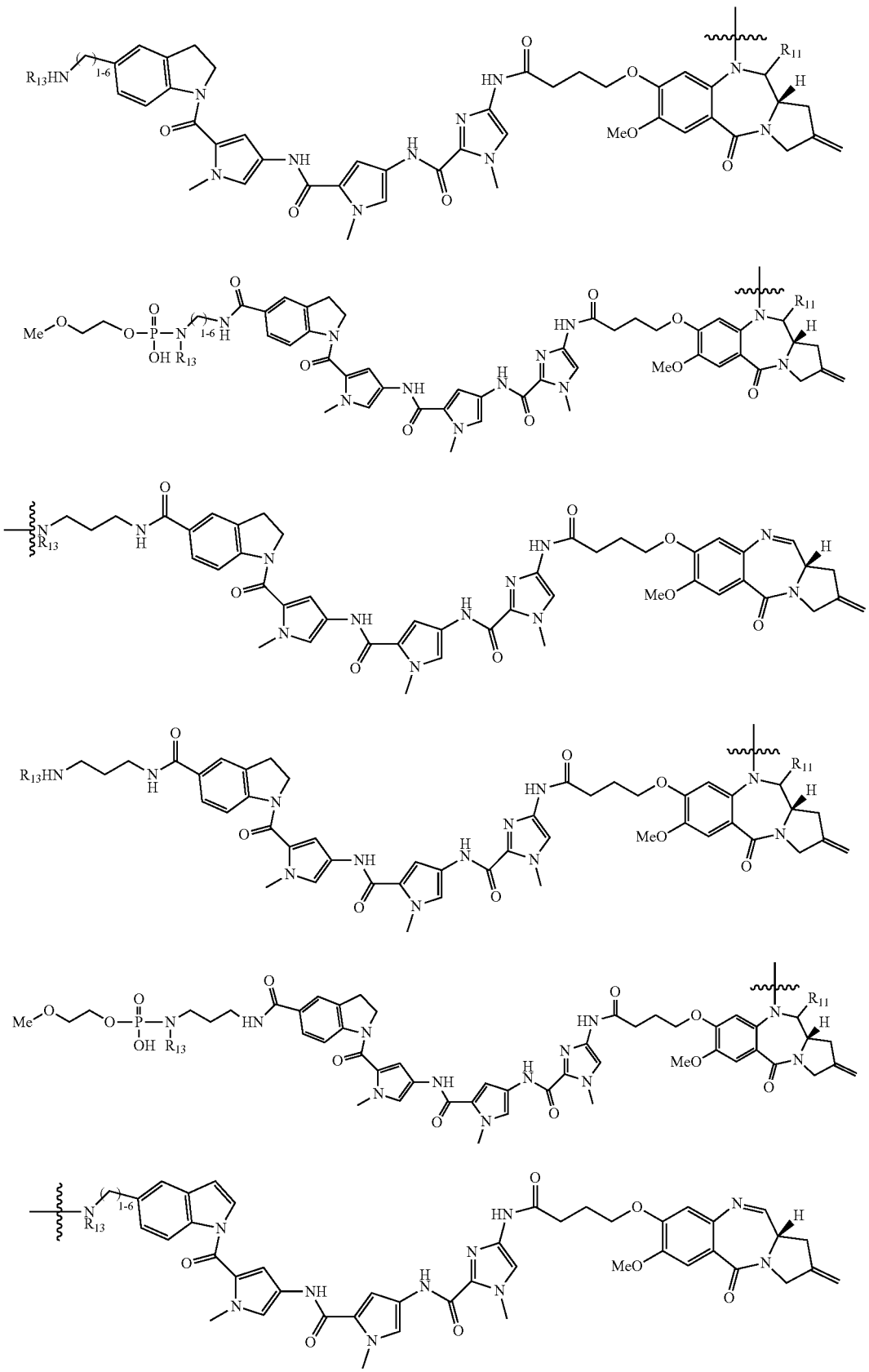

TABLE 1A-continued
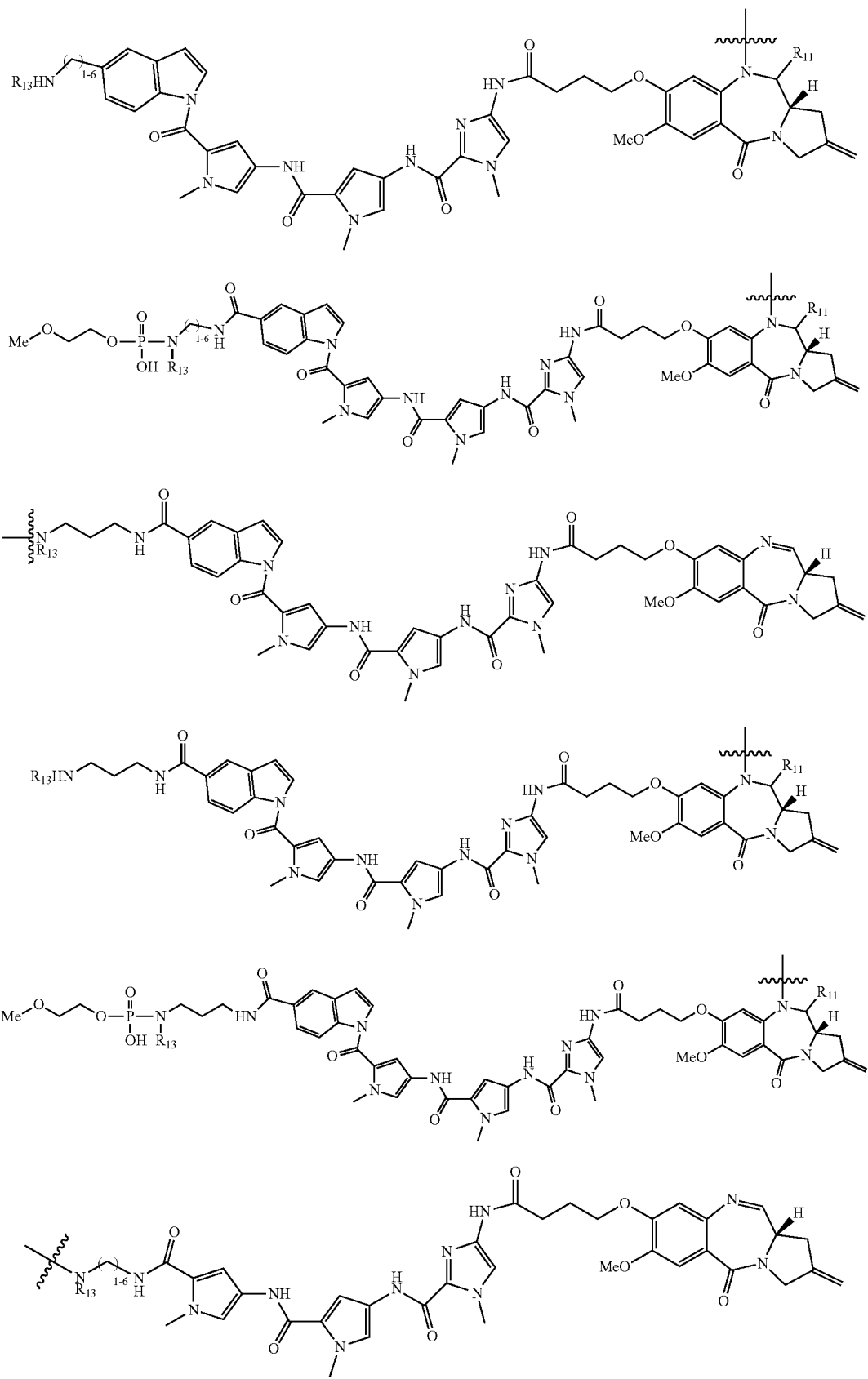

TABLE 1A-continued
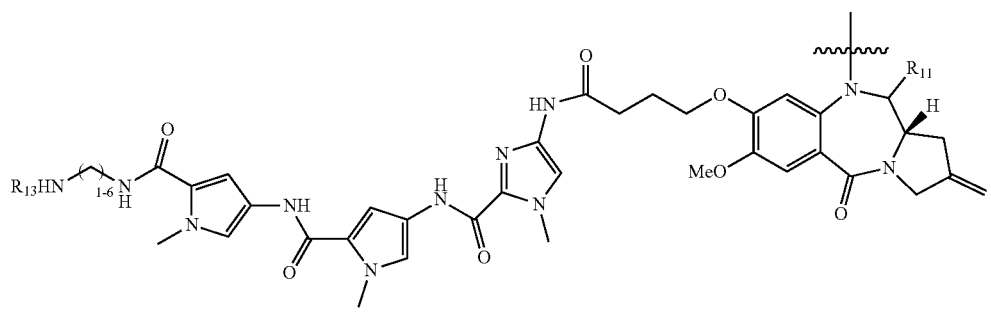
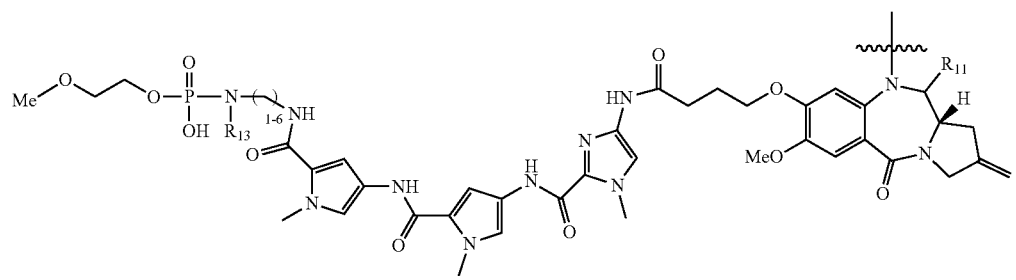
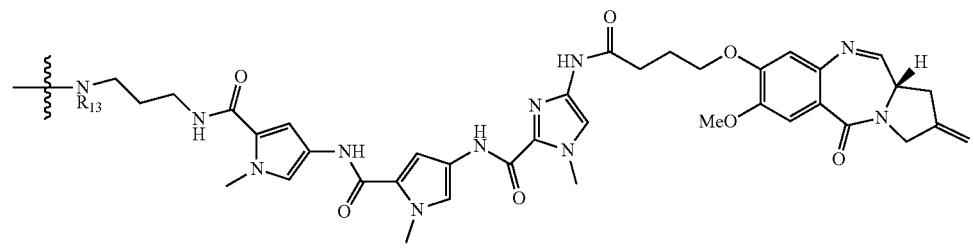
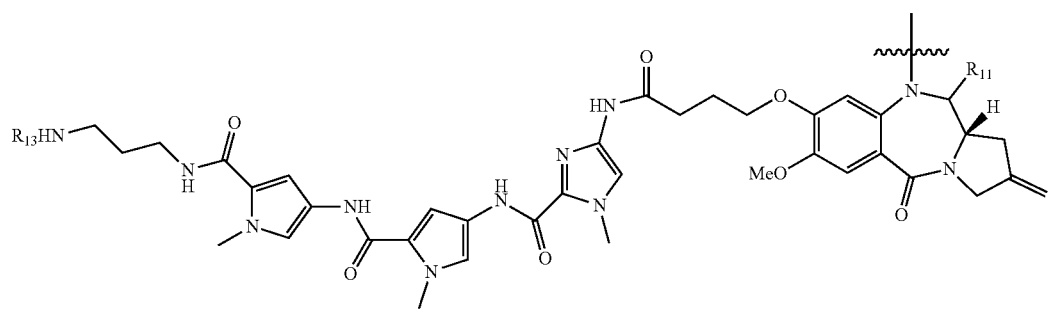
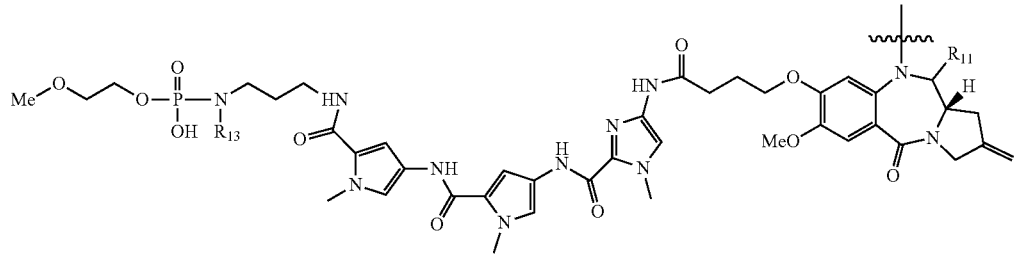

TABLE 1A-continued
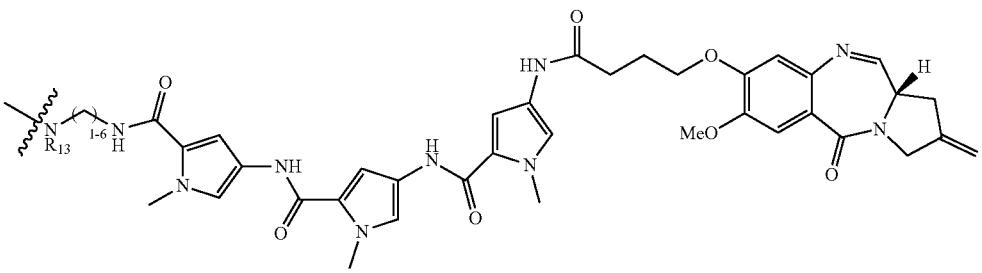
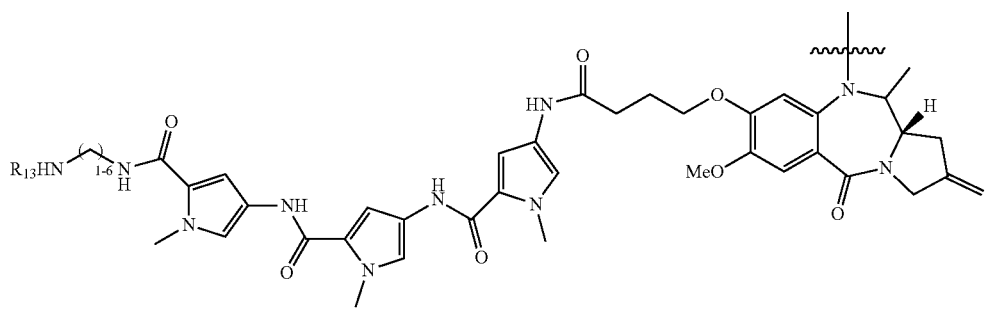
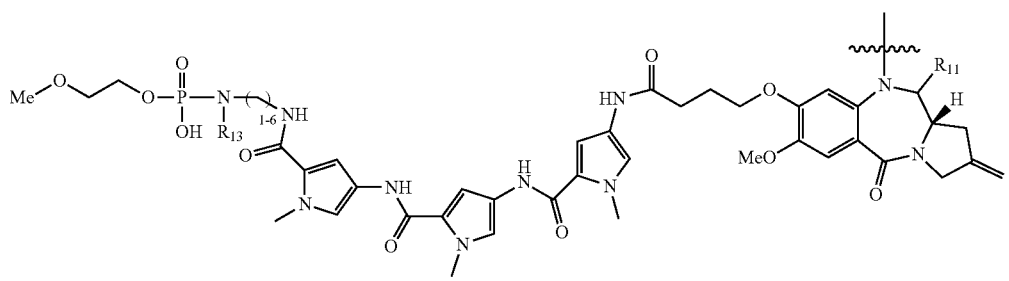
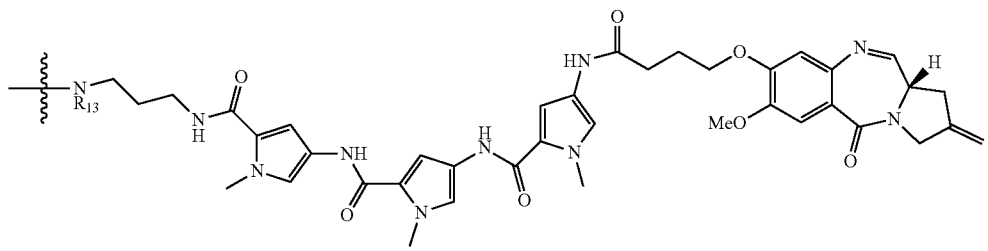
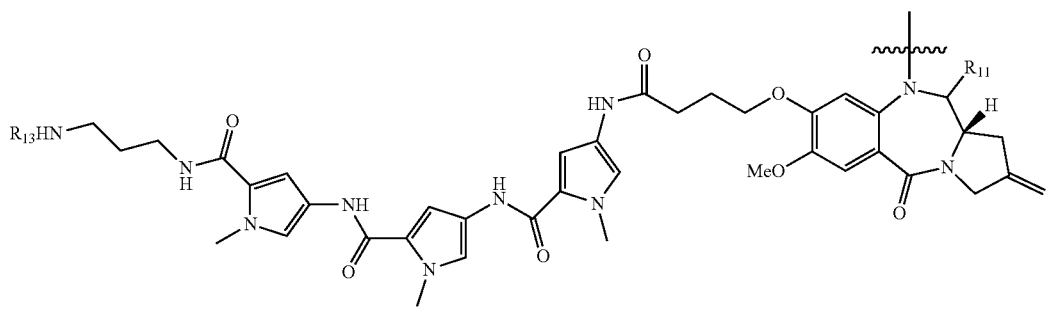

TABLE 1A-continued
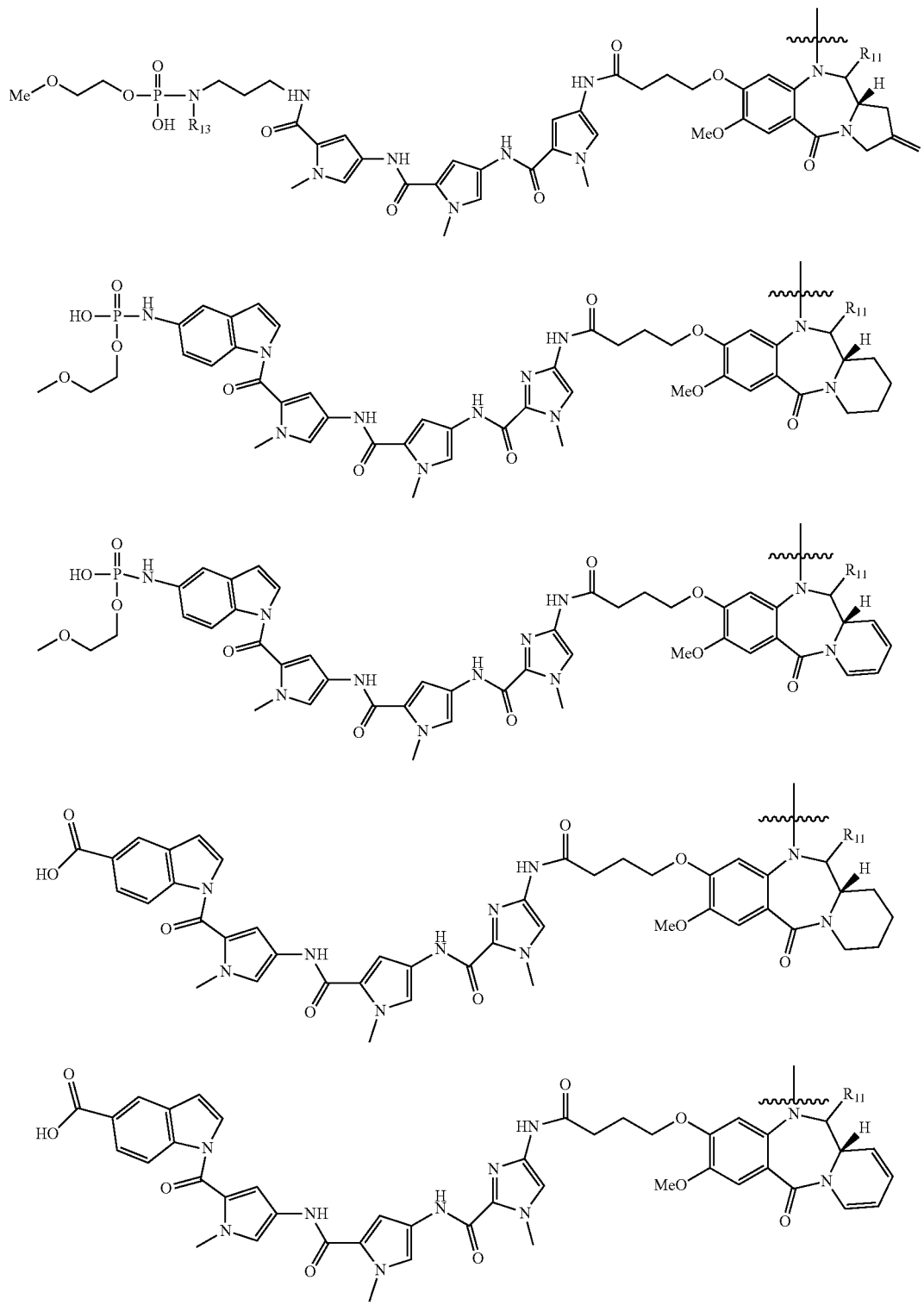
Representative examples of conjugates of Formula (I) include those listed in Table 2, a tautomer thereof, a pharmaceutically acceptable salt or solvate thereof, or a pharmaceutically acceptable salt or solvate of the tautomer.

TABLE 2
| Conjugate No. | Structure |
|---|---|
| Conjugate No. 5 (Example 1) | 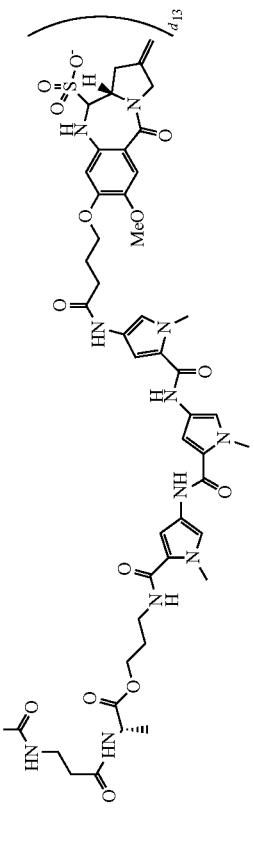 |
| Conjugate No. 8 (Example 2) | 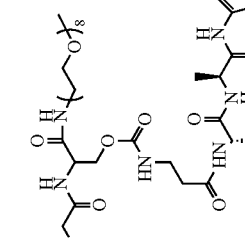 |
| Conjugate No. 14 (Example 4) | 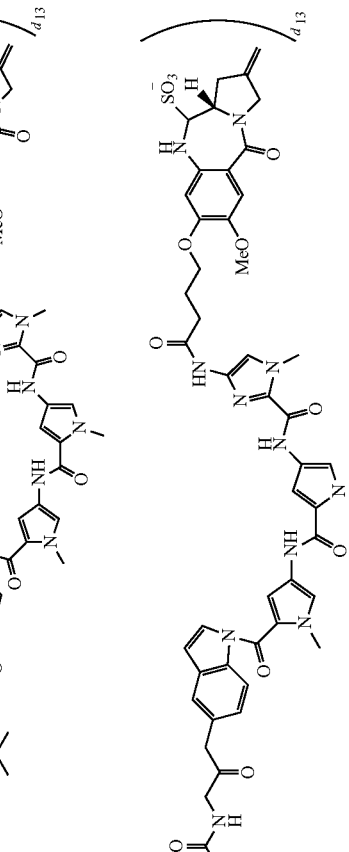 |

TABLE 2-continued

| Conjugate No. | Structure |
|---|---|
| Conjugate No. 22 (Example 5) | (structure with Trastuzumab) |
| Conjugate No. 28 (Example 6) | (structure with Trastuzumab) |
| Conjugate No. 34 (Example 7) | (structure with Trastuzumab) |

TABLE 2-continued
| Conjugate No. | Structure |
|---|---|
| Conjugate No. 35 (Example 8) | 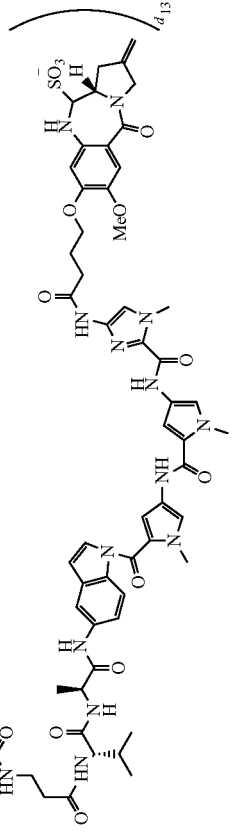 |
| Conjugate No. 101 | 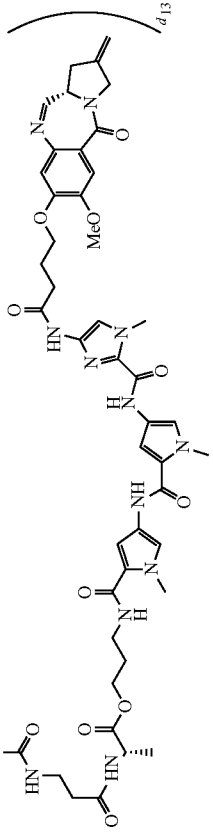 |

TABLE 2-continued
| Conjugate No. | Structure |
|---|---|
| Conjugate No. 102 | 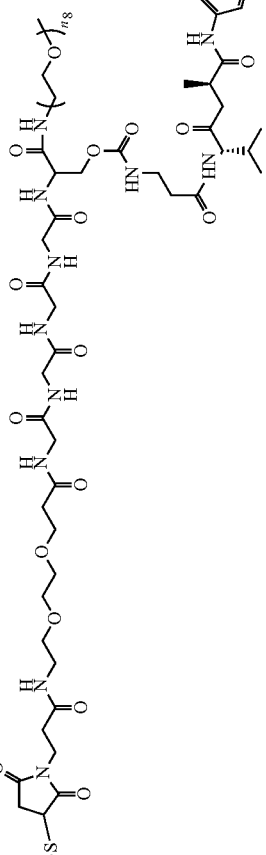 |

TABLE 2-continued
| Conjugate No. | Structure |
|---|---|
| Conjugate No. 103 | 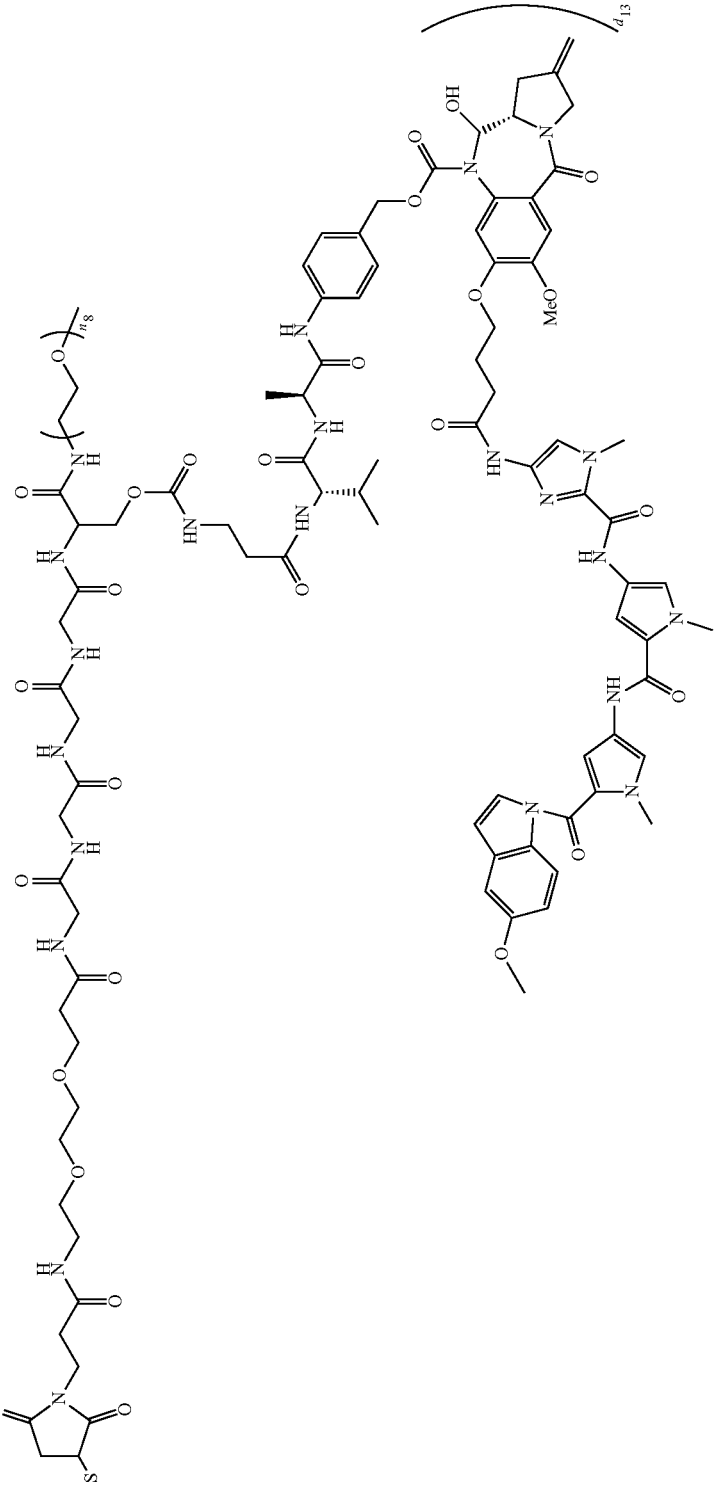 |
| Conjugate No. 104 | 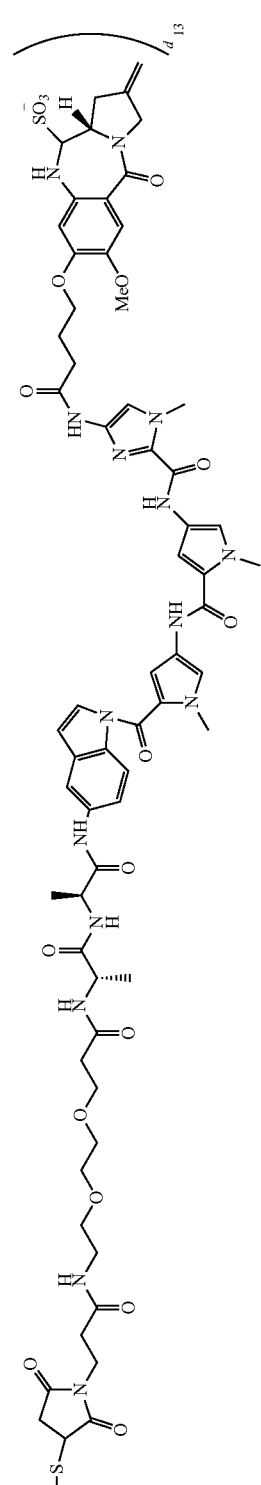 |

TABLE 2-continued
| Conjugate No. | Structure |
|---|---|
| Conjugate No. 105 | 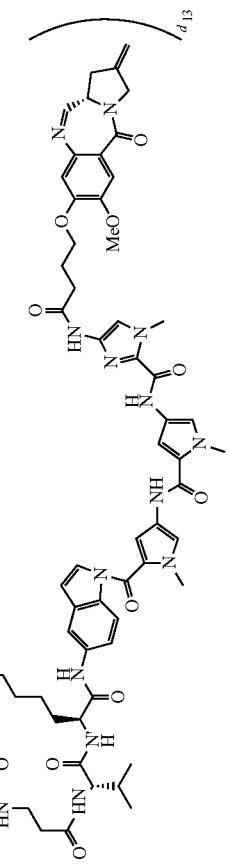 |
| Conjugate No. 106 | 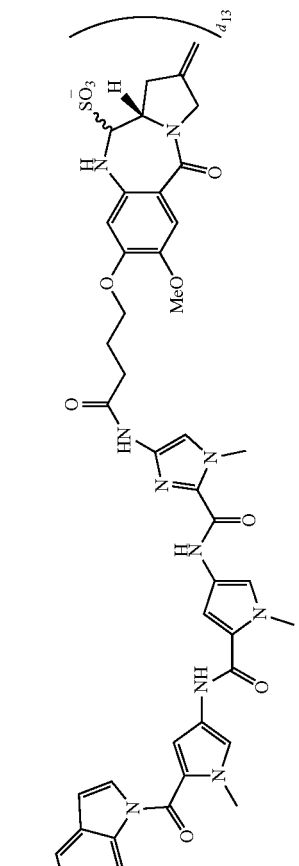 |
| Conjugate No. 107 | 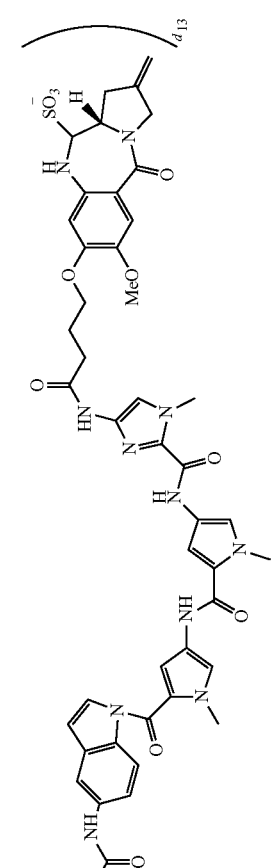 |

TABLE 2-continued
| Conjugate No. | Structure |
|---|---|
| Conjugate No. 108 | 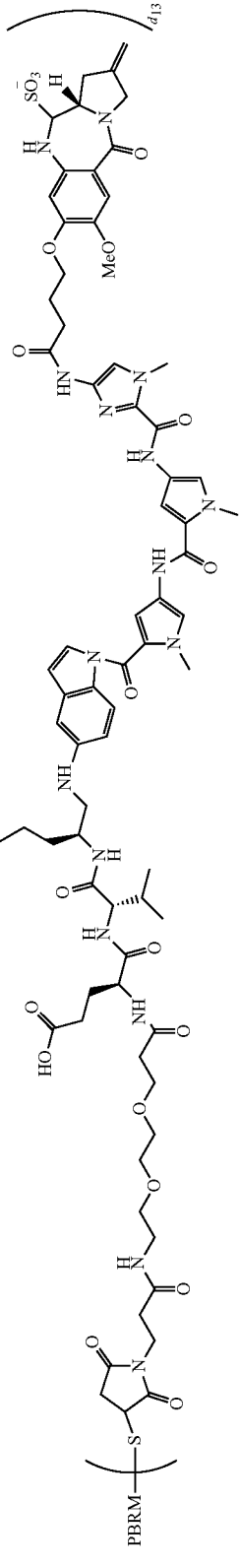 |
| Conjugate No. 109 | 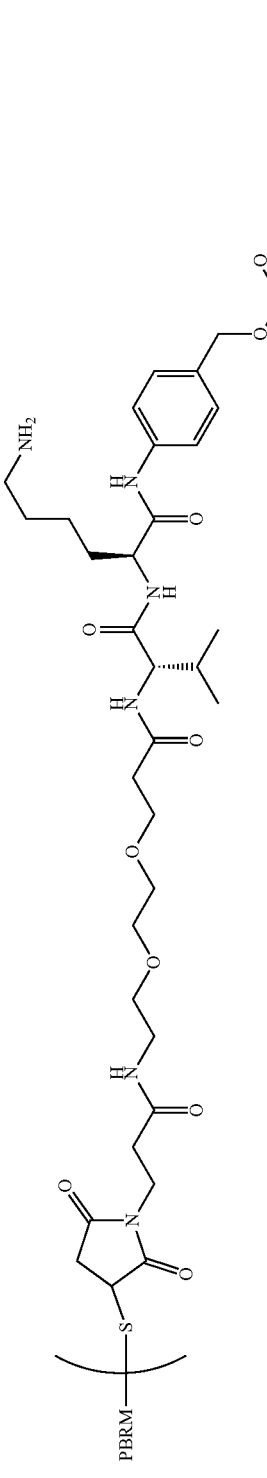 |

TABLE 2-continued

| Conjugate No. | Structure |
|---|---|
| Conjugate No. 110 | 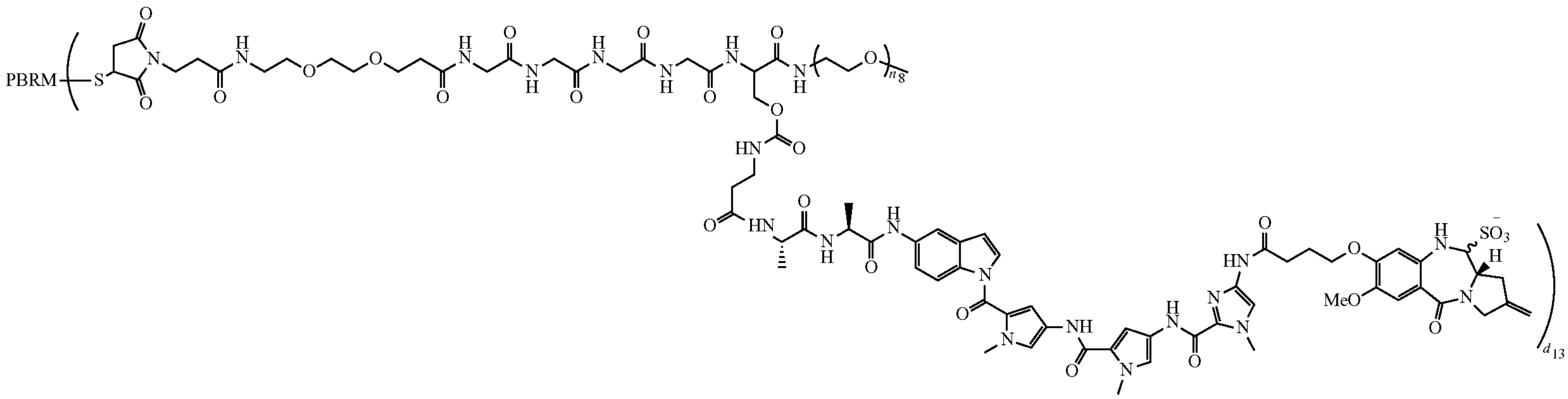 |
| Conjugate No. 111 | 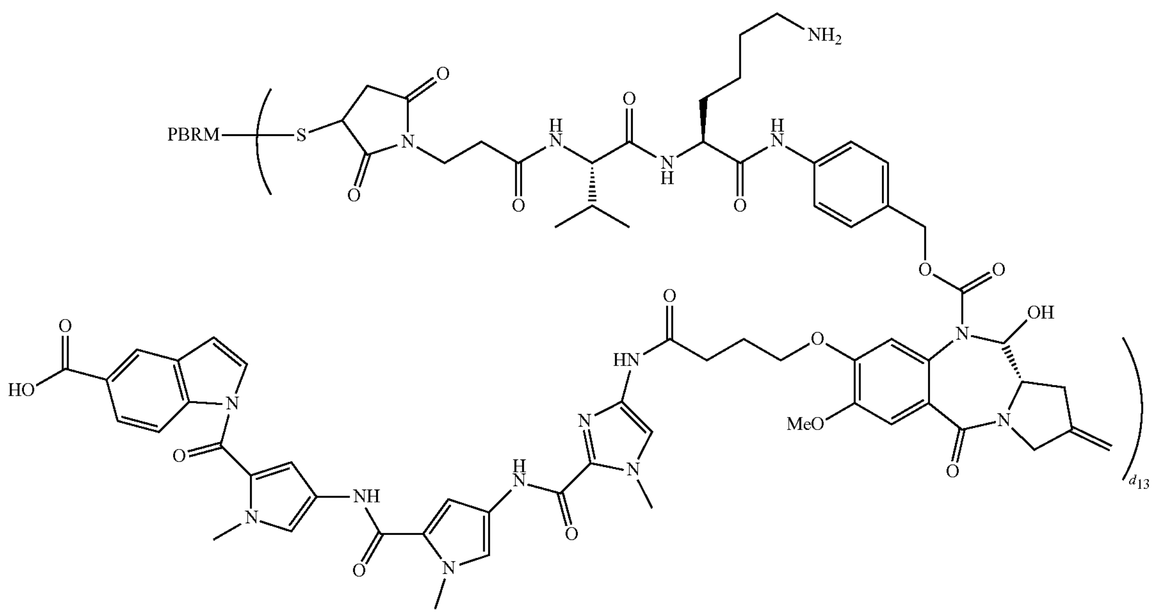 |

TABLE 2-continued
| Conjugate No. | Structure |
|---|---|
| Conjugate No. 112 | 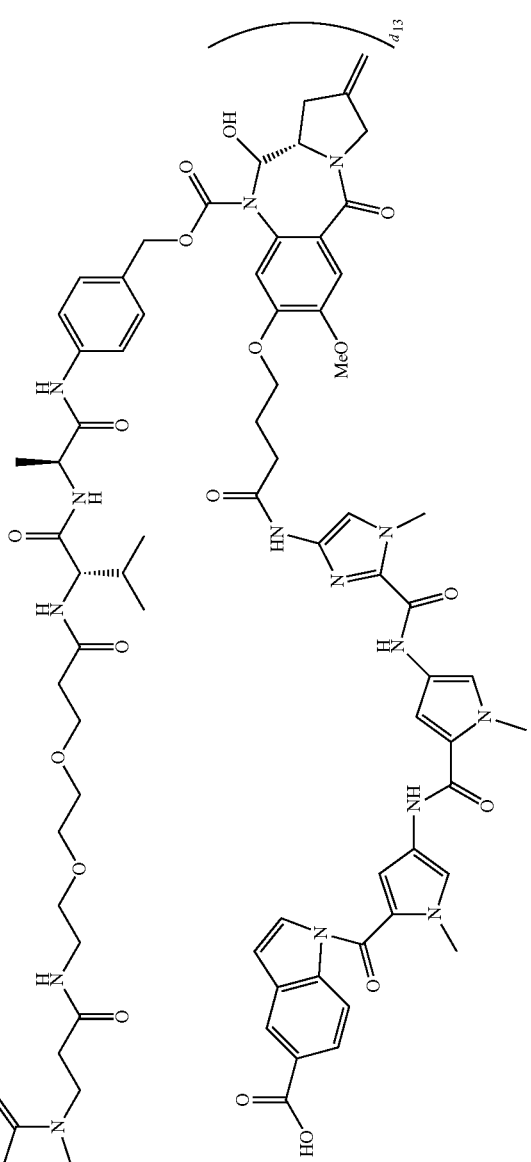 |

TABLE 2-continued
| Conjugate No. | Structure |
|---|---|
| Conjugate No. 113 | 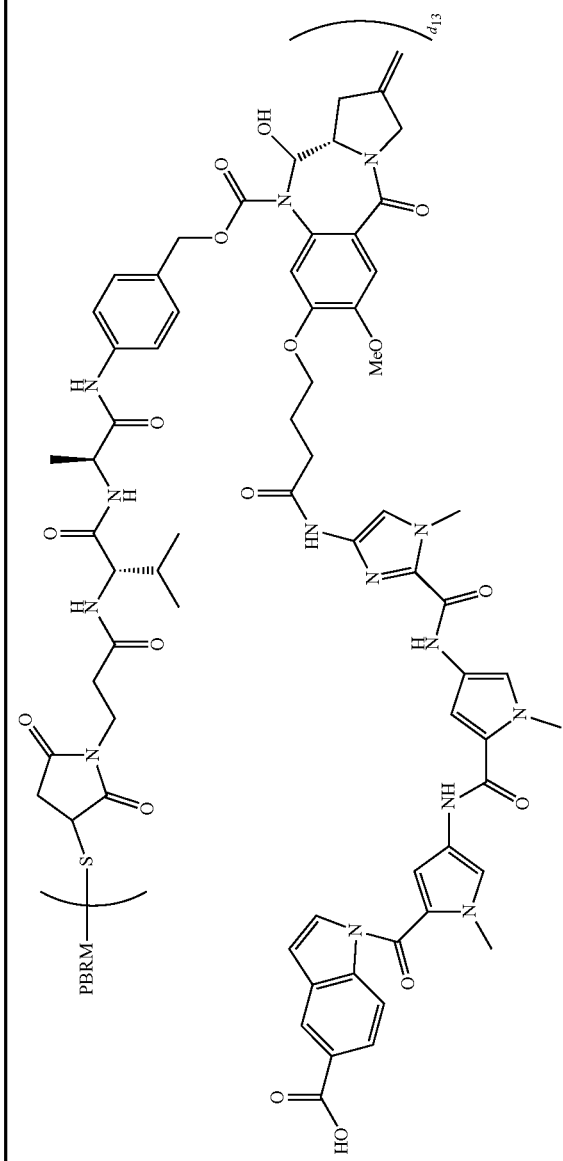 |

TABLE 2-continued
| Conjugate No. | Structure |
|---|---|
| Conjugate No. 114 | 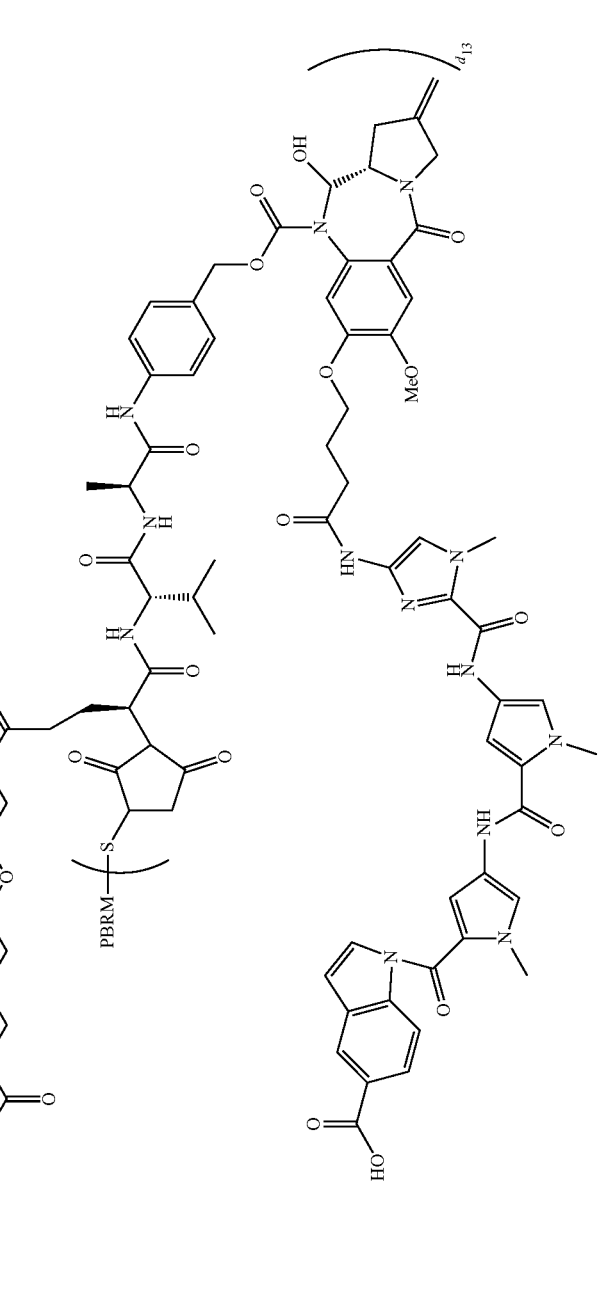 |
| Conjugate No. 115 | 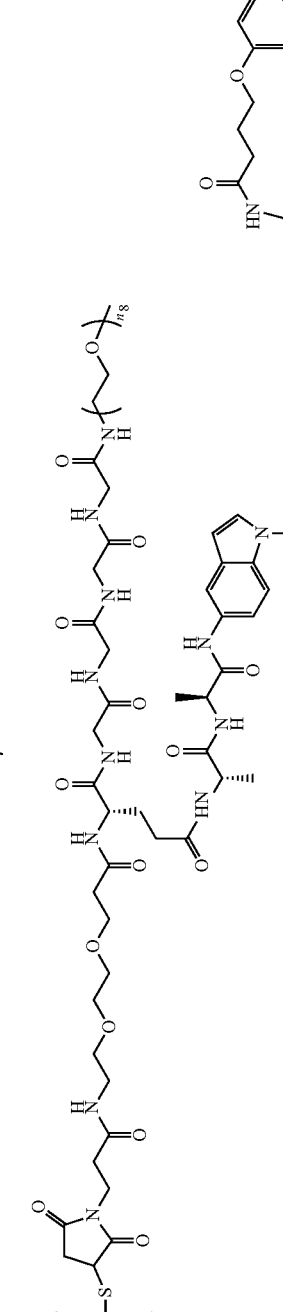 |

TABLE 2-continued
| Conjugate No. | Structure |
|---|---|
| Conjugate No. 116 | 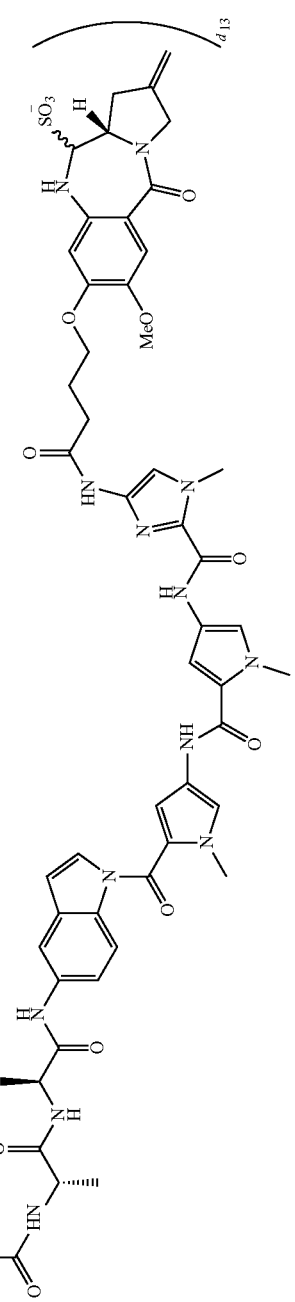 |
| Conjugate No. 118 | 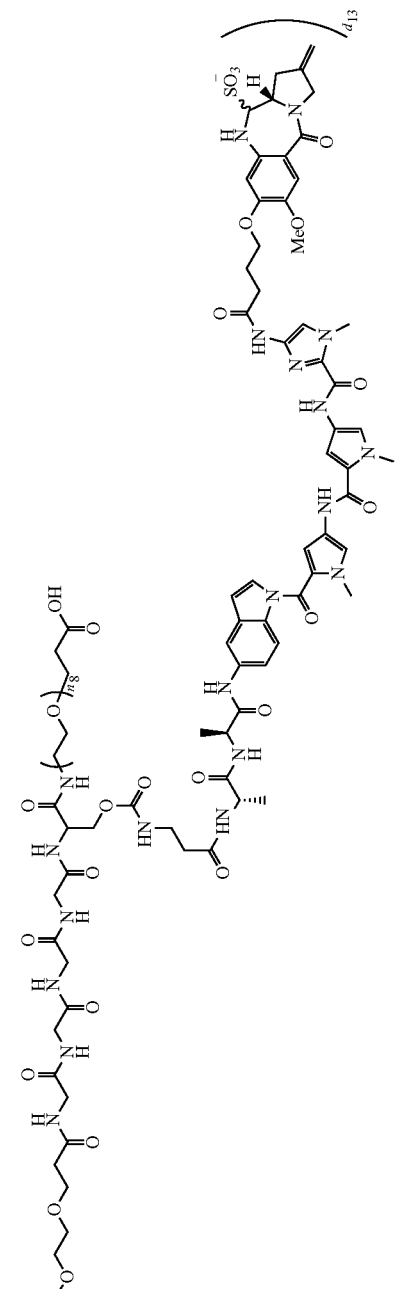 |

TABLE 2-continued
Structure
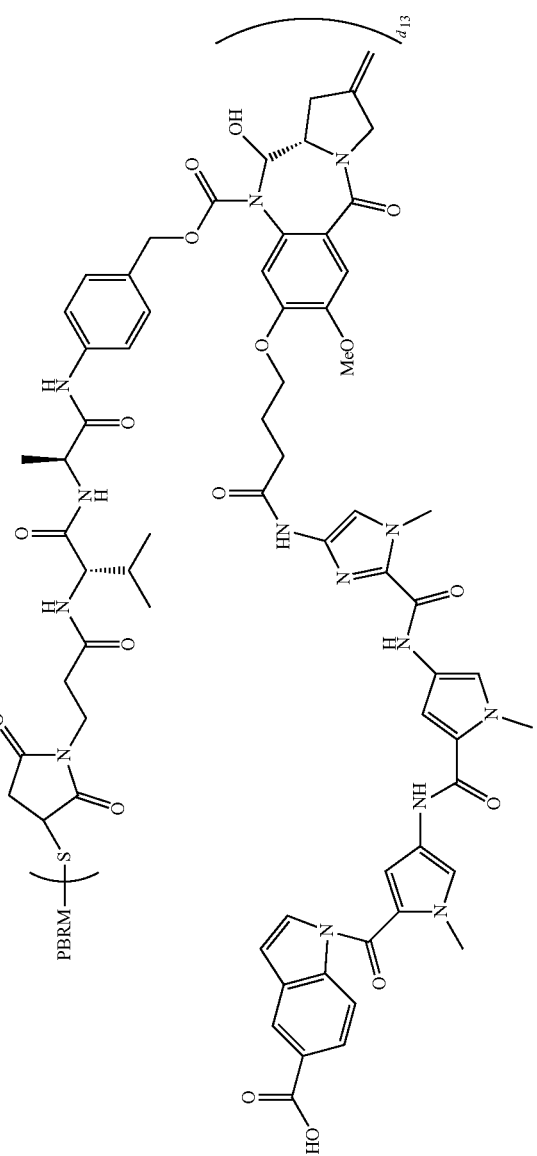

TABLE 2-continued
| Conjugate No. | Structure |
|---|---|
| 281 | 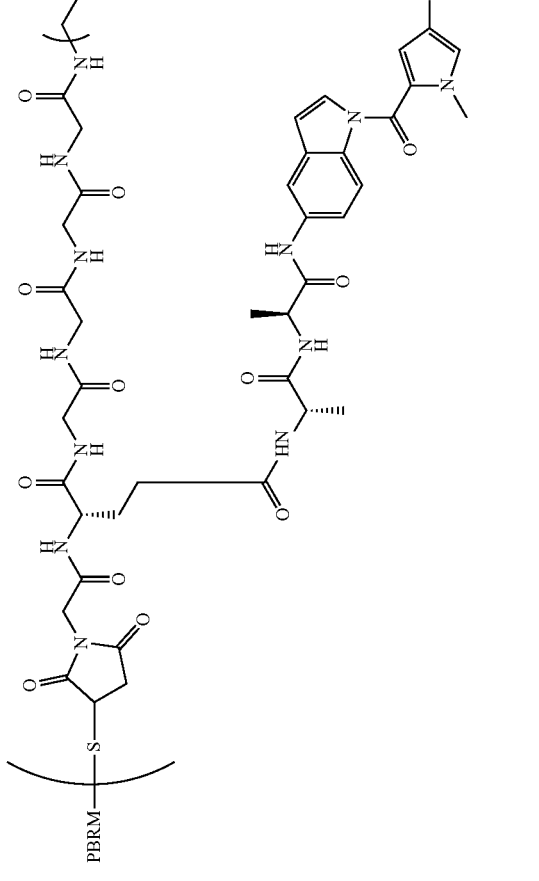 |
| 282 | 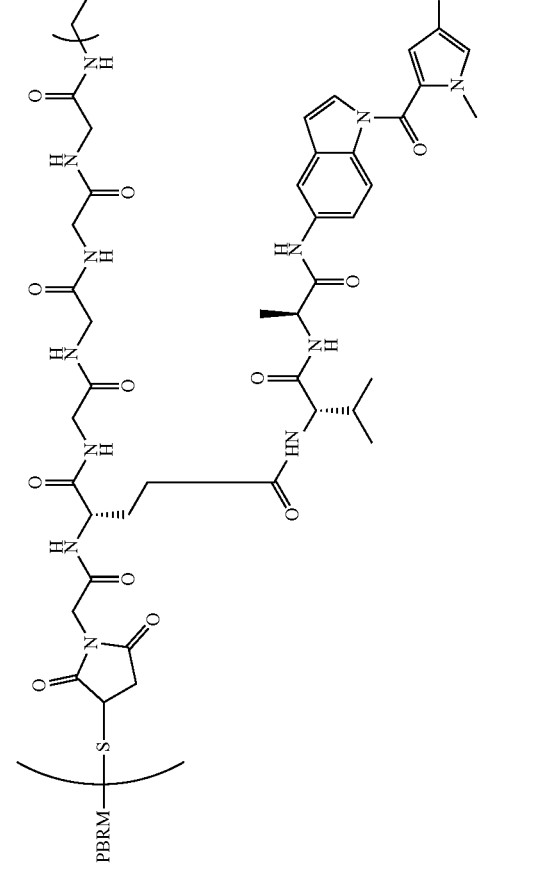 |

TABLE 2-continued
| Conjugate No. | Structure |
|---|---|
| 283 | 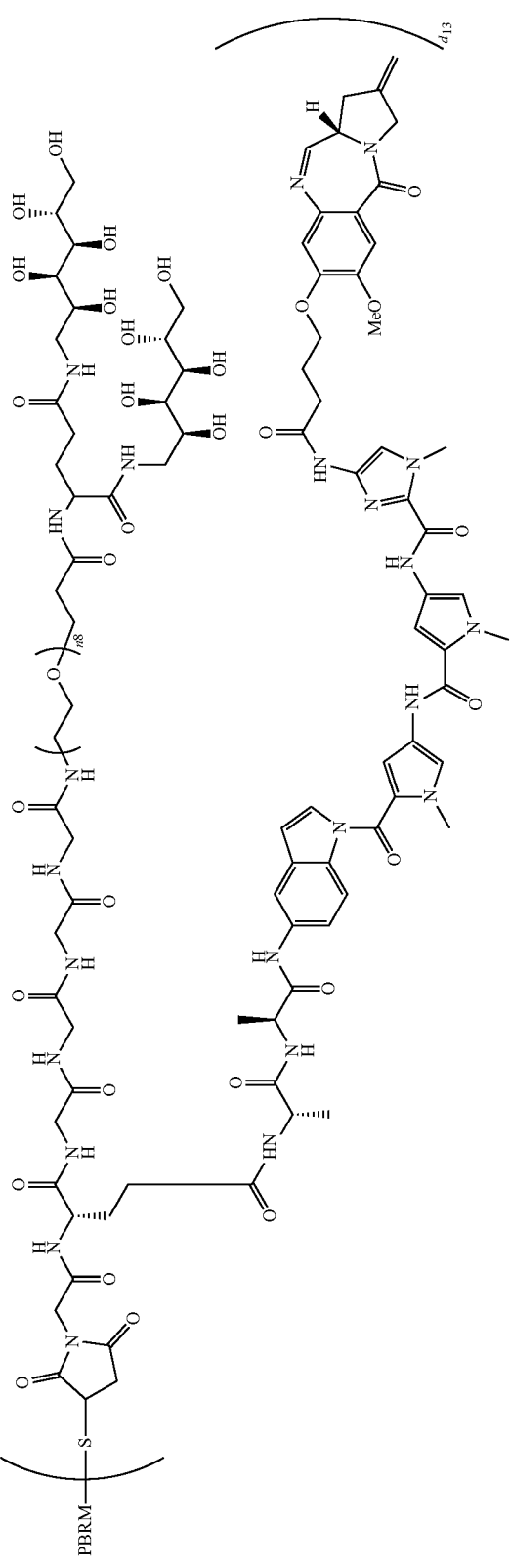 |
| 284 | 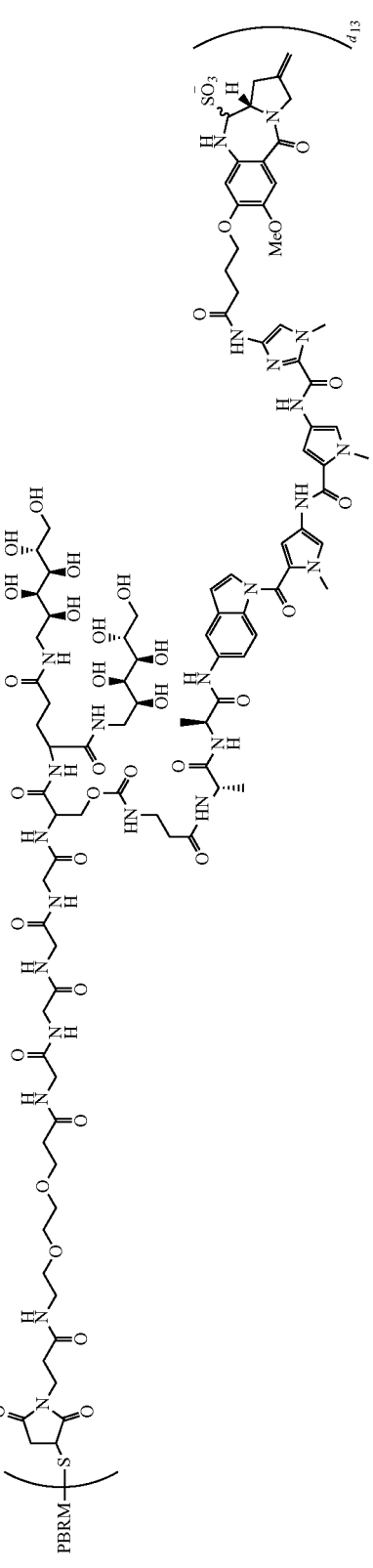 |

TABLE 2-continued
| Conjugate No. | Structure |
|---|---|
| 285 | 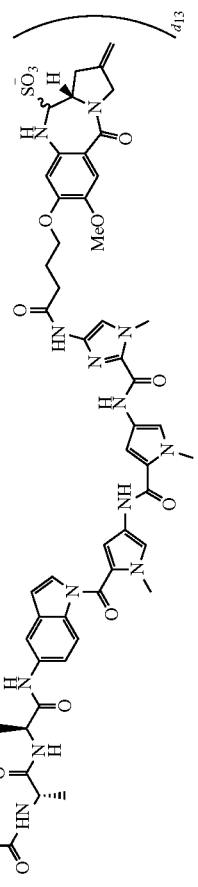 |
| 286 | 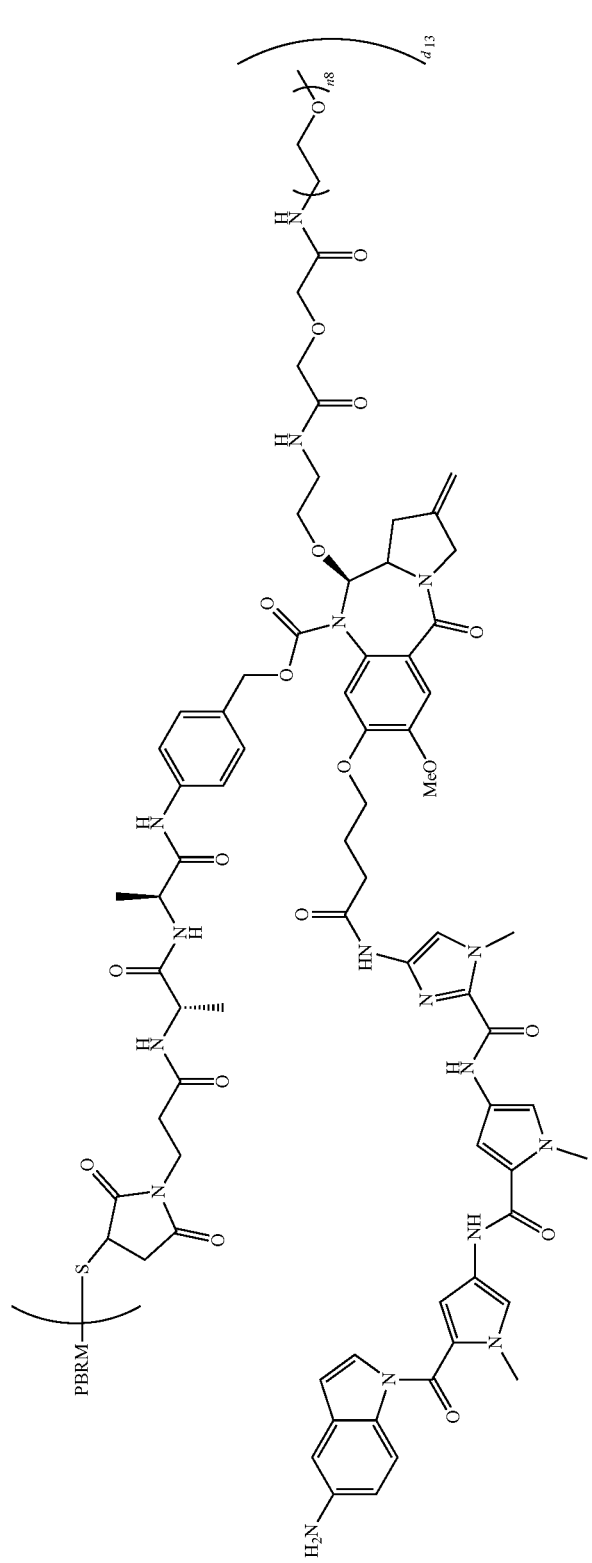 |

TABLE 2-continued
| Conjugate No. | Structure |
|---|---|
| | 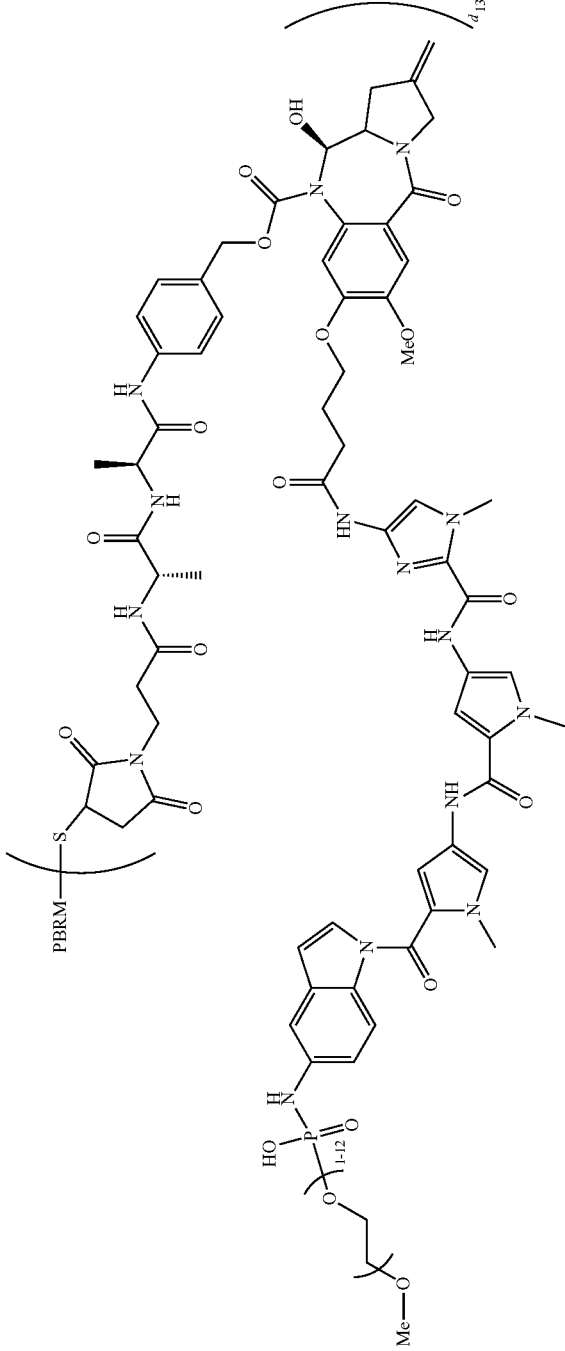 |

TABLE 2-continued
| Conjugate No. | Structure |
|---|---|
| | 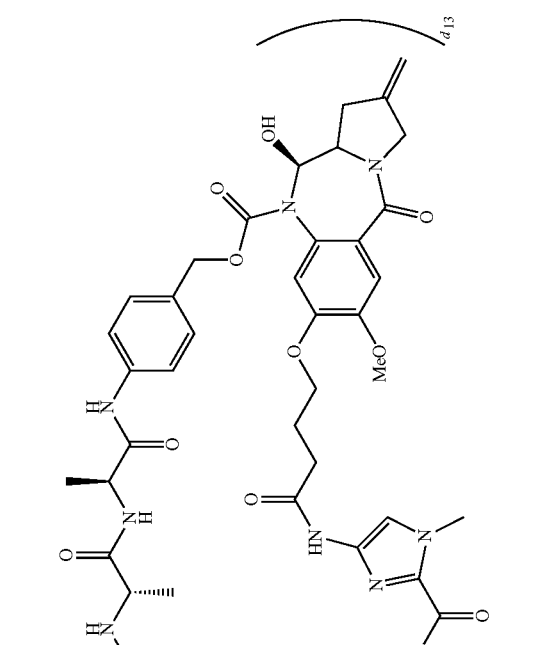 |

TABLE 2-continued
| Conjugate No. | Structure |
|---|---|
|  | 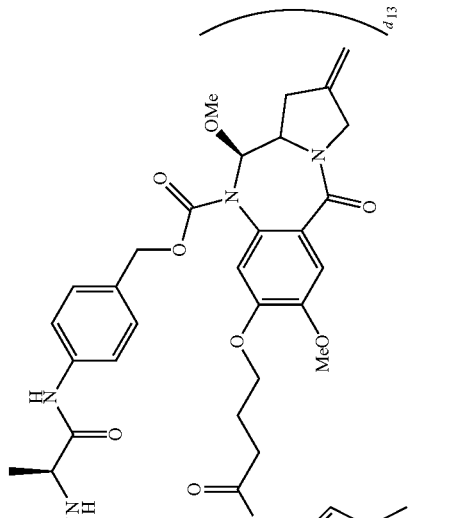 |

TABLE 2-continued
Conjugate No. | Structure
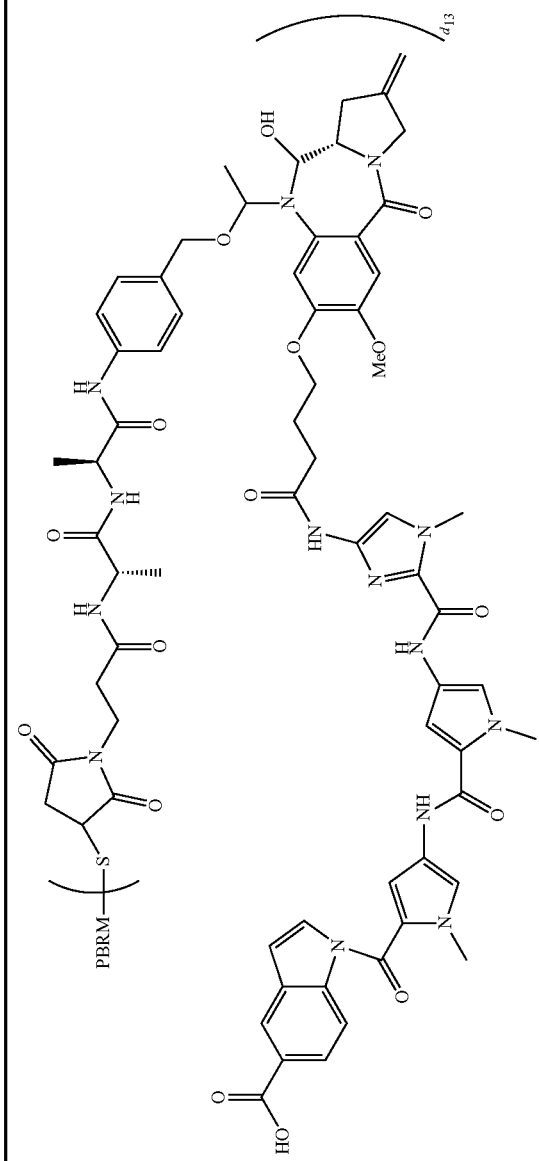

wherein $n_8$=6, 8 or 12 and, preferably, $d_{13}$ is 3 to 5.
In some embodiments, the PBD conjugates is a conjugate of any one of Formulae (XIVa) to (XIVx):
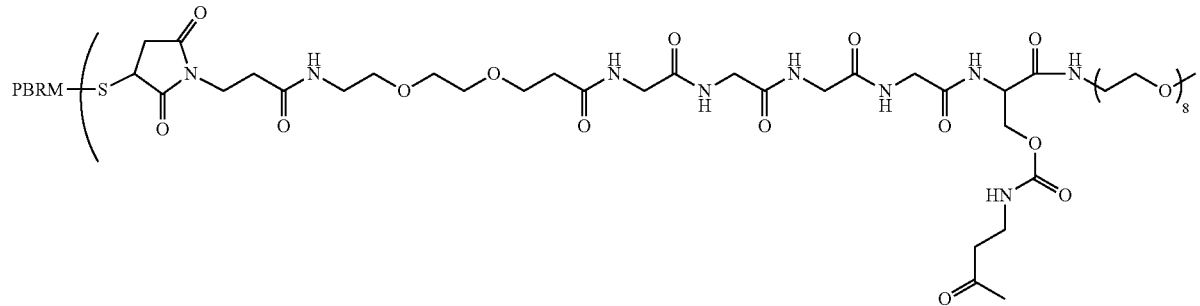
(XIVa)
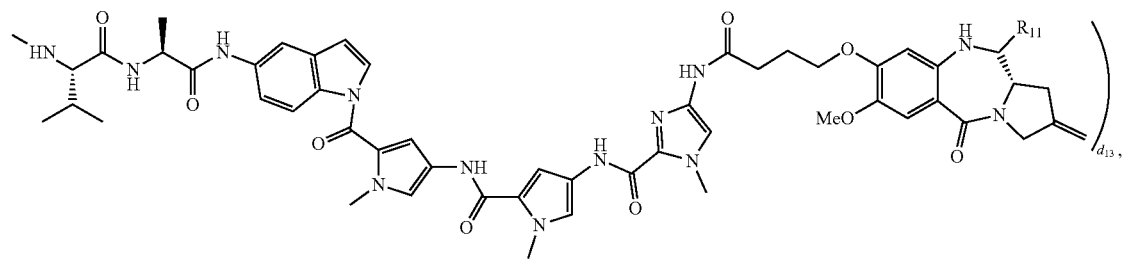
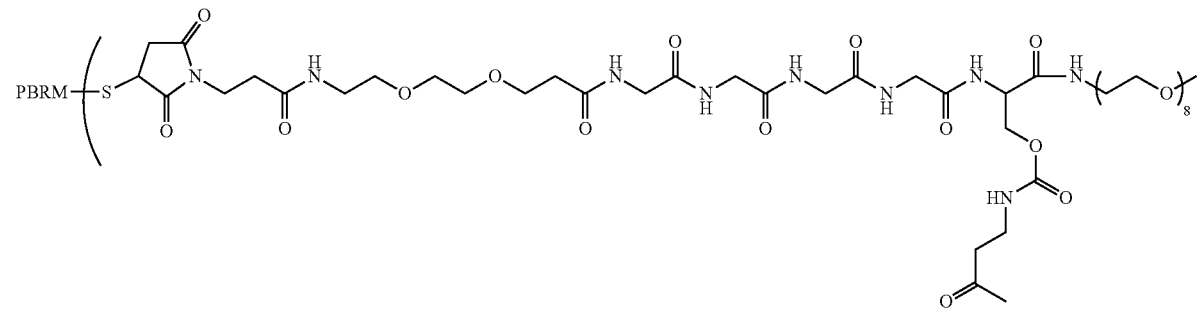
(XIVb)
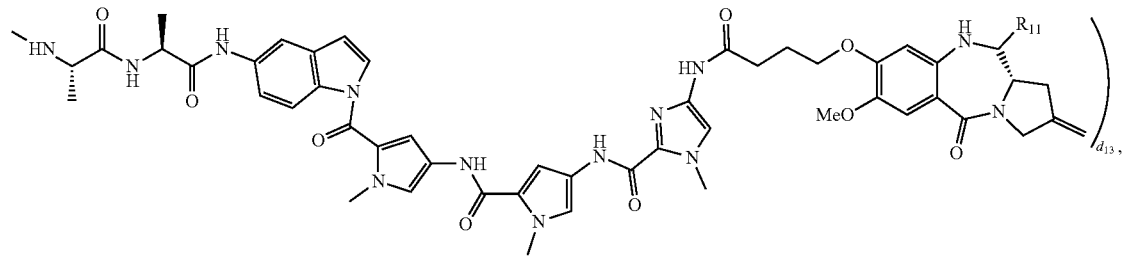
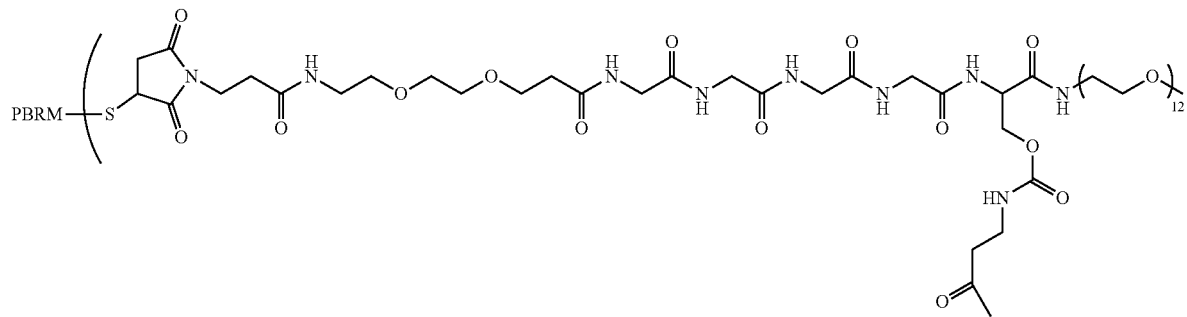
(XIVc)

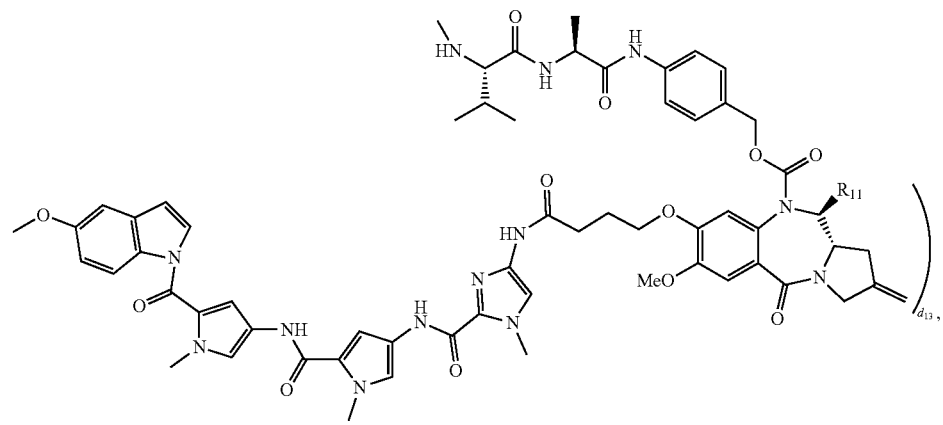
(XIVd)
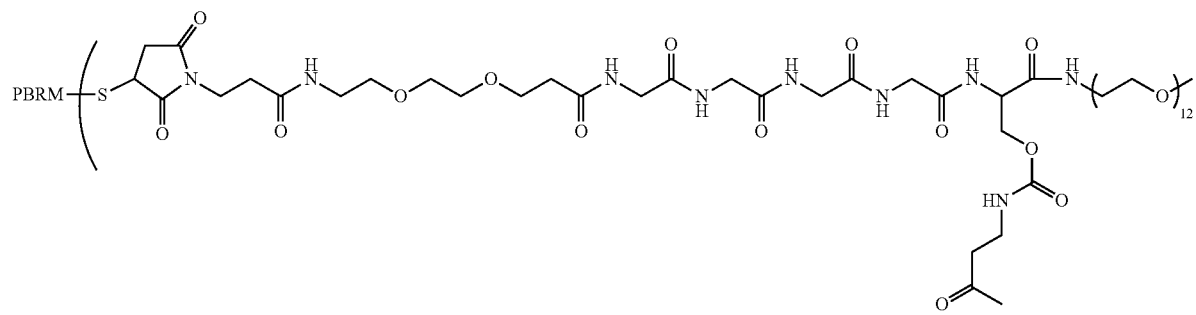
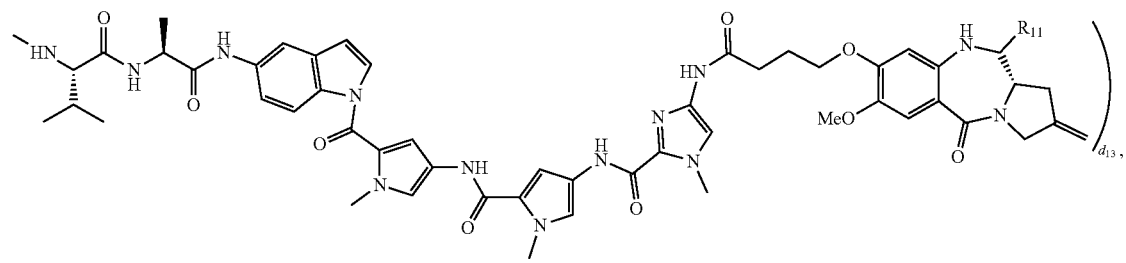
(XIVe)
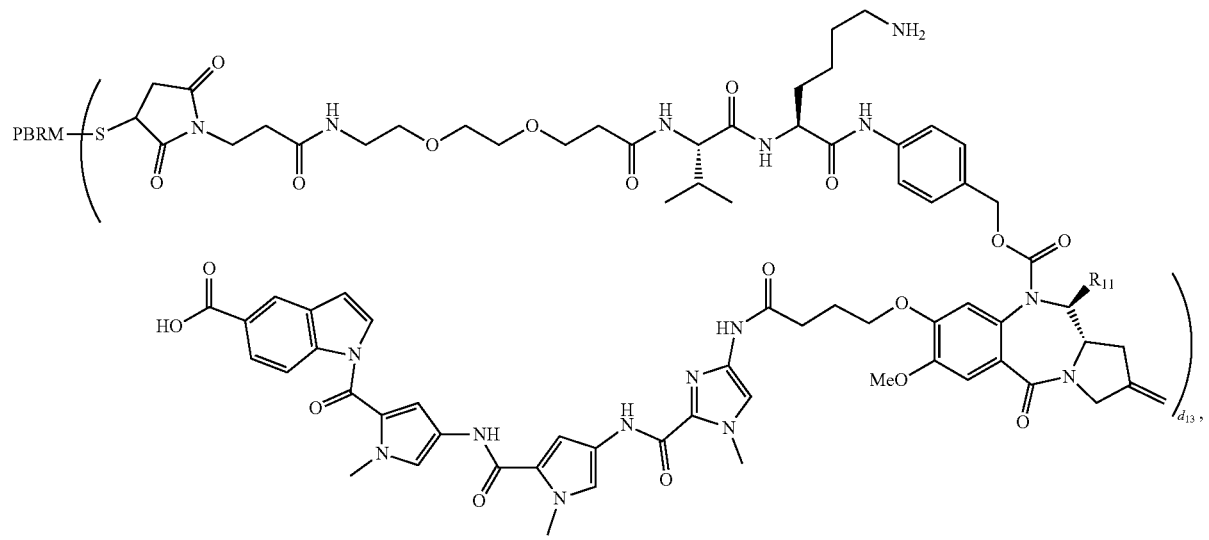

-continued
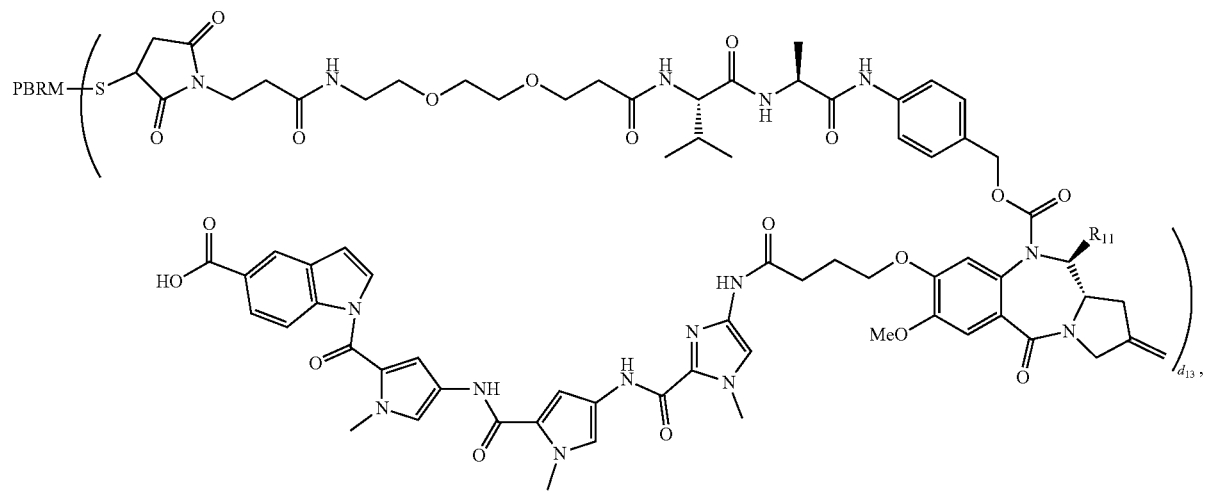
(XIVf)
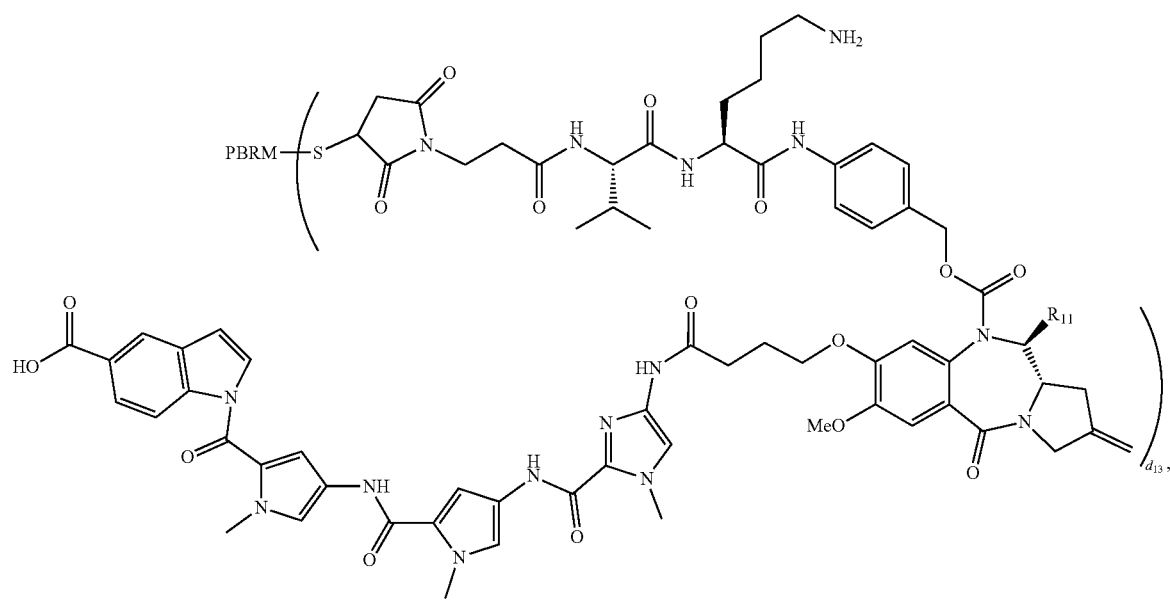
(XIVg)

(XIVh)
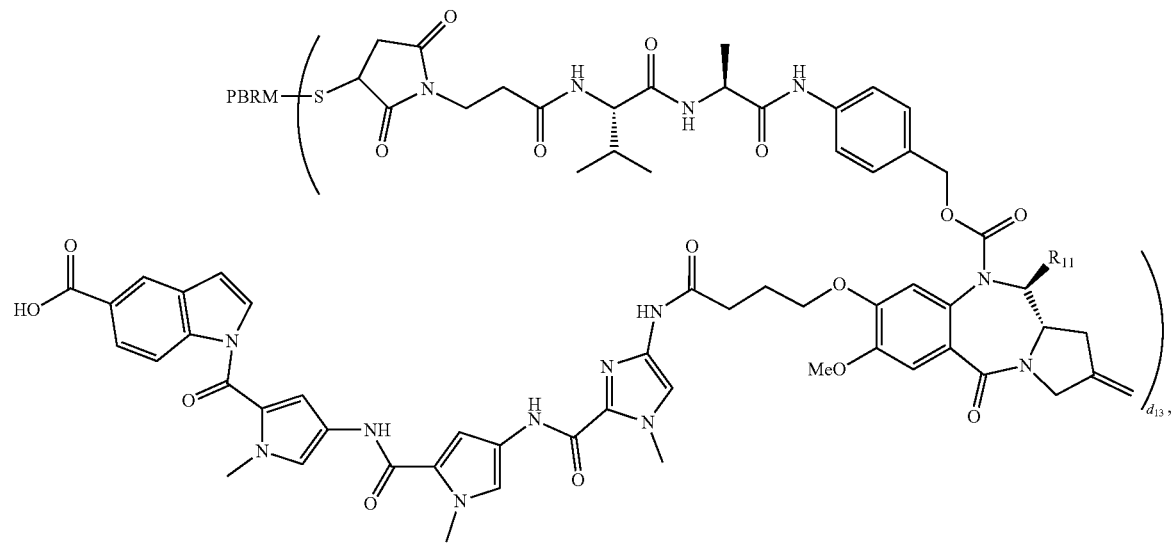
(XIVi)
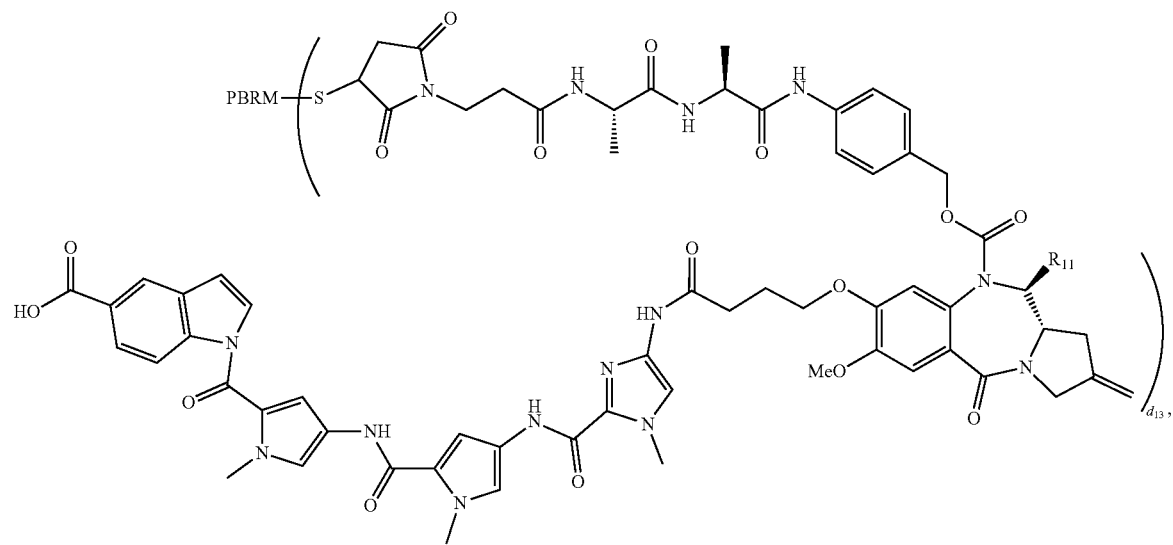
(XIVj)
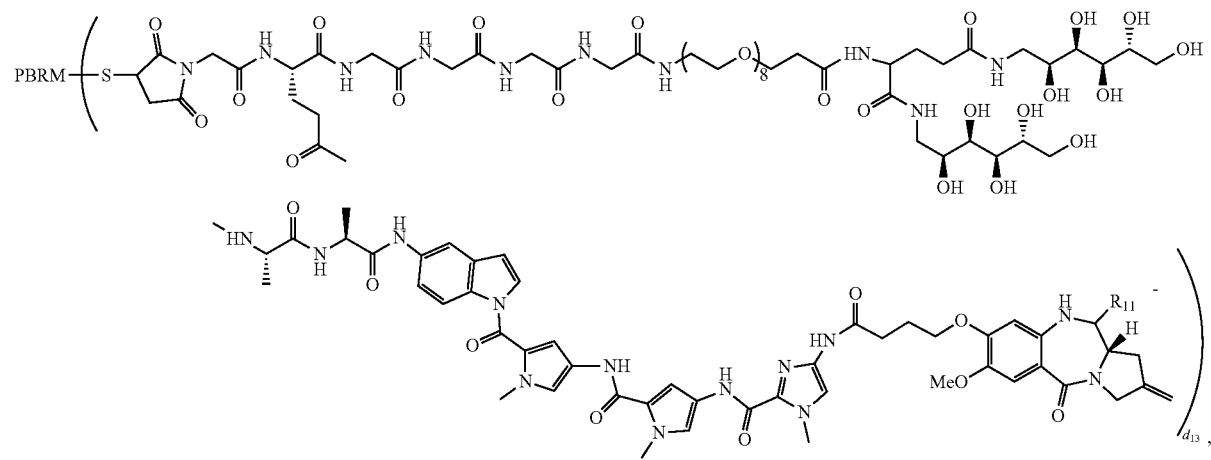

(XIVk)
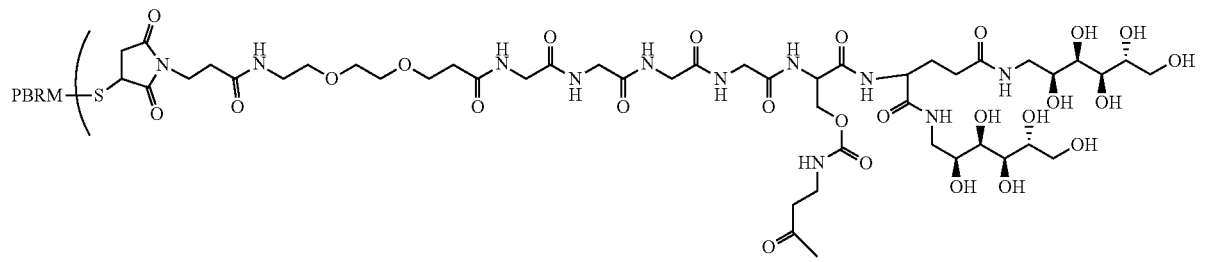
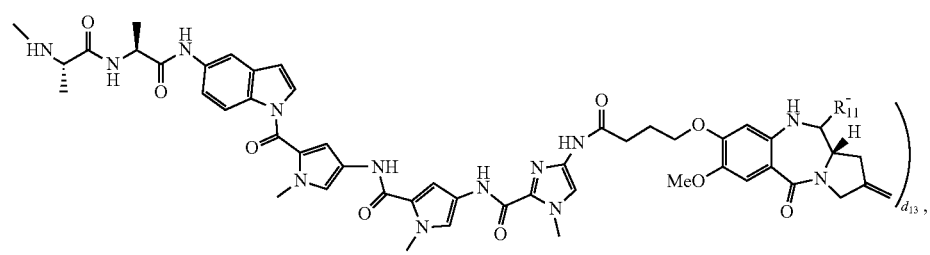
(XIVl)
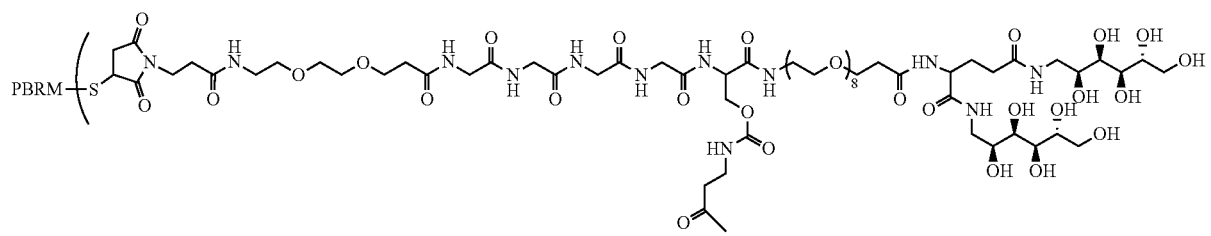
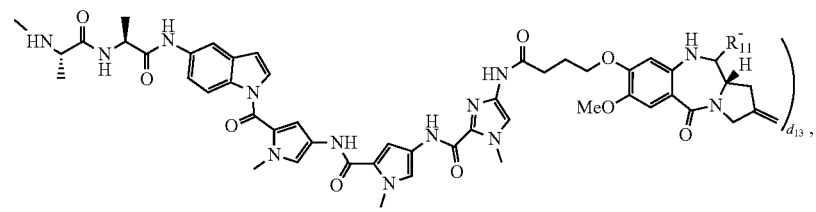
(XIVm)
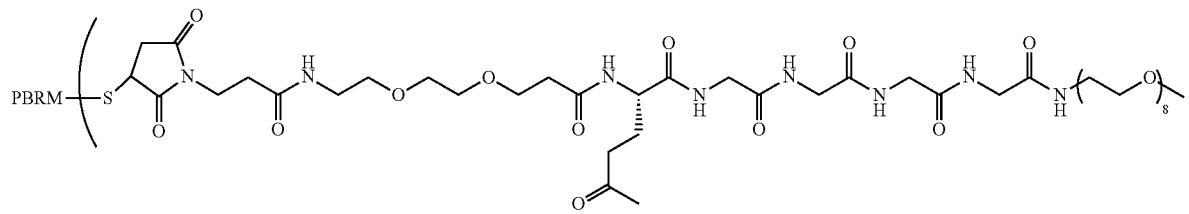
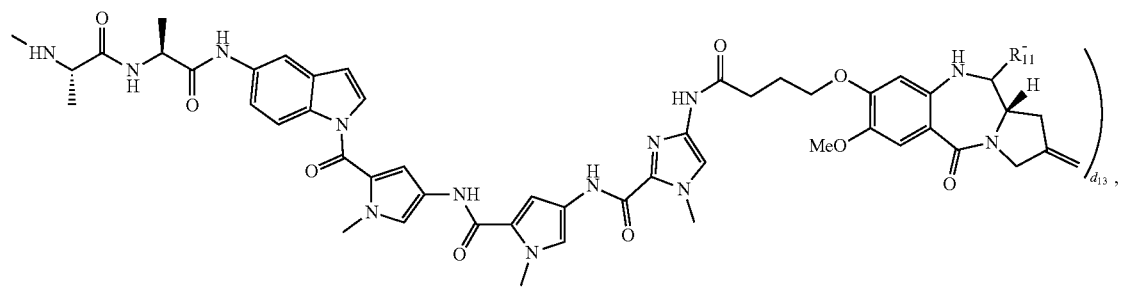

(XIVn)
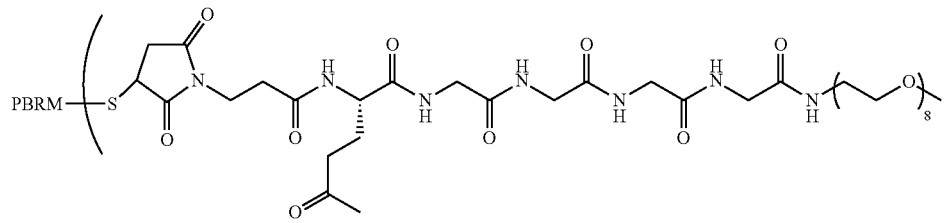
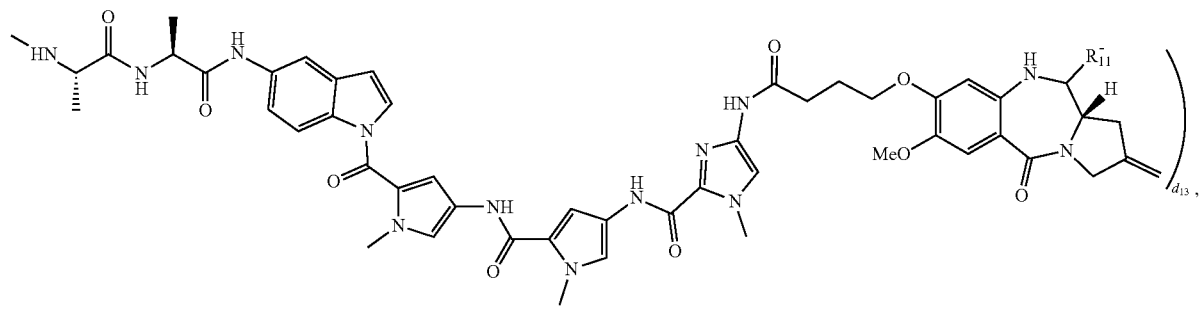
(XIVo)
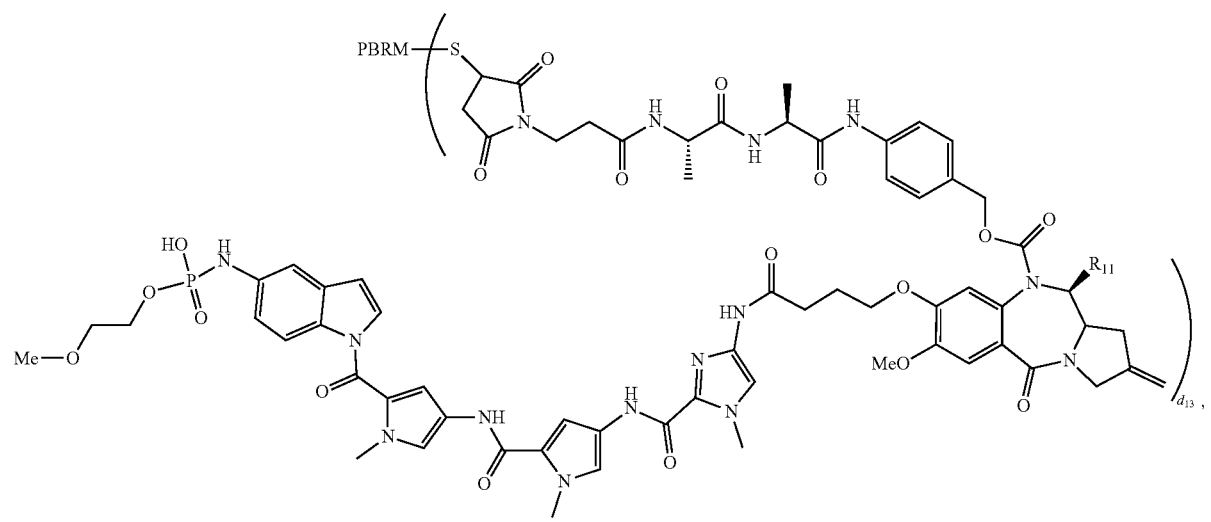
(XIVp)
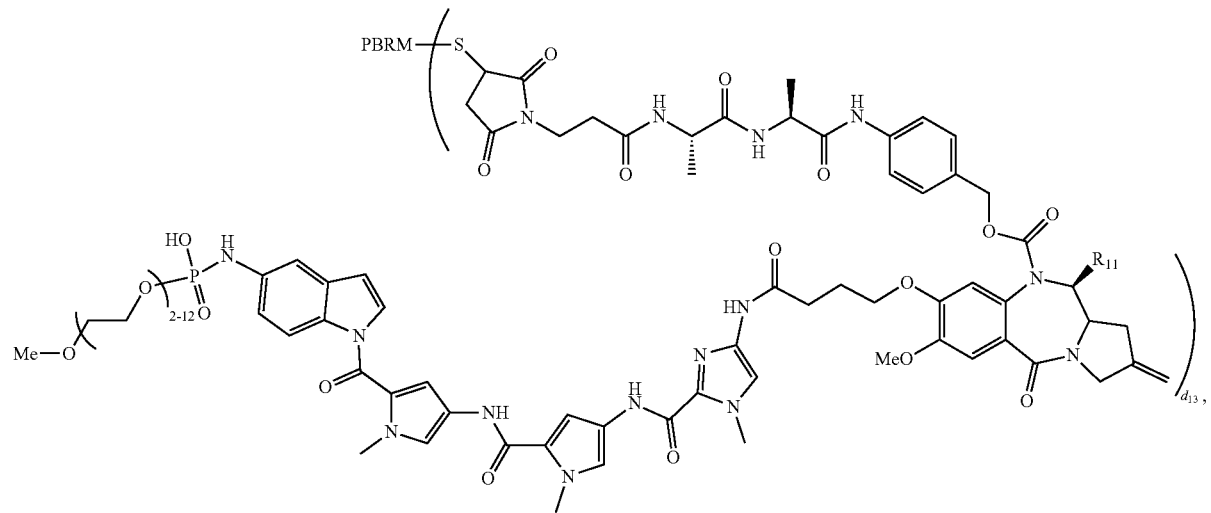

(XIVq)
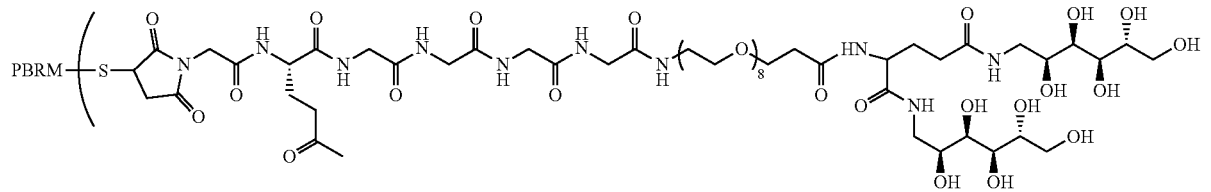
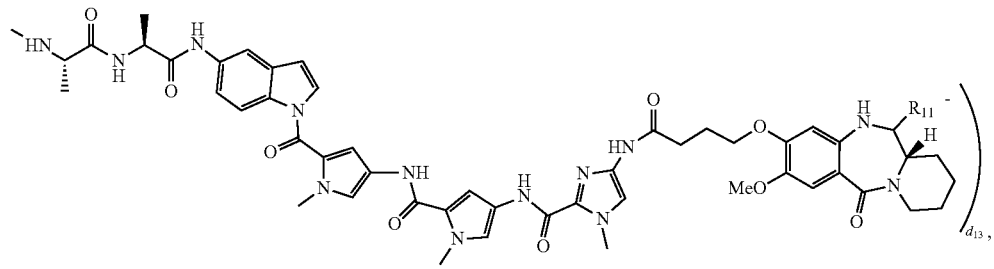
(XIVr)
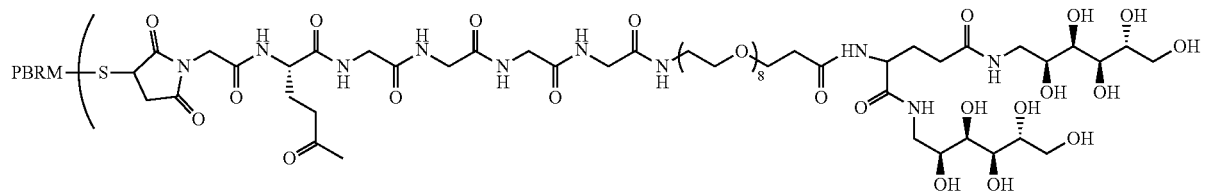
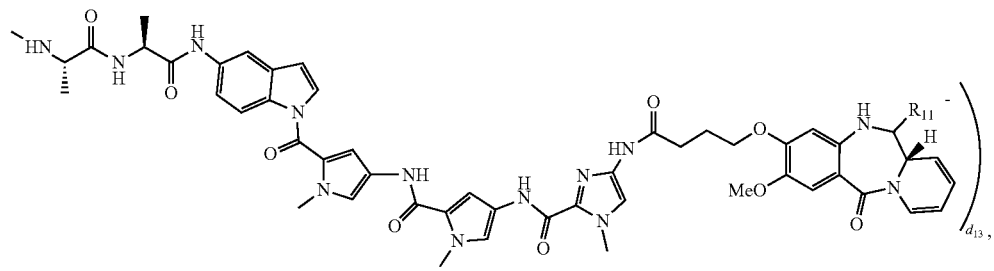
(XIVs)
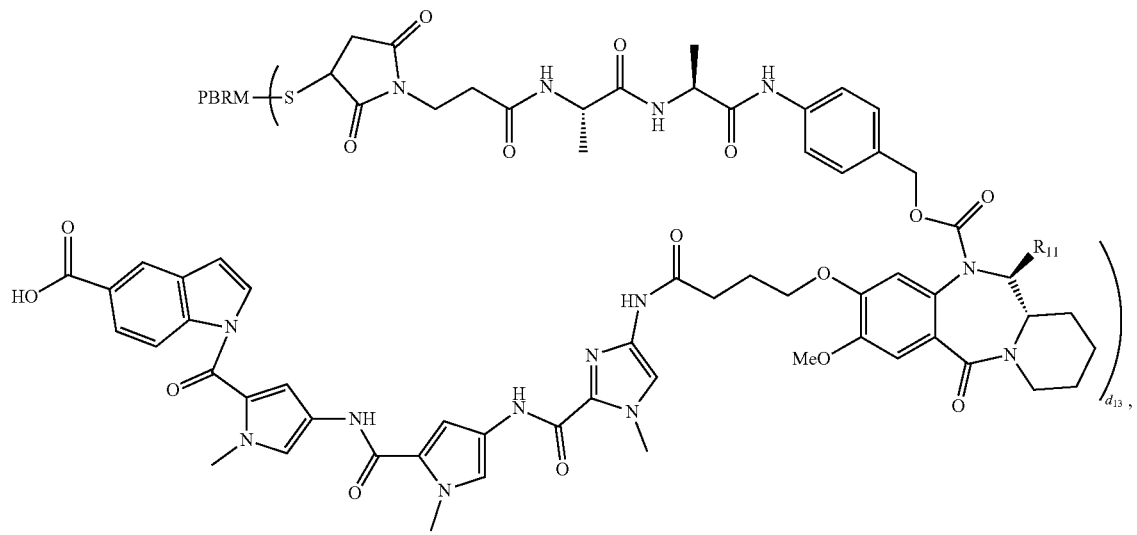

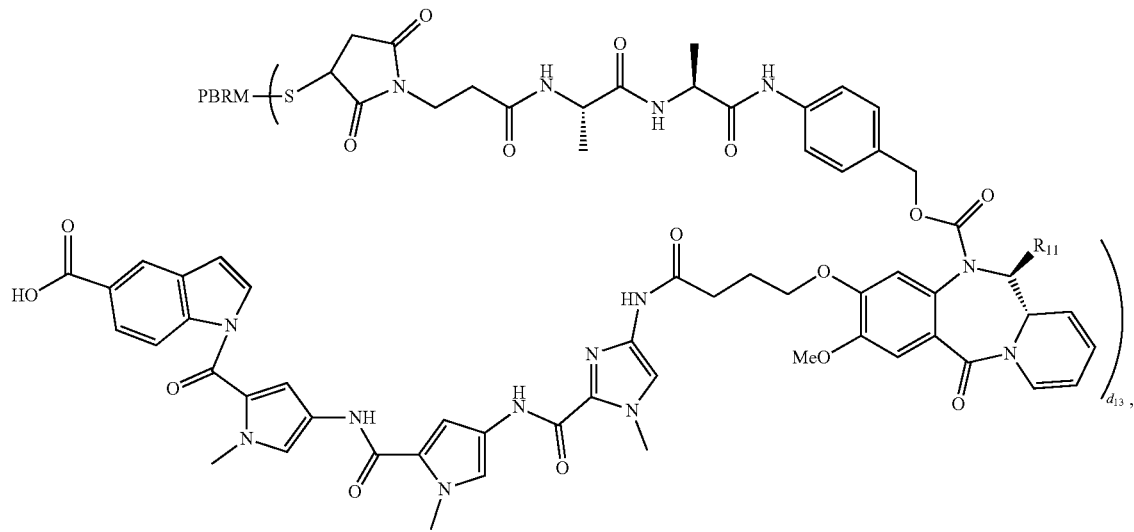
(XIVt)
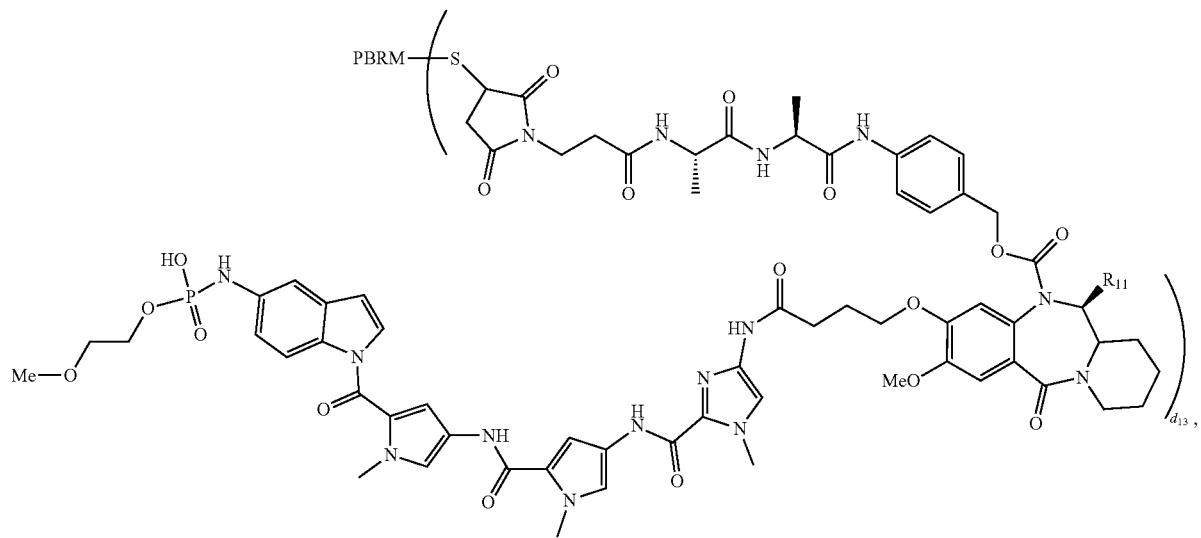
(XIVu)

-continued
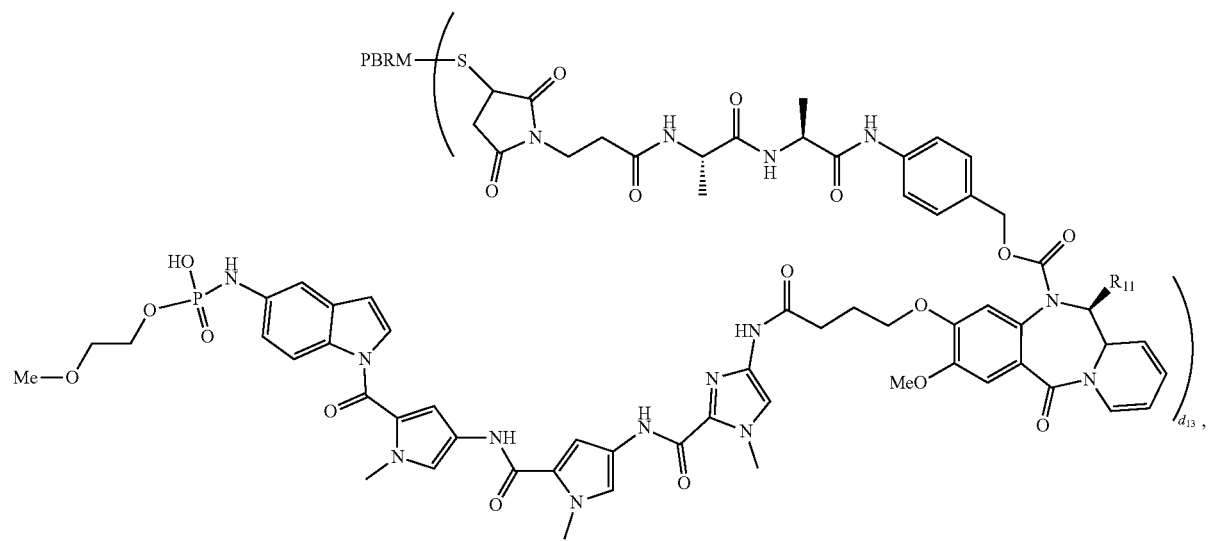
(XIVv)
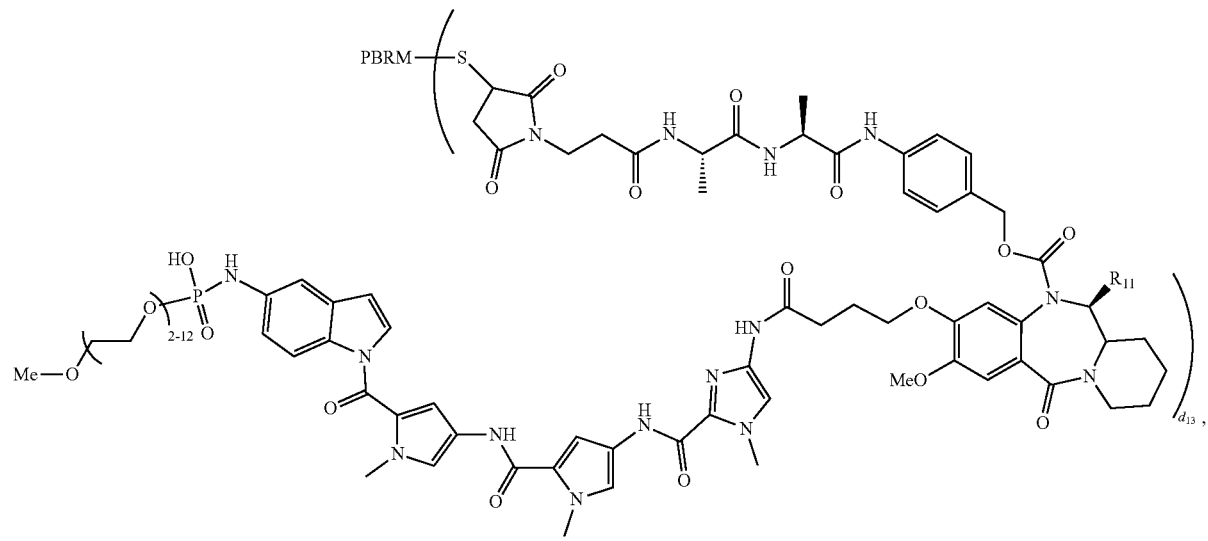
(XIVw)

(XIVx)

pharmaceutically acceptable salt or solvate thereof, or a pharmaceutically acceptable salt or solvate of the tautomer.

In some embodiments, the PBD conjugate is of Formula (XIVa), a tautomer thereof, a pharmaceutically acceptable salt or solvate thereof, or a pharmaceutically acceptable salt or solvate of the tautomer.

In some embodiments, the PBD conjugate is of Formula (XIVa).

In some embodiments, the PBD conjugate is of Formula (XIVb), a tautomer thereof, a pharmaceutically acceptable salt or solvate thereof, or a pharmaceutically acceptable salt or solvate of the tautomer.

In some embodiments, the PBD conjugate is of Formula (XIVb).

In some embodiments, the PBD conjugate is of Formula (XIVc), a tautomer thereof, a pharmaceutically acceptable salt or solvate thereof, or a pharmaceutically acceptable salt or solvate of the tautomer.

In some embodiments, the PBD conjugate is of Formula (XIVc).

In some embodiments, the PBD conjugate is of Formula (XIVd), a tautomer thereof, a pharmaceutically acceptable salt or solvate thereof, or a pharmaceutically acceptable salt or solvate of the tautomer.

In some embodiments, the PBD conjugate is of Formula (XIVd).

In some embodiments, the PBD conjugate is of Formula (XIVe), a tautomer thereof, a pharmaceutically acceptable salt or solvate thereof, or a pharmaceutically acceptable salt or solvate of the tautomer.

In some embodiments, the PBD conjugate is of Formula (XIVe).

In some embodiments, the PBD conjugate is of Formula (XIVf), a tautomer thereof, a pharmaceutically acceptable salt or solvate thereof, or a pharmaceutically acceptable salt or solvate of the tautomer.

In some embodiments, the PBD conjugate is of Formula (XIVf).

In some embodiments, the PBD conjugate is of Formula (XIVg), a tautomer thereof, a pharmaceutically acceptable salt or solvate thereof, or a pharmaceutically acceptable salt or solvate of the tautomer.

In some embodiments, the PBD conjugate is of Formula (XIVg).

In some embodiments, the PBD conjugate is of Formula (XIVh), a tautomer thereof, a pharmaceutically acceptable salt or solvate thereof, or a pharmaceutically acceptable salt or solvate of the tautomer.

In some embodiments, the PBD conjugate is of Formula (XIVh).

In some embodiments, the PBD conjugate is of Formula (XIVi), a tautomer thereof, a pharmaceutically acceptable salt or solvate thereof, or a pharmaceutically acceptable salt or solvate of the tautomer.

In some embodiments, the PBD conjugate is of Formula (XIVi).

In some embodiments, the PBD conjugate is of Formula (XIVj), a tautomer thereof, a pharmaceutically acceptable salt or solvate thereof, or a pharmaceutically acceptable salt or solvate of the tautomer.

In some embodiments, the PBD conjugate is of Formula (XIVj).

In some embodiments, the PBD conjugate is of Formula (XIVk), a tautomer thereof, a pharmaceutically acceptable salt or solvate thereof, or a pharmaceutically acceptable salt or solvate of the tautomer.

In some embodiments, the PBD conjugate is of Formula (XIVk).

In some embodiments, the PBD conjugate is of Formula (XIVl), a tautomer thereof, a pharmaceutically acceptable salt or solvate thereof, or a pharmaceutically acceptable salt or solvate of the tautomer.

In some embodiments, the PBD conjugate is of Formula (XIVl).

In some embodiments, the PBD conjugate is of Formula (XIVm), a tautomer thereof, a pharmaceutically acceptable salt or solvate thereof, or a pharmaceutically acceptable salt or solvate of the tautomer.

In some embodiments, the PBD conjugate is of Formula (XIVm).

In some embodiments, the PBD conjugate is of Formula (XIVn), a tautomer thereof, a pharmaceutically acceptable salt or solvate thereof, or a pharmaceutically acceptable salt or solvate of the tautomer.

In some embodiments, the PBD conjugate is of Formula (XIVn).

In some embodiments, the PBD conjugate is of Formula (XIVo), a tautomer thereof, a pharmaceutically acceptable salt or solvate thereof, or a pharmaceutically acceptable salt or solvate of the tautomer.

In some embodiments, the PBD conjugate is of Formula (XIVo).

In some embodiments, the PBD conjugate is of Formula (XIVp), a tautomer thereof, a pharmaceutically acceptable salt or solvate thereof, or a pharmaceutically acceptable salt or solvate of the tautomer.

In some embodiments, the PBD conjugate is of Formula (XIVp).

In some embodiments, the PBD conjugate is of Formula (XIVq), a tautomer thereof, a pharmaceutically acceptable salt or solvate thereof, or a pharmaceutically acceptable salt or solvate of the tautomer.

In some embodiments, the PBD conjugate is of Formula (XIVq).

In some embodiments, the PBD conjugate is of Formula (XIVr), a tautomer thereof, a pharmaceutically acceptable salt or solvate thereof, or a pharmaceutically acceptable salt or solvate of the tautomer.

In some embodiments, the PBD conjugate is of Formula (XIVr).

In some embodiments, the PBD conjugate is of Formula (XIVs), a tautomer thereof, a pharmaceutically acceptable salt or solvate thereof, or a pharmaceutically acceptable salt or solvate of the tautomer.

In some embodiments, the PBD conjugate is of Formula (XIVs).

In some embodiments, the PBD conjugate is of Formula (XIVt), a tautomer thereof, a pharmaceutically acceptable salt or solvate thereof, or a pharmaceutically acceptable salt or solvate of the tautomer.

In some embodiments, the PBD conjugate is of Formula (XIVt).

In some embodiments, the PBD conjugate is of Formula (XIVu), a tautomer thereof, a pharmaceutically acceptable salt or solvate thereof, or a pharmaceutically acceptable salt or solvate of the tautomer.

In some embodiments, the PBD conjugate is of Formula (XIVu).

In some embodiments, the PBD conjugate is of Formula (XIVv), a tautomer thereof, a pharmaceutically acceptable salt or solvate thereof, or a pharmaceutically acceptable salt or solvate of the tautomer.

In some embodiments, the PBD conjugate is of Formula (XIVv).

In some embodiments, the PBD conjugate is of Formula (XIVw), a tautomer thereof, a pharmaceutically acceptable salt or solvate thereof, or a pharmaceutically acceptable salt or solvate of the tautomer.

In some embodiments, the PBD conjugate is of Formula (XIVw).

In some embodiments, the PBD conjugate is of Formula (XIVx), a tautomer thereof, a pharmaceutically acceptable salt or solvate thereof, or a pharmaceutically acceptable salt or solvate of the tautomer.

In some embodiments, the PBD conjugate is of Formula (XIVx).

In some embodiment the PBD drug moiety (D) of the PBD conjugate exhibits bystander killing effects. In these embodiments the PBD drug moiety is highly membrane-permeable whereas its hydrolysis products has a low level of permeability and is locked in the cell.

In some embodiments, the PBD drug moiety (D) of the PBD conjugate is not a subtract for P-gp efflux pumps.

Pharmaceutical Compositions

Also included are pharmaceutical compositions comprising one or more conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

The pharmaceutical compositions of the conjugates described herein can be included in a container, pack, or dispenser together with instructions for administration.

In some embodiments, the compositions can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the active compounds (e.g., conjugates or drugs of the disclosure) are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

In some embodiments, the combination therapy can include one or more conjugates disclosed herein coformulated with, and/or coadministered with, one or more additional antibodies, which can be the same as the antibody used to form the conjugate or a different antibody.

In some embodiments, the combination therapy can include one or more therapeutic agent and/or adjuvant. In certain embodiments, the additional therapeutic agent is a small molecule inhibitor, another antibody-based therapy, a polypeptide or peptide-based therapy, a nucleic acid-based therapy and/or other biologic.

In certain embodiments, the additional therapeutic agent is a cytotoxic agent, a chemotherapeutic agent, a growth inhibitory agent, an angiogenesis inhibitor, a PARP (poly (ADP)-ribose polymerase) inhibitor, an alkylating agent, an anti-metabolite, an anti-microtubule agent, a topoisomerase inhibitor, a cytotoxic antibiotic, any other nucleic acid damaging agent or an immune checkpoint inhibitor. In one embodiment, the therapeutic agent used in the treatment of cancer, includes but is not limited to, a platinum compound (e.g., cisplatin or carboplatin); a taxane (e.g., paclitaxel or docetaxel); a topoisomerase inhibitor (e.g., irinotecan or topotecan); an anthracycline (e.g., doxorubicin (ADRIAMYCIN®) or liposomal doxorubicin (DOXIL®)); an anti-metabolite (e.g., gemcitabine, pemetrexed); cyclophosphamide; vinorelbine (NAVELBINE®); hexamethylmelamine; ifosfamide; etoposide; an angiogenesis inhibitor (e.g., Bevacizumab (Avastin®)), thalidomide, TNP-470, platelet factor 4, interferon or endostatin); a PARP inhibitor (e.g., Olaparib (Lynparza™)); an immune checkpoint inhibitor, such as for example, a monoclonal antibody that targets either PD-1 or PD-L ((Pembrolizumab (Keytruda®), atezolizumab (MPDL3280A) or Nivolumab (Opdivo®)) or CTA-4 (Ipilimumab (Yervoy®), a kinase inhibitor (e.g., sorafenib or erlotinib), a proteasome inhibitor (e.g., bortezomib or carfilzomib), an immune modulating agent (e.g., lenalidomide or IL-2), a radiation agent, an ALK inhibitor (e.g. crizotinib (Xalkori), ceritinib (Zykadia), alectinib (Alecensa), dalantercept (ACE-041), brigatinib (AP26113), entrectinib (NMS-E628), PF-06463922 TSR-011, CEP-37440 and X-396) and/or a biosimilar thereof and/or combinations thereof. Other suitable agents include an agent considered standard of care by those skilled in the art and/or a chemotherapeutic agent well known to those skilled in the art.

In some embodiments, the immune checkpoint inhibitor is an inhibitor of CTLA-4. In some embodiments, the immune checkpoint inhibitor is an antibody against CTLA-4. In some embodiments, the immune checkpoint inhibitor is a monoclonal antibody against CTLA-4. In other embodiments, the immune checkpoint inhibitor is a human or humanized antibody against CTLA-4. In one embodiment, the anti-CTLA-4 antibody blocks the binding of CTLA-4 to CD80 (B7-1) and/or CD86 (B7-2) expressed on antigen presenting cells. Exemplary antibodies against CTLA-4 include, but are not limited to, Bristol Meyers Squibb's anti-CTLA-4 antibody ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA4 antibody clone BNI3 from Abcam.

In some embodiments, the anti-CTLA-4 antibody is an anti-CTLA-4 antibody disclosed in any of the following patent publications (herein incorporated by reference): WO 2001014424; WO 2004035607; US2005/0201994; EP 1212422 B1; WO2003086459; WO2012120125; WO2000037504; WO2009100140; WO200609649; WO2005092380; WO2007123737; WO2006029219; WO20100979597; WO200612168; and WO1997020574. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014; and/or U.S. Pat. Nos. 5,977,318, 6,682,736, 7,109,003, and 7,132,281, incorporated herein by reference). In some embodiments, the anti-CTLA-4 antibody is for example, those disclosed in: WO 98/42752; U.S. Pat. Nos. 6,682,736 and 6,207,156; Hurwitz et al, Proc. Natl. Acad. Sci. USA, 95(17): 10067-10071 (1998); Camacho et al, J. Clin. Oncol., 22(145): Abstract No. 2505 (2004) (antibody CP-675206); Mokyr et al, Cancer Res., 58:5301-5304 (1998) (incorporated herein by reference).

In some embodiments, the CTLA-4 inhibitor is a CTLA-4 ligand as disclosed in WO1996040915.

In some embodiments, the CTLA-4 inhibitor is a nucleic acid inhibitor of CTLA-4 expression. In some embodiments, anti-CTLA4 RNAi molecules may take the form of the molecules described by Mello and Fire in PCT Publication Nos. WO 1999/032619 and WO 2001/029058; U.S. Publication Nos. 2003/0051263, 2003/0055020, 2003/0056235, 2004/265839, 2005/0100913, 2006/0024798, 2008/0050342, 2008/0081373, 2008/0248576, and 2008/055443; and/or U.S. Pat. Nos. 6,506,559, 7,282,564, 7,538,095, and 7,560,438 (incorporated herein by reference). In some instances, the anti-CTLA4 RNAi molecules take the form of double stranded RNAi molecules described by Tuschl in European Patent No. EP 1309726 (incorporated herein by reference). In some instances, the anti-CTLA4 RNAi molecules take the form of double stranded RNAi molecules described by Tuschl in U.S. Pat. Nos. 7,056,704 and 7,078,196 (incorporated herein by reference). In some embodiments, the CTLA4 inhibitor is an aptamer described in PCT Publication No. WO2004081021.

Additionally, the anti-CTLA4 RNAi molecules of the present disclosure may take the form be RNA molecules described by Crooke in U.S. Pat. Nos. 5,898,031, 6,107,094, 7,432,249, and 7,432,250, and European Application No. EP 0928290 (incorporated herein by reference).

In some embodiments, the immune checkpoint inhibitor is an inhibitor of PD-L1. In some embodiments, the immune checkpoint inhibitor is an antibody against PD-L1. In some embodiments, the immune checkpoint inhibitor is a monoclonal antibody against PD-L1. In other or additional embodiments, the immune checkpoint inhibitor is a human or humanized antibody against PD-L1. In one embodiment, the immune checkpoint inhibitor reduces the expression or activity of one or more immune checkpoint proteins, such as PD-L1. In another embodiment, the immune checkpoint inhibitor reduces the interaction between PD-1 and PD-L1. Exemplary immune checkpoint inhibitors include antibodies (e.g., an anti-PD-L1 antibody), RNAi molecules (e.g., anti-PD-L1 RNAi), antisense molecules (e.g., an anti-PD-L1 antisense RNA), dominant negative proteins (e.g., a dominant negative PD-L1 protein), and small molecule inhibitors. Antibodies include monoclonal antibodies, humanized antibodies, deimmunized antibodies, and Ig fusion proteins. An exemplary anti-PD-L1 antibody includes clone EH12. Exemplary antibodies against PD-L1 include: Genentech's MPDL3280A (RG7446); Anti-mouse PD-L1 antibody Clone 10F.9G2 (Cat #BE0101) from BioXcell; anti-PD-L1 monoclonal antibody MDX-1105 (BMS-936559) and BMS-935559 from Bristol-Meyer's Squibb; MSB0010718C; mouse anti-PD-L1 Clone 29E.2A3; and AstraZeneca's MEDI4736. In some embodiments, the anti-PD-L1 antibody is an anti-PD-L1 antibody disclosed in any of the following patent publications (herein incorporated by reference): WO2013079174; CN101104640; WO2010036959; WO2013056716; WO2007005874; WO2010089411; WO2010077634; WO2004004771; WO2006133396; WO201309906; US 20140294898; WO2013181634 or WO2012145493.

In some embodiments, the PD-L1 inhibitor is a nucleic acid inhibitor of PD-L1 expression. In some embodiments, the PD-L1 inhibitor is disclosed in one of the following patent publications (incorporated herein by reference): WO2011127180 or WO2011000841. In some embodiments, the PD-L1 inhibitor is rapamycin.

In some embodiments, the immune checkpoint inhibitor is an inhibitor of PD-L2. In some embodiments, the immune checkpoint inhibitor is an antibody against PD-L2. In some embodiments, the immune checkpoint inhibitor is a monoclonal antibody against PD-L2. In other or additional embodiments, the immune checkpoint inhibitor is a human or humanized antibody against PD-L2. In some embodiments, the immune checkpoint inhibitor reduces the expression or activity of one or more immune checkpoint proteins, such as PD-L2. In other embodiments, the immune checkpoint inhibitor reduces the interaction between PD-1 and PD-L2. Exemplary immune checkpoint inhibitors include antibodies (e.g., an anti-PD-L2 antibody), RNAi molecules (e.g., an anti-PD-L2 RNAi), antisense molecules (e.g., an anti-PD-L2 antisense RNA), dominant negative proteins (e.g., a dominant negative PD-L2 protein), and small molecule inhibitors. Antibodies include monoclonal antibodies, humanized antibodies, deimmunized antibodies, and Ig fusion proteins.

In some embodiments, the PD-L2 inhibitor is GlaxoSmithKline's AMP-224 (Amplimmune). In some embodiments, the PD-L2 inhibitor is rHIgM12B7.

In some embodiments, the immune checkpoint inhibitor is an inhibitor of PD-L1. In some embodiments, the immune checkpoint inhibitor is an antibody against PD-1. In some embodiments, the immune checkpoint inhibitor is a monoclonal antibody against PD-1. In other embodiments, the immune checkpoint inhibitor is a human or humanized antibody against PD-1. In some embodiments, the inhibitors of PD-1 biological activity (or its ligands) disclosed in U.S. Pat. Nos. 7,029,674; 6,808,710; or U.S. Patent Application Nos: 20050250106 and 20050159351 can be used in the combinations provided herein. Exemplary antibodies against PD-1 include: Anti-mouse PD-1 antibody Clone J43 (Cat #BE0033-2) from BioXcell; Anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda®, pembrolizumab, lambrolizumab, h409A1 1); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011 or hBAT-1), CureTech Ltd.

Additional exemplary anti-PD-1 antibodies are described by Goldberg et al, Blood 1 10(1): 186-192 (2007), Thompson et al, Clin. Cancer Res. 13(6): 1757-1761 (2007), and Korman et al, International Application No. PCT/JP2006/309606 (publication no. WO 2006/121168 A1), each of which are expressly incorporated by reference herein. In some embodiments, the anti-PD-1 antibody is an anti-PD-1 antibody disclosed in any of the following patent publications (herein incorporated by reference): WO014557; WO2011110604; WO2008156712; US2012023752; WO2011110621; WO2004072286; WO2004056875; WO20100036959; WO2010029434; WO201213548; WO2002078731; WO2012145493; WO2010089411; WO2001014557; WO2013022091; WO2013019906; WO2003011911; US20140294898; and WO2010001617.

In some embodiments, the PD-1 inhibitor is a PD-1 binding protein as disclosed in WO200914335 (herein incorporated by reference).

In some embodiments, the PD-1 inhibitor is a peptidomimetic inhibitor of PD-1 as disclosed in WO2013132317 (herein incorporated by reference).

In some embodiments, the PD-1 inhibitor is an anti-mouse PD-1 mAb: clone J43, BioXCell (West Lebanon, N.H.).

In some embodiments, the PD-1 inhibitor is a PD-L1 protein, a PD-L2 protein, or fragments, as well as antibody MDX-1 106 (ONO-4538) tested in clinical studies for the treatment of certain malignancies (Brahmer et al., J Clin Oncol. 2010 28(19): 3167-75, Epub 2010 Jun. 1). Other blocking antibodies may be readily identified and prepared by the skilled person based on the known domain of interaction between PD-1 and PD-L1/PD-L2, as discussed above. In some embodiments, a peptide corresponding to the IgV region of PD-1 or PD-L1/PD-L2 (or to a portion of this region) could be used as an antigen to develop blocking antibodies using methods well known in the art.

In some embodiments, the immune checkpoint inhibitor is an inhibitor of IDO1. In some embodiments, the immune checkpoint inhibitor is a small molecule against IDOL. Exemplary small molecules against IDO1 include: Incyte's INCB024360, NSC-721782 (also known as 1-methyl-D-tryptophan), and Bristol Meyers Squibb's F001287.

In some embodiments, the immune checkpoint inhibitor is an inhibitor of LAG3 (CD223). In some embodiments, the immune checkpoint inhibitor is an antibody against LAG3. In some embodiments, the immune checkpoint inhibitor is a monoclonal antibody against LAG3. In other or additional embodiments, the immune checkpoint inhibitor is a human or humanized antibody against LAG3. In additional embodiments, an antibody against LAG3 blocks the interaction of LAG3 with major histocompatibility complex (MHC) class II molecules. Exemplary antibodies against LAG3 include: anti-Lag-3 antibody clone eBioC9B7W ($C_9B7W$) from eBioscience; anti-Lag3 antibody LS-B2237 from LifeSpan Biosciences; IMP321 (ImmuFact) from Immutep; anti-Lag3 antibody BMS-986016; and the LAG-3 chimeric antibody A9H12. In some embodiments, the anti-LAG3 antibody is an anti-LAG3 antibody disclosed in any of the following patent publications (herein incorporated by reference): WO2010019570; WO2008132601; or WO2004078928.

In some embodiments, the immune checkpoint inhibitor is an antibody against TIM3 (also known as HAVCR2). In some embodiments, the immune checkpoint inhibitor is a monoclonal antibody against TIM3. In other or additional embodiments, the immune checkpoint inhibitor is a human or humanized antibody against TIM3. In additional embodiments, an antibody against TIM3 blocks the interaction of TIM3 with galectin-9 (Gal9). In some embodiments, the anti-TIM3 antibody is an anti-TIM3 antibody disclosed in any of the following patent publications (herein incorporated by reference): WO2013006490; WO201155607; WO2011159877; or WO200117057. In another embodiment, a TIM3 inhibitor is a TIM3 inhibitor disclosed in WO2009052623.

In some embodiments, the immune checkpoint inhibitor is an antibody against B7-H3. In one embodiment, the immune checkpoint inhibitor is MGA271.

In some embodiments, the immune checkpoint inhibitor is an antibody against MR. In one embodiment, the immune checkpoint inhibitor is Lirilumab (IPH2101). In some embodiments, an antibody against MR blocks the interaction of KIR with HLA.

In some embodiments, the immune checkpoint inhibitor is an antibody against CD137 (also known as 4-1BB or TNFRSF9). In one embodiment, the immune checkpoint inhibitor is urelumab (BMS-663513, Bristol-Myers Squibb), PF-05082566 (anti-4-1BB, PF-2566, Pfizer), or XmAb-5592 (Xencor). In one embodiment, an anti-CD137 antibody is an antibody disclosed in U.S. Published Application No. US 2005/0095244: an antibody disclosed in issued U.S. Pat. No. 7,288,638 (such as 20H4.9-IgG4 [1007 or BMS-663513] or 20H4.9-IgG1 [BMS-663031]); an antibody disclosed in issued U.S. Pat. No. 6,887,673 [4E9 or BMS-554271]; an antibody disclosed in issued U.S. Pat. No. 7,214,493; an antibody disclosed in issued U.S. Pat. No. 6,303,121; an antibody disclosed in issued U.S. Pat. No.

6,569,997; an antibody disclosed in issued U.S. Pat. No. 6,905,685; an antibody disclosed in issued U.S. Pat. No. 6,355,476; an antibody disclosed in issued U.S. Pat. No. 6,362,325 [1D8 or BMS-469492; 3H3 or BMS-469497; or 3E1]; an antibody disclosed in issued U.S. Pat. No. 6,974,863 (such as 53A2); or an antibody disclosed in issued U.S. Pat. No. 6,210,669 (such as 1D8, 3B8, or 3E1). In a further embodiment, the immune checkpoint inhibitor is one disclosed in WO 2014036412. In another embodiment, an antibody against CD137 blocks the interaction of CD137 with CD137L.

In some embodiments, the immune checkpoint inhibitor is an antibody against PS. In one embodiment, the immune checkpoint inhibitor is Bavituximab.

In some embodiments, the immune checkpoint inhibitor is an antibody against CD52. In one embodiment, the immune checkpoint inhibitor is alemtuzumab.

In some embodiments, the immune checkpoint inhibitor is an antibody against CD30. In one embodiment, the immune checkpoint inhibitor is brentuximab vedotin. In another embodiment, an antibody against CD30 blocks the interaction of CD30 with CD30L.

In some embodiments, the immune checkpoint inhibitor is an antibody against CD33. In one embodiment, the immune checkpoint inhibitor is gemtuzumab ozogamicin.

In some embodiments, the immune checkpoint inhibitor is an antibody against CD20. In one embodiment, the immune checkpoint inhibitor is ibritumomab tiuxetan. In another embodiment, the immune checkpoint inhibitor is of atumumab. In another embodiment, the immune checkpoint inhibitor is rituximab. In another embodiment, the immune checkpoint inhibitor is tositumomab.

In some embodiments, the immune checkpoint inhibitor is an antibody against CD27 (also known as TNFRSF7). In one embodiment, the immune checkpoint inhibitor is CDX-1127 (Celldex Therapeutics). In another embodiment, an antibody against CD27 blocks the interaction of CD27 with CD70.

In some embodiments, the immune checkpoint inhibitor is an antibody against OX40 (also known as TNFRSF4 or CD134). In one embodiment, the immune checkpoint inhibitor is anti-OX40 mouse IgG. In another embodiment, an antibody against 0×40 blocks the interaction of OX40 with OX40L.

In some embodiments, the immune checkpoint inhibitor is an antibody against glucocorticoid-induced tumor necrosis factor receptor (GITR). In one embodiment, the immune checkpoint inhibitor is TRX518 (GITR, Inc.). In another embodiment, an antibody against GITR blocks the interaction of GITR with GITRL.

In some embodiments, the immune checkpoint inhibitor is an antibody against inducible T-cell COStimulator (ICOS, also known as CD278). In one embodiment, the immune checkpoint inhibitor is MEDI570 (MedImmune, LLC) or AMG557 (Amgen). In another embodiment, an antibody against ICOS blocks the interaction of ICOS with ICOSL and/or B7-H2.

In some embodiments, the immune checkpoint inhibitor is an inhibitor against BTLA (CD272), CD160, 2B4, LAIR1, TIGHT, LIGHT, DR3, CD226, CD2, or SLAM. As described elsewhere herein, an immune checkpoint inhibitor can be one or more binding proteins, antibodies (or fragments or variants thereof) that bind to immune checkpoint molecules, nucleic acids that downregulate expression of the immune checkpoint molecules, or any other molecules that bind to immune checkpoint molecules (i.e. small organic molecules, peptidomimetics, aptamers, etc.). In some instances, an inhibitor of BTLA (CD272) is HVEM. In some instances, an inhibitor of CD160 is HVEM. In some cases, an inhibitor of 2B4 is CD48. In some instances, an inhibitor of LAIR1 is collagen. In some instances, an inhibitor of TIGHT is CD112, CD113, or CD155. In some instances, an inhibitor of CD28 is CD80 or CD86. In some instances, an inhibitor of LIGHT is HVEM. In some instances, an inhibitor of DR3 is TL1A. In some instances, an inhibitor of CD226 is CD155 or CD112. In some cases, an inhibitor of CD2 is CD48 or CD58. In some cases, SLAM is self-inhibitory and an inhibitor of SLAM is SLAM.

In certain embodiments, the immune checkpoint inhibitor inhibits a checkpoint protein that include, but are not limited to CTLA4 (cytotoxic T-lymphocyte antigen 4, also known as CD152), PD-L1 (programmed cell death 1 ligand 1, also known as CD274), PDL2 programmed cell death protein 2), PD-1 (programmed cell death protein 1, also known as CD279), a B-7 family ligand (B7-H1, B7-H3, B7-H4) BTLA (B and T lymphocyte attenuator, also known as CD272), HVEM, TIM3 (T-cell membrane protein 3), GAL9, LAG-3 (lymphocyte activation gene-3; CD223), VISTA, KIR (killer immunoglobulin receptor), 2B4 (also known as CD244), CD160, CGEN-15049, CHK1 (Checkpoint kinase 1), CHK2 (Checkpoint kinase 2), A2aR (adenosine A2a receptor), CD2, CD27, CD28, CD30, CD40, CD70, CD80, CD86, CD137, CD226, CD276, DR3, GITR, HAVCR2, HVEM, IDO1 (indoleamine 2,3-dioxygenase 1), IDO2 (indoleamine 2,3-dioxygenase 2), ICOS (inducible T cell costimulator), LAIR1, LIGHT (also known as TNFSF14, a TNF family member), MARCO (macrophage receptor with collagenous structure), OX40 (also known as tumor necrosis factor receptor superfamily, member 4, TNFRSF4, and CD134) and its ligand OX40L (CD252), SLAM, TIGHT, VTCN1 or a combination thereof.

In certain embodiments, the immune checkpoint inhibitor interacts with a ligand of a checkpoint protein that comprises CTLA-4, PDL1, PDL2, PD1, BTLA, HVEM, TIM3, GAL9, LAG3, VISTA, KIR, 2B4, CD160, CGEN-15049, CHK1, CHK2, A2aR, a B-7 family ligand, CD2, CD27, CD28, CD30, CD40, CD70, CD80, CD86, CD137, CD226, CD276, DR3, GITR, HAVCR2, HVEM, IDO1, IDO2, ICOS (inducible T cell costimulator), LAIR1, LIGHT, MARCO (macrophage receptor with collagenous structure), OX-40, SLAM, TIGHT, VTCN1 or a combination thereof.

In certain embodiments, the immune checkpoint inhibitor inhibits a checkpoint protein that comprises CTLA-4, PDL1, PD1 or a combination thereof.

In certain embodiments, the immune checkpoint inhibitor inhibits a checkpoint protein that comprises CTLA-4 and PD1 or a combination thereof.

In certain embodiments, the immune checkpoint inhibitor comprises pembrolizumab (MK-3475), nivolumab (BMS-936558), pidilizumab (CT-011), AMP-224, MDX-1 105, durvalumab (MED14736), MPDL3280A, BMS-936559, IPH2101, TSR-042, TSR-022, ipilimumab, lirilumab, atezolizumab, avelumab, tremelimumab, or a combination thereof.

In certain embodiments, the immune checkpoint inhibitor is nivolumab (BMS-936558), ipilimumab, pembrolizumab, atezolizumab, tremelimumab, durvalumab, avelumab, or a combination thereof.

In certain embodiments, the immune checkpoint inhibitor is pembrolizumab.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). In some embodiments, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the conjugate in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the conjugates to an accessible diseased tissue. The rate of entry of an active agent into the circulation has been shown to be a function of molecular weight or size. The use of a conjugate of this disclosure can localize the drug delivery in certain cells, such as cancer cells via the specificity of PBRMs.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired conjugates in a pharmaceutically acceptable carrier or diluent. Acceptable carriers, diluents, and/or excipients for therapeutic use are well known in the pharmaceutical art. In some embodiments, buffers, preservatives, bulking agents, dispersants, stabilizers, dyes, can be provided. In addition, antioxidants and suspending agents can be used Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any conjugate, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

In some embodiments, a drug or its derivatives, drug-conjugates or PBRM-drug conjugates can be evaluated for their ability to inhibit tumor growth in several cell lines using Cell titer Glo. Dose response curves can be generated using SoftMax Pro software and $IC_{50}$ values can be determined from four-parameter curve fitting. Cell lines employed can include those which are the targets of the PBRM and a control cell line that is not the target of the PBRM contained in the test conjugates.

In one embodiment, the conjugates are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutically acceptable carrier. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The conjugates and compositions described herein may be administered in appropriate form, preferably parenterally, more preferably intravenously. For parenteral administration, the conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

Dosage levels of the order of from between about 0.001 mg and about 140 mg per kilogram of body weight per day are useful in the treatment of the above-indicated conditions (between about 0.05 mg and about 7 g per subject per day). In some embodiments, the dosage administered to a patient is between about 0.001 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. The amount of conjugate that can be combined with the carrier materials to produce a single dosage form varies depending upon the host treated and the particular mode of administration. Dosage unit forms can generally contain from between about 0.001 mg and about 100 mg; between about 0.01 mg and about 75 mg; or between about 0.01 mg and about 50 mg; or between about 0.01 mg and about 25 mg; of a conjugate.

For intravenous administration, the dosage levels can comprise ranges described in the preceding paragraphs, or from about 0.01 to about 200 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of a compound.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments, about one to about four weeks after treatment, the patient can receive a second course of treatment. Specific clinical protocols with regard to route of administration, excipients, diluents, dosages, and times can be determined by the skilled artisan as the clinical situation warrants.

In other embodiments, the therapeutically effective amount may be provided on another regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the recommendations of the relevant regulatory bodies and judgment of a health-care practitioner. The therapeutically effective amounts described herein refer to total amounts administered for a given time period; that is, if more than one different conjugate described herein is administered, the therapeutically effective amounts correspond to the total amount administered. It is understood that the specific dose level for a particular subject depends upon a variety of factors including the activity of the specific conjugate, the age, body weight, general health, sex, diet, time of administration, route of administration, and rate of excretion, combination with other active agents, and the severity of the particular disease undergoing therapy.

In some embodiments, a therapeutically effective amount of a conjugate disclosed herein relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of conjugates disclosed herein may be, by way of nonlimiting example, from about 0.1 mg/kg body weight to about 50 mg/kg body weight, from about 0.1 mg/kg body weight to about 100 mg/kg body weight or from about 0.1 mg/kg body weight to about 150 mg/kg body weight. Common dosing frequencies may range, for example, from twice daily to once a month (e.g., once daily, once weekly; once every other week; once every 3 weeks or monthly). For example, conjugates disclosed herein can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). For example, conjugates disclosed herein can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 19 mg/kg, or 20 mg/kg) for treating cancer.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The conjugates can also be administered to a subject in combination with other therapeutic compounds to increase the overall therapeutic effect. The use of multiple compounds to treat an indication can increase the beneficial effects while reducing the presence of side effects. In some embodiments, the conjugates are used in combination with chemotherapeutic agents, such as those disclosed in U.S.

Pat. No. 7,303,749. In other embodiments the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine.

The present disclosure also provides pharmaceutical kits comprising one or more containers filled with one or more of the conjugates and/or compositions of the present disclosure, including, one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products. The compositions described herein can be packaged as a single dose or for continuous or periodic discontinuous administration. For continuous administration, a package or kit can include the conjugates in each dosage unit (e.g., solution or other unit described above or utilized in drug delivery), and optionally instructions for administering the doses daily, weekly, or monthly, for a predetermined length of time or as prescribed. If varying concentrations of a composition, of the components of the composition, or the relative ratios of the conjugates or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle. The packaging means of a kit may itself be geared for administration, such as a syringe, pipette, eye dropper, or other such apparatus, from which the formulation may be applied to an affected area of the body, injected into a subject, or even applied to and mixed with the other components of the kit.

Methods of Use

In some aspects, the present disclosure provides a method of treating a subject in need thereof (preferably mammals, most preferably humans and includes males, females, infants, children and adults) by administering a pharmaceutically effective amount of the conjugate (e.g., the antibody-drug conjugate (ADC)) of the present disclosure. In some embodiments, the conjugate (e.g., the antibody-drug conjugate (ADC)) of the present disclosure is administered in the form of soluble linear polymers, copolymers, conjugates, colloids, particles, gels, solid items, fibers, films, etc. Biodegradable biocompatible conjugates of the present disclosure can be used as drug carriers and drug carrier components, in systems of controlled drug release, preparations for low-invasive surgical procedures, etc. Pharmaceutical formulations can be injectable, implantable, etc.

In some aspects, the present disclosure provides a method of treating or preventing a disease or disorder in a subject in need thereof, comprising administering to the subject a pharmaceutically effective amount of a conjugate (e.g., an antibody-drug conjugate (ADC)) of the present disclosure; wherein said conjugate releases one or more PBD drug moieties upon biodegradation.

In some embodiments, the disease or disorder to be treated is a hyperproliferative disease, e.g., cancer.

In some embodiments, the conjugate (e.g., the antibody-drug conjugate (ADC)) of the present disclosure can be administered in vitro, in vivo and/or ex vivo to treat patients and/or to modulate the growth of selected cell populations including, for example, cancer.

In some aspects, the present disclosure provides a method of treating cancer, comprising administering to the subject a pharmaceutically effective amount of a conjugate (e.g., an antibody-drug conjugate (ADC)) of the present disclosure. In some embodiments, the particular types of cancers that can be treated with the conjugates of the present disclosure include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias; and (3) lymphomas such as Hodgkin's disease, non-Hodgkin's Lymphoma, Multiple myeloma, Waldenstrom's macroglobulinemia, Heavy chain disease, and Polycythemia vera.

In some embodiments, the conjugate (e.g., the antibody-drug conjugate (ADC)) of the present disclosure can be administered in vitro, in vivo and/or ex vivo to treat autoimmune diseases.

In some aspects, the present disclosure provides a method of treating an autoimmune disease, comprising administering to the subject a pharmaceutically effective amount of a conjugate (e.g., an antibody-drug conjugate (ADC)) of the present disclosure. In some embodiments, the autoimmune diseases that can be treated with the conjugates of the present disclosure include, but are not limited to, systemic lupus, rheumatoid arthritis, psoriasis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like.

In some aspects, the present disclosure provides a conjugate disclosed herein for use in the manufacture of a medicament useful for treating or lessening the severity of disorders, such as, characterized by abnormal growth of cells (e.g., cancer).

In some embodiments, the PBD drug moiety is locally delivered to a specific target cell, tissue, or organ.

In some aspects, the present disclosure provides a method of treating a disease or disorder in a subject, comprising preparing an aqueous formulation of at least one conjugate of the present disclosure and parenterally injecting said formulation in the subject.

In some aspects, the present disclosure provides a method of treating a disease or disorder in a subject, comprising preparing an implant comprising at least one conjugate of the present disclosure, and implanting said implant into the subject. In some embodiments, the implant is a biodegradable gel matrix.

In some aspects, the present disclosure provides a method for treating of a subject in need thereof, comprising administering a conjugate according to the methods described above.

In some aspects, the present disclosure provides a method for eliciting an immune response in a subject, comprising administering a conjugate as in the methods described above.

In some aspects, the present disclosure provides a method of diagnosing a disease in a subject, comprising steps of:

administering a conjugate of the present disclosure, wherein the conjugate further comprises a detectable molecule; and detecting the detectable molecule.

In some embodiments, the step of detecting the detectable molecule is performed non-invasively. In some embodiments, the step of detecting the detectable molecule is performed using suitable imaging equipment.

In some embodiments, the present disclosure provides a method for treating an animal comprises administering to the animal a biodegradable biocompatible conjugate of the present disclosure as a packing for a surgical wound from which a tumor or growth has been removed.

The biodegradable biocompatible conjugate packing will replace the tumor site during recovery and degrade and dissipate as the wound heals.

In some embodiments, soluble or colloidal conjugates of the present disclosure are administered intravenously. In some embodiments, soluble or colloidal conjugates of the present disclosure are administered via local (e.g., subcutaneous, intramuscular) injection. In some embodiments, solid conjugates of the present disclosure (e.g., particles, implants, drug delivery systems) are administered via implantation or injection.

In some embodiments, conjugates of the present disclosure comprising a detectable label are administered to study the patterns and dynamics of label distribution in animal body.

In some embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In some embodiments, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In another embodiment, conjugates comprising a detectable label are administered to study the patterns and dynamics of label distribution in animal body.

In some embodiments, any one or more of the conjugates disclosed herein may be used in practicing any of the methods described herein.

Diagnostic and Prophylactic Formulations

The PBD antibody conjugates disclosed herein are used in diagnostic and prophylactic formulations. In one embodiment, a PBD antibody conjugate disclosed herein is administered to patients that are at risk of developing one or more of the aforementioned diseases, such as for example, without limitation, cancer. A patient's or organ's predisposition to one or more of the aforementioned indications can be determined using genotypic, serological or biochemical markers.

In another embodiment of the disclosure, a PBD antibody conjugate disclosed herein is administered to human individuals diagnosed with a clinical indication associated with one or more of the aforementioned diseases, such as for example, without limitation, cancer. Upon diagnosis, a PBD antibody conjugate disclosed herein is administered to mitigate or reverse the effects of the clinical indication associated with one or more of the aforementioned diseases. All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

Definitions

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. In some embodiments, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. The term "heterocycloalkyl" refers to a saturated or unsaturated nonaromatic ring system having one or more heteroatoms (such as O, N, S, P, or Se) as ring atoms, such as a 3-8 membered monocyclic, 7-12 membered bicyclic (fused, bridged, or spiro rings), or 11-14 membered tricyclic ring system (fused, bridged, or spiro rings) having, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like. In the case of multicyclic non-aromatic rings, only one of the rings needs to be non-aromatic (e.g., 1,2,3,4-tetrahydronaphthalenyl or 2,3-dihydroindole). The terms "cycloalkylene" and "heterocycloalkylene" refer to the corresponding divalent groups, respectively.

The term "optionally substituted alkyl" refers to unsubstituted alkyl or alkyl having designated substituents replacing one or more hydrogen atoms on one or more carbons of the hydrocarbon backbone. Such substituents can include, In some embodiments, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, "alkyl linker" or "alkylene linker" is intended to include $C_1$, $C_2$, $C_3$, $C_4$, $C_5$ or $C_6$ straight chain (linear or branched) saturated divalent aliphatic hydrocarbon groups and $C_3$, $C_4$, $C_5$ or $C_6$ branched saturated aliphatic hydrocarbon groups. In some embodiments, $C_1$-$C_6$ alkylene linker is intended to include $C_1$, $C_2$, $C_3$, $C_4$, $C_5$ and $C_6$ alkylene linker groups. Examples of alkylene linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. In some embodiments, the term "alkenyl" includes straight chain alkenyl groups (e.g., ethenyl, propenyl, butenyl, pentenyl, hexenyl, heptenyl, octenyl, nonenyl, decenyl), and branched alkenyl groups.

In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, In some embodiments, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. In some embodiments, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, In some embodiments, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. In some embodiments, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with one or more aromatic rings and do not contain any heteroatom in the ring structure. Examples include phenyl, naphthalenyl, etc. The term "arylene" refers to the corresponding divalent groups, such as phenylene.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable aromatic heterocyclic ring, such as a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. The term "heteroarylene" refers to the corresponding divalent groups.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, In some embodiments, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. In some embodiments, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, In some embodiments, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In some embodiments, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., 1-4 heteroatoms selected from N, O and S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, In some embodiments, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

As used herein, the term "bis-oxy-alkylene" refers —O-alkylene-O—, in which alkylene can be linear or branched, e.g., —CH$_2$—, —CH(CH$_3$)$_2$—, or —(CH$_2$)$_2$—.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, In some embodiments, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. In some embodiments, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to —NH$_2$. "Alkylamino" includes groups of compounds wherein the nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to two alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g. 3-chloroperoxybenzoic acid (m-CPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present disclosure can be converted to N-hydroxy or N-alkoxy compounds. In some embodiments, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

Furthermore, the structures and other compounds discussed in this disclosure include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, and their solvates, if applicable. A salt, In some embodiments, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, In some embodiments, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, In some embodiments, a monohydrate, a di-hydrate, a tri-hydrate, etc.

It may be convenient or desirable to prepare, purify, and/or handle a corresponding solvate of an active compound. Compounds of the disclosure include compounds where a nucleophilic solvent ($H_2O$, $R^4OH$, $R^4NH_2$, $R^4SH$) adds across the imine bond of the PBD moiety, which is illustrated below where the solvent is water or an alcohol ($R^4OH$, where $R^4$ is an ether substituent as described above):

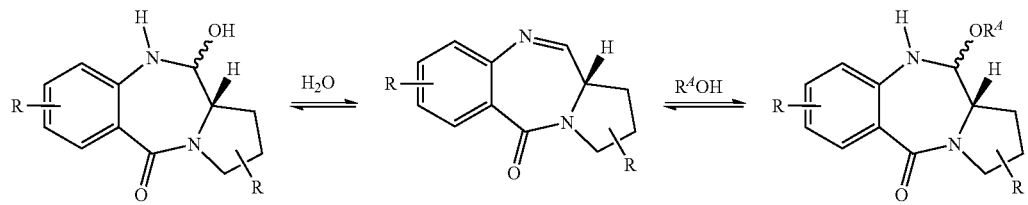

These forms can be called the carbinolamine and carbinolamine ether forms of the PBD. The balance of these equilibria depend on the conditions in which the compounds are found, as well as the nature of the moiety itself.

These compounds may be isolated in solid form, In some embodiments, by lyophilisation.

As defined herein, the term "derivative" refers to compounds that have a common core structure, and are substituted with various groups as described herein. In some embodiments, all of the compounds represented by Formula (I) are pyrrolo[2, 1-c][1, 4]benzodiazepines compounds (PBDs), and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96,3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present disclosure provides methods for the synthesis of the compounds of any of the Formulae and conjugates thereof described herein. The present disclosure also provides detailed methods for the synthesis of various disclosed conjugates of the present disclosure according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001: Greene, T. W., Wuts, P. G. M., *Protective Groups in Organic Synthesis*, 4$^{th}$ Edition, Wiley-Interscience, 2007; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

"Protein based recognition-molecule" or "PBRM" refers to a molecule that recognizes and binds to a cell surface marker or receptor such as, a transmembrane protein, surface immobilized protein, or proteoglycan. Examples of PBRMs include but are not limited to, antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, c-Kit, MUC1, MUC13 and anti-5T4) or peptides (LHRH receptor targeting peptides, EC-1 peptide), lipocalins, such as, In some embodiments, anticalins, proteins such as, In some embodiments, interferons, lymphokines, growth factors, colony stimulating factors, and the like, peptides or peptide mimics, and the like. The protein based recognition molecule, in addition to targeting the conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, In some embodiments, tyrosine, histidine, cysteine, or lysine. In some embodiments, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. In some embodiments, the ligand can preferentially associate with the cell surface molecule with a $K_d$ of less than about 50 nM, less than about 5 nM, or less than 500 pM. Techniques for measuring binding affinity of a ligand to a cell surface molecule are well-known; In some embodiments, one suitable technique, is termed surface plasmon resonance (SPR). In some embodiments, the ligand is used for targeting and has no detectable therapeutic effect as separate from the drug which it delivers. In another embodiment, the ligand functions both as a targeting moiety and as a therapeutic or immunomodulatory agent (e.g., to enhance the activity of the active drug or prodrug).

Synthetic Methods

The conjugates of this disclosure having any of the Formulae described herein may be prepared according to the procedures illustrated in Scheme 1 and the Examples, from commercially available starting materials or starting materials which can be prepared using literature procedures.

Any available techniques can be used to make the conjugates or compositions thereof, and intermediates and components (e.g., scaffolds) useful for making them. For example, semi-synthetic and fully synthetic methods may be used.

The general methods of producing the conjugates or scaffolds disclosed herein are illustrated in Scheme 1 below. More specific methods of syntheses of the conjugates are described in the Examples and for the scaffolds in application U.S. 62/572,010 filed Oct. 13, 2017. The variables (e.g., $M^P$, $M^A$, $W^D$, $L^D$, and $L^{P'}$, etc.) in these schemes have the same definitions as described herein unless otherwise specified.

Scheme 1

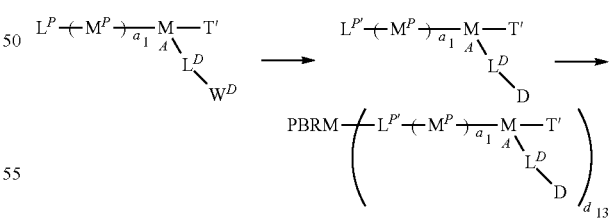

The synthetic processes of the disclosure can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

PBD compounds used for the conjugates of the present disclosure can be prepared in a variety of ways using commercially available starting materials, compounds known in the literature, as described in co-pending application U.S. Ser. No. 15/597,453 filed May 17, 2017, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present disclosure.

Conjugates of the present disclosure can be conveniently prepared by a variety of methods familiar to those skilled in the art. The conjugates of the disclosure with each of the formulae described herein may be prepared according to the following procedures from commercially available starting materials or starting materials which can be prepared using literature procedures. These procedures show the preparation of representative conjugates of this disclosure.

Conjugates designed, selected and/or optimized by methods described above, once produced, can be characterized using a variety of assays known to those skilled in the art to determine whether the conjugates have biological activity. For example, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below. Conjugates of the present disclosure can also be prepared in a variety of ways using commercially available starting materials, compounds, antibodies, and antibody fragments each of which are known in the literature, or from readily prepared intermediates, by employing standard synthetic methods and procedures either known to those skilled in the art, or which will be apparent to the skilled artisan in light of the teachings herein. In some embodiments, for the synthesis of conjugates of compounds of Formula (IV), where the antibody or antibody fragment is directly or indirectly linked to the compound at position E" or D", methods and linkers disclosed in WO2011/13063, WO2011/130616, WO2015/159076, WO2015/052535, WO2015/052534, WO2015/052321, WO2014/130879, WO2014/096365, WO2014/057122, WO2014/057073, WO2013/164593, WO2013/055993, WO2013/055990, WO2013/053873, WO2013/053871, WO2013/041606, WO2011/130616, and WO2011/130613 may be used. Each of these publications is incorporated herein by reference in its entirety.

As another example, for the synthesis of conjugates of compounds of Formula (IV), where the antibody or antibody fragment is directly or indirectly linked to the compound at position $R''_7$, methods and linkers disclosed in WO2014140174(A1) and WO2016/037644 may be used. Each of these publications is incorporated herein by reference in its entirety.

As another example, for the synthesis of conjugates of compounds of Formula (IV), where the antibody or antibody fragment is directly or indirectly linked to the compound at position $R''_{10}$, methods and linkers disclosed in WO 2013/055987, WO 2016/044560, WO 2016/044396, WO2015/159076, WO2015/095227, WO2015/095124, WO2015/052535, WO2015/052534, WO2015/052322, WO2014/174111, WO2014/096368, WO2014/057122, WO2014/057074, WO2014/022679, WO2014/011519, WO2014/011518, WO2013/177481, WO2013/055987, WO2011/130598, and WO2011/128650 may be used. Each of these publications is incorporated herein by reference in its entirety.

Also included are pharmaceutical compositions comprising one or more conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). In some embodiments, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the compound or conjugate to an accessible diseased tissue. The rate of entry of an active agent into the circulation has been shown to be a function of molecular weight or size. The use of a conjugate (e.g., an antibody-drug conjugate (ADC)) of this disclosure can localize the drug delivery in certain cells, such as cancer cells via the specificity of antibodies.

A "pharmaceutically acceptable formulation" means a composition or formulation that allows for the effective distribution of the conjugates in the physical location most suitable for their desired activity. In some embodiments, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include an effective amount of the desired conjugates in a pharmaceutically acceptable carrier or diluent. Acceptable carriers, diluents, and/or excipients for therapeutic use are well known in the pharmaceutical art. In some embodiments, buffers, preservatives, bulking agents, dispersants, stabilizers, dyes, can be provided. In addition, antioxidants and suspending agents can be used. Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "effective amount", as used herein, refers to an amount of a pharmaceutical agent to treat, ameliorate, or prevent an identified disease or condition, or to exhibit a detectable therapeutic or inhibitory effect. The effect can be detected by any assay or method known in the art. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician. In a preferred aspect, the disease or condition to can be treated via gene silencing.

For any conjugate, the effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

In some embodiments, a drug or its derivatives, drug-polymer conjugates or ADCs (including antibody-drug-polymer conjugates and antibody-drug conjugates) can be evaluated for their ability to inhibit tumor growth in several cell lines using CellTiter Glo®. Dose response curves can be generated using SoftMax Pro software and $IC_{50}$ values can be determined from four-parameter curve fitting. Cell lines employed can include those which are the targets of the antibody and a control cell line that is not the target of the antibody contained in the test conjugates.

In some embodiments, the PBD conjugates of the disclosure are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The PBD conjugates and compositions described herein may be administered in appropriate form, preferably parenterally, more preferably intravenously. For parenteral administration, the compounds, conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

For PBD conjugates disclosed herein, the appropriate dosage levels will depend on several factors, such as, In some embodiments, the type of disease to be treated, the severity and course of the disease, whether the compound is administered for preventing or therapeutic purposes, previous therapy, the patient's clinical history. Depending on the type and severity of the disease, about 100 ng to about 25 mg (e.g., about 1 µg/kg to 15 mg/kg, about 0.1-20 mg/kg) of the compound is an initial candidate dosage for administration to the patient, whether, In some embodiments, by one or more separate administrations, or by continuous infusion. A typical daily dosage might range from about 1 µg/kg to 100 mg/kg or more, depending on the factors mentioned above. An exemplary dosage of compound to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of a compound. Other dosage regimens may be useful. The progress of this therapy is easily monitored by conventional techniques and assays. Ranges disclosed herein are expressed as amount administered based on the subject's weight, and one skilled in the art can easily express it as amount administered per body surface area of the subject. In some embodiments, 1 mg/kg body weight for a human adult is equivalent to about 37 mg/m² and 1 mg/kg body weight for a human child is equivalent to about 25 mg/m².

For PBD conjugates disclosed herein, dosage levels of the order of from between about 0.01 mg and about 200 mg per kilogram of body weight per day are useful in the treatment of the target conditions (between about 0.05 mg and about 7 g per subject per day). In some embodiments, the dosage administered to a patient is between about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight.

The amount of conjugate that can be combined with the carrier materials to produce a single dosage form varies depending upon the host treated and the particular mode of administration. Dosage unit forms can generally contain from between about 0.01 mg and about 200 mg; between 0.01 mg and about 150 mg; between 0.01 mg and about 100 mg; between about 0.01 mg and about 75 mg; or between about 0.01 mg and about 50 mg; or between about 0.01 mg and about 25 mg; of a conjugate. In some embodiments, the PBD compound or conjugate of the disclosure can be administered to a subject in need thereof (e.g., a human patient) at a dose of about 100 mg, 3 times daily, or about 150 mg, 2 times daily, or about 200 mg, 2 times daily, or about 50-70 mg, 3-4 times daily, or about 100-125 mg, 2 times daily.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments about one to about four weeks after treatment, the patient can receive a second course of treatment. Specific clinical protocols with regard to route of administration, excipients, diluents, dosages, and times can be determined by the skilled artisan as the clinical situation warrants.

It is understood that the specific dose level for a particular subject depends upon a variety of factors including the activity of the specific compound or conjugate, the age, body weight, general health, sex, diet, time of administration, route of administration, and rate of excretion, combination with other active agents, and the severity of the particular disease undergoing therapy.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The PBD conjugates disclosed herein can also be administered to a subject in combination with other therapeutic compounds to increase the overall therapeutic effect. The use of multiple compounds to treat an indication can increase the beneficial effects while reducing the presence of side effects. In some embodiments, the conjugates are used in combination with chemotherapeutic agents, such as those disclosed in U.S. Pat. No. 7,303,749, U.S. 2016/0031887 and U.S. 2015/0133435, each of which is herein incorporated by reference by its entirety. In other embodiments, the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine.

The present disclosure also provides pharmaceutical kits comprising one or more containers filled with one or more of the compounds, conjugates and/or compositions of the present disclosure, including, one or more chemotherapeutic agents. Such kits can also include, In some embodiments, other compositions, a device(s) for administering the compositions, and written instructions in a form prescribed by a governmental agency regulating the manufacture, use or sale of pharmaceuticals or biological products.

In another aspect, the PBD conjugates of the disclosure are used in methods of treating animals (preferably mammals, most preferably humans and includes males, females, infants, children and adults).

The conjugates of the disclosure may be used to provide a PBD conjugate at a target location.

The target location is preferably a proliferative cell population. The antibody is an antibody for an antigen present in a proliferative cell population.

In some embodiments, the antigen is absent or present at a reduced level in a non-proliferative cell population compared to the amount of antigen present in the proliferative cell population, for example a tumor cell population.

The target location may be in vitro, in vivo or ex vivo.

The antibody-drug conjugate (ADC) of the disclosure include those with utility for anticancer activity. In particular, the ADC includes an antibody conjugated, i.e. covalently attached by a linker, to a PBD moiety.

At the target location the linker may not be cleaved. The ADC of the disclosure may have a cytotoxic effect without the cleavage of the linker to release a PBD drug moiety. The ADC of the disclosure selectively deliver cytotoxic agent to tumor tissue whereby greater selectivity, i.e., a lower efficacious dose, may be achieved.

In a further aspect, a conjugate as described herein is for use in the treatment of a proliferative disease. A second aspect of the present disclosure provides the use of a conjugate compound in the manufacture of a medicament for treating a proliferative disease.

One of ordinary skill in the art is readily able to determine whether or not a candidate conjugate treats a proliferative condition for any particular cell type. In some embodiments, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumors (e.g. histiocytoma, glioma, astrocytoma, osteoma), cancers (e.g. lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

In some embodiments, the treatment is of a pancreatic cancer.

In some embodiments, the treatment is of a tumor having $\alpha_v\beta_6$ integrin on the surface of the cell.

It is contemplated that the ADC of the present disclosure may be used to treat various diseases or disorders, e.g. characterized by the overexpression of a tumor antigen. Exemplary conditions or hyperproliferative disorders include benign or malignant tumors; leukemia, hematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer.

Autoimmune diseases for which the ADC compounds may be used in treatment include rheumatologic disorders (such as, In some embodiments, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, In some embodiments, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, In some embodiments, ANCA-associated vasculitis, including Churg-Strauss vasculitis, Wegener's granulomatosis, and polyarteriitis), autoimmune neurological disorders (such as, In some embodiments, multiple sclerosis, opsoclonus myoclonus syndrome, myasthenia gravis, neuromyelitis optica, Parkinson's disease, Alzheimer's disease, and autoimmune polyneuropathies), renal disorders (such as, In some embodiments, glomerulonephritis, Goodpasture syndrome, and Berger's disease), autoimmune dermatologic disorders (such as, In some embodiments, psoriasis, urticaria, hives, pemphigus vulgaris, bullous pemphigoid, and cutaneous lupus erythematosus), hematologic disorders (such as, In some embodiments, thrombocytopenic purpura, thrombotic thrombocytopenic purpura, post-transfusion purpura, and autoimmune hemolytic anemia), atherosclerosis, uveitis, autoimmune hearing diseases (such as, In some embodiments, inner ear disease and hearing loss), Behcet's disease, Raynaud's syndrome, organ transplant, and autoimmune endocrine disorders (such as, In some embodiments, diabetic-related autoimmune diseases such as insulin-dependent diabetes mellitus (IDDM), Addison's disease, and autoimmune thyroid disease (e.g. Graves' disease and thyroiditis)). More preferred such diseases include, In some embodiments, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

The term "treatment," as used herein in the context of treating a condition, pertains generally to treatment and therapy, whether of a human or an animal (e.g., in veterinary applications), in which some desired therapeutic effect is achieved, In some embodiments, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The subject/patient in need thereof may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, In some embodiments, a fetus. In one preferred embodiment, the subject/patient is a human.

In some embodiments, the patient is a population where each patient has a tumor having $\alpha v \beta 6$ integrin on the surface of the cell.

In certain embodiments, in practicing the method of the present disclosure, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative of the linkers, drug molecules and antibodies or antibody fragments, and methods for preparing same. These are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples ACN Acetonitrile
Alloc Allyloxycarbonyl
AcOH Acetic acid
DABCO 1,4-Diazabicyclo[2.2.2]octane
DCHA 2-Methylindol-1-ylacetic acid
DCM Dichloromethane
EEDQ 2-Ethoxy-1-ethoxycarbonyl-1,2-dihydroquinoline
EDCI N1-((ethylimino)methylene)-N3,N3-dimethylpropane-1,3-diamine hydrochloride
EDTA Ethylenediaminetetraacetic acid
DIEA N,N-Diisopropylethylamine
DMA N,N-Dimetylacetamide
DMF Dimethylformamide
EDC 1-Ethyl-3-[3-dimethylaminopropyl]carbodiimide hydrochloride
HOAt 1-Hydroxy-?-azabenzotriazole
HOBt Hydroxybenzotriazole
NHS 1-Hydroxypyrrolidine-2,5-dione (i.e., N-hydroxysuccinimide)
TEA Triethylamine
TEAA Triethylammonium acetate
TCEP Tris[2-carboxyethyl] phosphine
THF Tetrahydrofuran
MI Maleimide or maleimido
MTT 4-Methyltrityl
RP-HPLC Reverse-phase high performance liquid chromatography
SEC Size exclusion chromatography
WCX Weak cation exchange chromatography General Information Tumor growth inhibition (% TGI) was defined as the percent difference in median tumor volumes (MTVs) between treated and control groups.

Treatment efficacy was determined from the incidence and magnitude of regression responses of the tumor size observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm3 for three consecutive measurements during the course of the study. An animal with a CR response at the termination of a study was additionally classified as a tumor-free survivor (TFS). Animals were monitored for regression responses.

HPLC purification was performed on a Phenomenex Gemini 5 μm 110 Å, 250×10 mm, 5 micron, semi-preparation column.

Whenever possible the drug content of the conjugates was determined quantitatively by chromatography.

The protein content of the protein-drug conjugates was determined spectrophotometrically at 280 nm or by ELISA.

Antibody-drug conjugates, can be purified (i.e., removal of residual unreacted drug, antibody, or starting materials) by extensive diafiltration. If necessary, additional purification by size exclusion chromatography can be conducted to remove any aggregated antibody-drug conjugates. In general, the antibody-drug conjugates as purified typically contain <5% (e.g., <2% w/w) aggregated antibody-drug conjugates as determined by SEC; <0.5% (w/w) (e.g., <0.1% w/w) free (unconjugated) drug as determined by RP-HPLC or LC-MS/MS; <1% (w/w) of free drug conjugate as determined by SEC and/or RP-HPLC and <2% (w/w) (e.g., <1% w/w) unconjugated antibody or antibody fragment as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by RP-HPLC or back-calculation from DAR measured by CE-SDS.

RP-HPLC, or CE-SDS were used to characterize the specificity and distribution of the cysteine bioconjugation sites in the PBRM-drug conjugates. The results gave the positional distribution of the drug-conjugates on the heavy (H) and light (L) chains of the PBRM.

To determine the concentration of the free drug in a biological sample, an acidified sample was treated with acetonitrile. The free drug was extracted and the acetonitrile supernatant was analyzed. To determine the concentration of conjugated AF-HPA, the sample was subjected to exhaustive basic hydrolysis followed by immunocapture using anti-IgG1 antibody magnetic beads. The acetonitrile supernatant containing the released AF-HPA and AF was analyzed RP-HPLC. The total antibody was measured using the unique peptide after digestion. Analysis of free AF and AF-HPA was conducted by RP-HPLC using a C-4 column, an acetonitrile gradient and UV detection. Peak areas are integrated and compared to AF and AF-HPA standards. The method is quantitative for AF-HPA and AF in plasma and tissue homogenates and linear over the concentration ranges of 0.1 to 150 ng/mL. The total drug (AF-HPA) released after hydrolysis with NaOH was measured under the same condition with the dynamic range from 1 ng/mL to 5000 ng/mL. The total antibody standards range from 0.1 µg/mL to 100 µg/mL.

General Procedure A: Partial selective reduction of protein (antibody)

The partial selective reduction of the inter-chain disulfide groups or unpaired disulfide in the relevant antibody prior to conjugation with the polymer-drug conjugate is achieved by using a reducing agent, such as, In some embodiments, TCEP, DTT or p-mercaptoethanol. When the reduction is performed with an excess of the reducing agent, the reducing agent is removed prior to conjugation by SEC. The degree of conversion of the antibody disulfide groups into reactive sulfhydryl groups depends on the stoichiometry of antibody, reducing agent, pH, temperature and/or duration of the reaction. When some but not all of the disulfide groups in the antibody are reduced, the reduced antibody is a partially reduced antibody.

General Procedure B: Conjugation of Partially Reduced Antibody with Drug Conjugate The conjugation of the partially reduced antibody to the drug conjugate is conducted under neutral or slightly basic conditions (pH 6.5-8.5) at antibody concentrations of 1-10 mg/mL and drug conjugate concentrations of 0.5-10 mg/mL. The drug conjugate is typically used in 1-5.0 fold excess relative to the desired protein-drug conjugate stoichiometry. When the antibody is conjugated to the maleimido group of the drug conjugate, the conjugation is optionally terminated by the addition of a water-soluble maleimido blocking compound, such as, In some embodiments, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol, and the like.

The resulting antibody-drug conjugate is typically purified by diafiltration to remove any unconjugated polymer-drug conjugate, unconjugated drug and small molecule impurities. Alternatively or additionally, appropriate chromatographic separation procedures such as, In some embodiments, size-exclusion chromatography, hydrophobic interaction chromatography, ion chromatography such as, In some embodiments, WCX chromatography; reversed phase chromatography, hydroxyl apatite chromatography, affinity chromatography or combinations thereof may be used to purify the antibody-drug conjugate. The resulting purified polymer-drug conjugate is typically formulated in a buffer at pH 5.0-6.5.

Other antibody-drug conjugates are synthesized with methods similar to the procedure described herein, involving other antibodies and/or antibody fragments. Also antibody-drug conjugates with varying ratios of drug to antibody are obtained by varying the number of antibody sulfhydryl groups and drug load.

Example 1. Synthesis of Trastuzumab Conjugate 5

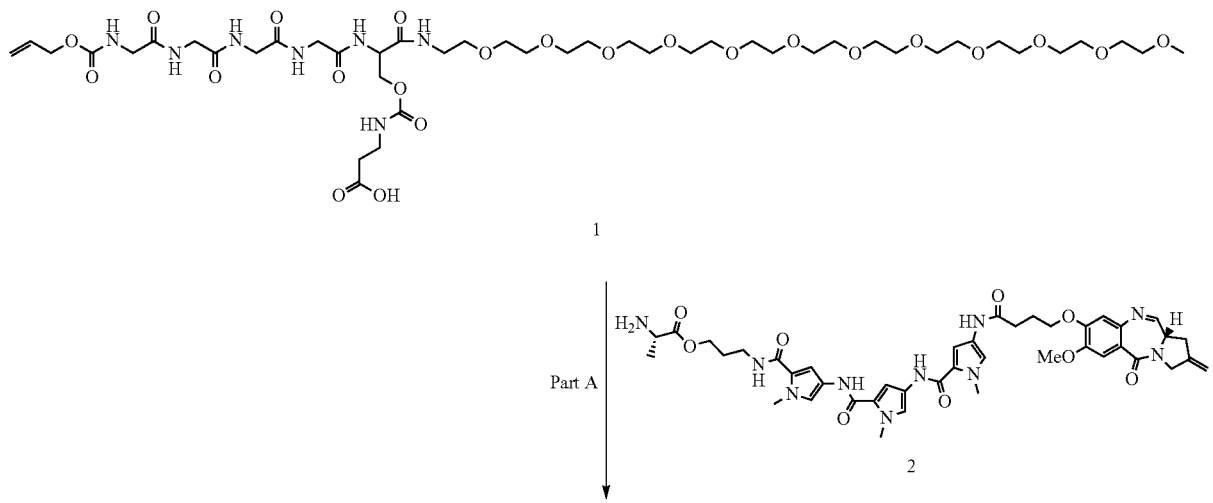

-continued

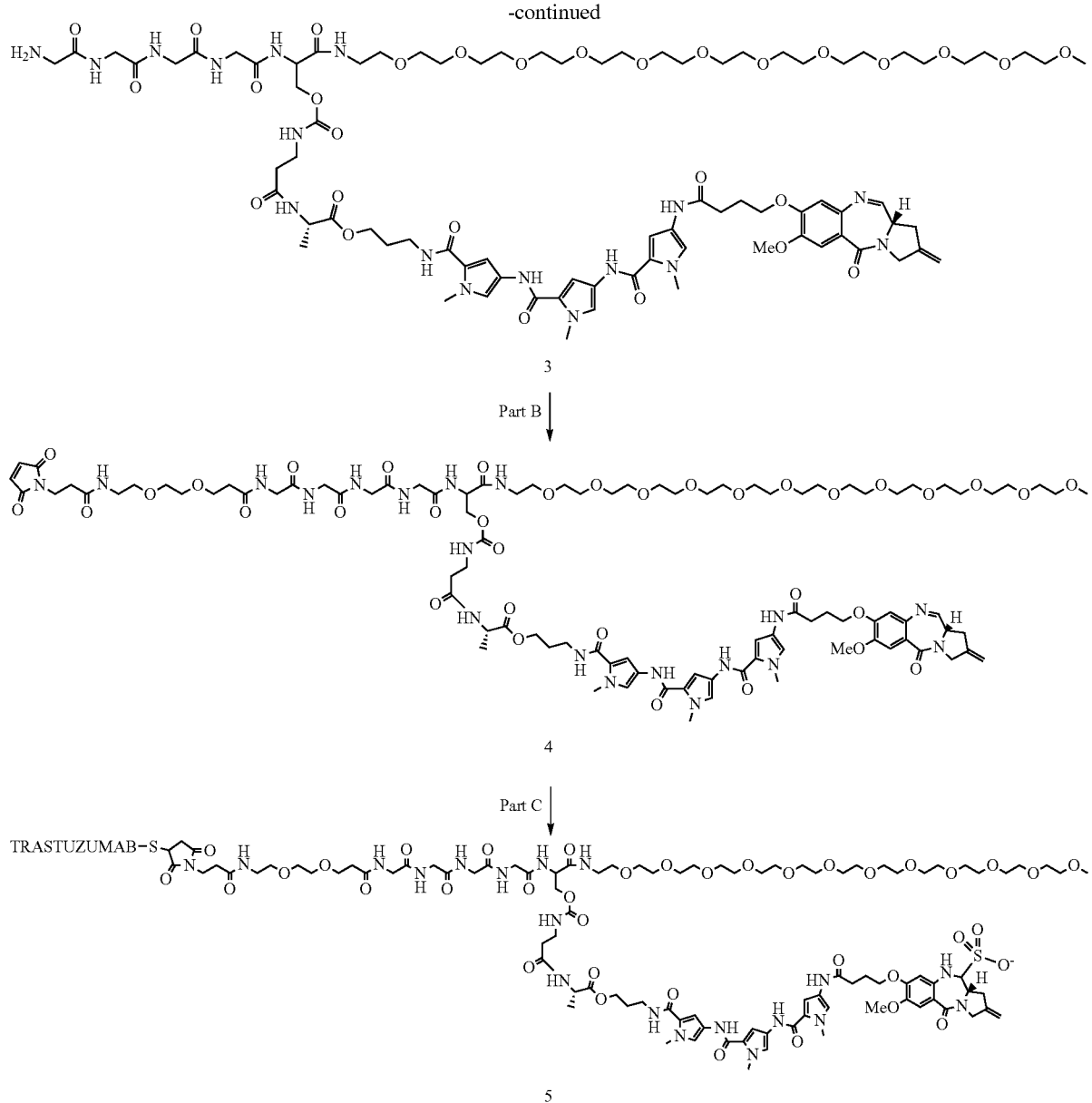

Part A:

To an ice-cold solution of compound 1 ((2.5 mg, 2.327 µmol, prepared as described in U.S. 62/425,895) in water (80 µL) was added a solution of 1-hydroxypyrrolidine-2,5-dione (NHS) (0.536 mg, 4.65 µmol) in water (20µ), then EDC (1.339 mg, 6.98 µmol) was added. The reaction mixture was allowed to warm up to room temperature over 30 min. To this mixture was added a solution of compound 2 (PC-5-129, prepared as described in U.S. Ser. No. 15/597,453) (2.82 mg, 3.14 µmol) in NMP/water (1:1, 40 µL), followed by the addition of EDC (1.339 mg, 6.98 µmol). The reaction mixture was allowed to warm up to room temperature slowly. After about 1.5 h, the crude product was purified by HPLC (10-70% acetonitrile/water containing 0.1% HOAc) to afford the desired Alloc-protected intermediate (2.5 mg, 1.3 µmol, 57% yield). ESI MS calc for $C_{86}H_{129}N_{17}O_{31}$ (M+2H) 948.0; found 948.1. This purified Alloc-protected intermediate was dissolved in $CHCl_3$ (150 µL) degassed by stirring at −78 C under high vacuum The reaction mixture was warmed to room temperature and treated with pyrrolidine (0.26 µmol) in $CHCl_3$ (10 µL), then with a solution of $Pd(PPh_3)_4$ (0.132 µmol) in $CHCl_3$, then allowed to stir at room temperature. After 1.5 h, the mixture diluted with acetonitrile (100 µL), neutralized with HOAc (1 µL) and then purified by HPLC (C-18, 10-70% acetonitrile/water containing 0.1% HOAc) to afford compound 3 (1.5 mg, 0.828 µmol, 63% yield. ESI MS calc for (M+H) 1810.88; found 1810.9.

Part B:

To a solution of compound 3 (2.2 mg, 0.377 µmol) in a mixture of NMP (125 µL)/DMSO (50 µL) and TEA (0.166 µL, 1.19 µmol) was added 2,5-dioxopyrrolidin-1-yl 3-(2-(2-(3-(2,5-dioxo-2,5-dihydro-1H-pyrrol-1-yl)propanamido)ethoxy)ethoxy)propanoate (1.0 mg, 2.4 µmol) in NMP (6.5 µL) at 0° C., and the resulting mixture was stirred at room temperature. After 3 hours additional 2,5-dioxopyrrolidin- 1-yl 3-(2-(2-(3-(2,5-dioxo-2,5-dihydro-1H-pyrrol-1-yl)pro-panamido)ethoxy)ethoxy)propanoate (2 equivalents) was added and the mixture was stirred overnight. The reaction mixture was neutralized with acetic acid, diluted with water and purified by HPLC (RP C18 column containing 0.1% HOAc (10-70% B over 35 min) to afford compound 4 (1 mg, 40% yield). ESI MS calc for $C_{96}H_{143}N_{19}O_{35}$ (M+2H) 1061; found 1061.5.

Part C:

Conjugate 5 was prepared from Trastuzumab and compound 4 as described in U.S. Ser. No. 15/597,453. The purified conjugate had a PBD to trastuzumab ratio of 6.3 as determined by UV-Vis using molar extinction$_{310\ nm}$=37,500 cm$^{-1}$M$^{-1}$ and 6280=25,394 cm$^{-1}$M$^{-1}$ for compound 2 and $\varepsilon_{280\ nm}$=226,107 cm$^{-1}$M$^{-1}$ for trastuzumab).

Example 2. Synthesis of Trastuzumab Conjugate 8

To a solution of compound 6 (88 mg, 0.078 mmol, prepared as described in U.S. 62/425,895) and compound 7 (60 mg, 0.060 mmol, prepared as described in U.S. Ser. No. 15/597,453) in NMP (2 mL) was added NHS (9.8 mg, 0.084 mmol), EDC (16 mg, 0.084 mmol), and DIEA (14.8 µL, 0.084 mmol) in succession. The mixture was stirred overnight at room temperature then purified by HPLC (0.1% formic acid in water:ACN, 10-90% B over 20 min) and lyophilized to afford the desired intermediate maleimide as a pale yellow solid (54.8 mg, 43% yield). ESI MS calc for $C_{97}H_{134}N_{22}O_3$ (M+2H) 1051.5; found 1051.3. Compound 8 was prepared from this intermediate maleimide using the procedure described in U.S. Ser. No. 15/597,453. The purified conjugate 8 had a PBD to trastuzumab ratio of 4.7 as determined by UV-Vis using molar extinction 322 m= 38,072 cm$^{-1}$M$^{-1}$ and 280=34,191 cm$^{-1}$M$^{-1}$ for compound 7 and $C_{280\ nm}$=226,107 cm$^{-1}$M$^{-1}$ for trastuzumab).

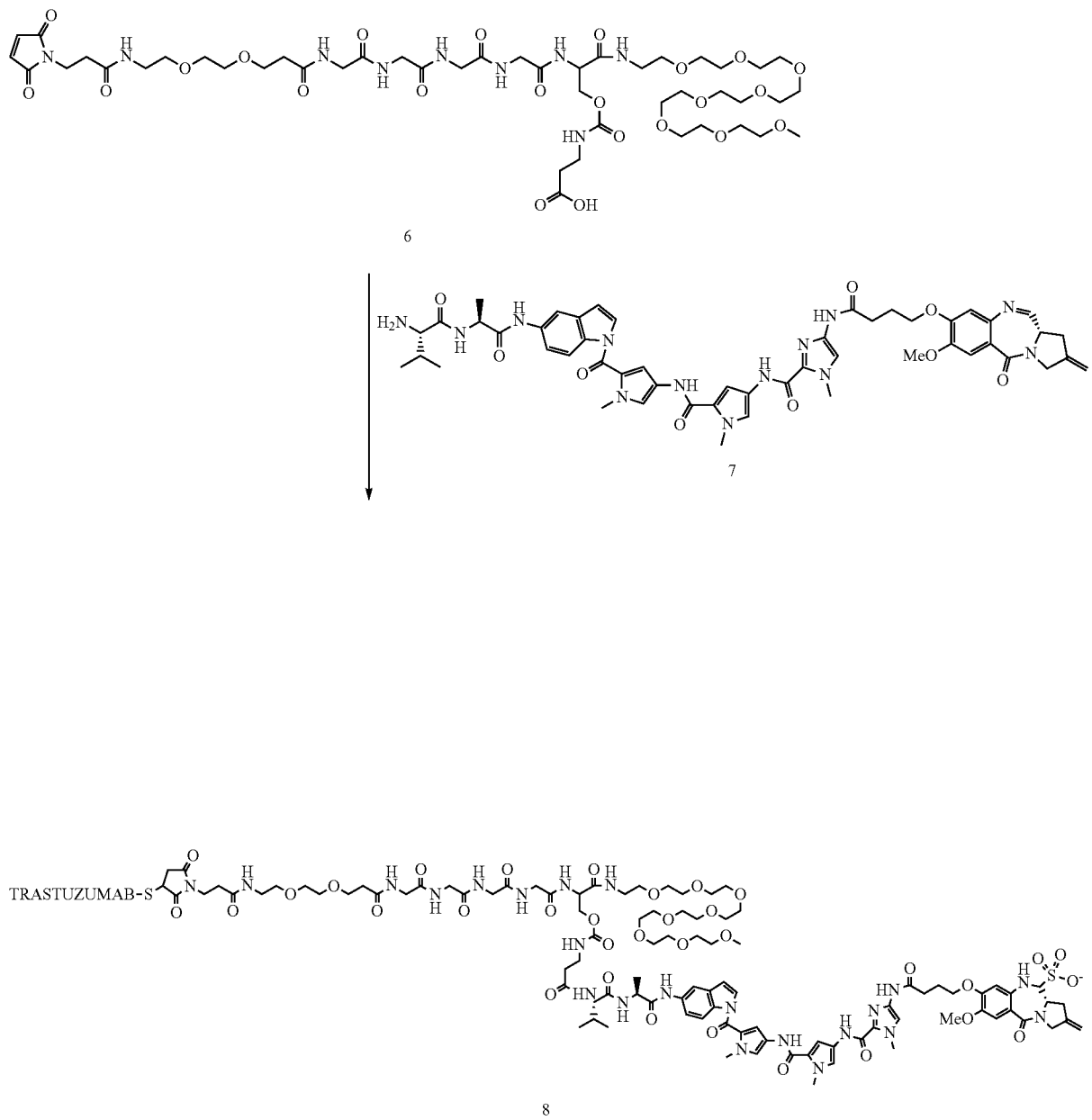

Example 3: Synthesis of Trastuzumab Conjugate 8A
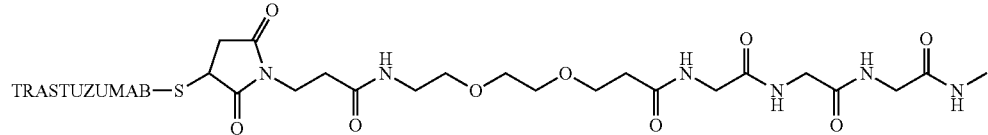
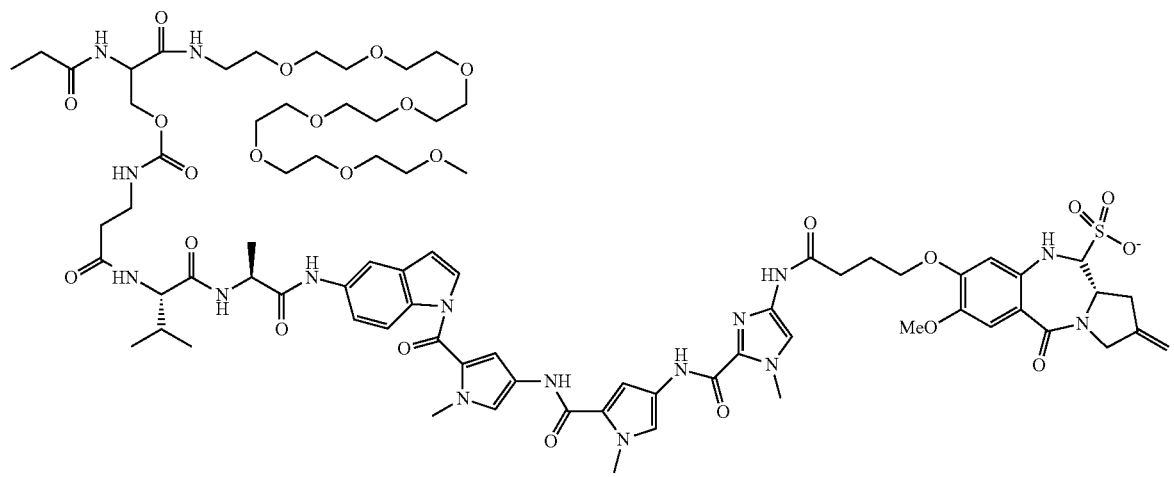
Conjugate 8A was prepared as described in Example 2 and had a PBD to trastuzumab ratio of 4.7 as determined by UV-Vis using molar extinction $\varepsilon_{322\ nm}=38,072\ cm^{-1}M^{-1}$ and $\varepsilon_{280\ nm}=34,191\ cm^{-1}M^{-1}$ for compound 7 and E280 n=226,107 $cm^{-1}M^{-1}$ for trastuzumab).
Example 4. Synthesis of Trastuzumab Conjugate 14
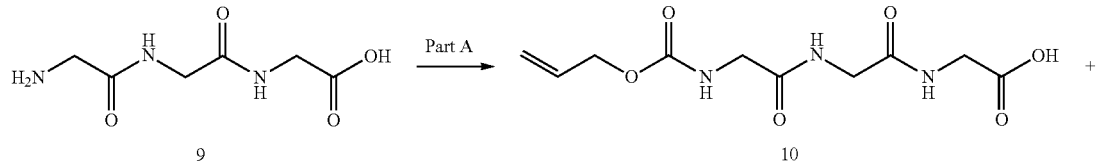
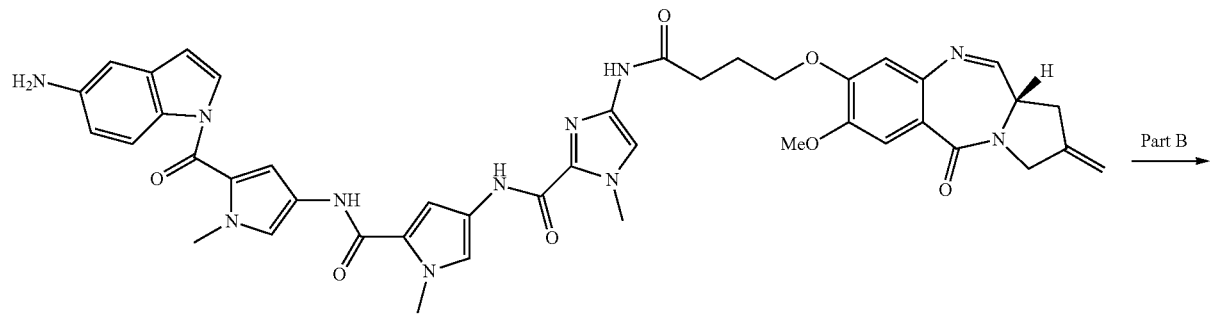

-continued

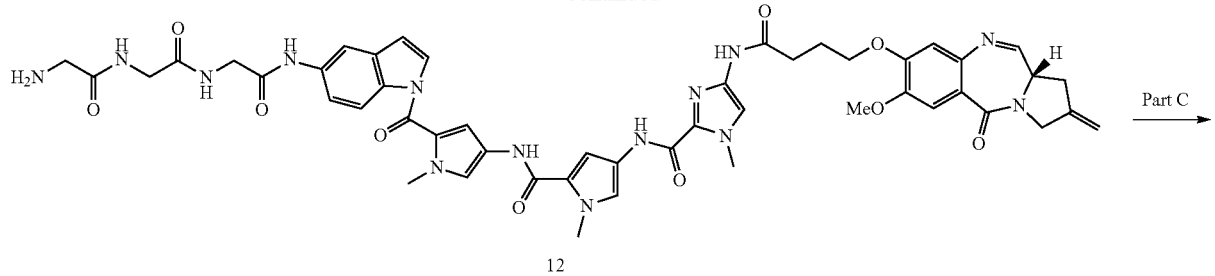

12

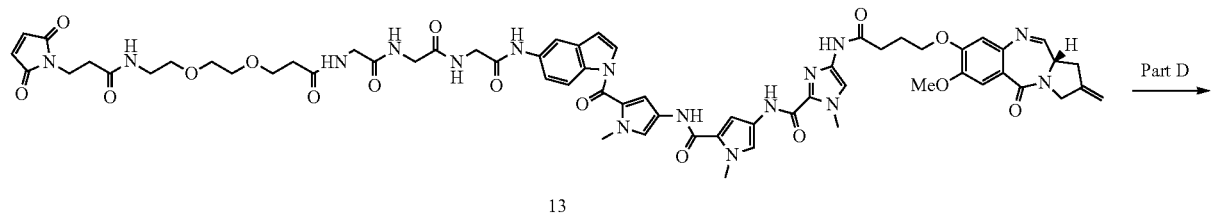

13

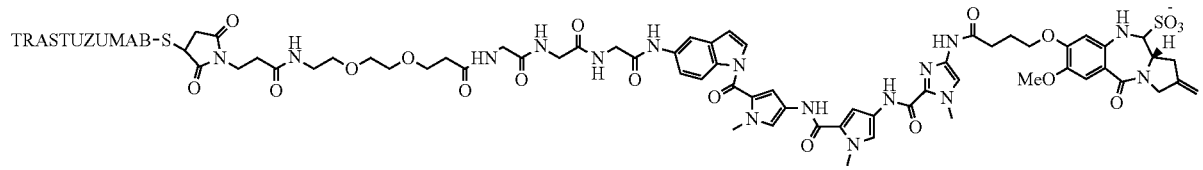

14

Part A:

To a solution of compound 9 (0.5 g, 2.64 mmol) and NaHCO₃ (0.222 g, 2.64 mmol) in water (10 mL) was added a solution of allyl (2,5-dioxopyrrolidin-1-yl) carbonate (0.526 g, 2.64 mmol) in acetone (10 mL). The mixture was then stirred overnight at room temperature. Acetone was removed under vacuum and the pH was adjusted to 1-2 with 1 N HCl and then extracted with EtOAc (2×30 mL). The organic phase was concentrated under vacuum. The residue was suspended in acetonitrile and concentrated under vacuum to afford compound 10 as a colorless solid (0.498 g). ESI MS: calc for $C_{10}H_{16}N_3O_6$ (M+H) 274.1; found 274.0.

Part B:

To a solution of compound 10 (13.23 mg, 0.048 mmol) and compound 11 (40 mg, 0.048 mmol; prepared as described in U.S. Ser. No. 15/597,453) in THF (1.0 mL) and DMA (0.2 mL) was added EEDQ (14.97 mg, 0.061 mmol) and the mixture was stirred overnight. Additional DMA and EEDQ (2 equivalents) was added and the mixture was stirred for another 20 h. The crude product was purified on silica gel (0-15% MeOH/DCM) to afford the Alloc-protected compound 11 intermediate (47 mg, 0.043 mmol, 90% yield). ESI MS: calc for $C_{53}H_{56}N_{14}O_{12}$ (M+H) 1081.4; found 1080.8. This intermediate was then dissolved in a mixture DCM (1 mL) and DMF (0.5 mL) and treated with triphenylphosphine (2.85 mg, 10.87 μmol) and pyrrolidine (4.49 μl, 0.054 mmol) under argon. The resulting mixture was stirred at room temperature for 10 min, followed by the addition of tetrakis(triphenylphosphine)palladium(0) (2.51 mg, 2.174 μmol) and the solution was stirred at room temperature for 20 min. The crude product was then purified on silica gel (0-20% MeOH/DCM) to afford compound 12 (26 mg, 0.026 mmol, 60.0% yield). ESI MS: calc for $C_{49}H_{53}N_{14}O_{10}$ (M+H) 997.4; found 997.0.

Part C:

To a solution of compound 12 (26 mg, 0.026 mmol in DMF (2.0 ml) was added HOBt (3.88 mg, 0.029 mmol), 2,5-dioxopyrrolidin-1-yl 3-(2-(2-(3-(2,5-dioxo-2,5-dihydro-H-pyrrol-1-yl)propanamido)ethoxy)ethoxy)propanoate (12.20 mg, 0.029 mmol), triethylamine (4.0 μL, 0.029 mmol). The mixture was stirred for 2 h at room temperature. The crude product was purified on HPLC (0.1% formic acid 10-90% ACN/water) to afford compound 13 (8.6 mg, 6.58 μmol, 25.2 yield). ESI MS: calc for $C_{49}H_{53}N_{14}O_{10}$ (M+H) 1307.5; found 1306.8.

Part D:

Conjugate 14 was prepared from Trastuzumab and compound 13 as described in Example 1. The purified conjugate had a PBD to trastuzumab ratio of 3.0 as determined by UV-Vis using molar extinction $\varepsilon_{322\ nm}$=38,072 cm⁻¹M⁻¹ and 280 m=34,191 cm⁻¹M⁻¹ for compound 7 and 6280 m=226,107 cm⁻¹M⁻¹ for trastuzumab).

Example 5. Synthesis of Trastuzumab Conjugate 22
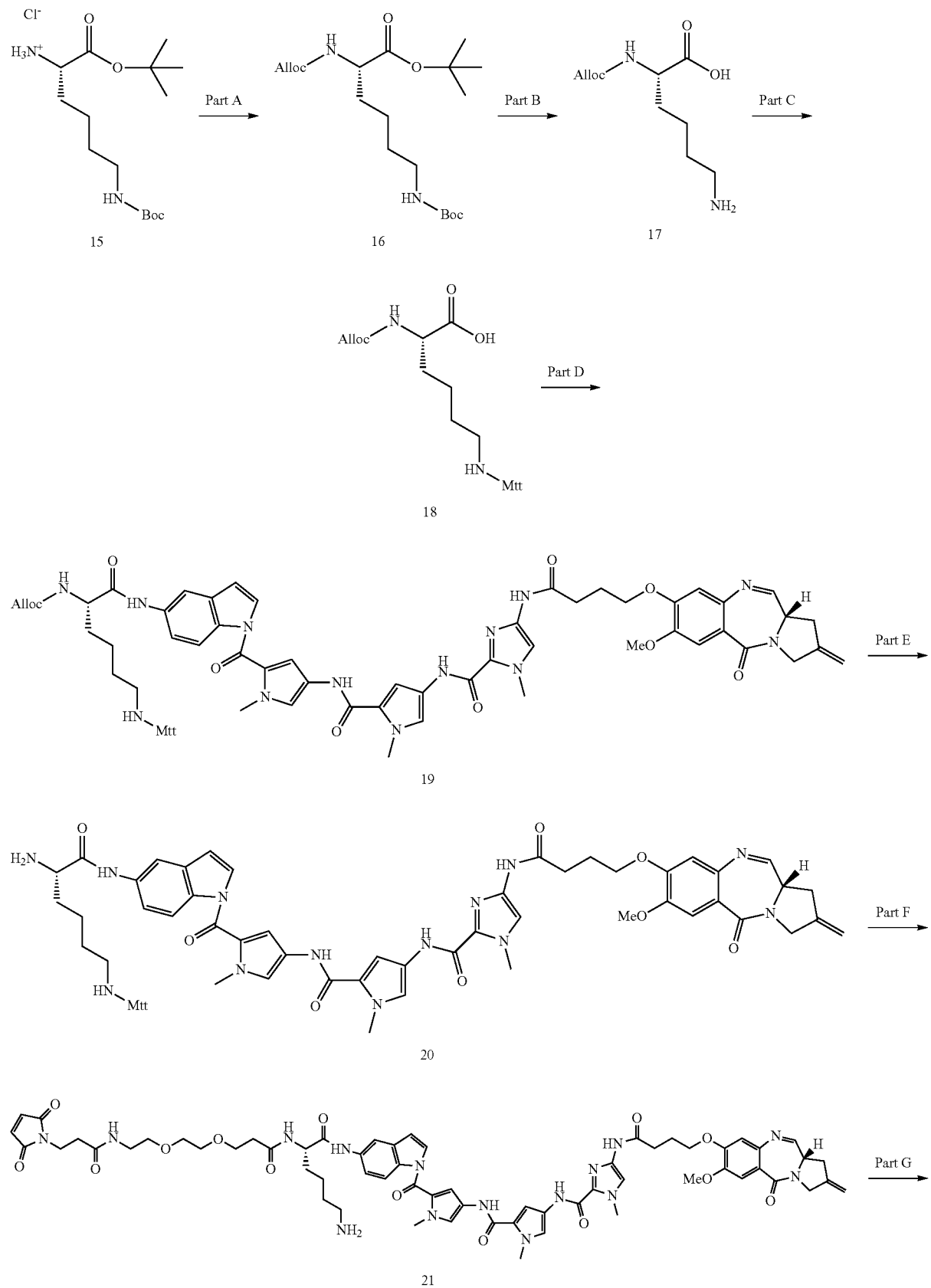

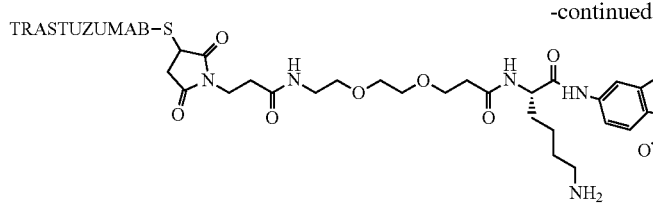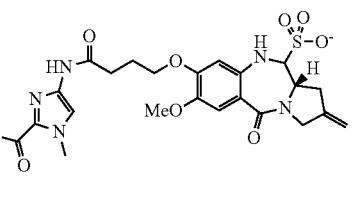

22

Part A:

To an ice-cold mixture of (S)-tert-butyl 2-amino-6-((tert-butoxycarbonyl)amino)hexanoate hydrochloride 15 (1.0 g, 2.95 mmol) and sodium bicarbonate (0.545 g, 6.49 mmol) in a solution of ACN (10 mL) and water (15 mL) was added a solution of allyl (2,5-dioxopyrrolidin-1-yl) carbonate (0.646 g, 3.25 mmol) in ACN (5 mL). The ice bath was removed and the mixture was stirred overnight at room temperature. Acetonitrile was removed under vacuum and the reaction mixture was diluted with EtOAC (60 mL) and washed with brine. The organic phase was dried over $MgSO_4$, filtered and concentrated under vacuum. The crude product was purified on silica gel (Hex:EtOAc, 0-80% B) to afford compound 16 (1.09 g, 2.82 mmol, 96% yield). ESI MS: calc for $C_{19}H_{34}N_2NaO_6$ (M+Na) 409.2; found 409.0.

Part B:

To an ice-cold solution of compound 16 (1.09 g, 2.82 mmol) in DCM (15 mL) was added TFA (2.0 mL). The resulting solution was stirred at room temperature for 3 h, then the solvent was removed under vacuum and the residue was placed under high vacuum overnight to yield compound 17 that was used in the next step without further purification (1.293 g, 2.82 mmol, 100% yield). ESI MS: calc for $C_{10}H_{19}N_2O_4$ (M+H) 231.1; found 231.0.

Part C:

To a solution of compound 17 (1.293 g, 2.82 mmol) in DCM (15 mL) under argon at room temperature, was added triethylamine (2.163 mL, 15.52 mmol). After 10 minutes, (chloro(p-tolyl)methylene)dibenzene (0.867 g, 2.96 mmol) was added as a solid and stirred overnight under argon at room temperature. The solvent was removed under vacuum, and the crude product was purified on silica gel (0-30% MeOH in DCM) to afford compound 18 (0.826 g, 1.697 mmol, 60.2% yield). ESI MS: calc. for $C_{30}H_{33}N_2O_4$ (M−H) 485.2; found 484.9.

Part D:

To a solution of compound 18 (29.5 mg, 0.061 mmol) and compound 11 (50 mg, 0.061 mmol) in a mixture of THF (1.0 mL) and DMA (0.2 mL) was added EEDQ (18.71 mg, 0.076 mmol) and the resulting mixture was stirred overnight. Additional DMA and EEDQ (0.2 equivalents) was added, and the reaction was stirred an additional 20 h. The crude product was purified on silica gel (0-15% MeOH/DCM) to afford compound 19 (47 mg, 0.036 mmol, 60.0% yield). ESI MS: calc for $C_{73}H_{76}N_{13}O_{10}$ (M+H$_2$O+H) 1312.6; found 1311.9.

Part E:

To a solution of compound 19 (47 mg, 0.036 mmol) in DCM (3 mL) was added triphenylphosphine (2.38 mg, 9.08 µmol) and pyrrolidine (3.75 µL, 0.045 mmol) under argon and the mixture was stirred at room temperature for 10 min. To this mixture was added tetrakis(triphenylphosphine)palladium(0) (2.098 mg, 1.815 µmol). The resulting solution was stirred at room temperature for 2 h, then the solvent was removed under vacuum and the residue was purified on silica gel (0-20% MeOH/DCM) to afford compound 20 (30 mg, 0.025 mmol, 68.3% yield). ESI MS: calc for $C_{69}H_{74}N_3O_9$ (M+NH$_4$) 1227.6; found 1227.8.

Part F:

To a solution of compound 20 (30 mg, 0.025 mmol) in DMF (2.0 mL) was added HOBt (5.02 mg, 0.037 mmol), 2,5-dioxopyrrolidin-1-yl 3-(2-(2-(3-(2,5-dioxo-2,5-dihydro-1H-pyrrol-1-yl)propanamido)ethoxy)ethoxy)propanoate (15.82 mg, 0.037 mmol), and triethylamine (5.18 µl, 0.037 mmol). The mixture was stirred 16 h at room temperature. The crude product was purified by HPLC (0.1 Formic Acid, 10-90% ACN/Water) to afford the desired MTT-protected maleimide intermediate (28 mg, 0.018 mmol, 74.3% yield). ESI MS: calc for $C_{83}H_{93}N_6O_{14}$ (M+NH$_4$) 1537.7; found 1537.8.

To a solution of the MTT-protected maleimide intermediate (28 mg, 0.018 mmol) in DCM (1.4 mL) was added 2,2,2-trifluoroethanol (0.4 mL, 5.49 mmol) and acetic acid (0.2 mL, 3.50 mmol) and the resulting mixture was stirred at room temperature for 2 h. The crude product was purified on silica gel (0-15% MeOH/DCM) to afford compound 21 (9.2 mg, 7.28 µmol, 39.5% yield). ESI MS: calc for $C_{63}H_{74}N_{15}O_{14}$ (M+H) 1264.5; found 1264.7.

Part G:

Compound 22 was prepared from Trastuzumab and compound 21 as described in Example 2. The purified conjugate had a PBD to trastuzumab ratio of 3.6 as determined by UV-Vis using molar extinction 322 m=38,072 cm$^{-1}$M$^{-1}$ and $\varepsilon_{280\ nm}$=34,191 cm$^{-1}$M for compound 7 and $\varepsilon_{280\ nm}$=226,107 cm-'M-' for trastuzumab.

Example 6. Synthesis of Trastuzumab Conjugate 28
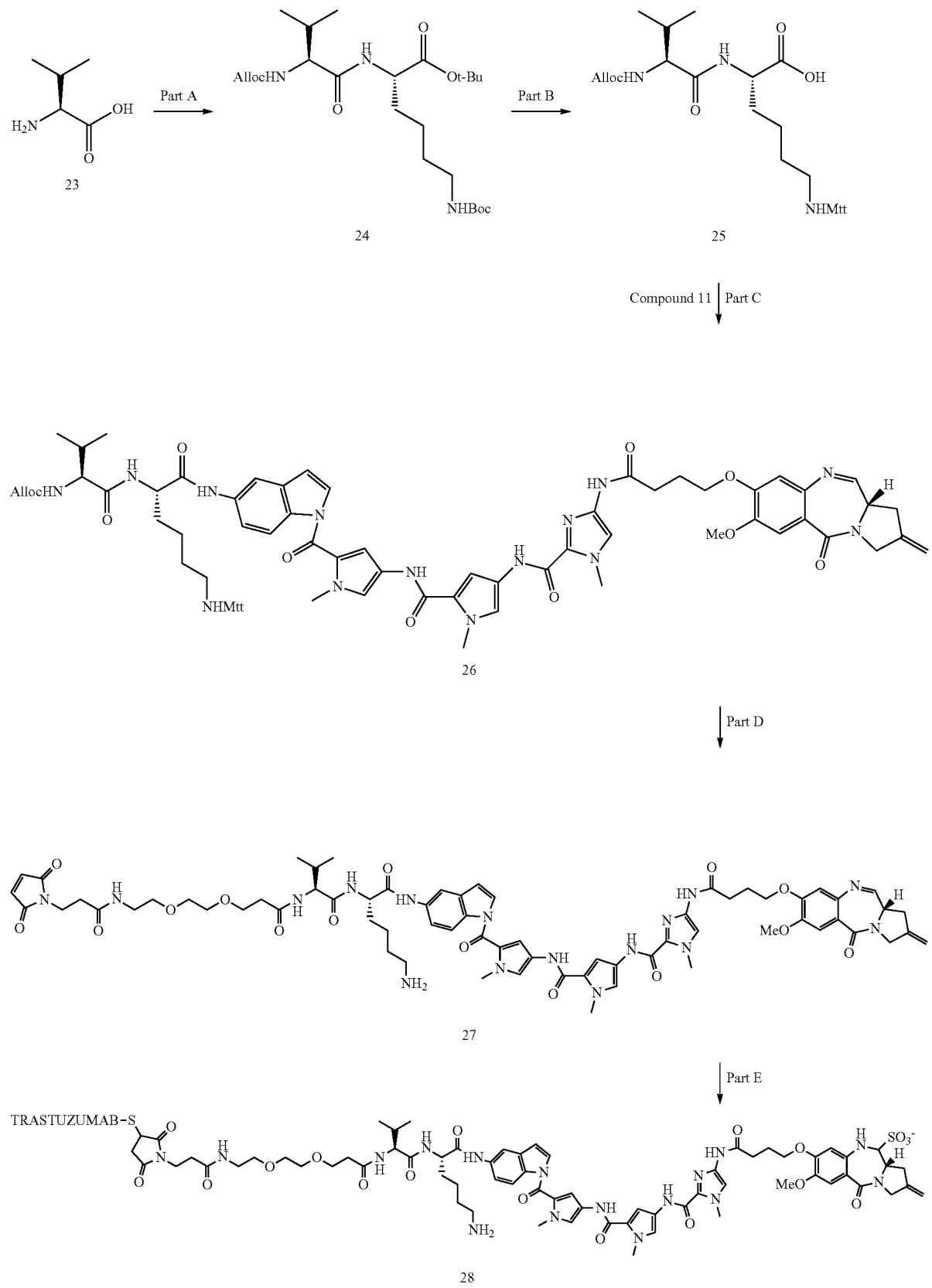

Compound 23 (1 g, 8.54 mmol) and NaHCO$_3$ (0.717 g, 8.54 mmol) were dissolved in acetone (42.7 mL) and water (42.7 mL). Allyl (2,5-dioxopyrrolidin-1-yl) carbonate (1.700 g, 8.54 mmol) was dissolved in acetone (5 mL), and added to the reaction mixture, which was then stirred for 12 h at room temperature. The reaction mixture was then concentrated under reduced pressure, acidified by the dropwise addition of concentrated HCl to pH 3, and extracted with EtOAc. The combined organic layers were washed with brine, dried over Na$_2$SO$_4$, and concentrated to provide crude Alloc-Val-OH (1.85 g, 9.19 mmol, 108% yield) ESI MS: C$_9$H$_{14}$NO$_4^-$ (M–H) 200.1; found 200.0 (negative mode), which was used in the next step without further purification.

To the crude Alloc-Val-OH (0.929 g, 4.62 mmol) was added HOAt (0.754 g, 5.54 mmol), (S)-tert-butyl 2-amino-6-((tert-butoxycarbonyl)amino)hexanoate hydrochloride (1.565 g, 4.62 mmol), and EDCI (1.062 g, 5.54 mmol), under argon was adding Et$_3$N (3.22 mL, 23.08 mmol) and DMF (46.2 mL) and the resulting mixture was stirred overnight at room temperature. The crude reaction mixture was diluted with water and extracted with DCM. The combined organic layers were washed with brine and dried over Na$_2$SO$_4$, then concentrated and purified on silica gel (100% DCM) to provide compound 24 (1.48 g, 3.05 mmol, 66.0% yield) ESI MS: C$_{24}$H$_{43}$N$_3$NaO$_7^+$ (M+Na) 508.3; found 508.0.

Part B:

To compound 24 (0.7152 g, 1.473 mmol) in DCM (2.95 mL), was added TFA (5.60 mL, 73.6 mmol) and the solution was stirred at room temperature for 6 hours. The reaction mixture was concentrated under reduced pressure to obtain the deprotected material as an oil (TFA salt), which was used directly in the next step. ESI MS: C$_{15}$H$_2$N$_3$O$_5^+$ (M+H) 330.2; found 330.0.

The material from the previous step (485 mg, 1.473 mmol), in DMF (14.7 mL) under argon at room temperature, was added Et$_3$N (1.13 mL, 8.10 mmol) followed by the additional of (chloro(p-tolyl)methylene)dibenzene (453 mg, 1.547 mmol) after 10 minutes and the reaction stirred at room temperature for 12 hours. The solvent was removed under reduced pressure, and the crude product was purified on silica gel (0-30% MeOH in DCM) to provide compound 25 (549.2 mg, 0.938 mmol, 63.7% yield). ESI MS: C$_{35}$H$_{42}$N$_3$O$_5^-$ (M–H) 584.3; found 583.8.

Part C:

Compounds 11 (50 mg, 0.061 mmol, prepared as described in U.S. Ser. No. 15/597,453), compound 25 (35.5 mg, 0.061 mmol) and EEDQ (19.46 mg, 0.079 mmol) were dissolved in THF (908 µl) and DMF (303 µl) and stirred at room temperature for 12 hours. The reaction mixture was concentrated, and the crude product was purified on silica gel (0-20% MeOH in DCM) to provide the coupled product (37.3 mg, 0.027 mmol, 44.2% yield). ESI MS: C$_{78}$H$_{85}$N$_{14}$O$_{11}^+$ (M+H) 1393.7; found 1393.7.

To the coupled product (37.3 mg, 0.027 mmol) were added DABCO (15.01 mg, 0.134 mmol), and Pd(PPh$_3$)$_4$ (3.09 mg, 2.68 µmol) and DCM (1.33 mL) and the mixture was stirred for 20 minutes at room temperature before purification on silica gel (0-40% MeOH in DCM) to provide compound 26 (6.8 mg, 5.19 µmol, 19.40% yield). ESI MS: C$_{74}$H$_{81}$N$_{14}$O$_9^+$ (M+H) 1309.6; found 1308.8

Part D:

Compound 26 (6.8 mg, 5.19 µmol) was dissolved in DMF (1 mL), and then triethylamine (0.525 mg, 5.19 µmol) and 2,5-dioxopyrrolidin-1-yl 3-(2-(2-(3-(2,5-dioxo-2,5-dihydro-1H-pyrrol-1-yl)propanamido)ethoxy)ethoxy)propanoate (2.209 mg, 5.19 µmol) were added and the mixture stirred at room temperature for 1 hour. The reaction mixture was concentrated on high vacuum and purified on silica gel (0-30% MeOH in DCM) to provide the MTT protected intermediate (4.5 mg, 2.78 µmol, 53.5% yield). ESI MS: C$_{88}$H$_{99}$N$_{16}$O$_{15}^+$ (M+H) 1619.8; found 1618.8.

The MTT protected intermediate (2.5 mg, 1.543 µmol) was dissolved in DCM (700 µl), 2,2,2-trifluoroethanol (200 µl, 2.74 mmol) and HOAc (100 µl, 1.748 mmol) and stirred at room temperature for 1 hour. The concentrated reaction mixture was purified by reverse phase RP-HPLC (0.1% HOAc, 10-100% ACN in H$_2$O), to obtain compound 27 (1.38 mg, 1.012 µmol, 65.6% yield). ESI MS: CO$_8$H$_{83}$N$_{16}$O$_{15}^+$ (M+H) 1363.6; found 1363.8.

Part E:

Compound 28 was prepared from Trastuzumab and compound 27 as described in Example 2. The purified conjugate had a PBD to trastuzumab ratio of 3.9 as determined by UV-Vis using molar extinction $\varepsilon_{322\ nm}$=38,072 cm$^{-1}$M$^{-1}$ and $\varepsilon_{280\ nm}$=34,191 cm$^{-1}$M$^{-1}$ for compound 7 and $\varepsilon_{280\ nm}$=226,107 cm$^{-1}$M$^{-1}$ for trastuzumab.

Example 7. Synthesis of Trastuzumab Conjugate 34

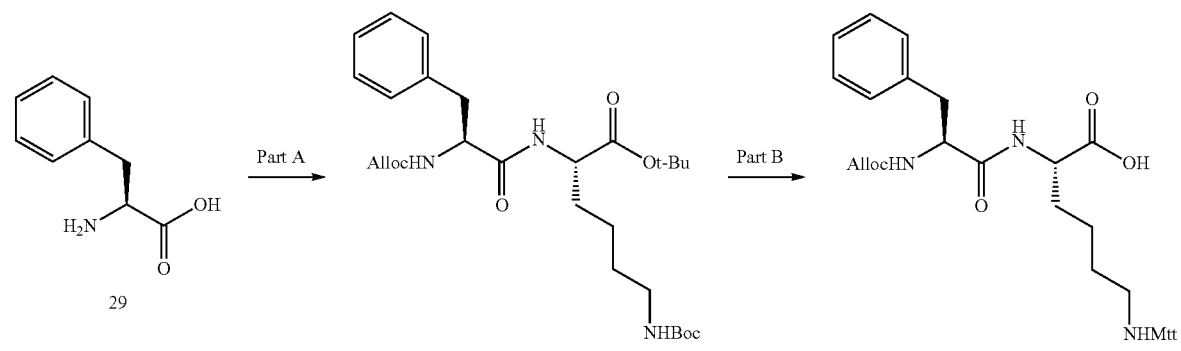

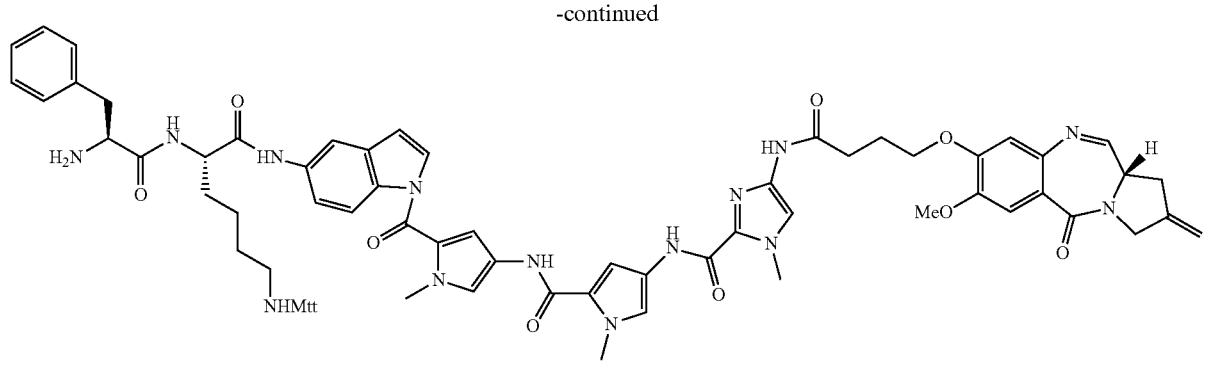

32

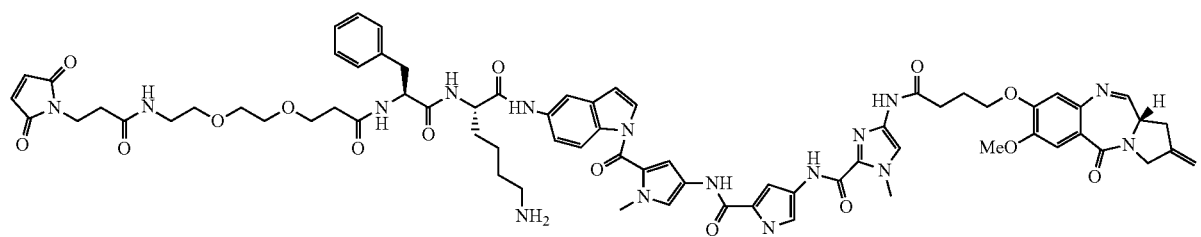

33

↓ Part E

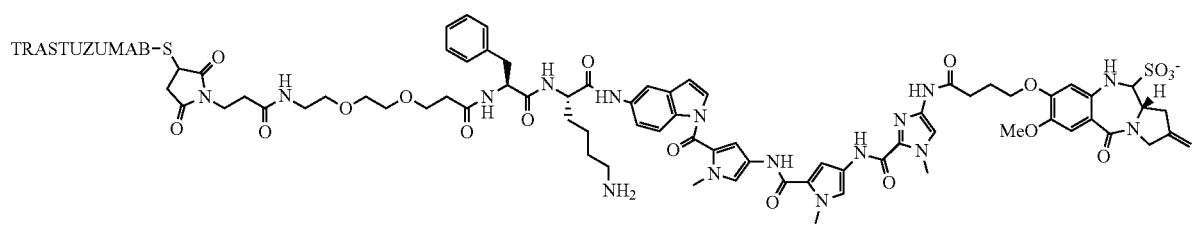

34

Part A:

To compound 29 (0.579 g, 2.3223 mmol, prepared from the DCHA salt) was added HOAt (0.379 g, 2.79 mmol), (S)-tert-butyl 2-amino-6-((tert-butoxycarbonyl)amino)hexanoate hydrochloride (0.787 g, 2.322 mmol), and EDCI (0.534 g, 2.79 mmol), under argon was added Et$_3$N (1.618 mL, 11.61 mmol) and DMF (23.22 mL) and the resulting mixture was stirred for 12 hours at room temperature. The reaction mixture was diluted with water and extracted with DCM. The combined organic layers were washed with brine, dried over Na$_2$SO$_4$, concentrated, and purified on silica gel (0-30% MeOH in DCM) to provide compound 30 (1.239 g, 2.322 mmol, 100% yield). ESI MS: $C_{28}H_{43}N_3NaO_7^+$ (M+Na) 556.3; found 555.9.

Part B:

To compound 30 (558 mg, 1.046 mmol) in DCM (21 mL) at room temperature, and was added TFA (1192 µl, 15.68 mmol). After 6 hours, additional TFA (2 mL) was added. The reaction mixture was concentrated under reduced pressure to give the deprotected intermediate (395 mg, 1.046 mmol, 100% yield). ESI MS: $C_{19}H_{28}N_3O_5^+$ (M+H) 378.2; found 378.0.

To the deprotected intermediate (0.395 g, 1.046 mmol), in DMF (10.46 mL) under argon at room temperature, was added Et₃N (0.802 mL, 5.75 mmol). After 10 minutes, (chloro(p-tolyl)methylene)dibenzene (0.322 g, 1.098 mmol) was added and the reaction was stirred for 12 hours at room temperature, concentrated under reduced pressure, and the crude product was purified on silica gel (0-30% MeOH in DCM) to provide compound 31 (0.2845 g, 0.449 mmol, 42.9% yield). ESI MS: $C_{39}H_{42}N_3O_5^-$ (M–H) 632.3; found 631.7 (M–H) negative mode.

Part C:

Compounds 11 (75 mg, 0.091 mmol, compound 31 (57.6 mg, 0.091 mmol), and EEDQ (29.2 mg, 0.118 mmol) dissolved in THF (1.36 mL) and DMF (454 µl) was stirred at room temperature for 12 hours. The reaction mixture was concentrated under reduced pressure, then purified on silica gel (0-20% MeOH in DCM) to provide the Alloc protected intermediate (66.5 mg, 0.046 mmol, 50.8% yield). ESI MS: $C_{82}H_{85}N_{14}O_{11}^+$ (M+H) 1441.7; found 1441.8.

To the Alloc protected intermediate (66.5 mg, 0.046 mmol), triphenylphosphine (3.02 mg, 0.012 mmol), pyrrolidine (4.74 µl, 0.058 mmol) and DCM (1538 µl) under argon was added Pd(PPh₃)₄ (5.33 mg, 4.61 µmol), and the resulting mixture was stirred at room temperature for 30 min, followed by purification on silica gel (0-35% MeOH in DCM) to provide compound 32 (62.6 mg, 0.046 mmol, 100% yield). ESI MS: $C_{78}H_{81}N_{14}O_9^+$ (M+H) 1357.6; found 1357.7.

Part D:

To compound 32 (62.6 mg, 0.046 mmol) was added Et₃N (6.43 µl, 0.046 mmol), DMF (922 µl) and 2,5-dioxopyrrolidin-1-yl 3-(2-(2-(3-(2,5-dioxo-2,5-dihydro-1H-pyrrol-1-yl)propanamido)ethoxy)ethoxy)propanoate (19.62 mg, 0.046 mmol), and the mixture was stirred at room temperature for 15 minutes, concentrated on high vacuum, then purified on silica (0-35% MeOH in DCM) to provide the MTT protected intermediate (77 mg, 0.046 mmol, 100% yield). ESI MS: $C_{92}H_{99}N_{16}O_{15}^+$ (M+H) 1667.8; found 1667.7.

To the MTT protected intermediate (77 mg, 0.046 mmol) was added DCM (2100 µl), 2,2,2-trifluoroethanol (600 µl, 8.23 mmol) and HOAc (300 µl, 5.25 mmol) and the reaction mixture was stirred at room temperature for 2 hours, concentrated under reduced pressure, then purified by RP-HPLC (10-100% ACN in H₂O with 0.1% HCO₂H) to provide 33 (4 mg, 2.83 µmol, 6.14% yield). ESI MS: $C_{72}H_{83}N_{16}O_{15}^+$ (M+H) 1411.6; found 1411.7.

Part E:

Compound 34 was prepared from Trastuzumab and compound 33 as described in Example 2 The purified conjugate had a PBD to trastuzumab ratio of 4.0 as determined by UV-Vis using molar extinction E322 m=38,072 cm⁻¹M⁻¹ and 628) m=34,191 cm⁻¹M⁻¹ for compound 7 and $\epsilon_{280\ nm}$=226,107 cm⁻¹M⁻¹ for trastuzumab.

Example 8. Synthesis of Trastuzumab Conjugate 35

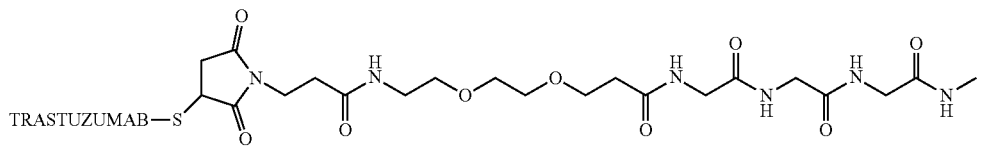

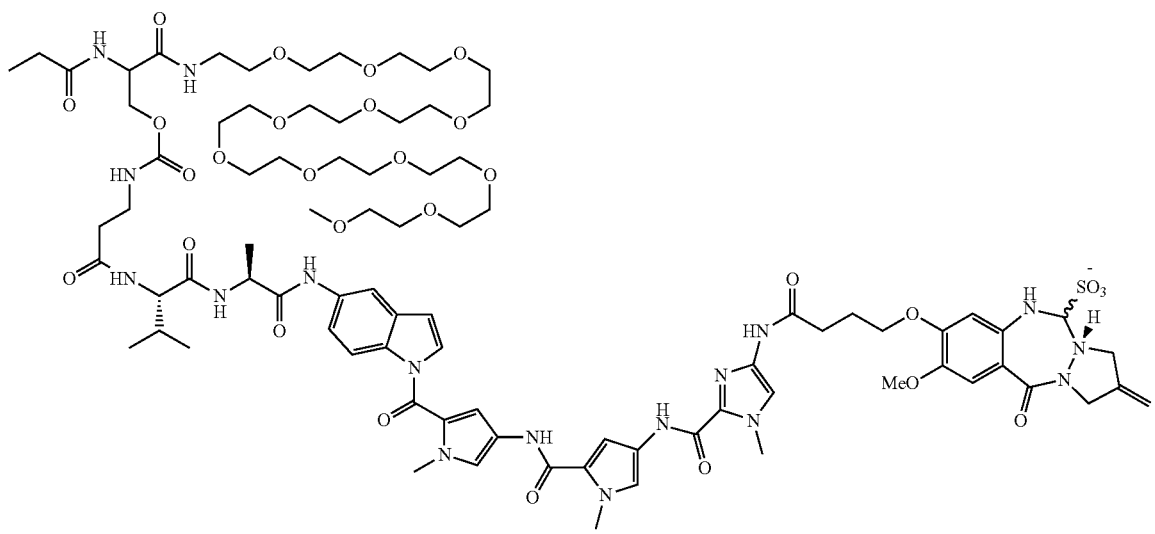

Trastuzumab conjugate 35 was prepared as described in Example 2 except that the corresponding PEG12 compound was used instead of the PEG8 compound. The purified conjugate had a PBD to trastuzumab ratio of 5.2 as determined by UV-Vis using molar extinction $\epsilon_{322\ nm}$=38,072 cm⁻¹M⁻¹ and E280 m=34,191 cm⁻¹M⁻¹ for compound 7 and $\epsilon_{280\ nm}$=226,107 cm⁻¹M⁻¹ for trastuzumab.

Example 9. Synthesis of Trastuzumab Conjugate 36

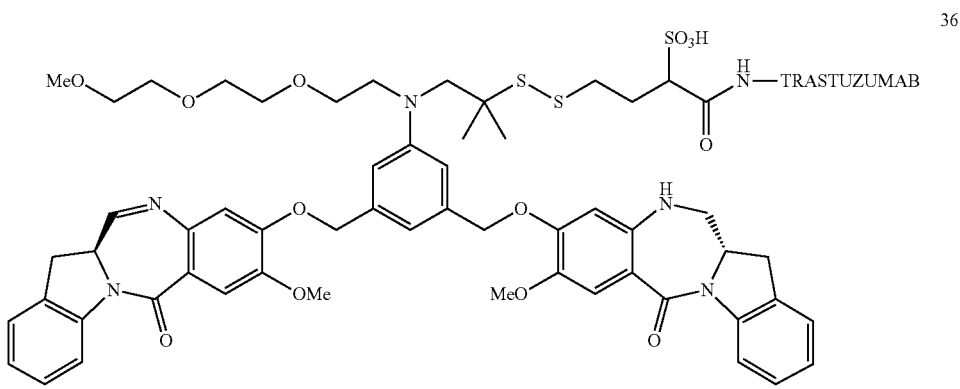

Conjugate 36 was prepared as described in US 2016/0082114A1 except that trastuzumab was used. The purified conjugate 36 had a IGN to anti-Trop2 antibody ratio of 2.3 as determined by UV-Vis using molar extinction $\varepsilon_{330\,nm}=15,484$ cm$^{-1}$M$^{-1}$ and $\varepsilon_{280\,nm}=30,115$ cm–1M–1 for IGN (according to WO2012/128868A1) and $\varepsilon_{280\,nm}=226,107$ cm–1M–1 for Trastuzumab antibody).

Example 10. Cell Viability Assay for Antibody-Drug Conjugates

PBD conjugates were evaluated for their antiproliferation properties in tumor cell lines in vitro using CellTiter-Glo® (Promega Corp). Cells were plated in black walled 96-well plate and allowed to adhere overnight at 37° C. in a humidified atmosphere of 5% $CO_2$. BT474, SKBR3, NCI-N$_{87}$ cells (HER2 expressing cells), JIMT1 cells (HER2 medium expression level cells) and MCF7 cells (HER2 low expressing levels cells) and were plated at a density of 5,000 cells per well. The next day the medium was replaced with 50 μL fresh medium and 50 μL of 2× stocks of PBD compounds or antibody-PBD conjugate were added to appropriate wells, mixed and incubated for 72 h. CellTiter-Glo® reagent was added to the wells at room temperature and the luminescent signal was measured after 10 min using a SpectraMax M5 plate reader (Molecular Devices). Dose response curves were generated using SoftMax Pro software. IC$_{50}$ values were determined from four-parameter curve fitting.

Table I gives illustrative results for the antiproliferation properties of the PBD and conjugates.

TABLE I

| Compound No. | BT474 IC$_{50}$ (nmol/L) | SKBR3 IC$_{50}$ (nmol/L) | N87 IC$_{50}$ (nmol/L) | JIMT1 IC$_{50}$ (nmol/L) | MCF7 IC$_{50}$ (nmol/L) |
|---|---|---|---|---|---|
| 8 | 0.21 | 0.03 | 0.08 | 96 | 43 |
| 8A | 0.06 | 0.01 | 0.04 | 300 | 253 |
| 14 | 300 | 0.048 | 0.260 | 300 | 300 |
| 22 | 2.45 | 0.020 | 0.11 | 300 | 300 |
| 28 | 0.619 | 0.020 | 0.063 | 300 | 300 |
| 34 | 0.598 | 0.013 | 0.070 | 28.400 | 3.410 |
| 35 | 0.27 | 0.0184 | 0.0324 | 0.154 | 3 |

As shown in Tables I, the antibody-drug conjugates show efficacy in the tested cell lines.

Example 11. Tumor Growth Response to Administration of Antibody-Drug Conjugates

Female CB-17 SCID mice were subcutaneously implanted with Calu-3 cells (n=10 for each group). Test compounds or vehicle were dosed IV as a single dose on day 1. Tumor size was measured at the times indicated in FIG. 1 using digital calipers. Tumor volume was calculated and was used to determine the delay in tumor growth. Tumor volumes are reported as the mean±SEM for each group.

FIG. 1 provides the results for the tumor response in mice subcutaneously implanted with Calu-3 cells (n=10 for each group) after IV administration of vehicle; and the Trastuzumab-drug conjugates: Example 4, Conjugate 14; Example 6, Conjugate 28; and Example 7, Conjugate 34; each at 1 mg/kg as a single dose at day 1; and Example 5, Conjugate 22, at 3 mg/kg as a single dose at day 1. The results show that on day 90, Conjugate 22 resulted in 1 partial response; Conjugate 28 in 5 partial responses and 2 complete responses; and Conjugate 34 in 6 partial responses and 2 complete responses.

Figure 2:
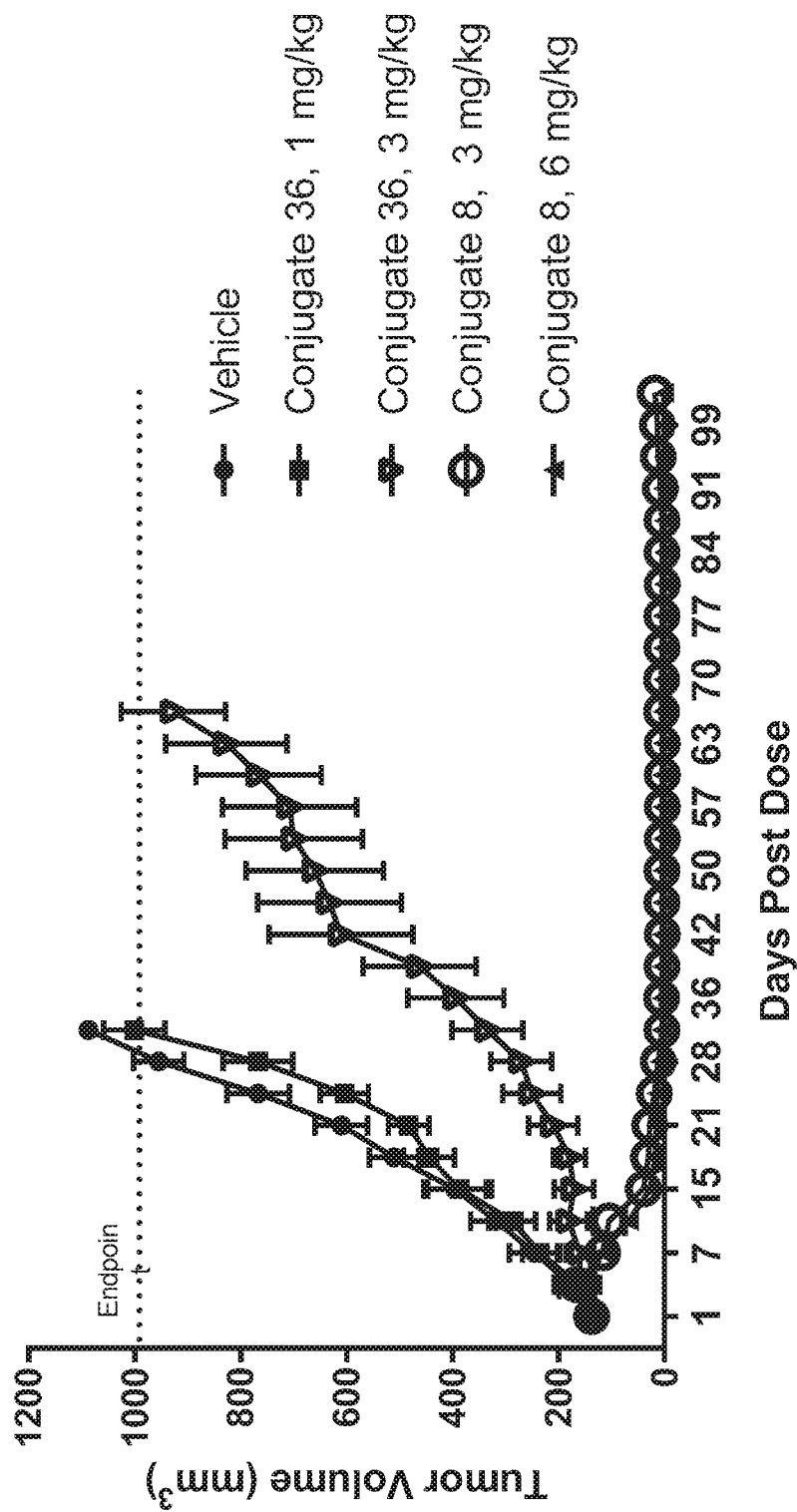
FIG. 2 is a plot of tumor volume vs. time, showing the tumor response in mice inoculated subcutaneously with Calu-3 cells (n=10 for each group) after IV administration as a single dose on day 1 of vehicle or trastuzumab-PBD conjugates: Example 2, Conjugate 8, at 3 mg/kg and 6 mg/kg; and Example 9, Conjugate 36, at 1 mg/kg and 3 mg/kg.

FIG. 2 provides the results for the tumor response in mice subcutaneously implanted with Calu-3 cells (n=10 for each group) after IV administration of vehicle; and the Trastuzumab-drug conjugates: Example 2, Conjugate 8 at 3 mg/kg and 6 mg/kg each as a single dose at day 1; and Example 8, Conjugate 36 at 1 mg/kg and 3 mg/kg each as a single dose at day 1. The results show that on day 102, Conjugate 8 at 3 mg/kg resulted in 1 partial response, 9 complete responses and 9 tumor-free survivals; and at 6 mg/kg resulted in 10 complete responses and 10 tumor-free survivals; and Conjugate 36 at 3 mg/kg in 1 partial response.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A conjugate of Formula (II):

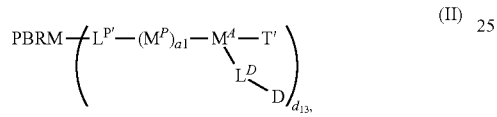

or a pharmaceutically acceptable salt or solvate thereof, wherein:
PBRM denotes a protein based recognition-molecule;
each occurrence of D is independently a PBD drug moiety of Formula (IV),

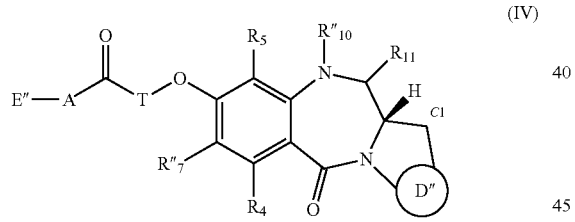

a tautomer, pharmaceutically acceptable salt or solvate thereof, or a pharmaceutically acceptable salt or solvate of the tautomer, wherein:
E" is a direct or indirect linkage to the PBRM (e.g., antibody or antibody fragment), E or

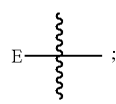

in which

denotes direct or indirect linkage to the PBRM via a functional group of E;
D" is D' or

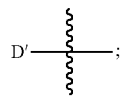

in which

denotes direct or indirect linkage to the PBRM via a functional group of D';
R"$_7$ is a direct or indirect linkage to the PBRM (e.g., antibody or antibody fragment), R$_7$ or

in which denotes direct or indirect linkage to the PBRM via a functional group of R$_7$;
R"$_{10}$ is a direct or indirect linkage to the PBRM, R$_{10}$ or in which

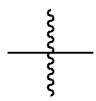

denotes direct or indirect linkage the PBRM via a functional group of $R_{10}$; and wherein the PBD drug moiety (D) is directly or indirectly linked to the PBRM (e.g., antibody or antibody fragment) via a functional group of one of E″, D″, R″$_7$, and R″$_{10}$;

in which D′ is D1, D2, D3, or D4:

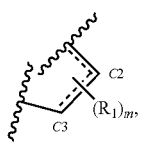
(D1)

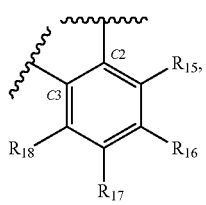
(D2)

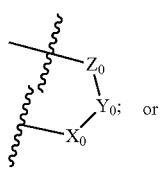
(D3)

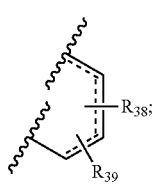
(D4)

wherein the dotted line between C2 and C3 or between C2 and C1 in D1 or the dotted line in D4 indicates the presence of a single or double bond; and m is 0, 1 or 2;

when D′ is D1, the dotted line between C2 and C3 is a double bond, and m is 1, then $R_1$ is:

(i) $C_{6-10}$ aryl group, optionally substituted by one or more substituents selected from —OH, halo, —NO$_2$, —CN, —N$_3$, —OR$_2$, —COOH, —COOR$_2$, —COR$_2$, —OCONR$_{13}$R$_{14}$, $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—OR$_a$, 3- to 14-membered heterocloalkyl, 5- to 12-membered heteroaryl, bis-oxy-$C_{1-3}$ alkylene, —NR$_{13}$R$_{14}$, —S(=O)$_2$R$_{12}$, —S(=O)$_2$NR$_{13}$R$_{14}$, —SR$_{12}$, —SO$_x$M, —OSO$_x$M, —NR$_9$COR$_{19}$, —NH(C=NH)NH$_2$;

(ii) $C_{1-5}$ alkyl;

(iii) $C_{3-6}$ cycloalkyl;

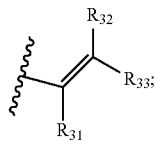
(iv)

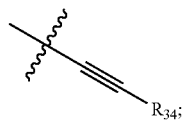
(vi)

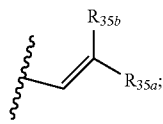
(vii)

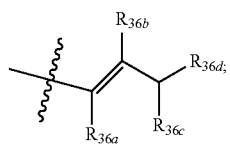
(viii)

or (viii) halo;

when D′ is D1, the dotted line between C2 and C3 is a single bond, and m is 1, then $R_1$ is:

(i) —OH, =O, =CH$_2$, —CN, —R$_2$, —OR$_2$, halo, =CH—R$_6$, =C(R$_6$)$_2$, —O—SO$_2$R$_2$, —CO$_2$R$_2$, —COR$_2$, —CHO, or —COOH; or

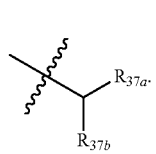
(ii)

when D′ is D1 and m is 2, then each $R_1$ independently is halo and either both $R_1$ are attached to the same carbon atom or one is attached to C2 and the other is attached to C3;

T is $C_{1-10}$ alkylene linker;

A is

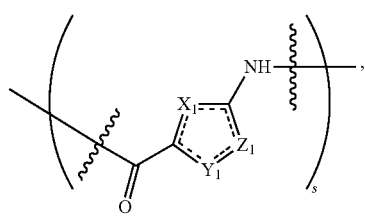

wherein the —NH group of A is connected to the —C(O)-T- moiety of Formula (IV) and the C=O moiety of A is connected to E; and each independently is

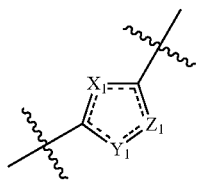

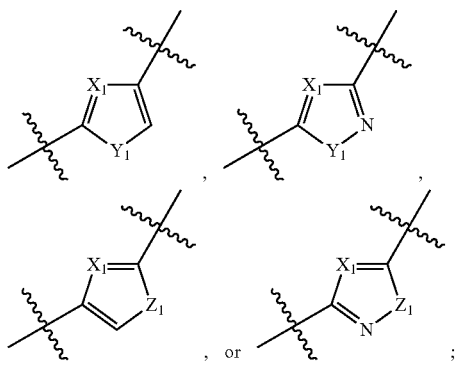
, , , or ;

E is E1, E2, E3, E4, —OH, —NH—(C$_{1-6}$ alkylene)-R$_{13a}$, —O—(CH$_2$)$_3$—NH$_2$, —O—CH(CH$_3$)—(CH$_2$)$_2$—NH$_2$ or —NH—(CH$_2$)$_3$—O—C(=O)—CH(CH$_3$)—NH$_2$:

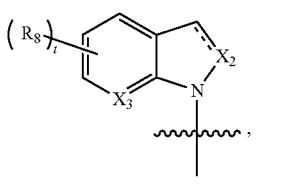 (E1)

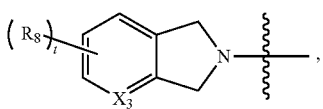 (E2)

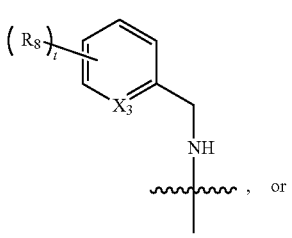 (E3)

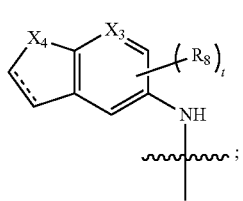 (E4)

wherein the dotted line in E1 or E4 indicates the presence of a single or double bond;

each occurrence of R$_2$ and R$_3$ independently is an optionally substituted C$_{1-8}$ alkyl, optionally substituted C$_{2-8}$ alkenyl, optionally substituted C$_{2-8}$ alkynyl, optionally substituted C$_{3-8}$ cycloalkyl, optionally substituted 3- to 20-membered heterocycloalkyl, optionally substituted C$_{6-20}$ aryl or optionally substituted 5- to 20-membered heteroaryl, and, optionally in relation to the group NR$_2$R$_3$, R$_2$ and R$_3$ together with the nitrogen atom to which they are attached form an optionally substituted 4-, 5-, 6- or 7-membered heterocycloalkyl or an optionally substituted 5- or 6-membered heteroaryl;

R$_4$, R$_5$ and R$_7$ are each independently —H, —R, —OH, —SH, —NHR$_2$—, —NR$_2$R$_3$, —NO$_2$, —SnMe$_3$, halo or a polyethylene glycol unit —(OCH$_2$CH$_2$)$_r$—OR$_a$; or R$_4$ and R$_7$ together form bis-oxy-C$_{1-3}$ alkylene;

each R$_6$ independently is —H, —R$_2$, —CO$_2$R$_2$, —COR$_2$, —CHO, —CO$_2$H, or halo;

each R$_8$ independently is —OH, halo, —NO$_2$, —CN, —N, —COOH, —COOR$_2$, —COR$_2$, —OCONR$_{13}$R$_{14}$, —CONR$_{13}$R$_{14}$, —CO—NH—(C$_{1-6}$ alkylene)-R$_{13a}$, C$_{1-10}$ alkyl, C$_{3-10}$ cycloalkyl, C$_{2-10}$ alkenyl, C$_{2-10}$ alkynyl, a polyethylene glycol unit —(OCH$_2$CH$_2$)$_r$—OR$_a$, 3- to 14-membered heterocycloalkyl, 5- to 12-membered heteroaryl, —S(=O)$_2$R$_{12}$, —S(=O)$_2$NR$_{13}$R$_{14}$, —SO$_x$M, —OSO$_x$M, —NR$_9$COR$_{19}$, —NH(C=NH)NH$_2$, —R$_{20}$—R$_{21}$—NR$_{13}$R$_{14}$, —R$_{20}$—R$_{21}$—NH—P(O)(OH)—(OCH$_2$CH$_2$)$_{n9}$—OCH$_3$, or —O—P(O)(OH)—(OCH$_2$CH$_2$)$_{n9}$—OCH$_3$;

each R$_9$ independently is C$_{1-10}$ alkyl, C$_{3-10}$ cycloalkyl, C$_{2-10}$ alkenyl or C$_{2-10}$ alkynyl;

R$^{10}$ is —H or a nitrogen protecting group;

R$^{11}$ is -QR$^Q$ or -SO$_x$M, or R$^{10}$ and R$^{11}$ taken together with the nitrogen atom and carbon atom to which they are respectively attached, form a N=C double bond;

each R$_{12}$ independently is C$_{1-7}$ alkyl, 3- to 20-membered heterocycloalkyl, 5- to 20-membered heteroaryl, or C$_{6-20}$ aryl;

each occurrence of R$_{13}$ and R$_{14}$ are each independently H, C$_{1-10}$ alkyl, 3- to 20-membered heterocycloalkyl, 5- to 20-membered heteroaryl, or C6-20 aryl;

each R$_{13a}$ independently is —OH or —NR$_{13}$R$_{14}$;

R$_{15}$, R$_{16}$, R$_{17}$ and R$_{18}$ are each independently —H, —OH, halo, —NO$_2$, —CN, —N$_3$, —OR$_2$, —COOH, —COOR$_2$, —COR$_2$, —OCONR$_{13}$R$_{14}$, C$_{1-10}$ alkyl, C$_{3-10}$ cycloalkyl, C$_{2-10}$ alkenyl, C$_{2-10}$ alkynyl, a polyethylene glycol unit —(OCH$_2$CH$_2$)$_r$—OR$_a$, 3-14 membered heterocycloalkyl, 5- to 12-membered heteroaryl, —NR$_{13}$R$_{14}$, —S(=O)$_2$R$_{12}$, —S(=O)$_2$NR$_{13}$R$_{14}$, —SR$_{12}$, —SO$_x$M, —OSO$_x$M, —NR$_9$COR$_{19}$ or —NH(C=NH)NH$_2$;

each R$_{19}$ independently is C$_{1-10}$ alkyl, C$_{3-10}$ cycloalkyl, C$_{2-10}$ alkenyl or C$_{2-10}$ alkynyl;

each R$_{20}$ independently is a bond, C$_{6-10}$ arylene, 3-14 membered heterocycloalkylene or 5- to 12-membered heteroarylene;

each R$_{21}$ independently is a bond or C$_{1-10}$ alkylene;

R$_{31}$, R$_{32}$ and R$_{33}$ are each independently —H, C$_{1-3}$ alkyl, C$_{2-3}$ alkenyl, C$_{2-3}$ alkynyl or cyclopropyl, wherein the total number of carbon atoms in the R$_1$ group is no more than 5;

R$_{34}$ is —H, C$_{1-3}$ alkyl, C$_{2-3}$ alkenyl, C$_{2-3}$ alkynyl, cyclopropyl, or phenyl wherein the phenyl is optionally substituted by one or more of halo, methyl, methoxy, pyridyl or thiophenyl;

one of $R_{35a}$ and $R_{35b}$ is —H and the other is a phenyl group optionally substituted with one or more of halo, methyl, methoxy, pyridyl or thiophenyl;

$R_{36a}$, $R_{36b}$, $R_{36c}$ are each independently —H or $C_{1-2}$ alkyl;

$R_{36d}$ is —OH, —SH, —COOH, —C(O)H, —N=C=O, —NHNH$_2$, —CONHNH$_2$,

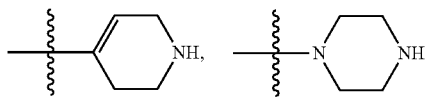

NHR$^N$, wherein R$^N$ is —H or $C_{1-4}$ alkyl;

$X_4$ is NH, O or S;

$X_5$ is NH, O or S;

Q is O, S or NH;

when Q is S or NH, then R$^Q$ is —H or optionally substituted $C_{1-2}$ alkyl; or when Q is O, then R$^Q$ is —H or optionally substituted $C_{1-2}$ alkyl, —SO$_x$M, —PO$_3$M, —(CH$_2$—CH$_2$—O)$_{n9}$CH$_3$, —(CH$_2$—CH$_2$O)$_{n9}$—(CH$_2$)$_2$—R$_{40}$, —C(O)—(CH$_2$—CH$_2$—O)$_{n9}$CH$_3$, —C(O)O—(CH$_2$—CH$_2$—O)$_{n9}$CH$_3$, —C(O)NH—)—(CH$_2$—CH$_2$—O)$_{n9}$CH$_3$, —(CH$_2$)$_n$—NH—C(O)—CH$_2$—O—CH$_2$—C(O)—NH—(CH$_2$—CH$_2$—O)$_{n9}$CH$_3$, —(CH$_2$)$_n$—NH—C(O)—(CH$_2$)$_n$—(CH$_2$—CH$_2$—O)$_{n9}$CH$_3$, a sugar moiety,

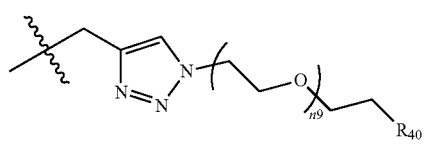

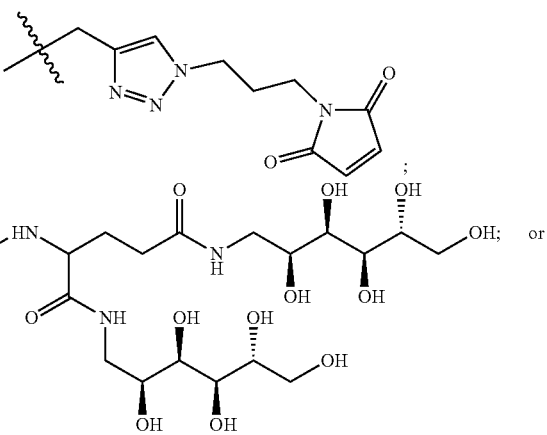

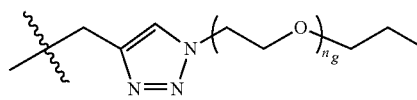

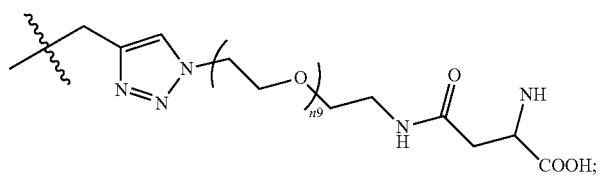

$R_{37a}$ and $R_{37b}$ are each independently is —H, —F, $C_{1-4}$ alkyl, $C_{2-3}$ alkenyl, wherein the alkyl and alkenyl groups are optionally substituted by $C_{1-4}$ alkyl amido or $C_{1-4}$ alkyl ester; or when one of $R_{37a}$ and $R_{37b}$ is —H, the other is —CN or a $C_{1-4}$ alkyl ester;

$R_{38}$ and $R_{39}$ are each independently H, $R_{13}$, =CH$_2$, =CH—(CH$_2$)$_{s1}$—CH$_3$, =O, (CH$_2$)$_{s1}$—OR$_{13}$, (CH$_2$)$_{s1}$—CO$_2$R$_{13}$, (CH$_2$)$_{s1}$—NR$_{13}$R$_{14}$, O—(CH$_2$)$_2$—NR$_{13}$R$_{14}$, NH—C(O)—R$_{13}$, O—(CH$_2$)s-NH—C(O)—R$_{13}$, O—(CH$_2$)s-C(O)NHR$_{13}$, (CH$_2$)$_{s1}$OS(=O)$_2$R$_{13}$, O—SO$_2$R$_{13}$, (CH$_2$)$_{s1}$—C(O)R$_{13}$ and (CH$_2$)$_{s1}$—C(O)NR$_{13}$R$_{14}$;

$X_0$ is CH$_2$, NR$_6$, C=O, BH, SO or SO$_2$;

$Y_0$ is O, CH$_2$, NR$_6$ or S;

$Z_0$ is absent or (CH$_2$)$_n$;

each $X_1$ independently is CR$_b$, or N;

each $Y_1$ independently is CH, NR$_a$, O or S;

each $Z_1$ independently is CH, NR$_a$, O or S;

each $R_a$ independently is H or $C_{1-4}$ alkyl;

each $R_b$ independently is H, OH, $C_{1-4}$ alkyl, or $C_{1-4}$ alkoxyl;

$X_2$ is CH, CH$_2$ or N;

$X_3$ is CH or N;

each M independently is H or a monovalent pharmaceutically acceptable cation;

n is 1, 2 or 3;

$n_9$ is 1, 2, 3, 4, 5, 6, 8, 12 or 24; each r independently is an integer from 1 to 200;

s is 1, 2, 3, 4, 5 or 6;

$s_1$ is 0, 1, 2, 3, 4, 5 or 6;

t is 0, 1, or 2;

$R_{40}$ is —SO$_3$H, —COOH, —C(O)NH(CH$_2$)$_2$SO$_3$H or —C(O)NH(CH$_2$)$_2$COOH;

each x independently is 2 or 3;

L$^{P'}$ is a divalent linker moiety connecting the PBRM to M$^P$; of which the corresponding monovalent moiety L$^P$ contains a functional group W$^P$ that is capable of forming a covalent bond with a functional group of the PBRM;

M$^P$ is a Stretcher unit;

$a_1$ is an integer from 0 to 1;

M$^A$ comprises a peptide moiety that contains at least two amino acids;

T' is a hydrophilic group and the

between T' and $M^A$ denotes direct or indirect attachment of T' and $M^A$;

each occurrence of $L^D$ is independently a divalent linker moiety connecting D to $M^A$ and comprises at least one cleavable bond such that when the bond is broken, D is released in an active form for its intended therapeutic effect; and $d_{13}$ is an integer from 1 to 20.

2. The conjugate of claim 1, wherein $L^P$, when not connected to PBRM, comprises a terminal group $W^P$, in which each $W^P$ independently is:

(1)

—SH;

(2)

—$SR^{1A}$;

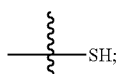

(3)

—$N_3$;

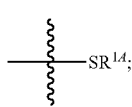

(4)

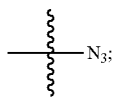

(5)

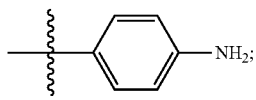

(6)

—NH $R^{1J}$;

(7)

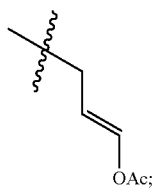

NHNH$_2$;

(8)

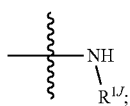

—O—NH$_2$;

(9)

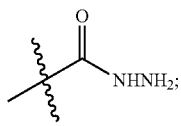

SH

NH $R^{1J}$;

(10)

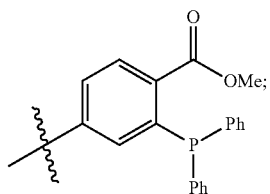

(11)

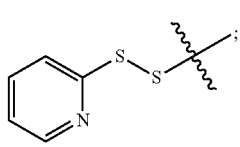

(12)

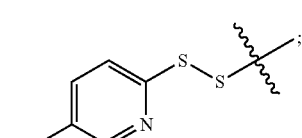

(13)

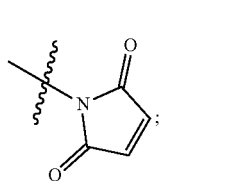

(14)

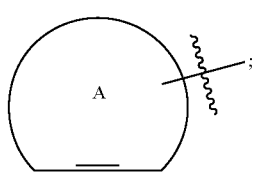

(15)

HO— 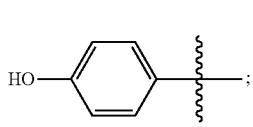 ;

(16)

$R^{2J}$ 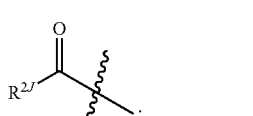 ;

(17)

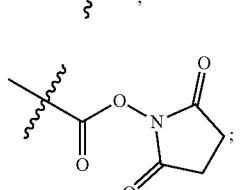

(18)

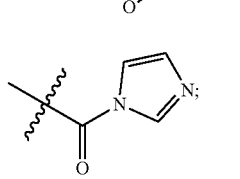

(19)

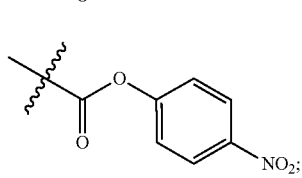

NO$_2$;

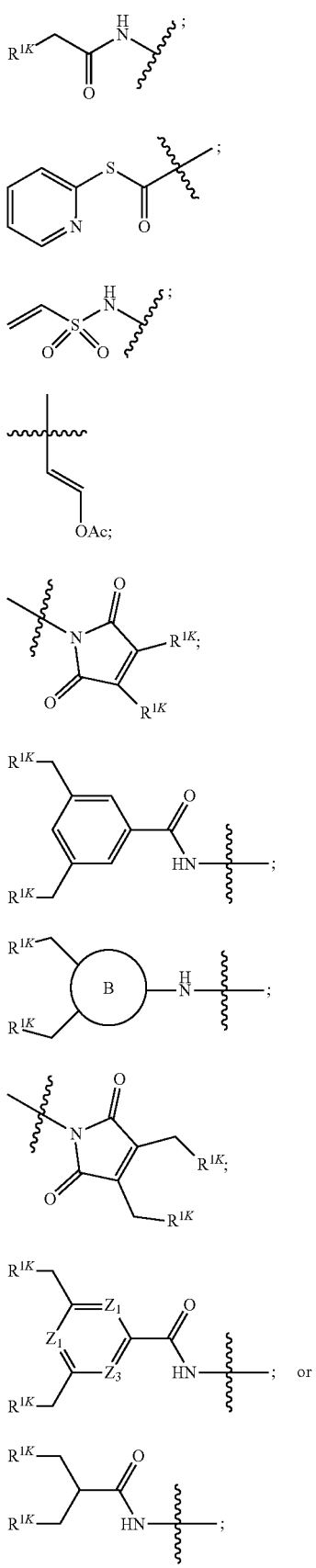
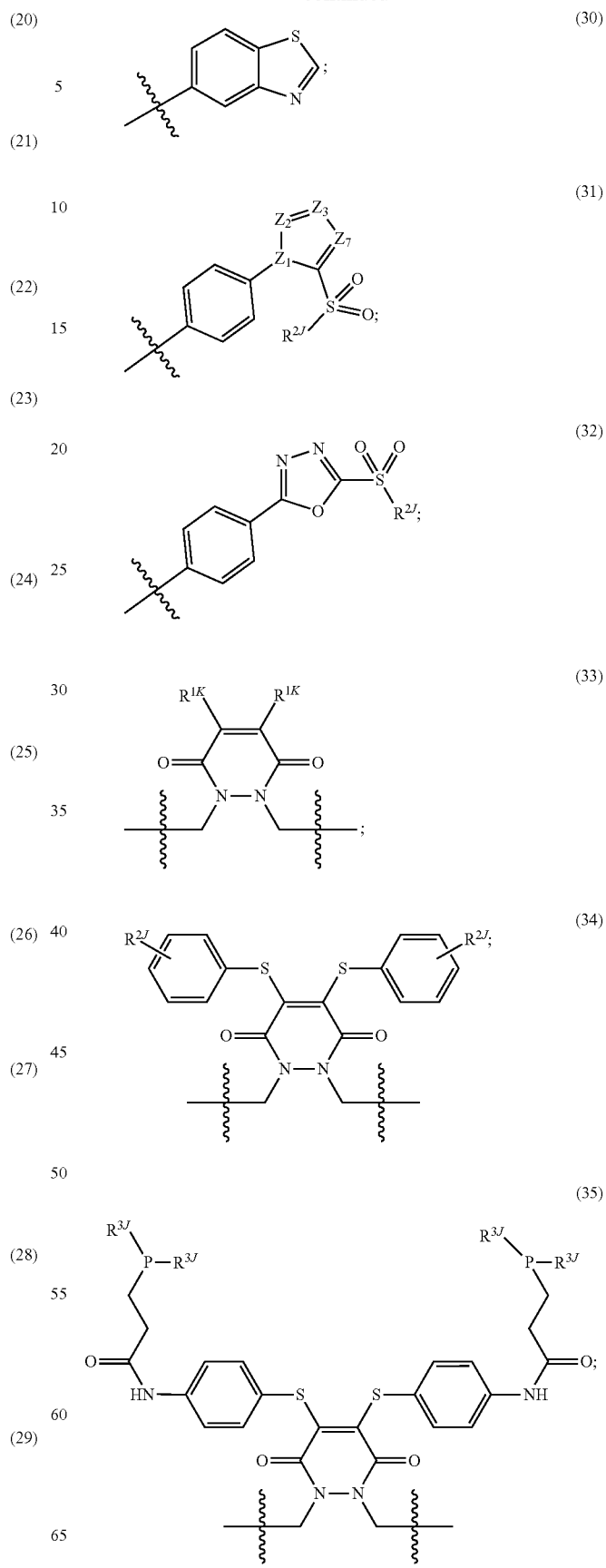

-continued

(36) 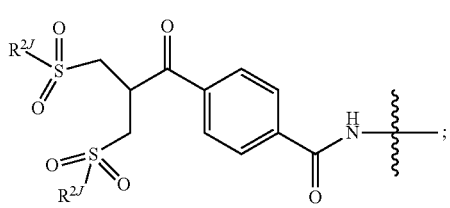

(37) 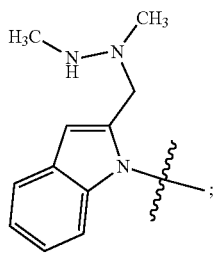

(38) 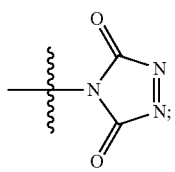

(39) 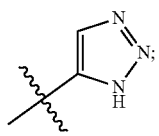

(40) 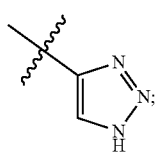

(41) 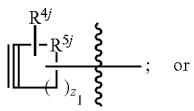 ; or

(43) 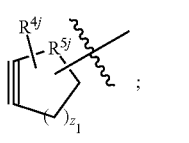 ;

wherein
$R^{1K}$ is a leaving group;
$R^{1A}$ is a sulfur protecting group;
ring A is cycloalkyl or heterocycloalkyl;
ring B is cycloalkyl, heterocycloalkyl, aryl, or heteroaryl;
$R^{1J}$ is hydrogen or an aliphatic, heteroaliphatic, carbocyclic, or heterocycloalkyl moiety;
$R^{2J}$ is hydrogen, an aliphatic, aryl, heteroaliphatic, or carbocyclic moiety;
$R^{3J}$ is $C_{1-6}$ alkyl;
$Z_1$, $Z_2$, $Z_3$ and $Z_7$ are each independently a carbon or nitrogen atom;
$R^{4j}$ is hydrogen, halogen, OR, —$NO_2$, —CN, —$S(O)_2R$, $C_{1-24}$ alkyl (e.g., $C_{1-6}$ alkyl), or 6-24 membered aryl or heteroaryl, wherein the C1-24 alkyl (e.g., $C_{1-6}$ alkyl), or 6-24 membered aryl or heteroaryl, is optionally substituted with one or more aryl or heteroaryl; or two $R^{4j}$ together form an annelated cycloalkyl, heterocycloalkyl, aryl, or heteroaryl; R is hydrogen, alkyl, heteroalkyl, cycloalkyl, or heterocycloalkyl R is hydrogen or an aliphatic, heteroaliphatic, carbocyclic, or heterocycloalkyl moiety;

$R^{5j}$ is $C(R^{4j})_2$, O, S or NR; and $z_1$ is an integer 1, 2, 3, 4, 5, 6, 7, 8, 9 or 10.

3. The conjugate of claim 1, wherein $M^P$ is:

(1) 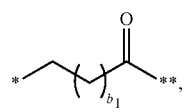

(2) 

(3) 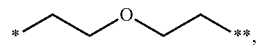

(4) 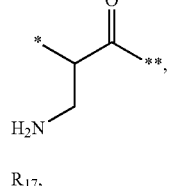

(5) $R_{17}$, (6) 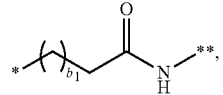

(7) $*$—$CH_2$—$C(O)$—$N(R_{23})$—$R_{17}$—$**$, (8) 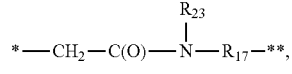

(9) 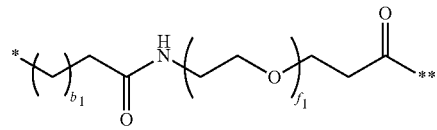

(10) 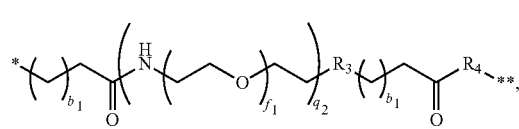

(11) 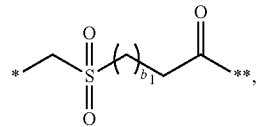

(12) 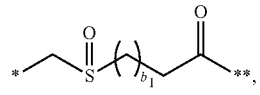, or

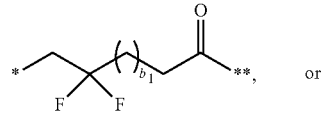

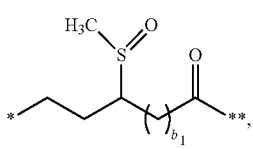

(13)

wherein * denotes attachment to $L^{P'}$ or $L^P$ and ** denotes attachment to $L^M$;

$R_3$, $R_5$, $R_{17}$, and $R_{23}$ are as defined herein;

$R_4$ is a bond or $-NR_5-(CR_{20}R_{21})-C(O)-$;

each $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

each $b_1$ independently is an integer from 0 to 6;

$e_1$ is an integer from 0 to 8, each $f_1$ independently is an integer from 1 to 6; and $g_2$ is an integer from 1 to 4.

4. The conjugate of claim 3, wherein $M^P$, when present, is:

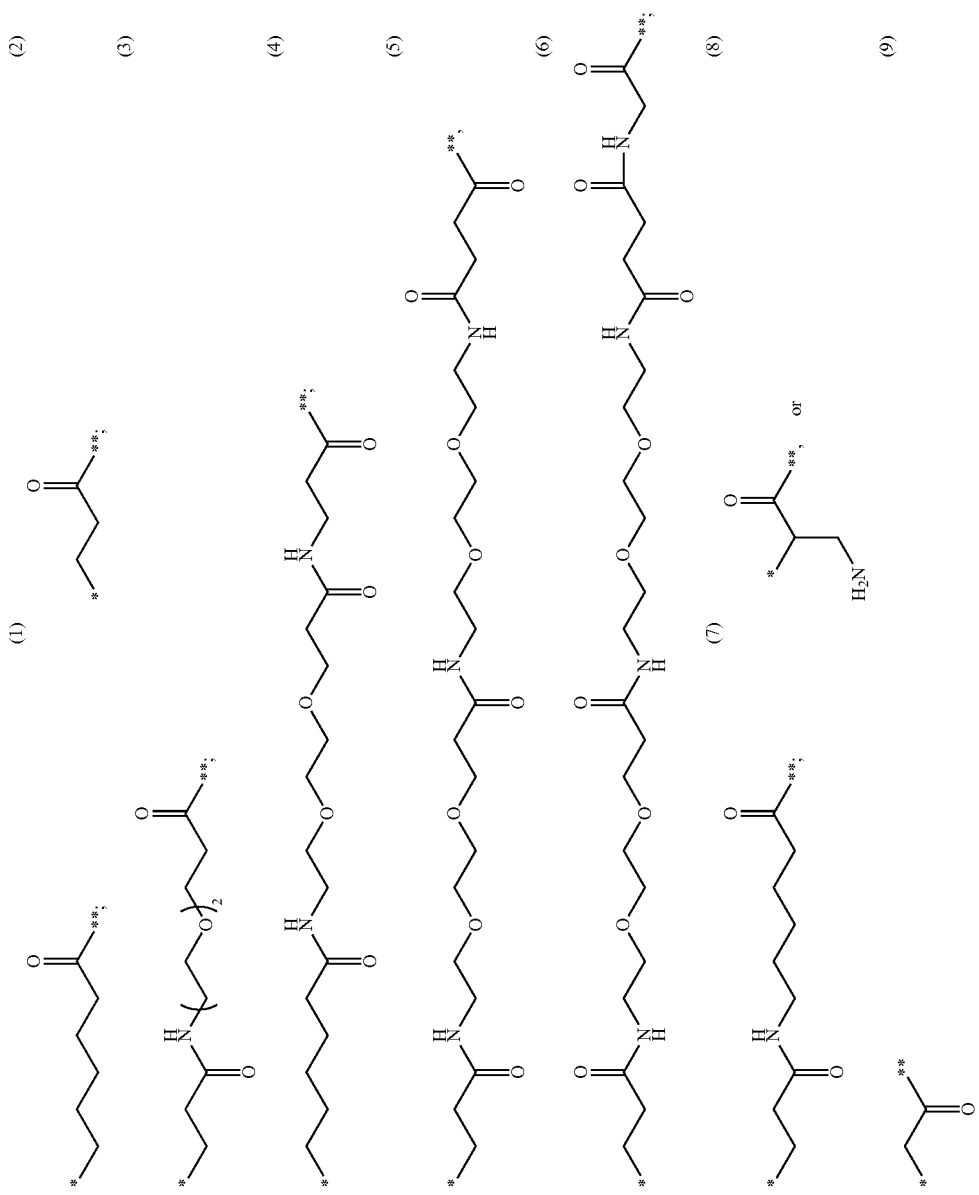

wherein * denotes attachment to $L^{P'}$ or $L^P$ and ** denotes attachment to $L^M$.

5. The conjugate or scaffold of claim 1, wherein $M^A$ comprises a peptide moiety that contains from three to about ten amino acids selected from glycine, serine, glutamic acid, aspartic acid, lysine, cysteine and a combination thereof.

6. The conjugate of claim 1, wherein $L^D$ comprises a peptide of 1 to 12 amino acids, wherein each amino acid is independently selected from alanine, β-alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof.

7. The conjugate of claim 1, wherein the hydrophilic group comprises a polyalcohol or a derivative thereof, a polyether or a derivative thereof, or a combination thereof.

8. The conjugate of claim 1, wherein T' comprises one or more of the following fragments of the formula:

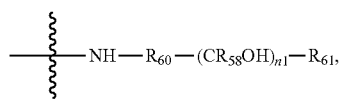

in which n$_1$ is an integer from 0 to about 6;

each $R_{58}$ is independently hydrogen or $C_{1-8}$ alkyl;

$R_{60}$ is a bond, a $C_{1-6}$ alkyl linker, or —CHR$_{59}$— in which $R_{59}$ is H, alkyl, cycloalkyl, or arylalkyl;

$R_{61}$ is CH$_2$OR$_{62}$, COOR$_{62}$, —(CH$_2$)$_{n2}$COOR$_{62}$, or a heterocycloalkyl substituted with one or more hydroxyl;

$R_{62}$ is H or $C_{1-8}$ alkyl; and n$_2$ is an integer from 1 to about 5.

9. The conjugate of claim 8, wherein T' comprises:

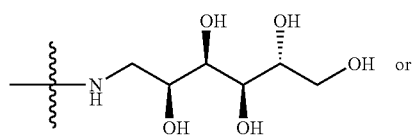

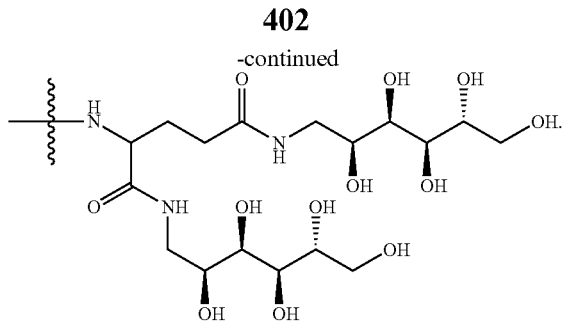

10. The conjugate of claim 1, wherein T' comprises

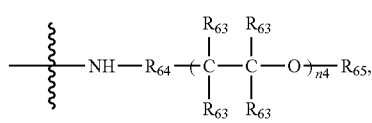

in which n$_4$ is an integer from 1 to about 25;

each $R_{63}$ is independently hydrogen or $C_{1-8}$ alkyl;

$R_{64}$ is a bond or a $C_{1-8}$ alkyl linker;

$R_{65}$ is H, $C_{1-8}$ alkyl, —(CH$_2$)$_{n2}$COOR$_{62}$, or —(CH$_2$)$_{n2}$COR$_{66}$;

$R_{62}$ is H or $C_{1-8}$ alkyl;

$R_{66}$ is

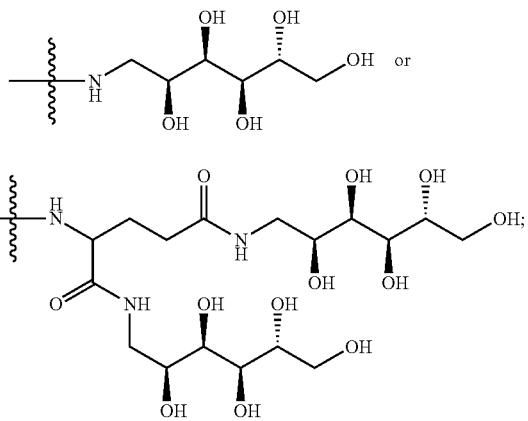

and n$_2$ is an integer from 1 to about 5.

11. The conjugate of claim 1, wherein T' comprises:

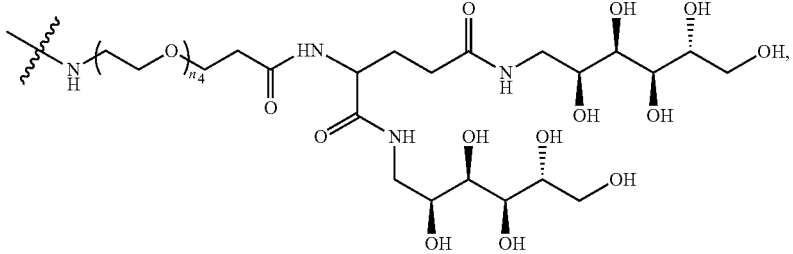

in which n$_4$ is an integer from about 2 to about 20.

12. The conjugate of claim 1, wherein the PBD drug moiety (D) is of any one of formulae (V-1), (V-2), (V-3), (VII), (VII-1), (VII-2), (VII-3), (IX-a), (IX-b), (IX-c), (IX-d), (IX-e), (IX-f), (IX-g), (IX-h), (IX-i), (IX j), (IX-k), (IX-l), (IX-m), (IX-n), (IX-o), (IX-p), (IX-q), or (IX-r):
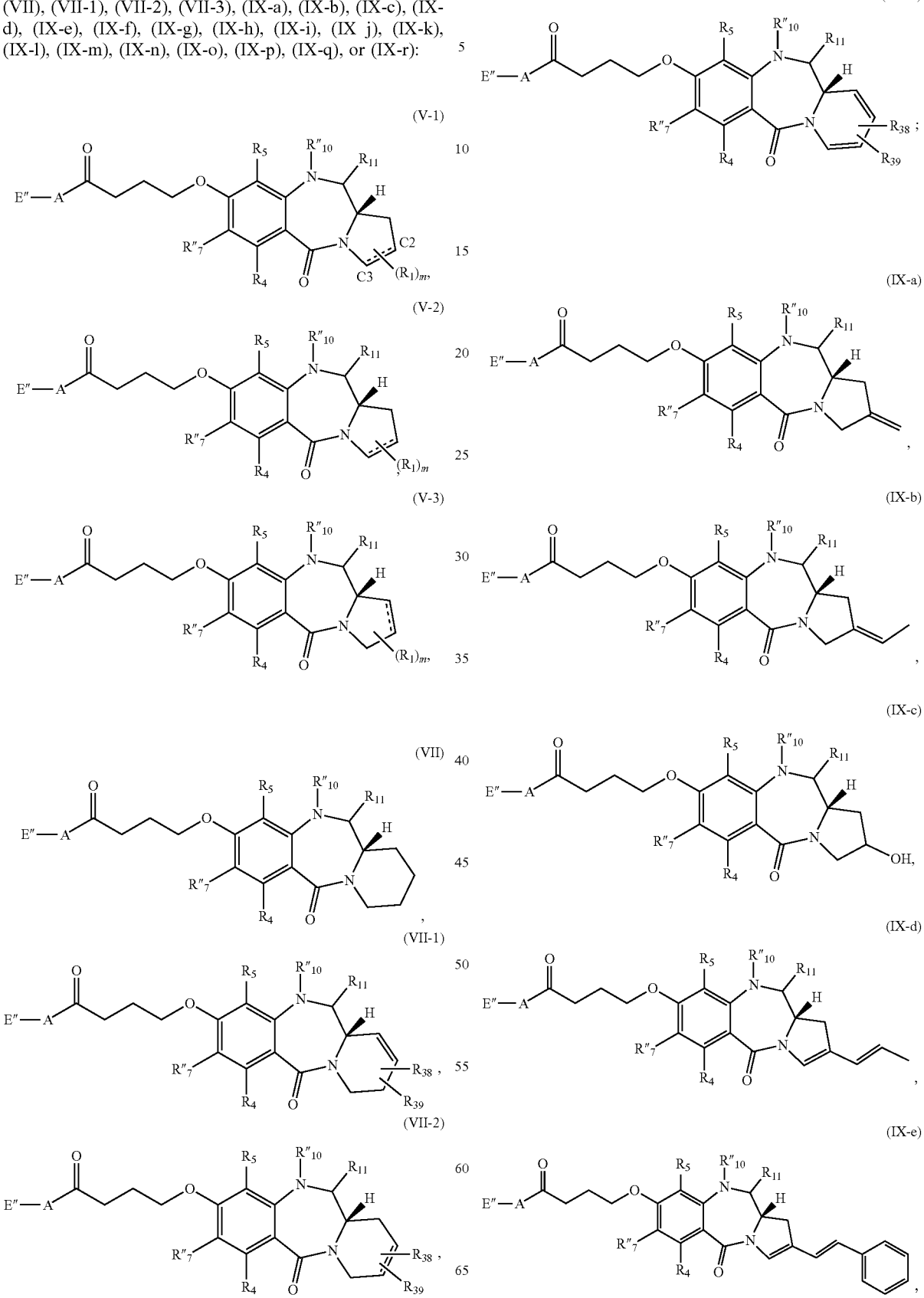

405
-continued
(IX-f)
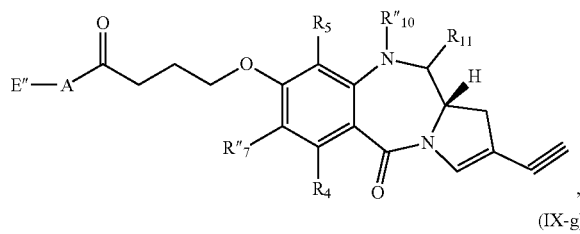
(IX-g)
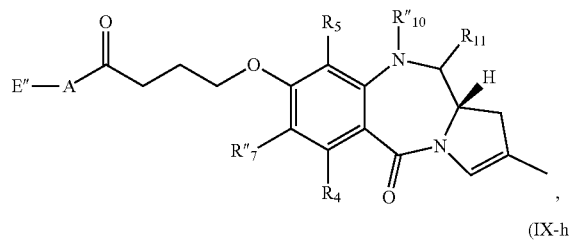
(IX-h)
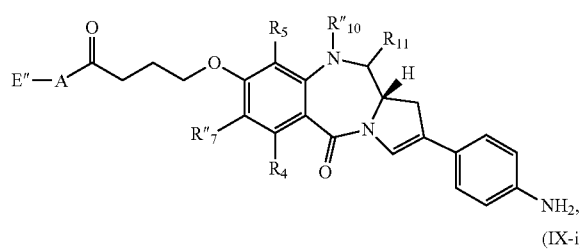
(IX-i)
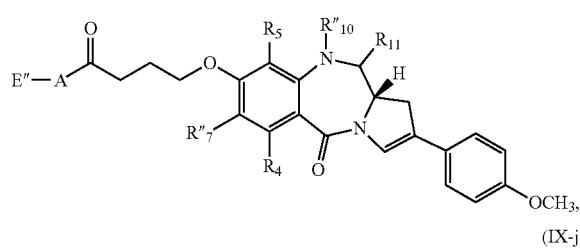
(IX-j)
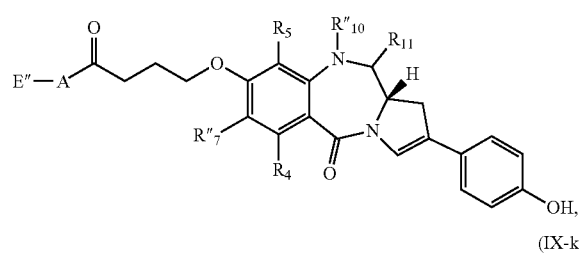
(IX-k)
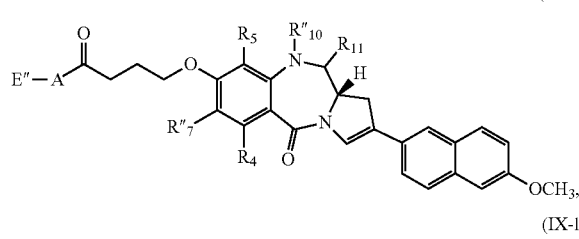
(IX-l)
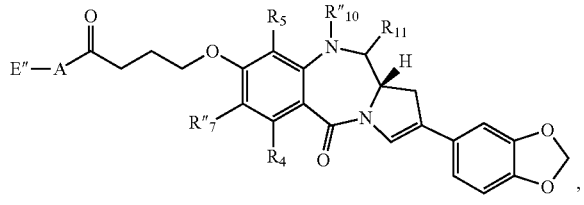
406
-continued
(IX-m)
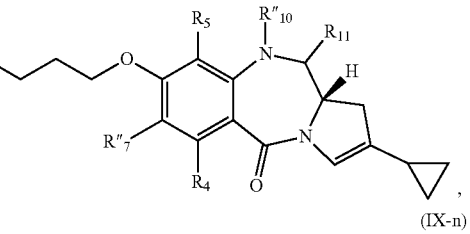
(IX-n)
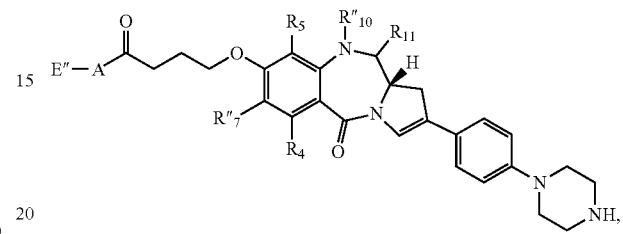
(IX-o)
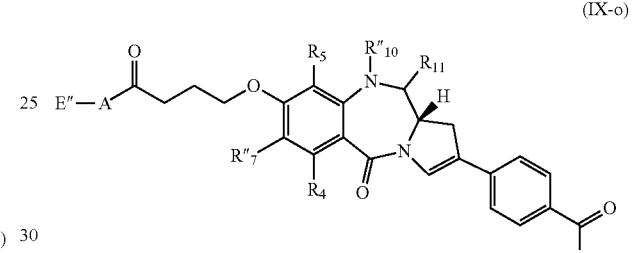
(IX-p)
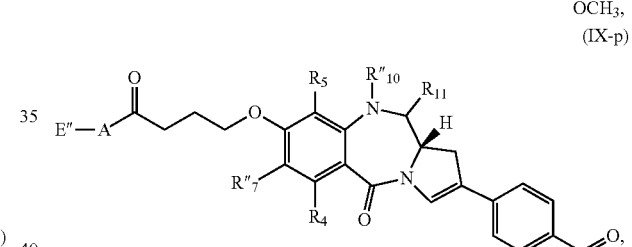
(IX-q)
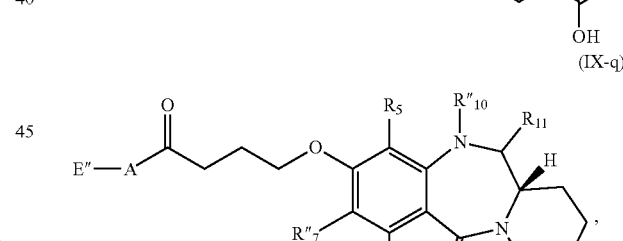
(IX-r)
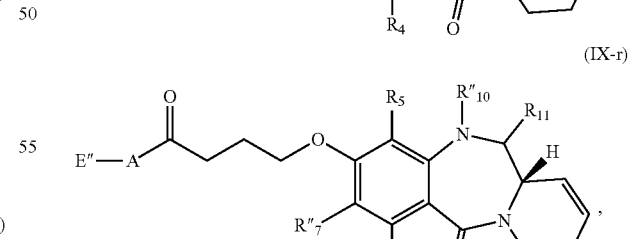
a tautomer, pharmaceutically acceptable salt or solvate thereof, or a pharmaceutically acceptable salt or solvate of the tautomer.
13. The conjugate of claim 1, wherein T is $C_{2-4}$ alkylene linker.

14. The conjugate of claim 1, wherein A is
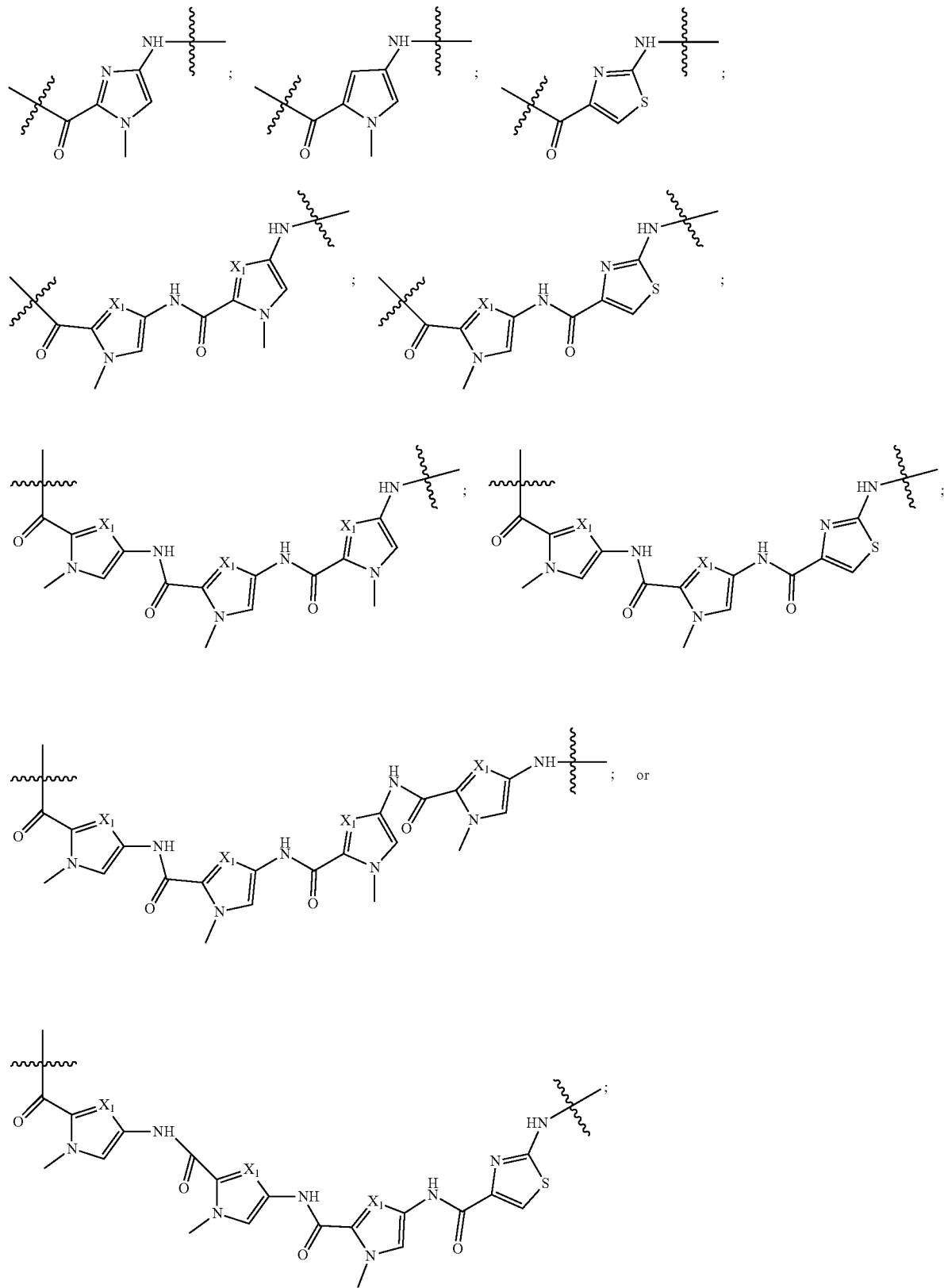
wherein each $X_1$ independently is CH or N.

15. The conjugate of claim 1, wherein E is

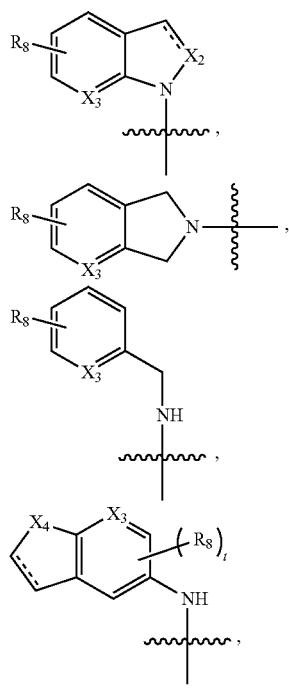

—OH, or —NH—(C$_{1-6}$ alkylene)-OH.

16. The conjugate of claim 1, wherein

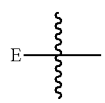

is

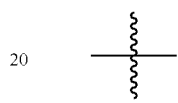

in which

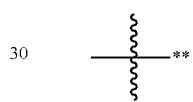

denotes a direct or indirect linkage to the PBRM, L$^C$, or L$^D$, and

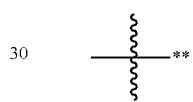

denotes a direct or indirect linkage to a remaining portion of D (e.g., a direct or indirect linkage to A).

17. The conjugate of claim 1, wherein the PBD drug moiety (D), prior to being connected to another portion of the conjugate, corresponds to a compound of any one of Formula (XIIIa) to (XIIIm):

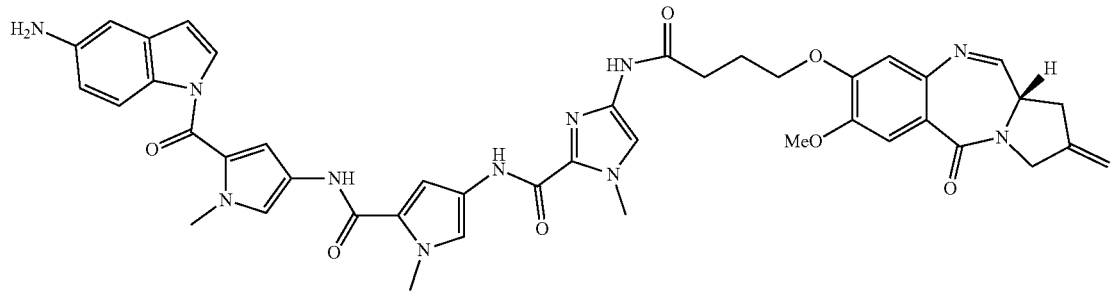
(XIIIa)

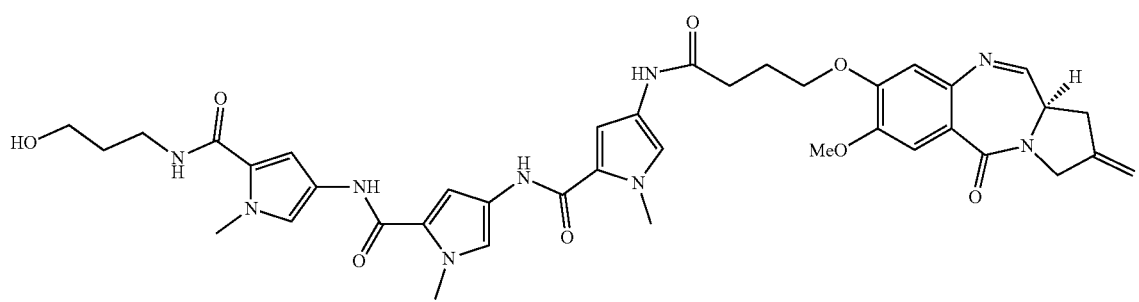
(XIIIb)

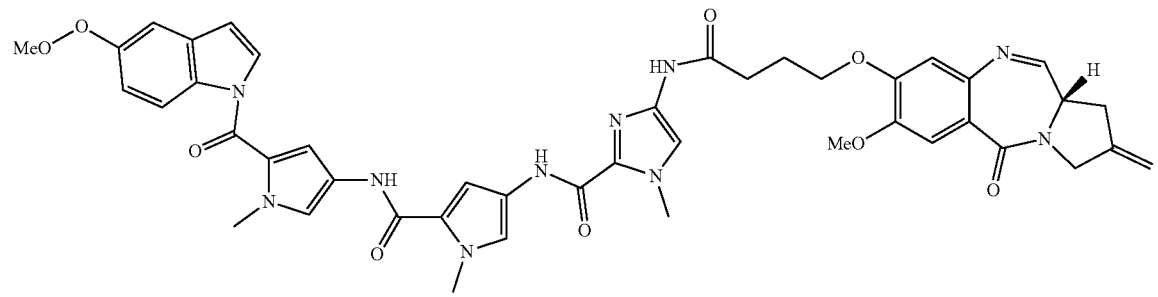
(XIIIc)
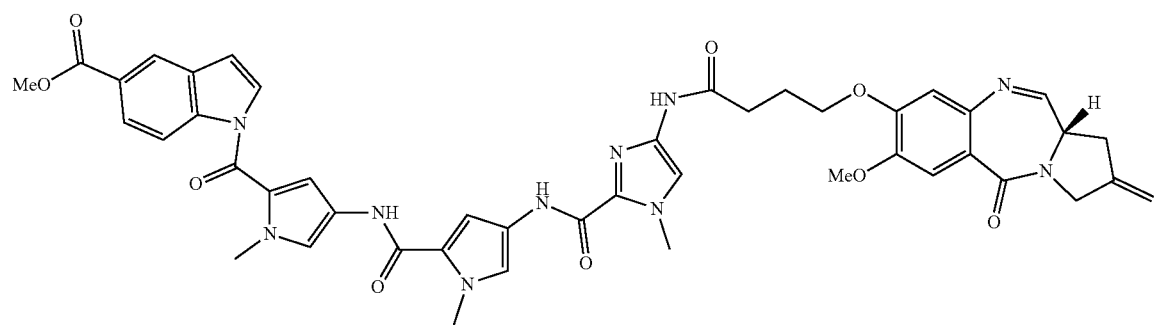
(XIIId)
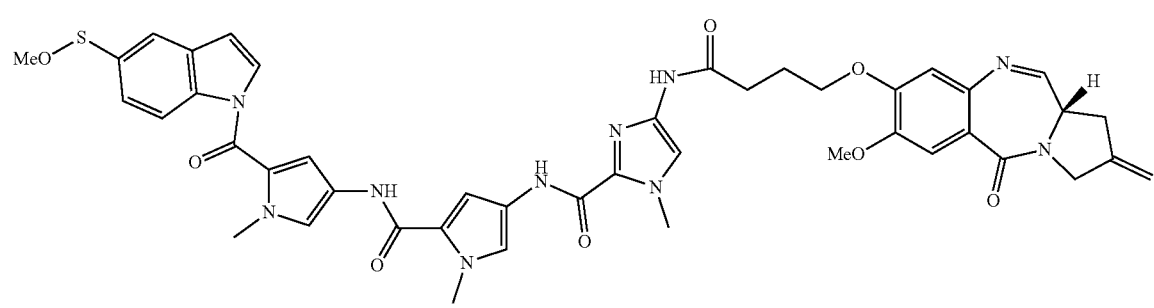
(XIIIe)
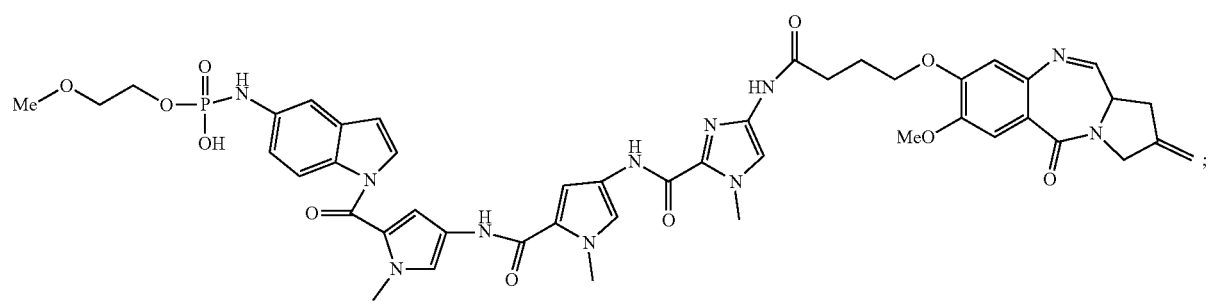
(XIIIf)
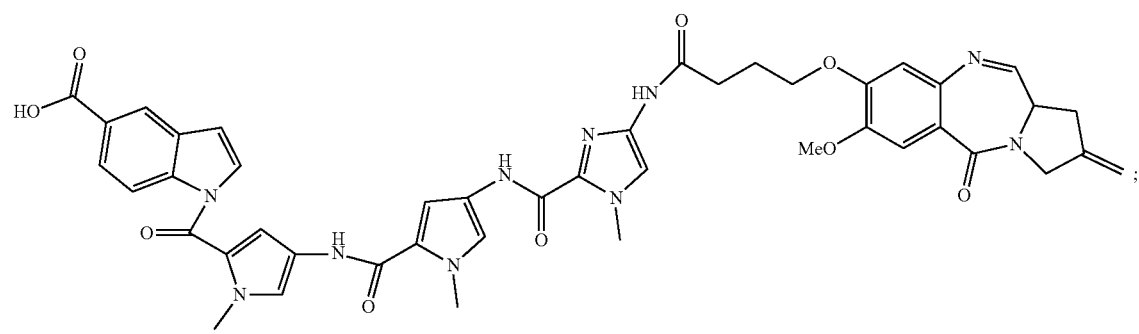
(XIIIg)

-continued
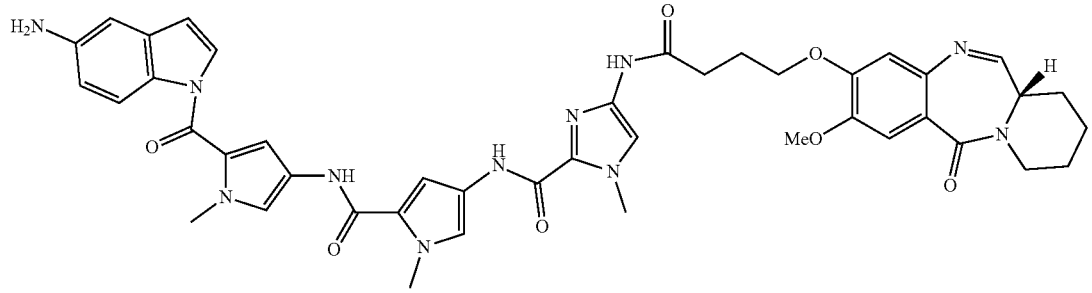
(XIIIh)
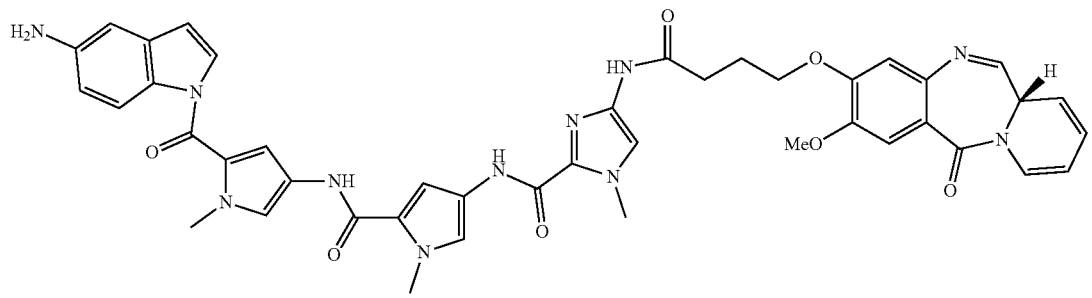
(XIIIi)
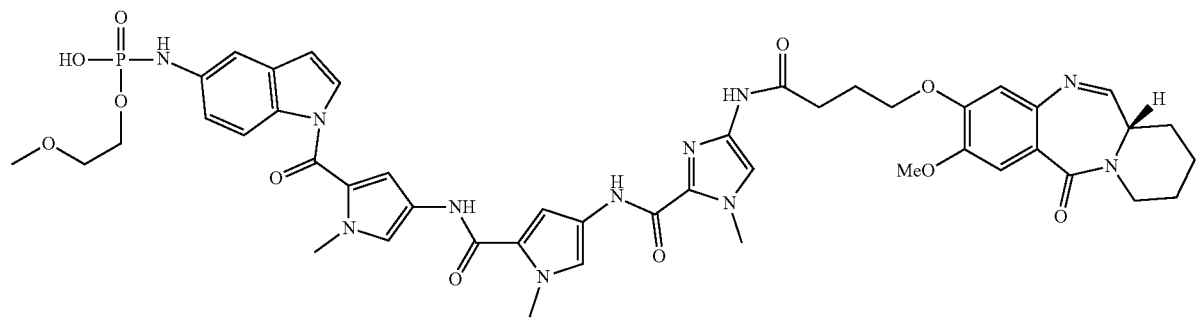
(XIIIj)
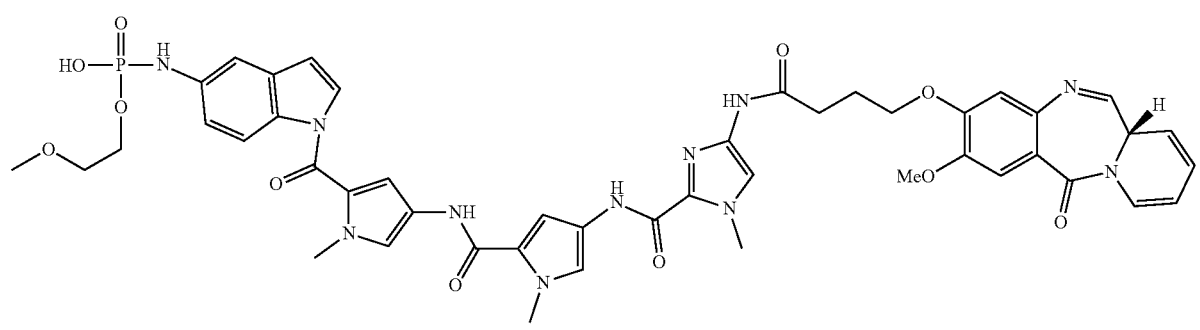
(XIIIk)
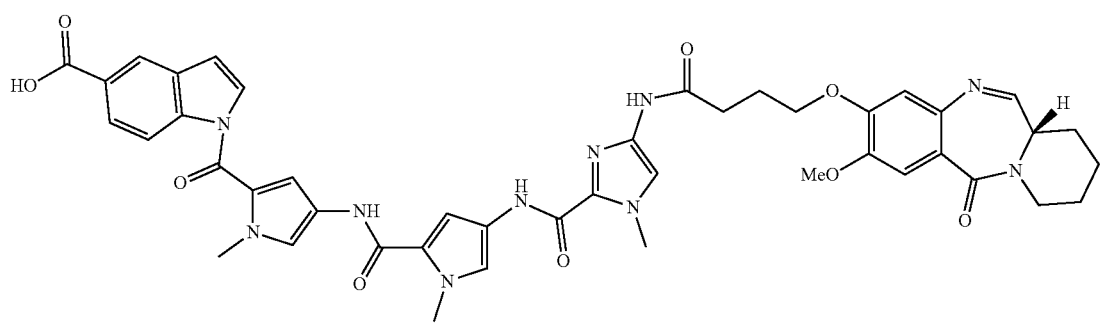
(XIIIl)

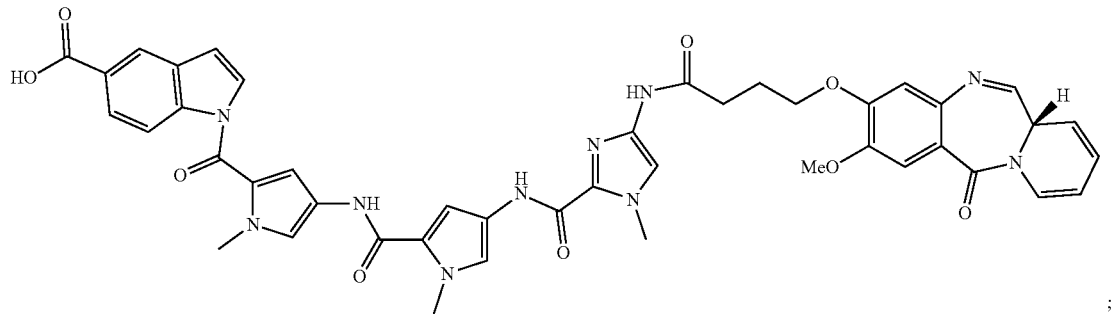
(XIIIm)
a tautomer, pharmaceutically acceptable salt or solvate thereof, or a pharmaceutically acceptable salt or solvate of the tautomer.
18. The conjugate of claim 1, being a conjugate of Formula (XIVa) to (XIVx):

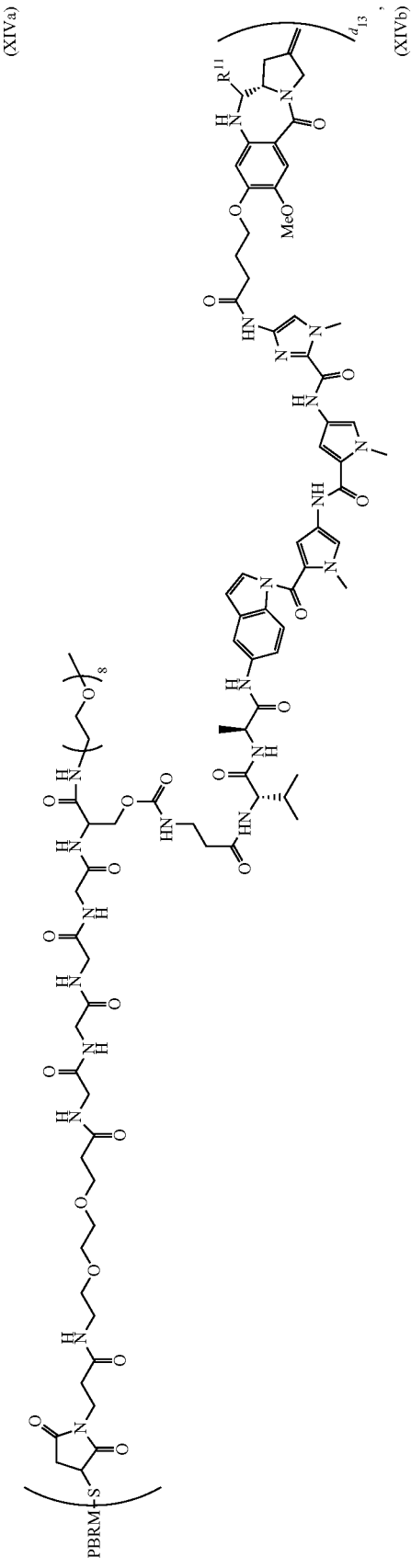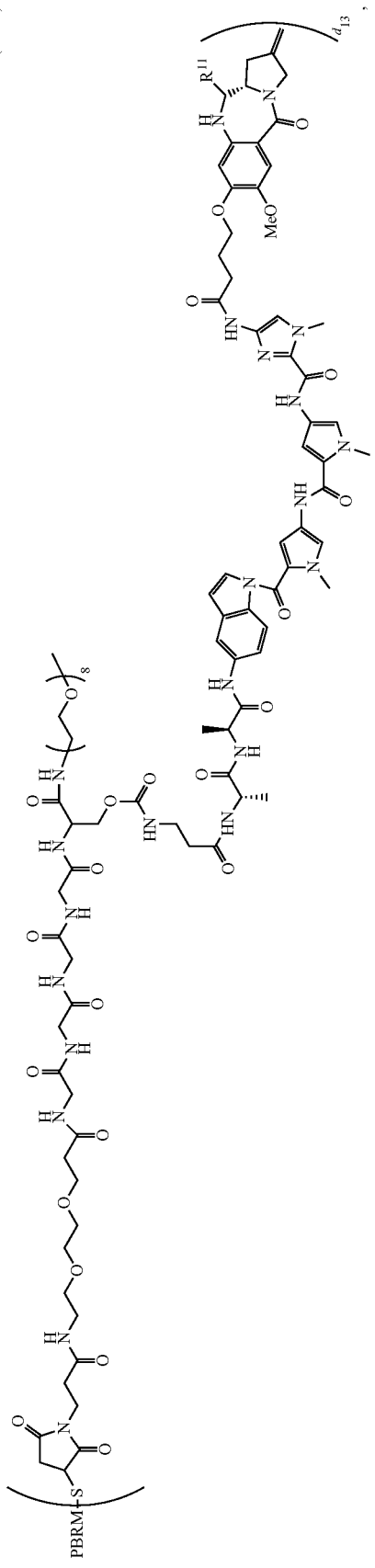

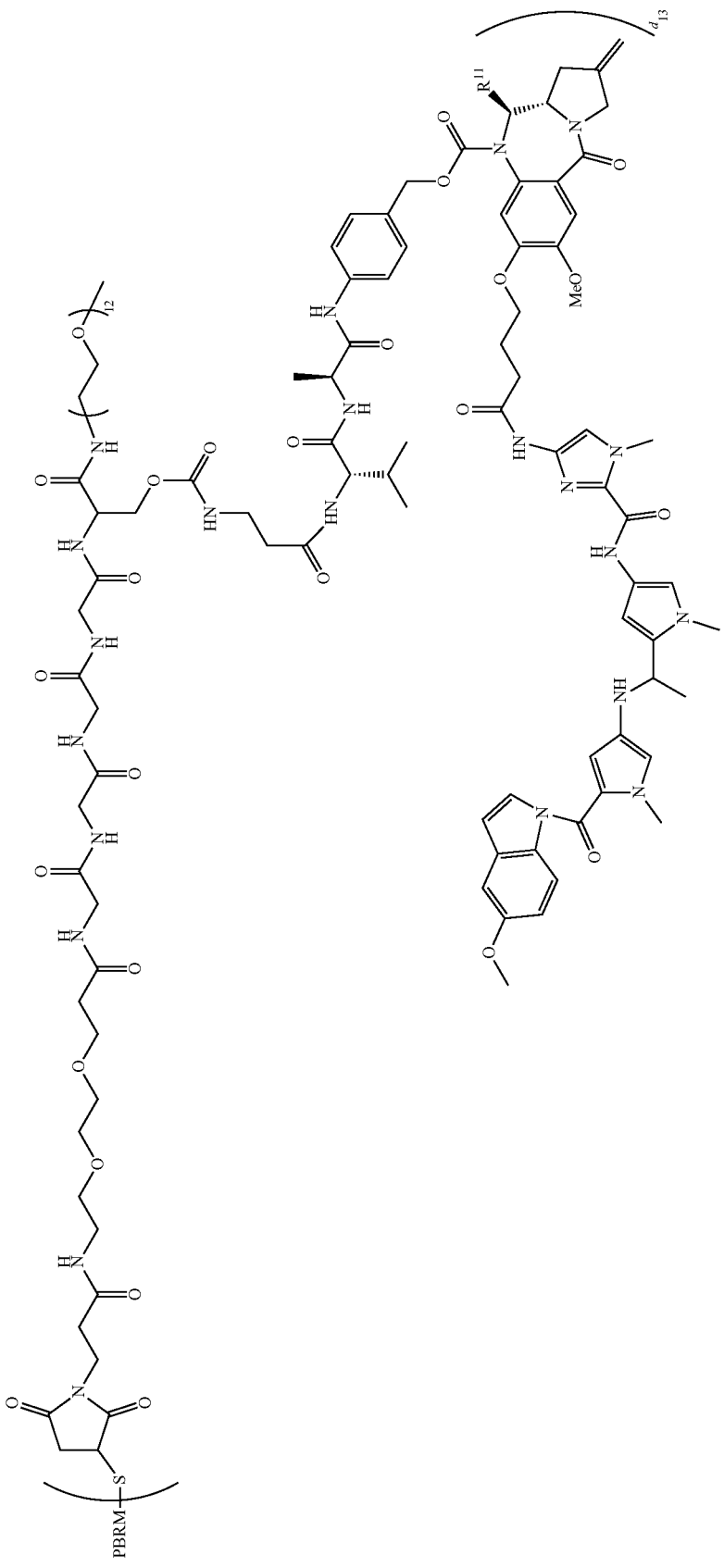

-continued
(XIVd)
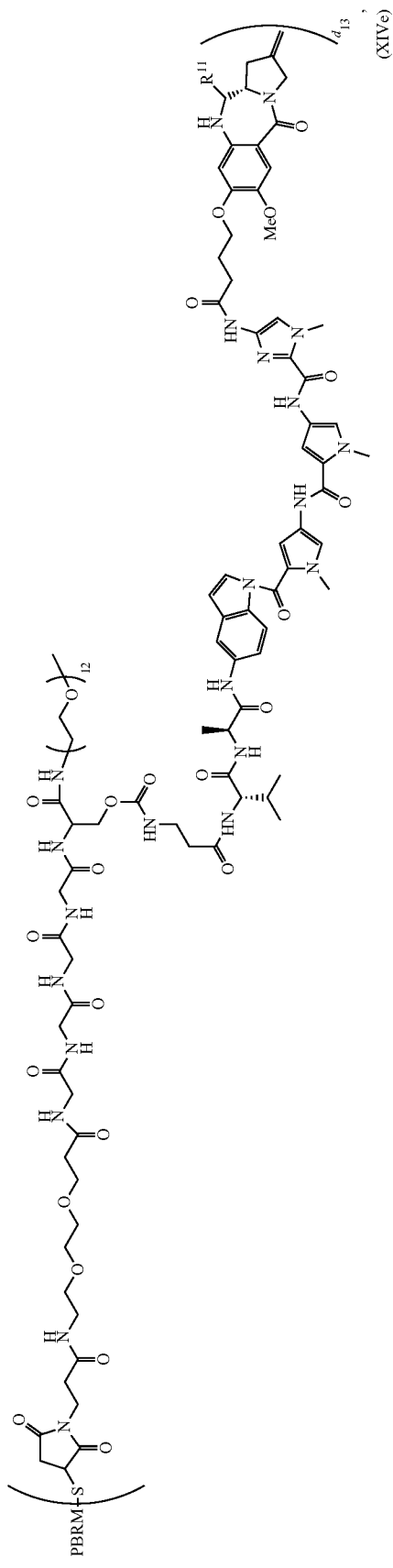
(XIVe)
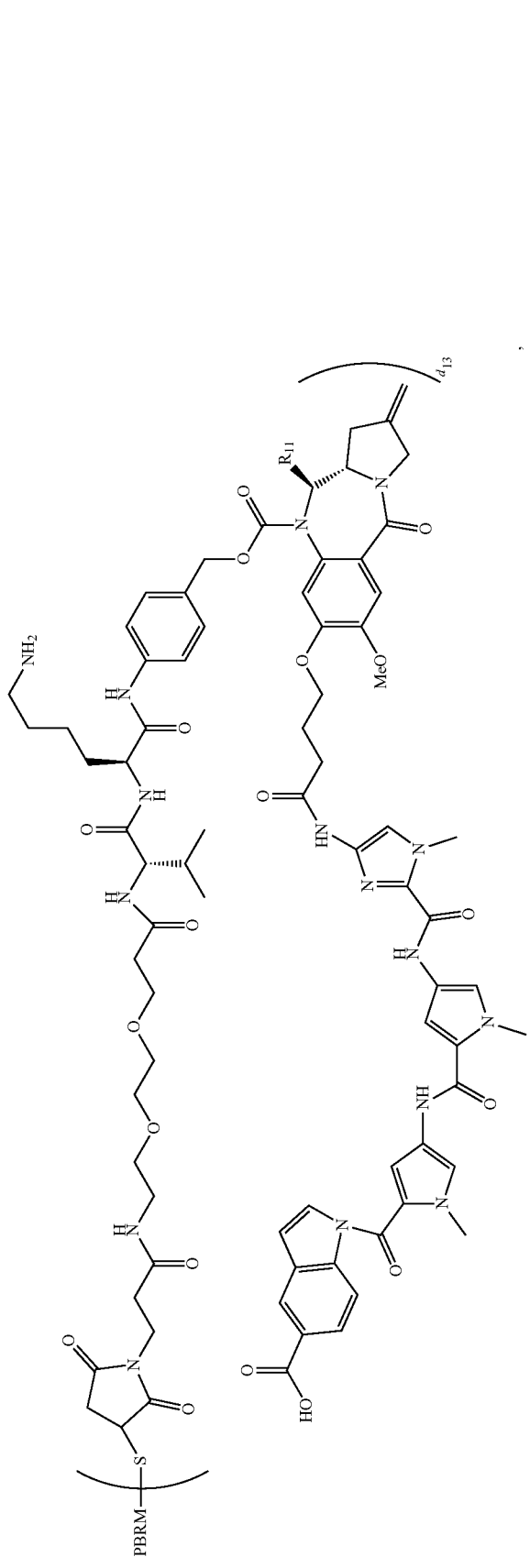

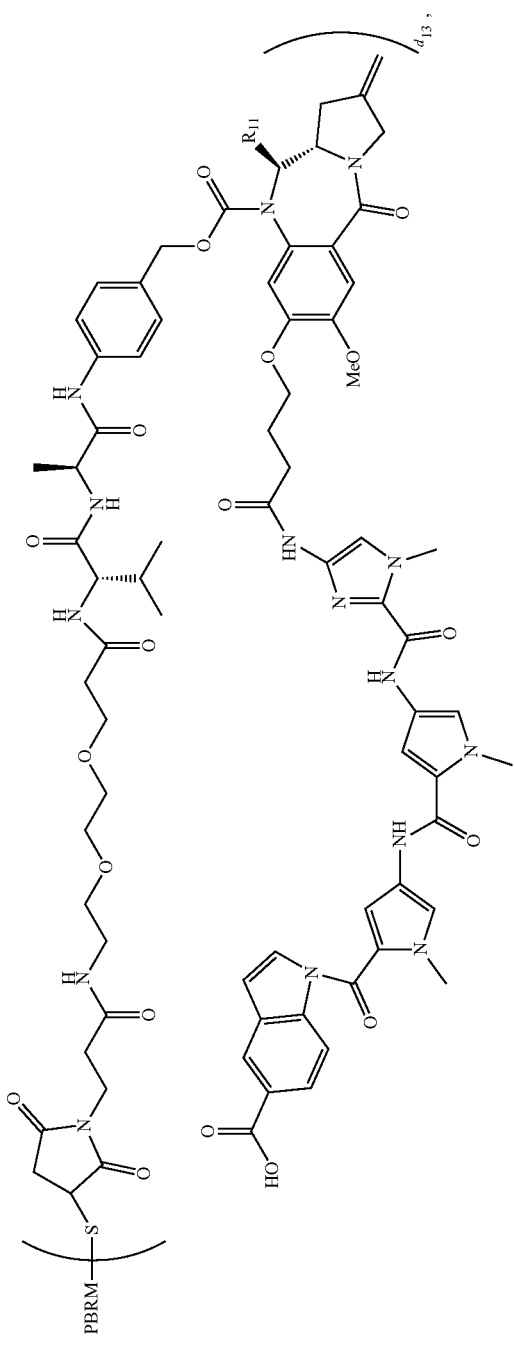
(XIVf)
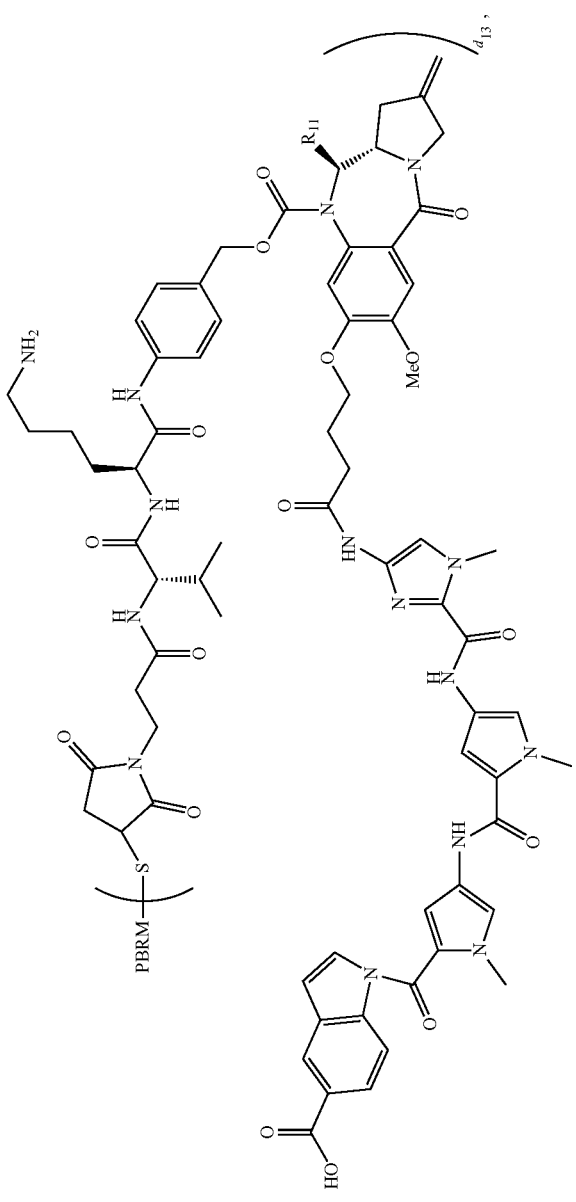
(XIVg)

425
(XIVh)
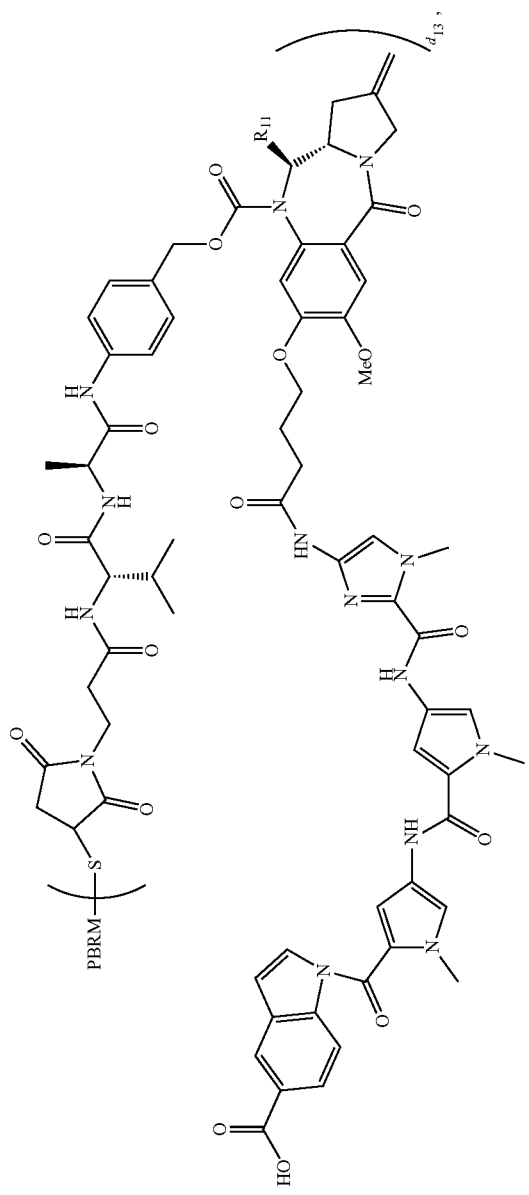
426
(XIVi)
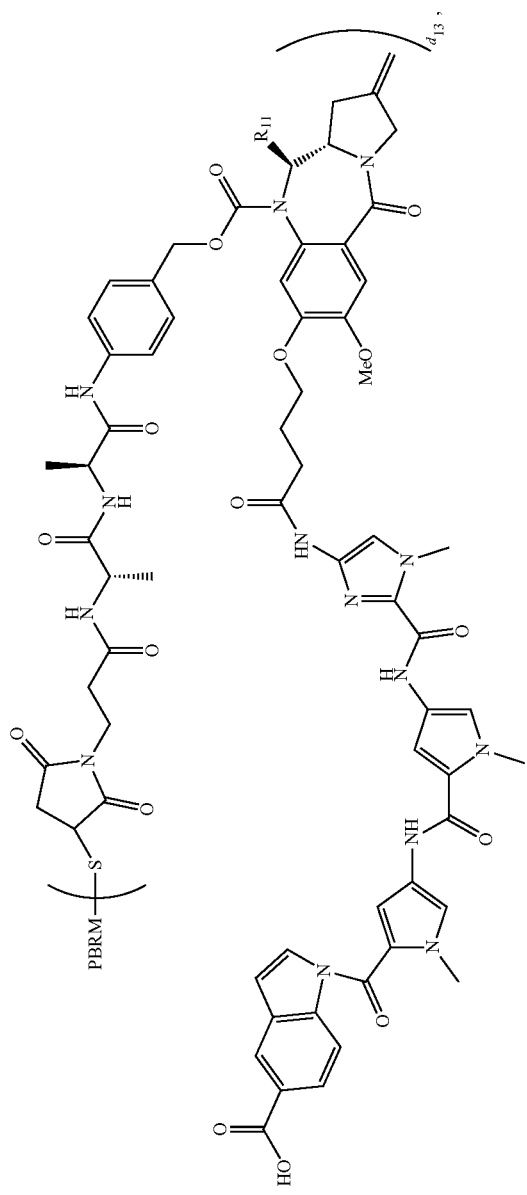

427
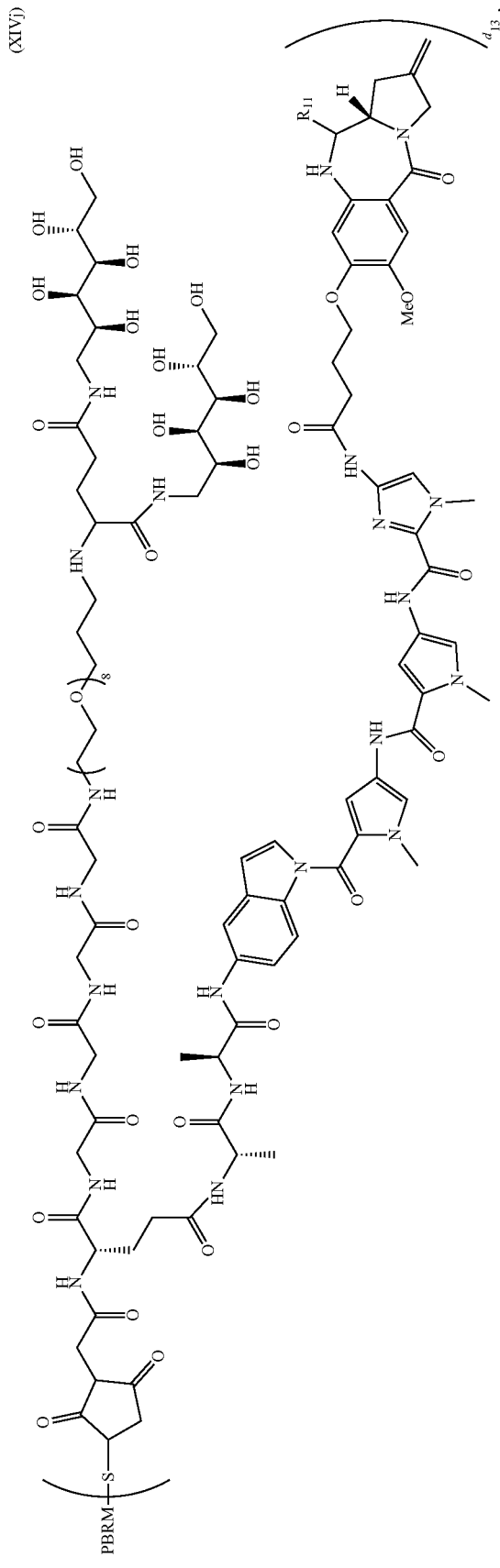
(XIVj)
428
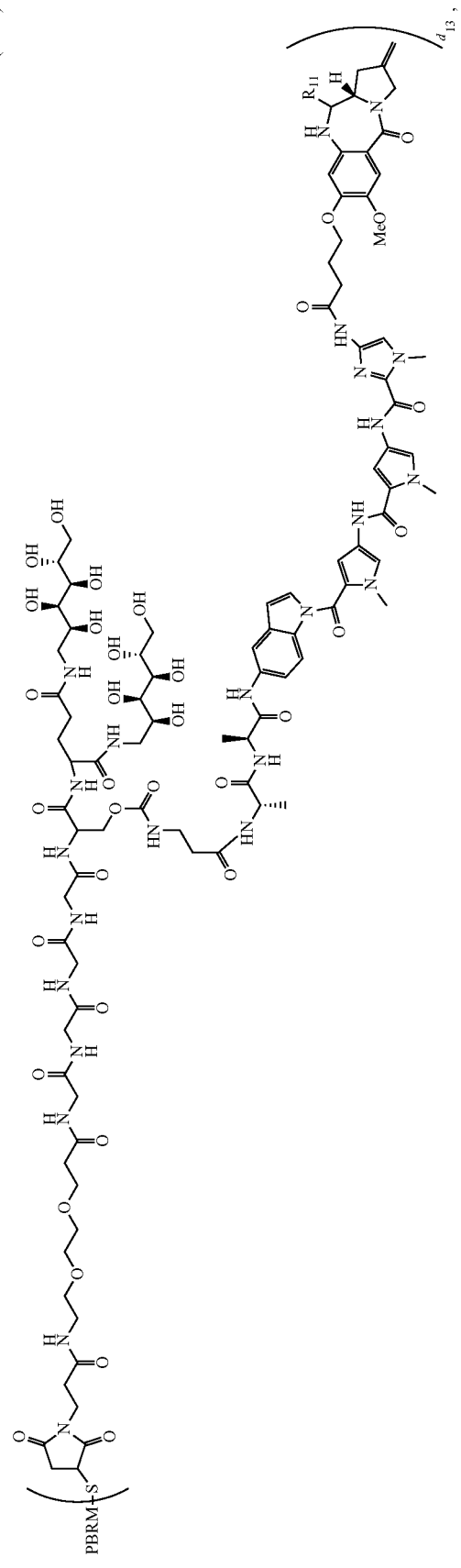
(XIVk)

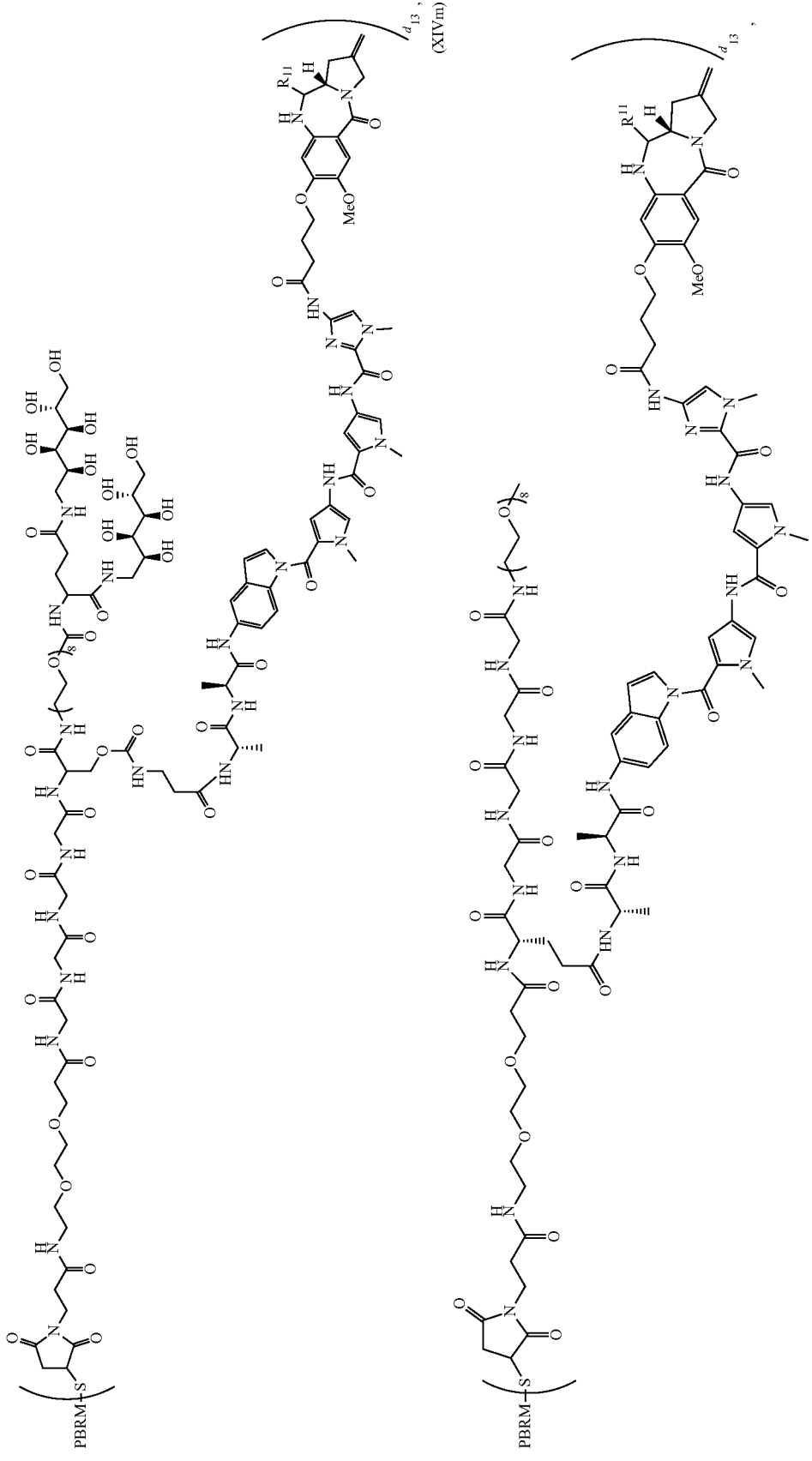

431
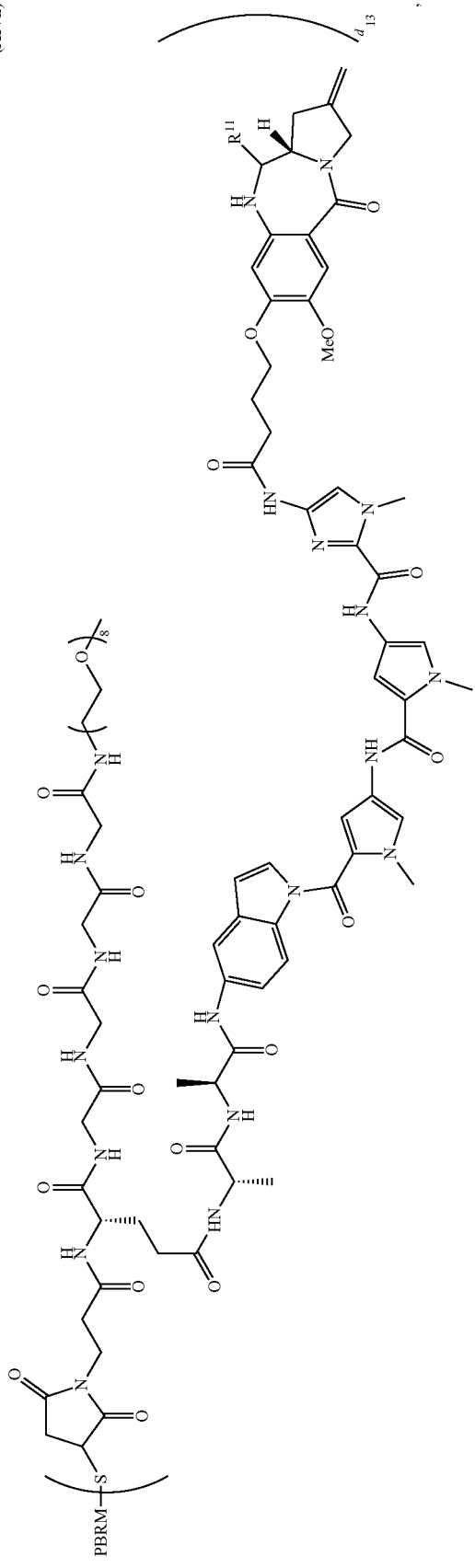
(XIVn)
432
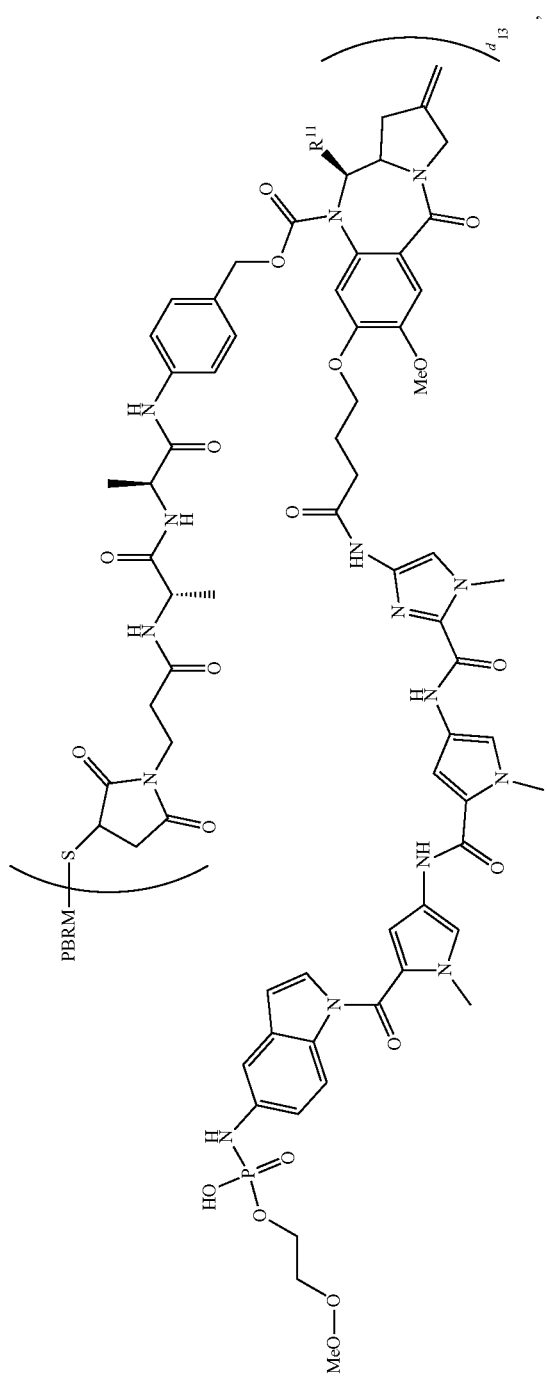
(XIVo)

433
(XIVp)
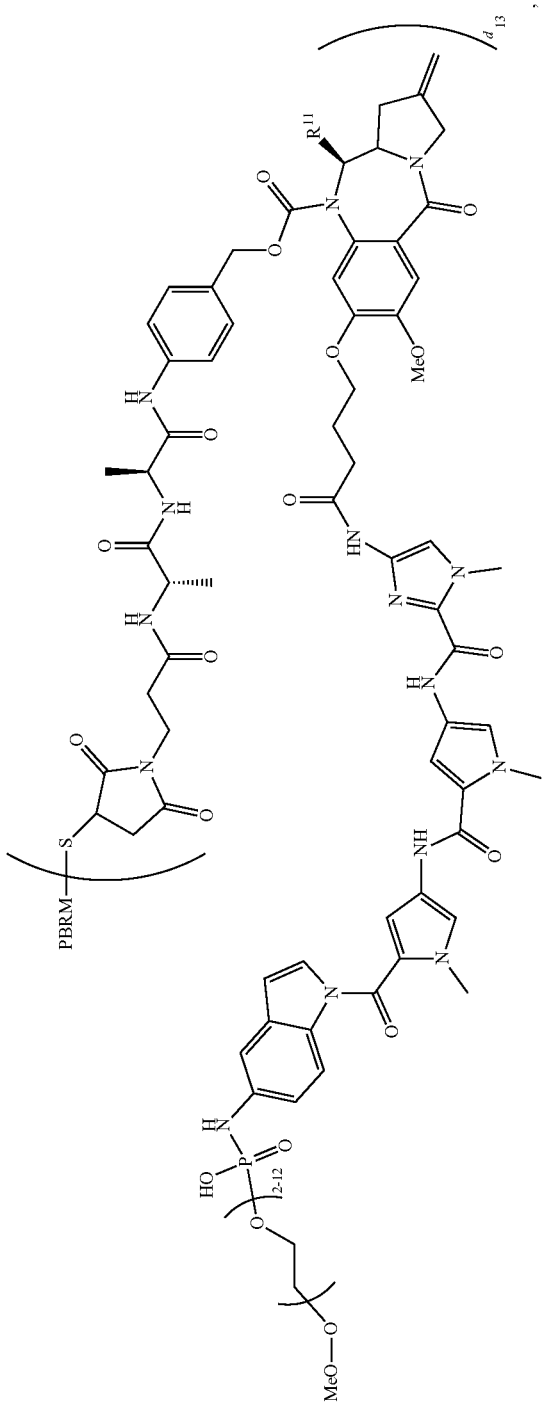
434
(XIVq)
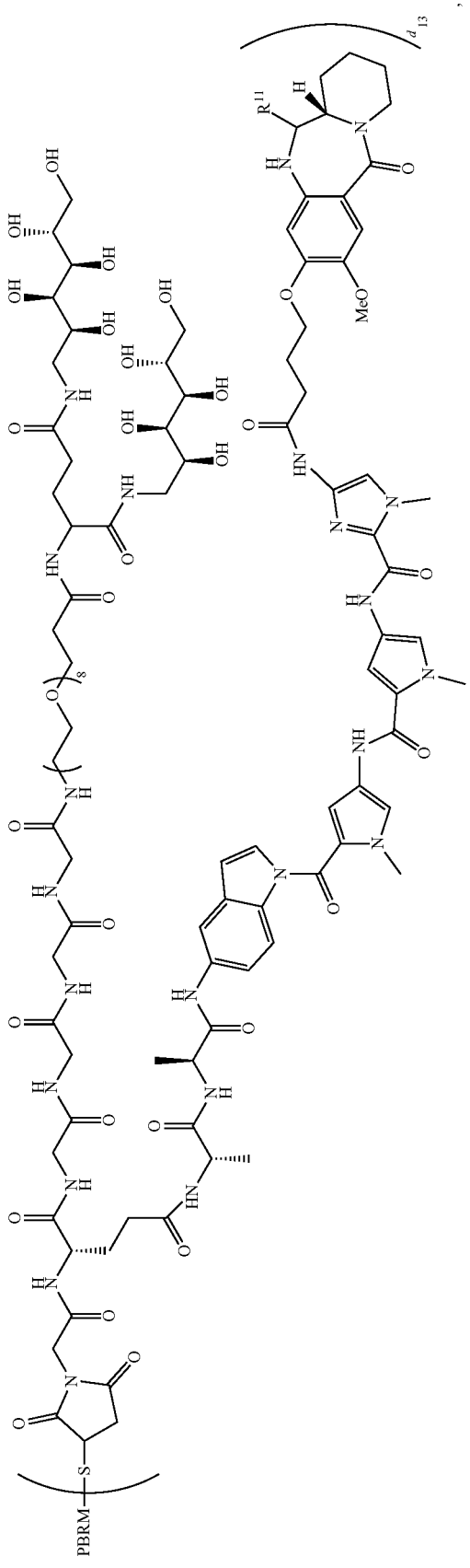

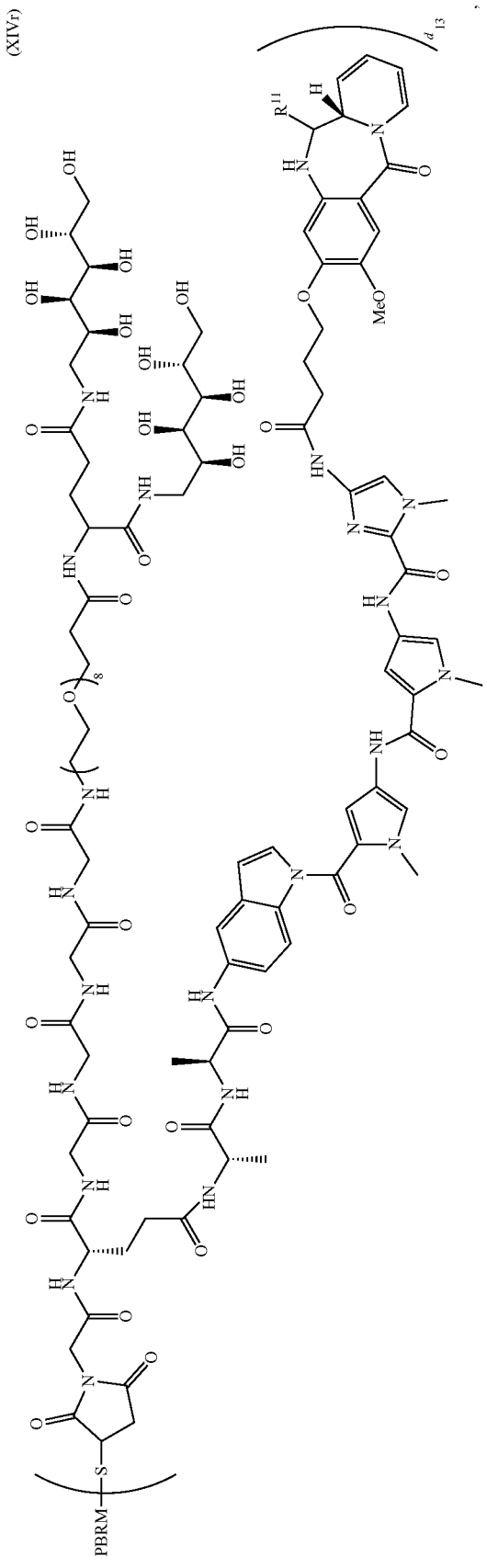
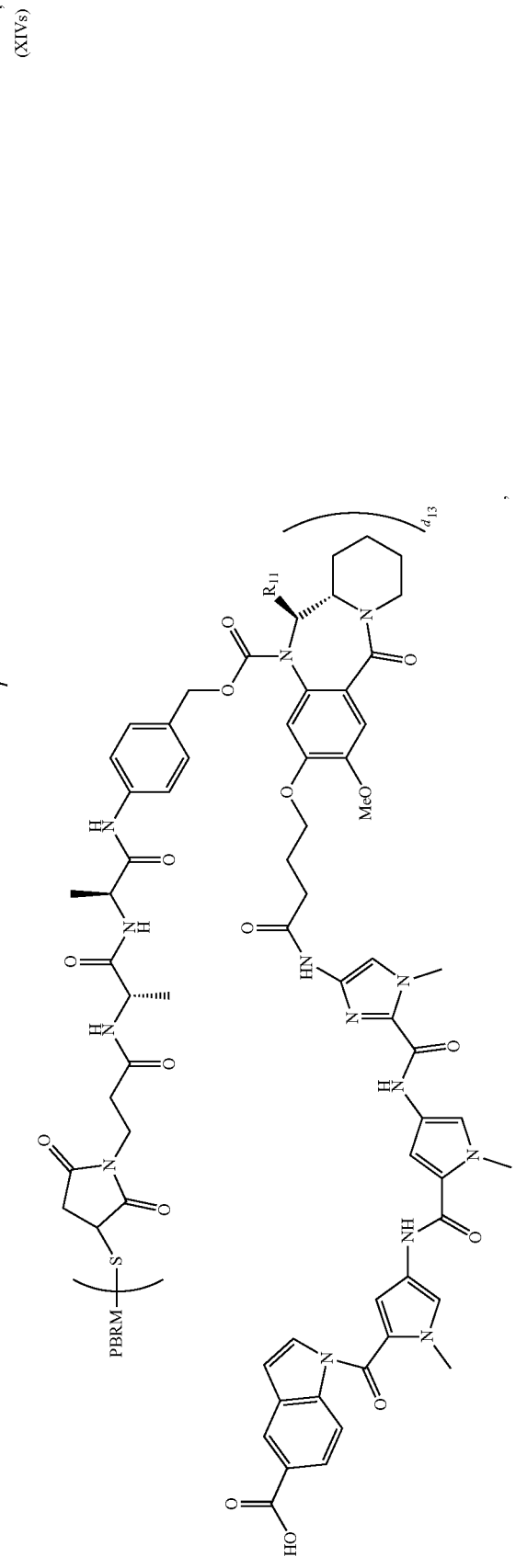

(XIVt)
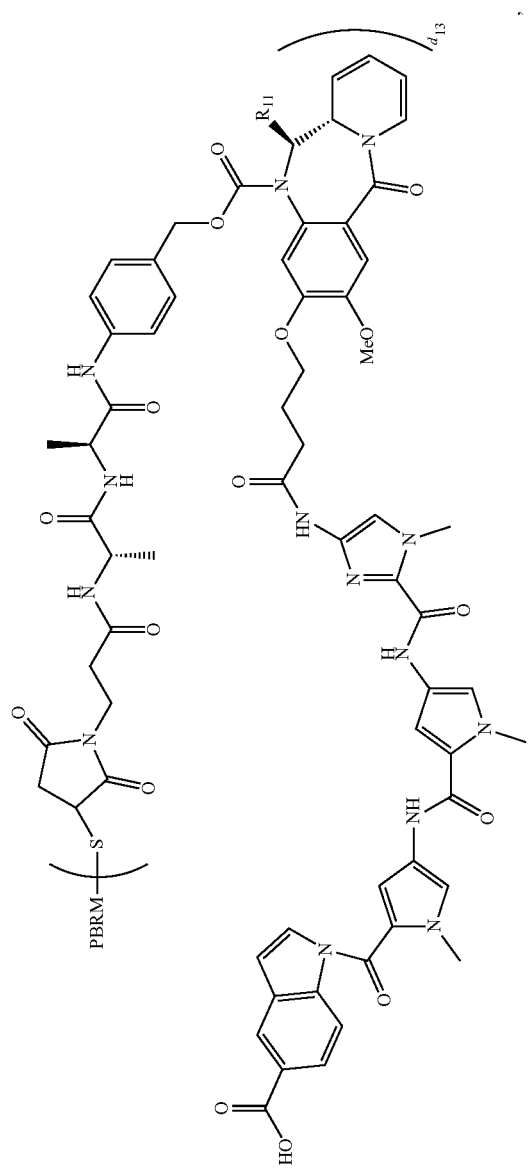
(XIVu)
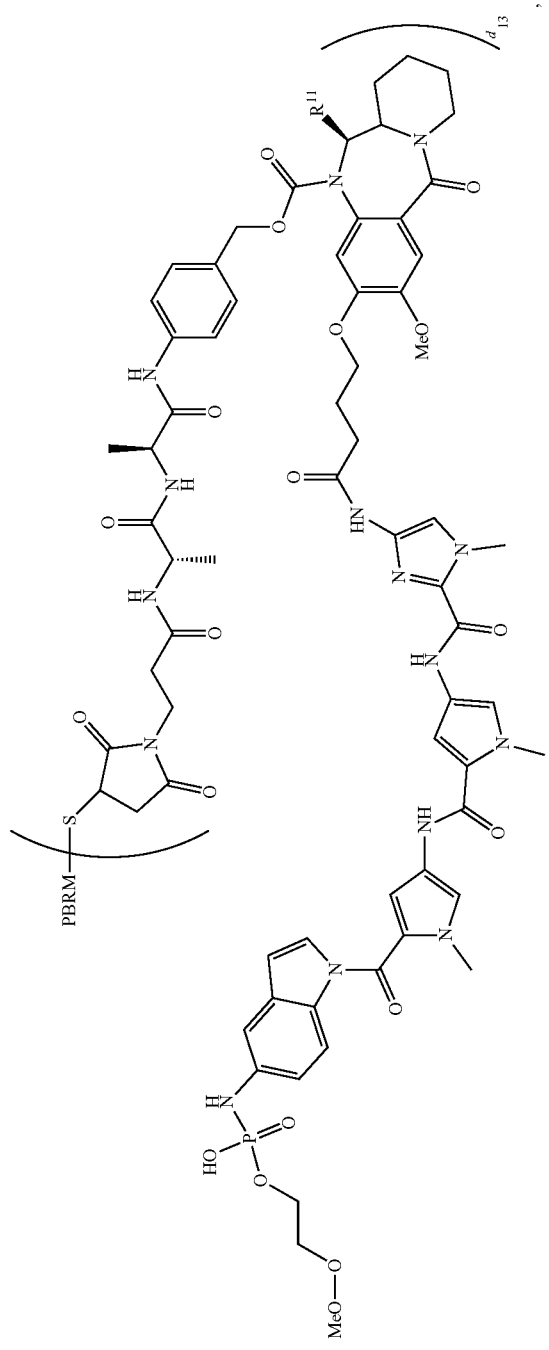

-continued
(XIVv)
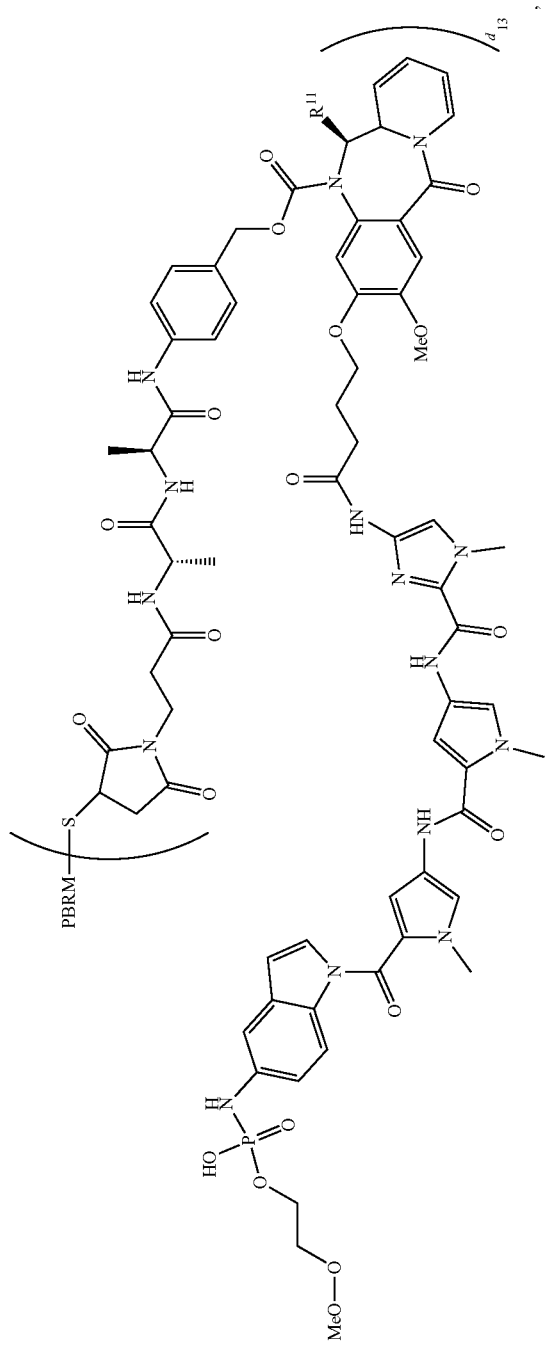
(XIVw)
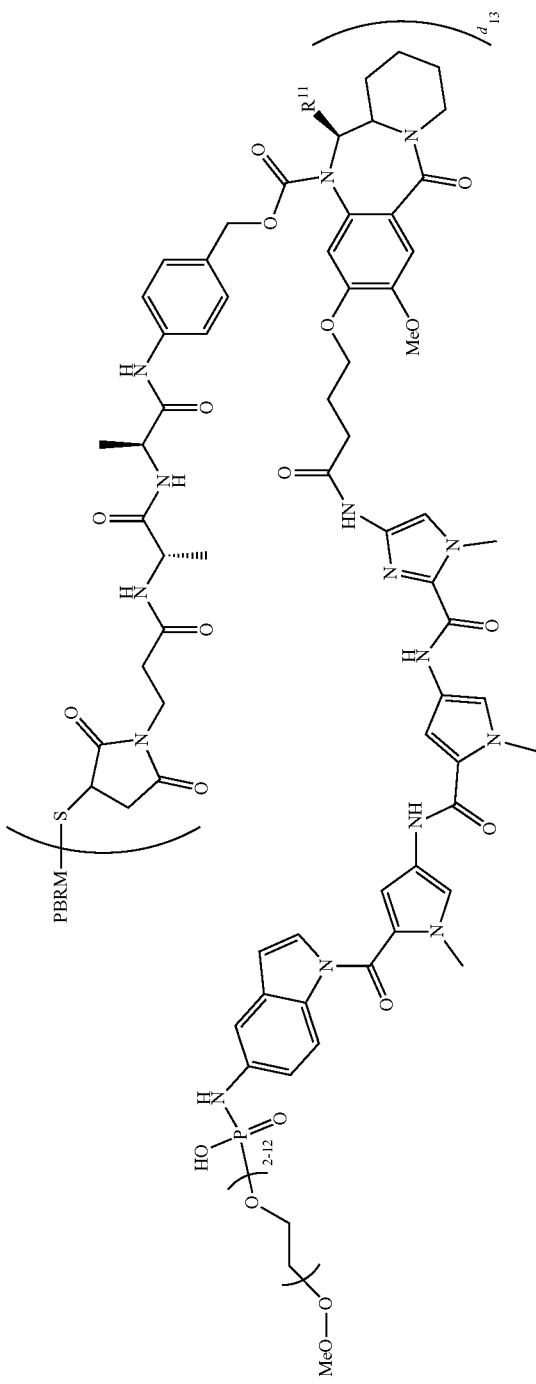

(XIVx)
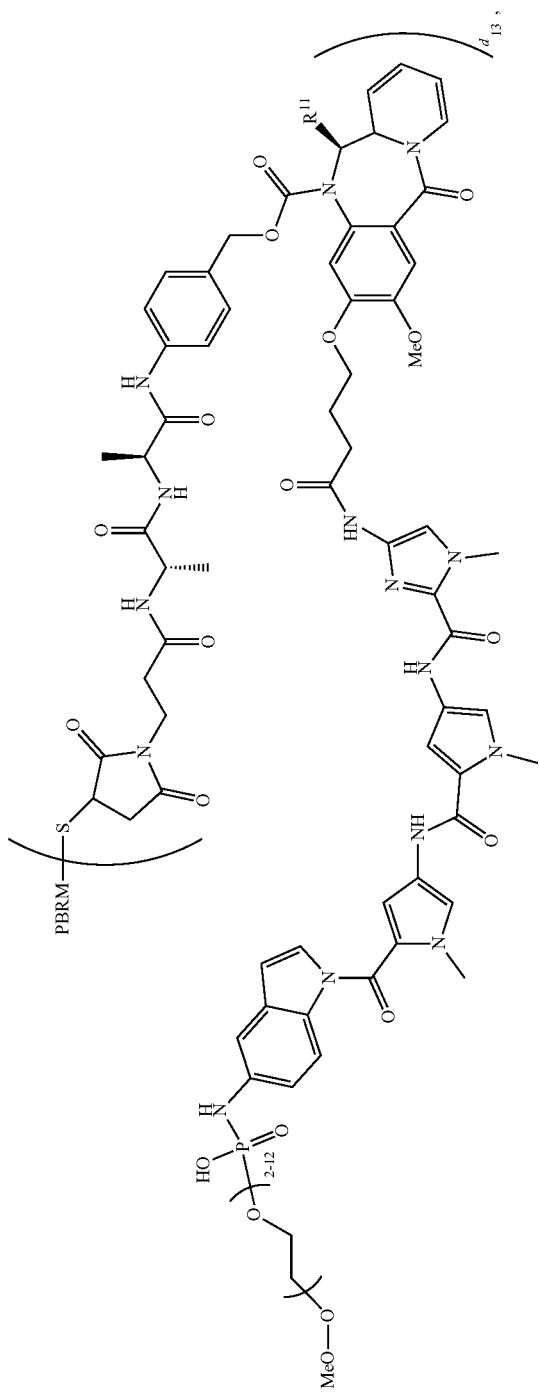

or a tautomer, pharmaceutically acceptable salt or solvate thereof, or a pharmaceutically acceptable salt or solvate of the tautomer, wherein $d_{13}$ is 3 to 5.

19. A conjugate being selected from Formulae (XIVi), (XIVj) and (XIVo):

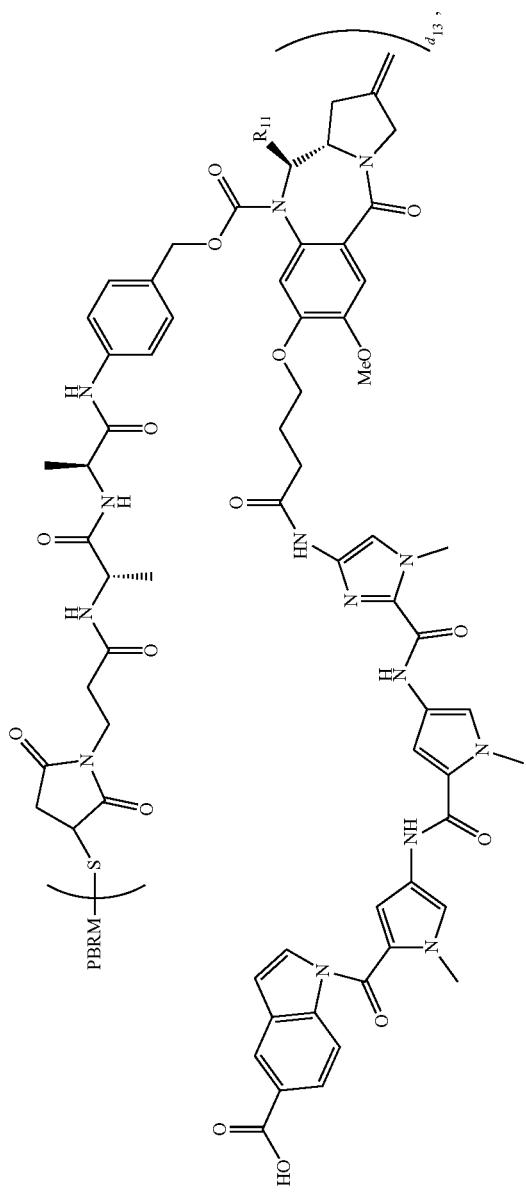
(XIVi)
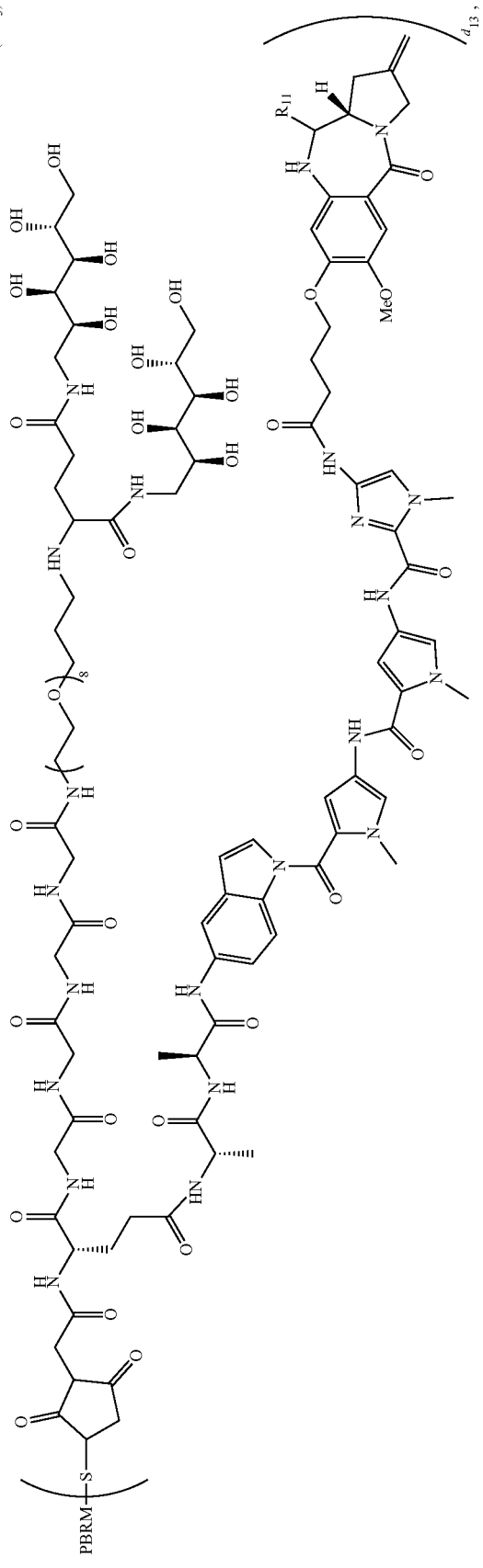
(XIVj)

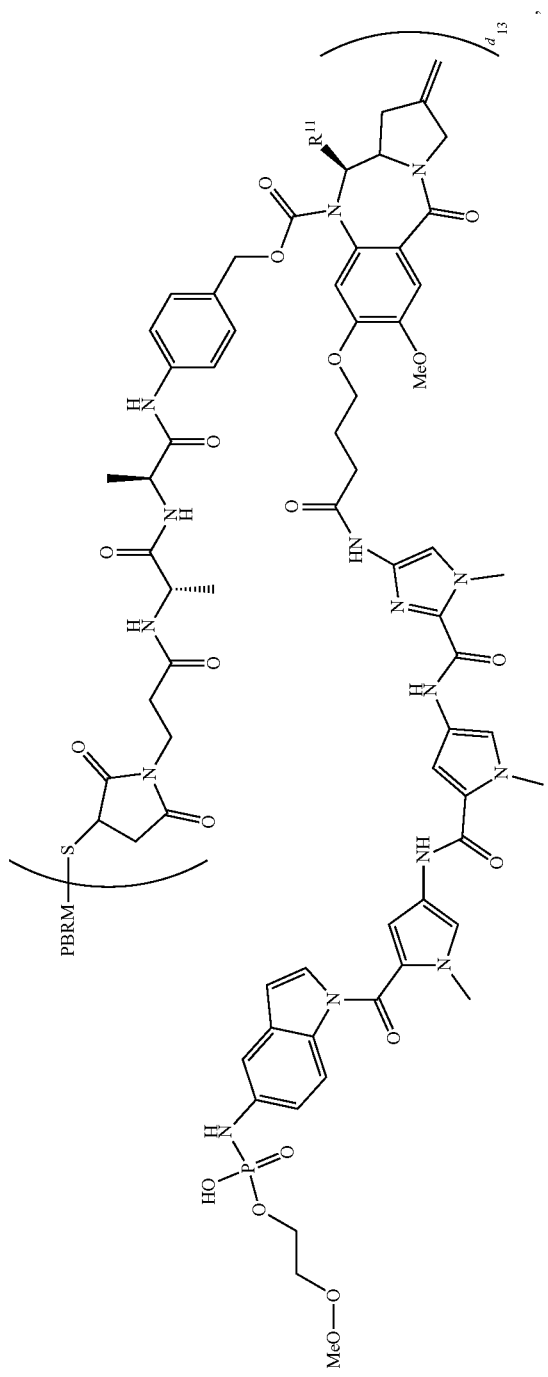
(XIVo) and or a tautomer, pharmaceutically acceptable salt or solvates thereof, or a pharmaceutically acceptable salt or solvate of the tautomer.

20. A pharmaceutical composition comprising the conjugate of claim 1 and a pharmaceutically acceptable carrier.

21. A method of treating a disease or disorder, comprising administering to a subject in need thereof a pharmaceutically effective amount of the conjugate of claim 1, wherein the disease or disorder is cancer.

* * * * *

UNITED STATES PATENT AND TRADEMARK OFFICE
CERTIFICATE OF CORRECTION

PATENT NO. : 11,638,760 B2
APPLICATION NO. : 16/766914
DATED : May 2, 2023
INVENTOR(S) : Joshua D. Thomas et al.

It is certified that error appears in the above-identified patent and that said Letters Patent is hereby corrected as shown below:

In the Claims

At Column 388, Claim number 1, Line number 13 and 14:
"-H, -R, -OH, -SH, -NHR$_2$ , -NR$_2$R$_3$, -NO$_2$, -SnMe$_3$, halo or"
Should read:
-- -H,-R$_2$, -OH, -OR$_2$, -SH, -SR$_2$, -NH$_2$, -NHR$_2$, -NR$_2$R$_3$, -NO$_2$, -SnMe$_3$, halo or --

At Column 388, Claim number 1, Line number 20:
"-N, -COOH, -COOR$_2$, -COR$_2$, -OCONR$_{13}$R$_{14}$,"
Should read:
-- -N$_3$, OR$_2$, -COOH, -COOR$_2$, -COR$_2$, -OCONR$_{13}$R$_{14}$, --

At Column 388, Claim number 1, Line number 25:
"bered heteroaryl, -S(=O)$_2$R$_{12}$, -S(=O)$_2$NR$_{13}$R$_{14}$"
Should read:
-- bered heteroaryl, -S(=O)$_2$R$_{12}$, -S(=O)$_2$NR$_{13}$R$_{14}$, -SR$_{12}$ --

At Column 388, Claim number 1, Line number 43:
"20-membered heteroaryl, or C6-20 aryl;"
Should read:
-- 20-membered heteroaryl, or C$_{6-20}$ aryl; --

At Column 390, Claim number 1, Line number 2:
"X$_5$ is NH, O or S;"
Should read:
-- X$_8$ is NH, O or S; --

Signed and Sealed this
Ninth Day of January, 2024

Katherine Kelly Vidal
*Director of the United States Patent and Trademark Office*

At Column 389, Claim number 1, third diagram:
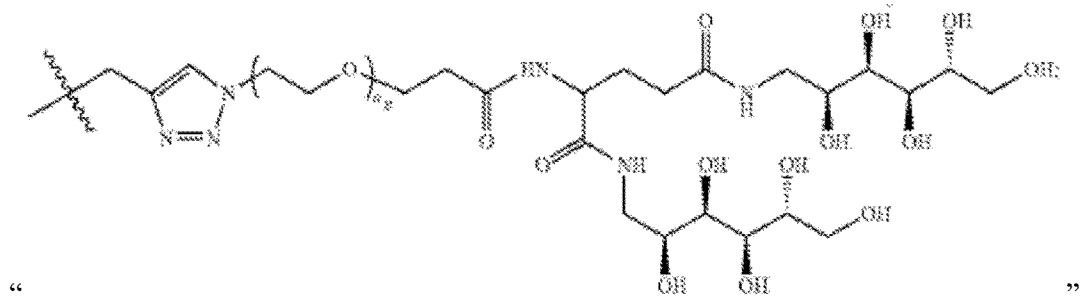
"
Should read:
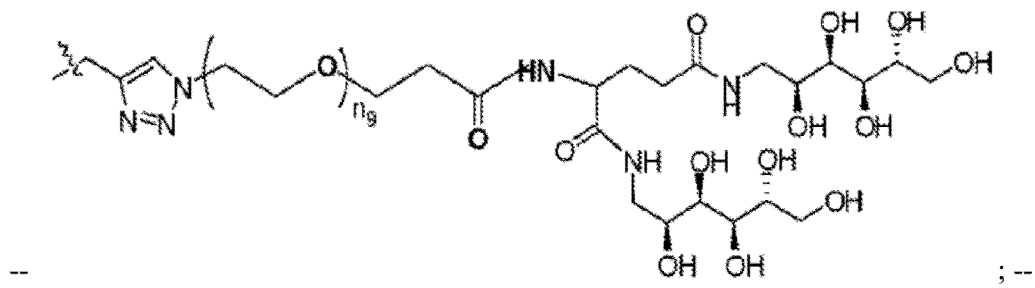
;--
At Column 393, Claim number 2, Line number 55, diagram number (28):
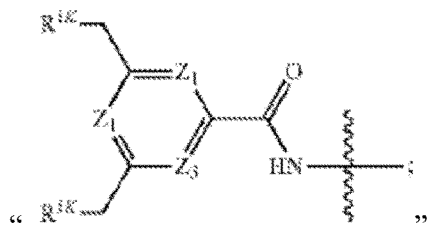
"
Should read:
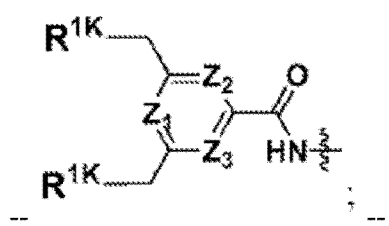
;--
At Column 396, Claim number 2, Line 66:
"heteroaryl, wherein the C1-24 slkyl (e.g. $C_{1-6}$ alkyl), or"
Should read:
-- heteroaryl, wherein the $C_{1-24}$ alkyl (*e.g.,* $C_{1-6}$ alkyl), or --

At Column 396, Claim number 3, Line number 48, diagram 9:
"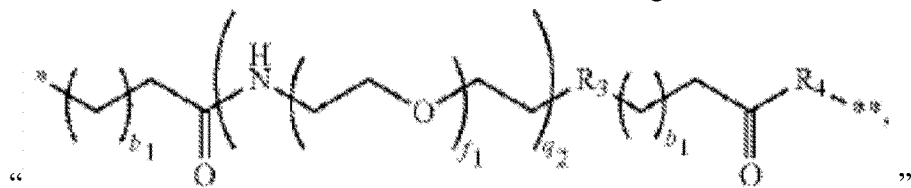"
Should read:
--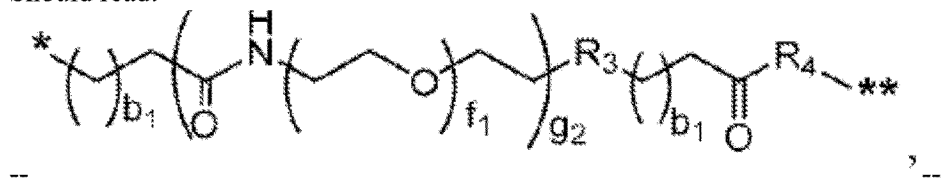,--
At Column 419, Claim number 18, diagram (XIVc):
"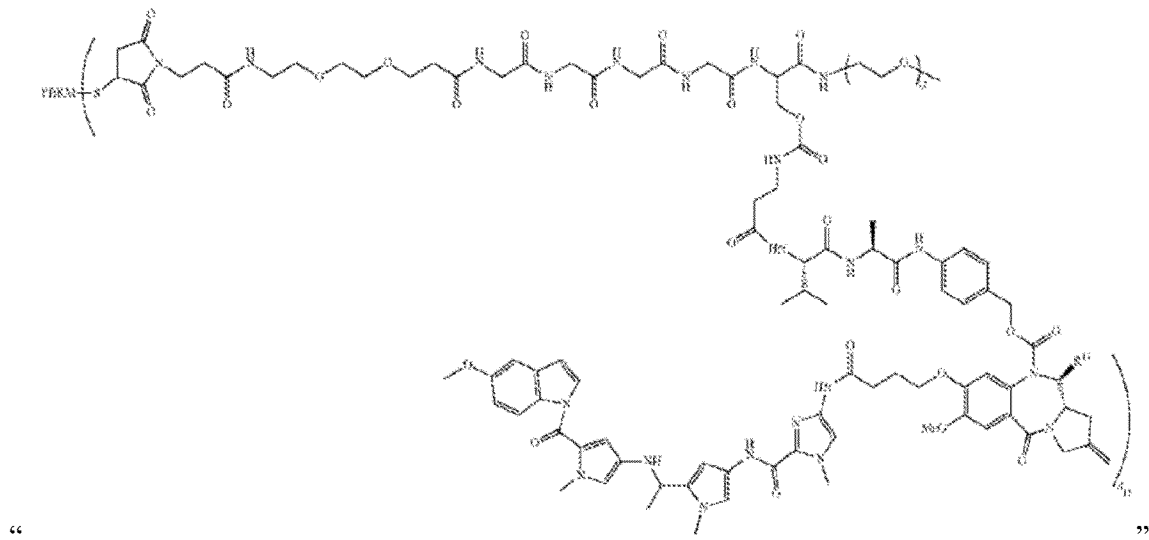"
Should read:
--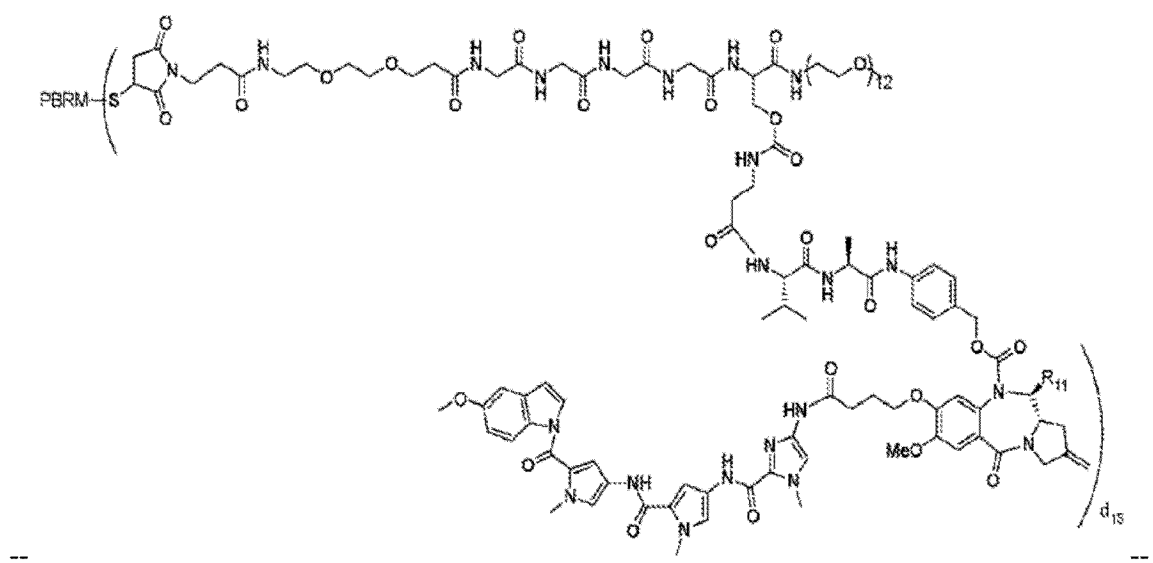,--

CERTIFICATE OF CORRECTION (continued)
U.S. Pat. No. 11,638,760 B2

At Column 427, Claim number 18, diagram (XIVj):

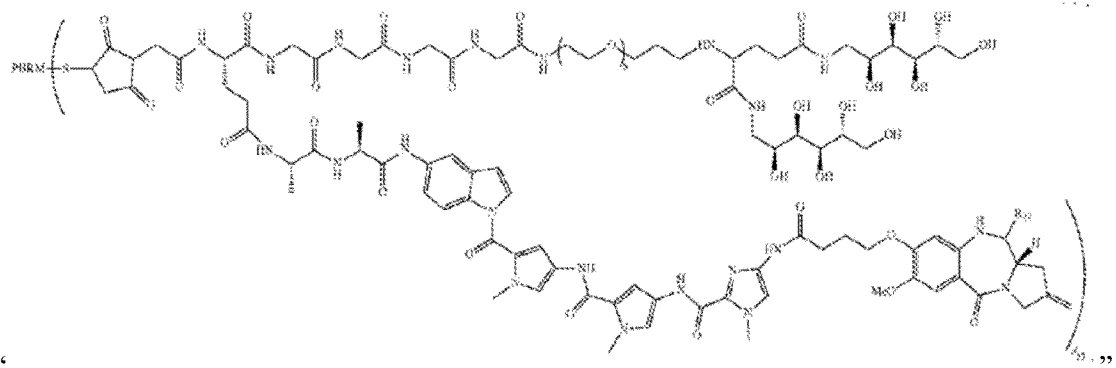

"

Should read:

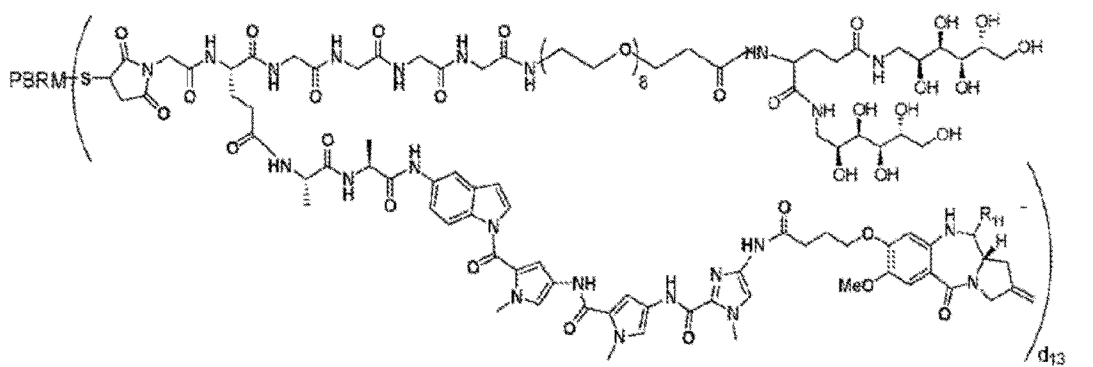

--

At Column 431, Claim number 18, diagram number (XIVo):

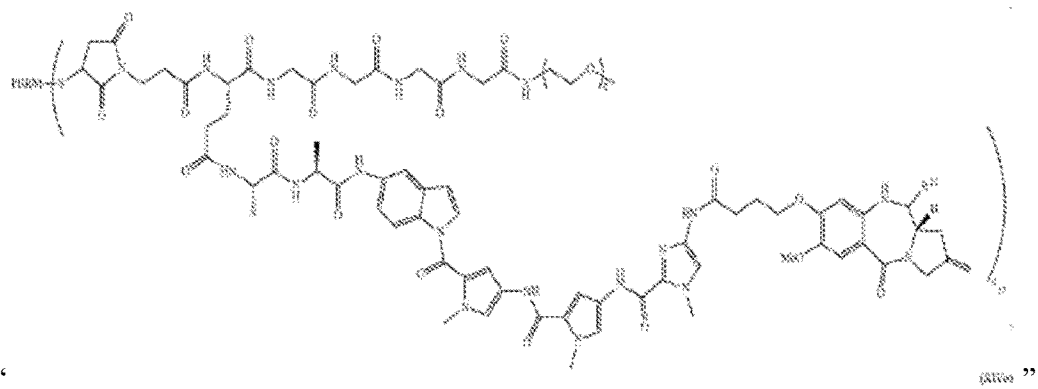

"

CERTIFICATE OF CORRECTION (continued)
U.S. Pat. No. 11,638,760 B2

Should read:

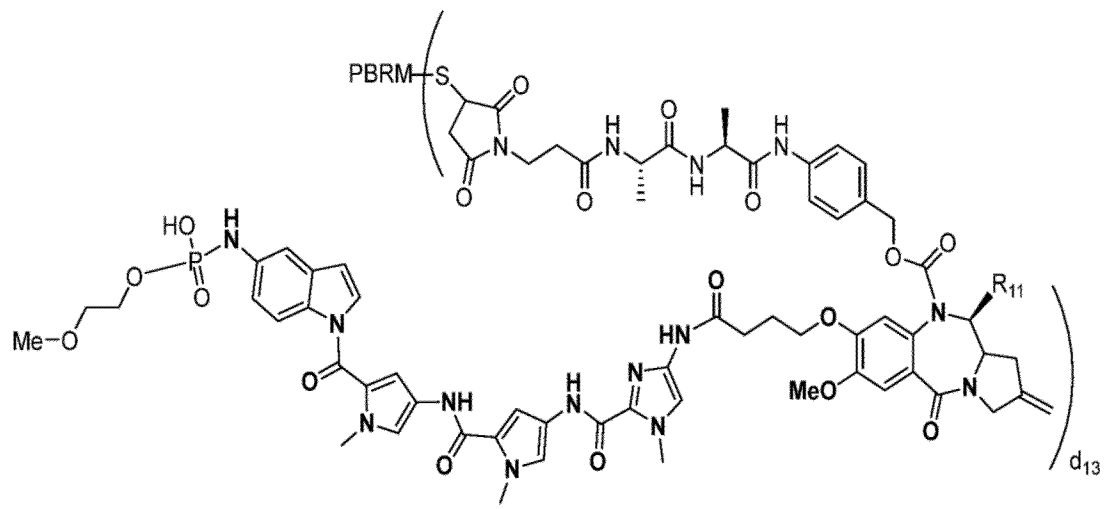

--   -   --

At Column 432, Claim number 18, diagram (XIVp):

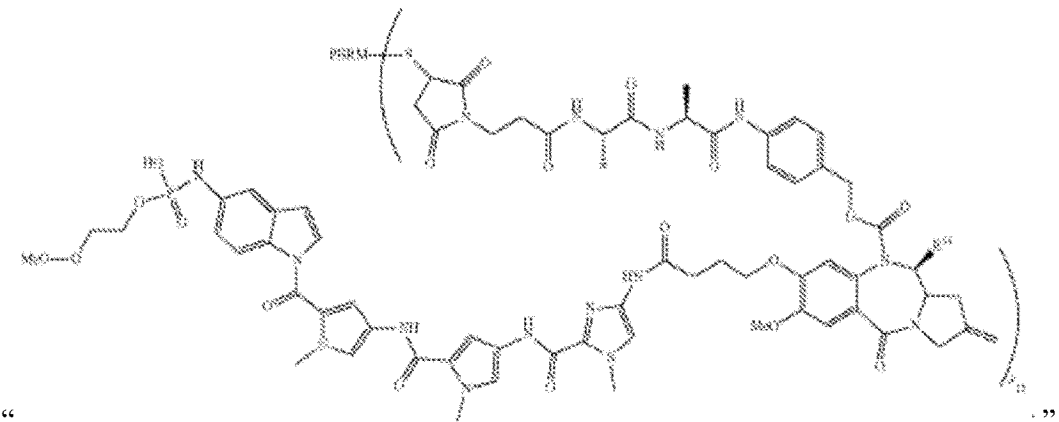

"   ."

Should read:

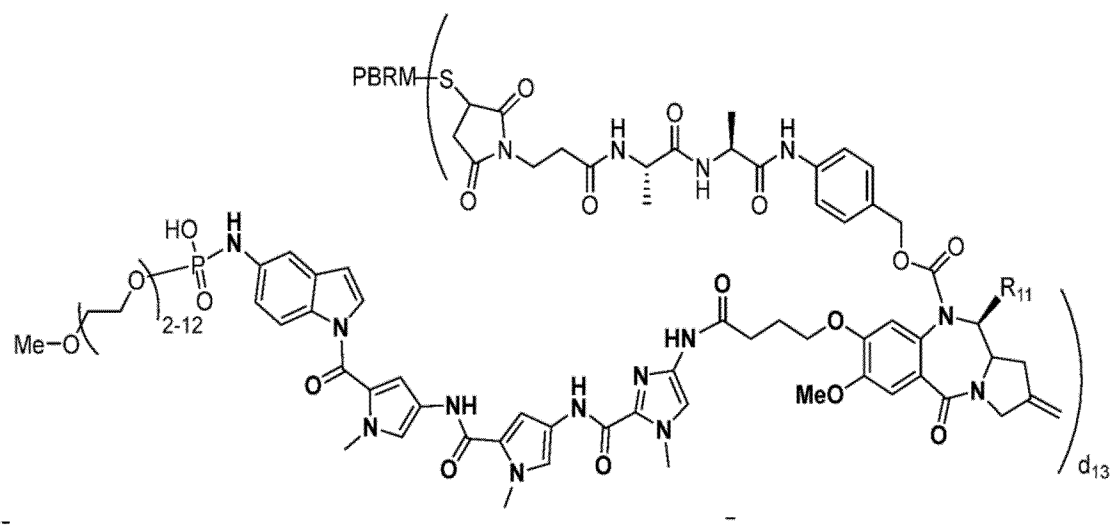

--   -   --

CERTIFICATE OF CORRECTION (continued)
U.S. Pat. No. 11,638,760 B2

At Column 433, Claim number 18, diagram (XIVq):

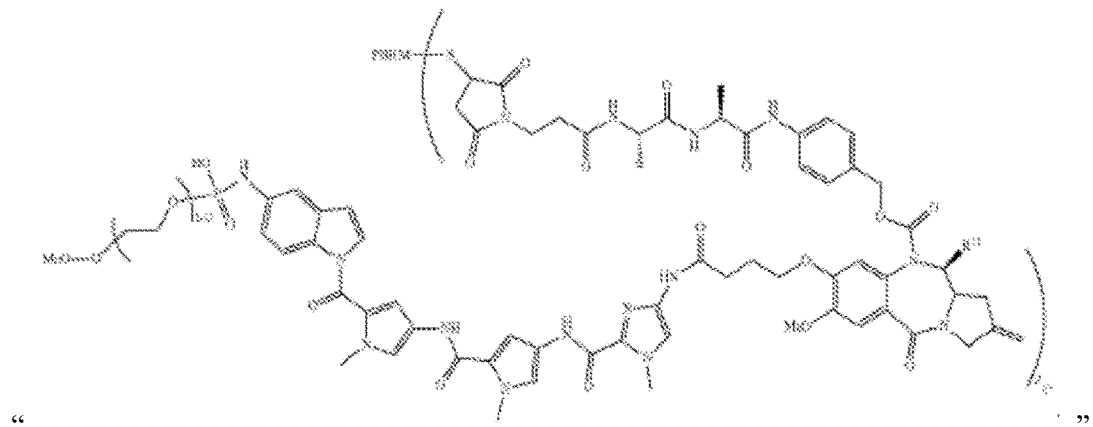

"

"

Should read:

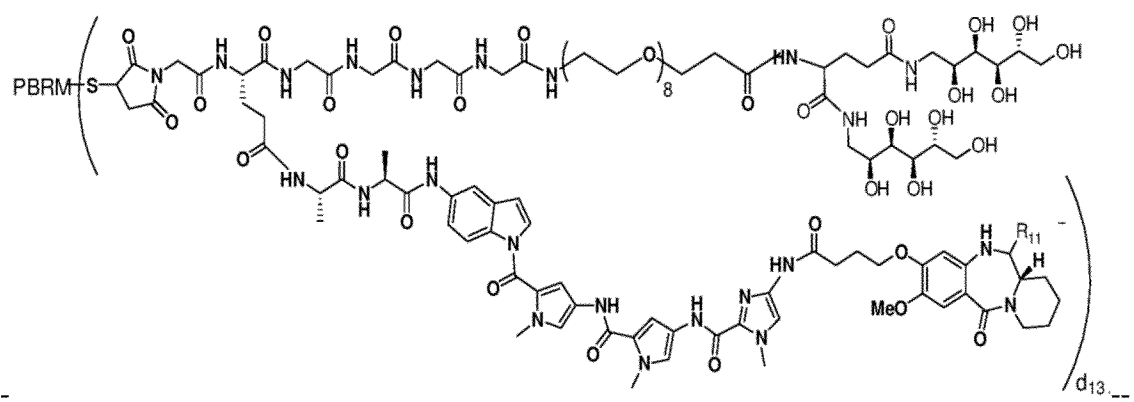

--

At Column 438, Claim number 18, diagram (XIVu):

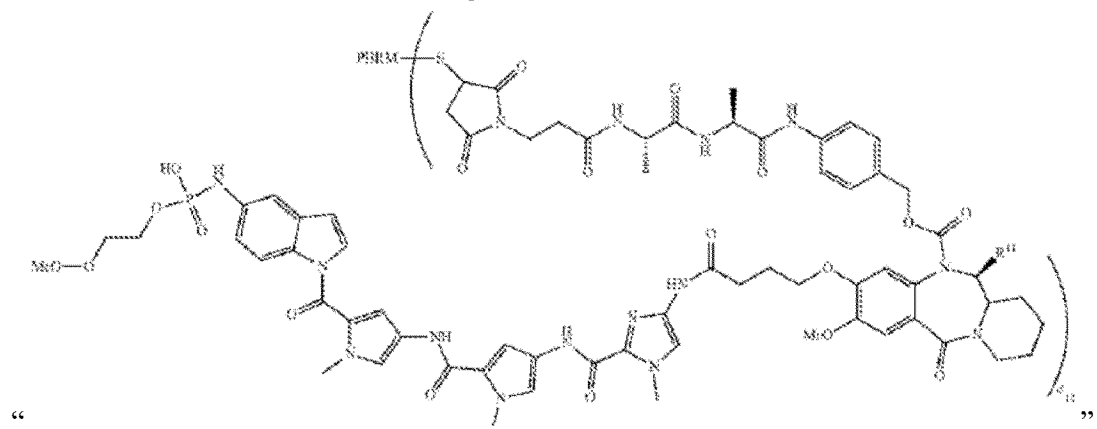

"

"

CERTIFICATE OF CORRECTION (continued)
U.S. Pat. No. 11,638,760 B2

Should read:

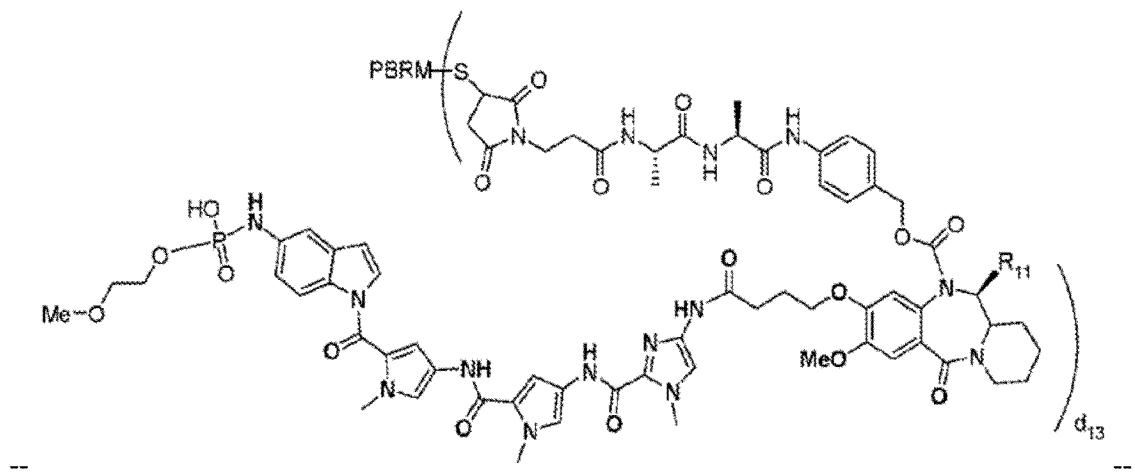

--                                                                                                           --

At Column 439, Claim number 18, diagram (XIVv):

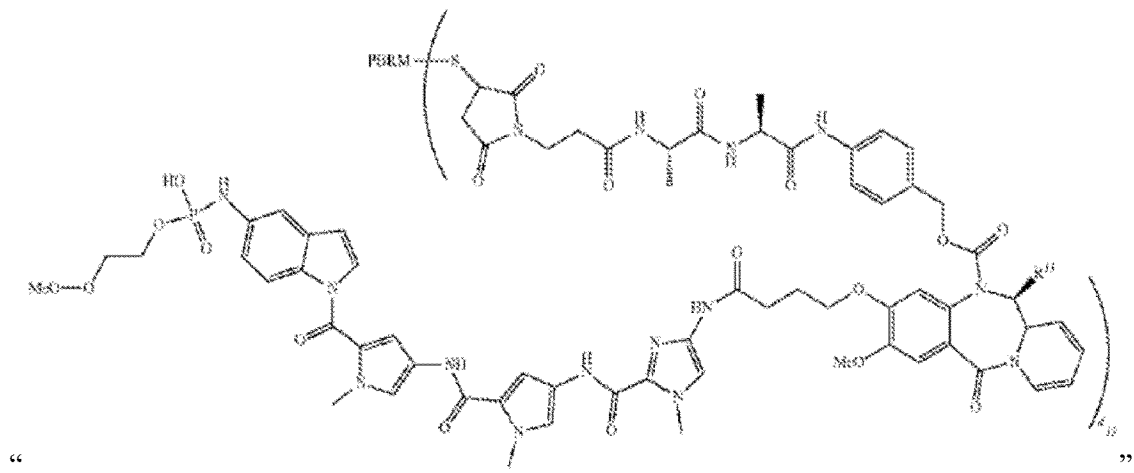

"                                                                                                            "

Should read:

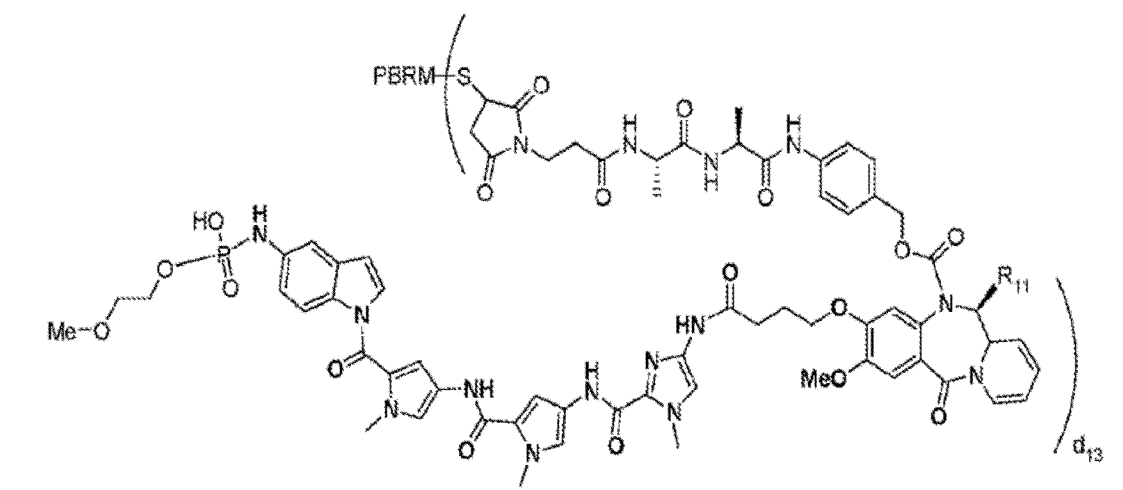

--                                                                                                           --

CERTIFICATE OF CORRECTION (continued)
U.S. Pat. No. 11,638,760 B2

At Column 440, Claim number 18, diagram (XIVw):

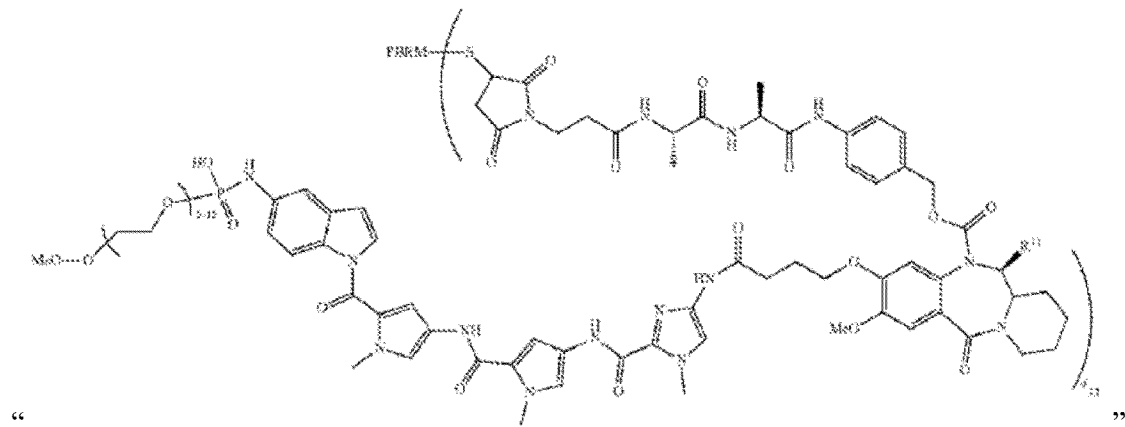

"

Should read:

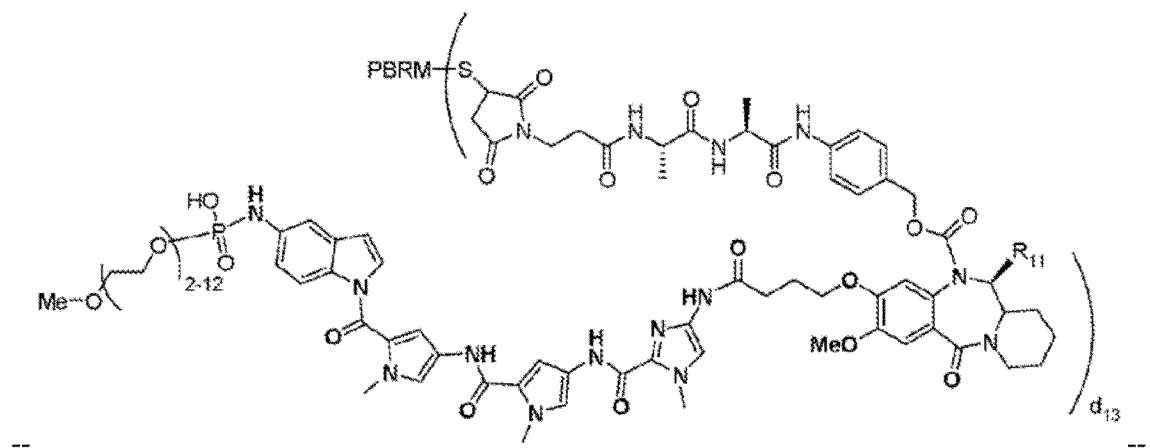

--

At Column 441, Claim number 18, diagram (XIVx):

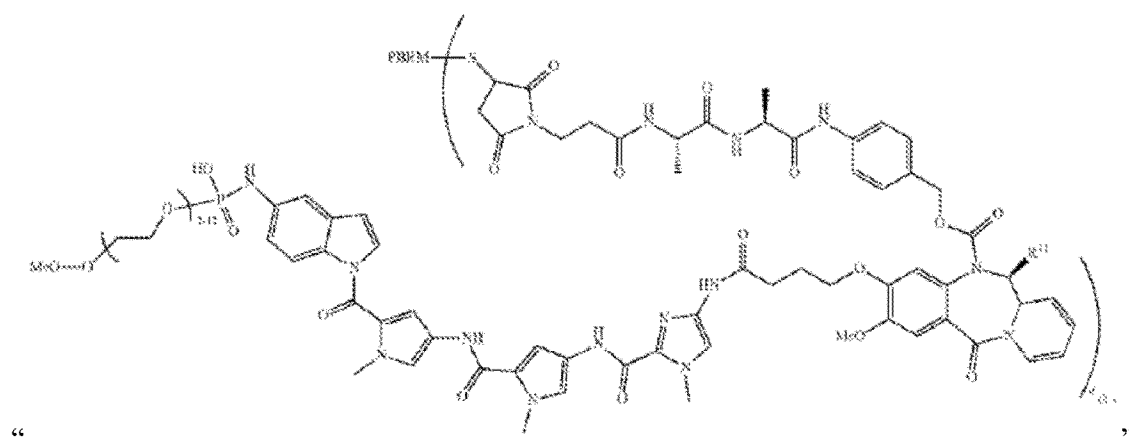

"                                                                           "

CERTIFICATE OF CORRECTION (continued)
U.S. Pat. No. 11,638,760 B2

Should read:

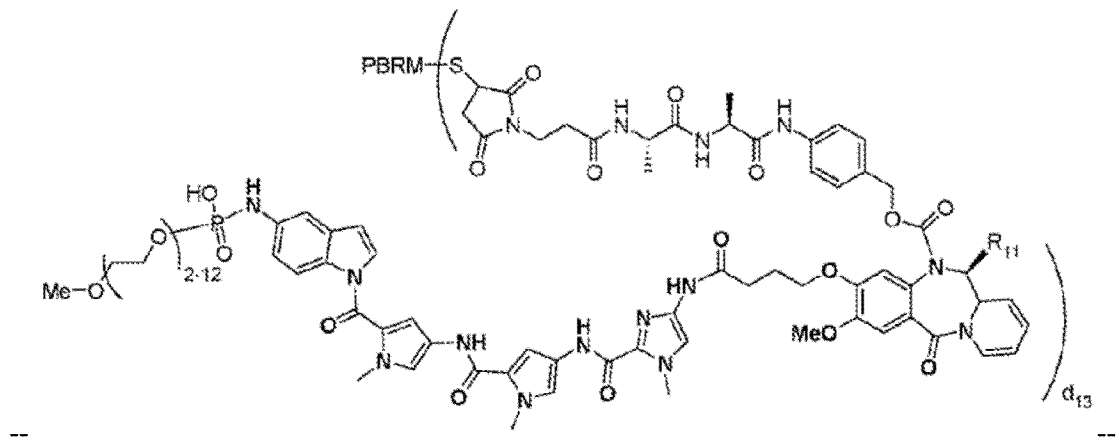
--

At Column 446, Claim number 19, diagram (XIVj):

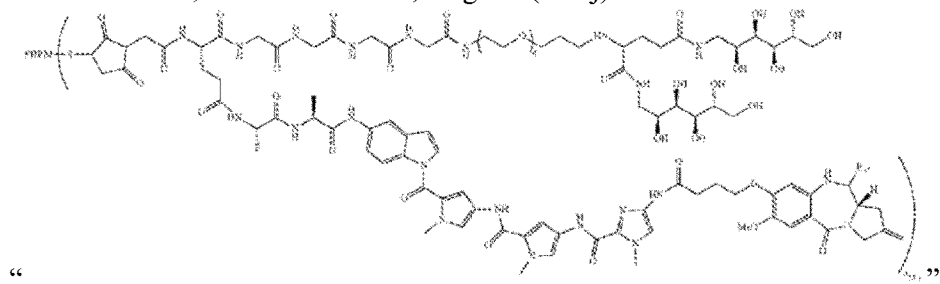
"

Should read:

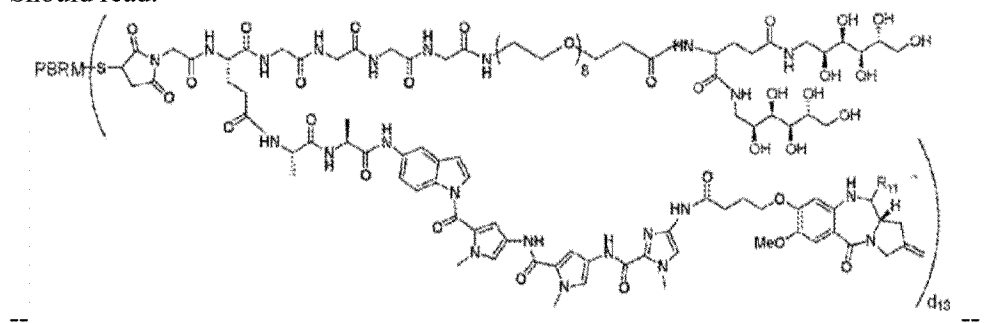
--

At Column 447, Claim number 19, diagram (XIVo):

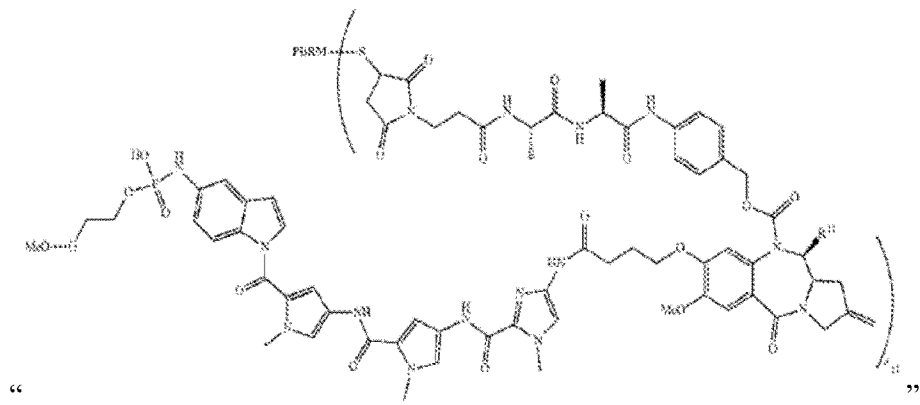
"

CERTIFICATE OF CORRECTION (continued)
U.S. Pat. No. 11,638,760 B2

Should read:

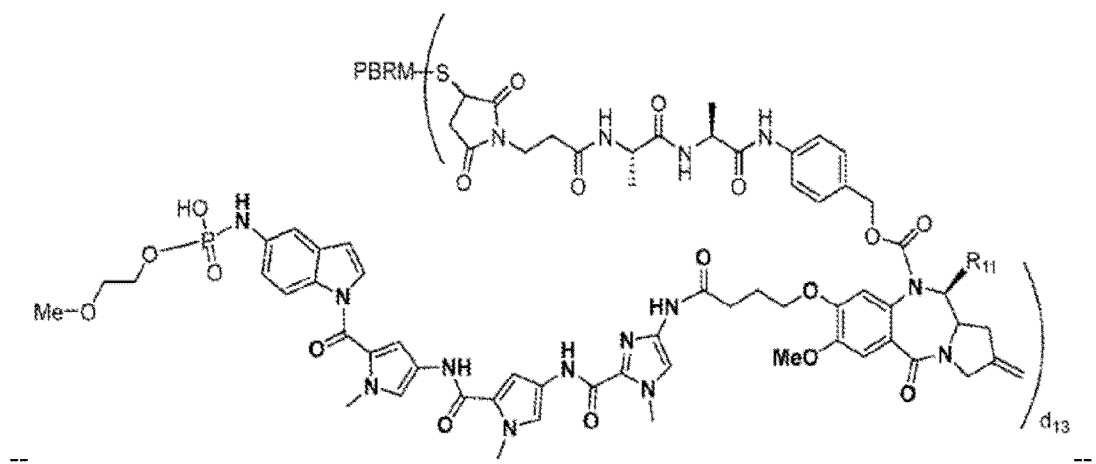

-- --

SEQUENCE LISTING

<160> NUMBER OF SEQ ID NOS: 29

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 10
<212> TYPE: PRT
<213> ORGANISM: Homo sapiens

<400> SEQUENCE: 5

Gly Tyr Thr Phe Thr Gly Tyr Asn Ile His
1               5                   10

<210> SEQ ID NO 6
<211> LENGTH: 17
<212> TYPE: PRT
<213> ORGANISM: Homo sapiens

<400> SEQUENCE: 6

Ala Ile Tyr Pro Gly Asn Gly Asp Thr Ser Tyr Lys Gln Lys Phe Arg
1               5                   10                  15

Gly

<210> SEQ ID NO 7
<211> LENGTH: 10
<212> TYPE: PRT
<213> ORGANISM: Homo sapiens

<400> SEQUENCE: 7

Gly Glu Thr Ala Arg Ala Thr Phe Ala Tyr
1               5                   10

<210> SEQ ID NO 8
<211> LENGTH: 11
<212> TYPE: PRT
<213> ORGANISM: Homo sapiens

<400> SEQUENCE: 8

Ser Ala Ser Gln Asp Ile Gly Asn Phe Leu Asn
1               5                   10

<210> SEQ ID NO 9
<211> LENGTH: 7

```
<212> TYPE: PRT
<213> ORGANISM: Homo sapiens

<400> SEQUENCE: 9

Tyr Thr Ser Ser Leu Tyr Ser
1               5

<210> SEQ ID NO 10
<211> LENGTH: 9
<212> TYPE: PRT
<213> ORGANISM: Homo sapiens

<400> SEQUENCE: 10

Gln Gln Tyr Ser Lys Leu Pro Leu Thr
1               5

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19
```

```
000

<210> SEQ ID NO 20

<400> SEQUENCE: 20

000

<210> SEQ ID NO 21
<211> LENGTH: 7
<212> TYPE: PRT
<213> ORGANISM: Homo sapiens

<400> SEQUENCE: 21

Gly Ala Ser Ser Arg Ala Thr
1               5

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25
<211> LENGTH: 9
<212> TYPE: PRT
<213> ORGANISM: Homo sapiens

<400> SEQUENCE: 25

Phe Thr Phe Ser Ser Tyr Ser Met Asn
1               5

<210> SEQ ID NO 26
<211> LENGTH: 17
<212> TYPE: PRT
<213> ORGANISM: Homo sapiens

<400> SEQUENCE: 26

Tyr Ile Ser Ser Ser Ser Ser Thr Ile Tyr Tyr Ala Asp Ser Val Lys
1               5                   10                  15

Gly

<210> SEQ ID NO 27
<211> LENGTH: 8
<212> TYPE: PRT
<213> ORGANISM: Homo sapiens

<400> SEQUENCE: 27

Gly Gly His Gly Tyr Phe Asp Leu
1               5

<210> SEQ ID NO 28
```

```
<211> LENGTH: 12
<212> TYPE: PRT
<213> ORGANISM: Homo sapiens

<400> SEQUENCE: 28

Arg Ala Ser Gln Ser Val Ser Ser Ser Tyr Leu Ala
1               5                   10

<210> SEQ ID NO 29
<211> LENGTH: 9
<212> TYPE: PRT
<213> ORGANISM: Homo sapiens

<400> SEQUENCE: 29

Gln Gln Tyr His His Ser Pro Leu Thr
1               5
```